US010519444B2

(12) United States Patent
Lee et al.

(10) Patent No.: US 10,519,444 B2
(45) Date of Patent: Dec. 31, 2019

(54) METHODS OF REDUCING EXPRESSION OF X-INACTIVATION ESCAPEE GENES AND AUTOSOMAL GENES

(71) Applicant: The General Hospital Corporation, Boston, MA (US)

(72) Inventors: Jeannie T. Lee, Boston, MA (US); Hsueh-Ping Chu, Weymouth, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 15/780,509

(22) PCT Filed: Dec. 1, 2016

(86) PCT No.: PCT/US2016/064438
§ 371 (c)(1),
(2) Date: May 31, 2018

(87) PCT Pub. No.: WO2017/096053
PCT Pub. Date: Jun. 8, 2017

(65) Prior Publication Data

US 2018/0346906 A1 Dec. 6, 2018

Related U.S. Application Data

(60) Provisional application No. 62/261,698, filed on Dec. 1, 2015.

(51) Int. Cl.
*C12N 15/113* (2010.01)
*A61K 31/713* (2006.01)
*A61K 45/06* (2006.01)

(52) U.S. Cl.
CPC .......... *C12N 15/113* (2013.01); *A61K 31/713* (2013.01); *A61K 45/06* (2013.01); *C12N 2310/11* (2013.01); *C12N 2310/111* (2013.01); *C12N 2310/113* (2013.01); *C12N 2310/315* (2013.01); *C12N 2310/321* (2013.01); *C12N 2310/322* (2013.01); *C12N 2310/3231* (2013.01); *C12N 2310/341* (2013.01); *C12N 2310/3521* (2013.01); *C12N 2310/3533* (2013.01)

(58) Field of Classification Search
None
See application file for complete search history.

(56) References Cited

U.S. PATENT DOCUMENTS 5,801,154 A * 9/1998 Baracchini ............. C07H 21/00 435/325
2014/0142160 A1 5/2014 Lee et al.

OTHER PUBLICATIONS

Azzalin and Lingner, "Telomere functions grounding on TERRA firma," Trends Cell Biol, 2015, 25: 29-36.
Azzalin, et al., "Telomeric Repeat Containing RNA and RNA Surveillance Factors at Mammalian Chromosome Ends," Science, 2007, 318: 798-801.
Bacher et al., "Transient colocalization of X-inactivation centres accompanies the initiation of X inactivation," Nature Cell Biology, 2006, 8: 293-299.
Balk et al., "Telomeric RNA-DNA hybrids affect telomere-length dynamics and senescence," Nat Struct Mol Biol, 2013, 20: 1199-1205.
Berletch et al., "Escape from X inactivation in mice and humans," Genome Biology, 2010, 11: 213.
Berletch et al., "Genes that escape from X inactivation," Human Genetics, 2011, 130: 237-245.
De Jesus et al., "Telomerase at the intersection of cancer and aging," Trends in Genetics, 2013, 29: 513-520.
Blackburn et al., "Telomeres and telomerase: the path from maize, Tetrahymena and yeast to human cancer and aging," Nature Medicine, 2006, 12: 1133-1138.
Brown et al., "The human XIST gene: analysis of a 17 kb inactive X-specific RNA that contains conserved repeats and is highly localized within the nucleus." Cell, 1992, 71, 527-542.
Carrel and Willard, "X-inactivation profile reveals extensive variability in X-linked gene expression in females," Nature, 434: 400-404.
Chu et al., "Genomic maps of long noncoding RNA occupancy reveal principles of RNA-chromatin interactions," Molecular Cell, 2011, 44: 667-678.
De Silanes et al., "Identification of TERRA locus unveils a telomere protection role through association to nearly all chromosomes," Nat Commun, 2014, 5: 4723.
Deng et al., "X chromosome regulation: diverse patterns in development, tissues and disease," Nat Rev Genet, 15: 367-378.
Deng et al., "TERRA RNA binding to TRF2 facilitates heterochromatin formation and ORC recruitment at telomeres," Molecular Cell, 2009, 35: 403-413.
Disteche, "Dosage compensation of the sex chromosomes," Annual Review of Genetics, 2012, 46: 537-560.
Dixon et al., "Topological domains in mammalian genomes identified by analysis of chromatin interactions," Nature, 2012, 485: 376-380.
Doksani and de Lange, "The role of double-strand break repair pathways at functional and dysfunctional telomeres," Cold Spring Harbor Perspectives in Biology, 2014, 6: a016576.
Filippova et al., "Boundaries between chromosomal domains of X inactivation and escape bind CTCF and lack CpG methylation during early development," Dev Cell, 2005, 8: 31-42.

(Continued)

*Primary Examiner* — Tracy Vivlemore
(74) *Attorney, Agent, or Firm* — Fish & Richardson P.C.

(57) ABSTRACT

Inhibitory nucleic acids, e.g., antisense oligonucleotides (ASO) against PAR-TERRA RNA or other chromosome-specific TERRA transcripts (i.e., inclusive of chromosome-specific subtelomeric sequences), and methods of use thereof to downregulate expression of escapee genes on the inactive X chromosome, expression from the active X chromosome, subtelomeric autosomal loci (e.g., FSHD locus), or expression of autosomal genes involved in growth control and apoptosis, e.g., in cells and subjects with supernumerary X chromosomes and/or cancer and other human diseases.

10 Claims, 38 Drawing Sheets
(33 of 38 Drawing Sheet(s) Filed in Color)

Specification includes a Sequence Listing.

(56) References Cited

OTHER PUBLICATIONS

Heinz et al., "Simple combinations of lineage-determining transcription factors prime cis-regulatory elements required for macrophage and B cell identities," Molecular Cell, 2010, 38: 576-589.
Horvath et al., "Deletion of an X-inactivation boundary disrupts adjacent gene silencing," PLoS Genetics, 2013, 9: e1003952.
Kharchenko et al., "Design and analysis of ChIP-seq experiments for DNA-binding proteins," Nature Biotechnology, 2008, 26: 1351-1359.
Kung et al., "Locus-Specific Targeting to the X Chromosome Revealed by the RNA Interactome of CTCF," Molecular Cell, 2015, 57: 361-375.
Le et al., "TERRA, hnRNP A1, and DNA-PKcs Interactions at Human Telomeres," Frontiers in Oncology, 2013, 3: 91.
Lee, "Gracefully ageing at 50, X-chromosome inactivation becomes a paradigm for RNA and chromatin control," Nat Rev Mol Cell Biol, 2011, 12: 815-826.
Lee et al., "Tsix, a gene antisense to Xist at the X-inactivation centre," Nat Genet, 1999, 21: 400-404.
Lingner et al., "Reverse transcriptase motifs in the catalytic subunit of telomerase," Science, 1997, 276: 561-567.
Lopes et al., "Clustered transcripts that escape X inactivation at mouse XqD," Mammalian Genome, 2011, 22: 572-582.
Luke et al., "The Rat1p 5' to 3' exonuclease degrades telomeric repeat-containing RNA and promotes telomere elongation in *Saccharomyces cerevisiae*," Molecular Cell, 2008, 32: 465-477.
Maguire, "The mechanism of meiotic homologue pairing," Journal of Theoretical Biology, 1984, 106: 605-615.
Maicher et al., "Deregulated telomere transcription causes replication-dependent telomere shortening and promotes cellular senescence," Nucleic Acids Res, 40: 6649-6659.
Merkenschlager and Odom, "CTCF and cohesin. linking gene regulatory elements with their targets," Cell, 2013, 152: 1285-1297.
Penny et al., "Requirement for Xist in X chromosome inactivation," Nature, 1996, 379: 131-137.
Pfeiffer and Lingner, "TERRA promotes telomere shortening through exonuclease 1-mediated resection of chromosome ends," PLoS Genetics, 2012, 8: e1002747.
Pfeiffer et al., "The THO complex component Thp2 counteracts telomeric R-loops and telomere shortening," EMBO J, 2013, 32: 2861-2871.
Pinter et al., "Spreading of X chromosome inactivation via a hierarchy of defined Polycomb stations," Genome Research, 2012, 22: 1864-1876.
Redon et al., "The non-coding RNA TERRA is a natural ligand and direct inhibitor of human telomerase," Nucleic Acids Res, 2010, 38: 5797-5806.
Redon et al., "A three-state model for the regulation of telomerase by TERRA and hnRNPA1," Nucleic Acids Res, 2013, 41: 9117-9128.
Reig-Viader et al., "Telomeric repeat-containing RNA and telomerase in human fetal oocytes," Hum Reprod, 2013, 28: 414-422.
Reig-Viader et al., "Telomeric repeat-containing RNA (TERRA) and telomerase are components of telomeres during mammalian gametogenesis," Biol Reprod, 2014, 90: 103.
Rockmill and Roeder, "Telomere-mediated chromosome pairing during meiosis in budding yeast," Genes & Development, 1998, 12: 2574-2586.
Sandell et al., "Transcription of a yeast telomere alleviates telomere position effect without affecting chromosome stability," PNAS, 1994, 91: 12061-12065.
Schoeftner and Blasco, "Developmentally regulated transcription of mammalian telomeres by DNA-dependent RNA polymerase II," Nature Cell Biology, 2007, 10: 228-236.
Schoubben et al., "Tetrasomy and pentasomy of the X chromosome," Eur J Pediatr, 2011, 170(10):1325-7.
Sfeir and de Lange, "Removal of shelterin reveals the telomere end-protection problem," Science, 2012, 336: 593-597.
Shin et al., "CEAS: cis-regulatory element annotation system," Bioinformatics, 2009, 25: 2605-2606.
Simon et al., "High-resolution Xist binding maps reveal two-step spreading during X-chromosome inactivation," Nature, 2013, 504: 465-469.
Simon et al., "The genomic binding sites of a noncoding RNA," PNAS, 2011, 108: 20497-20502.
Soriano et al., "High rate of recombination and double crossovers in the mouse pseudoautosomal region during male meiosis," PNAS, 1987, 84: 7218-7220.
Starmer and Magnuson, "A new model for random X chromosome inactivation," Development, 2009, 136: 1-10.
Sun et al., "Jpx RNA activates Xist by evicting CTCF," Cell, 2013, 153: 1537-1551.
Targaltia et al., "48,XXYY, 48,XXXXY and 49,XXXXY syndromes: not just variants of Klinefelter syndrome," Acta Paediatr, Jun. 2011, 100(6):851-60.
Trapnell et al., "Differential analysis of gene regulation at transcript resolution with RNA-seq," Nature Biotechnology, 2013, 31: 46-53.
Visootsak and Graham, "Klinefelter syndrome and other sex chromosomal aneuploidies," Orphanet J Rare Dis, 2006, 1: 42.
Wang et al., "Role of TERRA in the Regulation of Telomere Length," Int J Biol Sci, 2015, 11: 316-323.
Wutz, "Gene silencing in X-chromosome inactivation: advances in understanding facultative heterochromatin formation," Nat Rev Genet, 2011, 12: 542-553.
Xiang et al., "Synaptonemal complex extension from clustered telomeres mediates full-length chromosome pairing in Schmidtea mediterranea," PNAS, 2014, 111: E5159-5168.
Xu et al., "Evidence that homologous X-chromosome pairing requires transcription and CTCF protein," Nat Genet, 2007, 39: 1390-1396.
Xu et al., "Transient homologous chromosome pairing marks the onset of X inactivation," Science, 2006, 311: 1149-1152.
Yang et al., "Global survey of escape from X inactivation by RNA-sequencing in mouse," Genome Research, 2010, 20: 614-622.
Yu et al., "Telomeric transcripts stimulate telomere recombination to suppress senescence in cells lacking telomerase," PNAS, 2014, 111: 3377-3382.
Zhang et al., Model-based analysis of ChIP-Seq (MACS). Genome Biology, 2008, 9: R137.
Zhao et al., "Polycomb proteins targeted by a short repeat RNA to the mouse X chromosome," Science, 2008, 322: 750-756.
International Search Report and Written Opinion mailed in PCT/US2016/064438, 13 pgs.
Zhang et al., "Telomeric RNAs mark sex chromosomes in stem cells," Genetics 182.3: 685-698 (2009).
Basu et al., "X chromosome inactivation: A silence that needs to be broken," Genesis 49.11: 821-834 (2011).

* cited by examiner

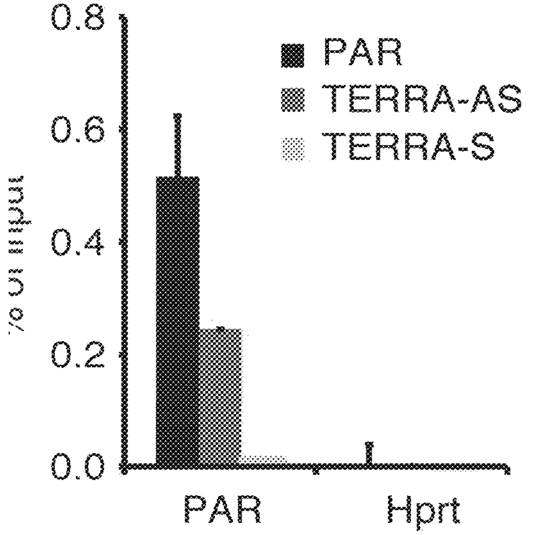
FIG. 2C
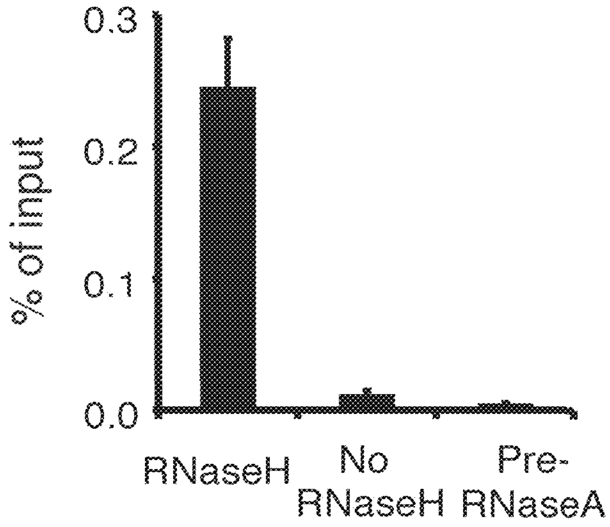
FIG. 2D
| | Number of PAR-TERRA binding sites | | | | | | | | | |
|---|---|---|---|---|---|---|---|---|---|---|
| | ES_d0 | | | ES_d3 | | ES_d7 | | MEF | | |
| | TERRA | PAR | Sense | TERRA | PAR | TERRA | PAR | TERRA | PAR | Sense |
| Normalized to input | 4054 | 2304 | 78 | 2125 | 5373 | 1884 | 3199 | 500 | 440 | 544 |
| Normalized to sense | 4076 | - | - | - | - | - | - | 492 | - | - |
| Normalized to no-RNase H | 3880 | - | - | - | - | - | - | 492 | - | - |
FIG. 2E

TERRA ChIRT-seq

- Promoter (≤ 1000 bp): 1.8 %
- Promoter (1000-2000 bp): 1.8 %
- Promoter (2000-3000 bp): 1.8 %
- Downstream (≤ 1000 bp): 1.7 %
- Downstream (1000-2000 bp): 1.6 %
- Downstream (2000-3000 bp): 1.4 %
- 5'UTR: 0.6 %
- 3'UTR: 1.4 %
- Coding exon: 0.7 %
- Intron: 40.1 %
- Distal intergenic: 47.2 %

PAR ChIRT-seq

- Promoter (<=1000 bp): 1.8 %
- Promoter (1000-2000 bp): 2.0 %
- Promoter (2000-3000 bp): 1.9 %
- Downstream (<=1000 bp): 1.6 %
- Downstream (1000-2000 bp): 1.6 %
- Downstream (2000-3000 bp): 1.3 %
- 5'UTR: 0.3 %
- 3'UTR: 0.9 %
- Coding exon: 0.4 %
- Intron: 40.4 %
- Distal intergenic: 47.8 %

Number of binding sites

| ES d0 | total | ChrX |
|---|---|---|
| TERRA | 4054 | 86 |
| PAR | 2304 | 84 |

| MEF | total | ChrX |
|---|---|---|
| TERRA | 500 | 94 |
| PAR | 440 | 30 |

Immortalized female MEF (tetraploid)

CHIRT Replicate 1

| Name of library | Total reads | Reads after PCR duplicates removal | Uniquely mapped reads in mm10 | % Uniquely mapped reads in mm10 |
|---|---|---|---|---|
| ES_d0 PAR-AS | 32464373 | 31255733 | 30472507 | 97.49 |
| ES_d0 TERRA-AS | 28932181 | 23905938 | 22631527 | 94.67 |
| ES_d0 TERRA-S | 46282449 | 44747817 | 43894751 | 98.09 |
| ES_d0 TER (no RNAseH) | 41852461 | 34807415 | 32453318 | 93.24 |
| ES_d0 input | 45396054 | 41983022 | 41545697 | 98.96 |
| ES_d3 input | 30065363 | 27270315 | 26488296 | 97.13 |
| ES_d3 PAR-AS | 41668524 | 35614418 | 28292145 | 79.44 |
| ES_d3 TERRA-AS | 33458866 | 27658177 | 23664357 | 85.56 |
| ES_d7 input | 37132369 | 35901389 | 12171677 | 33.90 |
| ES_d7 PAR-AS | 36815663 | 34240958 | 32758921 | 95.67 |
| ES_d7 TERRA-AS | 33045601 | 27014673 | 23824033 | 88.19 |
| MEF PAR-AS | 31682605 | 28971390 | 25213047 | 87.03 |
| MEF TERRA-AS | 35059769 | 32329303 | 7773238 | 24.04 |
| MEF TERRA-S | 38609175 | 32433255 | 19840775 | 61.17 |
| MEF TERRA (no RNAseH) | 43253571 | 33402120 | 26037320 | 77.95 |
| MEF input | 46619652 | 40321599 | 39755914 | 98.60 |

CHIRT Replicate 2

| Name of library | Total reads | Reads after PCR duplicates removal | Uniquely mapped reads in mm10 | % Uniquely mapped reads in mm10 |
|---|---|---|---|---|
| ES_d0 PAR | 11537196 | 7807554 | 6826109 | 87.43 |
| ES_d0 PAR RNase A | 15826305 | 14859144 | 12993461 | 87.44 |
| ES_d0 TERRA | 14094905 | 12515985 | 10725993 | 85.70 |
| ES_d0 TERRA RNaseA | 13627224 | 12411472 | 10985881 | 88.51 |
| ES_d0 sense | 14950599 | 13133452 | 10864427 | 82.72 |
| ES_d0 sense RNase A | 13903763 | 12050175 | 10459053 | 86.80 |
| ES_d0 TERRA no Rnase H | 13666488 | 10053384 | 8013263 | 79.71 |
| MEF PAR | 17210856 | 13251314 | 11195046 | 84.48 |
| MEF PAR RNase A | 14849691 | 12367944 | 9990314 | 80.78 |
| MEF TERRA | 13684453 | 8039976 | 6620225 | 82.34 |
| MEF TERRA RNaseA | 12206274 | 6923577 | 5602706 | 80.92 |
| MEF sense | 12117053 | 8649137 | 7467591 | 86.34 |
| MEF sense RNase A | 15981875 | 11504737 | 9553319 | 83.04 |
| MEF TERRA no Rnase H | 12542949 | 8715062 | 6604865 | 75.79 |

FIG. 9C

SEQUENCE LISTING

```
<160> NUMBER OF SEQ ID NOS: 61

<210> SEQ ID NO 1
<211> LENGTH: 151450
<212> TYPE: DNA
<213> ORGANISM: Homo sapiens

<400> SEQUENCE: 1

gctcaatgca acctccacct cccgggttca cgccattctc ctgcctcagc ctcctgagta     60

gctggcacta caggtgccca tcacgcaccc aggtagtttt tgtgttttta atagagacgg    120

ggtttcacca tgttggtcag gctggtctcg aactcctgac ctcatgttcc acccgccttc    180

gcctcccaaa gtgctgggat gacaggcgtg agtcactgca cactcggctg tttttttttc    240

ttttgagatg gagtctcggt ctatcattca gactggagtg cagtggcacg atgtcagctc    300

aatgcaacct ccatctcccg gcttcaagca gttctcctgc ctgagcctcc cgagtaactg    360

ggactacagg cgcctgccac acacccagct aagttttgta tttttagtag agatgggatt    420

tcaccatgtt ggtcaggctg ctctcaagct cctgacctca tgatccaccc acctcggcct    480
```

-continued

```
cccaaagtgc tgggaagaca ggcgaagtca ccacgcccag ccaccccatc tctattttaa    540
agaaaatgaa aacgtattat catcggtcct atgatcacca acatttggcc caaacaaagt    600
cacaatactt ggaaattcgg gggtgaaact gcagccgccg cgtcccgaac ttcagaaggg    660
tcccgtcagc accacagcag cttctgattg agcgcgatga cgtcactgac gaagccgtct    720
gcgccgatga agtcccccgc gatgatgttg gtgcaccgtg aacccggccc cgggcactgc    780
tctcggaccc acgcgctcag ccgcggaagg ttgggcagcg tcatcttctc cagggactcg    840
gacgggtgcg ccagaacgta ctgcaggttc tccgtgaggt tgatgccggc cacgaacaac    900
cctcctgcaa cggtgagggt ggggagaggt tacacggtca cgggcctcac ccgcctgttt    960
ctccctccta gtcacattat tagaggttcg catctcagga attaagagtt gaaagcacca   1020
tgtccaacaa ggaaattggg tgagctttgc ttataaagcg tggtgggcag tagacaaccc   1080
caaagatgct cacgtcgtaa caccgtgtgg gagacagaat aatgtcccca aagatgtcca   1140
catcctaatc cccatgtgat agacagaata atggccccaa agatgtccac gtcctaatcc   1200
ccatgtgata gacagaataa tgtccccaaa gatgtccacg tcctaatccc catgtgatag   1260
acaggataat ggccccaaag atgtccacgt cctgatcccc atgtgataga cagaataatg   1320
tccccaaaga tgtccacgtc ctaatcccca tgtgggagac agaataatgt ccccaaagat   1380
gtccacgtcg taatccccat gtgatagaca gaataatggc cccaaagatg tccacgtcct   1440
aatccccatg tgatagacag aataatgtcc ccaaagatgt ccacgtccta atccccatgt   1500
gggagacaga ataatgtccc caaagatgtc cacgtcctaa tccccatgtg atagacagaa   1560
taatgtcccc aaagatgtcc acgtcctaat ccccatgtga tagacagaat aatgtcccca   1620
aagatgtcca cgtcctaatc cccatgtgat agacagaata atggccccaa agatgtccac   1680
gtcctaatcc ccatgtggga gacagaataa tgtccccaaa gatgtccacg tcctaatccc   1740
catgtgatag acagaataat gtccccaaag atgtccacgt cctaatcccc atgtgggaga   1800
cagaataatg tccccaaaga tgtccacgtc ctaatcccca tgtgatagac agaataatgt   1860
ccccaaagat gtccacgtcc taatccccat gtgatagaca gaataatgtc cccaaagatg   1920
tccacgtcct aatccccatg tgatagacag aataatgtcc ccaaagatgt ccacgtccta   1980
atccccatgt gggagacaga ataatgtccc caaagatgtc cacgtcctaa tccccatgtg   2040
atagacagaa taatgtcccc aaagatgtcc acgtcctaat ccccatgtga tagacagaat   2100
aatgtcccca aagatgtcca cgtcctaatc cccatgtgat agacagaata atgtccccaa   2160
agatgtccac gtcctaatcc ccatgtgata gacagaataa tggccccaaa gatgtccacg   2220
tcctaatccc catgtgatag acagaataac agccccaaag atgtccacgt cctaatcccc   2280
atgtgggaga cagaataatg tccccaaaga tgtccacgtc ctaatcccca tgtgatagac   2340
agaataatgt ccccaaagat gtccacgtcc taatccccat gtgggagaca gaataacagc   2400
cccaaagatg tccacgtcct aatccccatg tgatagacag aataatgtcc ccaaagatgt   2460
ccacgtccta atccccatgt gggagacaga ataacagccc caaagatgtc cacgtcctaa   2520
tccccatgtg ggagacagaa taatgtcccc aaagatgtcc acgtcctaat ccccatgtgg   2580
gagacagaat aatggcccca aagatgtcca cgtcctaatc cccatgtggg agacagaata   2640
atggccccaa agatgtccac gtcctaatcc ccatgtgata gacaggataa tgtccccaaa   2700
gatgtccacg tcctgatccc catgtgatag acagaataat gtccccaaag atgtccacgt   2760
cctaatcccc atgtgataga cagaataatg tccccaaaga tgtccacgtc ctaatcccca   2820
tgtgatagac agaataatgg ccccaaagat gtccacgtcc taatccccat gtgatagaca   2880
```

```
gaataatgtc cccaaagatg tccacgtcct gatccccatg tgggagacag aataatgtcc   2940
ccaaagatgt ccacgtccta atccccatgt gatagacagg ataatgtccc caaagatgtc   3000
cacgtcctaa tccccatgtg atagacagaa taatgtcccc aaagatgtcc acgtcctaat   3060
ccccatgtga tagacagaat aatggcccca aagatgtcca cgtcctaatc cccatgtggg   3120
agacagaata atgtccccaa agatgtccac gtcctaatcc ccatgaggta gacaggataa   3180
tggccccaaa gatgtccacg tcctaatccc atgtgggaga cagaataata tggccccaaa   3240
cttgtccaca ttcttatccc ccatgtgata gacaggaaga atgctgttgt cttgggcact   3300
aagtctgtgc catctcttat gaggcttata gagagggttg acgttgacca gtgattctca   3360
aagtggggtc cctgcaatag ttagaaatgc aaatttgggg gctccaccta catctgctga   3420
gccggaatct cctgcaagcc atatttgaag aagctccccc agaggtaggt tccagtgccc   3480
ctgtgttgac cagctggact gattccacag ccagagacgg caaaggcaac agacgtttat   3540
ggccaagttc tctcagtggt ttttaacacg tatttctagg ctgggcacgg tggctcatgc   3600
ctgtcatccc agcacgttga gaggttgagg ccggtggatc atgaggtcag gagttcaaga   3660
ccagcctgac caacacgctg aaaccctttc tctagtaaaa acacatccaa aaattagctc   3720
agcatggtgg tacgtgcccg taatcccagc tactcgggag gctgaggcag gagaatcact   3780
tgaatccagg aggtggaggt tgcagtgagc cgagatcacg ccattgcact ccagcctggg   3840
tgacagagca agactctgtc tcaaaaacaa aacaaaacaa acaaaaaaag gccgggcaca   3900
gtggctcaag cctgtaatcc caccactttg ggaggccaag gcgggcagat cacctgaggt   3960
cgggagttcg agaccagcct gatcaacatg gagaaacccc atctctacta aaaataaaaa   4020
ttagccgggc gtggtgggag gctgaggcgg gagaattgct cgaacccagg aggcgaaggc   4080
tgcagtgagc caagattgcg ccattgcact ctagcctggg caacaagagc aaaactctgt   4140
ctcaaaaaac aaacacacaa acaaaaaaat tttccgcctg gcaccgtggc tcacgcctgt   4200
catcccagca ctttgggaga ctgagacggg cagatcatga ggtcaggagt tcgagaccag   4260
cccgaccaac atggtgaaac cctgtctcta ctaaaaatac aaaaaaaaat tagccgggtg   4320
tggtggcggg cgcctgtagt cccagctact caggaggctg aggcaggaga atggcttgaa   4380
cccgggagac ggaggttgca gtgagccgag atcgcgccac tgcactccga ccggggcaac   4440
aagagtgaga ctccacctca aaaaaaaaaa aaagacattt ctgaagtctc taaacctcgt   4500
tcctgtgtga gggcaagaga ccaagttgaa aaaacctgct cctttgcccg gcccgtgact   4560
gggtttcatg ctgcccctgt gggaagcagc cctcgcggcc gtgaagatca ccttgagaga   4620
acccagccgc aggctgcagg accgagacgg ccccacctgc caccgtcccc gcggggagga   4680
ccttcctccc tccctccctc aggctcctgc ctccggagga cacggggccg tggctgccga   4740
cgctgtctgc acctcacacc ccgtcggtgg cttttttaca aaaattgtgg tgaaattcac   4800
gtacaaaaaa gttacctttt ttttttttc ccaagatgga gtctcgctct gttgcccagg   4860
ctggagtgct gtggcgcgat ttcggctcac ggcagcctcc gcccccgggt tcaagcaatt   4920
ctcctgcctc agcctcccga ggagctggga ttacaggtgc acacaaccac gcccagctaa   4980
atctttttgt atttttacta gagatggggt ttcaccagac tggtcgcaaa ctcctgatct   5040
caattaatcc acctgcctcg gcctcccaaa gtggtgggat tacaggcgtg agccactgca   5100
ccgaaattca cgattttaaa ttgcacaact cggctgggaa tggtggttca agcagatcgc   5160
ttgaccccag aagtttgatt ttgtcttgtt ttgttttgag acagagtctc gctctgttgc   5220
```

```
ccaggctgga gtacactggc tcgatctcgg cccactgcaa cctccgcctt cctggttcaa   5280
gtgattcccc tgcctcagcc tcctgagtag ctgggattat aggcgcgcat caccatgcct   5340
ggctaatttt tctcttttt gttttgtttt gagatggagt cttgctcctg tcgcccaggc   5400
tggagtgcag tggcgcgacc atggatcaca gcaacctccg cctcctggat tcaagcattt   5460
ctcctgcctc agcctcccaa gtagatggga ttacaggtgc ctattttttt ttttttttg   5520
agacagagtt ccactctgtc gcccaggctg gagttcagtg gcgtgatctc ggctcactgc   5580
aagctccgcc tcccgagttc acaccattct cctacctcag cctccggagt agctgggatt   5640
acaggcgccc gccaccacgc ccggctaatt ttttgtattt ttagtagaga cggggtttct   5700
ccatgttagc cgggatggtc tcgatctcct gacctcatga tccgcccgcc tcggcctccc   5760
gaagtgctgg gattacaggc gtgagccacc gcgcccggcc tgtgcccgct aatttttgta   5820
tttttgctag agaagaggtt tcgccatgtt ggccaggctg gtctccaaac tcctgacctc   5880
aggtgatcca cccaccttgg cctcccaaag tgctgtgatc acaggtgtga gccaccgcac   5940
ctggctgaca ccaggagttt gagaccagcc tggccaacac agtgagaccc cttctctaat   6000
caaagaatta actaaaaaaa ataaagtgga ttcacgttgt gcaactccga cctctcccta   6060
gttccagaac attctcatcg tcctaaaagg agagaccctg tttccatgaa gcagtcagtc   6120
ctcatttccc ctccgcagcc cccggcaacc acaaatcctc tttctgtctc tggattggca   6180
tgttctgggc atttcctgta aatggattca cacactacgt gtccttttgt gtctggcttc   6240
tctcactgag cgtgatgtct taaggtttgt gcccgctgca tccttgtcag agcctcgttc   6300
tttttcatgg ctgtgtaata ttccaccgcg tggatggacc acaccttgtt gatccctccc   6360
cccgccaatg tacatggact gctttctccc tgggtgcttc ttaagtagag acagggtttc   6420
atcacattgg tcaggccggt ctcgaactcc cgacctcagg tgatctgccc gcctcagcct   6480
cccaaagtgc taggatgaca ggcatgaacc actgcgcccg gccgctaagt tttatttcta   6540
gtaaagttgg ggtctcacta tgttggccag gctggtctca aactcccgac ctcaggtgat   6600
ccacccgcct cggcctcccg aagtgctggg attacaggta cagggattac cacgcccagc   6660
tcatggattc cttttaaatt gttttcacgt aaaagtgaag gcaagtccat gtggacccgg   6720
cctgccgcag ggcgtcacgg gaggctgtgt ggaatctacc cccacgaggg gcgacctggt   6780
acctgggcgg ccgcagctct tcatggtctc caggtatcgg atgagggcct cggtcttcac   6840
cctgtttccc caccagtagg ggactcctgg ccacagctcg tggtgccggc gcaaggagct   6900
ctcgtcttca taggagacga tgacctgttg gccccgggac cacagctgcc gcagtgtcgg   6960
cacctcctgc aaaggaccag agttaagggg tgcaggggag agaggagagc cgggggcacc   7020
tgggagagcg gagggctggg aagtcgggac accggcccaa cacgagtata aaccaaaaat   7080
gaaattctgg ccgggcgcag tggctgacgc ctgtaatccc agcactttgg gaggccgagg   7140
tgggtggatc acctgaggtc aggagtttga gaccagcccg ggcaacatgg tgaaacccca   7200
tctctactaa aaatacaaaa attggccggg tgcggtggtg cacgcctgtc atcccggcta   7260
gtcagaaggc tgaggtagga gaatcgtttg aacctgggag gcagaggttg cggtgagccg   7320
aggtttcgct attgcactcc agcctgggag acagaccgag actccctctc aaataaataa   7380
ataaattaag tatggccagg tgcaggggct catgcctgta atcccagcac tttgggagga   7440
cacggcggga ggatcactcg aggccaggaa ttcgagcctg ggctgcacag ggtgaccctg   7500
tctctatttt tatatattta tttattttta ttttttattt tttgagacgg atctcgctct   7560
gtctcccagg ctggaatgca gtggcgcgat ctcggctcac tgcaacctcc accccccggg   7620
```

-continued

```
ttcacaccat tctcctgcct cagcctcccg agtagctggg actacaggcg cccgccacca   7680
cgcccggcta attgtttgta ttttgtgtta gtagagacgg ggtttcaccg tgttagccag   7740
gatggtctcg atgtcctgac ctcatgatcc gcccgcctcg gcctcccaaa gtcctgggat   7800
gacaggtgtg agccactgcg tccggcacac ccaccgccac acccagataa ttttggtatt   7860
tttagtagag acggggtttc accatgttgg ccaggatagt ctcaatctct tgacctcgtg   7920
atccgcccgc ctcggcctcc caaagtcctg ggatgacaag cgtgagccac cacacccagc   7980
ctaattgttg tatttttagt agacaccagg tttcaccatg ttggccagga tagtctcgat   8040
ctcttgacct cgtgatccac ccgcctcggc ctcccaaagt gctgggatga caggcgtgag   8100
ccaccgcgcc cggctgacgc tgcacacatt tctaaacccg tcaagggaag cagatctcac   8160
caggagccac ccccaccgggt cagccagggc cccccacact gcgggagagc aggcagcccc   8220
cgttcgacgg cttcacctgc tacaggaatc atggcagcac ccacacccag ggcacagcaa   8280
atggagtctg aggctgacga tgcccctgcc ccgggagaga cgtgcggata tccttcccct   8340
cctcacccca cgaggacaca gcatgtcccc gaagatgttc ttgatacagg cgaccaggta   8400
ctcgtgcagg tcctcgctca gcccctcgaa gtttctgcag gccaggatga ccacctcgcg   8460
tggatgccgc tccagccact ccgagatttc cgtgagtgtg tcctggggag gggggtgctg   8520
ggctgagtcc tgcacgactc caacaccaca gggaaggcgg ggtgtggcgg ctcacgcctg   8580
tcatcccagc aatttgggag gccgaggcgg gtggatcacc tgaggttagg agtttgagac   8640
cagcctagcc aacatggtga aaccccgtat ctactaaaaa tacaaaaatt agctgggcgt   8700
ggtgtccggc gtctgtaatc ccagctactt ggaaggctga ggcaggagaa ttgcctgaac   8760
ccaggaggca gaggttgcag tgagctgaga ttgcaccact gcactccagc ctgggcgaca   8820
cagcaagact ccatctccaa aaaaaaaaag caaaaaaaaa agaaatctcc gtaacggatt   8880
ggcggggtca gtgtctcctg tctggtgtat aggtgacgtc acccttccat taaagaccgg   8940
gcgtttcctg tccacatctg catgtggctg tttcatcccc acgggagctt ggccacctcc   9000
cgccgtcccc cttgcttccc acctcagccc ggccgcacct gcaccagcgc ccggccgcct   9060
cccgctgtcc cccttgcttc ccacctcagc ccggccgcac ctgcaccagt gcccggccgc   9120
ctcccgctgt ccccccttgct tcccacctca gcccggccgc acctgcacca gtgcccggcc   9180
gcctcccact ctccccattg cgtcccacct cagcccggcc gcacctccac cagcgccgtt   9240
gtgtacacca tatggacaaa gtgcaggttc ttctccgagc cctccagcat gtgggctatc   9300
cgcaggtcca ggtaccgcac cccggcatcc agctgctctg tgacgtccag tgcctgtgga   9360
cagaggctgc tgtcatgtct gcctggctga gcgccgcgtc tggggggctc aggaatgggc   9420
tgtggggttg gcccacccgc atgtcctgct gcccactggg acgtggatgt cgtaacaaca   9480
gctgtttgta tgtgctggga gcgctgcagc cacggggacc tgcatttgga aaacctcatc   9540
tccggggacc tggccttttt tttttttttt tgagacggag tctcgctctg tcacccaggc   9600
tggagtgcag tggtgcaatc tgggctcact gcaagctccg cctcccgggt tcatgccgtt   9660
ctcctgcctc agcctcccca gtagctggga ctgcaggcgc ccgccaccgc gcccagctaa   9720
ttttgttttg tatttttagt agagatgtgg tttcaacatg ttagccagga cggtctcgat   9780
ctcctgacct cgtgatccac ccaccttggc ctcccaaagt gctgggatta caggcgtgag   9840
ccaccgcgcc cggcctctac taaaaatttt aaaaatcagc ctgggtgtgg tggtgtacac   9900
ctgtagtccc agctgcccgg gaggctgagg aaggaggatc ctttgatcct gggaggccca   9960
```

-continued

```
ggctgcagga agctgagatc gcaccaccgc actccagtct gggtgagaga gcgagactcc  10020
atctctaaag gaatgaatga atgtgattat tagggagaaa ggggcctgtc tccctgtttc  10080
ccagggacta gcagatgcct gactgcaaac tgcagacccg cctcaggtcc taaagacacg  10140
agaaatgagt ccttgtctgt cttgagtgca ggcatgaaag gggttgtctc ggccgggcgc  10200
ggtggctgac gcctgtaatc ccagcacttt gggaggctga ggcgggtgga tcacgaggtc  10260
aggagttcga gaccatcctg gctaacacag tgaaaccctg actctactca aaataccaaa  10320
aattagccgg gcgtggtcgc gggagcctgt agtcccagct actcaggagg ctgagacagg  10380
agaatggcgt gaacccggga ggcggagctt gcagtgagcc gagatggcac caactgcact  10440
ccagcctggg cggcagtgag actccgtctc aaaaaaaaaa aaaagaaaaa gaaagaaaaa  10500
gaaaggtgtt gtctctgctg ggatgcaaca gggcgagacc ctctccctct gcagctctca  10560
gtggaggcct gcgatgctca cggcattagc tttacgccat ttaataaaat gctgggccgg  10620
gcgcggtggc tcacgcctgt aatcccagca ctttcggagg ctggggcggg cagatcatga  10680
ggtcaggaga tcaagaccat cctgactaac acggtaaaac cccatctcta ctaaaaatac  10740
aaaaaattag ccaggtgtgg tgacaggtgc ctgtagaccc aggtacttag gaggatgagg  10800
caggagaatc gcttgaaccc aggcagcgga ggttgcagtg agccgagatc acgccactgc  10860
actccagccc gggtaagaag agtgagaccc tgtctcaaaa aataaataaa taaaaacact  10920
gttcccctct cttccacctc tggggagggg ttctgggtgg gcagcaggtt ttgttttaat  10980
cctgtctccg cagctgggat aggaacctgc ctcctgagcc cacagggcac cactcaaacc  11040
ctacctgggt gaggggccat ttcagcacca cggggccgtg ggccccacat agctgacagg  11100
ccaggtcagc agcacggggc acagaccgta cctgggtgac ggaccatttc agcacgacag  11160
ggcgcgtgat gcagggcaag gccttgttca gcagctgcag cagccgggac tcctcgtgcg  11220
aaatgggga cttcttgttc aggcagtacg tcatcgtgtc gtggctccct gagagcaaag  11280
cacacacgcg gacatgtcac cacgagtccg tccccgccac ctgctgtgag tcgctccaca  11340
gcccgcctac agcacaggct gctgcccgcc cacagcacag gcacaggtat ggcgggaggg  11400
gtgcacgctg acccccaaaa ctcacgtcca ctggaacctg ggaacacgac ccgtgttgaa  11460
acagggtctc tgcagatatc attaggttga aatgagatca tcctggagta gggcgggccc  11520
ccaaatccag tgacaggtgt ccgtctaaga cacaagagga ggagacagac acagaggagg  11580
aggcctcgtg gagacggagg cagagactgg agtgatgcgg ccacaagccc agggatgcct  11640
ggagccccca ggagctggga gaggcaggaa ggatccccca ctctagagcc tctagaagga  11700
actgaataca atttcaatga cttgagtggt gatccccaaa agagctgttc aagtcctaac  11760
cccctgccca gaacctgtga atgggatcct gtttggaaat agggtcttta cacatgctct  11820
caaaatgctc aagatgaagt catcttggct ttgtgctggg tcctaaatgc aatgacaggt  11880
gtccttagga gacacagacc cagaggagga ggccacgtgg agatggaggc agagactgga  11940
gtgatgcggc cacaagccca gggatgcctg gagcccccag gagctgggag aggcaggaag  12000
gaccctcccc tagagcctca ggaggacgtg tggtcctgcc catatcttga cttcagattt  12060
ctgtatctag aactgggaga gagtaaattt ctgttctttg ccgcctcctg acgtgtgctc  12120
acttgttatg gtaaccgcaa gaaacacaga cctttgtaga gtttgactga tggctgacgt  12180
ttgcatttcc tgcctatgac acgtagttgt tatttcttaa atatagatat aaatatatct  12240
atatttaaga tatatatatt taagatatat atgacatata tctatatata aacatatata  12300
gtatctatat ctataaacaa agatatatag tatctatatc cataaacata tatagtatct  12360
```

atatctatat ataaacatat atagtatcta tatctatata taaacatata tagtatctat 12420
atctatatat aaacatatat agtatctata tctatatata aacatatata gtatctatat 12480
ctatatataa acatatatag tatctatatc tatatataaa catatatagt atatattcta 12540
tatataaaca tatatagtgt atatatatct atatataaac atatattagt atatatttac 12600
ataaatacat atttttgcat aaatatgtat ttatataaat atataaaata tatatccaca 12660
tattatgttt ataaatataa tatataaatg tacttatgta tcatatattt atataaatat 12720
atgatatata ttttatattt tacatttact tatttatata ttatatataa atataaatat 12780
gtatgtttat atataaatat gtacacttac atataaatgt gtgtgtgtat atacatattt 12840
gcagagatgg ggcctcacta tgttgcccag gctgctctca aactcctaaa ctcaagtgat 12900
cctcctgcct tggcttccca aagtgctggg attacaggcg tgagccacca cgcccggcct 12960
tccccccttta aatcccctga ggaacgtgaa gccccctttac atcctctgag gaacgtggac 13020
cccctttaaa tccccagacc ccgagaggca ttggaacgaa gccacagtca cctgctcccc 13080
cgatcttgag ctaaggtgtt aaggaaggag accagtactt ctcctgctgc cccctacccc 13140
caccttgcct agtttataag acaggagaaa gcaaaaggtt ggaaagaaac agaagtaaga 13200
taaatagcca gacaaccttg gcaccaccac ccagccctgg gagttaaaat aatatcaatc 13260
cataacctaa accacttctg ttatctgtaa atgccagacg ttgtatgaaa aagcgttaca 13320
aaactttctg ttctgttagc tgacacatgt agccccccagt cacgttcccc acacttgctt 13380
gatttatcac gacccccttca cgtggacccc tcagagttgt aagcctttaa aaaggccaag 13440
aatttctttt ttaaggagct cggctcttaa gatgtgagtc tgccgaagct cccggccaaa 13500
gaaacctctt ctttctttaa tccggtgtct gagttttgtc tgcggctggt cctgctacag 13560
tatcacccct ggaagctact tactaggtca gctctagact gacagatgcc ccgcatctct 13620
acaaattaac ctaagatgtc gggtgcaata gctcatgtct gcaatgccag cactttggga 13680
ggccgaggca ggtggattgc ctgaggtcgg gagttcgaga ccagcttgac caacatggtg 13740
aaaccccatc tctgctaaaa atacaaaaat cagccaggca tagtggagcg tgcctgtaat 13800
cccagctact cgggaggctg aggcaggaga atcgcttgaa cccaggaggc agaggttgcg 13860
atgagctgag gtggagccac tgcactcgag cctgggcgat aagagcaaaa ctccgtctca 13920
aaaaaaaaaa attaacctca ggatgtcaca ctggggcacc ataactcatt ccctacattg 13980
caaggaagaa cgcgatcagt gctcgatgcc acttcagtaa cccacatgaa ttcctgaaaa 14040
acagctttca tcatcacccc ctctcctgat gtgcactttc tttagaagct cccgtctcga 14100
cgttgttctc cacagccact tcctaaggcg agttggaggg tttcctgggc tgcagtcctc 14160
aaatgtggct caaggaaacc ccctacttat attaattttg tctaagttta tttccttagg 14220
ttgacaatac gtatctgtgt gcatgtgtat gtgtgtccgt atgcctatat gtgagtgtgc 14280
atgtgtgtgc ctgtgtttaa acatgtacct gtgttcctgt gtgcatggac gtgtgtctac 14340
gtgtgtgcat gtgtgtacac gcgtgtgcat gtgcatgtgt gcctgtgtac acgtgtgcat 14400
atgtgcattc atgtatgtct atgtgaatag gtgcaaatgt gtacatgtgt atgtctgtgt 14460
gcatgcatgt acgtgtgtac acgtgtatac atgcattgca tagacgtgtc tctgcgtgca 14520
taggtgcaaa tgtttatgtg tgcacgtgtg tctgtgcatg tacatgtcta cacctgtgta 14580
tatctgcagg tgtatatatg tgtgcatagg tgcaaatata tatatacatg tgtgcatgtg 14640
tgtacatgtg tacacgtgtg catgtgcatg tgtacacacc cgcacatgtg catgcatgtg 14700

```
tatgtgcatc catgtgtgta tgagcctatg tgcatgtata catgtgtgca ttagtatgtg  14760
cctacatcca tgtatacatg tgcctgcatg tgtgtacacc tgtgtgtgtg catgtatatg  14820
catccatgtg catatgtgtg gggatgtgca tgtgtgcatg catgtatgtg tgtgcgcatg  14880
catgtgtgtg tgtatgtatg tgtctgtgtg tgcctgcatg tgtgcctatg tgcacctatg  14940
tatgtgatat ggctcggctg tgtccccacc caaatctcat cttgaattgt agctcccata  15000
attcccatct gtcatgggag ggacctggtg ggaggtcacc gaatcacggg gcgggtcttt  15060
cccatgctgt tctcgtgatc gtgaataagt ctcacgagat ctgatggttg tacaaagggc  15120
agttctccag cacacgctct gttggctgcc accatgtaac atgtgacttt gctccgcatt  15180
caccttctgc cgtgattgtg aggcctcccc agccaggtgg aactgagtcc attaaacctc  15240
ttttataaat tacccagtct cgggtatgtc tttgttagca gcgtgagaac agaccaacac  15300
agtatgcaca tgcgtatgtg tgcagatgtg catgtgtgtg tgcagatgtg catgtgtgtg  15360
tgcagatgtg cgtgtgcaga tgtgcatgtg tgcgtgtgtg cgtgtgtgcg tgtgtgcatg  15420
tatgcctgtg tatgtgtgca catgtgtgca tgcctgtgtg tatgcatgtc tgtgcatgtc  15480
catgactatg tacatatgtg tatgcacaca cgtgtgcact gtgtgtatgt gtgtgtccac  15540
atcagtgtgc tttctaggat ttccctacac ccaggattgc tcctacagcc agcgtcccca  15600
ctggggaatg cagacgccac agctcccgcc ccaccctgcc gtcacctggg atagaggcaa  15660
cggcccctgc cccaccccaa cctcacctgg gatggagagg tggtggaggg gcacatccca  15720
gagccgggga cacagtgccg acatccagtc ctcgttggca tttctgcagt gcagcctcga  15780
gaagctgttg gaagcgctca cctgcccacc catcagaggt gagccctggg caacctgagg  15840
aaggagaaga ggaaaagagg tttttttacgg tgacttcagg tcaggagttc gagaccagcc  15900
tggccaactt gacaaaaccc catctctact aaaaatacaa aaattagctg ggcgtggtgg  15960
tgggcacctg tggcacctgt catcccagct actcgggagg ctgaggcagg agaatcgctt  16020
gaacccggga ggtggaggtt acagtgagcg gagatcccgc cactgcactc caggctgggc  16080
aacaagagtg aaactccata tccaaaaaag aaaaaaaaaa aagagagaga gagagaggaa  16140
aaggggtcct tggaagcatt ttttgcagct ccaaaaaatg tttcttgtct agcgtgaaag  16200
ccctggctct tagacccggc ttggcaacct ttaatatgca aatgcgagcc tttagctggt  16260
ccagcccaca tggcgattcc caccgttgcc ctcttgccct cgcccccacc cgtgcctgac  16320
accaaggccg cccccacccg ggcctgacac caaggccgcc cccacccggg cctggcaaca  16380
cggccgcccc cacccgggcc tggcaccacg gccgccccca cccgggcctg acaccaaggc  16440
cgcccccacc cgggcctgac accacggccg cccccactac cctcaggcgt gtggaacatc  16500
atggcgccct acatttgcat attacggaac tggggtgggc gggccaggtt tttcgcgggc  16560
tacgtgaatg acaggcctgg tcagaccaat cccctcagcg ctatgcaaat gagtcacgcc  16620
tcctccaggc accgtataac acgggctggt ctcctgcctg gggtttggag cccccgtccc  16680
tctgtctcag tccaggggag ccacttcttt ctgccttctc gccttggttt tttttttttt  16740
gagacgcagt ttcgctcttg ttgcccaggc tgcagtgaaa tggcgcgatc tcggctcacc  16800
gcaacctccg cggtgctggg attacaggcg tgagccactg cccggacctc ccttctttcc  16860
tattaaactc tccgctcctt aaaaccactc cacgtgtgtc cgtgtcgcct acacacacac  16920
acacacacac acatacacac ataacagaat atatacatat atacatatta tatacataac  16980
atatatataa catatataat atatacatat aatatatatt atacatataa tatatacata  17040
tataatatat atataatata tatataacat acatgtataa catatataca tatataatat  17100
```

agacatatat aacacataca taacatatat acatatatac atcactatat atacatatat 17160
aagtatatat atataatata ctgttgaaaa taagggaagt gaccctttcc ataaggacat 17220
tttagacaac ttgtaaattc tttctctgcc tctgaagtgt atataacttt tttggttggt 17280
cttttttttt tttttttgac acagtttccc tctcgttgcc caggctggac tgcaatggcg 17340
cgatcgcggc tcactgcaac ctccgcctcc caggttcaag caattctcct gcctcagcct 17400
ccagagtagc tgggattaca ggcgcccgcc accacacctg cttaattttt gtatttttgg 17460
tagagacggg gtttcactat cttggtcagg ctagtcttga actcctgacc tcaggtgatc 17520
tgcctgcctc ggcctcccaa agtgctggga ttactggcgt gagccacggt gcccagctgt 17580
atgtacggtt tttttttgt tttgttttgt tttttttaaa gacagggttt cactcttgtt 17640
acccaggctg gagtgcaatg atgcaatctc ggctcactgc aacctccgcc tcccaggttc 17700
aagcaattct cctgcctcag cctccagagt agctgggatt acaggcgtcc gccaccacgc 17760
ccggcaatgt atgtaagatt tttaatcatt tagattaaaa ctgattagat taaaatcatt 17820
agatctaatt gatttaatca aatcaattag aattgttgat cttgagccca gaaatcagcc 17880
tgttgacagt ttcacatctg aggaatgttt cctggtggac ctgaggcctc ctcttagaaa 17940
tgagacctgg aggggccggg cacggtggct cacgcctgtc atcccatcac tttgggaggc 18000
tgaggtgggt ggatcacctg aggtcagggg ttcgagacca gcctggccaa catggtgaaa 18060
ccccatttct actaaaagta caaaaagtag ccggccgtgg tggcgcacgc ctgtaatccc 18120
agctactcag gaggctgagg cttgaacccg ggaggcgggg gctgtagtga gccacaatca 18180
caccattgca ctccagcctg ggtgacaaag tgagactctg tctcaagaaa aaagaaatgg 18240
gacagagagg aagggaagaa gccccggcct cctggagaag agacaaactt cagctgcctg 18300
caaactgcaa acccaccttg agtcccacac gcagggggag ttcggaattc gaattgttgg 18360
tctcgagccc agaatgaaag gcctggtctc cctgggccgc aagaaaggac gagatcctct 18420
cggtctgcag ctcctggcgg ctgcccgcgt tggcttcaca aggttctgta ataatcctgc 18480
tgccttctct tccacactga ggccaggctt cccaggtggc tgcagatttt gttcttattt 18540
acatcttccc aaaagccttc ctcccagacc ctaagccaac accagctaca tgaactcaga 18600
tcttccctgc tgcccggaag gagggaggga gggagggagg gagggagggt cccgggagcc 18660
tgctgggccc aggaggagga gcccattctt tatcagcccg ggggatgtca gctcagcctc 18720
tttctccaag agaagcaacc acacctgtac cgcggctccg ggtccccagg agggagctgg 18780
ccccttctct gcagccagct ggaaaaggcc caggacggct tcccctcccc ctgcacgccc 18840
cccgctccgc ctgcacggcc ccccctcccc ctgcacggcc cccctccgcc tgcacggccc 18900
cccctccccc tgcacggcct cccctccccc tgcacggcct cccttccccc tgcacggccc 18960
ccctccccct gcacggcctc ccctccccct gcacggcctc ccctccccct gcacggcctc 19020
ccctccccct gcacggcccc ccttccccct gcacggcctc ccctccccct gcacggcctc 19080
cgctgccccc tgcacgtacc cccctccgcc tgcacggcct cccttccccc tgcacggcct 19140
cccttccccc tgcacggcct cccctccccc tgcacggcct cccctccccc tgcacggcct 19200
cccctccccc tgcacggcct cccctccccc tgcacgtctt cccctccgcc tgcacggcct 19260
cccttccccc tgcacggcct cccttccccc tgcacggccc cccttccccc tgcacggcct 19320
cccctccccc tgcacggcct cccttccccc tgcacggcct ccgctgcccc ctgcacgtac 19380
ccccctccgc ctgcacggcc tcccttcccc ctgcacggcc tcccttcccc ctgcacggcc 19440

-continued

```
ccccttcccc ctgcacggcc tcccctcccc ctgcacggcc tccgctgccc cctgcacgta  19500
ccccccctccg cctgcacggc ctcccttccc cctgcacggc ctcccctcct cctgcacggc  19560
ctcccctccc cctgcacgtc ttcccctctg cctgcacggc ctcccttccc cctgcacggc  19620
ctcccttccc cctgcacggc ccccttccc cctgcacggc ctcccctccc cctgcacggc  19680
ctcccttccc cctgcacggc ctcccctcct cctgcacggc ctcccctctg cctgcagggc  19740
tgtgcagtga tctgcctgga gcatcccagc agggccgctg tgagcctccg gatgcccagg  19800
gtcccggggc cgcggggtgg aggggaggtt aaaatgcagg tctgggcggg gcccgctggc  19860
tcacgcctgt aattcgagca cttcaacact ttgggaggcc gaggcgggcg gatcacctga  19920
ggtcaggagt tcgaaaccgg cctggccaac atggcaaaac cccatcactg gtaaaaatac  19980
aaaaatcatt tagccgtgct ggcgcgcgcc tgtagtccca gctactggga ggctgaggca  20040
ggagaatcgc ttgaacccgg gaggcggagg ttgcagtgag ccgagatcgc gccattgcac  20100
tccagcctgg gagacagagt gagactcccg ttcaaaaaca aaaaaccttc gtctccacat  20160
cctcttatct taatgcagat attcctttct actaataact cttttttttct tcttttttttt  20220
tttttcagag acagggtctc gctctgttgc gcagactggt gtgcagtgtc atgatctcag  20280
cttactgcag cctccgcctc ctggattcaa gctattcgcc tgcctcagcc tccagcacag  20340
ctgggattac aagcacttgc caccattccc agctaatttt ttgtattttt ggtagcaacg  20400
ggggtctcac catgttggcc aggctggtct cgaactcctg acttcaggtg atccgcccgc  20460
cttggcttcc caaagtgctg ggatgacagg cgtgagccac cgtgcccggc ctaataataa  20520
ctctttcaac caattgccag tcagaaaatt ttaaaatcta ccttatgacc tggaagcccg  20580
cctcaccacc agtggagcag tcccaccttc accgattgaa cctgtcaggc ctctgagccg  20640
aagctcagcc attatcaccc ctgtgacttg cacatatacg tccaggtggc ctgcaggagc  20700
caagaagtct ggagcagcca aggaaaaacc acagagaagt aaaacagcca gttcctgcct  20760
taactggtta actaaaatta caacatttta ctatcgtgag ttctccctgc cctaccttag  20820
ccgatcaatc gactttgtgc cgttcgtcct ctggacaatg agtcttatga tctgtgcacc  20880
acgcaccttg caatccctcc tctgctgaca atagataacc accttttgct gtaattttcc  20940
attacctacc caactcctat tgagccaccc ctcccccatc tcccttcgct gactctctct  21000
tcggactcag cccacttgca cccaagtgaa tgaaccgctt tatcgctcac acaaagcctg  21060
ttcgggggtc tcttcgcacc gacgcgcttg acagaaccaa ggttcgtctt acacgtatgg  21120
attcatgtct gacgtttcct taaaatgcat aataccaaga tgtcctccga ccacctaggg  21180
cacaggtcgt caggacctcc tgaggctcgg tcacaggcgc gtcctcaacc ttagcaaaac  21240
acactttttt tttttttttt ttgagacgga gtcttgctct gtctcccagg ctggagtgca  21300
gtggtgcaat ctcggctcac tgcaacctcc gcttcccagg ttcaagcaat tctcctatct  21360
cagcctccca agtagctggg actacaggcg cccaccacca cacccaggta atttctgtat  21420
ttttagtaga gacagggttt caccttgttg gtcaggctgg tcttgaactc ctgacgtcag  21480
gtgatctgcc cgccttggcc tcccaaagtg ctgggatgac aggcgtgagc caccgtgccc  21540
ggccagcaaa acacactttc taaatgtcct gagacctgtc tcagatactt tttggttcag  21600
aagactcgag gaaatcagtg tctcctagga caggctggac ccaaagctgt acactcacat  21660
cctctgtgtc atgacggatt ccatccattc cggctactgt catactccct ccctcccatc  21720
acagtccctt cccccgtcac agtccctccc ctcccgtcac cttcatcata tcccaggtcc  21780
cctgaccact gaggggtgtc ccctcctgtc cccacgtccc ccgacccctc ccctcacatc  21840
```

-continued

```
ccaagtcccc tgaccactga ggggtgtcca ctcctgtccc cacacctgtc cccatgtcct  21900
cctgagccct ccctcacatc ccaggtcccc tgaccactga ggggtgtccg ctcctatccc  21960
cacacctgtc cccacattcc ccctgacccc tcccctcaca tcccaggtcc cctgaccact  22020
gaggggtgtc ccctcctatc cccacacctg tccccacgtt ccccctgacc cctcccctca  22080
catcccaggt cccctgacca ctgaggggtg tccactcctg tccccacacc tgtccccatg  22140
tcctcctgag ccctcccctc acatcccagg tcccctgacc actgaggggt gtccactcct  22200
gtccccacgt gccctgaccc ctcccctcac atcccaggtc ccctgaccac tgaggggtgt  22260
ccactcctgt ccccacgtgc cctgacccct cccctcacat cccaggtccc ctgaccactg  22320
aggggtgtcc actcctgtcc ccacacctgt ccccatgtcc tcctgagccc tcccctcaca  22380
tcccaggtcc cctgaccact gaggggtgtc cactcctgtc cccacgtgcc ctgacccctc  22440
ccctcacatc ccaggtcccc tgaccactga ggggtgtcca ctcctgtccc cacacctgtc  22500
cccatgtcct cctgagccct cccctcacat cccaggtccc ctgaccactg aggggtgtcc  22560
actcctgtcc ccacgtgccc tgacccctcc cctcacatcc caggtcccct gaccactgag  22620
gggtgtcccc tcctgtcccc acacctgtcc ccacgttccc caacccctcc cctcacatcc  22680
caggtcccct gaccactgag gggtgtcccc tcctatcccc acatctgtcc ccacgttccc  22740
cctgacccct cccctcacat cccaagtccc ctgaccactg aggggcgccc cctcctgtcc  22800
ccaggtcccc cgacgccttc cccacacatg acaaagtgga gcaggaagga gccccggggg  22860
cggcccccac tcccagccac ctctgccatc tcgtccggac ggcacagcgg agtggggtct  22920
ggaggccgtc ccacggagca ctgacccttc ctgggggagg tcctctccac cctggccttc  22980
acggtcgcgg cgggacagcg cagatgacgg acgggcccag acgcccggtg acccgccagg  23040
cggggtgaga cacctacacc ttcccgcccg ctgagtcctc gggagactca cgtcccagag  23100
gcgtgagtgg ccgtgacgcg cacattcaac gcacggggtg aatggttgct gggtgaatca  23160
acggaaggac aggggtgctc agatcccagc attcccagtg ccccaacatc ccccaccgtcc  23220
cagctgtccc gacccgtccc cacgcaggcc ccggcggcag ggtgaggacg tccaaccggc  23280
caagcaagtc gtggccccccg ggctcatttc ataaccgtcc tgggctgttt ccacactggc  23340
tccgcggctc tgacccggca gagaattcac ggtctgcaag gggtgcaggc cgcctgtggc  23400
tgccaacgtc caggccacag atcccaggcg accctccccc tgaacccccct gcccgtgccc  23460
ccagctaagg gtcccaggag gaggagaagg agcctcaatg acggaagcgc gggttcctga  23520
ttcccagccc acaacaggca cagacggcac ccgccacgtc ccccgtaggg gacttgccat  23580
caggagaacg gggtagacac actcaccttc cagccgctgg aatcccagag ctcctggcag  23640
ctcccgccgg gtctctgcgg gacactcttc ctaaaacaca cccagtccgc tgcgattggc  23700
tgtggcgcgg acactcctgc caccaggagg agggacagcc cgccccccgcc acggatctgt  23760
ccccaccgca ggagcgggac cggctgggct gcaaacaccg ccctgaactc ccacggggac  23820
cccacagacc aggactgggg accggaagac ccctcccagg ggaccccacg gtgtgtccca  23880
acaaggtgtc cccggggtcc cccggtcagg ggcttagaga cagcaaggac gtcccagagg  23940
tgtgtgccca cgggttctct gtggtcagag gggcccttgc aggggacatt gaggtgtctg  24000
actgacgggc cccactcggg ccactggccg cggctgcggt gggtctcccg gagcccccag  24060
gacggggtga acaggtgctt tcatctcggc cctggggtca acgcatgggg ccggcagtcc  24120
caagcctgca ggctctgagc gccttggcca gcaaacccac cgggatcttc cccctgcagg  24180
```

-continued

```
ttccgacctc tcccgccccg cgtggcccgg accctgggca gcccgtgccg cctccgtcgg  24240
tggaagtggc tcctcccagc gcagcccacg cctgcgatct cccccccga gccaacctgg  24300
agctgaccag gagcccaggt caggggtctg tccagggccc cgttcctgcc tcctcctggc  24360
tgcttccggt ccaccccgca ggtgctcccc acgcaccccg ctgtctccca ccccgggctg  24420
gactccagga cagggccagt gtgggcttca gagagtgcac ggaacgtttg gggccgcag  24480
tggacggctc aaagggctgc cttgggatcc catgttcccg ggtggaattc tcccgcatag  24540
ccacggctgg ggcttctctc cctgcacccc atttctgtcc cggctccctg tttcctccct  24600
caccccagct gtggggtacc ttgagggcgg ctgctgtcct ggcacaggga catctggtcg  24660
gcctacaagc cacaggccac cggcctctcc gcctctttcc atcctaactc aggccccgtc  24720
acctccccac actccgccct cccccctgct cctcctcccc ctcctccttc ctccccctgc  24780
tccttctcca tcctctccct ccttcttcct gtccattgag actccccctc tctgcccaaa  24840
gcccccctgtg gcttcctctt ggcccatctg tttcctccct cccccctcctc cctcctcctc  24900
ctccctcctc ccttcactga ggccctgcgg ggacaccagc ctcctggttc ccgcctcctt  24960
ccacagccct gggagagtct ataaaatgac ctgtgccctg gtgtggcacg ggagcaggaa  25020
gcggcttcca cgcctcctcc cacagtcaca gggcccggcc cttcctcccg ctgtgcccca  25080
gagtcatgag gaccagaggt cacagggccc ggcccttcct ctgtgtcctg gtgtgatgtg  25140
gactgtggtc acagggcccg gcccttcctc tgtgtcctgg tgtgatgtgg actgtggtca  25200
cagggcccgg cccttcctcc gtgtcctggt gtgatgtgga ctgtggtcat gaggcccggc  25260
ccttcctctg tgtcctggtg tgatgtggac tgtggtcaca gggcccggcc cttcctctgt  25320
gtcctggtgt gatgtggact gtggtcacgg ggcccggccc ttcctctgtg tcctggtgtg  25380
atgtggactg tggtcatgag gcctggccct tcctctgtgt cctggtgtga tgtggactgt  25440
ggtcacaggg cccggccctt cctctgtgtc ctggtgtgat gtggactgtg gtcacagggc  25500
ccggcccttc ctccgtgtcc tggtgtgatg tggactgtgg tcatgaggcc cggcccttcc  25560
tctgtgtcct ggtgtgatgt ggactgtggt cacagggccc ggcccttcct ccgtgtcctg  25620
gtgtgatgtg gactgtggtc acagggcccg gcccttcctc tgtgtcctgg tgtgatgtgg  25680
actgtggtca tgaggcctgg cccttcctct gtgtcctggt gtgatgtgga ctgtggtcac  25740
ggggcccggc ccttcctctg tgtcctggtg tgatgtggac tgtggtcacg ggcccggcc  25800
cttcctctgt gtcctggtgt gatgtggact gtggtcacgg ggcccggccc ttcctctgtg  25860
tcctggtgtg atgtggactg tggtcacggg gcccggccct tcctctgtgt cctggtgtga  25920
tctggactgt ggtcacgggg cccggccctt cctctgtgtc ctggtgtgat ctggactgtg  25980
gtcacgaggc ccggcccttc ctctgtgtcc tggtgtgatg tggactgtgg tcacagggcc  26040
cggcccttcc tctgtgtcct ggtgtgatct ggactgtggt cacagggccc ggcccttcct  26100
ctgtgtcctg gtgtgatctg gactgtggtc atgaggcctg gcccttcctc cgtgtcctgg  26160
tgtgatgtgg actgtggtca cagggcccgg cccttcctct gtgtcctggt gtgatgtgga  26220
ctgtggtcac agggcccggc ccttcctccc gctgtgcccc agagtcatga ggaccagagg  26280
tcacagggcc cggcccttcc tctgtgtcct ggtgtgatgt ggactgtggt cacagggccc  26340
ggcccttcct ctgtgtcctg gtgtgatgtg gactgtggtc acagggcccg gcccttcctc  26400
tgtgtcctgg tgtgatgtgg actgtggtca cggggcccgg cccttcctct gtgtcctggt  26460
gtgatgtgga ctgtggtcac ggggcccggc ccttcctctg tgtcctggtg tgatgtggac  26520
tgtggtcacg gggcccggcc cttcctctgt gtcctggtgt gatctggact gtggtcacgg  26580
```

ggcccggccc ttcctctgtg tcctggtgtg atctggactg tggtcacgag gcccggccct 26640
tcctctgtgt cctggtgtga tgtggactgt ggtcacaggg cccggccctt cctctgtgtc 26700
ctggtgtgat gtggactgtg gtcacggggc ccggcccttc ctctgtgtcc tggtgtgatg 26760
tggactgtgg tcacggggcc cggcccttcc tctgtgtcct ggtgtgatgt ggactgtggt 26820
catggggccc ggcccttcct ctgtgtcctg gtgtgatgtg gactgtggtc atgaggcccg 26880
gcccttcctc tgtgtcctgg tgtgatgtgg actgtggtca cagggcctgg cccttcctct 26940
gtgtcctggt gtgatgtgga ctgtggtcat gaggcctggc ccttcctccg tgtcctggtg 27000
tgatgtggac tgtggtcaca gggcctggcc cttcctctgt gtcctggtgt gatgtggact 27060
gtggtcacag ggcccggccc ttcctctgtc ctggtgtgat gtggactgtg gtcacagggc 27120
ccggcccttc ctctgtgtcc tggtgtgatg tggactgtgg tcacagggcc cggcccttcc 27180
tctgtgtcct ggtgtgatgt ggactgtggt catgaggcct ggcccttcct ctgtgtcctg 27240
gtgtgatgtg gactgtggtc acagggcccg gcccttcctc tgtgtcctgg tgtgatgtgg 27300
actgtggtca cagggcccgg cccttcctct gtgtcctggt gtgatgtgga ctgtggtcat 27360
gaggcctggc ccttcctctg tgtcctggtg tgatgtggac tgtggtcatg aggcctggcc 27420
cttcctctgt gtcctggtgt gatgtggact gtggtcacag ggcccggccc ttcctctgtg 27480
tcctggtgtg atgtggactg tggtcacagg gcccggccct tcctctgtgt cctggtgtga 27540
tctggactgt ggtcatgagg cccggccctt cctctgtgtc ctggtgtgat gtggactgtg 27600
gtcacagggc ccggcccttc ctctgtgtcc tggtgtgatg tggactgtgg tcacggggcc 27660
cggcccttcc tctgtgtcct ggtgtgatgt ggactgtggt cacggggccc ggcccttcct 27720
ccgtgtcctg gtgtgatgtg gactgtggtc acagggcccg gcccttcctc cgtgtcctgg 27780
tgtgatgtgg actgtggtca tgaggcccgg cccttcctct gtgtcctggt gtgatgtgga 27840
ctgtggtcac agggcctggc ccttcctctg tgtcctggtg tgatgtggac tgtggtcatg 27900
aggcccggcc cttcctctgt gtcctggtgt gatgtggact gtggtcacag ggcccggccc 27960
ttcctctgtg tcctggtgtg atgtggactg tggtcatgag gcccggccct tcctctgtgt 28020
cctggtgtga tgtggactgt ggtcatgagg cccggccctt cctctgtgtc ctggtgtgat 28080
gtggactgtg gtcacagggc ccggcccttc ctccgtgtcc tggtgtgatg tggactgtgg 28140
tcacagggcc cggcccttcc tctgtgtcct ggtgtgatgt ggactgtggt cacagggccc 28200
ggcccttcct ccgtgtcctg gtgtgatgtg gactgtggtc acagggcccg gcccttcctc 28260
tgtgtcctgg tgtgatgtgg actgtggtca tgaggcccgg cccttcctct gtgtcctggt 28320
gtgatgtgga ctgtggtcac agggcccggc ccttcctctg tgtcctggtg tgatgtggac 28380
tgtggtcaca gggcccggcc cttcctctgt gtcctggtgt gatgtggact gtggtcatga 28440
ggcccggccc ttcctctgtg tcctggtgtg atgtggactg tggtcacagg gcccggccct 28500
tcctctgtgt cctggtgtga tgtggactgt ggtcacaggg cccggccctt cctctgtgtc 28560
ctggtgtgat gtggactgtg gtcacagggc ccggcccttc ctctgtgtcc tggtgtgatg 28620
tggactgtgg tcacagggcc tggcccttcc tcccgctgtg ccccagggtc atgaggaccg 28680
gaggtcacag tgcccggccc ttcctctgtc ctggtgtgat gtggactgtg gtctcggggc 28740
ccagcccttc ctccctctgt gtcctgggcg gccaggtgtg ggctggacac gaggggagga 28800
catcacgtgg gctgagggac gtgtcgtccg tgcctcggtg ctgcctgtgt tctgcgagcc 28860
gagggttgtg aagggtgctt gagtgaagtg ggccaagtgt gagcccctgt aaatggctgt 28920
gacttccctg ttgaccgtgc ccttgtgtcc gacaaggggt gtttgcaaac ccctcccaag 28980
gccgggcacg gaagcccttg gtccagctgc ttcctggaat ggaaaaccct ctcctgcact 29040
agaaaatccc atgaccccgc gtttgagttt cgaatattta gcatggggag cacccctcca 29100
atggctagga gagacaccag gcggagataa aggtttgact atttaccagt cctgcatcca 29160
cggccggcct gcaggcccca cccaggcgga ggtaaggatt tgattattta tggatcccgg 29220
gtgctgcagg ccccacccag gcggaggtaa ggatttgatt atttatgggt cccgggtcct 29280
gcaggtccca cgcaggcgga ggtaaggatt tgattattta tgggtcccgg gtgctgcagg 29340
ccccgcccag gcggaggtaa ggatttgatt atttatgggt cccgggtgct gcaggcccca 29400
cccaggcgga ggtaaggatt tgattattta tgggtcccgg gtgctgcagg ccccacccag 29460
gcggaggtaa ggatttgatt atttatgggt cccgggtgct gcaggccccg cccaggcgga 29520
ggtaagggtt tgattattta tgggtcccgg gtgctgcagg tcccacgcag gcggaggtaa 29580
ggatttgatt atttatgggt cccgggtgct gcaggcccca cccaggcgga ggtaaggatt 29640
tgattattta tgggtcccgg gtgctgcagg tcccacgcag gcggaggtaa ggatttgatt 29700
atttatgggt cccgggtgct gcaggcccca cccaggcgga ggtaaggatt tgattattta 29760
tgggtcccgg gtgctgcagg ccccgcccag gcggaggtaa ggatttgatt atttatgggt 29820
cccgggcgct gcaggcccca cccaggcgga ggtaaggatt tgattattta tggatcccgg 29880
gtgctgcagg ccccacccag gcggaggtaa ggatttgatt atttatgggt cccgggtcct 29940
gcaggccccg cccaggcgga ggtaaggatt tgattattta tgggtcccgg gcgctgcagg 30000
ccccacccag gcggaggtaa ggatttgatt atttatgggt cccgggtcct gcaggccccg 30060
cccaggcgga ggtaaggatt tgattattta tgggtcccgg gtgctgcagg ccccacccag 30120
gcggaggtaa ggatttgatt atttatgggt cccgggtcct gcaggcccca cccaggcgga 30180
ggtaaggatt tgattattta tgggtcccgg gtcctgcagg ccccacccag gcggagctaa 30240
ggatttgatt atttatgggt cccgggccct gcaggccccg cccaggcgga ggtaaggatt 30300
tgattattta tgggtcccgg gtcctgcagg ccccacccag gcggaggtaa ggatttgatt 30360
atttatgggt cccgggcgct gcaggcccca cccaggcgga ggtaaggatt tgattattta 30420
tgggtcccgg gtgctgcagt ccccgcccag gcggaggtaa ggatttgatt atttatgggt 30480
cccgggtgct gcaggcccca cccaggcgga ggtaaggatt tgattattta tgggtcccgg 30540
gtcctgcagg ccccacccag gcggaggtaa ggatttgatt atttatgggt cccgggtcct 30600
gcaggccccg cccaggcgga ggtaaggatt tgattattta tgggtcccgg gtcctgcagg 30660
ccccgcccag gcggaggtaa ggatttgatt atttatggat cccgggtcct gcaggccccg 30720
cccaggcgga ggtaaggatt tgattattta tgggtcccgg gtgctgcagt ccccacccag 30780
gcggaggtaa ggatttgatt atttatgggt cccgggtcct gcaggccccg cccaggcgga 30840
ggtaaggatt tgattattta tgggtcccgg gtgctgcagg ccccgcccag gcggaggtaa 30900
ggatttgatt atttatgggt cccgggtcct gcaggccccg cccaggcgga ggtaaggatt 30960
tgattattta tgggtcccgg gtcctgcagg ccccacccag gcggaggtaa ggatttgatt 31020
atttatggat cccgggtgct gcaggcccca cccaggcgga ggtaaggatt tgattattta 31080
tgggtcccgg gcgctgcagg ccccacccag gcggaggtaa ggatttgatt atttatgggt 31140
cccgggtcct gcaggcccca cccaggcgga gctaaggatt tgattattta tgggtcccgg 31200
gtcctgcagg tcccacgcag gcggaggtaa ggatttgatt atttatgggt cccgggtcct 31260
gcaggccccg cccaggcgga ggtaaggatt tgattattta tgggtcccgg gtgctgcagg 31320
ccccacccag gcggaggtaa ggatttgatt atttatgggt cccgggtgct gcaggcccca 31380
cccaggcgga ggtaaggatt tgattattta tgggtcccgg gtgctgcagg ccccgcccag 31440
gcggaggtaa ggatttgatt atttatgggt cccgggtgct gcaggccccg cccaggcgga 31500
ggtaaggatt tgattattta tgggtcccgg gtcctgcagg ccccacccag gcggaggtaa 31560
ggatttgatt atttatgggt cccgggtgct gcaggccccg cccaggcgga ggtaaggatt 31620
tgattattta tgggtcccgg gtcctgcagg ccccgcccag gcggaggtaa ggatttgatt 31680
atttatgggt cccgggtgct gcaggcccca cccaggcgga ggtaaggatt tgattattta 31740
tgggtcccgg gtcctgcagg tcccacccag gcggaggtaa ggatttgatt atttatgggt 31800
cccgggccct gcaggcccca cccacactgg gtggtgagga atgcagcaga gagggaccct 31860
gggccagcac ctttattggg tccaaggtat tatcccaccc tgtttccggc tcgcagttgt 31920
cacgggtggt tgagagccag cagggagggt ctctgagagg tggcaccgtg cgggcgtcgc 31980
cgggaacaga ggcacaaagc tgggagcccc ggacccgggt ttcaacagca tggggcagcc 32040
gcacggctca cggggcctca ggccgggccg tgacgggctc agagcacacc tgcgtgagcc 32100
gagaccggag gctacgtgat ctcattctgc aggtgcgatt cccgaagctg ctctgttccg 32160
agctgccttg tttaaaaccg tcgccgggcc gggcgtggtg gctcacgcct gtcatccgaa 32220
cactctggga ggcccagacg cgtggattgc ctgagctgag ctctggagtt cgagaccagc 32280
ctgggcaaca tggtgaaatc ccgtctctac taaaaaaaaa aaaaaaaaaa aaaatagccg 32340
ggcgaggtgg cgggtgcctg taatcccagc tactccagag gctgaggcag agaatcgctt 32400
gaaaagggga ggcggaggtt gcagtgagcc gagatcgcgc ccctgcactc cagcttggtc 32460
tccgtctcaa aaaataaaaa ataaaagtaa agtcatcaat tctgttttcc cctgtccttg 32520
ccgagaagca aaatgacatg aaaaggatag agaattgtgt ctccgaagct gagtcttacc 32580
cctttaccag agaaaagaca caactttggg aggccaaggc gggcggatgg ccaacatgat 32640
gaaaccttgt ctctaccaaa aaaaaaaaaa tacaaaattt agctgggcct ggtggcacgc 32700
gtctgtaatc ccatctaccg ggaaggctga gataatcgcg gctcactgca acctccatct 32760
cccgggttca agcgattctc ctgcctcagc ctcccaagta gctgggatta caggcacccg 32820
ccaccacgcc cggctaattt agtagagaca gggtttcatc atgttggcca ggctggtctc 32880
aaactcccga cctcaggcaa tccgcccacc ttggcctccc aaagtgctgg gatgacaggc 32940
gtgagccacc gcacccggcc agagatactg atttttatga gcaacacgta taggcttcct 33000
aaatcacacc gctggaaaaa gtattctcca cgtctgtagc tcctctctct gctggtttgg 33060
gggttcagga agcagggcgc gattttgcat tataagtatc gactaaagaa tggtaaggct 33120
ggctgggtgc agcggctcac gcctgtcatc ccagcagttt gggaggctga ggcaggtgga 33180
tccgtgaggt cgggagttca agaccagcct ggccaacatg gtgaaacccc gtctctacta 33240
aaaatacaaa aattagccag ccatagtggt gaatgcctgt aatcccagct actggggagg 33300
ctgaggcggg agaattgcgt gaacccagga ggcagaggtt gcagtgagtc gaggttgtgc 33360
cactgcactc cagcctgggc tgcaatagtg aaactccatc tcaaaaaaaa aaaaaaaaaa 33420
ggacaggtgc ggtgcctcac gcctgtcatc tcagcacttt gggaggctga ggcgggcaga 33480
tcacttcagg tcaggagttc gagaccaaaa atataaaaaa ttagccgggt gtggtgatgc 33540
tcacctgtaa tcctagctcc ttgagaggct gaggcaggag aatcacttga acccggaagg 33600
cggaagttgg agtgagccaa gatctagcca tggcactcca gcgtggggga cagaaccaga 33660

-continued

```
ctctgtttca aaaaaacaaa caaacaaaca aaaaacaaaa caaaaaaaga atggtgaggc 33720
tgcaaaggac agctttgttt ctcataaggg gttaggcgca ggggagctat tcctacagcc 33780
tgggaagcag agtcagaagc cagaagcaga cacctccaga gaggggcaga aggaacagga 33840
atcagccggg cgcgatggct cacgcctgtc atcccagcac tttgggaggc cgaggcaggt 33900
ggatcacgag gtcaggagat cgacaccatc ctggctaaca cggtgaaacc ccgtctctac 33960
taaaaataca aaaaattagc cgggcgtggt ggcgggcgcc tgtagtccca gctactcggg 34020
aggctgaggc aggagaatgg cgtgaacccg ggaggcggag cttgcagtga gtggagatcg 34080
tgccattgca ctccagcctg gggacagca atagactccg tctccaaaaa gaaaagaaaa 34140
gaaaaaaaga aagaagaaag agagagagag agagagggag ggagggaggg aaggaaaaga 34200
aagagaaaga aaaaagtgcc cgtttcctct ggcacaaggg tgcccgtgcc acagctgagc 34260
tggagaagga agtcagggat gaggagtgga gtcaggtatg cggccctctc acccctgatg 34320
ccaggcgcac ctgcccacct ggtcccatgc taatcattca tactccaagt ccccacgctt 34380
aaaattgtaa cacagcccta aatgtcccaa aatgtcctct gatcacacac agcaggagaa 34440
tcactcgact ttgcatagag ttgtcaaaac acatacaaat atatgctacc acacaccggt 34500
attgaacgtt aaaatcgatt accattttcc actgatcaag tcaacagaga ttgaaaaacc 34560
agcacttttg ggagaggccg aggcaggcag atcgcttgag cccaggagtt ccagacgagc 34620
ctgagcaaca tggcaagacc ctgtctctac aaaaaatata aaaattagct gggcgtagtg 34680
gtgtgcactt gtaggaccag ctacagagac ctcttccctc ctcctgtagt cccagctact 34740
caggaggctg aggagggagg atcacttgag tctaggaggt cgaggctgca ctccagcctg 34800
ggggacacag tgaaatcctg tgtctaccaa aaaaggtgaa aagagaaact tctgtctaca 34860
atattgatgg ttcctgaagt tgcctcccaa catattttaa gttcggccta aagatttctc 34920
tgtacatagt gaactgtgac gtaacaggag gtgtcaacag accagaacct actcttgtgg 34980
caatcactga atctcagcca aaggcagcca aatgttccaa ccgggttcaa acaaggtaaa 35040
cgccaaccca cacccaatgc agctgtttct ctgctttctg tgtgtcctgt ccttttcttt 35100
ctttctttct atctttcttt ctttcttttt ctttctttct ttcttttctt tctttccttt 35160
ctttctttct tctttctttc tttctttctt ttctttcttt cttttctttc tctctctctc 35220
tttcttttttc tttctttctt ctttctttct ttcttttttt ttgtggaaac agagtctcgc 35280
tctgtcaccc aggctggagt gcaatggcgc gatctcgggt cactgccagc tccgcctccc 35340
gggttcacgc cattctctgc ctcagcctcc tgagtagctg agactacagg caccagccat 35400
catgcccggc taattttttg tatttttagt agagacgggg tttcactgtg ttagccagga 35460
tggtctcgat ctcctgacct cgtgatccac ccacctaggc ctcccaaagt gctgggatga 35520
caggcctgag ccaccgcgcc cggcccactt tattttattt tttattttta tttttcagac 35580
agaatctcgg tctgtcaccc aggctggagt gcaatggcgc gatctcggct cactgcaacc 35640
ttcacctcct gggttcaagc gattctcctg cctcagcctc ccaaagtgct gagattacag 35700
gcatgagcca ccgcacccag cctaagactt atttttcttc cacatcccca aaactacagc 35760
gtctgcaaat ccacacgggc gttcccgacc ggacctggat tccccactgt ccccaaccct 35820
gccccttaga ggcggttcag acgccgccga ccttgaagcc aacgacagac acctgttgtt 35880
tccacgcagg gaagaagcca cagctcaggg tacaagaagc ctgtgctggc tcaggttgat 35940
ctttttcttt ttatttttga gacagagtct cactctgtct cccaggctgg agtgcagtgg 36000
cacgatcttg gctcactgca acctccgcct tccaggttca agtgattctc ctgcctcagc 36060
```

-continued

```
ctcccaagtg agtacctggg attacaggtg cccgccacca cacccggcta atttttgta  36120
tttttagcag agactgtttt tcaccatgtt ggccaggctg gtctcgaact cctgacctca  36180
tgtgatccac ctgcctcggc ctcccaaagt gctgggatta caggcgtgag ccaccgcgtc  36240
cggcccctga ttcagttttt gaccacagct ggtttcctct tttatttcag gtatacaggc  36300
catatacact gattgttgta aaatatattc catcttactc ttcttcatat acacatatat  36360
atatttcatt tccttttttg agacactcca gcctgggtga aagagcgaga ctccatctca  36420
aaaataaata aataaataaa taaataaata aataaataaa ataaaaaata aaactccgcg  36480
gccgggcgcg gtggctcacg cctgtcatcc cagcactttg ggaggccgag gcgggtggat  36540
cacgaggtca gaggatggag accatcctgg ctaacatggt gaaacctcgt ctctactaaa  36600
aatacaaaaa atcagccggg tgtggtggcg ggcgcctgta gtcccagcta ctcgggaggc  36660
tgaggcagaa ttacttgaac ccgggaggtg gaggttgtgg tgagccgaga tcacgccact  36720
gcactccagc ctgggtgaca gacctagaga gagagattat ctcaaaaaaa aaaaaaaaaa  36780
aagatcctgc caagcttgtg actactaaat gccactgcag tgcacacttt gaaatgggta  36840
agttgacatt atataatttc acattgaatg attaaaaaca aaaatgcaaa ttgtatgtaa  36900
aattcaatga ttaattaaat tgcaaattga atgattacaa ataagtattg actatgaata  36960
ggttaccttt tctgaagaat aggagaggtt aaaaaagaca ttttttcctt ttttacttta  37020
taaacatctt tacagttgaa tttttatttt tatttattta taattattat tttttgtaga  37080
gacaggacct ggctatgttg ccccggctgg tctctaaatc tggggctcaa gcgatccccc  37140
aacctcagcc tcccaaggtg ctgggattac aggcgtgagc cacttcaccg gcctgtttgc  37200
attttaaaaa taagcttgca tcacttttta gataaaaatt aactacagat aacctcaact  37260
gaccctagca ggaactggag tctctgctcc tcctctgagg ccctcagctc cccgtgggtg  37320
ggggctctct aggcagcccc caggaacagg tgggcctcct tggtaacccc cagagacccc  37380
caaccctggc atcctgcagg gtggccgggc agggagggag ctagggagct gggcaaggcg  37440
ggtcccacag gaaagggctc tactccctga gattgaaacc atttttgcaa aaacaatttt  37500
tctttctttt ttttttttt aagacagagt ctcgctctgt cacccaggct gcagggcagt  37560
ggcgcgatct cggctcactg caaccttcgc ctcccatgtt cgagccattc acctgtctca  37620
agctcctggg tagctgggac cacaggcacc caccaccata ctcggctagt tttcgtattt  37680
ttattagaga cggggtttta ccacattggc caggctggtc tcaaacccct gacgctgtga  37740
tcctcccacc tcagcctccc agagtggtgg gattacaggc atgagccacc gcgcccggcc  37800
tgataaaatt gtaagtgaga acattagggc agtgaaggag agctaacctc actgagtccg  37860
tcttgcttcg aacttccacg ctgtctgcaa gctgtctcca agctgtctcc aagctgtcct  37920
tcttcactca tgggtgtcac ccacactatc tttgggagga acttagttta tagtttagct  37980
ttgacacgaa gatgataata gccctttccc agtgcaaacc tccttcttgc ctggggacta  38040
ggccgtgttt acaggactaa gagattatcc cctggattag aaatgatggt ttaggactct  38100
ggcctctgga ggctgcaagt ttctgaccct cctcaaattg ctcctgctca catcgctttt  38160
gtgaaaccta caatcagtgc tgagatatgt cacagaccct tcactggacg gatcagctgg  38220
caccacccag atgatcaacc ggctaatctg gtctgcggcc cccacccagg aactgactca  38280
gcgccagacg acagcttcga ctccctgtga ttccatctct gacccaacca atcagcactc  38340
cccactttct gacctcctac ccagcaaatt atcctgaaaa actccagtcc cagggtctct  38400
```

-continued

```
ggggagacgg atttgaggaa taaggaaact ccggcctccc acgcagccgg ctgggattgc  38460
agctttgtgg tagtgataaa tcactctgtc cacgcagccg gcgaggtgag cccettgggc  38520
ggtgacagga agaccaagga ggataaagaa aagccagctc ctgggggcgc gaggtcacag  38580
ccgtggctcg gacgggaacc ccaaggtcaa aggatagcag gggcaggagg tgccggcctt  38640
ggaaggcagc ggcagattcc acagaagcct ctggagtcct cgtcccaggc agacgccgtg  38700
caccgcctgg aggtggtggg aagagcgcac acagcttgca aaggccgggg tacgtcgcca  38760
gaggggcaca ggcgcaaggg ggcctggctg gcccagaaga ggggtccccg gaaccccagg  38820
tccatgtcag ggccggagcc tgcccagatc cattttccct gctgattccc aaggtgctct  38880
gtgcccccag agaactgctt tgaaacccac atacctcacg gtggggccca ccccaaaagc  38940
ccatccctgg gcttcatgag gtgtggtttg agaccctata tttttttctg ttttgagacg  39000
gagtttcgct cttgttgccc gggctggagt gcaatggtgc catctcggct cactgcaagc  39060
tccgcctccc gggttcaagc gattctcctg cctcagcctc cggagtagct gggatgacgg  39120
gcacccgcca ccatgtctgg ctaatttctt ttatttttag tagagacggc gtttcaccat  39180
cttggccagg ctggtcttga actcctgacc tcgtgatcca cctgcctcag cctcccaaag  39240
tgctgggatt gcaggcttca tttttttttt tttttttttt tttttgagat ggagtctcgc  39300
tctgtcgccc aggctggagt gcagtggcgt gatctcggct caccacaacc tccacctcct  39360
gggttcaagc aattatttat ctgcctcagc ctcccgagta gctgggacta caggcacccg  39420
ccaccacacc cggctaattt tttgtatttt tagtagagac ggggtttcac caggttagtc  39480
aggatggtct cgacctcctg acctcgtgat ccgcctgcct tggcctccca aagtgctggg  39540
attacaggcg tgagccactg cgccccgcta ttgttctaag cctaaagggg gaaggccttg  39600
tgagctgtgc ttcgtactgg ttttttttttc acattacacc aggttcaagc aattctcctg  39660
cctcagccag gctggtctca aactcctgac ctcatgatcc gcccacctcg gtctcccaaa  39720
gtgctcggat tacaggtgtg agccaccgcg cccggccaca gttaaccatt ttcaccgtgc  39780
ccggccagaa ttaactattc taatgggtcc attcactagc atttagcacc tgtttccgca  39840
ggggccgggt ctgtgcaaac cacaccccgg aggtcgagga agctgagagc tgaaggaaga  39900
agctgactaa tccagattct ccgaaagaaa tacttagcag agatgtaaga acagaagccg  39960
tgtctgcgag gagagtggat cccggtcgtc cctgcagacc cagggcttca ccccagggag  40020
gaatatgcag gaaaacgttg gtgggaggga ggggggccct cacggtcagg gaaggtgcct  40080
cagggacagc cacgtgcacc tgccccaggg cagggtttat ggtccaggct attgaggtca  40140
cattggagaa agtagcaaaa tcatcttaga gaccttccca gagcagcggt tggtcagaag  40200
tgaacaggtg gatcagcatt ccagatggag ttgctctctc ttccacaaac actcactgtc  40260
agatgcaacc cccactctct ctagctaccc cccccagcta cccccactgt ctctagctcc  40320
ccccactgtc tctagctacc ccacctctct ctagctatcc ccccctctag ctacccccac  40380
tgtctctagc tccccccact gtctctagct acccccgcct ctctctagct atccccctct  40440
ctaactactc cccacctctc tctagctatc cccctctcta gctaccccac ctctctctag  40500
ctatccccct ctctagctac cccacctctc tctagctacc cccacctctc tctagctacc  40560
ccccccagct acccccactc tctctagcta ccccacctct ctctagctat ccccctctct  40620
agctacccca cctctctcta gctaccccca cctctctcta gctacccccc ccagctaccc  40680
ccactctctc tagctacccc acctctctct agctatcccc ctctctagct accccacctc  40740
tctctagcta tccccctctc tagctacccc acctctctct agctatcccc ctctctagct  40800
```

```
accccacctc tctctagcta tccccctctc tagctacccc acctctctct agctaccccc  40860
ccctctctag ctatccccac tctctctagc tatccccctc tctagctacc cccactgtct  40920
ctagctacac cccctctagc tacccccact gtctctagct ccccccactc tctctagcta  40980
ccccacctct ctctagctat cccccctctct agctacccc actctctagc taccccacct  41040
ctctgtagct accccacctc tctctagcta cccccctctc tttagctcca gcacattctc  41100
atgactccac aaggagacca tgtgtcagaa ccccgttcct tttcatggct gcatactatt  41160
ccactctgtg gacagagcac attttgtgtg tcccttcctc tcatgacggc ctgtgctctc  41220
tcctgaatgc accatgcatg caggtgacgt gtgtgcaaag ccattgcctg gcaggtccca  41280
gagaccctct gctggctccc aagcaggtcc cctcccacct cacgggtgac cacgctgagg  41340
ttcaggacag atgaggcagg ttgctgagat gaggggcaag cccagccctg tgggggccca  41400
gctgggtgcc cgggtggctc acgtcaccag aggggcctcc tgctgcacct ttgagccaat  41460
ggcactgagc atggggtggg tctctatgag ctggttcaca cagacacccc cacacccacc  41520
ccatggatgt gggagcctcc accatttccc ctaggggttc gcagcctctc cccaactaga  41580
gacccccctcc ctgggagtcc ctcaagggct ccccaccccc atacccatac accattgcag  41640
tgttggcagc tggaagcccc ccaggggccc ttagggacct gaggacagga atggagggag  41700
gaagcttccc tgtgtgtggt tcctgtttgc tctgtgaggt gaggtgtgga cacccacagt  41760
cagcaggtca gagggacctg caaggtcagg cagcgtctcc caggctggcc aggggccagg  41820
gttagggttg gaagaccggg atggtctgtg gaatccccat gctcaccccc caccgccgat  41880
taccctggga gggcagtggc cacagtcagg tcccagcagc agagcccagc tctgggggtg  41940
gatgcagggg gtgctgcagg ggccggctgt accatcccag gcggtcttgg ggggtcacga  42000
tgtccccaac acggtgggag ggaggcagag gcccccctca aactcctgac ctcaggtgat  42060
ccaaccgcct cagcctccca aagcgccggg atcacaggca tgagccaccg tgcccggcca  42120
ctttccgctt atttttacag cactgatttt gcagaagtct tttgctttag ggccctggcc  42180
ccggccccta tgccacctcg caccccctcca cccctctctg cccggatcct ggcctccccg  42240
tactcatcca ggctgccctc agccttccca tgcagtcctg gacaatacaa ggagctccgt  42300
ccacactggc tccggcacgt ggagagggaa acctggctcc tcggctcaag gaaagtactt  42360
tttttttttt tgagatggag tttcactctt gtcgcccagg ctggagcgat ctcggctcac  42420
tgcaacctcc acctccccgg ttcaagcgat tctcctgcct cagcctcccg agtagcggga  42480
attacaggtg cccgccacca cgcccagcta atttttgtat ttttagtaca gatggggttt  42540
tgccaagttg gccaggatgg tctcaaactc ctgaactcag gtgatccacc cgcctctgcc  42600
tcccaaagtg ctgggattac gggcgtgagc caccgcgccc agccaagcaa agtatttttt  42660
aaagctctgt cttgtggtaa atctcacagc aggtgaaagc atctcgattc atagaataac  42720
ctgggcgttg gcctcacagt tgcagcagca accagccggg cctcccgtcg caactccatc  42780
cgagctccca gactccccac cctcctgtcc accctgcctg gcttgagaca ggtggatcac  42840
ctgaggtcag gagttcaaga gcagcctggc caacacggtg aaacctcatc tctactaaaa  42900
atataaaaat tagccgggcg tggtggctca cacctataat cccagcactt tgggaggctg  42960
aggcgggcgg atcgggaggt caggagttcg agaccagcct ggccaacatg gcaaaaccct  43020
aaaagaacaa aaattagccg ggcgtggtgg cgggcgcctg tggttccagc tacttgggag  43080
gctgaggcag gagaatcgct agaacccggg aggcggaggt tgcagtgagc tgagtttgtg  43140
```

-continued

```
ccactggact ccagcctggg tgacagagca acactccgtc tcaaaaaaaa aaacacaaag  43200
tgctaattat atatatattt accacaattt ggaaacattg ttcgccgggc gcagtggctc  43260
acgcctgtca tcccagcact ttgggaggcc gaggcgggcg gatcatgagt tcaggagatt  43320
gagaccatcc tggttaacac agtgaaaccc cgtctctact aaaaatacaa aaaattagcc  43380
aggcgtggtg gcgggcgcct gtagtccgag ctactcggga ggctgaggca ggagaacggc  43440
gtgagcccgg gaggcggagc ttgcagtgag ctgagatcac accactgcac tccagcctgg  43500
gcgacagagc gagactccgt ctcaaaaaaa ataaaatgct cattatatac atatttacgc  43560
caattagaaa accttgttca tcctatcagt cacttctggg cggggagtta gaattccgca  43620
gagacgcctt ctgtctcgca cagatgactt ctgggagggc cggtgagctt acggggccat  43680
gaggtgtgta agggggatct gcacagcccc aggcaggact tatgccacac agaggcccag  43740
tgcttggtcc ctcggctgtg actgacgtcc ccacggcagc cacaaccgag ctgactttga  43800
agaacggctg cctttattgc ccgctgtgaa cccgacgctg ctgcgggaat gagcgtgcgg  43860
ggggccgctg acgccggccc agcacccccg cacggaggcc aacgcacgaa gctgccctgg  43920
gagcggctct cggctcagcc agtgaagggg taaacggggg cctcctctca ccccaaagcc  43980
cgtgacccct ggatggagcc gggatgctgc gatcagttcc aaggctgtgg ccgaaacacc  44040
gtgttaccgg cagagtaagg ccagaacaat gctggaggct ttaaaaccca cacgttaaaa  44100
acacaatttt tgtttgtttg tttgttttga gacggagtct cgctctgtcg cccaggctgg  44160
agtgcagtgg cacgatctcg gctcactgca acctccgcct cccaggttca tgccattctc  44220
ctgcctcaga ctcccgagta gctgggacta caggcaggtg ccaccacgcc cagataattt  44280
ttttttgta ttttttagta gagacggggt ttcaccaggt tagccaggat ggtctcgatc  44340
tcctgacctc atgatcctcc tgcctcggcc tcccaaagtg ctgagatgac aggcatgagc  44400
cactgggccc ggcctaaaaa cacaatttct atctaacacc cgggggcata aaacctttga  44460
aactggccgg gcgcagcggc tcgcacctgt catcccagca ctttgggagg ccgaggccgg  44520
cggatcacct gaggtcggga gttcgagacc agtctgacca acatggtgaa accccgtctc  44580
tactaaaaat acaaaattag ccgggtgtgg tggtgcctcc ctgtaatccc agctactcag  44640
gcggctgagg tgagagaatc acttgaaccc aggaggcgga ggttgcagtg agccgagatc  44700
acgccactgc actgcagccc aggcaacagg agcgaaactc catctcaaaa aaaaaaagtt  44760
tggaaacgtt tgttttctag gaaacagaaa caataacctc cgtctgtctg cagacatcgc  44820
ccaccctgcc cgagcttccc accgaggtta aagatgagct ctcgcccgcg gccccaggag  44880
ggactctcgg cagaaaaccc ttacggaacc ttgaagatgt gtccagcccg gggctcccgt  44940
aacaagtgct ccggactcag gcggtccgcc gcggaggtca cgtagaggtt gtcgtagccg  45000
ggtccccgaa gcagcaggag gtgaccctgt acacaggcag ctccaccgtg cacagcacct  45060
tccctgtgag cgagcgtggg ggctgagcct gagcacccca ggccgcctgc ctggccgttc  45120
ctcctgaccc tgggcccaac ccccgggcag catgggtgtc tctgtggcac ctggagctgc  45180
cagattggca cctgcctagc caggcccagc cgcacctgct ctagtgagct ctgtagtctc  45240
cccagattca tgccaagtag gatctcagaa tgggaaatta tttggaaata gggtgtttgc  45300
agaggtaatt agtaggtcag agcaggttag ggtgggtcct acatccaatc accagtgtcc  45360
ttctaagaga cagaagagca gacacagaca cagaggagga ggccacgtgg agacggaggc  45420
agagactgga gtgatgcggc ctcaagccca gggatgcctg gagcccccag gagctgggag  45480
aggcaggaag gaccctcccc tagagtctca atacaattga agtggattga actgtggttc  45540
```

-continued

```
ccaaaaagat ctgtctacac cctaatatcc acaacctagg aatgagacct tgtatagaaa  45600
tagggtgttt caagatctag ttagtgaagg atcttgagat gagatcatcc tggagtaggg  45660
tggatcctaa atgcaatgac aggtgtcctt ctagagacag aagaggagac acagacacag  45720
tggatgaggc ctcgtggaga cggaggcaga gactggagtg atgcggccac aagcccaggg  45780
acgcctggag cccccaggag ccgggagagg caggaaggac cctccactac agctcctgga  45840
gggagtacgg ccctgaaact cctcggtctc agactcctgc tctgcaggac tgggggaggt  45900
gacttcctgt ttcttaggca gccagtcctt ggttgcggca gccccaggac ctagcacacc  45960
tgcagaggga acctgggagt ccgtgccgtc gggaaacgga ggccccttag tctctacaaa  46020
ttcgcgattg ctgcccggcc ccgacttctg aagccagaac gctgcagacg cagtggacac  46080
ccgatgtggc caagcctcat acggccccgc catccggcac acacctgtct cggggtcaag  46140
gcgtatcacc ttgcctctat cgacgcagag gccacccaga gcttccccgc agcgtccacg  46200
cacacgccgg ccggcatgcc ctgctccgga tgcagccggt acaggagcct ccggttcact  46260
gcaatgagag gaccgggatg ggcaggggcc ttcccagccc tggtgagtgc cctgctgagt  46320
gccaggagca ggcagacctc aggcaggccc gtgaccctcc tggatgtgag tggagcctgg  46380
aggaggtgca cctagctcgt tgggagcctt ggacgtggct ggatcctgat gcgtacagac  46440
cccgtttggc gaacagctgt aggctgaaaa ttaatgtccc caaatacagc tgaccagggc  46500
acacacctcc tcaaacgccg gcccaaggac atcacccttt aaacagcatc caatctctct  46560
cctagttccc accgaggatt atgaacgaag ccttgatgta cacctgttga ctttgtggaa  46620
gatgggagac ttctctccca acccgaagca cttccagccc agaaacccca gtgacacctg  46680
gtcgaaggcc ttgtaccttg gcctttcttt cctcaggtgg aaatgagaag aaagaacatg  46740
gccccaagga cagacaccag ataactgggg acttggctgt ccaccagctg ggaactgaga  46800
gttatgcctg ctccagtggc ccatcctgct agaaaaaaga tgtctttacc aggaaaacgg  46860
gatgtggcag tcctcaccca cccacaggat gacctggtcc ccaccaacat ccagggataa  46920
ccttgaaccc atcgacatcc agggataacc ttgtcccagt caacatccag ggatgacttt  46980
gtccccaccc acatgtggag gtgacctcgt ccccatcaac attcaccaaa catgcagaga  47040
tcaccttgtc cccaccaacg tccggggata atcttgtcct catcaacata caggactgac  47100
cttgtcccga taagcaccca gggatgacct tgtccccact aacaagcaga gataaccttg  47160
tcccaatcaa catccaggat gaccttgtcc ccactgacat gcagagatca ccttatcccc  47220
accaacatcc agggataacc ttgagtcaat caacatccag gatgacctca tccccaccca  47280
catgcagaga tcaccttgtt cccaccaaca tccggggata accttgaatc aatcaacaac  47340
cttgaaccaa tcaacatcca ggatgacctt gtccctatca acatccagga cgaccttgtc  47400
cccacccaca tgcagagatc accttgtccc caccaacatc cagggataac cttgtcccaa  47460
tcaacatcca ggatgacctt gtccaccacc cacatgcgga gatgacctcg tccccatcaa  47520
cattcaccaa acatgtagag atcaccttgt ccccaccaac atccaaggtt aaccttgaac  47580
caatcaacat caggatgacc ttgtccccac ccacatgcag agatgacctc gtccccatca  47640
acattcacca aacatgcaga gatccccttg ctctcgccaa cgtccgggga taatcttgtc  47700
cccatcaaca tccagaatga ccttgtcttc accaacatcc gggactgacc ttgtcctgat  47760
aagcacccag ggatgaactt gtccccacta acaagcagag atgaccttgt cccaatcaac  47820
atccaggatg acttcgtccc catcgatatg cacagattct agggaaaaga aagagagatc  47880
```

-continued agactgtcac tgtgtctatg tagaaaggaa agacataaga gactccattt tgaaaaagac 47940
ctgtccttta aacaattgct ttgctgagat gttgttaatt tgtagctttg ccccagccac 48000
tttgccccaa cctggagctc acaaaaacat gtgttgtatg aaatcaaggt ttaagggatc 48060
cagggcggtg caggacgtgc cttgttaaca agatgttcac gagcggtata cttggtaaaa 48120
gtcatcgcca tcctctagtc tcaataaacc aggggcacag tgccctgcgg aaagccgcag 48180
ggacctctgc tcttgaaagc cgggtattgt ccaaggtttc tccccatgtg atagtctgaa 48240
atatggcctc gtgggaaggg aaagagctga ccatccccca gctcaacacc cataaagggt 48300
ctgtgctgag gaggattagt aaaagaggaa ggcctctttg cagttgagat aagaggaagg 48360
catctgtctc ctgctcgtcc ctggacaata gaatgtctcg gtgtaaaccg attgtatatt 48420
ccatctactg agatagggta aaactgcctt atggctggag gtgggacatg ctggcggcaa 48480
cactgctctt taaggcgttg agatgtttat gtatgtgcac atcaaagcac agcacttttt 48540
tctgtacctt gtttatgatg cagagacatt tgttcacgtt ttcctgctga ccctctctcc 48600
actattaccc tattgtcctg ccacatcccc ctctccccga taatgatcaa taagtactaa 48660
gggaactcag aggcaggtgc cggcgcgggt cctctgtatg ctgagcgccg gtcccctggg 48720
cccattttc tttctctcta ctttatctct gtgtctcttt cttttttcaa gtctctcgtt 48780
cctcctgatg agaaatgccc acaggtgtgg aggggcaggc caccccttca aggatgcaca 48840
tggaaggatg cacagaggag gatgcacatg ggaggatgca catgagttgt acagaatgga 48900
tgagtcccta cacacaggag actccttcct gtcacaacct gagacccgct cttcctgtca 48960
cggcccgaga caccctcttc ctgtcacggc ccgagacccc ctcttcctgt cacggcccga 49020
gaccccctct tcctgtcacg gcccgagact ccctcttcct gtcacggccc gagactccct 49080
cttcctgtca caacctgaga cccgctcttc ctgtcacggc ccgagacccg ctcttcctgt 49140
cacggcccga gactccctct tcctgtcacg gcccgagatc ccctcttcct gtcacggccc 49200
gagactccct cttcctgtca cggccggaga ccccctcttc ctgtcacggc ccgagacccc 49260
ctcttcctgt cacggcccga gaccccctct tcctgtcacg gcccgagacc ccctcttcct 49320
gtcacggccc gagaccccct cttcctgtca cggcccgaga ccccctcttc ctgtcacggc 49380
ccgagactcc ctcttcctgt cacggcccga gatcccctct tcctgtcacg gcccgagacc 49440
ccctcttcct gtcacggccg gagaccccct cttcctgtca cggcccgaga ccccctcttc 49500
ctgtcacggc ccgagacccc ctcttcctgt cacggcccga gactccctct tcctgtcacg 49560
gcccgagact ccctcttcct gtcacaacct gagacccgct cttcctgtca cggcccgaga 49620
cccgctcttc ctgtcacggc ccgagactcc ctcttcctgt cacggcccga gatcccctct 49680
tcctgtcacg gcccgagact ccctcttcct gtcacggccg gagaccccct cttcctgtca 49740
cggcccgaga ccccctcttc ctgtcacggc ccgagacccc ctcttcctgt cacggcccga 49800
gaccccctct tcctgtcacg gcccgagacc ccctcttcct gtcacggccc gagaccccct 49860
cttcctgtca cggcccgaga ctccctcttc ctgtcacggc ccgagatccc ctcttcctgt 49920
cacggcccga gaccccctct tcctgtcacg gccggagacc ccctcttcct gtcacggccc 49980
gagaccccct cttcctgtca cggcccgaga ctccctcttc ctgtcacggc ccgagacccc 50040
ctcttcctgt cacggcccga gaccccctct tcctgtcacg gcccgagacc ccctcttcct 50100
gtcacggccc gagactccct cttcctgtca cggcccgaga ctccctcttc cggtcacggc 50160
ccgagatccc ctcttcctgt catggcctga gttgttttc aggtttcttt gggatcccct 50220
tggctacaaa caggtccact cagtcagctg aggggcttag aattctattt ttggtttacc 50280

```
ccactatcag gaggttgtct gagataagcc agcccctccc acccttgcag gcacagtgtg  50340
caagcataag atctcgtgct ggccgccatt caggtggcag ccacagggat ggtccagacg  50400
tggctctcca accgtcctta gaccacacaa agctttagga tttctggggt cccaatgcag  50460
actctaaagg ttgcatagtc tggtctctat ctgccctcaa tgagacctag gcccagtgca  50520
gactctaaag gttgcatagt ctggtcccta tctgccctca atgagaccta ggcccagtgc  50580
agactcgaaa ggttgcacag tctgctctct atctgtcctc aatgagactt aggcacaatg  50640
cagactctaa acgttgcaca gtctgctctc tatctgccct caatgagacc taggcccaat  50700
gcatactcta aaggttgcac agtctgctct ctatctgccc tcaatgagac ctaggcccaa  50760
tgcagactct aaaggttgca tagtctggtc tctatctgcc ctcaatgaga cctaggccca  50820
atgaagactc taaaggttgc gcagtctgct ctctatctgt cctcaatgag acctaggccc  50880
agtgcagact ataaaggttg cacagtctgg tctctatctg tcctcaatga gacctaggcc  50940
caatgcagac tctaaaggtt gcacagtctg ctctctatct gtcctcaatg agacctaggc  51000
caagtgcaga ctctaaagct tgcacagtct gctctctatc tgacctcaat gagacctagg  51060
cccaatgcag actataaagg ttctacagtc tgctctctat ctgtcctcaa tgagacctag  51120
gcccaatgca gactctaaag gttgcacact ctggtctcta tctgtcctca atgagaccta  51180
ggcccagtgc agactgtaaa gtttgcatag tctgctctct atctgtcctc aatgagacct  51240
aggtccaatg cagactctaa aggttgcaca gtctgctctc tatctgtcct cgatgagacc  51300
taggcctagt gcagactcta aaggttgcac agtctgctct ctatctgctc tcaatgagac  51360
ctaggcccaa tgcagactct aaaggttgca cagtctgctc tctatctgtc ctcaatgaga  51420
cctaggccca atgcagactc taaaggttgc acagtctgct ctctatttgt cctcaatgag  51480
acccaggccc aatgcagact ctaaaggttg cacagtctgc tctctatcgg tcctcaatga  51540
gaccgaggcc ctatgcagac tctaaaggtt acacagtgtg ctctctatca gtcctcagtg  51600
agacctagac ccaatggaga ctctaaagtt tgcaaagtct gctctctatc tctcctcagt  51660
gagacctaga cccaatgcag actctaaagg ttgcacagta tggtctctat ctgccctcaa  51720
tgagacctag gctcagtgca gactttaaag tttgcacagt ctgctctgta tctgtcctca  51780
atgagaccta ggcccaatgc agactctaaa ggttgcacag tctgccctct atctgtcctc  51840
aatgagacct aggcccaatg cagactctaa agttttaaca gtctggtctc tatctatcct  51900
caatgagacc taggcccaat gccgaatcta gaggttgcac agtgtgctct ctgtctgctc  51960
tcaatgagac ctagacccaa tgcagactct aaaggttgca cagtctgctc tctaactgcc  52020
ctcaatgaga cctaagccca atgcagactc taaaggttgc acagtctggt cgctatctgt  52080
cctcaatgag acccagaccc aatgcagact ctaaaggttg cacagtctgc tctatatctg  52140
tcctcaatga gacctaggaa aagtgccgac tctaatggtt gcctagtctg ctctttatct  52200
gtcctcaatg agacctaggc ccaatgcaga ctctaaaggt tgcacagtcc ggtctctatc  52260
tgtcctcaat gagacctagg cccaatgccg actctaaagt ttgcacagtg tgctctctat  52320
ctgctctcaa tgagacctag gcccaatgca gactctacag gtagcacagt ctgctctcta  52380
actgccctca atgacaccta ggcccaatgc agactctaaa cgttgcatag tctggtctct  52440
acctgccctc aatgagacct aggcccaatg cagactctaa aggttgcaca gtctgctctc  52500
tatctgtcct caatgagacc taggccaagt gcagactcta aagcttgcac agtctgctct  52560
ctatctgacc tcaatgagac ctaggcccaa tgcagactac aaaggttcta cagtctgctc  52620
```

```
tctatctgtc ctcaatgaga cctaggccca atgcagactc taaaggttgc acactctggt  52680
ctctttctgt cctcaatgag acctaggcca aatgcagact ctaaaggttg cacagtctgc  52740
tctctaactg tcctcaatga gacataggcc caatgcagac tctaaaggtt gcacagtctg  52800
ctctctatgt gtcctcaatg agacctaggc tcagtgcaga ctctaaaggt tgcatagtat  52860
gctctctatc tgtcctcaat gagatctaag cccaatgcag actctaaggg ttgccgagcc  52920
tgctctctat ctgccctcaa tgagacctag gcccaatgca gactctaaag gttgcacagt  52980
ctgctgtcta tctgacctca aggagaccta ggcccaatgc agactctaaa ggttgcacag  53040
tctggtctct atctgtcctc aatgacacct aggcccagtg cagactctaa agtttgcaca  53100
gtctgctctc tgtctgtcct caaagagacc taggcccagt gcagactcta aaggttgcac  53160
agtctgctct ctatctgtcc tcaatgagac ctaggcccaa tgcagactct aaaggttgca  53220
cagtctgctc tctatctgcc ctcaatgaga cctaggccca atgcaaactc taaagttgca  53280
cagtctggtc tctatctgtc ctcaatgaga cctaggccca atgcggactc taaaggttgc  53340
acagtgtgct ctccatctgt cctcaatgag acctaggccc aatgcagact ctaaaggttg  53400
cacagtctgc tctctatctg ccctcaatga gacctaggcc caatgcagac tctaaaggtt  53460
gcacagtctg ctctctatct gctctcaatg agacctaggc ccaatgcaga ctctaaaggt  53520
tgcacagtct ggtctctatc tgtcctgaat gaggcccagg cccaatgcag actgtaaagg  53580
ttgcacagtc tgctctctat ctgtcctcaa tgagacctag gctcagtgca gcctctaaag  53640
tttgcatagt ctgctctcta tctgtcctca atgagaccta ggtccaatgc agactctaaa  53700
ggttgcacag tctgctctct atctgtcctc aatgagacct aggcctagtg cagactctaa  53760
aggttgcaca gtctgttctc tatctgtcct caatgagacc taggccaagt gcagactcta  53820
aagcttgcac agtctgctct gtatctgacc tcaatgagac ctaggcccaa tgcagactat  53880
aaaggttcta cagtctgctc tctatctgtc ctcaatgaga cctaggccca atgcagactc  53940
taaaggttgc acactctggt ctctatctgc cctcaatgag acctaggccc aatgaagact  54000
ctaaaggttg cgcagtctgc tctctatctc tcctcaatga gacctaggcc caatgcagac  54060
tctaaaggtt gtacagtctg ctctctatct gtcctcaatg agacctaggc ccaatgcaga  54120
ctctaaaggt tgcacagtct gctctctatt tgtcctcaat gagacccagg cccaatgcag  54180
actctaaagg tggcacagtc tgctctctat cggtcctcaa tgagaccgag gccctatgca  54240
gactctaaag gttacacagt gtgctctcta tctgtcctca gtgagaccta ggcccaatgc  54300
agactctaaa gtttgcgcag tctgctctct atgtgtcctc aatgagacct agggccagtg  54360
cagactctaa aggttgcata gtctgctctc tatcagtcct cagtgagacc tagacccaat  54420
ggagactcta aagtttgcaa agtctgctct ctatctctcc tcagtgagac ctagatccaa  54480
tgcagactct aaaggttgca cactctggtc tctttctgtc ctcaatgaga cctaggccaa  54540
atgcagactc taaaggttgc acagtctgct ctctaactgt cctcaatgag acataggccc  54600
aatgcagact ctaaaggttg cacagtctgc tctctatgtg tcctcaatga gacctaggct  54660
cagtgcagac tctaaaggtt gcatagtatg ctctctatct gtcctcaatg agatctaagc  54720
ccaatgcaga ctctaagggt tgccgagcct gctctctatc tgccctcaat gagacctagg  54780
cccaatgcag actctaaagg ttgcacagtc tgctgtctat ctgacctcaa ggagacctag  54840
gcccaatgca gactctaaag gttgcacagt ctggtctcta tctgtcctca atgacaccta  54900
ggcccagtgc agactctaaa gtttgcacag tctgctctct gtctgtcctc aaagagacct  54960
aggcccagtg cagactctaa atgttgcaca gtctgctctc tatctgtcct caatgagacc  55020
```

taggcccaat gcagactcta aaggttgcac agtctgctct ctatctgccc tcaatgagac 55080
ctaggcccaa tgcaaactct aaagttgcac agtctggtct ctatctgtcc tcaatgagac 55140
ctaggcccaa tgcggactct aaaggttgca cagtgtgctc tccatctgtc ctcaatgaga 55200
cctaggccca atgccgactc tagaggttgc acagtgtgct ctctatctgc tctcaatgag 55260
acctaggccc aatgcagact ctaaaggttg cacagtctgc tctctaactg ccctcaatga 55320
gacctagacc caatgcaaac tctaaaggtt gcacagtctg gtcgctatct gtcctcaatg 55380
agacccaggc ccaatgcaga ctctaaaggt tgcacagtct gctctatatc cgtcctcaat 55440
gagacctagg accagtgccg actctaatgg ttgcctagtc tgctctttat ctgtcctcaa 55500
tgagacctag gcccaatgca gactctaaag gttgcacagt ccggtctcta tctgtcctca 55560
atgagaccta ggcccaatgc cgactctaaa gtttgcacag tgtgctctct atctgctctc 55620
aatgagacct aggcccaatg cagactctaa aggtagcaca gtctgctctc taactgccct 55680
caatgacacc taggcccaat gcagactcta aacgttgcat agtctggtct ctatctgccc 55740
tcaatgagac ctaggcccaa tgcagactct aaaggttgca cagtctgctc tctatctgtc 55800
ctcaatgaga cctaggccaa gtgcagactc taaagcttgc acagtctgct ctctatctga 55860
cctcaatgag acctaggccc aatgcagact ataaaggttc tacagtctgc tctctatctg 55920
acctcaatga gacctaggcc caatgcagac tataaaggtt ctacagtctg ctctctatct 55980
gtcctcaatg agacctaggc ccaatgcaga ctctaaaggt tgcacagtct gctctctaac 56040
tgtcctcaat gagacatagg cccaatgcag actctaaagg ttgcacagtc tgctctctat 56100
gtgtcctcaa tgagacctag gcccagtgca gactctaaag gttgcatagt atgctctcta 56160
tctgtcctca atgagatcta agcccaatgc agactctaag ggttgccgag cctgctctct 56220
atctgccctc aatgagacct aggcccaatg cagactctaa aggttgcaca gtccgctctc 56280
tatctgtcct caatgagacc taggcccaat agagactcta aaggttgcac agtctgctct 56340
ctatctgtcc tcaatgagac ccaggcccaa tgcagactct aaacgttgca tagtctgctc 56400
tctatctgtc cgcaattaga cctagaccca atgcagactc taaaggttgc acagtctgct 56460
gtctatatga cgtcaaggag acctaggccc aatgcagact ctaaaggttg cacagtctgg 56520
tctctatctg tcctcaatga cacctaggcc cagtgcagac tctaaagttt gcacagtctg 56580
ctctctgtct gtcctcaaag agacctaggc ccagtgcaga ctctaaaggt tgcacagtct 56640
gctctctatc tgtcctcaat gagacctagg cccaatgcag actctaaagg tggcacagtc 56700
tgctctctat ctgccctcaa tgagacctag gcccaatgca aactctaaag gttgcacagt 56760
ctggtctcta tctgtcctca atgagaccta ggcccaatgc ggactctaaa ggttgcacag 56820
tgtgctctcc atctgtcctc aatgagacct aggcccaatg cagactctaa aggttgcaca 56880
gtctgctctc tatctctcct caatgagacc taggcccaat gcagactcta aagtttgcac 56940
agtcggctct ctatctgccc acaatgagac ctaggcccaa tgcagactct aaaggttgca 57000
cagtctgctc tctatgtgtc ctcaatgaga cctaggccca gtgcagactc taaaggttgc 57060
acagtctgct ctctatctgc cctcaatgag acctaggccc aatgcagact gtaaaggttg 57120
cacagtctgc tctctatctg ctctcaatga gacctaggcc caatgcagac tctaaaggtt 57180
gcacagtctg gtctctatct ctcctgaatg aggcccaggt ccaatgcaga ctgtaaaggt 57240
tgcacagtct gctctctatc tgtcctcaat gagacctagg ctcagtgcag cctctaaagt 57300
ttgcatagtc tgctctctat ctgtcctcaa tgagacctag gtccaatgca gactctaaag 57360
gttgcacagt ctgctctcta tctgtcctca atgagaccta ggcctagtgc agactctaaa 57420
ggttgcacag tctgctctct atctgccctc aatgagacct aggcccaatg cagactctaa 57480
aggttgcaca gtctgctctc catctgtcct caatgagacc taggcccaat gcagactcta 57540
aaggttgcac agtctgctct ccatctgtcc tcaatgagac ctaggcccaa tgcagactct 57600
aaaggttgca cagtctgctc tctatttgtc ctcaatgaga cccaggccca atgcagactc 57660
taaaggttgc acagtctgct ctctatcggt cctcaatgag accgaggccc tatgcagact 57720
ctaaaggtta cacagtgtgc tctctatctg tcctcaatga gacctaggcc caatgcagac 57780
tctaaagttt gcgcagtctg ctctctatct gtcctcaatg agacctaggg ccagtgcaga 57840
ctctaaaggt tgcatagtct gctctctatc agtcctcagt gagacctaga cccaatgcag 57900
actctaaagt ttgcaaagtc tgctctctat ctctcctcag tgagacctag acccaatgca 57960
gactctaaag gttgcacagt atggtctcta tctgtcctca atgagaccta ggcccagtgc 58020
agactctaaa ggttgcacag tctgctctct atcggtcctc aatgagacct aggcccaatg 58080
cagactctaa agtttgcaca gtctgccctc tatctgtcct caatgagacc taggcccagt 58140
gcagactcta aaggttgcac agtctgctct ctatctgtcc tcaatgagac ccaggcccaa 58200
tgcagactct aaaggttgca cagtctgctc tatatctgtc ctcaatgaga cctaggacca 58260
ctgccgactc taatggttgc ctagtctgct ctctatctgt cctcaatgag aactaggccc 58320
aatgcagact ctaaaggttg cacagtctgg tctctatctg tcctcaatga gacctaggcc 58380
caatgccgac tctaaaggtt gcacagtatg ctctctatct gctctcaatg agacataggc 58440
ccaatgcaga ctctaaaggt tgcacagtct gctctctatc tgccctcaat gagacctagg 58500
cccaatgcag actctaaagg ttgcacagtc tgctctccat ctgtcctcaa tgagacctag 58560
gcccaatgca gactctaaag gttgcacagt ctgctctcta tttctcctca atgagaccca 58620
ggcccaatgc agactctaaa ggtggcacag tctgctctct atcggtcctc aatgagaccg 58680
aggccctatg cagactctaa aggttacaca gtgtgctctc tatctgtcct cagtgagacc 58740
taggcccaat gcaaactcta aagtttgcgc agtctgctct ctatctgtcc tcaatgagac 58800
ctagggccag tgcagactct aaaggttgca tagtctgctc tctatcagtc ctcagtgaga 58860
cctagaccta atgcagactc taaagtttgc aaagtctgct ctctatctct cctcagtgag 58920
acctagaccc aatgcagact ctaaaggttg cacagtatgg tctctatctg ccctcaatga 58980
gacctaggcc cagtgcagac tctaaaggtt tcacagtctg ctctctatct gtcctcaatg 59040
agacctaggc ccaatgcaga ctctaaagtt tgcacagtct ggtctctatc tgtcctcaat 59100
gagacctagg cccaatgccg actctagagg ttgcacagtg tgctctctat ctgctctcaa 59160
tgagacctag gcccaatgca gactctaaag gttgcacagt ctgctctcta actgccctca 59220
atgagaccta ggcccaatgc agactctaaa ggttgcacag tctgttctct atctgtcctc 59280
agtgagacct aggccaagtg cagactctaa agcttgcaca gtctgctctc tatctgacct 59340
caatgagacc taggcccaat gcagactcta aaggttgcac agtctgctct ctatctgtcc 59400
tcaatgagac ctaggcccaa tgcaaactct aaaggttgca cactctggtc tctttctgtc 59460
ctcaatgaga cctaggccaa atgcagactc taaaggttgc acagtctgct ctctaactgt 59520
cctcaatgag acataggccc aatgcagact ctaaaggttg cacagtctgc tctctatgtg 59580
tcctcaatga gacctaggcc cagtgcagac tctaaaggtt gcatagtatg ctctctatct 59640
gtcctcaatg agatctaggc ccaatgcaga ctctaagggt tgccgagcct gctctctatc 59700
tgccctcaat gagacctagg cccaatgcag actctaaagt ttgcacagtc cgctccctat 59760

-continued

```
ctgtccttaa tgagacctag gcccaataga gactctaaag gttgcacagt ctgctctcta  59820
tctgtcctca atgagaccca ggcccaatgc agactctaaa cgttgcatag tctgctctct  59880
atctgtccgc aattagacct aggcccaatg caaactctaa acgttgcaca gtctgctgtc  59940
tatctgtccg caattagacc taggcccaat gcagactcta aaggttgcag agtctgctgt  60000
ctatctgacc tcaaggagac ctaggcccaa tgcagactct aaaggttgca cagtctggtc  60060
tctatctgtc ctcaatgaca cctaggccca gtgcagactc taaagtttgc acagtctgct  60120
ctctgtctgt cctcaaagag acctaggccc agtgcagact ctaaaggttg cacagtctgc  60180
tctctatctg tcctcactga tacctaggcc caatgcagac tctaaaggtt gcacagtctg  60240
atctctattt gtcctcaatg agacccaggc ccaatgcaga ctctaaaggt tgcacagtct  60300
gctctctatc ggtcctcaat gagacctagg cccaatgcag actctaaagg ttgcacagtc  60360
tgctctctat ctgccctcaa tgagacctag gccctatgca aacgctaaag gttgcacagt  60420
gtggtctcta tctgtcctca atgagaccta ggcccaatgc agactctaaa ggttgcacag  60480
tgtgctctcc atcagtcctc aatgagacct aggccaaatg cagactctaa aggttgcaca  60540
gtctgctctc tatgtgtcct caatgagacc taggcccagt gcagactcta aagtttgcac  60600
agtctgctct ctatcggccc tcaatgagac ctaggcccaa ttcagactct aaaggttgca  60660
cagtctgctc tctatctgct ctcaatgaga cctaggccca atgcaaactc taaaggttgc  60720
acagtctggt ctctatctct cctgaatgag acccaggccc aatgcagact gtaaaggttg  60780
cacagtctgc tctctatctg tcctcaatga gacccaggcc cagtgcagac tgtaaagttt  60840
gcatagtctg ctctctatct gtcctcaatg agacctaggt ccaatgcaga ctctaaaggt  60900
tgcacagtct gctctctatc tgtcctcgat gagacctagg cctagtgcag actctaaagg  60960
ttgcacagtc tgctctctat ctgccctcaa tgagacctag gcccaatgca gactctaaag  61020
gttgcacagt ctgctctcta tttttcctca atgagaccca ggcccaatgc agactctaaa  61080
ggttgcacag tctgctctct atctgtcctc aatgagaccg aggccctatg cagactctaa  61140
aggttacaca gtgtgctctc tatctgtcct cagtgagacc taggcccaat gcagactcta  61200
aagtttgcgc agtctgctct ctatctgtcc tcaatgagac ctagggccag tgcagactct  61260
aaaggttgca tagtctgctc tctatcagtc ctcagtgaga cctagaccca atggagactc  61320
taaagtttgc aaagtctgct ctctatctct cctcagtgag acctagaccc aatgcagact  61380
ctaaaggttg cacagtctgg tctctatctg ccctcaatga gacctaggct cagtgcagac  61440
tttaaagttt gcacagtctg ctctgtatct gtcctcaatg agacctaggc ccattgcaga  61500
ctctaaaggt tgcacagtct gccctctatc tgtcctcaat gagacctagg cccaatgcag  61560
actctaaagt ttcaacagtc tggtctctat ctgtcctcaa tgagacctag gcccaatgcc  61620
gactctagag gttgcacagt gtgctctcta tctgctctca atgagaccta gacccaatgc  61680
agactctaaa ggttgcacag tctggtctct atctgccctt aatgagacct acactcccag  61740
gagtctgcag aacagggtgt gtgtaagttt tctggggccg ctcaaggaaa cgggggatta  61800
aaaaatatta tcctcacagt gctggcatgt tggcctacac agagccctgc tcgccgtgaa  61860
cgtcaggact tcctgcgtga tctcttcaag tccgattggg agccctttga ctcgcccccct  61920
gtctgtgctg gagaattcag agcccactga ctcatctttc tttgtggcct gggagagttg  61980
tggagaacat gccgtacctt cgcggtgccg cacggatctt cctgctccct ccctcgggag  62040
tctcgcaggg accccatctc gttttaatgt tttgtcaata cggcacccac gagaacgttg  62100
```

-continued

```
cagggaagac accactgtgg ccgtaaacca cagaaactag agctgaagtg gccccaggtg  62160
gcctccagtc aagtggtatc caaattcttc accctgaggc cctttattta ttattattat  62220
tattagagac ggagtttcgc tcttgttacc caggctggag tgcaatggtg tgatatcagc  62280
tcaccgcaac ctccgcctcc cgggttcaag caattctccg gcctcagcct cccaagtagc  62340
tgggattaca ggtgggcgcc accacgcctg gctaattttt tgtattttta gagatgggga  62400
ttctctatgt tggtcaggct ggtctcgaac tcccaacctc aggtgagctg ctggccttgg  62460
cctcccaaag tgctgggatt acaggcgtgc accaccacac ccatccctat cttattcttt  62520
ttctctcacc agggacccca aatttggaag aaccataatc atgtttattg acatcatgtt  62580
aaattaaggt tcccacgttt attaataaaa gaaatatatc attagcctgg ccttttaaat  62640
ttttcttaat ttaatttttt ttttttttga ggcagggtct cactctgtca cccaggctgg  62700
agtgcaatgg taccatcatg gctcaccaca gcccccgct cctaggctca agcaatcctc  62760
ttgcctcagc ctcctgagta tctggggatt ataggtgcac accatcacac tcagccaatt  62820
aaaaaaaaat ttctagtaga gatggggtct caccaagttg tccaggctgg tctcacactt  62880
ctgagctcaa gtaatcctcc tgctttggcc tcccaaagtg ctcggattac aggggtaagc  62940
taccacattc agcctttatt tttattttta atggaggtaa aagccacata acataaaatt  63000
taccctttca actacttctt ttttttagat ggaggcttgc tctgttgccc aggctggagt  63060
gcagtggcac aatctcagct cacttcaacc tctacctccc gggttcaagt gattcccctg  63120
cctcagcctc ccaagtagct gggatcacag gcacccgcca ccacacctgg caattttttt  63180
gtattttagt agagacgggg tttcactgtg ttggccaaga cggtgtcgat ctcctgacct  63240
cgtgatccgc ctgcctcggc ctcccaaagt gctgggatta caggcatgag ccaccgcgcc  63300
cggccccttt aaagtatttt taaggataca cttcagcagt gttcatcata tccgcattgt  63360
tgtataacag atgtttacaa cttcttcatc ttacaaaaca gaaactgtgt ccacatcaaa  63420
ccagggtgcc ccattccccc ggcccctggc acccaccatt ctactgtctg tctctatgaa  63480
ttccactctt ccagagacct cataggagtg ggatcacaca gcactttttt gtctggctta  63540
tcttgttaac aacaggtgag tccatgtggt agcctgtctc atcattcctt ccttttttagg  63600
gctgattcat atttcattat atggatgaac cacattttct ttttccagtc atgctgtaac  63660
aggatgagtc acagtcaaaa ctcctcagac accagattaa agaaggaaga ggttttttta  63720
tttggccggg agattcggca gactcgtgtc ttaagagccg agctccccga aaaagaaatt  63780
cctagccctt ttaagggcta agaactctaa ggggtctatg tgaaagagtc ataatagatc  63840
aagtaagtgt gaggaacgtg agtgggggct acatacatca gctaagagaa caaaaagttt  63900
ttattttttt attttttttg agacggaatc tcgctctgtg gcccaggctg gagtgcagtg  63960
gtgtgatctc agctcacttc aagctccgcc tcccgggttc acagcattct cctgcctcag  64020
cctccccagt agctgggact acaggcgccc gccaccgcgc ccggctaatt ttttgtattt  64080
ttagtagaca cggggtttca tcatgttaac caggatggtc tcgatctcct gaccttgtga  64140
tccacccgcc tcggcctccc aaagtgctgg gattagaggc tggagccacc gtgcccggcc  64200
tgcacccagc taatttttttg tatttttagt agagatgggg tttcaccgtg ttagccagga  64260
tggtctccat ctcctgacct catgatccgc ccacctcggc ctcccaaagt cctgggatta  64320
caggcgtgag ccaccgcgcc cggccagaac aaaaagtttt acagtgcttt ctcatacaat  64380
gtctggaatt tacagatagc accagtagtt ttggtcagcg gttaatacta ttattatttt  64440
aatcaccagg gccaggtggt ggcaccaagg tcgtctagct atttatctta cttttgtttc  64500
```

```
tttccaactt tttgctttct ctcttttctc ttgtcttata aactagggaa aaggggaggt  64560
tggggagaaa ctggaaagga caacaggaga agtggtggtg tcataacata atgcgatcat  64620
gggcaccggg ctgcttccat cttttggcta ttgtgaatac tgctgtaacg accacggttg  64680
tgcaataatc ccttccagac tctgctttca atctttttgg atttagtcgg agaagtaatg  64740
tgattgctgg ttcataggtg gttccatttc tggttattta tttatttttt aagagacaga  64800
gttttatatg ttgcccaggc tggccttgaa ctcctgggct tcagtgatcc ccttccctca  64860
gcctcccaag tagccggtag tgcagctgca catcaccaca cccaagtgat ttttagttgt  64920
tatttttctg gttttgtttt tgcggagatg gagtttcact gtgccgccca gggtggagtg  64980
cggtggcata atcggctcac tgcagcctcc acctcctggt tcaggcgctt ctcctgcctt  65040
agcctcccga gtagctggga ctataggcat ctgtcaccac actcagctaa ttattttgtg  65100
tttgcttccc cccaccccgc ccccccgaga tggagtcttc ctttgtcacc caggctggag  65160
tgcagtggcg cgatctcggc tcaatgcaac ctctgcctcc ggggttcaag caattctcct  65220
gcctcagcct cccgggtagc tgggattcct ggcacccaca accacgcccg gctaattttt  65280
tatttttagt agagacggag tttcaccatg ttggccaggc tggtctcgaa ctcctgactt  65340
tgtgatccac ctgcctcggg ctcccaaagt gctgggatga caggtgtgag ccactgtgcc  65400
cagcctgata tttagtgctt ttttgaggag gctccatagt gttttccacg gtggccacac  65460
cattttctag tcctacaggc aatccacgag ggctccaatt tccacacatc cttgttaaca  65520
ctatttttgt ttcactgtag catttcatgg atgtgaggtg ctatcactgt ggttttgatg  65580
tgtatttctc taatgattac tgatgttgag gatccttcca tgtttgtttg ctacttgtat  65640
atcttttctg gagaaatatc tattcaggtc gtttgctcat ttttcaatca gttaacttgt  65700
ttttcaattg ttcagttgca ggagctcttt atatgtgctg gacgaatatc cgacgtacca  65760
gacatataat ctgcagttat ttcctcttat tccatgtctt gcctttccac tgttgtttcc  65820
tgtgcagaaa tgtttaacct cgaagttgga ccatttgtct atttgtgctt ttgttgcctg  65880
tgcttatctg ggctttggat aggccagagg taaacggcag gtgttactgc accaagttca  65940
taaaatcgag cccaaaacaa aggagtcgac acagtaatta gctggtgtgt cgccttggcg  66000
agaatatata tgacttttgc tgagaatttt cattaatgtt tattttctat ttttattttt  66060
tgagatggag tctcgctctg tcgcccaggc cggagtgcag tggtgcaatc tcagctcact  66120
gcaagctcca cctcccgggc tcacgctgtt ctcctgcctc agcctcccga gtagctggga  66180
ctacaggcgc ccgccaccgc gcccggagaa ttttttgtat ttttagtaga gatggggttt  66240
cactgtgttg gccaggatgg tcttgatctc ctgacctcgt gatccacctg ccttggcctc  66300
ccaaagtgct gggattacag gcgtgagcca ccgcgcccgg ccattaatgt ttattttgac  66360
gcaacttcac agttacatta aggcaacaat atggcacaaa gaattccttc gtatcaggca  66420
ttcacattcc ccaaacgctg gcggtctaca ccggcttcat cctggatcag aaccaagtgg  66480
agggactgct gtttctgtgg gctggtttcc tgggggctgc cataaccagt gaccagaaac  66540
cgggtgggta cgtcaacagg aatttatcat ctcccagtct cggatgtcga tgttgaagcc  66600
ctaaccccca ctgcctcaga acgtgagtgt atttggcctc atagtattag aacgaggctg  66660
tcagggtggg ccctaaagca acctgctgtt ctcatgagag gaagtgtgga cacacacaga  66720
agagacgata gggatacttg tgcacagtga aaagacccta tgagcgtaca ccagacggcg  66780
tccgcaagcc gaggagagga gaaaccagcc ctgctgacaa caccttgctc tcggacctca  66840
```

-continued

```
gcctccaggt ctgtgggaag ataattttca gtgaagccct ccagtcttgg taccttatgg  66900
cggccctgaa cactcataca gacgggtaca tttactgtcc ctgttcttct gccgaggaaa  66960
tggaggcaca gagacgttta gtgagcttga cccatgcggg agggccagga gcggtcaagg  67020
ttggattgga acaaaccacc ctttttgcag cactcacgtt cttaggcacg acgcctgctt  67080
ccttaggtgc tctgcaaaga gaatacggca gagtgcaccc cgaacacgca acggtacagt  67140
cacaaagatg acactggctc caagtgtctt cagcaaaatg ggaacgtgtc agaagagtag  67200
gggggtcgct gcgggaacag ggttggccca aggcagccgc cggtcccgag cagcatgcgc  67260
gatgcgggct gggcaggacc ccgtggcccc tccgccgccc tctcagtccg cgcgagggcc  67320
ccactcgggg ctcggccggg ctccgggaac gcggtctgcg gtccaggggc cgcgagcctc  67380
cgccgctcct cggcctcgtg ggcccgggcg ctgggtgggg ccgcgggtgg gcgtcagggg  67440
ccaggctggg cgccgaggtc tgcaaagggg cggagaagac ggccttgggc tccgcgcaga  67500
acctgcgagt gggcggcggt gcacctccca cccgggtcac ctcggtgcca cccatgcctg  67560
cctcagtgca ggcggaccca cggccctcca cgccctccct cgctcgcgtg ctgcccggct  67620
ggccgctgtt cgcatcctct cgctaactcc gtggggtccc gcccattcgg gcgactgccc  67680
cggctgcagc ccacccgcta atctcggcta tcttccctca ctcagttctt cgcctccacc  67740
agcttcggct cttttcgtca cccctcttta ctccccgttc ctctccgtca ctttccgtca  67800
tctccgaata ggctcggccg gctgcatctc accatttcgc tttcctcttt gtcgccctct  67860
gataaatttc gtgactcttc gtcactgtcc gtcagtcccc gtcactttcc gtcaattctc  67920
gccactttcc gtcgctctcc gccgcccttc agctccgctc ggctcttctc cgtcagacat  67980
cgtctacttt cgtcactctc cgtcaccctc cgtcactctc cgtctgctcc ctaccccgca  68040
ctccgggtgg agaaagcctc agggactttt cctgccctta gcccttttcc gtccctctcc  68100
gatcctgctg tctgtcagtc cctggttatt tctggtctgc tcgtgactct gtcctcctcc  68160
cttcactcct gggagggtgg cctggtccct cctgagaggc ctctccccac tacccggcct  68220
gaatgatggt ggtgagcggg aggtctcgag gtgatcccga gggaaggagc gggggtctga  68280
gggtggtccc gagagggacc cgaggggtgg agcgggggga gggtctggag atggccccga  68340
ggaggtcccg ataggaggag cggcagtctg gggggtggtgc cgagggaaga agccgtctgg  68400
tgtggtctgg aaaatgggag caggggggtct ggggtggtcc cgaggggagg agcgggggtc  68460
tggggtggtc ccgaggggag gagcgggggt ctgaggtggt cccgagggga ggagctgggg  68520
gttctgggtg tggtcccgtg ggtaggaggg ggggtctggg gatggtccta agaggaggag  68580
caggggggtct gggggtggtc ccgaggggag gagcgggggt ctggggtggt cccgagggga  68640
ggagcggggg tctggggtgg tcccgagggg aggagcgggg gtctggggtg gtcccgaggg  68700
gaggagctgg gggttctggg tgtggtcccg tgggtaggag ggggggtctg gggatggtcc  68760
taagaggagg agcagggggt ctgggggtgg tcccgagggg aggagcgggg gtctggggtg  68820
gtcccgaggg gaggagcggg ggtctggggt ggtcccgagg ggaggagcgg gggtctgggg  68880
tggtcccgag gggaggagct gggggttctg ggtgtggtcc cgtgggtagg aggggggggtc  68940
tgggtgtggt cccgagggga ggagctgggg gttctgggtg tggtcccgtg ggtaggaggg  69000
ggggtctggg gatggtccta agaggaggag caggggggtct gggggtggtc ccgaggggag  69060
gagcgggggt ctggggtggt cccgagggga ggagcggggg tctggggtgg tcccgagggg  69120
aggagctggg ggttctgggt gtggtcccgt gggtaggagg gggggtctgg gtgtggtccc  69180
gaggggagga gctgggggtt ctgggtgtgg tcccgtgggt aggagggggg gtctggggat  69240
```

```
ggtcctaaga ggaggagcag ggggtctggg ggtggtcccg aggggaggag cgggggtctg  69300
gggtggtccc gaggggagga gcgggggtct gaggtggtcc cgaggggagg agctgggggt  69360
tctgggtgtg gtcccgtggg taggaggggg ggtctgggga tggtcctaag aggaggagca  69420
gggggtctgg gggtggtccc gaggggagga gcgggggtct ggggtggtcc cgaggggagg  69480
agcgggggtc tggggtggtc ccgaggggag gagcaggggg tctgggggtg gtcccgaggg  69540
gaggagcggg ggtctggggt ggtcccgagg ggaggagctg gggttctgg gtgtggtccc  69600
gtgggtagaa ggggggtct ggggatggtc ctaagaggag gagcaggggg tctgggggtg  69660
gtcccgaggg gaggagcggg ggtctggggt ggtcccgagg ggaggagctg gggttctgg  69720
gtgtggtccc gtgggtagga gggggggtc tggggatggc cctaagagga ggagcggggg  69780
tctgcgtgtg gttttcaggg gtggagcatg gggtctccct gtggttcgga gggtggagca  69840
gggggtctgg ggttggtact tttgggcggg acagcgctat ttctcttttt ggtccggttc  69900
ccatctgctg atctgggggt ccttgtgatc ctgacaggtg gggccgaatg ggagggtcaa  69960
ggtgagggga aggaaggagt ggcagcctgg tcccaaggga gcaggaaagg gtttgtggtt  70020
cagttctgat gtgtgaccca tccataggag aatggacacc tcagactctc tcaatcctgg  70080
ccagtggcag gtcccagtag ctgccttccc tggctgtcct tgaggctcac tggaggatac  70140
ttctttttca ttctggcaaa ttttaaaaaa ttcttctata gatctcagtg agttcaaagc  70200
tgcctgtgtg caggcataga tccgttcttt gctgagcttc cactctagtc ggctgaaagg  70260
aaagggtaat atagctggaa aaggtatcct ggggtgatta gaggattcta catttcatct  70320
tagaaaggga tattgacagg agaccagaac ttccagatcc tcttgaattt caagaactac  70380
ttccaagcct ggacaatatc gggaggcctc atctctacaa aataaaaatt aagaaattcg  70440
ccacgtgcga tggcacactc ctgtagtccc acctactctg gaggctgagg cgggaagatc  70500
gcttgagctt gggagtccga ggctgcagtc agctgtgatc atgccactgc actccagcct  70560
gggtgacaga gcaagaccct gaaaaaaaaa aagggaggga gggaaggagg gagggaggga  70620
ggaaggaagg aatgaaggaa ggaaggaaat ggcttaagct cagagagctg tgtgtggccc  70680
ccagctccca acccctacca aagggcctgc aaacccacgg aggggcaggt tgtcttgagc  70740
tggagctacg gggacggggg gacctgaact gtcggggtta gggttagggt taggctttga  70800
gatttcgggt tacagaatat agatgggttt ggtcctggga aaattccagg tctgggtttt  70860
gcagttgggg gttggtctca ggtgagatgc ggcaggttta cagtgtttgc aaggtatgta  70920
cagatttata tggtgctatt gcttgaatgt gttctccaga tttcatgtgt tggcaatttt  70980
ttttcttttc tttttgacat ggtgtcttgc tctgtcatct atcacccagg ctggagtgca  71040
atcgtgggat ctcggctcgc tgcaacctct gcctcccagg ttcgagcgat tctcacacct  71100
cagcctcctg gtagctggca ttgtggcagg acaagccgca gacaaaattc ctcagacact  71160
gggttaaaga aggaagggct ttactctgcc aggagcatcg gcacacttgc gcctgaagag  71220
ccaagctccc cgaaaacgaa attcctagcc cttttaaggg tttacaactc taaggggttt  71280
acgtgaaagg gttgtgatag atcgaggaag cgtggggaac gtgactgggg gctacacgca  71340
tcagataaca gaacagaaag ttttgcaggg cttcctcata cagtgtctgg aatttacaga  71400
taacacaagt agtttaggtc aggggttaat attattatta ttattatttt aaccaccagg  71460
gtcgggtggt gctgccaagg tcatctagct atttatctta cttctgtttt tttttttttt  71520
taagcttttt gctttctccc tttttccctg ttttataaac taaggaagcg gtgtggggaa  71580
```

-continued

```
gggaagggca gcaggaggag tggtggtctc cttccttagg attacaagca ccgggcctca  71640
ttcctggcta acgtttttttg ttttttttt gtatttgtat tagagatggg gtttcaccat  71700
gttggccagg ctggtcttga actcctgacc tcagctgatc gcctgccttg gcctctgaaa  71760
gtgctgggat taaaagcaca aggcagctgg gcgcggtggc tcaggcctgc aatcctagca  71820
ctttgggaga ccgagatggg tggatcacga ggtcaggaga tcgagaccat cctggctaac  71880
atggtgaaac cctgtctcta caaagaaata caaaaaaaaa aaaaaaatta gctgggcgtg  71940
gtggcgggcg cctgtagtcc cagctactca ggaggctgag gcaggagaat ggcgtgaacc  72000
cgggaggcag agcttgcagt gagccgagat agcgccactg cactccagcc tgggcgacag  72060
agcgagactc cgtctcaaaa aaaaaaaaaa aaaaagcaca aggcatcgcg cccagccatg  72120
tgttggcaat ttaatccccg aattcatgtc ctgattggag atatggcctt tgggaggcaa  72180
ttaggattag ataatgttat taggttgggt ccccagtcat gggactcgtg gctttataag  72240
atgaggaaga gagactggag cggacacgca gtcttgccct ctcctccctc gcccgcacac  72300
tcttgctctc ccctccccctg ccatgtgcag ccctccactg ggctgtgatg ctctaggcct  72360
ccccagccac cagaacttgc cctcccctcc tcggccatga gtggacacag actcccgccc  72420
tcccgccatg tgccgccctc cactgggctg ggatgctctg ggccatgtgc tgcctggggt  72480
ccaggggccg ttagtctccg ccgctcctcg gcctcgtggg cccgggcgct gggtggggcc  72540
gcgggtgggc gtcaggggcc aggctgggcg ccgaggtctg caaaggggcg gagaagacgg  72600
ccttgggctc cgcgcagaac ctgcgagtgg gcggcggtgc acctcccgcc cgggtcacct  72660
cggtgccacc catgcctgcc tcagtgcagg cggacccacg gccctccacg ccctccctcg  72720
ctcgcgtgct gcccggctgg ccgctgttcg catcctctcg ctaactccgt ggggtcccgc  72780
ccattcgggc gactgccccg gctgcagccc acccgctaat ctcggctatc ttccctcact  72840
cagttcttcg cctccaccag cttcggctct tttcgtcacc cctctttact cctcgttcct  72900
ctccgtcact ttccgtcatc tccgattagg ctcggccggc tgcatctcac catttcgctt  72960
tcctctttgt cgccctctga taaatttcgt gactcttcgt cactgtccgt cagtccccgt  73020
cactttccgt caattctcgc cactttccgt cactctccgc cgcccttcag ctccgctcgg  73080
ctcttctccg tcagacatcg tctactttcg tcactctccg tcaccctccg tcactctccg  73140
tctgctccct accccgcact ccgggtggag aaagcctcag ggacttttcc tgcccttagc  73200
ccttttctgt ccctctccga tcctgctgtc tgtcagtccc tggttatttc tggtctgctc  73260
gtgactctgt cctcctccct tcactcctgg gagagtggcc tggtccctcc tgagaggcct  73320
ctccccacta cccggcctga atgatggtgg tgagcgggag gtctcgaggt gatcccaagg  73380
gaaggagcgg gggtctgggg gtggcggcga gggggttccg aggggaggag cgagcgtctg  73440
gggatggttc cgagagggac ccgaggggtg taccgggggt agggtctgga ggtggcccga  73500
agggggtccc gacaggagga gcggcagtct gggggtggcg ctgagggaag gagcagtcgc  73560
gtggtccgga ggacaggagc agggagtctg ggggtggttt cgtggggagg agcagggggt  73620
ctgggggtgg tcccgagggg aggagcgggg gatggcgccg agggaaggag ctgtctggtg  73680
tggtccggag gacaggaaca gtggatctgg gggtggtcct gatgggagga gcgggggtct  73740
gggggtggtc ccgaggggaa gcgtgggggt ctgtgggtgg tccttagggg aggagcgggg  73800
gtctgggggt ggtcctgtgg ggaggagcag ggggttctgg gggcggtcct gatgggagga  73860
gcgggggtct gggggtgatc ccgaggggaa gcgtgggggt ctgtgggtgg tccttagggg  73920
aggagcgggg gtctggggat gatcctgagg ggaggagctg gggtctgggg atggcgccga  73980
```

gggaaggagc tgtccggtgt ggtccggagg acaggaacag tggatctggg ggcggtcccg 74040
tggggaggag cagggagtct gggggtggtt ttcagggatg gagcatgggg cctccctgtg 74100
gtccagaggg tggagcaggg agtctggggg tggtacttat gggcgggaca gcactatttc 74160
tctttttggt ccggttccca tctgctgatc tgggggtcct tgtgatcctg acaggtgggg 74220
cagaatggga gggtcaaggt gaggggaagg gatattgaca ggaggtcaga acttcaagat 74280
cctcttgaat ttcaagaact acttccaagc ctggacaata tcgagaggcc tcatctctac 74340
aaaataaaaa ttaagaaatt cgctgggtgc aatggcacac tcctgtagtc ccacctactc 74400
tggaggctga ggagggaaga taacttgagc ctgggagtcc gaggctgcag tcagctgtga 74460
tcatgccact gcactccagc ctgggtgaca gagcaagacc ctgaaaaaaa aaagggaggg 74520
agggaaggag ggagggaggg aggaaggaag ggaagggagg gaggaaggaa ggaatgaagg 74580
aagaaaatgg cttaagctca gagagctgta tgtggccccc agctcccacc cccaccagag 74640
ggcctgcaaa cccacggagg ggcaggttgt cttgagctgg aaccacaggg gcggggggac 74700
ctcaactgta ggggttaggg ttagggttag gctttgaggt ttcgggttac agaatataga 74760
tgggtttggt cctgggaaaa ttccaggttg agttttgtag ttgggggttg gtctcaggtg 74820
agatacggca ggtttacttg ggcctgaaga gccgagctcc ccgaaaacga aattcctggc 74880
ccttttaagg gtttacgact ctaaggggtt cacgtgaaag ggtcgtgata gatcgaggaa 74940
gcatcggaac gtgactgggg gctacacgca tcagataaca gaacagaaag ttttgcaggg 75000
cttcctcata cagtgtctgg aatttacaga taacacaagt agtttaggtc aggggttaat 75060
attattatta ttattatttt aaccaccagt gccgggtggt gctgccaagg tcgtctagct 75120
atttatctta cttctgtttt ttttatcttt ttgctttctc ccttttttccc tgtttcataa 75180
actagagaag ggggtgtggg gaagggaagg gcagcagaag tggcggtctc ctcccttagg 75240
attacaggca ccctgcgtta acctcaaaat tgtctcagtc ccaaagaagg ggctagattt 75300
tcttttatac ttttgtttag aaaggggagt ggcggtctag ttaaaagaat tttacataag 75360
taaatcaggc aaaatgttaa aaggataaat ggttacagga aagtaaacag ttccaggtgc 75420
aggtgcttta agactattac aaggtgatag acgcgggtaa ttgggcgtta tcaatcggac 75480
gaattcctgg ggactgcgga tgtagctcgc cacagtaggt tgtcagttaa ttgcattctc 75540
ggatgtcctg ggagtcagct tgcacgagtt aagtctttga ggaaggggct gccagtgaaa 75600
gagccaagat ggagtctgtc cggttctctc agttaaggga gagtcctttc aggtggaaag 75660
aaggctaggt gattgaagga aagggagagt ctaaaaacag ggttagcaaa aatgaggttg 75720
ggcattacag ttgtaccctc catcgcctct tccaatctca agcaattcca taacttggaa 75780
aacctcaggc aaggacttcc tggaatatgt ccactgtaac gaccaggttt tccagtgtgt 75840
tatctacacc ctgtaacgct gttaggtaca taatgtttca gcaatctttg ttcttcacca 75900
gcactctgag tacatgaaaa aggccaagat gcttcttcag ggatgaattt tgctactttt 75960
taaaggagac ttaagaggca cttttggcac tctaagtctt tcttcaaatg atgaaatttg 76020
ttacctattt aactcattgc tgtgacgcgt tttccaattc tatgttccct tggtttttgt 76080
tgtatttttt tctgcatgaa ctctacatca tttactcact ctgaacgaca gaataaaaga 76140
aattggccac catatcatac tcggaaggac aatcatggcc atgagacaca aaggactccc 76200
agccctgggc ccaggccccc ctcacgcatg cagccatcgc ggcactgtgc ctgagtgggc 76260
catatgcatg gtggggaccc gatgctggga gacacagctc agggcacagg ggccccaaga 76320
agccatagct ggggaaagct cattcccgac agggctcagc tccaacctga aactagagtc 76380
ccaccctggg gtttccatgg tggtggtaaa ccaaccacag attttgggga tatgactgct 76440
ccctttgcca cgatagcttc ttccacgtgc ccctggcctg atgaccagac cactagagag 76500
gggaggcccg agtcccaggg atgggtgggt tgcaggcaga gctggggctg gatggacggt 76560
gagtggtgag agctcaaggt gcagaagggg ctcctgtcgg ggactgggtt aacagggacc 76620
gggacaaata gacggggact cccgagatga gaaagacctt ttcgtacaaa gtgtttgcat 76680
cagtacctca caatgaaaag aataagataa ataacagtac aaaaaagcaa tcaccagatc 76740
agctcaaggc actctttgaa gtcccccctg tgtagggaag ttggaagaca tatctgtgtg 76800
gcccatagag agtagatccc aaagacagaa ggcccaagtc cctaaatccc cacaggggaa 76860
ctgtgttaca gaccaggagc tcatgtacag ggctgtccca gggcccctaa attccagaag 76920
ggaactgggt tagagwccag gggctsatgy aacgggctgt ccctggtccc ctaaatcccc 76980
acaggggaac tgggttagag atgaggagct cattttccgg gctgtccagg tcccctaaat 77040
cccagatggg aactgggtta tcraccaggt gctcttctag ggttgtctcc agggtcctag 77100
tgtgtctgga attggtgggt tcttggtctc actgacttca agaatgaaga cgcggaacct 77160
cgcggtgagt gttacagttc ttaaaggtgg cgcgtccgga gtttgtttct tctgatgttc 77220
agatgtgttc tgagtttctt ctttctggtg gggttgtggt ctcactggct caggagtgaa 77280
gctgcagacc tttgcggtga gtgtcacagc tcataaaggc agtgtggacc caaagagtga 77340
gcartagcaa gatttattgc aaagagtgaa agaacgaagc ttccacagta tggaaaggga 77400
ccccattggg ttgccactgc tggctcaggc agtctgcttt tattctctaa tctgctccca 77460
cccacatcct gctgataggt ccactttcag agggttaggg ttagggttag ggttagggtt 77520
agggttaggg ttagggttag ggttagggtt agggttaggg ttagggttag ggttagggtc 77580
ctttagagtc tgcattaggc ctatgtctca ttgaggacag ttagagagca gactgtgcta 77640
cctttagagt ctgcatttgg cctaggtctc attgagtaca gaaagagacc agagtgtgca 77700
acctttagag tctgcattgg gcctgggtct cattgaggac agatagagag gagactgtag 77760
aacctttata gtctgcattg ggcctaggtc tcattgaggt cagataggga gcagactggg 77820
caagctttag agtctgcact tggcctaggt ctcattgagg acagatagag aacagactgt 77880
gcaaccttta gagtctgcat tgggcctagg tctcattgag ggcagttaga gagcagactg 77940
tgcaaccttt agagtctgca ttgggcctag gtctcattga gagcagatag agagcacact 78000
gtgcaacctc tagagtcggc attgggccta ggtctcattg aggacagata gagaccagac 78060
tgtgcaaact ttagagtctg cattgggcct aggtctcatt gaggacagat acagggcaga 78120
ctgtgcaacc tttagagtct gcattgggcc taggtctcat tgaggtcaga tagagagcag 78180
actgtgcaac ctttagagtc tgcactgggc ctaggtctca ttgagggcag atagagacca 78240
tactgtgcaa cctttagagt ctgcattggg tctaggtctc actgaggaga gatagagagc 78300
agactttgca aactttagag tctgcattag gtctaggtct cactgaggac tgatagagag 78360
cagattatgc aacctttaga gtctgcactg gccctaggtc tcattgagga cagatagaga 78420
gcagactgcg caaactttag agtctgcatt gggcctaggt ctcattgagg acagatagag 78480
agcacactgt gtaaccttta gagtctgcat agggcctcgg tctcattgag gaccgataga 78540
gagcagactg tgccaccttt agagtctgca ttgggcctgg gtctcattga ggagaaatag 78600
agagcagact gtgcaacctt tagagtctgc attgggccta ggtctcattg aggacagatg 78660
gagagcagac tgtgcaacct ttagagtctg cattgggcct aggtctcatt gagggcacat 78720
agagagcaga ctgtgcaacc tttagagtct gcattgggcc taggtctcat tgagagaaga 78780
tagagagcat acagtgcaac ctttagagtc ggcattgggc ctaggtctca ttgagggcac 78840
atagagagca gactgtgcaa cctttagagt ctgcattggg cctaggtctc attgagagaa 78900
gatagagagc atacagtgca acctttagag tcggcattgg gcctaggtct cattgaggac 78960
agatagagac cagactgtga aacctttaga gtctgcattg ggcctaggtc tcattgagga 79020
cagatagaga gcagagtagg caaccattag agtcggcact ggtcctaggt ctcattgagg 79080
acagatatag agcagactgt gcaaccttta gagtctgcat tgggcctggg tctcattgag 79140
gacagataga gagcagactg tgcaaccttt agaggctgca ctgggcctag gtctcattga 79200
ggacagatag agggcagact gtgcaacctt tagagtctgc attgggccta ggtctcattg 79260
aggaccgata gagagcagac tgtgcaacct ttagagtctg cactgggcct aggtctcatt 79320
gagggcagat agagaccata ctgtgcaacc tttagagtct gcattgggcc taggtctcac 79380
tgaggagaga tagagagcac actgtgtaac ctttagagac tgcatagggc ctcggtctca 79440
ttgaggaccg atagagagca gactgtgcca cctttagagt ctgcattggg cctgggtctc 79500
attgaggaca aatagagagc agactgtgca acctttagag tctgcattgg gcctaggtct 79560
cattgaggac agatggagag cagactgtgc aacctataga gtctgcattg ggcctaggtc 79620
tcattgagga cagatggaaa gcagactgtg caacctttag agtctgcatt ggacctaggt 79680
ctcattgagg acagatagag agcagactat gcaaacttta gaggctggac tgagcctagg 79740
tctcattgag gacagataga gagcagactg tgcaaccttt acagtctgca ttgggcctgg 79800
gcctcattca ggacagatag agaccagact gtgcaacctt tagagtctgc attgggccta 79860
ggtctcattg agagtagata gagagcagac tgtgcaacct ttagagtcta cattgggcct 79920
aggtctcatt gagggcagat agagagcaga ctgtgcaacc tttagagtct gcacttggcc 79980
taggtctcat tgaggacaca tagagagcag actgtgcaac ctttagagtc tgcattgggc 80040
ctaggtctca ttgagggcag atagagagca gactgtgcaa actttagagt ttgcattggg 80100
cctaggtctc attgaggaga gatagagagc agactgtgca acctttagag tctgcattgg 80160
gcctaggtct cattgaggac agatggagag cacactgtgc aacctttaga gtccgcattg 80220
ggcctaggtc tcattgagga cagatagaga ccagactgtg caacctttag agtttgcatt 80280
gggcctaggt ctcattgagg gcagatagag agcagactgt gcaaccttta gagtctgcat 80340
tgggcctagg tctcattgag gaccgataga gagcagactg tgcaaccttt agactctgca 80400
ttgggcctgg gtctcattga ggacaaatag agaacagact gtgcaacctt tagagtctgc 80460
attgggccta ggtatcagtg aggacagata gagaggagac tgtgcaacct ttagagtctg 80520
cactgggcct aggtctcttt gaggacagac agagagcaga ctgtgcaaac tttagagtct 80580
gcactgggcc taggtgtcat tgaggacaga tagagaccag actgtgcaac ctttagagtc 80640
tgcattgggc ctaggtctcc ttgaggtcag atagacagca gaatctgcaa cctttagagt 80700
ctgcattggg cctaggtcta attgcggaca gatagacagc agactgtgca acgtttagag 80760
tctgcattgg gcctaggtct aattgcggac agatagagag cagactatgc aacgtttaga 80820
gtctgcattg ggcctgggtc tcattgagga cagatagaga gcagactgtg caacctttag 80880
agtctctatt gggcctaggt ctcattgagg acagataggg agaggactgt gcaaccttta 80940
gagtctgcat tgggcctagg tctcattgag ggcagataga gagcaggctc gggaacccctt 81000
agagtctgca ttgggcctag atctcattga ggacagatag agagcatact atgcaacctt 81060

-continued

```
tagagtctgc actgggccta ggtctcattg aggacacata gagagcagac tgtgcaacct  81120
ttagagtctg cattgggcct atgtctcatt gaggacagtt agagagcagg ctgtgcaacc  81180
tttacagtct gcatttggcc taggtctcat tgaggacaga aagagaccag agtgcgcaaa  81240
ctttagagtc tgcattgggc ctaggtctca ttgaggacag atagagagca gactgtagaa  81300
cctttatagt ctgcattggg cctaggtctc attgaggtca gatagagagc agactgtgca  81360
agctttagag tctgcacttg gcctaggtct cattgaggac agatagagaa cagactgtgc  81420
aacctttaga gtctgcattg ggcctaggtc tcattgaggg cagttagaga gcagactgtg  81480
caacctttag agtctgcatt gggcctaggt ctcattgaga gcagatagag agcacactgt  81540
gcaacctcta gagtcggcat tgggcctagg tctcattgag gacagataga gaccagactg  81600
tgcaaacttt agagtctgca ttgggcctag gtctcattga ggacagatag agggcagact  81660
gtgcaacctt tagagtctgc attgagccta ggtctcattg aggacagata gagagcagac  81720
tgtgcaacct ttcgagtctg cactgggcct aggtctcatt gagggcatat agagaccata  81780
ctgtgcaaac tttagagtct gcattgggtc taggtctcac tgaggagaga tagagagcag  81840
actttgcaaa ctttagagtc tgcattaggt ctaggtctca ctgaggactg atagagagca  81900
gactatgcaa ctttagagtc tgcactggcc ctaggtctca ttgaggacag atagagagca  81960
gactgcgcaa actttagagt ctgcattggg tctaggtctc attgaggaca gatagagagc  82020
acactgtgta acctttagag tctgcataga gcctcggtct cattgaggac cgatagagag  82080
cagactgtgc cacctttaga gtctgcattg ggcctgggtc tcactgagga gaaatagaga  82140
gcagactgtg caacctttag agtctgcatt gggcctaggt ctcattgagg acagatggag  82200
agcagactgt gcaaccttta gagtctgcat tgggcctagg tctcattgag ggcagataga  82260
gagcagactg tgcaaccttt agagtctgca ttgggcctag gtctcattga gagcagatag  82320
agagcatact gtgcaacctt tagagtcggc attgggccta ggtctcattg aggacagata  82380
gagaccagac tgtgcaacct ttagagtctg cattgggcct aggtctcatt gaggacagat  82440
agagagcaga ctatgcaacc attagagtcg acactggtcc taggtctcat tgaggacaga  82500
tatagagcag actgtgcaac ctttagagtc tgcattgtgc ctgggtctca ttgaggacag  82560
atagagagca gactaggcaa ccattagagt cgacactggt cctaggtcta attgaggaca  82620
gatatagtgc agactgtgca acctttagag tctgcattgg gcctgggtct tattgaggac  82680
agatagagac cagactgtgc aacctttaga gtctgcactg ggcctaggtc tcattgagga  82740
cagatagagg gcagactgtg caacctttag agtctgcatt gggcctaggt ctcattgagg  82800
acagatagag agcagactgt gcaaccttta gagtctgcac tgggcctagg tctcattgag  82860
ggcagataga gaccatactg tgcaaccttt agaatctgca ttgggtctag gtctcactga  82920
ggagagatag agagcagact ttgcaaactt tagagtctgc attgggtcta ggtctcactg  82980
aggactgata gagagcagac tatgcaacct ttagagtctg cactggcact aggtctcatt  83040
gaggacagat acagagcaga ctgcgcaaac tttagagtct gcattgggcc taggtctcat  83100
tgaggacaga tagagagcac actgtgtaac ctttagagtc tgcatagggc ctcggtctct  83160
atgaggaccg atagagagca gactgtgcaa cctttagagt ctgcattggg cctgggtctc  83220
attgaggaca aatagagagc agactgtgca acctttagag tctgcattgg gcctaggtct  83280
cattgaggag agatggagag cagactgtgc aacctttaga gtctgcattg ggcctaggtc  83340
tcattgagag cagatagaga gcagagtgtg caacctttag agtctgcatt gggcctaggt  83400
ctcattgagg gcagatagag accagactgt gcaaccttta gagtctgcat tgggcctagg  83460
```

```
tctcattgag gacagataga gggcagactg tgcaaccttt agagtctgca ttgggcctag  83520
gtctcattga ggacagatag agagcagact ttgcaaactt tagagtctgc actgggccta  83580
ggtctcattg agggcatata gagaccatac tgtgcaaact ttagagtctg cattgggtct  83640
aggtctcact gaggagagat agagagcaga ctttgcaaac ttcagagtct gcattaggtc  83700
taggtctcac tgaggactga tagagagcag actatgcaac tttagagtct gcctggccct  83760
aggtctcatt gaggacagat agagagcaga ctgcgcaaac tttagagtct gcattgggcc  83820
taggtctcac tgaggacaga tagagagcac actgtgtaac ctttagagtt tgcatagggc  83880
ctcggtctca ttgaggaccg atagagagca gactgtgcaa cctttagagt ctgcattggg  83940
cctgggtctc attgaggaaa aatagagagc agactgtgca acctttagag tctgcattgg  84000
gcctaggtct cattgagggc agatagagag cagactgtgc aacctttaga gtctgcacta  84060
gggctaggtc tcatcgagga cagatagaga gcagactgtg caacatttag agtctgcatt  84120
ggacctaggt ctcactgagg acagatagag agcagactat gcaaacttta cagtctgcac  84180
tgggcctagg tctcattgag gacagataga gagcagactg tgcaaccttt acagtctgca  84240
ttgggcctgg gtctcattca ggagagatag agaccagaat gtgcaacctt tagagtttgc  84300
attgggccta ggtctcttga gagcagatag agagcagact gtgcaacctt tacagtctgc  84360
attgggccta ggtctcattg agggccgata gagagcagac tgtgcaaact ttagagtctg  84420
cactgggcct aggtctgatt gaggacacat agagagcaga ctgtgcaacc tttagagtct  84480
gcatttggcc taggtctcat tgaggacaga tggagagcac actgtgcaac ctttagagtc  84540
cgcattgggc ctaggtctca ttgaggacag atagagacca gactgtgcaa cctttagagt  84600
ttgcattggg cctaggtctc attgagggca gatagagagc agactgtgca acctttagag  84660
tctgcattgg gcctaggtct cattgaggac cgatagagag cagactgtgc aacctttaga  84720
ctctgcattg ggcctgggtc tcattgagga caaatagaga acagactgtg caacctttag  84780
agtctgcatt gggcctaggt atcagtgagg acagatagag aggagactgt gcaaccttta  84840
gagtctgcac tgggcctagg tctctttgag gacagacaga gagcagactg tgcaaacttt  84900
agagtctgca ctgggcctag gtgtcattga ggacagatag agaccagact gtgcaacctt  84960
tagagtctgc attgggccta ggtctccttg aggtcagata gacagcagaa tctgcaacct  85020
ttagagtctg cattgggcct aggtctaatt gcggacagat agacagcaga ctgtgcaacg  85080
tttagagtct gcattgggcc taggtctaat tgcggacaga tagagagcag actatgcaac  85140
gtttagagtc tgcattgggc ctgggtctca ttgaggacag atagagagca gactgtgcaa  85200
cctttagagt ctctattggg cctaggtctc attgaggaca gatagggaga ggactgtgca  85260
acctttagag tctgcattgg gcctaggtct cattgagggc agatagagag caggctcggg  85320
aacccttaga gtctgcattg ggcctagatc tcattgagga cagatagaga gcatactatg  85380
caacctttag agtctgcact gggcctaggt ctcattgagg acacatagag agcagactgt  85440
gcaaccttta gagtctgcat tgggcctatg tctcattgag gacagttaga gagcaggctg  85500
tgcaaccttt acagtctgca tttggcctag gtctcattga ggacagaaag agaccagagt  85560
gcgcaaactt tagagtctgc attgggccta ggtctcattg aggacagata gagagcagac  85620
tgtagaacct ttatagtctg cattgggcct aggtctcatt gaggtcagat agagagcaga  85680
ctgtgcaagc tttagagtct gcacttggcc taggtctcat tgaggacaga tagagaacag  85740
actgtgcaac ctttagagtc tgcattgggc ctaggtctca ttgagggcag ttagagagca  85800
```

gactgtgcaa cctttagagt ctgcattggg cctaggtctc attgagagca gatagagagc 85860
acactgtgca acctctagag tcggcattgg gcctaggtct cattgaggac agatagagac 85920
cagactgtgc aaactttaga gtctgcattg ggcctaggtc tcattgagga cagatagagg 85980
gcagactgtg caacctttag agtctgcatt gagcctaggt ctcattgagg acagatagag 86040
agcagactgt gcaacctttc gagtctgcac tgggcctagg tctcattgag ggcatataga 86100
gaccatactg tgcaaacttt agagtctgca ttgggtctag gtctcactga ggagagatag 86160
agagcagact ttgcaaactt tagagtctgc attaggtcta ggtctcactg aggactgata 86220
gagagcagac tatgcaactt tagagtctgc actggcccta ggtctcattg aggacagata 86280
gagagcagac tgcgcaaact ttagagtctg cattgggtct aggtctcatt gaggacagat 86340
agagagcaca ctgtgtaacc tttagagtct gcatagagcc tcggtctcat tgaggaccga 86400
tagagagcag actgtgccac ctttagagtc tgcattgggc ctgggtctca ctgaggagaa 86460
atagagagca gactgtgcaa cctttagagt ctgcattggg cctaggtctc attgaggaca 86520
gatggagagc agactgtgca acctttagag tctgcattgg gcctaggtct cattgagggc 86580
agatagagag cagactgtgc aacctttaga gtctgcattg ggcctaggtc tcattgagag 86640
cagatagaga gcatactgtg caacctttag agtcggcatt gggcctaggt ctcattgagg 86700
acagatagag accagactgt gcaaccttta gagtctgcat tgggcctagg tctcattgag 86760
gacagataga gagcagacta tgcaaccatt agagtcgaca ctggtcctag gtctcattga 86820
ggacagatat agagcagact gtgcaacctt tagagtctgc attgtgcctg ggtctcattg 86880
aggacagata gagagcagac taggcaacca ttagagtcga cactggtcct aggtctaatt 86940
gaggacagat atagtgcaga ctgtgcaacc tttagagtct gcattgggcc tgggtcttat 87000
tgaggacaga tagagaccag actgtgcaac ctttagagtc tgcactgggc ctaggtctca 87060
ttgaggacag atagagggca gactgtgcaa cctttagagt ctgcattggg cctaggtctc 87120
attgaggaca gatagagagc agactgtgca acctttagag tctgcactgg gcctaggtct 87180
cattgagggc agatagagac catactgtgc aacctttaga atctgcattg ggtctaggtc 87240
tcactgagga gagatagaga gcagactttg caaactttag agtctgcatt gggtctaggt 87300
ctcactgagg actgatagag agcagactat gcaaccttta gagtctgcac tggcactagg 87360
tctcattgag gacagataca gagcagactg cgcaaacttt agagtctgca ttgggcctag 87420
gtctcattga ggacagatag agagcacact gtgtaacctt tagagtctgc atagggcctc 87480
ggtctctatg aggaccgata gagagcagac tgtgcaacct ttagagtctg cattgggcct 87540
gggtctcatt gaggacaaat agagagcaga ctgtgcaacc tttagagtct gcattgggcc 87600
taggtctcat tgaggagaga tggagagcag actgtgcaac ctttagagtc tgcattgggc 87660
ctaggtctca ttgagagcag atagagagca gagtgtgcaa cctttagagt ctgcattggg 87720
cctaggtctc attgagggca gatagagacc agactgtgca acctttagag tctgcattgg 87780
gcctaggtct cattgagagc agatagagag cagactgtgc aacctttaga gtctgcattg 87840
ggcctaggtc tcattgagga cagatggaga gcacactgtg caacctttag agtccgcatt 87900
gggcctaggt gtcattgagg acagatagag accagactgt gcaaccttta gagtctgcat 87960
tgggcctagg tctccttgag gtcagataga cagcagactc tgcaaccttt agagtctgca 88020
ttgggcctag gtctaattgc ggacagatag acagcagact gtgcaacgtt tagagtctgc 88080
attgggccta ggtctaattg cggacagata gagagcagac tatgcaacgt ttagagtctg 88140
cattgggcct gggtctcatt gaggacagat agagagcaga ctgtgcaacc tttagagtct 88200

-continued

```
ctattgggcc taggtctcat tgaggacaga tagggagcgg actgtgcaac ctttagagtc  88260
tgcattgggc ctaggtctca ttgacggcag acagagagca ggctcggcaa cccttagagt  88320
ctgcattggg cctagatctc attgaggaca gatagagagc atactatgca acctttagag  88380
tctgcactgg gcttagttct cattgaggaa acatagagag cagactgtgc aacctttaga  88440
gtctgcatta ggcctatgtc tcattgagga cagttagaga gcagactgtg ctacctttag  88500
agtctgcatt tggcctaggt ctcattgagt acagaaagag accagagtgt gcaaccttta  88560
gagtctgcat tgggcctggg tctcattgag gacagataga gaggagactg tagaaccttt  88620
atagtctgca ttgggcctag gtctcattga ggtcagatag ggagcagact gggcaagctt  88680
tagagtctgc acttggccta ggtctcattg aggacagata gagaacagac tgtgcaacct  88740
ttagagtctg cattgggcct aggtctcatt gagggcagtt agagagcaga ctgtgcaacc  88800
tttagagtct gcattgggcc taggtctcat tgagagcaga tagagagcac actgtgcaac  88860
ctctagagtc ggcattgggc ctaggtctca ttgaggacag atagagacca gactgtgcaa  88920
actttagagt ctgcattggg cctaggtctc attgaggaca gatggagagc agactgtgca  88980
acctttagag tctgcattgg gcctaggtct cattgagggc acatagagag cagactgtgc  89040
aacctttaga gtctgcattg ggcctaggtc tcattgagag aagatagaga gcatacagtg  89100
caacctttag agtcggcatt gggcctaggt ctcattgagg gcacatagag agcagactgt  89160
gcaaccttta gagtctgcat tgggcctagg tctcattgag agaagataga gagcatacag  89220
tgcaaccttt agagtcggca ttgggcctag gtctcattga ggacagatag agaccagact  89280
gtgaaacctt tagagtctgc attgggccta ggtctcattg aggacagata gagagcagag  89340
taggcaacca ttagagtcgg cactggtcct aggtctcatt gaggacagat atagagcaga  89400
ctgtgcaacc tttagagtct gcattgggcc tgggtctcat tgaggacaga tagagagcag  89460
actgtgcaac ctttagaggc tgcactgggc ctaggtctca ttgaggacag atagagggca  89520
gactgtgcaa cctttagagt ctgcattggg cctaggtctc attgaggacc gatagagagc  89580
agactgtgca acctttagag tctgcactgg gcctaggtct cattgagggc agatagagac  89640
catactgtgc aacctttaga gtctgcattg ggcctaggtc tcactgagga gagatagaga  89700
gcacactgtg taacctttag agactgcata gggcctcggt ctcattgagg accgatagag  89760
agcagactgt gccaccttta gagtctgcat tgggcctggg tctcattgag gacaaataga  89820
gagcagactg tgcaaccttt agagtctgca ttgggcctag gtctcattga ggacagatgg  89880
agagcagact gtgcaaccta tagagtctgc attgggccta ggtctcattg aggacagatg  89940
gaaagcagac tgtgcaacct ttagagtctg cattggacct aggtctcatt gaggacagat  90000
agagagcaga ctatgcaaac tttagaggct ggactgagcc taggtctcat tgaggacaga  90060
tagagagcag actgtgcaac ctttacagtc tgcattgggc ctgggcctca ttcaggacag  90120
atagagacca gactgcgcaa cctttagagt ctgcattggg cctaggtctc attgagagta  90180
gatagagagc agactgtgca acctttagag tctacattgg gcctaggtct cattgagggc  90240
agatggagag cagactgtgc aacctttaga gtctgcactt ggcctaggtc tcattgagga  90300
cacatagaga gcagactgtg caacctttag agtctgcatt gggcctaggt ctcattgagg  90360
gcagatagag agcagactgt gcaaacttta gagtttgcat tggcctagg tctcattgag  90420
gagagataga gagcagactg tgcaaccttt agagtctgca ttgggcctag gtctcattga  90480
ggacagatgg agagcacact gtgcaacctt tagagtccgc attgggccta ggtctcattg  90540
```

-continued

```
aggacagata gagaccagac tgtgcaacct ttagtgtttg cattgggcct aggtctcatt  90600
gagggcagat agagagcaga atgtgcaacc cttagagtct gcattgggcc taggtctcat  90660
tgaggacaga tagagagcag actgtgcaac ctttagagtc tgcactgggc ctaggtctct  90720
ttgaggacag acagagagca gactgtgcaa actttagagt ctgcactggg cctaggtctc  90780
attgaggaca catagagagc agactgtgca acctttagag tctgcattgg gcctatgtct  90840
cattgaggac agttagagag cagactgtgc aaactttaga gtctgcattt ggcctacgtc  90900
tcattgagga caaaaagaga ccagagtgtg caacctttag agtcggcatt gggactcggt  90960
ctcattgagg acagatagag agcagactgt agaaccttca tagtctgcat tgggcctagg  91020
tctcattgag gtcagataga gagcagactg tgcaagcttt agagtctgca cttggcctag  91080
gtctcattga ggacagatag agagcagact gtgcaaactt tagagtctgc attgggccta  91140
ggtctcattg agggcagata gagaccagac tatgcaacgt ttagagtctg cattgggcct  91200
aggtgtcatt gagggcagtt agagagcaga ctgtgcaacc tttagaatct gcattgggcc  91260
taggtctcat tgagagcaga tagagagcac actgtgcaaa ctttagagtc ggcattgggc  91320
ctaggtctca ttgaggacag atagagaccg gactgtgcaa cctttagagt ctgcattggg  91380
cctaggtctc attgaggaca gatagagagc acactaggca accattagag tccgcactgg  91440
tcctaggtct cattgaggac agatatagag cagactgtgc aacctttaga gtctgcattg  91500
ggcctgggtc tcattgagga cagatagcga ccagactgta caacctttag agtctgcatt  91560
gggcttaggt ctcattgagg gcagttagag agcagactgt gcaaccttta gagtctgcat  91620
tgggcctagg tctcattgag agcagataga gagcacactg tgcaacctct agagtcggca  91680
ttgggcctag gtctcattga ggacagatag agaccagact gttgaaactt tagaggctgc  91740
attgggccta ggtctcattg aggacagata gagggcagac tgtgcaacct ttagagtctg  91800
caatggacct aggtctcatt gaggacagat acggagcaga ctgtgcaaac tttaaagtct  91860
gcactgagcc taggtctcat tgagggcaga tagagaccag actgtgcaac ctttagagtc  91920
tgcattgggt ctaggtctca ctgaggcgag atagagagca gactttgcaa actttagagt  91980
ctccattggg tctaggtctc actgaggact gataggagca gactatgcaa cctttagagt  92040
ctgcactggc cctaggtctc attgaggaca gatagagagc agactgcgca aactttagag  92100
tctgcattgg gcctaggtct cactgaggac agatagagag cacactgtgt aacctttaga  92160
gtctgcatag agcctcggtc tcattgagga cagatagaga gcagactgtg caacctttag  92220
agtctctatt gggcctagat ctcattgagg acagataggg agcggactgt gcaaccttta  92280
gagtctgcat tgggcctagg tctcattgag ggcagataga gagcaggctc ggcaaccctt  92340
agagtctgca ttgggcctag atcttattga ggacagatag agagcatact atgcaacctt  92400
gagagtctgc actgggccta ggtctcattg aggacacata gagagcagac tgtgcaacct  92460
ttagagtctg cattgggcct atgtctcatt gaggacagtt agagagcaga ctgtgcaacc  92520
tttagagtct gcatttggcc taggtctcat tgaggacaga aagagaccag agtgtgcaac  92580
ctttagagtt tgcattgggc ctaggtctca ttgaggacag atagagagca gactgtagaa  92640
cctttatagt ctgcattggg cctaggtctc attgaggtca gatagagagc agactgtgca  92700
agctttagag tctacacttg gcctaggtct cattgaggac agatagagaa cagactgtgc  92760
aaactttaga gtctgcattg ggcctaggtc tcattgaggg cagttagaga gcagactgtg  92820
caacctttag agtctgcatt gggcctaggt ctcattgaga gcagatagag agcacactgt  92880
gcaacctcta gagtcggcat tgggcctagg tctcattgag gacagataga gaccagactg  92940
```

-continued

```
tgcaaacttt agagtctgca ttgggcctag gtctcattga ggacagatag agggcagact  93000
gtgcaacgtt tagagtctgc attgggccta ggtctcattg aggacagata gagagcagac  93060
tgtgaaacct ttagagtctg cactgggcct aggtctcatt gagggcagat agagaccata  93120
ctgtgcaacc tttagagtct gcattgggtc taggtctcac tgaggagaga tagagagcag  93180
actttgcaaa ctttagagtc tacattaggt ctacgtctca ctgaggactg atagagagca  93240
gactatgcaa cctttagagt ctgcactggc cctaggtctc attgaggaca catagagagc  93300
agactgcgca aactttagag tttgcattgg gcctaggtct cactgaggac agatagagag  93360
cacactgtgt aacctttaga gtctgcgtag ggcctcggtc tcattgagga ccgatagaga  93420
gcagactgtg ccacctttag agtctgcatt gggcctgggt ctcatggagg agaaatagag  93480
agcagactgt gcaaccttta gagtctgcat tgggcctagg tctcattgag gacagatgga  93540
gagcagactg tgcaaccttt agagtctgca ttgggtctat gtctcattga gggcagatag  93600
agaccagact gtgcaacctt tagagtttgc attgggccta ggtctcattg agggcagata  93660
gagagcagac tgtgccacct ttagagtcta cattgggcct aggtctcatt gaggacagat  93720
agagagcaga ctgtgcaacc tttatagtct gcactgggcc taggtctctt tgaggacaga  93780
cagagagcag actgtgcaaa ctttagagtc tgcactgggc ctaggtgtca ttgaggacag  93840
atagagacca gactgtgcaa cctttagagt ctgcattggg cctaggtctc cttgaggtca  93900
gataggcagc agactgtgca acctttagag tctgcattgg gtctaggtct aattgcggac  93960
agatggagag cagactatgc aaagtttaca gtctgcattg ggcctgggtc tcattgagga  94020
cagatagaga gcagactgtg caacctttag agtctctatt gggcctaggt ctcattgagg  94080
acagatagag agcagactgt gcaaccttta gagtctgcat tgggcctagg tctcattgag  94140
ggcagataga gagcaggctc ggcaaccctt agagtctgcg ttgggcttag atctcattga  94200
ggacagatag agagcatact atgcaacctt tagagtctgc actgggccta ggtctcattg  94260
aggacacata gagagcagac tgtggaacct ttagagtctg cattgggcct atgtctcaat  94320
gaggacagtt agagagcaga ctgtgcaacc tttagagtct gcattgggcc taggtctcat  94380
tgaggacaga tagagagcag actgtagaac ctttatagtc tgcattgggc ctaggtctca  94440
ttgaggtcag atagagagca gactgtgcaa gctttagagt ctgcacttgg cctaggtctc  94500
attgaggaca gatagagagc agactgtgca acctttagag tctgcattgg gcctaggtct  94560
tattgagggc agatagagac cagactatgc aacgtttaga gtctgcattg ggcctaggtg  94620
tcattgaggg cagttagaga gcagactgtg ctacctttag agtctgcatt aggcctaggt  94680
ctcattgaga gcagatagag agcacactgt gcaaacttta gagtcggcat tgggcctagg  94740
tctcattgag gacagataga gaccggactg tgcaaccttt agagtctgca ttgggcctag  94800
gtctcattga ggacagataa agagcagact aggcaaccat tagagtcggc actggtccta  94860
agtctcattg aggacagata tagaggagac tgtgtaacct ttagagtctg cattgggcct  94920
gggtctcatt gaggacagat agagaacaga ctgtgcaacc tttagagtct gcattgggtc  94980
taggtctcat tgagggcagt tagagagcag actgtgccac ctttagagtc tgcattgggc  95040
ctaggtctca tcgacagcag atagagagca cactgtgcaa cctctagagt cggcattggg  95100
cctaggtctc attgaggaca gatagagacc agactgttaa aactttagag tctgcattgg  95160
gcctaggtct aattgaggac agatagaggg cagactgtgc aacctttaga gtctgcattg  95220
ggcctaggtc tcattgaggg cagatagaga gcaggctcgg gaacccttag agtctgcatt  95280
```

-continued

```
gggcctagat ctcattgagg acagatagag agcatactat gcaaccttta gagtctgcat  95340
tgggcctagg tctcattgag agcacataga gagcagactg tgcaaccttt agagtctgca  95400
ttgggcctat gtctcattga ggacagttag agagcaggct gtgcaacctt tacagtctgc  95460
atttggccta ggtctcattg aggacagaaa gagaccagag tgcgcaaact ttagagtctg  95520
cattgggcct aggtctcatt gaggacagat agagagcaga ctgtagaacc tttatagtct  95580
gcattgggcc taggtctcat tgaggtcaga tagagagcag actgtgcaag ctttagagtc  95640
tgcacttggc ctaggtctca ttgaggacag atagagaaca gactgtgcaa cctttagagt  95700
ctgcattggg cctaggtctc attgagggca gttagagagc agactgtgca acctttagag  95760
tctgcattgg gcctaggtct cattgagagc agatagagag cacactgtgc aacctctaga  95820
gtcggcattg ggcctaggtc tcattgagga cagatagaga ccagactgtg caaactttag  95880
agtctgcatt gggcctaggt ctcattgagg acagatagag ggcagactgt gcaaccttta  95940
gagtctgcat tgagcctagg tctcattgag gacagataga gagcagactg tgcaaccttt  96000
cgagtctgca ctgggcctag gtctcattga gggcatatag agaccatact gtgcaaactt  96060
tagagtctgc attgggtcta ggtctcactg aggagagata gagagcagac tttgcaaact  96120
ttagagtctg cattaggtct aggtctcact gaggactgat agagagcaga ctatgcaact  96180
ttagagtctg cactggccct aggtctcatt gaggacagat agagagcaga ctgcgcaaac  96240
tttagagtct gcattgggtc taggtctcat tgaggacaga tagagagcac actgtgtaac  96300
ctttagagtc tgcatagagc ctcggtctca ttgaggaccg atagagagca gactgtgcca  96360
cctttagagt ctgcattggg cctgggtctc actgaggaga aatagagagc agactgtgca  96420
acctttagag tctgcattgg gcctaggtct cattgaggac agatggagag cagactgtgc  96480
aacctttaga gtctgcattg ggcctaggtc tcattgaggg cagatagaga gcagactgtg  96540
caacctttag agtctgcatt gggcctaggt ctcattgaga gcagatagag agcatactgt  96600
gcaaccttta gagtcggcat tgggcctagg tctcattgag gacagataga gaccagactg  96660
tgcaaccttt agagtctgca ttgggcctag gtctcattga ggacagatag agagcagact  96720
atgcaaccat tagagtcgac actggtccta ggtctcattg aggacagata tagagcagac  96780
tgtgcaacct ttagagtctg cattgtgcat gggtctcatt gaggacagat agagagcaga  96840
ctaggcaacc attagagtcg acactggtcc taggtctaat tgaggacaga tatagtgcag  96900
actgtgcaac ctttagagtc tgcattgggc ctgggtctca ttgaggacag atagagacca  96960
gactgtgcaa cctttagagt ctgcactggg cctaggtctc attgaggaca gatagagggc  97020
agactgtgca acctttagag tctgcattgg gcctaggtct cattgaggac agatagagag  97080
cagactgtgc aacctttaga gtctgcactg ggcctaggtc tcattgaggg cagatagaga  97140
ccatactgtg caacctttag aatctgcatt gggtctaggt ctcactgagg agagatagag  97200
agcagacttt gcaaacttta gagtctgcat tgggtctagg tctcactgag gactgataga  97260
gagcagacta tgcaaccttt agagtctgca ctggcactag gtctcattga ggacagatac  97320
agagcagact gcgcaaactt tagagtctgc attgggccta ggtctcattg aggacagata  97380
gagagcacac tgtgtaacct ttagagtctg catagggcct cggtctctat gaggaccgat  97440
agagagcaga ctgtgcaacc tttagagtct gcattgggcc tgggtctcat tgaggacaaa  97500
tagagagcag actgtgcaac ctttagagtc tgcattgggc ctaggtctca ttgaggagag  97560
atggagagca gactgtgcaa cctttagagt ctgcattggg cctaggtctc attgagagca  97620
gatagagagc agagtgtgca acctttagag tctgcattgg gcctaggtct cattgagggc  97680
```

```
agatagagac cagactgtgc aacctttaga gtctgcattg ggcctaggtc tcattgagag  97740
cagatagaga gcagactgtg caacctttag agtctgcatt gagcctaggt ctcattgagg  97800
agagatagag agcagactgt gcaaccttta gagtctgcat tgggcctagg tctcattgag  97860
gacagatgga gagcacactg tgcaaccttt agagtccgca ttgggcctag gtgtcattga  97920
ggacagatag agaccagact gtgcaacctt tagagtctgc attgggccta ggtctccttg  97980
aggtcagata gacagcagac tctgcaacct ttagagtctg cattgggcct aggtctaatt  98040
gcggacagat agacagcaga ctgtgcaacg tttagagtct gcattgggcc taggtctaat  98100
tgcggacaga tagagagcag actatgcaac gtttagagtc tgcattgggc ctgggtctca  98160
ttgaggacag atagagagca gactgtgcaa cctttagagt ctctattggg cctaggtctc  98220
attgaggaca gatagggagc ggactgtgca acctttagag tctgcattgg gcctaggtct  98280
cattgacggc agacagagag caggctcggc aacccttaga gtctgcattg ggcctagatc  98340
tcattgagga cagatagaga gcatactatg caacctttag agtctgcact gggcttagtt  98400
ctcattgagg aaacatagag agcagactgt gcaaccttta gagtctgcat taggcctatg  98460
tctcattgag gacagttaga gagcagactg tgctaccttt agagtctgca tttggcctag  98520
gtctcattga gtacagaaag agaccagagt gtgcaacctt tagagtctgc attgggcctg  98580
ggtctcattg aggacagata gagaggagac tgtagaacct ttatagtctg cattgggcct  98640
aggtctcatt gaggtcagat agggagcaga ctgggcaagc tttagagtct gcacttggcc  98700
taggtctcat tgaggacaga tagagaacag actgtgcaac ctttagagtc tgcattcggc  98760
ctaggtctca ttgagggcag ttagagagca gactgtgcaa cctttagagt ctgcattggg  98820
cctaggtctc attgagagca gatagagagc acactgtgca acctctagag tcggcattgg  98880
gcctaggtct cattgaggac agatagagac cagactgtgc aaactttaga gtctgcattg  98940
ggcctaggtc tcattgagga cagatacagg gcagactgtg caacctttag agtctgcatt  99000
gggcctaggt ctcattgagg tcagatagag agcagactgt gcaaccttta gagtctgcac  99060
tgggcctagg tctcattgag ggcagataga gaccatactg tgcaaccttt agagtctgca  99120
ttgggtctag gtctcactga ggagagatag agagcagact ttgcaaactt tagagtctgc  99180
attaggtcta ggtctcactg aggactgata gagagcagat tatgcaacct ttagagtctg  99240
cactggccct aggtctcatt gaggacagat agagagcaga ctgcgcaaac tttagagtct  99300
gcattgggcc taggtctcat tgaggacaga tagagagcac actgtgtaac ctttagagtc  99360
tgcatagggc ctcggtctca ttgaggaccg atagagagca gactgtgcca cctttagagt  99420
ctgcattggg cctgggtctc attgaggaga aatagagagc agactgtgca acctttagag  99480
tctgcattgg gcctaggtct cattgaggac agatggagag cagactgtgc aacctttaga  99540
gtctgcattg ggcctaggtc tcattgaggg cacatagaga gcagactgtg caacctttag  99600
agtctgcatt gggcctaggt ctcattgaga gaagatagag agcatacagt gcaaccttta  99660
gagtcggcat tgggcctagg tctcattgag gacagataga gaccagactg tgaaaccttt  99720
agagtctgca ttgggcctag gtctcattga ggacagatag agagcagagt aggcaaccat  99780
tagagtcggc actggtccta ggtctcattg aggacagata tagagcagac tgtgcaacct  99840
ttagagtctg cattgggcct gggtctcatt gaggacagat agagagcaga ctgtgcaacc  99900
tttagaggct gcactgggcc taggtctcat tgaggacaga tagagggcag actgtgcaac  99960
ctttagagtc tgcattgggc ctaggtctca ttgaggaccg atagagagca gactgtgcaa 100020
```

-continued cctttagagt ctgcactggg cctaggtctc attgagggca gatagagacc atactgtgca 100080
acctttagag tctgcattgg gcctaggtct cactgaggag agatagagag cacactgtgt 100140
aacctttaga gactgcatag ggcctcggtc tcattgagga ccgatagaga gcagactgtg 100200
ccacctttag agtctgcatt gggcctgggt ctcattgagg acaaatagag agcagactgt 100260
gcaaccttta gagtctgcat tgggcctagg tctcattgag gacagatgga gagcagactg 100320
tgcaacctat agagtctgca ttgggcctag gtctcattga ggacagatgg aaagcagact 100380
gtgcaacctt tagagtctgc attggaccta ggtctcattg aggacagata gagagcagac 100440
tatgcaaact ttagaggctg gactgagcct aggtctcatt gaggacagat agagagcaga 100500
ctgtgcaacc tttacagtct gcattgggcc tgggcctcat tcaggacaga tagagaccag 100560
actgcgcaac ctttagagtc tgcattgggc ctaggtctca ttgagagtag atagagagca 100620
gactgtgcaa cctttagagt ctacattggg cctaggtctc attgagggca gatagagagc 100680
agactgtgca acctttagag tctgcacttg gcctaggtct cattgaggac acatagagag 100740
cagactgtgc aacctttaga gtctgcattg ggcctaggtc tcgttgaggg cagatagaga 100800
gcagactgtg caaactttag agtttgcatt gggcctaggt ctcattgagg agagatagag 100860
agcagactgt gcaaccttta gagtctgcat tgggcctagg tctcattgag gacagatgga 100920
gagcacactg tgcaaccttt agagtccgca ttgggcctag gtctcattga ggacagatag 100980
agaccagact gtgcaacctt tagtgtttgc attgggccta ggtctcattg agggcagata 101040
gagagcagaa tgtgcaaccc ttagagtctg cattgggcct aggtctcatt gaggacagat 101100
agagagcaga ctgtgcaacc tttagagtct gcactgggcc taggtctctt tgaggacaga 101160
cagagagcag actgtgcaaa ctttagagtc tgcactgggc ctaggtctca ttgaggacag 101220
atatagagga gactgtgtaa cctttagagt ctgcattggg cctgggtctc attgaggaca 101280
gatagagaac agactgtgca acctttagag tctgcattgg gtctaggtct cattgagggc 101340
agttagagag cagactgtgc cacctttaga gtctgcattg ggcctaggtc tcatcgacag 101400
cagatagaga gcacactgtg caacctctag agtcggcatt gggcctaggt ctcattgagg 101460
acagatagag accagactgt taaaacttta gagtctgcat tgggcctagg tctaattgag 101520
gacagataga gggcagactg tgcaaccttt agagtctgca ttgggcctag gtctcattga 101580
gggcagatag agagcaggct cgggaaccct tagagtctgc attgggccta gatctcattg 101640
aggacagata gagagcatac tatgcaacct ttagagtctg cattgggcct aggtctcatt 101700
gagagcacat agagagcaga ctgtgcaacc tttagagtct gcattgggcc tatgtctcat 101760
tgaggacagt tagagagcag gctgtgcaac ctttacagtc tgcatttggc ctaggtctca 101820
ttgaggacag aaagagacca gagtgcgcaa actttagagt ctgcattggg cctaggtctc 101880
attgaggaca gatagagagc agactgtaga acctttatag tctgcattgg gcctaggtct 101940
cattgaggtc agatagagag cagactgtgc aagctttaga gtctgcactt ggcctaggtc 102000
tcattgagga cagatagaga acagactgtg caacctttag agtctgcatt gggcctaggt 102060
ctcattgagg gcagttagag agcagactgt gcaaccttta gagtctgcat tgggcctagg 102120
tctcattgag agcagataga gagcacactg tgcaacctct agagtcggca ttgggcctag 102180
gtctcattga ggacagatag agaccagact gtgcaaactt tagagtctgc attgggccta 102240
ggtctcattg aggacagata gagggcagac tgtgcaacct ttagagtctg cattgagcct 102300
aggtctcatt gaggacagat agagagcaga ctgtgcaacc tttcgagtct gcactgggcc 102360
taggtctcat tgagggcata tagagaccat actgtgcaaa ctttagagtc tgcattgggt 102420

-continued ctaggtctca ctgaggagag atagagagca gactttgcaa actttagagt ctgcattagg 102480
tctaggtctc actgaggact gatagagagc agactatgca actttagagt ctgcactggc 102540
cctaggtctc attgaggaca gatagagagc agactgcgca aactttagag tctgcattgg 102600
gtctaggtct cattgaggac agatagagag cacactgtgt aacctttaga gtctgcatag 102660
agcctcggtc tcattgagga ccgatagaga gcagactgtg ccacctttag agtctgcatt 102720
gggcctgggt ctcactgagg agaaatagag agcagactgt gcaaccttta gagtctgcat 102780
tgggcctagg tctcattgag gacagatgga gagcagactg tgcaaccttt agagtctgca 102840
ttgggcctag gtctcattga gggcagatag agagcagact gtgcaacctt tagagtctgc 102900
attgggccta ggtctcattg agagcagata gagagcatac tgtgcaacct ttagagtcgg 102960
cattgggcct aggtctcatt gaggacagat agagaccaga ctgtgcaacc tttagagtct 103020
gcattgggcc taggtctcat tgaggacaga tagagagcag actatgcaac cattagagtc 103080
gacactggtc ctaggtctca ttgaggacag atatagagca gactgtgcaa cctttagagt 103140
ctgcattgtg catgggtctc attgaggaca gatagagagc agactaggca accattagag 103200
tcgacactgg tcctaggtct aattgaggac agatatagtg cagactgtgc aacctttaga 103260
gtctgcattg ggcctgggtc tcattgagga cagatagaga ccagactgtg caacctttag 103320
agtctgcact gggcctaggt ctcattgagg acagatagag ggcagactgt gcaaccttta 103380
gagtctgcat tgggcctagg tctcattgag gacagataga gagcagactg tgcaaccttt 103440
agagtctgca ctgggcctag gtctcattga gggcagatag agaccatact gtgcaacctt 103500
tagaatctgc attgggtcta ggtctcactg aggagagata gagagcagac tttgcaaact 103560
ttagagtctg cattgggtct aggtctcact gaggactgat agagagcaga ctatgcaacc 103620
tttagagtct gcactggcac taggtctcat tgaggacaga tacagagcag actgcgcaaa 103680
ctttagagtc tgcattgggc ctaggtctca ttgaggacag atagagagca cactgtgtaa 103740
cctttagagt ctgcataggg cctcggtctc tatgaggacc gatagagagc agactgtgca 103800
acctttagag tctgcattgg gcctgggtct cattgaggac aaatagagag cagactgtgc 103860
aacctttaga gtctgcattg ggcctaggtc tcattgagga gagatggaga gcagactgtg 103920
caacctttag agtctgcatt gggcctaggt ctcattgaga gcagatagag agcagagtgt 103980
gcaaccttta gagtctgcat tgggcctagg tctcattgag ggcagataga gaccagactg 104040
tgcaaccttt agagtctgca ttgggcctag gtctcattga gagcagatag agagcagact 104100
gtgcaacctt tagagtctgc attgagccta ggtctcattg aggagagata gagagcagac 104160
tgtgcaacct ttagagtctg cattgggcct aggtctcatt gaggacagat ggagagcaca 104220
ctgtgcaacc tttagagtcc gcattgggcc taggtgtcat tgaggacaga tagagaccag 104280
actgtgcaac ctttagagtc tgcattgggc ctaggtctcc ttgaggtcag atagacagca 104340
gactctgcaa cctttagagt ctgcattggg cctaggtcta attgcggaca gatagacagc 104400
agactgtgca acgtttagag tctgcattgg gcctaggtct aattgcggac agatagagag 104460
cagactatgc aacgtttaga gtctgcattg ggcctgggtc tcattgagga cagatagaga 104520
gcagactgtg caacctttag agtctctatt gggcctaggt ctcattgagg acagataggg 104580
agcggactgt gcaaccttta gagtctgcat tgggcctagg tctcattgac ggcagacaga 104640
gagcaggctc ggcaaccctt agagtctgca ttgggcctag atctcattga ggacagatag 104700
agagcatact atgcaacctt tagagtctgc actgggctta gttctcattg aggaaacata 104760

-continued gagagcagac tgtgcaacct ttagagtctg cattaggcct atgtctcatt gaggacagtt 104820
agagagcaga ctgtgctacc tttagagtct gcatttggcc taggtctcat tgagtacaga 104880
aagagaccag agtgtgcaac ctttagagtc tgcattgggc ctgggtctca ttgaggacag 104940
atagagagga gactgtagaa cctttatagt ctgcattggg cctaggtctc attgaggtca 105000
gatagggagc agactgggca agctttagag tctgcacttg gcctaggtct cattgaggac 105060
agatagagaa cagactgtgc aacctttaga gtctgcattc ggcctaggtc tcattgaggg 105120
cagttagaga gcagactgtg caacctttag agtctgcatt gggcctaggt ctcattgaga 105180
gcagatagag agcacactgt gcaacctcta gagtcggcat tgggcctagg tctcattgag 105240
gacagataga gaccagactg tgcaaacttt agagtctgca ttgggcctag gtctcattga 105300
ggacagatac agggcagact gtgcaacctt tagagtctgc attgggccta ggtctcattg 105360
aggtcagata gagagcagac tgtgcaacct ttagagtctg cactgggcct aggtctcatt 105420
gagggcagat agagaccata ctgtgcaacc tttagagtct gcattgggtc taggtctcac 105480
tgaggagaga tagagagcag actttgcaaa ctttagagtc tgcattaggt ctaggtctca 105540
ctgaggactg atagagagca gattatgcaa cctttagagt ctgcactggc cctaggtctc 105600
attgaggaca gatagagagc agactgcgca aactttagag tctgcattgg gcctaggtct 105660
cattgaggac agatagagag cacactgtgt aacctttaga gtctgcatag ggcctcggtc 105720
tcattgagga ccgatagaga gcagactgtg ccacctttag agtctgcatt gggcctgggt 105780
ctcattgagg agaaatagag agcagactgt gcaaccttta gagtctgcat tgggcctagg 105840
tctcattgag gacagatgga gagcagactg tgcaaccttt agagtctgca ttgggcctag 105900
gtctcattga gggcacatag agagcagact gtgcaacctt tagagtctgc attgggccta 105960
ggtctcattg agagaagata gagagcatac agtgcaacct ttagagtcgg cattgggcct 106020
aggtctcatt gaggacagat agagaccaga ctgtgaaacc tttagagtct gcattgggcc 106080
taggtctcat tgaggacaga tagagagcag agtaggcaac cattagagtc ggcactggtc 106140
ctaggtctca ttgaggacag atatagagca gactgtgcaa cctttagagt ctgcattggg 106200
cctgggtctc attgaggaca gatagagagc agactgtgca acctttagag gctgcactgg 106260
gcctaggtct cattgaggac agatagaggg cagactgtgc aacctttaga gtctgcattg 106320
ggcctaggtc tcattgagga ccgatagaga gcagactgtg caacctttag agtctgcact 106380
gggcctaggt ctcattgagg gcagatagag accatactgt gcaaccttta gagtctgcat 106440
tgggcctagg tctcactgag gagagataga gagcacactg tgtaaccttt agagactgca 106500
tagggcctcg gtctcattga ggaccgatag agagcagact gtgccacctt tagagtctgc 106560
attgggcctg ggtctcattg aggacaaata gagagcagac tgtgcaacct ttagagtctg 106620
cattgggcct aggtctcatt gaggacagat ggagagcaga ctgtgcaacc tatagagtct 106680
gcattgggcc taggtctcat tgaggacaga tggaaagcag actgtgcaac ctttagagtc 106740
tgcattggac ctaggtctca ttgaggacag atagagagca gactatgcaa actttagagg 106800
ctggactgag cctaggtctc attgaggaca gatagagagc agactgtgca acctttacag 106860
tctgcattgg gcctgggcct cattcaggac agatagagac cagactgcgc aacctttaga 106920
gtctgcattg ggcctaggtc tcattgagag tagatagaga gcagactgtg caacctttag 106980
agtctacatt gggcctaggt ctcattgagg gcagatagag agcagactgt gcaaccttta 107040
gagtctgcac ttggcctagg tctcattgag gacacataga gagcagactg tgcaaccttt 107100
agagtctgca ttgggcctag gtctcgttga gggcagatag agagcagact gtgcaaactt 107160

-continued tagagtttgc attgggccta ggtctcattg aggagagata gagagcagac tgtgcaacct 107220
ttagagtctg cattgggcct aggtctcatt gaggacagat ggagagcaca ctgtgcaacc 107280
tttagagtcc gcattgggcc taggtctcat tgaggacaga tagagaccag actgtgcaac 107340
ctttagtgtt tgcattgggc ctaggtctca ttgagggcag atagagagca gaatgtgcaa 107400
cccttagagt ctgcattggg cctaggtctc attgaggaca gatagagagc agactgtgca 107460
acctttagag tctgcactgg gcctaggtct ctttgaggac agacagagag cagactgtgc 107520
aaactttaga gtctgcactg ggcctaggtc tcattgagga cacatagaga gcagactgtg 107580
caacctttag agtctgcatt gggcctatgt ctcattgagg acagttagag agcagactgt 107640
gcaaacttta gagtctgcat ttggcctacg tctcattgag gacaaaaaga gaccagagtg 107700
tgcaaccttt agagtcggca ttgggactcg gtctcattga ggacagatag agagcagact 107760
gtagaacctt catagtctgc attgggccta ggtctcattg aggtcagata gagagcagac 107820
tgtgcaagct ttagagtctg cacttggcct aggtctcatt gaggacagat agagagcaga 107880
ctgtgcaaac tttagagtct gcattgggcc taggtctcat tgagggcaga tagagaccag 107940
actatgcaac gtttagagtc tgcattgggc ctaggtgtca ttgagggcag ttagagagca 108000
gactgtgcaa cctttagaat ctgcattggg cctaggtctc attgagagca gatagagagc 108060
acactgtgca aactttagag tcggcattgg gcctaggtct cattgaggac agatagagac 108120
cggactgtgc aacctttaga gtctgcattg ggcctaggtc tcattgagga cagatagaga 108180
gcacactagg caaccattag agtccgcact ggtcctaggt ctcattgagg acagatatag 108240
agcagactgt gcaaccttta gagtctgcat tgggcctggg tctcattgag gacagatagc 108300
gaccagactg tacaaccttt agagtctgca ttgggcttag gtctcattga gggcagttag 108360
agagcagact gtgcaacctt tagagtctgc attgggccta ggtctcattg agagcagata 108420
gagagcacac tgtgcaacct ctagagtcgg cattgggcct aggtctcatt gaggacagat 108480
agagaccaga ctgttgaaac tttagaggct gcattgggcc taggtctcat tgaggacaga 108540
tagagggcag actgtgcaac ctttagagtc tgcaatggac ctaggtctca ttgaggacag 108600
atacggagca gactgtgcaa actttaaagt ctgcactgag cctaggtctc attgagggca 108660
gatagagacc agactgtgca acctttagag tctgcattgg gtctaggtct cactgaggcg 108720
agatagagag cagactttgc aaactttaga gtctccattg ggtctaggtc tcactgagga 108780
ctgataggag cagactatgc aacctttaga gtctgcactg gccctaggtc tcattgagga 108840
cagatagaga gcagactgcg caaactttag agtctgcatt gggcctaggt ctcactgagg 108900
acagatagag agcacactgt gtaaccttta gagtctgcat agagcctcgg tctcattgag 108960
gacagataga gagcagactg tgcaaccttt agagtctcta ttgggcctag atctcattga 109020
ggacagatag ggagcggact gtgcaacctt tagagtctgc attgggccta ggtctcattg 109080
agggcagata gagagcaggc tcggcaaccc ttagagtctg cattgggcct agatcttatt 109140
gaggacagat agagagcata ctatgcaacc ttgagagtct gcactgggcc taggtctcat 109200
tgaggacaca tagagagcag actgtgcaac ctttagagtc tgcattgggc ctatgtctca 109260
ttgaggacag ttagagagca gactgtgcaa cctttagagt ctgcatttgg cctaggtctc 109320
attgaggaca gaaagagacc agagtgtgca acctttagag tttgcattgg gcctaggtct 109380
cattgaggac agatagagag cagactgtag aacctttata gtctgcattg ggcctaggtc 109440
tcattgaggt cagatagaga gcagactgtg caagctttag agtctacact tggcctaggt 109500
ctcattgagg acagatagag aacagactgt gcaaccttta gagtctgcat tgggcctagg 109560
tctcattgag ggcagataga gaccagactg tgcaaccttt agagtttgca ttgggcctag 109620
gtctcattga gggcagatag agagcagact gtgccacctt tagagtctac attgggccta 109680
ggtctcattg aggacagata gagagcagac tgtgcaacct ttatagtctg cactgggcct 109740
aggtctcttt gaggacagac agagagcaga ctgtgcaaac tttagagtct gcactgggcc 109800
taggtgtcat tgaggacaga tagagaccag actgtgcaac ctttagagtc tgcattgggc 109860
ctaggtctcc ttgaggtcag ataggcagca gactgtgcaa cctttagagt ctgcattggg 109920
tctaggtcta attgcggaca gatggagagc agactatgca aagtttacag tctgcattgg 109980
gcctgggtct cattgaggac agatagagag cagactgtgc aacctttaga gtctctattg 110040
ggcctaggtc tcattgagga cagatagaga gcagactgtg caacctttag agtctgcatt 110100
gggcctaggt ctcattgagg gcagatagag agcaggctcg gcaaccctta gagtctgcgt 110160
tgggcttaga tctcattgag gacagataga gagcatacta tgcaaccttt agagtctgca 110220
ctgggcctag gtctcattga ggacacatag agagcagact gtggaacctt tagagtctgc 110280
attgggccta tgtctcaatg aggacagtta gagagcagac tgtgcaacct ttagagtctg 110340
cattgggcct aggtctcatt gaggacagat agagagcaga ctgtagaacc tttatagtct 110400
gcattgggcc taggtctcat tgaggtcaga tagagagcag actgtgcaag ctttagagtc 110460
tgcacttggc ctaggtctca ttgaggacag atagagagca gactgtgcaa cctttagagt 110520
ctgcattggg cctaggtgtc attgagggca gatagagacc agactatgca acgtttagag 110580
tctgcattgg gcctaggtgt cattgagggc agttagagag cagactgtgc tacctttaga 110640
gtctgcatta ggcctaggtc tcattgagag cagatagaga gcacactgtg caaactttag 110700
agtcggcatt gggcctaggt ctcattgagg acagatagag accggactgt gcaaccttta 110760
gagtctgcat tgggcctagg tctcattgag gacagataaa gagcagacta ggcaaccatt 110820
agagtcggca ctggtcctaa gtctcattga ggacagatat agaggagact gtgtaacctt 110880
tagagtctgc attgggcctg ggtctcattg aggacagata gcgaccagac tgtgcaacct 110940
ttagagtctg cattgggtct aggtctcatt gagggcagtt agagagcaga ctgtgccacc 111000
tttagagtct gcattgggcc taggtctcat cgacagcaga tagagagcac actgtgcaac 111060
ctctagagtc ggcattgggc ctaggtctca ttgaggacag atagagacca gactgttaaa 111120
actttagagt ctgcattggg cctaggtcta attgaggaca gatagagggc agactgtgca 111180
acctttagag tctgcattgg gcctaggtct cattgaggac agatacagag cagactgtgc 111240
aaactttaaa gtctgcactg aacctaggtc tcattgaggg cagatagaga ccataatgtg 111300
caacctttag agtctgcatt gggtctaggt ctcactgagg agagatagag agcagacttt 111360
gcaaacttta gagtctccat tgggtctagg tctcactgag gactgataga gagcagacta 111420
tgcaaccttt agagtctgca ctggccctag gtctcattga ggacacatag agagcagact 111480
gcgcaaactt tagagtctgc attgggccta ggtctcactg aggacagata gagagcacac 111540
tgtgtaacct ttagagtctg catagggcct cggtctcatt gaggaccgat agagagcaga 111600
ctgtgccacc tttagagtct gcattgggcc tgggtctcat tgaggacaaa tagagagcag 111660
actgtgcaac ctttagagtc tgcattgggc ctaggtctca ttgaggacag atagagagca 111720
gactgtgcaa cctttagagt ctgcattggg cctaggtctc attgagggca gatagagagc 111780
agactgtgca acctttagag tctgcactgg gcctaggtct catcgaggac agatagagag 111840
cagactgtgc aacctttaga gtctgcattg gacctaggtc tcattgagga cagatagaga 111900
gcagactatg caaactttac agtctgcact gggcctaggt ctcattgagg acagatagag 111960
accagagtgt gcaaccttta gagtctgcat tgggcctagg tctcattgag gacagacaga 112020
gagcagactg tagaaccttt atagtctgca ttgggcctag gtctcattga ggtcagatag 112080
agagcagact gtgcaagctt tagagtctgc acttggccta ggtctcattg aggacagata 112140
gagagcagac tgtgcaacct ttagagtctg cattgggcct aggtctcatt gaggacagat 112200
agagaccaga ctgtgcaacc tttatagtct gcactgggcc taggtctcat tgaggagaga 112260
tagagagcag actgcgcaac ctttagagtc ttcattgggc ctaggtctca ttgagggcag 112320
atagagacca gagtgttcaa cctttagagt ctgcattggg cctaggtctc attgaggaca 112380
gatagagagc agactgtaga aactttatag tctgcattgg gcctaggtct cattgaggtc 112440
agatagagaa cagactgtgc aagctttaga gtctgcactt ggcctaggtc tcattgagga 112500
cagatagaga acagactgtg caacctttag agtctgcact aggcctaggt ctcattgagg 112560
acagatagag agcagactgt gcaaccttta gagtctgcat tggacctagg tctcattgag 112620
gacagataga gagcagacta tgcaaacttt agaggctgca ctgagcctag gtctcattga 112680
ggacagatag agagcagact gtgcaacctt tacagtctgc attggatctg ggcctcattc 112740
aggacagata gagaccagac tgtgcaacct ttagagtctg cattgggcct aggtctcatt 112800
gagagcagat agagagcaga ctgtgcaacc tttagagtct gcattgggcc taggtctcat 112860
tgagggcaga tagagagcag actgtgcaaa ctttagagtc tgcattgggc ctaggtctca 112920
ttgaggagag atagagagca gactgtgcaa cctttagagt ctgcattggg cctaggtctc 112980
attgaggaca gatggagagc acactgtgca acctttagag tccgcattgg gcctaggtct 113040
cattgaggac agatagagac cagactgtgc aactttagag tctgcattgg gcctaggtct 113100
cattgagggc agatagagag cagactgtgc aacctttaga gtctgcactg ggcctaggtc 113160
tcattgagga cagatagaga gcagactgtg caacctttag agtctgcact gtgcctaggt 113220
ctctttgagg acagacagag agcagactgt gcaaacttta gagtctgcac tgggcctagg 113280
tgtcattgag gacagataga gaccagactg tgcaaccttt agagtctgca ttgggcctaa 113340
gtctccttga ggtcagatag acagcagact gtgcaacctt tagagtctgc attgggccta 113400
ggtctaattg cggacagaca gagagcagac tatgcaacgt ttagagtctg cattgggcct 113460
gggtctcatt gaggacagat agagtgcaga ctgtgcaacc tttagagtct ctattgggcc 113520
taggtctcat tgaggacaga tagagagcgg actgtgcaac ctttagagtc tgcattgggc 113580
ctaggtctca ttgagggcag atagagagca ggctcggcaa cccttagagt ctgcattggg 113640
cttagatctc attgaggaca gatagagagc atactatgca acctttagag tctgcactgg 113700
gcctaggtct cattgaggac acatagagag cagactgtgc aacctttaga gtctgcattg 113760
ggcctatgtc tcattgagga cagttagaga gcagactgtg caacctttag agtctgcatt 113820
tggcctaggt ctcattgagg acagaaagag accagagtgt gcaaccttta gagtctgcat 113880
tgggcctagg tctcattgag gacagataga gagcagactg tagaaccttt atagtctgca 113940
ttgggcctag gtctcattga ggtcagatag agagcagact gtgcaagctt tagagtctgc 114000
acttggccta ggtctcattg aggacagata gagagcagac tgtgcaacct ttagagtctg 114060
cattgggcct aggtctcatt gagggcagat agagaccaga ctatgcaacg tttagagtct 114120
gcattgggcc taggtgtcat tgagggcagt tagagagcag actgtgctac ctttagagtc 114180
tgcattgggc ctaggtctca ttgagagcag atagagagca cactgtgcaa actttagagt 114240

```
cggcattggg cctaggtctc attgaggaca gatagagacc ggactgtgca acctttagag 114300
tctgcattgg gcctaggtct cattgaggac agataaagag cagactaggc aaccattaga 114360
gtcggcactt ttcctaggtc tcattgagga cagatataga gcagactgtg caacctttag 114420
agtctgcatt gggtctgggt ctcattgagg acagatagcg accagactgt gcaaccttta 114480
gagtctgctt tgggcttagg tctcattgag ggcagttaga gagcagactg tgcaaccttt 114540
agagtctgca ttgggtctag gtctcattga gagcagatag agagcacact gtgcaacctc 114600
tagagtcggc attgggccta ggtctcattg aggacagata gagaccagac tgttaaaact 114660
ttagagtctg cattgggcct aggtctcatt gaggacagat agagggcaga ctgtgcaacc 114720
tttagagtct gcattggtcc taggtctcat tgaggacaga tagagagcag actgcgcaaa 114780
ctttagagtc tgcattgggc ctaggtctca ctgaggacag atagagagca cactgtgtaa 114840
cctttagagt ctgcataggg cctcggtctc attgaggacc gatagagagc agactgtgca 114900
acctttagag tctgcattgg gcctgggtct cattgaggac aaatagagag cagactgtgc 114960
aacctttaga gtctgcattg ggcctaggtc tcattgagga cagatagaga gcagactgtg 115020
caacctttag agtctgcatt gggcctaggt ctcattgagg gcagatagag agcagactgt 115080
gcaaccttta gagtctgcac taggcctagg tctcatcgag gacagataga gagcagactg 115140
tgcaaccttt agagtctgca ttggacctag gtctcattga ggacagatag aaagcagact 115200
atgcaaactt tacagtctgc actgggccta ggtctcattg aggacagata gagaccagag 115260
tgtgcaacct ttagagtctg cattgggcct aggtctcatt gaggacagat agagagcaga 115320
ctgtagaacc tttatagtct gcattgggcc taggtctcat tgaggtcaga tagagagcag 115380
actgtgcaag ctttagagtc tgcacttggc ctaggtctca ttgaggacag atagagagca 115440
gactgtgcaa cctttagagt ctgcattggg cctaggtctc attgaggaca gatagagacc 115500
agactgtgca acctttatag tctgcactgg gcctaggtct cattgaggac agatagagag 115560
cagactgcgc aacctttaga gtcttcattg gtcctaggtc tcattgaggg cagatagaga 115620
ccagactatg caacctttag agtctgcatt gggcctaggt ctcattgagg gcagatagag 115680
agcagactgt gcaaccttta gagtatgcat tgggcctagg tctcattgag ggcagataga 115740
gagcagactg tgcaacgttt agagtctgca ttgtgcctaa gtctcattga ggacagatag 115800
agagcagact gtgcaacctt tcgagtctgc actgggccta ggtctcattg agggcagata 115860
gggaccagag tatgcaacct ttagagtctg cactgggcct aggtctcatt gagggcagat 115920
agagaccaga ctatgcaacc tttagagtct gcattgggac cccagaaatc ctaaactttg 115980
tgtggtctaa ggacggttgg agagccacgt ctggaccatc cctgtggctg ccacctgaat 116040
ggcggccagc acgagatctt atgcttgcac actgtgcctg caagggtggg aggggctggc 116100
ttatctcaga caacctcctg atagtggggt aaaccaaaaa tagaattcta agcccctcag 116160
ctgactgagt ggacctgttt gtagccaagg ggatcccaaa gaaacctgaa aaacaactca 116220
ggccgtgaca ggaagagggg atctcgggcc gtgacaggaa gagggagtct cgggccgtga 116280
caggaagagg gagtctcggg ccgtgacagg aagagggagt ctcgggccgt gactggaaga 116340
gggggtctcg ggccgtgaca ggaagagggg gtctcgggcc gtgacaggaa gagggggtct 116400
cgggccgtga caggaagagg gggtctcggg ccgtgacagg aagagggggt ctcgggccgt 116460
gacaggaaga gggggtctcg ggccgtgaca ggaagaggga gtctcgggcc gtgacaggaa 116520
gagggagtct cgggccgtga taggaagagg gagtctcggg ccgtgacagg aagaggggat 116580
ctcgggccgt gacaggaaga gggagtctcg ggccgtgaca ggaagagggt atctgtcctc 116640
```

aatgagacct aggcccaatg cagactctaa agtttgcaca ctctggtctc tttctgtcct 116700
caatgagacc taggccaaat gcagactcta aaggttgcac agtctgctct ctaactgtcc 116760
tcaatgagac ataggcccaa tgcagactct aaaggttgca cagtctgctc tctatgtgtc 116820
ctcaatgaga cctaggccca gtgcagactc taaaggttgc atagcatgct ctctatctgt 116880
cctcaatgat atctaggccc aatgcagact ctaagggttg ccgagcctgc tctctatctg 116940
ccctcaatga gacctaggcc caatgcagac tctaaaggtt gcacagtccg ctccctatct 117000
gtcctcaatg agacctaggc ccaatagaga ccctaaaggt tgcacagtct gctctctatc 117060
tgtcctcaat gagacccagg cccaatgcag actctaaacg ttgcatagtc tgctctctat 117120
ctgtccgcaa ttagacctag gcccaatgca gactctaaac gttgcacagt ctgctgtcta 117180
tctgtccgca attagaccta ggcccaatgc agactctaaa ggttgcagag tctgctgtct 117240
gtctgacctc aaggagacct aggcccaatg cagactctaa aggttgcaca gtctggtctc 117300
tatctgtcct caatgacacc taggcccagt gcagactcta aagtttgcac attctgctct 117360
ctgtctgtcc tcaaagagac ctagggccag tgcagactct aaaggttgca cagtctcctc 117420
tctatttgtc ctcactgata cctaggccca ttgtagactc taaaggttgc acagtctgcc 117480
ctctatctgt cctcaatgag acctaggccc aatgcagact ctaaagtttc aacagtctgg 117540
tctctatctg tcctcaatga gacctaggcc caatgccgac tctagaggtt gcacagtgtg 117600
ctctctatct gctctcaatg agacctaggc ccaatgcaga ctctaaaggt tgcacagtct 117660
gctctctaac tgccctcaat gagacctaag cccaatgcag actctaaagg ttgcacagtc 117720
tggtcgctat ctgtcctcaa tgagacccag gcccaatgca gactctaaag gttgcacagt 117780
ctgctctata tctgtcctca atgagaccta ggaccagtgc cgactctaat ggttgcctag 117840
tctgctctct atctgtcctc aatgagacgt aggcccaatg cagactctaa aggttgcaca 117900
gtccggtctc tatctgtcct caatgagacc taggcccaat gccgactcta aagtttgcac 117960
agtgtgctct ctatctgctc tcaatgagac ctaggcccaa tgcagactct aaaggttgca 118020
cagtctgctc tctaactgcc ctcaatgaga cctaggccca atgcagactc taaacgttgc 118080
atagtctggt ctctatctgc cctcaatgag acctaggccc aatgcagact ctagagtttg 118140
cacagtctgc tctctatctg tcctcaatga gacctaggcc aagtgcagac tctaaagctt 118200
gcaccgtctg ctctctatct gacctcaatg agacctaggc ccaatgcaga ctataaagtt 118260
tctacagtct gctctctatc tgtcctcaat gagacctagg cccaatgctg actctaaagg 118320
ttgcacactc tggtctgttt ctgtcctcaa tgagacctag gccaaatgca gactctaaag 118380
gttgcacagt ctgctctcta actgtcctca atgagacata ggcccaatgc agactctaaa 118440
ggttgcacag tctgctctct atgtgtcctc aatgagacct aggcccaatg cagactctaa 118500
aggttgcata gtatgctctc tatctgtcct caataagatc taggcccaat gcagactcta 118560
agggttgccg agcctgctct ctatctgccc tcaatgagac ctaggcccaa tgcagactct 118620
aaaggttgca cagtccgctc tctatctgtc ctcaatgaga cctaggccca atagagactc 118680
taaaggttgc acagtctgct ctctatctgt cctgaatgag acccaggccc aatgcagact 118740
ctaaacgttg catagtctgc tctctatctg tccgcaatta gacctaggcc caatgcagac 118800
tctaaaggtt gcacagtctg ctgtctatct gacctcaagg agacctaggc ccaatgcaga 118860
ctctaaaggt tgcacagtct ggtctctttc tgtcctcaat gacacctagg cccagtgcag 118920
actctaaagt ttgcacagtc tgctctctgt ctgtcctcaa agagacctag gcccagtgca 118980

-continued gactctaaag gttgcacagt ctgctctcta tctgtcctca atgagaccta ggcccaatgc 119040
agactctaaa ggttgcacag tttgctctct atctgccctc aatgagacct aggtccaatg 119100
caaactctaa agtttgcaca gtctggtctc tatctgtcct caatgagacc taggcccaat 119160
gccgactcta gaggttgcac agtgtgctct ctatctgctc tcaatgagac ctatgcccaa 119220
tgcagactct aaaggttgcg cagtctgctc tctaaatgcc ctcaatgaga cctaggccca 119280
atgcagactc tagaggttgc acagtctgct ctctatctgt cctcaatgag acctaggccc 119340
agtgcagact ctaaaggttg ctcagtctgc tctctatctg tcctcaatga gacccaggca 119400
caatgcagac tctaaaggtt gcacagtctg ctctatatct gtcctcaatg agacctagga 119460
ccagtgccga ctctaatggt tgcctagtct gctctctatc tgtcctgaat gagacctagg 119520
cccaatgccg actctaaagg ttgcacagta tgctctctat ctgctctcaa tgagacctag 119580
gcccaatgca gactctaaag gttgcacagt ctgctctcta tctgtcctca atgagaccta 119640
ggcccagtgc agactctaaa ggttgcacag tctgctctct atctgccctc aatgagacct 119700
aggcccaatg cagactctaa agtttgcaca gtctggtctc tatctgtcct caatgagacc 119760
caggcccaat gcagactgta aaggttgcac agtctgctct atatgtgtcc tcaatgagac 119820
ctaggcccag tgccgactct aaaggttgcc tagtctgctc tctatctgtc ctcaatgaga 119880
cctaggtcca atgcagtccc taaaggttgc acagtctgct ctctatttgt cctcagtgag 119940
acccaggccc aatgcagact ctaaaggttg cacagtctgc tctccatcgg tcctcaatga 120000
gaccgaggcc caattcggac tctaaaggtt gcacagtctg ctctctatct gtcttcaatg 120060
agacctaggc ccaatgcaga ctctaaagtt tgcacagtct gctctctgtc tgccctcaat 120120
gagccctaga cccaatgcag actctaaagg ttgcacagtc tgctctctat ctgtcctcaa 120180
tgagacctag gcccaatgca gactctaaag gttgcacagt ctgctctcta actgccctca 120240
atgagaccta ggcccaatgc agactctaat ggttgcacag tctgctctct atctgtcctc 120300
aatgagactc aggctcaatg cagtctctaa aggttgcaca gtctgctctc tatctgtcct 120360
caatgagacc taggcccaat gcagactcta aaggttgcac cgtctgctct ctatctgccc 120420
tcaatgagac ctaggcccaa tgcagactct aaaggttgta cagtcggctc tctacctgcc 120480
ctcattgaga cctaggccca atgcagactg taaaggttgc accgtctgtt ctctatctgc 120540
cctcaatgag acgtaggccc aatgcagact ctaaaggttg tgcagtctgc tctctatgtg 120600
ccctcaatga gacctaggcc caatgcagac tctaaaggtt gcacagtctg ctctctatct 120660
gtcctcaatg agacccaggc tcaatgcagt ctctaaaggt tgcacagtgt gctctctatc 120720
tgacctcaat gagaccttgg cccaatgcag actctaaagg ttgcacagtc ggctctctac 120780
ctgccctcaa tgagacctag gcccaatgca gattctaaag gttgcacagt ctgctctcta 120840
tcggtcctca atgagaccga ggctctatgc agactctaaa ggttacacag tgtgctctct 120900
atctgtcctc aatgagaccc agacccaatg cagactctaa agtttgcgca gtctgctctc 120960
tatctgtcct caatgagacc tagggccagt gcagactcta aagttgcata gtctgctctc 121020
tatcagtcct cagtgagacc tagacctaat gcagactcta aagtttgcaa agtctgctct 121080
ctatctctcc tcagtgagac ctagacccaa tgcagactct aaagtttgca cagtatggtc 121140
tctatatgcc ctcaatgaga cctaggccca gtgcagactc gaaaggttgc acagtctgct 121200
ctctatctgt cctcaatgag acctaggctc aatgcagact ctaaaggttg cacagtctgc 121260
cctctatctg tcctcaatga gacctaggcc caatgcagac tctaaagttt gcacagtctg 121320
gtctctatct gtcctcaatg agacctaggc ccaatgccga ctctagaggt tgcacagtgt 121380
gctctctatc tgctctcaat gagacctagg cccaatgcag actctaaagg ttgcacagtc 121440
tgctctctaa ctgccctcaa tgagacctag gcccaatgca gactctaaag gttgcacagt 121500
ctgttctcta tctgtcctca atgagaccta ggccaagtgc agactctaaa gcttgcacag 121560
tctgctctct atctgacctc aaagagacct aggcccaatg cagactataa aggttctaca 121620
gtctgctctc tatctgtcct caatgagacc taggcccaat gcagactcta aagtttgcgc 121680
actctggtct ctttctgtcc tcaatgagac ctaggccaaa tgcagactgt aaaggttgca 121740
cagcctgctc tctaactgtc ctcaatgaga cataggccca atgcagactc taaaggttgc 121800
acagtctgct ctctatgtgt cctcaatgag acctaggccc agtgcagact ctaaaggttg 121860
catagtatgc tctctatctg tcctcaatga gatctaggcc caatgcagac tctaagggtt 121920
cccgagcctg ctctctatct gccctcaatg agacctaggc ccaatgcaga ctctaaaggt 121980
tgcacagtcc tctccctatc tgtcctcaat gagacctagg cccaatagag actctaaagg 122040
ttgcacagtc tgctctctat ctgtcctcaa tgagacccag gcccaatgca gactctaaac 122100
gttgcatagt ctgctctcta tctgtccgca attagaccta ggcccaatgc agactctaaa 122160
cgttgcacag tctgctgtct atctgtccgc aattagacct aggcccaatg cagactctaa 122220
aggttgcaga ttctgctgtc tatctgacct caaggagacc taggcccaat gcagactcta 122280
aaggttgcac agtctggtct ctatctgtcc tcaatgacac ctaggcccag tgcagactct 122340
aaagtttgca cagtctgctc tctgtctgtc ctcaaagaga cctaggccca gtgcagactc 122400
taaaggttgc acagtctcct ctctatctgt cctcactgat acctaggccc aatgcagact 122460
ctaaaggttg cacagtctgt tctctatttg tcctcaatga gacccaggcc caatgcagag 122520
tctaaaggtt gcacagtctg ctctctatcg gtcctcaatg agacctaggc ccaatgcaga 122580
ctctaaaggt tgcacagtct gctctctatc tgccctcaat gagacctagg cccaatgcaa 122640
actctaaagg ttgcacagtc tggtctctat ctgtcctcaa tgagacctag gcccaatgcg 122700
gactctaaag gttgcacagt gtgctctcca tctgtcctca atgagaccta ggccaaatgc 122760
agactctaaa ggttgcacag tctgctctct atgtgtcctc aatcagacct aggcccagtg 122820
cagactctaa agtttgcaca gtctgctctc tatcggccct caatgagacc taggcccaat 122880
gcagactgta aaggttgcac agtctgctct ctatctgctc tcaagagacc taggcccaat 122940
gcaaactcta aaggttgcac attctggtct ctatctctcc tgaatgagac ccaggcccaa 123000
tgcagactgt aaaggttgca cagtctgctc tctatctgtc ctcaatgaga cctaggccca 123060
gtgcagactg taaagtttgc atagtctgct ctctatctgt cctcagtgag acctaggtcc 123120
aatgcagact ctaaatgttg cacagtctgc tctctatctg tcctcgatga gacctagccc 123180
tagtgcagac tctaaaggtt gcacagtctg ctctctatct gccctcaatg agacctaggc 123240
ccaatgcaga ctctaaaggt tgcacagtcg gctctccatt tttcctcaat gagacccagg 123300
cccaatgcag actctaaagg ttgcacagtc tgctctctat cggtcctcaa tgagaccgag 123360
gccctatgca aactctaaag gttacacagt gtgctctcta tctgtcctca gtgagaccta 123420
ggcccaatgc agactctaaa gtttgcgcag tctgctctct atctgtcctc aatgagacct 123480
agggccaggc agactctaaa gttgcatagt ctgctctcta tcagtcctca gtgagaccta 123540
gacctaatgc agactctgaa gtttgcaaag tctgctctct atctctcctc agtgagacct 123600
agacccaatg cagactctaa agtttgcaca gtatggtctc tatatgccct caatgagacc 123660
taggcccagt gcagactcta aagtttgcaa agtctgctct ctatctgtcc tcaatgagac 123720

-continued ctaggcccaa tgcagactct aaaggttgca cagtctgccc tctatctgtc ctcaatgaga 123780
cctaggccca atgcagactc taaagtttgc acagtctggt ctctatctgt cctcaatgag 123840
acctaggccc aatgccgact ctagagtttg cacagtgtgc tctctatctg ctctcaatga 123900
gacctaggcc caatgcagac tctaaagttt gcacagtctg ctctctaact gccctcaatg 123960
agacctaggc ccaatgcaga ctctaaaggt tgcacagtct gttctctatc tgtcctcaat 124020
gagacctagg acaagtgcag actctaaagc ttgcacagtc tgctctctat ctgacctcaa 124080
tgagacctag gcccaatgca gactataaag gttctacagt ctgctctcta tctgtcctca 124140
atgagaccta ggcccaatgc agactctaaa gtttgcacac tctggtctct ttctgtcctc 124200
aatgagacct aggccaaatg cagactctaa aggttgcaca gtctgctctc taactgtcct 124260
caatgagaca taggcccaat gcagactcta aaggttgcac agtctgctct ctatgtgtcc 124320
tcaatgagac ctaggcccag tgcagactct aaaggttgca tagcatgctc tctatctgtc 124380
ctcaatgata tctaggccca atgcagactc taagggttgc cgagcctgct ctctatctgc 124440
cctcaatgag acctaggccc aatgcagact ctaaaggttg cacagtccgc tccctatctg 124500
tcctcaatga gacctaggcc caatagagac cctaaaggtt gcacagtctg ctctctatct 124560
gtcctcaatg agacccaggc ccaatgcaga ctctaaacgt tgcatagtct gctctctatc 124620
tgtccgcaat tagacctagg cccaatgcag actctaaacg ttgcacagtc tgctgtctat 124680
ctgtccgcaa ttagacctag gcccaatgca gactctaaag gttgcagagt ctgctgtctg 124740
tctgacctca aggagaccta ggcccaatgc agactctaaa ggttgcacag tctggtctct 124800
atctgtcctc aatgacacct aggcccagtg cagactctaa agtttgcaca ttctgctctc 124860
tgtctgtcct caaagagacc tagggccagt gcagactcta aaggttgcac agtctcctct 124920
ctatttgtcc tcactgatac ctaggcccat tgtagactct aaaggttgca cagtctgccc 124980
tctatctgtc atcaatgaga cctaggccca atgcagactc taaagtttca acagtctggt 125040
ctctatctgt cctcaatgag acctaggccc aatgccgact ctagaggttg cacagtgtgc 125100
tctctatctg ctctcaatga gacctaggcc caatgcagac tctaaaggtt gcacagtctg 125160
ctctctaact gccctcaatg agacctaagc ccaatgcaga ctctaaaggt tgcacagtct 125220
ggtcgctatc tgtcctcaat gagacccagg cccaatgcag actctaaagg ttgcacagtc 125280
tgctctatat ctgtcctcaa tgagacctag gaccagtgcc gactctaatg gttgcctagt 125340
ctgctctcta tctgtcctca atgagacgta ggcccaatgc agactctaaa ggttgcacag 125400
tccggtctct atctgtcctc aatgagacct aggcccaatg ccgactctaa agtttgcaca 125460
gtgtgctctc tatctgctct caatgagacc taggcccagt gcagactcta aaggttgcac 125520
agtctgctct gtatcggtcc ataatgagac ctaggcccaa tgcagactct aaaggttgca 125580
cagtctgccc tctatctgtc ctcaatgaga cctaggccca atgcagactc taaagtttgc 125640
acagtctggt ctctatctgt cctcaatgag acctaggccc aatgccgact ctagaggttg 125700
cacagtgtgc tctctatctg ctctcaatga gacctaggcc caatgcagac tctaaaggtt 125760
gcgcagtctg ctctctaaat gccctcaatg agacctaggc ccaatgcaga ctctagaggt 125820
tgcacagtct gctctctatc tgtcctcaat gagacctagg cccagtgcag actctaaagg 125880
ttgcacagtc tgctctctat ctgtcctcaa tgagacccag gcacaatgca gactctaaag 125940
gttgcacagt ctgctctata tctgtcctca atgagaccta ggaccagtgc cgactctaat 126000
ggttgcctag tctgctctct atctgtcctc aatgagacct aggcccaatg cagactctaa 126060
aggttgcaca gtctggtctc tatctgtcct caatgagacc taggcccaat gccgactcta 126120
aaggttgcac agtatgctct ctatctgctc tcaatgagac ctaggcccaa tgcagactct 126180
aaaggttgca cagtctgctc tctatctgtc ctcaatgaga cctaggccca gtgcagactc 126240
taaaggttgc acagtctgct ctctatctgc cctcaatgag acctaggccc aatgcagact 126300
ctaaaggttg cacagtctgg tctctatctg tcctcaatga gacccaggcc caatgcagac 126360
tgtaaaggtt gcacagtctg ctctatatgt gtcctcaatg agacctaggc ccagtgccga 126420
ctctaaaggt tgcctagtct gctctctatc tgtcctcaat gagacctagg tccaatgcag 126480
tccctaaagg ttgcacagtc tgctctctat ttgtcctcag tgagacccag gcccaatgca 126540
gactctaaag gttgcacagt ctgctctcca tcggtcctca atgagaccga ggcccaattc 126600
ggactctaaa ggttgcacag tctgctctct atctgtcttc aatgagacct aggcccaatg 126660
cagactctaa agtttgcaca gtctgctctc tgtctgccct caatgagccc tagacccaat 126720
gcagactcta aaggttgcac agtctgctct ctatctgtcc tcaatgagac ctaggcccaa 126780
tgcagactct aaaggttgca cagtctgctc tctatgtgcc ctcaatgaga cctaggccca 126840
atgcagactc taatggttgc acagtctgct ctctatctgt cctcaatgag actcaggctc 126900
aatgcagtct ctaaaggttg cacagtctgc tctctatctg tcctcaatga gacctaggcc 126960
caatgcagac tctaaaggtt gcaccgtctg ctctctatct gccctcaatg agacctaggc 127020
ccaatgcaga ctctaaaggt tgtacagtcg gctctctacc tgccctcatt gagacctagg 127080
cccaatgcag actgtaaagg ttgcaccgtc tgttctctat ctgccctcaa tgagacgtag 127140
gcccaatgca gactctaaag gttgtgcagt ctgctctcta tgtgccctca atgagaccta 127200
ggcccaatgc agactctaaa ggttgcacag tctgctctct atctgtcctc aatgagaccc 127260
aggctcaatg cagtctctaa aggttgcaca gtgtgctctc tatctgacct caatgagacc 127320
ttggcccaat gcagactcta aaggttgcac agtcggctct ctacctgccc tcaatgagac 127380
ctaggcccaa tgcagattct aaaggttgca cagtctgctc tctatcggtc ctcaatgaga 127440
ccgaggctct atgcagactc taaaggttac acagtgtgct ctctatctgt cctcaatgag 127500
acctagaccc aatgcagact ctaaagtttg cgcagtctgc tctctatctg tcctcaatga 127560
gacctagggc cagtgcagac tctaaagttg catagtctgc tctctatcag tcctcagtga 127620
gacctagacc taatgcagac tctaaagttt gcaaagtctg ctctctatct ctcctcagtg 127680
agacctagac ccaatgcaga ctctaaagtt tgcacagtat ggtctctata tgccctcaat 127740
gagacctagg cccagtgcag actcgaaagg ttgcacagtc tgctctctat ctgtcctcaa 127800
tgagacctag gctcaatgca gactctaaag gttgcacagt ctgccctcta tctgtcctca 127860
atgagaccta ggcccaatgc agactctaaa gtttgcacag tctggtctct atctgtcctc 127920
aatgagacct aggcccaatg ccgactctag aggttgcaca gtgtgctctc tatctgctct 127980
caatgagacc taggcccaat gcagactcta aaggttgcac agtctgctct ctaactgccc 128040
tcaatgagac ctaggcccaa tgcagactct aaaggttgca cagtctgttc tctatctgtc 128100
ctcaatgaga cctaggccaa gtgcagactc taaagcttgc acagtctgct ctctatctga 128160
cctcaatgag acctaggccc aatgcagact ataaaggttc tacagtctgc tctctatctg 128220
tcctcaatga gacctaggcc caatgcagac tctaaagttt gcgcactctg gtctctttct 128280
gtcctcaatg agacctaggc caaatgcaga ctgtaaaggt tgcacagcct gctctctaac 128340
tgtcctcaat gagacatagg cccaatgcag actctaaagg ttgcacagtc tgctctctat 128400
gtgtcctcaa tgagacctag gcccagtgca gactctaaag gttgcatagt atgctctcta 128460
tctgtcctca atgagatcta ggcccaatgc agactctaag ggttcccgag cctgctctct 128520
atctgccctc aatgagacct aggcccaatg cagactctaa aggttgcaca gtcctctccc 128580
tatctgtcct caatgagacc taggcccaat agagactcta aaggttgcac agtctgctct 128640
ctatctgtcc tcaatgagac ccaggcccaa tgcagactct aaacgttgca tagtctgctc 128700
tctatctgtc cgcaattaga cctaggccca atgcagactc taaacgttgc acagtctgct 128760
gtctatctgt ccgcaattag acctaggccc aatgcagact ctaaaggttg cagattctgc 128820
tgtctatctg acctcaagga gacctaggcc caatgcagac tctaaaggtt gcacagtctg 128880
gtctctatct gtcctcaatg acacctaggc ccagtgcaga ctctaaagtt tgcacagtct 128940
gctctctgtc tgtcctcaaa gagacctagg cccagtgcag actctaaagg ttgcacagtc 129000
tcctctctat ctgtcctcac tgatacctag gcccaatgca gactctaaag gttgcacagt 129060
ctgttctcta tttgtcctca atgagaccca ggcccaatgc agagtctaaa ggttgcacag 129120
tctgctctct atcggtcctc aatgagacct aggcccaatg cagactctaa aggttgcaca 129180
gtctgctctc tatctgccct caatgagacc taggcccaat gcaaactcta aaggttgcac 129240
agtctggtct ctatctgtcc tcaatgagac ctaggcccaa tgcggactct aaaggttgca 129300
cagtgtgctc tccatctgtc ctcaatgaga cctaggccaa atgcagactc taaaggttgc 129360
acagtctgct ctctatgtgt cctcaatcag acctaggccc agtgcagact ctaaagtttc 129420
cacagtctgc tctctatcgg ccctcaatga gacctaggcc caatgcagac tgtaaaggtt 129480
gcacagtctg ctctctatct gctctcaaga gacctaggcc caatgcaaac tctaaaggtt 129540
gcacattctg gtctctatct ctcctgaatg agacccaggc ccaatgcaga ctgtaaaggt 129600
tgcacagtct gctctctatc tgtcctcaat gagacctagg cccagtgcag actgtaaagt 129660
ttgcatagtc tgctctctat ctgtcctcag tgagacctag gtccaatgca gactctaaat 129720
gttgcacagt ctgctctcta tctgtcctcg atgagaccta gccctagtgc agactctaaa 129780
ggttgcacag tctgctctct atctgccctc aatgagacct aggcccaatg cagactctaa 129840
aggttgcaca gtctgctctc tgtttttcct caatgagacc caggcccaat gcagactcta 129900
aaggttgcac agtctgctct ctatcggtcc tcaatgagac cgaggccctt tgcaaactct 129960
aaaggttaca cagtgtgctc tctatctgtc ctcagtgaga cctaggccca atgcagactc 130020
taaagtttgc gcagtctgct ctctatctgt cctcaatgag acctagggcc aggcagactc 130080
taaagttgca tagtctgctc tctatcagtc ctcagtgaga cctagaccta atgcagactc 130140
tgaagtttgc aaagtctgct ctctatctct cctcagtgag acctagaccc aatgcagact 130200
ctaaagtttg cacagtatgg tctctatatg ccctcaatga gacctaggcc cagtgcagac 130260
tctaaagttt gcaaagtctg ctctctatct gtcctcaatg agacctaggc ccaatgcaga 130320
ctctaaaggt tgcacagtct gccctctatc tgtcctcaat gagacctagg cccaatgcag 130380
actctaaagt ttgcacagtc tggtctctat ctgtcctcaa tgagacctag gcccaatgcc 130440
gactctagag tttgcacagt gtgctctcta tctgctctca atgagaccta ggcccaatgc 130500
agactctaaa gtttgcacag tctgctctct aactgccctc aatgagacct aggcccaatg 130560
cagactctaa aggttgcaca gtctgttctc tatctgtcct caatgagacc taggacaagt 130620
gcagactcta aagcttgcac agtctgctct ctatctgacc tcaatgagac ctaggcccaa 130680
tgcagactat aaaggttcta cagtctgctc tctatctgtc ctcaatgaga cctaggccca 130740
atgcagactc taaagtttgc acactctggt ctctttctgt cctcaatgag acctaggcca 130800
aatgcagact ctaaaggttg cacagtctgc tctctaactg tcctcaatga gacataggcc 130860
caatgcagac tctaaaggtt gcacagtctg ctctctatgt gtcctcaatg agacctaggc 130920
ccagtgcaga ctctaaaggt tgcatagcat gctctctatc tgtcctcaat gatatctagg 130980
cccaatgcag actctaaggg ttgccgagcc tgctctctat ctgccctcaa tgagacctag 131040
gcccaatgca gactctaaag gttgcacagt ccgctcccta tctgtcctca atgagaccta 131100
ggcccaatag agaccctaaa ggttgcacag tctgctctct atctgtcctc aatgagaccc 131160
aggcccaatg cagactctaa acgttgcata gtctgctctc tatctgtccg caattagacc 131220
taggcccaat gcagactcta aacgttgcac agtctgctgt ctatctgtcc gcaattagac 131280
ctaggcccaa tgcagactct aaaggttgca gagtctgctg tctgtctgac ctcaaggaga 131340
cctaggccca atgcagactc taaaggttgc acagtctggt ctctatctgt cctcaatgag 131400
acctaggccc agtgcagact ctaaagtttg cacattctgc tctctgtctg tcctcaaaga 131460
gacctagggc cagtgcagac tctaaaggtt gcacagtctc ctctctattt gtcctcactg 131520
atacctaggc ccattgtaga ctctaaaggt tgcacagtct gccctctatc tgtcctcaat 131580
gagacctagg cccaatgcag actctaaagt ttcaacagtc tggtctctat ctgtcctcaa 131640
tgagacctag gcccaatgcc gactctagag gttgcacagt gtgctctcta tctgctctca 131700
atgagaccta ggcccaatgc agactctaaa ggttgcacag tctgctctct aactgccctc 131760
aatgagacct aagcccaatg cagactctaa aggttgcaca gtctggtcgc tatctgtcct 131820
caatgagacc caggcccaat gcagactcta aaggttgcac agtctgctct atatctgtcc 131880
tcaatgagac ctaggaccag tgccgactct aatggttgcc tagtctgctc tctatctgtc 131940
ctcaatgaga cgtaggccca atgcagactc taaaggttgc acagtccggt ctctatctgt 132000
cctcaatgag acctaggccc aatgccgact ctaaagttgg cacagtgtgc tctctatctg 132060
ctctcaatga gacctaggcc caatgcagac tctaaaggtt gcacagtctg ctctctaact 132120
gccctcaatg agacctaggc ccaatgcaga ctctaaacgt tgcatagtct ggtctctatc 132180
tgccctcaat gagacctagg cccaatgcag actctagagt ttgcacagtc tgctctctat 132240
ctgtcctcaa tgagacctag gccaagtgca gactctaaag cttgcacagt ctgctctcta 132300
tctgacctca atgagaccta ggcccaatgc agactataaa gtttctacag tctgctctct 132360
atctgtcctc aatgagacct aggcccaatg ctgactctaa aggttgcaca ctctggtctg 132420
tttctgtcct caatgagacc taggccaaat gcagactcta aagcttgcac agtctgctct 132480
ctaactgtcc tcaatgagac ataggcccaa tgcagactct aaaggttgca cagtctgctc 132540
tctatgtgtc ctcaatgaga cctaggccca atgcagactc taaaggttgc atagtatgct 132600
ctctatctgt cctcaataag atctaggccc aatgcagact ctaagggttg ccgagcctgc 132660
tctctatctg ccctcaatga gacctaggcc caatgcagac tctaaaggtt gcacagtccg 132720
ctctctatct gtcctcaatg agacctaggc ccaatagaga ctctaaaggt tgcacagtct 132780
gctctctatc tgtcctgaat gagacccagg cccaatgcag actctaaacg ttgcatagtc 132840
tgctctctat ctgtccgcaa ttagacctag gcccaatgca gactctaaag gttgcacagt 132900
ctgctgtcta tctgacctca aggagaccta ggcccaatgc agactctaaa ggttgcacag 132960
tctggtctct ttctgtcctc aatgacacct aggcccagtg cagactctaa agtttgcaca 133020
gtctgctctc tgtctgtcct caaagagacc taggcccagt gcagactcta aaggttgcac 133080
agtctgctct ctatctgtcc tcaatgagac ctaggcccaa tgcagactct aaaggttgca 133140
cagtttgctc tctatctgcc ctcaatgaga cctaggtcca atgcaaactc taaaggttgc 133200
acagtctggt ctctatctgt cttcaatgag acccaggccc aatgcagact ctaaagattg 133260
cacagtctgc tctctatcgg tcctcaatga gaccgaggcc ctatgcagac tctaaaggtt 133320
acacagtgtg ctctctatct gccctcaatg agacctaggc ccagtgcaga ctctaaaggt 133380
tgcacagtct gctctgtatc ggtccacaat gagacctagg cccaatgcag actctaaagg 133440
ttgcacagtc tgccctctat ctgtcctcaa tgagacctag gcccaatgca gactctaaag 133500
tttgcacagt ctggtctcta tctgtcctca atgagaccta ggcccaatgc cgactctagt 133560
ggttgcacag tgtgctctct atctgctctc aatgagacct aggcccaatg cagactctaa 133620
aggttgcgca gtctgctctc taaatgccct caatgagacc taggcccaat gcagactcta 133680
gaggttgcac agtctgctct ctatctgtcc tcaatgagac ctaggcccag tgcagactct 133740
aaaggttgca cagtctgctc tctatctgtc ctcaatgaga cccaggcaca atgcagactc 133800
taaaggttgc acagtctgct ctatatctgt cctcaatgag acctaggacc agtgccgact 133860
ctaatggttg cctagtctgc tctctatctg tcctcaatga gacctaggcc caatgcagac 133920
tctaaaggtt gcacagtctg gtctctatct gtcctcaatg agacctaggc ccaatgccga 133980
ctctaaaggt tgcacagtat gctctctatc tgctctcaat gagacctagg cccaatgcag 134040
actctaaagg ttgcacagtc tgctctctat ctgtcctcaa tgagacctag gcccagtgca 134100
gactctaaag gttgcacagt ctgctctcta tctgccctca atgagaccta ggcccaatgc 134160
agactctaaa ggttgcacag tctggtctct atctgtcctc aatgagaccc aggcccaatg 134220
cagactgtaa aggttgcaca gtctgctcta tatgtgtcct caatgagacc taggcccagt 134280
gccgactcta aaggttgcct agtctgctct ctatctgtcc tcaatgagac ctaggtccaa 134340
tgcagtccct aaaggttgca cagtctgctc tctatttgtc ctcagtgaga cccaggccca 134400
atgcagactc taaaggttgc acagtctgct ctccatcggt cctcaatgag accgaggccc 134460
aattcggact ctaaaggttg cacagtctgc tctctatctg tcttcaatga gacctaggcc 134520
caatgctgac tctaaagttt gcacagtctg ctctctgtct gccctcagtg ggccctagac 134580
ccaatgcaga ctctaaaggt tgcacagtct gctctctatc tgtcctcaat gagacctagg 134640
cccaatgcag actctaaagg ttgcacagtc tgctctctat gtgccctcaa tgagacctag 134700
gcccaatgca gactctaatg gttgcacagt ctgctctcta tctgtcctca atgagactca 134760
ggctcaatgc agtctctaaa ggttgcacag tctgctctct atctgtcctc aatgagacct 134820
aggcccaatg cagactctaa aggttgcacc gtctgctctc tatctgccct caatgagacc 134880
taggcccaat gcagactcta aaggttgtac agtcggctct ctacctgccc tcaatgagac 134940
ctaggcccaa tgcagactgt aaaggttgca ccgtctgttc tctatctgcc ctcaatgaga 135000
cgtaggccca atgcagactc taaaggttgc acagtctgct ctctatctgt cctcaatgag 135060
acccaggctc aatgcagtct ctaaaggttg cacagtgtgc tctctatctg acctcaatga 135120
gaccttggcc caatgcagac tctaaaggtt gcacagtcgg ctctctacct gccctcaatg 135180
agacctaggc ccaatgcaga ttctaaaggt tgcacagtct ggtctctatc tgcccttaat 135240
gagacctaca ctcccaggag tctgcagaac agggtgtgtg taagttttct ggggccgctc 135300
aaggaaacgg gggattaaaa aatattatcc tcacagtgct ggcatgttgg cctacacaga 135360
gccctgctcg ccgtgaacgt caggacttcc tgcgtgatct cttcaagtcc gattgggagc 135420
cctttgactc gtcccctgtc tgtgctggag aattcagagc ccactgactc atctttcttt 135480
gtggcctggg agagttgtgg agaacatgct gtaccttcgc ggtgccgcac ggatcttcct 135540
gctccctccc tcgggagtct cgcagggacc ccatctcgtt ttaatgtttt gtcaatacgg 135600
cacccacgag aacgttgcag ggaagacacc actgtggccg taaaccacag aaactagagc 135660
tgaagtggcc ccaggtggcc tccagtcaag cagtatccaa attcttcacc ctgaggccct 135720
ttatttatta ttattattat tagagacgga gtttcgctct tgttacccag gctggagtgc 135780
aatggtgtga tatcagctca ccgcaacctc cgcctcccgg gttcaagcaa ttctctggcc 135840
tcagcctccc aagtagctgg gattacaggt gggcgccacc acgcctggct aattttttgt 135900
atttttagag atggggattc tctatgttgg tcaggctggt ctcgaactcc caacctcagg 135960
tgagctgctg gccttggcct cccaaagtgc tgggattaca ggcgtgcacc accacaccca 136020
gccctatctt attctttttc tctcaccagg gaccccaaat ttggaagaac cataatcatg 136080
tttattgaca ttatgttaaa ttaaggttcc cacgtttatt aataaaagaa atatatcatt 136140
agcctggcct tttaaatttt tcttaattta attttttttt ttttttgagg cagggtctca 136200
ctctgtcacc caggctggag tgcaatggta ccatcatggc tcaccacagc cccccgctcc 136260
taggctcaag caatcctctt gcctcagcct cctgagtatc tggggattat aggtgcacac 136320
catcacactc agccaattaa aaaaaaattt ctagtagaga tggggtctca ccaagttgtc 136380
caggctggtc tcacacttct gagctcaagt aatcgtcctg ctttggcctc ccaaagtgct 136440
cggattacag gggtaagcta ccacattcag cctttatttt tatttttaat ggaggtaaaa 136500
gccacataac ataaaattta ccctttcaac tacttctttt ttttagatgg aggcttgctc 136560
tgttgcccag gctggagtgc agtggcacaa tctcagctca cttcaacctc tacctcccgg 136620
gttcaagtga ttcccctgcc tcagcctccc aagtagctgg gatcacaggc acccgccacc 136680
acacctggca aatttttttgt attttagtag agacggggtt tcactgtgtt ggccaagacg 136740
gtgtcgatct cctgacctcg tgatccgcct gcctcggcct cccaaagtgc tgggattaca 136800
ggcatgagcc accgcgcccg gccccttttaa agtattttta aggatacact tcagcagtgt 136860
tcatcatatc cgcattgttg tataacagat gtttacaact tcttcatctt acaaaacaga 136920
aactgtgtcc acatcaaacc agggtgcccc attcccccgg cccctggcac ccaccattct 136980
actgtctgtc tctatgaatt ccactcttcc agagacctca taggagtggg atcacacagc 137040
actttttgt ctggcttatc ttgttaacaa caggtgagtc catgtggtag cctgtctcat 137100
cattccttcc tttttagggc tgattcatat ttcattatat ggatgaacca cattttcttt 137160
ttccagtcat gctgtaacag gatgagtcac agtcaaaact cctcagacac cagattaaag 137220
aaggaagagg tttttttattt tggccgggag attcggcaga ctcgtgtctt aagagccgag 137280
ctccccgaaa aagaaattcc tagccctttt aagggctaag aactctaagg ggtctatgtg 137340
aaagagtcat aatagatcaa gtaagtgtga ggaacgtgag tgggggctac atacatcagc 137400
taagagaaca aaaagttttt attttttttat tttttttgag acggaatctc gctctgtggc 137460
ccaggctgga gtgcagtggc gtgatctcag ctcactgcaa gctccgcctc ccgggttcac 137520
accattctcc tgcctcagcc tccccagtag ctgggactac aggcgcccgc caccgcgccc 137580
ggctaatttt ttgtattttt agtagacacg gggtttcatc atgttaacca ggatggtctc 137640
gatctcctga ccttgtgatc cacccgcctc ggcctcccaa agtgctggga ttagaggctg 137700
gagccaccgt gcccggcctg cacccagcta atttttttgta tttttagtag agatggggtt 137760
tcaccgtgtt agccaggatg gtctcaatct cctgacctca tgatcctccc acctcggcct 137820
cccaaagtcc tgggattaca ggcgtgagcc accgcgcccg gccagaacaa aaagttttac 137880
agtgctttct catacaatgt ctggaattta cagatagcac cagtagtttt ggtcagcggt 137940

-continued

```
taatactatt attattttaa tcaccagggc caggtggtgg caccaaggtc gtctagctat 138000
ttatcttact tttgtttctt tccaactttt tgctttctct cttttctctt gtcttataaa 138060
ctagggaaaa ggggaggttg gggagaaagt gggaaggaca acaggagaag tggtggtgtc 138120
ataacataat gcgatcatgg gcaccgggct gcttccatct tttggctatt gtgaatactg 138180
ctgtaacgac cacggttgtg caataatccc ttccagactc tgctttcaat ctttttggat 138240
ttagtcggag aagtaatgtg attgctggtt cataggtggt tccatttctg gttatttatt 138300
tattttttaa gagacagagt tttatatgtt gcccaggctg gccttgaact cctgggcttc 138360
agtgatcccc ttccctcagc ctcccaagta gccggtagtg cagctgcaca tcaccacacc 138420
caagtgattt ttagttgtta tttttctggt tttgtttttg cggagatgga gtttcactgt 138480
gccgcccagg gtggagtgcg gtggcataat cggctcactg cagcctccac ctcctggttc 138540
aggcgcttct cctgccttag cctcccgagt agctgggact ataggcatct gtcaccacac 138600
ttagctaatt attttgtgtt tgcttccccc caccccgccc ccccgagatg gagtcttcct 138660
ttgtcaccca ggctggagtg cagtggcgcg atctcggctc aatgcaacct ctgcctccgg 138720
ggttcaagca attctcctgc ctcagcctcc cgggtagctg ggattcctgg cacccacaac 138780
cacgcccggc taattttttta tttttagtag agacggagtt tcaccatgtt ggccaggctg 138840
gtctcgaact cctgactttg tgatccacct gcctcgggct cccaaagtgc tgggatgaca 138900
ggtgtgagcc actgtgccca gcctgatatt tagtgctttt ttgaggaggc tccatagtgt 138960
tttccacggt ggccacacca ttttctagtc ctacaggcaa tccacgaggg ctccaatttc 139020
cacacatcct tgttaacact atttttgttt cactgtagca tttcatggat gtgaggtgct 139080
atcactgtgg ttttgatgtg tatttctcta atgattactg atgttgagga tccttccatg 139140
tttgtttgct acttgtatat cttttctgga gaaatatcta ttcaggtcgt ttgctcattt 139200
ttcaatcagt taacttgttt ttcaattgtt cagttgcagg agctctttat atgtgctgga 139260
cgaatatccg acgtaccaga catataatct gcagttattt cctcttattc catgtcttgc 139320
cttttcactg ttgtttcctg tgcagaaatg tttaacctcg aagttggacc atttgtctat 139380
ttgtgctttt gttgcctgtg cttatctggg ctttggatag gccagaggta aacggcaggt 139440
gttactgcac caagttcata aaatcgagcc caaaacaaag gagtcgacac agtaattagc 139500
tggtgtgtcg ccttggcgag aatatatatg actttgctg agaattttca ttaatgttta 139560
ttttctattt ttattttttg agatggagtc tcgctctgtc gcccaggccg gagtgcagtg 139620
gcgcaatctc agctcactgc aagctccacc tcccgggctc acgctgttct cctgcctcag 139680
cctcctgagt agctgggact acaggcgccc gccaccgcgc ccggagaatt ttttgtattt 139740
ttagtagaga tggggtttca ctgtgttggc caggatggtc ttgatctcct gacctcgtga 139800
tccacctgcc ttggcctccc aaagtgctgg gattacaggc gtgagccacc gcgcccggcc 139860
attaatgttt attttgacgc aacttcacag ttacattaag gcaacaatat ggcgcaaaga 139920
attccttcgt atcaggcatt cacattcccc aaacgctggc ggtctacaac agcttcatcc 139980
tggatcagaa ccaagtggag ggactgctgt ttctgtgggc tggtttcctg ggggctgcca 140040
taaccagtga ccagaaaccg ggtgggttcg tcaacaggaa tttatcatct cccagtctcg 140100
gatgtcgatg ttgaagccct aacccccact gcctcagaac gtgagtgtat ttggcctcat 140160
agtattagaa cgaggctgtc agggtgggcc ctaaagcaac ctgctgttct catgagagga 140220
agtgtggaca cacacagaag agacgatagg gatacttgtg cacagtgaaa agaccctatg 140280
agcgtacacc agacggcgtc cgcaagccga ggagaggaga aaccagccct gctgacaaca 140340
```

-continued

```
ccttgctctc ggacctcagc ctccaggtct gtgggaagat aattttcagt gaagccctcc 140400
agtcttggta ccttatggcg gccctgaaca ctcatacaga cgggtacatt tactgtccct 140460
gttcttctgc cgaggaaatg gaggcacaga gacgtttagt gaacttgacc catgtgggag 140520
ggccaggagc ggtcaaggtt ggattggaac aaaccaccct ttttgcagca ctcacgttct 140580
taggcacgac gcctgcttcc ttaggtgctc tgcaaagaga atacggcaga gtgcaccccg 140640
aacacgcaac ggtacagtca caaagatgac actggctcca agtgtcttca gcaaaatggg 140700
aacgtgtcag aagagtaggg gggtctctca tggcgtgaat acaaggcccc tagaaaggaa 140760
gagacagctc agcccaccac cctcagagga aggtcttggt tctgctttac cactgagtag 140820
tttcccacct ccgacaggag aaggcctcag tacctagacc tcaggaccta gaaggtctca 140880
gtacctaggc gacctcagta ccgacgaggt ctctgtacat aggagatctc cgtgcctagg 140940
agacctcagt atctaggagg tctcagcacc gtggcgacct cagcaccgag gcaacctcag 141000
taccgaggcg acctcaatac ctaggaggtc tcagcaccga ggcgacctca gcaccgagga 141060
gacttcagta ccgaggagat ctcagtaccc aggggacctc agtacctagt aggtcaaact 141120
gagagacgaa acgtagaggg gaggttgtca cgggctgggg gaggcggaaa ggagagctgt 141180
tcagcttgga aaggtgcaaa cgttctgcag acagacggtg gcgccgagcg caccacgcga 141240
tgtgctcagt cccaccgacc tgcgccctga aaacggccag tatggcaaac tccgtgtttt 141300
gtatattgtg ccacaaagaa gaaaaagtgt cttagggaga gagggaggga gagagggagg 141360
gcgaggagcg agggcgccgc ggccggcccc gccccgcccc gccgcgcagc cccctacagg 141420
ccgagcagct cgcgcggggt cccgcgtccc ccaggtcggc tcccgcccgg ggctgggccg 141480
ctgcgggaac agggttggcc caaggcagcc gccggtcccg agcagcatgc gcgatgcggg 141540
ctgggcagga ccccgtggcc cctccgccgc cctctcagtc cgcgcgaggg ccccactcgg 141600
ggctcggccg ggctccggga acgcggtctg cggtccaggg gccgcgagcc tccgccgctc 141660
ctcggcctcg tgggcccggg cgctgggtgg ggccgcgggt gggcgtcagg ggccaggctg 141720
ggcgccgagg tctgcaaagg ggcggagaag acgggcttgg gctccgcgca gaacctgcga 141780
gtgggcggcg gtgcacctcc cacccgggtc acctcggtgc cacccatgcc tgcctcagtg 141840
caggcggacc cacggccctc cacgccctcc ctcgctcgcg tgctgcccgg ctggccgctg 141900
ttcgcatcct ctcgctaact ccgtggggtc ccgcccattc gggcgactgc cccggctgca 141960
gcccacccgc taatctcggc tatcttccct cactcagttc ttcgcctcca ccagcttcgg 142020
ctcttttcgt caccccctctt tactccccgt tcctctccgt cactttccgt catctccgaa 142080
taggctcggc cggctgcatc tcaccatttc gctttcctct ttgtcgccct ctgataaatt 142140
tcgtgactct tcgtcactgt ccgtcagtcc ccgtcacttt ccgtcaattc tcgccacttt 142200
ccgtcgctct ccgccgccct tcagctccgc tcggctcttc tccgtcagac atcgtctact 142260
ttcgtcactc tccgtcaccc ttcgtcactc tccgtctgct ccctaccccg cactccgggt 142320
ggagaaagcc tcagggactt ttcctgccct tagccctttt ccgtccctct ccgatcctgc 142380
tgtctgtcag tccctggtta tttctggtct gctcgtgact ctgtcctcct cccttcactc 142440
ctgggagggt ggcctggtcc ctcctgagag gcctctcccc actacccggc ctgaatgatg 142500
gtggtgagcg ggaggtctcg aggtgatccc gagggaagga gcgggggtct gagggtggtc 142560
ccgagaggga cccgaggggt ggagcggggg gagggtctgg agatggcccc gaggaggtcc 142620
cgataggagg agcggcagtc tgggggtggt gccgagggaa gaagccgtct ggtgtggtct 142680
```

ggaaaatggg agcagggggt ctggggtggt cccgagggga ggagcggggg tctggggtgg 142740
tcccgagggg aggagcgggg gtctgaggtg gtcccgaggg gaggagcggg gggtctgggg 142800
gtggtcccgt gggtaggagg gggggtctgg ggatggtcct aagaggagga gcagggggtc 142860
tgggggtggt cccgagggga ggagcggggg tctggggtgg tcccgagggg aggagcgggg 142920
gtctggggtg gtcccgaggg gaggagcggg ggttctgggg gtggtcccga ggggaggagc 142980
gggggtctgg ggtggtcccg aggggaggag cgggggtctg gggtggtccc gaggggagga 143040
gcgggggtct ggggtggtcc cgaggggagg agctgggggt tctgggtgtg gtcccgtggg 143100
taggaggggg ggtctgggga tggtcctaag aggaggagca gggggtctgg gggtggtccc 143160
gaggggagga gcgggggtct ggggtggtcc cgaggggagg agcgggggtc tggggtggtc 143220
ccgaggggag gagcgggggt ctggggtggt cccgagggga ggagctgggg gttctgggtg 143280
tggtcccgtg ggtaggaggg ggggtctggg gatggtccta agaggaggag cagggggtcg 143340
ggggtggtcc cgaggggagg agcgggggtc tggggtggtc ccgaggggag gagcgggggt 143400
ctggggtggt cccgagggga ggagcggggg tctggggtgg tcctaagagg aggagcaggg 143460
ggtctggggg tggtcccgag gggaggagct gggggttctg ggtgtggtcc cgtgggtagg 143520
agggggggtc tggggatggt cctaagagga ggagcagggg gtctgggggt ggtcccgagg 143580
ggaggagcgg gggtctgggg tggtcccgag gggaggagcg ggggtctggg gtggtcccga 143640
ggggaggagc gggggtctgg ggtggtcccg aggggaggag ctgggggttc tgggtgtggt 143700
cccgtgggta ggaggggggg tctggggatg gtcctaagag gaggagcagg gggtctgggg 143760
tggtcccgag gggaggagcg ggggtctggg gtggtcccga ggggaggagc gggggtctgg 143820
gggtggtccc gaggggagga gcgggggtct ggggtggtcc cgaggggagg agctgggggt 143880
tctgggtgtg gtcccgtggg taggaggggg ggtctgggga tggccctaag aggaggagcg 143940
ggggtctgca tgtggttttc aggggtggag catggggtct ccctgtggtt cggagggtgg 144000
agcagggggt ctggggttgg tacttttggg cgggacagcg ctatttctct ttttggtccg 144060
gttcccatct gctgatctgg gggtccttgt gatcctgaca ggtggggccg aatgggaggg 144120
tcaaggtgag gggaaggaag gagtggcagc ctggtcccaa gggagcagga aagggtttgt 144180
ggttcagttc tgatgtgtga cccatccata ggagaatgga cacctcagac tctctcaatc 144240
ctggccagtg gcaggtccca gtagctgcct tccctggctg tccttgaggc tcactggagg 144300
atacttcttt ttcattctgg caaattttaa aaaattcttc tatagatctc agtgagttca 144360
aagctgcctg tgtgcaggca tagatccgtt ctttgctgag cttccactct agtcggctga 144420
aaggaaaggg taatatagct ggaaaaggta tcctggggtg attagaggat tctacatttc 144480
atcttagaaa gggatattga caggagacca gaacttccag atcctcttga atttcaagaa 144540
ctacttccaa gcctggacaa tatcgggagg cctcatctct acaaaataaa aattaagaaa 144600
ttcgccacgt gcgatggcac actcctgtag tcccacctac tctggaggct gaggcgggaa 144660
gatcgcttga gcttgggagt ccgaggctgc agtcagctgt gatcatgcca ctgcactcca 144720
gcctgggtga cagagcaaga ccctgaaaaa aaaaagggag ggagggaagg agggagggag 144780
ggaggaagga aggaatgaag gaaggaagga aatggcttaa gctcagagag ctgtgtgtgg 144840
cccccagctc ccacccccac caaagggcct gcaaacccac ggaggggcag gttgtcttga 144900
gctggagcta cggggacggg gggacctgaa ctgtcggggt tagggttagg gttaggcttt 144960
gagatttcgg gttacagaat atagatgggt ttggtcctgg gaaaattcca ggtctgggtt 145020
ttgcggttgg gggttggtct caggtgagat gcggcaggtt tacagtgttt gcaaggtatg 145080

-continued

```
tacagattta tatggtgcta ttgcttgaat gtgttctcca gatttcatgt gttggcaatt 145140
tttttctttt tctttttgac atggtgtctt gctctgtcat ctatcaccca ggctggagtg 145200
caatcgtggg atctcggctc gctgcaacct ctgcctccca ggttcgagcg attctcacac 145260
ctcagcctcc tggtagctgg cattgtggca ggacaagccg cagacaaaat tcctcagaca 145320
ctgggttaaa gaaggaaggg ctttactctg ccaggagcat cggcacactt gcgcctgaag 145380
agccaagctc cccgaaaacg aaattcctgg cccttttaag ggtttacaac tctaaggggt 145440
ttacgtgaaa gggttgtgat agatcgagga agcatgggga acgtgactgg gggctacacg 145500
catcagataa cagaacagaa agttttgcag ggcttcctca tacagtgtct ggaatttaca 145560
gataacacaa gtagtttagg tcaggggtta atattattat tattattatt ttaaccacca 145620
gggtcgggtg gtgctgccaa gatcatctag ctatttatct tacttctgtt tttttttttt 145680
tttttttaag ctttttgctt tctccctttt tccctgtttt ataaactaag gaagcggtgt 145740
ggggaaggga agggcagcag gaggagtggt ggtctccttc cttaggatta caagcaccgg 145800
gcctcattcc tggctaacgt tttttgtttt ttttttgtat ttgtattaga gatggggttt 145860
caccatgttg gccaggctgg tcttgaactc ctgacctcag gtgatcgcct gccttggcct 145920
ctgaaagtgc tgggattaaa agcacaaggc agctgggtgc ggtggctcag gcctgcaatc 145980
ctagcacttt gggagaccga gatgggtgga tcacgaggtc aggagatcga gaccatcctg 146040
gctaacatgg tgaaaccccg tctctacaaa gaaatacaaa aaaaaaaaaa aaaaaattac 146100
ctgggcgtgg tggcgggcgc ctgtagtccc agctactcag gaggctgagg caggagaatg 146160
gcgtgaaccc gggaggcaga gcttgcagtg agccgagata gcgccactgc actccagcct 146220
gggcgacaga gcgagactcc gtctcaaaaa aaaaaaaaaa aaaagcacaa gccatcgcgc 146280
ccagccatgt gttggcaatt taatccccga attcatgtcc tgattggaga tatggccttt 146340
gggaggcaat taggattaga taatgttatt aggttgggtc cccagtcatg ggactcgtgg 146400
ctttataaga tgaggaagag agactggagc ggacacgcag tcttgccctc tcctccctcg 146460
cccgcacact cttgctctcc cctcccctgc catgtgcagc cctccactgg gctgtgatgc 146520
tctaggcctc cccagccacc agaacttgcc ctcccctccc cggccatgag tggacacgga 146580
ctcccgccct cccgccatgt gccgccctcc actgggctgg gatgctctgg gccatgtgct 146640
gcctggggtc caggggccgt tagtctccgc cgctcctcgg cctcgtgggc ccgggcgctg 146700
ggtggggccg cgggtgggcg tcaggggcca ggctgggcgc cgaggtctgc aaaggggcgg 146760
agaagacggg cttgggctcc gcggagagac tgccaggggg cggcggtgca cctcccaccc 146820
gggtcacctc ggtgccacgc atgcctgcct cagtgcaggc ggacccacgg ccctccacgc 146880
cctccctcgc tcgcgtgctg cccggctggc cgctgttcgc atcctctcgc taactccgtg 146940
gggtcccgcc cattcgggcg actgccccgg ctgcagccca cccgctaatc tcggctatct 147000
tccctcactc agttcttcgc ctccaccagc ttcggctctt ttcgtcaccc ctctttactc 147060
ctcgttcctc tccgtcactt tccgtcatct ccgattaggc tcggccggct gcatctcacc 147120
atttcgcttt cctctttgtc gccctctgat aaatttcgtg actcttcgtc actgtccgtc 147180
agtccccgtc actttccgtc aattctcgcc actttccgtc actctccgcc gcccttcagc 147240
tccgctcggc tcttctccgt cagacatcgt ctactttcgt cactctccgt caccctccgt 147300
cactctccgt ctgctcccta ccccgcactc cgggtggaga aagcctcagg gggtcccgac 147360
aggaggagcg gcagtctggg ggtggcgctg agggaaggag cagtcgcgtg gtccggagga 147420
```

caggagcagg gagtctgggg gtggtttcgt ggggaggagc agggggtctg ggggtggttc 147480
ccaggggagg agcgggggtc tgggggtggt cctgagggga gaagaggggg gttactgggc 147540
gtggtttcgt ggggaggagc agggggtctg ggcgtggtcc cgagggcagg agcgggggtc 147600
tgggggtggt cccgagggga agcgtggggg tctggggatg gcgccgaggg aaggagctgt 147660
ctggtgtggt ccggaggaca ggaacagtgg atctgggggt ggtcctgagg ggaggagcgg 147720
gggtctgggg gtggtcccga ggggaagcgt gggggtctgt gggtggtcct taggggagga 147780
gcgggggtct gggggtggtc ctgtggggag gagcaggggg ttctgggggc ggtcctgatg 147840
ggaggagcgg gggtctgggg atgatcctga ggggaggagc tggggtctgg ggatggcgcc 147900
gagggaagga gctgtccggt gtggtccgga ggacaggaac agtggatctg ggggcggtcc 147960
cgtggggagg agcagggggt ctgggggtgg ttttcaggga tggagcatgg ggcctccctg 148020
tggtccagag ggtggagcag ggagtctggg ggtggtactt atgggcggga cagcactatt 148080 tctcttttttg gtccggttcc catctgctga tctgggggtc cttgtgatcc tgacaggtgg 148140
ggcagaatgg gagggtcaag gtgaggggaa gggatattga caggaggtca gaacttcaag 148200
atcctcttga atttcaagaa ctacttccaa gcctggacaa tatcgagagg cctcatctct 148260
acaaaataaa aattaagaaa ttcgctgggt gcgatggcac actcctgtag tcccacctac 148320
tctggaggct gaggagggaa gataacttga gcctgggagt ccgaggctgc agtcagctgt 148380
gatcatgcca ctgcactcca gcctgggtga cagagcaaga ccctgaaaaa aaaaagggag 148440
ggagggaagg agggagggag ggaggaagga agggaaggga gggaggaagg aaggaatgaa 148500
ggaagaaaat ggcttaagct cagagagctg tatgtggccc ccagctccca cccccaccag 148560
agggcctgca aacccacgga ggggcaggtt gtcttgagct ggaaccacag gggcgggggg 148620
acctcaactg taggggttag ggttagggtt aggctttgag gtttcgggtt acagaatata 148680
gatgggtttg gtcctgggaa aattccaggt tgagttttgt agttgggggt tggtctcagg 148740
tgagatacgg caggtttact tgggcctgaa gagccgagct ccccgaaaac gaaattcctg 148800
gcccttttaa gggtttacga ctctaagggg ttcacttgaa agggtcgtga tagatcgagc 148860
aagcatcgga acgtgactgg gggctacacg catcagataa cagaacagaa agttttgcag 148920
ggcttcctca tacagtgtct ggaatttaca gataacacaa gtagtttagg tcaggggtta 148980
atattattat tattattatt ttaaccacca gtgccgggtg gtgctgccaa ggtcgtctag 149040
ctatttatct tacttctgtt ttttttatct ttttgctttc tcccttttttc cctgtttcat 149100 aaactagaga agggggtgtg gggaagggaa gggcagcaga agtggcggtc tcctccctta 149160
ggattacagg caccctgcgt taacctcaaa attgtctcag tcccaaagaa ggggctagat 149220
tttcttttat actttttgttt agaaagggga gtggcggtct agttaaaaga attttacata 149280
agtaaatcag gcaaaatgtt aaaaggataa atggttacag gaaagtaaac agttccaggt 149340
gcaggtgctt taagactatt acaaggtgat agacgcgggt aattgggcgt tatcaatcgg 149400
acgaattcct ggggactgcg gatgtagctc gccacagtag gttgtcagtt aattgcattc 149460
tcggatgtcc tgggagtcag cttgcacgag ttaagtcttt gaggaagggg ctgccagtga 149520
aagagccaag atggagtctg tccggttctc tcagttaagg gagagtcctt tcaggtggaa 149580
agaaggctag gtgattgaag gaaagggaga gtctaaaaac agggttagca aaaatgaggt 149640
tgggcattac agttgtaccc tccatcgcct cttccaatct caagcaattc cataacttgg 149700
aaaacctcag gcaaggactt cctggaatat gtccactgta acgaccaggt tttccagtgt 149760
gttatctaca ccctgtaacg ctgttaggta cataatgttt cagcaatctt tgttcttcac 149820

-continued

```
cagcactctg agtacatgaa aaaggccaag atgcttcttc agggatgaat tttgctactt 149880

tttaaaggag acttaagagg cacttttggc actctaagtc tttcttcaaa tgatgaaatt 149940

tgttacctat ttaactcatt gctgtgacgc gttttccaat tctatgttcc cttggttttt 150000

gttgtatttt tttctgcatg aactctacat catttactca ctctgaacga cagaataaaa 150060

gaaattggcc accatatcat actcggaagg acaatcatgg ccatgagaca caaaggactc 150120

ccagccctgg gcccaggccc ccctcacgca tgcagccatc gcggcactgt gcctgagtgg 150180

gccatatgca tggtggggac ccgatgctgg gagacacagc tcagggcaca ggggccccaa 150240

gaagccatag ctggggaaag ctcattcccg acagggctca gctccaacct gaaactagag 150300

tcccaccctg ggtttccat ggtggtggta aaccaaccac agattttggg gatatgactg 150360

ctccctttgc cacgatagct tcttccacgt gcccctggcc tgatgaccag accactagag 150420

aggggaggcc cgagtcccag ggatgggtgg gttgcaggca gagctggggc tggatggacg 150480

gtgagtggtg agagctcaag gtgcagaagg ggctcctgtc ggggactggg ttaacaggga 150540

ccgggacaaa tagacgggga ctcccgagat gagaaagacc ttttcgtaca aagtgtttgc 150600

atcagtacct cacaatgaaa agaataagat aaataacagt acaaaaaagc aatcaccaga 150660

tcagctcaag gcactctttg aagtcccccc tgtgtaggga agttggaaga catatctgtg 150720

tggcccatag agagtagatc ccaaagacag aaggcccaag tccctaaatc cccacagggg 150780

aactgtgtta cagaccagga gctcatgtac agggctgtcc cagggcccct aaattccaga 150840

agggaactgg gttagagtcc aggggctcat gcaacgggct gtccctggtc ccctaaatcc 150900

ccacagggga actgggttag agatgaggag ctcattttcc gggctgtcca ggtcccctaa 150960

atcccagatg ggaactgggt tatcaaccag gtgctcttct aggggttgtc tcagggtcct 151020

agtgtgtctg gaattggtgg gttcttggtc tcactgactt caagaatgaa gacgcggaac 151080

ctcgcggtga gtgttacagt tcttaaaggt ggcgcgtccg gagtttgttt cttctgatgt 151140

tcagatgtgt tctgagtttc ttctttctgg tggggttgtg gtctcactgg ctcaggagtg 151200

aagctgcaga cctttgcggt gagtgtcaca gctcataaag gcagtgtgga cccaaagagt 151260

gagcaatagc aagatttatt gcaaagagtg aaagaacgaa gcttccacag tatggaaagg 151320

gaccccattg ggttgccact gctggctcag gcagtctgct tttattctct aatctgctcc 151380

cacccacatc ctgctgatag gtccactttc agagggttag ggttagggtt agggttaggg 151440

ttagggttag                                                        151450
```

<210> SEQ ID NO 2
<211> LENGTH: 146152
<212> TYPE: DNA
<213> ORGANISM: Mus musculus

<400> SEQUENCE: 2

```
gatcaataaa acactgctca gcgtgctacc tctatggaga gttcacttcg taccatatac     60

gttctctttg cgcgttccgc ttttctgcca cacttttctc tattccgtac aaacaatcct    120

aattaatatc tacaatttta acctctgata atacatttta cgtaagagtg gttgagtttg    180

gatatctatg ttatgaggtg atcaatggat tcacagtgtg tatgtggtta ccggcttctt    240

ttttaaaact acatccgggc tggtgagatg gctcagtggg taagagcacc cgactgctct    300

tccgaaggtc cagagttcaa atcccagcaa ccacatggtg gctcacaacc atccgtaaca    360

agatctgact ccctcttctg gagtgtctga agacagctac agtgtactta catataataa    420
```

-continued

```
ataaataaat ctttaaaaaa aaaaactaca tccatgtggt tttccggagg ttgttaattt    480
catgggtatt tagtcagctg ttctcatgac tgcgatacaa gtgagcatta tccattcctt    540
gaacaggaaa gagaagccga taaatattgt catcatgttc agtcctcatc atctcctttc    600
tgtgttgaga tcccttcacc cagctcatct gaaaacagtc gtcgaacgcg gaagggaatc    660
agccgagaga tactcactga caacattggc ttgtccggtg aatatggtgt actggagctc    720
gtaggagacc acgctgaact cgtcctctga ggtccagtgg acggtgatgg tgtcatagga    780
agcggtgcag agctcttctc taatcgtggg agcgttggga gctgtggaca tcacacgcat    840
gtcagcggag cagcagatac cattaggacg acaatttgga ggtattcgac tgttgaagca    900
ggtcttcctc ctaaacaggt ctagcacatt tactaacagg aggttttggt tccagagcgc    960
tcagccgtct acttaaagaa tgtttcaggg tttatctgtt gttgattttt ctaagcggtg   1020
tgactaaagc cagccagccg gccgctaaga cgtcacctcg atttatcatg agaatatatt   1080
tatgagagta agagaacaat agcttcttgt gtatgaagaa agatagatca gagaaaaagt   1140
aaccatggca gactttcata atgtcattct catttggtag gggtgggggg gtggaaatct   1200
tactaatcaa ggactatagg atcgacattt taggtattgt aggacagact tctgctctcg   1260
cacctactta accctgccat tagagcggat gtagatgatt tgtacgtaaa gagtacgacc   1320
agactctcat aaaatcttat ttacaaaaca gccacagggc ctgatttggc ttgaaaccca   1380
ctatgccaat ctctcgtcca cacgccacca gctattttaa aaaatatcac ggtgatctgc   1440
taagaaatca acaagtcatt taaattcttc ctttatcttt attttcttgt ccctgtttct   1500
acttggtctg tgttatttag gttagaatac agcgcggaca ttcatcttta taggactatc   1560
agatagcatt tcagagactg aagcacgtgt atgggtttta gaagataatc gactcaatgg   1620
taaagtgaat agacactgta ctagagagaa catagaagag agtaagacga tacctgttag   1680
gtaatccaga cactctagca gtttcttctc ccgggaaaaa tccaaggcaa aagtgtcaaa   1740
cgtgtcattg aggttgattt cgggaattag gacctgggag gatgcagttg ccatggagac   1800
tctgtcattt aaacaagaca ctgttttaag aaatgtcaag gtggctttta tcaccactgt   1860
gaaggagtga gaacaaaacc aaaggaaaag aaatatcagg gttttaaaaa gcacccccctc   1920
tgaaaaggcg tcacgtgcga acgcaaacaa cctcacagag aaagcagagg aattgggaga   1980
ggtaacccgg tgccaccccc cccccttctt taaaatatcc gaaaaagtcc ccacggaagc   2040
agaagaatct tcatatttcg tgctgctgtg tatttgacag cccggcccgg tcacatcgaa   2100
ccccggccag aagcgcacag cttcaggcat ctcttcacac atctgtctgg gaaactgtct   2160
gttcctttca gactcgcccc tgccccactt ccaaggggag tctccagaat ttcaaactgc   2220
atcaaaggca gagtgaagat taaaaaagaa tgtctccaga tcttggatta gtttaatcaa   2280
ttactagccc ctctctaaaa taaacatgaa aaggggggga ggggttgtct ggctctttct   2340
cgttctcccg ctattcgcct tttttcccct accgtcttcc caacagatgc cacgggaaat   2400
attcctgagc tttctcagaa attccccagt cggcacacaa tctcgtccct acgctcagat   2460
tttctggtga gtgctccctt gtataaagcg taaagcaagg tatgtgtgtc tgtctcctgt   2520
gtgctcttga gttcatttgg aaagtgactg acagcagaac aatctagcgg gtgctaaaat   2580
gcaagtaatt atgtttacac aaagaaaacc atgtcttgaa taatgctact actgagcata   2640
gagaatgatc tagacttatt ttgatgtgtt ttatggtttt gttgagttca agctgaaggc   2700
tgtcacggaa agggttttat catgtcgaag gaaagcgttc ttagctggag caaaccagcc   2760
gaagcttcca ttctctctgg cactcgacct ctaacagaaa acaagtcagt cggagagcaa   2820
```

-continued

```
ggccgaccgg tcagtcccac gcagatatga gccaccatca gcctgacagc ttcccagctg   2880
tccctgcacc cacctctcag tgatattctt tgctgtctgt agaaaacggg cgtggtcatt   2940
ttccttcagc gagtgctccg cttgcgagat gagcgatgca gacctctcaa ggcactgttt   3000
acagtttgca atctgctgag ctaacttgcg gagcctgatc acctggaacg agagaagcac   3060
ggcgggcgag gtcacacgtt aaggatcgat cgcttgggag gtggctcagg gctgaaccct   3120
tcagaggcgt gaggtctgtt ctgtctaagc agagagaggt tgaaatccgg aaggcaaatt   3180
tttggaactt gaactttcag tctttggaga agccttagtc acctgtttga tgaggagaca   3240
ctaattcgtg tcagtgtgac actaactcac actagcatcg ctcattactt ctctgttgaa   3300
ggggggaaag gtgtccgctg gcaagtgaca aacggtcacc gaatctcttc cttctgccat   3360
cctacctaat gacttcagga ccttagagaa ccctggaact ctctccatct caggttttca   3420
atatgccttt aagaaaataa aacatgtctg taggtgtgaa ttcgaggctt aagttaaaaa   3480
cagtgaaaaa aaaccctaca aagttctttg taatccacgt aataaagttg tgacatgaaa   3540
gcattaggta ttcctatttt ccatactgcc taaaacctgt gtatgaaatt aacagagagg   3600
gagcattttc ccattgattg atatttttct tattggactg atgagagaaa gccaaaaaaa   3660
gcacagctgg gccatttcct ctcactgtaa acgtcatttc cagtcacttt gtgcagcatg   3720
gtaaaaacac atcgttcatt gtaaaggtag gtcttgtccc tatcaggaga agtgtgtacc   3780
cgagtcgaac aaaataacac catttcacac cagatagaac agagcctctg gcaacattat   3840
ctagagagtc gaggcagccc tctagcctaa ctcagggtgt tagaacacat ctattaggaa   3900
ctgtcagagg aagggagaat tccagaagga taagttaata gtctcaacca taaaccagat   3960
gagtggaata tttaattata taacataaag aagatttaaa tggtacggcc aagttgaagg   4020
cagatgataa aattctcacc aaacgagatg aggtcagact actcttctgg cttcatttca   4080
tgtcactctc ttagcctttg aataggcaca gcagagacca cacgtctcaa aaatgacggc   4140
tcttcaatgt catatttttc aggtttttcc tctgaggcta tgtggagatt aacggtgatg   4200
tttaaggaca agaagaataa ccgaaacagg agatattgat gtaaaagaaa ttgagagcat   4260
actgtgaaac tgccacgatc ttctcgagtg gacttccatg tagagcgtac ttttcattac   4320
aggtcagttg acagttgcct cggagattca caaacactgt gtgcgataga atcagctggg   4380
gatctttccc aggaaaactc tagatgtctg ggcacatcct ctggcattct agttaaggag   4440
ctgccattgg cagagccaca gtaatttgca tttgaacgag caacgcatgt ttttaagtct   4500
ccgggtgatg aatgactagt atggtcggga ccagcatttc aaatatcaat ctcgctttaa   4560
tctttgagtc catggacatc tgtcatgctt gaatgtcact cagacccttt tgtcccttct   4620
tacctcgatg gaactcccca ggcagaggcc aaaactcagt ccccacggaa gcagaagaat   4680
attcatattt cgtgttgctg tgtatttaac agcctggccc ggtcacatcg aaccccagca   4740
agaagcgcat caatgataat aaaagataat aaaaaagaaa aacgaacgtg cacgcagatg   4800
ctttccaaaa gaatcaacgc tcacggaaac caaaaacaag tgtcctttga aaaaaaggaa   4860
aatcgaacgg tcacgaccac cgcattctcc tctgtcacca ccgggtggcg acagagagca   4920
cgccgggaaa aaaaaacttc ctccgagggg tcggattgcc caatttcttc tgtagctgtt   4980
ttctgtcaca taattgtcta cgagtttacc tccaaaactt attgattgca ttcccgtctg   5040
tgtgtttctt ctttgagtcc ttttttgtct gtgatttctt tatctctaaa ctgtttcttt   5100
tcaggtctgc gtcctcttct gcaaaacgaa tcttaccgga aattagataa tgctgctgat   5160
```

-continued

```
tttgctggct gtgcttttag aaactcaaga tttcttggct tgcttcggaa atgagctcag   5220
cacctcagtt ttaaagaaaa gaatctgaaa atagcttctt gttctccttg gtgtgctcta   5280
atggttttac ttttctgctt tcccctaacc aggctcctgg gctcagcgct ctgcaatcca   5340
atctcactgt ggactcctgt ctcatctctg tgtctctgag gcacctgtct ggtgtgataa   5400
tagaatgagt ggagtacggg tcctcttaac gactgacttg ttccagaacc tcagaactga   5460
agtctgccaa aagctatgat gccaggcaga catcggcaat actctcttcc cgtccctcgt   5520
aatgaataag aagccttctg cagtctgtgg cgctgaggca caggcctggt ttctgccttc   5580
catccgatcc aaagcaattc cagattcttc caggatgttt tttaggcaca ggcatcggaa   5640
ctgcaggcat gcccgtatct cttcaaccat gcctgtgctt ccagccacag ttgtggcatt   5700
gcactttcat gccattcctg cttcaccgaa atgctgctct catttcactc ttcaccgttg   5760
gagtccatgt ctattaatgg tgtatgtctg cagcggagtg agtgctacaa aagatggact   5820
ctacctataa tcatggccca aactggaata ccttttatta ctatcctcta gctcctgaaa   5880
ggaaacccca ggccgtgaaa ttcaagctgc agctgagtaa gggtaagtaa gtacggttgc   5940
tgcagaggta tgaaaaagtg ccactgcaat ctgaagatgg actcttagcg aagtccacat   6000
cggcaccttg ggaatctttc agtatgctac cttccatacc aaaggaactt tgtagatgtc   6060
taggttaaga atcttaaggg gttggggtgg tccaggatcg tctgggtaat ctctacataa   6120
ttcctaaggt ctttatgaca gagagacagg acggttcatg tcagtgaagt agatagcagg   6180
atgaagacag aaggcagagt gctaatgact tagttgtgag ccaaggacca tggatgacct   6240
ccagaaactt gacaagacaa gcatagctta ctaacattgc ctttaaccta tgtagccttt   6300
agtacagtga gactgctctc agacatcaga acagtaagat aatcaataag aaggttctaa   6360
gctacacagt tttggtaatg tgtaatagta cgatagaaac catcataaga agaatacaga   6420
accaattaaa caggagaaca gaggcttttt aaaaaaattt tttgagctac attgcataga   6480
ttaacaaata taccaaatgt aaatttctta cacttccaga ttactagacc gttaaattcg   6540
agaatttatc accacaaaaa taagtgtttg aggtgatgaa tatgttactt agcttgattt   6600
aattattata cattctattc atgaaccaca gaatcatgtc gtatccacca acatgtacac   6660
gtgtaacttg tcaatttaac attaaaacga taaattttct aaagaaattt atgtgggcat   6720
gtagagtatt gatcctggca tgcaaccact tgacaatagc agattatctt cttggaacat   6780
aatagcaact aaccatggca gaaaaacagg catctgagaa actaggagac gaaaggaatg   6840
agagatgagt ccacatgatg aaagaagatg cactatgcgg aagtatattc tcagtagatt   6900
ctaggtggac acttactgcc agaggcattg agcaaacatg gtgccatgct attgggaatt   6960
ttaagaaata tgaataattc tctttcggtt cttcactact ctttgtcgag tattttacta   7020
cagcaacaca aaatggacca aggcaggtag ttaagaaggg attatgacga atgcagagag   7080
tacgatttgt ttttaacttt caaagctgta gatgttggag agaaagtata tattcttcag   7140
gtgagaaata cagaaccttt ttatcaagga aaccatacct tgccttcttt aatctttgtt   7200
ccaataattt gtcttcgttg ctgaatgatt tcaatgagaa gatcacattc ttctgtcagt   7260
ttggcttctt gacgggatgc attgacctac aggatgaata aaatggcatt catcggaatt   7320
tgatcttagc cattctgagt ggctgtgagg tggaatctca gggttgtttt gatttgcatt   7380
tccctgatga ttaaggatgc tgaacctttt ttttttcagg tgcttctcag ccattcggta   7440
ttcctcaggt gatagcccaa aaaacttaga atacccaaga tacaagatac aatttgcaaa   7500
acacatgaaa ctcaagaaga acgaagacca aagtgtggac actttgcccc ttctcagaac   7560
```

```
tgggaacaaa acacccatgg aaggagttac agagacaaag tttggagctg agacgaaagg   7620
tggaccatct agagactgcc ttatccaggg atccacccca taatcagctt ccaaacgctg   7680
acaccattgc acacaccagc aagattttat cgaaaggacc cagatatagc tgacgaaatc   7740
caggcccatc catgttcctg aaaatgtgaa gactccattc tttttatggc agaatacaat   7800
tcccatatgt gtatatacca tattcttaaa atccactctt ctgtcaaggg aactttaggt   7860
tgattctata tcttagctat tgtaaatagt atagcaataa atatggctga gcaagtatct   7920
ctatgttagg atatggagtc ctttgggtac atgaccagga tttgtataac tagttgtgtg   7980
tgtgtgtgtg tgtgtgtgtg tgtgtatttg tataactagt tgtgtgtgtg tgtgtgtgtg   8040
tgtacccttc aaactgagct tcattgtgaa tacactactt tgcattgcca ccagcagtgt   8100
ataaaggttc ctttcacttc tgtattcaca ccagcatctg ttgttgtatc taataggact   8160
ttagaaacat tctttttttt ttttttttcc tcattggacc atgtctggct gaagtgagtt   8220
agccacctac aggctttcaa agcagaactt cccgattcat cctgccaaaa ggatatactc   8280
attcgagaga tggcttcctg ttggtacaca gaaggaacac tgaagtaagc ctgggacagg   8340
ataaagccaa tgtgtcagag acaggaaatc ttacttctga gtattcaggg agaaaggagc   8400
attgctcaat gcactaggaa ttctacaaaa atggttaccc ccccccctgag attacacagc   8460
ctaggaacca tgctggccct caatcagtgc aattttgaaa ctgcaccgct gcaccactaa   8520
acaattacac tttcctttta aggctgttaa cctttctgtc tggtagtttt aaacacagtt   8580
atctacactg tatatttgcc taaaagcagt ctttatggca ccatcacaag ctgggtcatt   8640
ccatactcat ttaaattaag ggaacccaga gaaaggaggc gacattcaca tatgatgtcc   8700
tgtaagtgtg gttatttgga ctccagagca cttgtctctg tatatctgta actttgattc   8760
tgcatctgat tataaagtgg atagttttat ttaaaaagca tggtccggct ctcccattta   8820
actcgaaaaa gagacacact aaaggagtta attccaaagt ggataaattg atattttggc   8880
cagtaagatg agggcatgag gggaaagctg cactcacgtc agctctgtgc cccactgtgc   8940
tctgccgacc aggtgcaaag agaaatatga ggatctgagg gtgctttggt ttttattgcc   9000
aaaggcagcc gtgatgaaca ttccagaccc tggggcagaa gttagacaga gctgccagaa   9060
ggaacaatga aagggatcct aatagtttag tttgtacata aaaccgagcc aaggagaact   9120
gagtaagcac agacggtatt actgtaatac atctgatatg tttacatcga cgttttactc   9180
tgcaactctc tcatagtgtg gcagttcttt tgcacctgtg ttctgggaat tctacaactt   9240
gaactggaga aaacaatttc actatagttt tggccataga agggtttatg aatgctgaca   9300
atgatccaat tacgttgtta accttttttgg gctttatgca tgaatgggag tttgctggta   9360
tagtttaata cgacccagag tccaactcca aataataccg cacagcaacc tgacaaggtg   9420
tcaaatggag tgggaatcta tcacttctct tgaagtagca atgaactaaa aatctcaata   9480
caactttaga tactacagtt gctcactaca ggatctagct catccagatt atacacgtcc   9540
aaatgatgta aacagcacgc atgtgtgtgt gtgtgtatgc ttatgtgtat gtttctctgt   9600
gtgcatttgt ggtgtgtgtg tgtgtgtgtg tgtgtgtgtg tgtgtgtgta tttgaatgct   9660
ggcctctatc caatgctctg gtctggatga tgcaattgcc attgtctcca aaaaaaaata   9720
gaatgttttc ccatttggaa atggcacaat taattgaagc agaaatgctc atctttactt   9780
gcagtttggc attatttcaa agtttataaa taatgatttt taggcttgat caatgattta   9840
aagtcttctg cacacctatc cattcatttt aacaaagaat tctctgcagt gttttacatc   9900
```

attcaagata atttatcccc atcaatcctc tagtaaaaaa actatgatta attcattcac 9960
aaaatatcta gtgctccata tgcaaatgat gggaggtcac agaaggccag aaaaggaaga 10020
aactttcaaa acagaccaaa aagggggtgg ggggaccaaa aagagagcca cagagaattg 10080
gaaaatccag tgaaggtgga ttacaggaca gaaagatggc ttgtcaggta agggagcttg 10140
cttctaggcc tgaggacttg aattcagtcc ttggaatata cacagtggag gagagggcca 10200
attgccaaaa ttgttttctg atcttcacat aagggatata gttaacatgt acattctcac 10260
acacatgtat aaacacacag acacacacag acacacacac ggttaaattt ttgaggcgat 10320
tacaaacaat gaggctagca cactgacaat ctgctggatt tgaccttggg taaggatgat 10380
tagtcagatg ggcctctatc ttccagaaac cacagttgca attatttaca agtttttact 10440
tgttccccat tactatctca atgtggattg atactcaaat caccaacaat tccccaattg 10500
gtcttttatg ttatatttgc tataaaaaca agagtaatgg ctcttggtat tttcttaagt 10560
aataaaatcg gctttctgat ttttctaaga aaattgggaa gacagtgtga taatgagagc 10620
tgtattccat atttgactta cacagagtaa attctgagac taattctgtt taaaatttaa 10680
atagaatatt tttccattta ttggtagtca gcagctcact atgttaccca ggctctccct 10740
gaagaatcca tcctctgcca gaaaatcccc agtgctgatt gtgtgtgtgt gtgtgtgtgt 10800
gtgtgtgtgt gtgtgatcac atccatatcc tgaccacaaa cctcaatcac ttctcataag 10860
cttgttttat gctccagata acagtaactt caaacttgac ctgagggagc ttttactgta 10920
atactctcct ggaggaaaca aagcagaaca gattaaaaac ctattgtttc taaaacccca 10980
gacagcaact taacacaaac agtttgttgg gaggctctct gaagttgctc tttcaatgcc 11040
tctcattccc aagccccaaa ctgccttgga ctttacactg tttcttttct agttttaaaa 11100
aaccagcact tacacaatca caaggccatt tcatttgctt gccctctttg gttaaataag 11160
ttattaaaac aatcagggag cggaccttca agagtttcca tttttaaaag aaagcggaag 11220
tgaacccctg ggaggagggg tgaacttatg aggatgtaac atttcctact aaggcctgag 11280
aaagaattca ttgattgaat ttacaacaat gaggagttac ctctgtgctg tgagttttct 11340
tagctcccgc tagcctggga atgttatttt cctcacgaat tctcagactc ggaagacatg 11400
gacaacttcg ggaagaggaa aaggaagaac tagagtctag gaacctatga tgtgaagcag 11460
gaaattcttt tcaactgtac tgactgaaaa gaatagcttg ctggtgccca acatattcca 11520
gcacctcttt ggaagtccct taatagtgtg gcattttccc atggatgggt gattattttg 11580
caggaagata aaataaaaaa ggtaaaggac aggaaagaac atggcgccaa atgaagtaaa 11640
aagaaataaa agaaagagat gactgctcct gggtatggta gaggagaaag gtttttatag 11700
atacgtgggg gagcatagcc agaggcaaga accttagaga gagagtctgg agtggacatg 11760
aacacactgc catgtgtcat gtgaggagaa aggtgaagga gggcaagaga gaggtgagag 11820
agaagaacca cgttcaggag tcaggaggct caaagttaca aagagaaagg ataaccaaag 11880
tggttggatt atttagggag gagcggcctg tgccagagag ttcagagtaa gggttgagga 11940
atgccaccca ggtgggtcct ataacaggga gggactggtg gatacaggga acttgggggc 12000
caggtctgtt gtgatatgtt agataggtat ctcagccatt tgtcccaggt ttcaaacata 12060
gcacagatta tttttcaaat agctacaaat atcaatttct gaaatgagtt aggttttaag 12120
tgcgaagcca acaaaatcta tgtgcttctt gaaatgttgt tgtaccttca agaaccaatt 12180
tccaactcag gtaccaaatg aaacgcttct caaccctcat ctctccagag ctgctcctta 12240
gctatctttc cttcatgcat gcctttcatt tttccagaag acacacacac acacacacac 12300

-continued

```
acacacacac tctctctctc tctctctctc tctctctctt tctttctttc ttcttttttt  12360
tttggttgtt tttttcggaa cagggtttct ctgtatagcc ctggatgtcc tttgtagatc  12420
aggctggcct cgaactcaga aatccacctg cctctgcctc ccaagtgctg ggattaaagg  12480
cgtgcgcccc caccgcccgg catccttttt ctttaatgct tcctgctccc tttttttatat  12540
accagggcat gatatcctct ttggttcaaa tagcttttat gactctgatg gctccttcct  12600
cagtcaatta tcacaaaata acttggaatt cctttttaaa aagtattctt tgagaatatt  12660
aacaattagg ataaatgtaa tagtagatac tgttcctgcc atttttctac tcataaataa  12720
ttacctagta cttacttaga atacacttac ttccactcca aaggatttac aaagcagcag  12780
gtaaatagat actcttaaat tttgttaaga attacttcta atggtatgta cgactgtttt  12840
taaaatggcc acaattaatt gagtaatttt ttttttaatg agtatcttaa ctagaacaat  12900
atctgatccc tggaaataaa taatctggtg gtaagtttct tgaatttatt tcccatctga  12960
aaattactat acatgatagg atataatttt acatcacatt acaatgaata atattttgta  13020
aattccagtc atactaaaat tgcattagga acatggcatt agttctgaaa acattaccag  13080
ccataatgca aaccagacac taatgctttg agaagtaact tgctgaaatg ggatgaaata  13140
atcacgcgat acataaacca tttataggat ttaccttaaa gcacaggtga tttgttttta  13200
ctgaagagaa ataattcttt cttattattc caaacatcaa gtgccatcgc atcataaaaa  13260
taaaatatgg cacatgaaca ttctattttt catcctttta ttcatattcg ctttgctatg  13320
aaataacgaa aacatcatgc atcttcacta ttatttccca tattgtctaa tcaacaaggt  13380
acaaacaaat gcagtttcag tagatgagaa aggtcaaggt tctgcaactt gcagtcgcct  13440
tcacgttgca tgctgcgcct gagcagcata aaagacagaa gtatcattta gtgccaaaag  13500
gaaagggtct gaggcatgaa cccgagagcc aatcctttca acttccattc tctaactttt  13560
ctttctccat ataccatatt catcagcact taagtgacca acagttaaaa cggatggttt  13620
aggcaaggaa aaacacctct cttgttagtc ctaaatactg cagaaattta gagcttgaaa  13680
aattggccaa cagacttact tctcagtaac cagttttaaa tttccaatca tgaagaggga  13740
gctcataagt aaaatcacaa cctttatgaa cacaaaatat tttaaacctt acacggaatc  13800
tccaatattt acataaaaga gaagctttta agctgagtgt atttgaaagc ttagctttat  13860
tgtgctgggg aatgtaccat catcaacacc attgaatgac ataaaataag ctgatatccc  13920
caaatccttt tttattagat attttcttca tttacatttc aaatgctatc ccgaaagtcc  13980
cctctacctt cccccaccc cccccgccc tgctccccga ccctcccaaa tactggaatt  14040
tttaaagaca gtacttctga aatctatagg acaagttcaa gtcctggcta ctcattaaat  14100
tccataagct ttcaggcaaa tcgtaccccc tttcctctct gtgtgtcttc atttctgtgg  14160
actggttgag atgtgtgcat gtggaagcct aaggacaacc ttgttgtcat ctctcagaca  14220
ccatcccacc atctaccttt ttttctttgg tggtcagggt ttctcattgg cctggaactt  14280
atcaagtatg ctagcctaaa cggtcagtga gggcctacct gctctccttg gcgcagagat  14340
tacaagcatg aaccaccctg acttgtgatt tgttttagaa acttaggttc tagggatcaa  14400
acttgggtcc tcatgcttgt aagtcaaacc ctttaatgcc tggacaattt cattggtccc  14460
cacttctttc ttcctttctt actttcactt gcacttgtca ctctggtaag tggcattctt  14520
tcctgtttgt accctgactc ctcgatggta atgtgatgga gaaatactga gttgacttct  14580
actcaggcta ttgtgttact taagtgtggt tgctctctgc tcctatgtga agctctttag  14640
```

aattagaacc agcccatgct cttccagtga gtgaaagact agatcacatt gcttaaaatc 14700
cttgaactta gatgtgcacc tgaataaagg taagcatagt tctgtcttta tgaaagatcc 14760
ataagtgata tcgatataac gtcttgtttg gttgttgtcg ttccagaatt ggggcagaag 14820
tgcagattga ttactgaata tctttgctat ctaaggttcg atatctatag ttatgcaaat 14880
acaaccaatt agaggatggg ctgtaaaaac tgtacatgtg aactacggcc acaatcaggg 14940
aaaggactcg tgctattatt ccatctttga ttctatctat gacatatggc tgagcaagta 15000
tctctatgtt aggatatgga gtcctttggg tacatgacca ggatttgtct aactagttgt 15060
gtgtgtgtgt gtgtgtgtgt gtgtgtgtgt gtgtgtgtgt gtgtgtctat ttctttttat 15120
tggggaattg agtcgattga tattaagaga tattaagtta aagtaattgt tgcttccaat 15180
tagtataaat atacaaagat aaatcataac aaaatattaa gaatgacaag aatagaaaac 15240
gtcctatttt attttactac acacacacac acacacacac acacacacaa acacacacac 15300
actttcacat gtttaatgta tatataggtt gacatattct gggttcacac atatgcaaag 15360
agtggtgagc catcaacgag aataaaagaa aaacgaacgt gcacgtagat gctttcaaaa 15420
ataatcaacg ctcacggaaa ccaaaaacaa gtgtcctttg aaaaaaagaa aatcgaaagg 15480
tcacgaccac cgcattctcc tctgtcacca ccgggtggcg acagagagca cgccgggaaa 15540
aaacttccac caaaggggtc ggatctgcct gcttcatccc ggccagggtg aggggaagcc 15600
ggccaggctg gcggatccga cccggcgagg cggtcgcgct ttccatcggt cggtccccgg 15660
gaggttgtac tttgtgagat acaggaagtg cctccatttt ggacaggaag tcgagcccag 15720
gcgctcatgg gagctgtagt gcgtctaggg cccagcgccg atctccgggg ccacccggtg 15780
gcgaaaaacg cgcaagtgca cccccggttc tctgcctcgt ggggacggat ctgggacccg 15840
aaggccagcc gcggttccag acctgcggtg cggccgtgtc ggcggcgtcc ccgggcagac 15900
gggggttcag gtccgcggcc gccgctccag gttgtacctg tagaagtgca gggacagagc 15960
ctctctctgt ctctctgtct atgtgtctaa gtctctctct gtccctctgt ctgactctaa 16020
gtctctcctc ctcctcctcc tcctcctcct cctcccttcc acccggggct gcctggcgtc 16080
ggcgtccgcc atcgagggac ccatcccggc ttccacgagt cccgcagccc ccggctctcc 16140
cttctccttc cttctccttc cttctcctgc ttccttcttc catcccggcc tgcctggtct 16200
ctgccgtggc ccgcgcagct cgggtctctg tgtctgtctg tccccctgtc ctggttctcc 16260
cttcttcttc catcccggcc tgcctggtct ctgccgtggc ccgcgcagct cgggtctctg 16320
tgtctgtctg tccccctgtc ctggttctcc cttctcctgc ttccttcttc catcccggcc 16380
tgcctggtct ctgccgtggc ccgcgcagct cgggtctctg tgtctgtctg tccccctgtc 16440
ctggttctcc cttctccttc cttcttccat cccggcctgc ctggtctctg ccatggcccg 16500
cgcagctcgg gtctctgcgt ctgtctgtcc ccctgtcctg gttctccctt ctccttcctt 16560
ctccctgctt ccttctcccc ggggaccaag cccgagtctg catccgaccg agatgcacca 16620
tcccggcttc cgtgtgtctc gccgtccccc ggtctctgtc tgtcaacctc ccttctcctt 16680
ccttcttcca cccagggacc aagcccgagt ccgtgtcccg cgcagtctgg gtctgtctgt 16740
ccccctgtcc ccctgtcccg gttcttcctt cttcctgctt ccttcttcca tcccggcctg 16800
cctggtctct gccgtggccc gcgcagctcg ggtctctgcg tctgtctgtc cccctgtccc 16860
ggttcttcct tctcctgctt ccttcttcca tcccggcctg cctggtctct gccgtggccc 16920
gcgcagctcg ggtctctgcg tctgtctgtc cccctgtcct ggttctccct tctccttcct 16980
tcttccatcc cggcctgcct ggtctctgcc atggcccgcg cagctcgggt ctctgcgtct 17040

-continued gtctgtcccc ctgtcccggt tcttccttct cctgcttcct tcttccatcc cggcctgcct 17100
ggtctctgcc gtggcccgcg cagctcgggt ctctgcgtct gtctgtcccc ctgtcctggt 17160
tctcccttct ccttccttct tccatcccgg cctgcctggt ctctgccgtg gcctgcgcag 17220
ctcgggtctc tgcgtctgtc tgtcccctg tcctggttct cccttctcct tccttctccc 17280
tgcttccttc tccccgggga ccaagcccga gtctgcatcc gaccgagatg caccatcccg 17340
gcttccgtgt gtctcgccgt cccccggtct ctgtctgtca acctcccttc tccttccttc 17400
ttccacccag ggaccaagcc cgagtccgtg tcccgcgcag tctgggtctg tctgtccccc 17460 tgtcccctg tcccggttct tccttcttcc tgcttccttc ttccatcccg gcctgcctgg 17520
tctctgccgt ggcccgcgca gctcgggtct ctgcgtctgt ctgtcccct gtcccggttc 17580 ttccttctcc tgcttccttc ttccatcccg gcctgcctgg tctctgccgt ggcctgcgca 17640
gctcgggtct ctgcgtctgt ctgtcccct gtcctggttc tcccttctcc ttccttctcc 17700
ctgcttcctt ctccccgggg accaagcccg agtctgcatc cgaccgagat gcaccatccc 17760
ggcttccgtg tgtctcgccg tcccccggtc tctgtctgtc tccctccctt ctccttcctt 17820
cttccaccca gggaccaagc ccgagtccgt gtcccgcgca gtctgggtct gtctgtcccc 17880 ctgtcccct gtcccggttc ttccttcttc ctgcttcctt cttccatccc ggcctgcctg 17940
gcctctgccg tggcccgcgc agctcgggtc tctgtgtctg tctgtccccc tgtcccctg 18000 tcctggttct cccttctcct tcttccatcc cggcctgcct ggtctctgcc gtggcccgcg 18060
cagctcgggt ctctgtgtct gtctgtcccc ctgtcccct gtcctggttc tcccttctcc 18120
ttcttccatc ccggcctgcc tggtctctgc cgtggcccgc gcagctcggg tctctgtctg 18180
tctgtccccc tgtcctggtt ctcccttctc cttccttctt ccatcccggc ctgcctggtc 18240
tctgccatgg cccgcgcagc tcgggtctct gtctgtctgt cccctgtcc tggttctccc 18300 ttctccttct tccatcccgg cctgcctggc ctctgccgtg gcccgcgcag ctcgggtctc 18360
tgcgtctgtc tgtcccctg tcctggttct cccttctcct tccttctccc tgcttccttc 18420
tccccgggga ccaagcccga gtctgcatcc gaccgagacg caccatcccg gcttccgtgt 18480
gtctcgccgt cccccggtct ctgtctgtca acctcccttc tccttccttc ttccacccag 18540
ggaccaagcc cgagtccgtg tcccgcgcag tctgggtctg tctgtccccc tgtcccctg 18600 tcccggttct tccttcttcc tgcttccttc ttccatcccg gcctgcctgg tctctgccgt 18660
ggcccgcgca gctcgggtct ctgcgtctgt ctgtcccct gtcccggttc ttccttctcc 18720
tgcttccttc ttccatcccg gcctgcctgg tctctgccgt ggcctgcgca gctcgggtct 18780
ctgcgtctgt ctgtcccct gtcctggttc tcccttctcc ttccttctcc ctgcttcctt 18840
ctccccgggg accaagcccg agtctgcatc cgaccgagat gcaccatccc ggcttccgtg 18900
tgtctcgccg tcccccggtc tctgtctgtc tccctccctt ctccttcctt cttccaccca 18960
gggaccaagc ccgagtccgt gtcccgcgca gtctgggtct gtctgtccca ctgtcccct 19020 gtcctggttc tcccttctcc ttccttctcc ctgcttcctt ctccctgggg accaagcccg 19080
agtctgcatc cgaccgagac gcaccatccc ggcttccgtg cgtctcgccg tccccgggtc 19140
tctccgtctc cttccttctt ccactttctt ccacccgggg accaagcccg agtccgtgtc 19200
ccgagcagct cgggtctctg tcatctctct gtcccccgt ctccctacct tctctgcctc 19260
atggggtcga atctgggacc cgaaccccag cccgggctcc cgacgagagg tgtggctctg 19320
tcattggggt ccccgggcag gcggcgtctc aggtctgcgt cctccgctcc cgttgtacct 19380
gtagaagtgt aggagacgag cctctctctg tctctgtctc tctgtctctc tgtctctgtg 19440
tctctctgtc tctgtgtcta agtctctctc ctcctcctcc cttccacccg gggctgcctg 19500
gcgtcggcgt ccgccatcga gggacccatc ccggcttccg cgagtcccgc agcccccggc 19560
tctcccttct ccttccttcc ttcagacccg gcctgcctgg tgcttggcca ccacctgtgc 19620
agccccgggt ctgtctctct gtctgtccat cctcgcttca ggccggggcc cagcccgaga 19680
gagaaaggcc cggcccgtgc atcctccctg cctccccccc ccccgctgtc tctgtctccc 19740
cccctctgtc ccatctccct ccctcctcac ccagcctgcc tggcgctgcc catggcctgt 19800
gcagcctggg tctgtgtgtc tgtcctggtc ctcactttct tccttcagac ccggcctgcc 19860
tggtgcttgg ccaccacctg tgcagctcag ggtctgtctg tctctgtccc agtgtcttcc 19920
tgtctgtcct ggtcactcac tgctttcttc cttcagacag acccggcctg cctggtgctt 19980
ggccaacacc tgtgcagctc agggtctgtc catctgtctc tgtcccagtc tctgcctgtc 20040
tgtccttcct cccttcagac agacccggcc tgcctggtgc ttggccacca cctgcgcagc 20100
tcaggtctgt ccatctgtct ctgtcccagt ctctgcctgt ctgtcccggt ctctccctcc 20160
ttaaaggaaa aatcttaaag gaaaaagagt gcagcccgct cctcccctcg cctgtgctcc 20220
cgctcttccc gactcccgaa ccgaccgcct gtcccggact cagtcagctc cggaccgagt 20280
ccgtctctct gtccttctgg cagaacgcag acacagctcg ccccagaccg cagccccggc 20340
tcggtccgtc cccggtcgtc ccggagcccg tgcacccgcg caccatccgc gtgtaagaca 20400
gcccgagtca gagtcagagt gcggatgtgc cgggtggggg atggggtggt gtgcgtgtga 20460
ggtagaccag aagtccagag agaggaaagg acgggcgggg gtgagggggg gggaagagcg 20520
ggagcacggg tgaggggagg agcgggctgg actctttttc ctttaagatt tttcctttaa 20580
gatttttcct ttaagatttt tcctttaaga tttttccttt aagatttttc cttgttaaga 20640
tttttccttg ttaagatttt tccttgttaa gatttttcct tgttaagatt tttccttgtt 20700
aagatctttt taagagacct tgctgtcttt tttttttttt ttactttttt tttccgcttt 20760
ctttttttgct tttttcttag gtcaatttttg ggggtgtgtc ctgacacttg aggggcgggt 20820
ctaaggtgtg gctttcttgg gtggcttttc cattctgtta agatttttcc tttttaaggt 20880
ctttttaaga gaccttgctg ccttcggtgt cttttttttt ttttactttt ccattctgac 20940
tttctctgtc tctctcgttg gggcctgtct tagatcggat ggggcgtgtt ctcacacttt 21000
aggggcgggt ctaagggaag aggggtgtgg tccgacactt tttatttaat tcttttttttc 21060
tccgctttct tgggtggctt ttccattctg actttctgtc tctctcagtg gggcgtgtct 21120
tagcgtgtca gaaggggcgt ggtctaatac tttgggggcg tgtctcagag caggaggggt 21180
gtggtctggc actttagggc gtgtcctgac acttaagggg cgggtctaag ggaagagggg 21240
tgtggtctgg tctgatactt ttttttaaat tccgctttct tgggtggctt ttccattctg 21300
tctctccctc tcagtggaga cagtggagcg tgtcttagcc cagaaggggc gtggtctaat 21360
actttggggg cgtgtctcag agcaggaggg gtgtggtctg gcactttttt ttaattcttt 21420
ttttcctctg ctttcccatt ctgactttct ctgtccctcc ctctcagtcg ggcgtgtctt 21480
agcccagaag gggcgtggtc taatacttat ttttcctttt tttacctttt ttcccgcttt 21540
cttgggtggc ttccattctg accttctctc tctctctttc tctctctctc tctcgttagc 21600
gcgtgtcctg acacttaagg ggcgggtcta agggaagagg ggtgtggtct gacacttttt 21660
aagatttttc ctttttaagg tcttttaaga gacttttctt tttttttttac tttttttttt 21720
tcgctttctt gggtggcttt tccattctga ctttctctgt ccctctctct cagcccagaa 21780

```
ggggcgtggt cttagacagg aaggggtctc atctcgcact ttgggggcct ttgggggcgt  21840
gtctcagagc aggaggggtg tggtctgacg ctttaggggc gtgtcttaaa ccgggagggg  21900
tgtggtctga cactttttta aaaacttttc cttttttttcc gctttcctgg gtggattttc  21960
cattctgact ttctctgtct ctcccattta gggttttttt ttttggtctc actattctca  22020
tcacactctc tgtctgggga tggcaggtag ggaggaaggg gcgtggtctc acgctttaga  22080
ggcgggtctt acactgggag gggtctgaag atggccttct ttttaaactc tcatctctgc  22140
cacagaaggc tgtgcttcct tcctttactc tttggaggca ggaaggaagg aagggccctg  22200
gtctcacgct ttaggggcgt tctttacatt ttctttaacg tccctgtctt ttctgttccg  22260
tctgtcgcag aaggaagaca cacacacatc tgcatatcca tttcaactgc aattttattg  22320
agggggacat ttctgtacgc agtcaggccc cgttggcgtg ctccttcctc cgtgagaatc  22380
gctccgtcct ggcggcctcg gcgacacgcg cacctggaaa agacgggaag agagggaggg  22440
ggggggggtca gcgtctgtgg acgggaccgt ggcgactcgc tgtttcagtg tgtgagtgtt  22500
tggacaccac gccggatttg agtgtgaggc ggcctcattg tgccaatcat cagttgcgtg  22560
tctgctgcct ccgtgtgcag acccgaggtt cctctgcatc tcattatgcc gctctgagtc  22620
taatctgaat atctgggcct ccgtgtgcag acctgaggtt cctctgcgtc taatctgaat  22680
atctgggcct ccgtgtgcag acccgaggtt cctctgcatc tcattatgcc gctctgagtc  22740
taatctgaat atctgggcct ccgtgtgcag acccgaggtt cctctgcatc tcattatgcc  22800
gctctgagtc taatctgaat atctgggcct ccgtgtgcag acccgaggtt cctctgcatc  22860
tcattatgcc gctctgcgtc taatctgaat atctgggcct ccgtgtgcag acccgaggtt  22920
cctctgcatc tcattatgcc gctctgcgtc taatctgaat atctgggcct ccgtgtgcag  22980
acctgaggtt cctctgcatc tcatcatgcc gctctgagtc taatctgaat atctgggcct  23040
ccgtgtgcag acccgaggtt cctctgcatc tcatcatgcc gctctgcgtc taatctgaat  23100
atctgggcct ccgtgtgcag acctgaggtt cctctgcatc tcattatgcc gctctgagtc  23160
taatctgaat atctgggcct ccgtgtgcag acccgaggtt cctctgcatc tcattatgcc  23220
gctctgagtc taatctgaat atctgggcct ccgtgtgcag acccgaggtt cctctgcatc  23280
tcattatgcc gctctgcgtc taatctgaat atctgggcct ccgtgtgcag acctgaggtt  23340
cctctgcatc tcattatgcc gctctgagtc taatctgaat atctgggcct ccgtgtgcag  23400
acctgaggtt cctctgcatc tcattatgcc gctctgagtc taatctgaat atctgggcct  23460
ccgtgtgcag acctgaggtt cctctgcatc tcatgccgct ctgcgggagt gtctcattga  23520
ctgcgtgatc atgcaactct gagcctggtt tgtcactgtc tctgtctgtc tgtctctctc  23580
ctgtctctct accttaaccc aaagctcacc ctctccctct gtctctatat ctctctgtct  23640
ctctctctgt ctgtccctaa ctctgtctct aactgtatct ctgtctgtct ccaactctga  23700
ccttctctct gcctctccgt cactgtctct cggtctctct gtgtctgtct cgttctctgt  23760
gtctctgtgt ctgtctctat atatctctgt ctcttactta ccctaatcct aaacctctgt  23820
ctctccatct ctgtgtctgt ctctgtctct ctgtctctgc gtctctgtat ctccgtgtct  23880
atctgtgtct ctctgtccct aactctgtct ccgactctgt ctctctctct gtctctatct  23940
ctgtgtctgt ctcactgtct gactctccgt gtctctacct tcaccctaaa cttaaccctc  24000
tctgtctctg tctctatctc tgtctctctg tctctgtcgc taactctatc tctgtctctg  24060
tgtttctctc tctatatctc tccatctgtc tctccatctc tgtctctatc tctctgtgtt  24120
```

```
tgccagtctc catcgtctgt gtctctgtgt ctctctgtct ctgtgtctgt ctcactttat  24180
atctctctat ctttctgtct tactgtctct gtgtctgttt ctgtctctct gtctcccttt  24240
ctctctgtca gtctggctct gtagctctgt ctgtttctct atctctccat cactgtctcc  24300
ctctctatct ctctctctct gtttctttct gtctcactgt ctctgtctct atgtctcact  24360
ctgcctgtct ctgactctgt gtctctaaat ctgtctctct gtctctgtct gtttcacttt  24420
ttctatctct ctctgtcttt ctgtctctct gtctcccttt ctctctgtca gtctggctct  24480
gtagctctgt ctgtctgttt ctctgtctct ccatcactgt ctccctctct atctgtctct  24540
ctctgtttct gtctgtcttt cggtctcatt gtctctgtct cagtgtctgt ctgtctcagt  24600
gtctgtatct ctctgtctcg cagtctctgt gtctctgttt ctgtctctat ctcgctgtct  24660
ctctgtctgt ctctctgtct ctgtctctct ctaactctgt ctaacactgt ctctgtgtct  24720
ctgtttctgt tttaacccta accctaacct caccctaacc ctaaacctct ctgtctctcc  24780
atctctgtct ctgtgtctct ctgtgtctgt ctctccgtgt ctctctacct taaccctaac  24840
ctcaccctaa ccctaaacct ctgtgtctct ccatctctgt ctctctgtct ctctgtgtct  24900
ctctgtctct gtctctccgt gtctctctac cttaacccta acctcaccct aaccctaaac  24960
ctctctgtct ctccatctct gtctctctct ctctgtgtct ctctgtctct gtctctccgt  25020
gtctctctac cataacacta acctcaccct aaccctaaac ctgtctgtct ctccatctct  25080
gtctctatct ctctgtgtct ctctgtctct gtctctccgt gtctctctac cataacccta  25140
acctcaccct aaccctaaac ctctctgtct ctccatctct ctctctgtgt ctccgtgtct  25200
ctctgtgtct ctctacctta accctaacct caccctaacc ctaaacctct gtgtgtctcc  25260
atctctgtct ctctgtctct ctgtgtctct ctgtctctgt ctctccgtgc ctctctacct  25320
taaccctaac ctcaccctaa ccctaaacct ctctgtctct ccatctctgt ctctgtgtct  25380
ctctgtctct gtgtctaagt ctctctcctc ctcctccctt ccacccgggg ctgcctggcg  25440
tcggcgtccg ccatcgaggg acccatcccg gcttccgcga gtcccgcagc ccccggctct  25500
cccttctcct tccttccttc agacccggcc tgcctggtgc ttggccacca cctgtgcagc  25560
cccgggtctg tctctctgtc tgtccatcct cgcttcaggc cggggcccag cccgagagag  25620
aaaggcccgg cccgtgcatc ctccctgcct cccccccccc cgctgtctct gtctcccccc  25680
ctctgtccca tctccctccc tcctcaccca gcctgcctgg cgctgcccat ggcctgtgca  25740
gcctgggtct gtgtgtctgt cctggtcctc actttcttcc ttcagacccg gcctgcctgg  25800
tgcttggcca ccacctgtgc agctcagggt ctgtctgtct ctgtcccagt gtcttcctgt  25860
ctgtcctggt cactcactgc tttcttcctt cagacagacc cggcctgcct ggtgcttggc  25920
caacacctgt gcagctcagg gtctgtccat ctgtctctgt cccagtctct gcctgtctgt  25980
ccttcctccc ttcagacaga cccggcctgc ctggtgcttg gccaccacct gcgcagctca  26040
ggtctgtcca tctgtctctg tcccagtctc tgcctgtctg tcccggtctc tccctcctta  26100
aaggaaaaat cttaaaggaa aaagagtgca gcccgctcct cccctcgcct gtgctcccgc  26160
tcttcccgac tcccgaaccg accgcctgtc ccggactcag tcagctccgg accgagtccg  26220
tctctctgtc cttctggcag aacgcagaca cagctcgccc cagaccgcag ccccggctcg  26280
gtccgtcccc ggtcgtcccg gagcccgtgc acccgcgcac catccgcgtg taagacagcc  26340
cgagtcagag tcagagtgcg gatgtgccgg gtgggggatg gggtggtgtg cgtgtgaggt  26400
agaccagaag tccagagaga ggaaaggacg ggcgggggtg aggggggggg aagagcggga  26460
gcacgggtga ggggaggagc gggctggact ctttttcctt taagattttt cctttaagat  26520
```

-continued

```
ttttccttta agatttttcc tttaagattt ttcctttaag atttttcctt gttaagattt  26580
ttccttgtta agatttttcc ttgttaagat ttttccttgt taagattttt ccttgttaag  26640
atctttttaa gagaccttgc tgtctttttt ttttttttta cttttttttt ccgctttctt  26700
ttttgctttt ttcttaggtc aattttgggg gtgtgtcctg acacttgagg ggcgggtcta  26760
aggtgtggct ttcttgggtg gcttttccat tctgttaaga tttttccttt ttaaggtctt  26820
tttaagagac cttgctgcct tcggtgtctt tttttttttt tacttttcca ttctgacttt  26880
ctctgtctct ctcgttgggg cctgtcttag atcggatggg gcgtgttctc acactttagg  26940
ggcgggtcta agggaagagg ggtgtggtcc gacacttttt atttaattct ttttttctcc  27000
gctttcttgg gtggcttttc cattctgact ttctgtctct ctcagtgggg cgtgtcttag  27060
cgtgtcagaa ggggcgtggt ctaatacttt gggggcgtgt ctcagagcag gaggggtgtg  27120
gtctggcact ttagggcgtg tcctgacact taaggggcgg gtctaaggga agaggggtgt  27180
ggtctggtct gatacttttt tttaaattcc gctttcttgg gtggcttttc cattctgtct  27240
ctccctctca gtggagacag tggagcgtgt cttagcccag aaggggcgtg gtctaatact  27300
ttgggggcgt gtctcagagc aggaggggtg tggtctggca cttttttttta attcttttt  27360
tcctctgctt tcccattctg actttctctg tccctccctc tcagtcgggc gtgtcttagc  27420
ccagaagggg cgtggtctaa tacttatttt tccttttttt accttttttc ccgctttctt  27480
gggtggcttc cattctgacc ttctctctct ctctttctct ctctctctct cgttagcgcg  27540
tgtcctgaca cttaaggggc gggtctaagg gaagaggggt gtggtctgac actttttaag  27600
atttttcctt tttaaggtct tttaagagac ttttcttttt tttttacttt ttttttttcg  27660
ctttcttggg tggcttttcc attctgactt tctctgtccc tctctctcag cccagaaggg  27720
gcgtggtctt agacaggaag ggtctcatc tcgcactttg gggggccttg ggggcgtgtc  27780
tcagagcagg aggggtgtgg tctgacgctt tagggggcgtg tcttaaaccg ggaggggtgt  27840
ggtctgacac tttttttaaaa actttttcctt tttttccgct ttcctgggtg gattttccat  27900
tctgactttc tctgtctctc ccatttaggg tttttttttt tggtctcact attctcatca  27960
cactctctgt ctggggatgg caggtaggga ggaaggggcg tggtctcacg ctttagaggc  28020
gggtcttaca ctgggagggg tctgaagatg gccttctttt taaactctca tctctgccac  28080
agaaggctgt gcttccttcc tttactcttt ggaggcagga aggaaggaag ggccctggtc  28140
tcacgcttta ggggcgttct ttacattttc tttaacgtcc ctgtcttttc tgttccgtct  28200
gtcgcagaag gaagacacac acacatctgc atatccattt caactgcaat tttattgagg  28260
gggacatttc tgtacgcagt caggccccgt tggcgtgctc cttcctccgt gagaatcgct  28320
ccgtcctggc ggcctcggcg acacgcgcac ctggaaaaga cgggaagaga gggagggggg  28380
ggggtcagcg tctgtggacg ggaccgtggc gactcgctgt ttcagtgtgt gagtgtttgg  28440
acaccacgcc ggatttgagt gtgaggcggc ctcattgtgc caatcatcag ttgcgtgtct  28500
gctgcctccg tgtgcagacc cgaggttcct ctgcatctca ttatgccgct ctgagtctaa  28560
tctgaatatc tgggcctccg tgtgcagacc tgaggttcct ctgcgtctaa tctgaatatc  28620
tgggcctccg tgtgcagacc cgaggttcct ctgcatctca ttatgccgct ctgagtctaa  28680
tctgaatatc tgggcctccg tgtgcagacc cgaggttcct ctgcatctca ttatgccgct  28740
ctgagtctaa tctgaatatc tgggcctccg tgtgcagacc cgaggttcct ctgcatctca  28800
ttatgccgct ctgcgtctaa tctgaatatc tgggcctccg tgtgcagacc cgaggttcct  28860
```

-continued

```
ctgcatctca ttatgccgct ctgcgtctaa tctgaatatc tgggcctccg tgtgcagacc  28920
tgaggttcct ctgcatctca tcatgccgct ctgagtctaa tctgaatatc tgggcctccg  28980
tgtgcagacc cgaggttcct ctgcatctca tcatgccgct ctgcgtctaa tctgaatatc  29040
tgggcctccg tgtgcagacc tgaggttcct ctgcatctca ttatgccgct ctgagtctaa  29100
tctgaatatc tgggcctccg tgtgcagacc cgaggttcct ctgcatctca ttatgccgct  29160
ctgagtctaa tctgaatatc tgggcctccg tgtgcagacc cgaggttcct ctgcatctca  29220
ttatgccgct ctgcgtctaa tctgaatatc tgggcctccg tgtgcagacc tgaggttcct  29280
ctgcatctca ttatgccgct ctgagtctaa tctgaatatc tgggcctccg tgtgcagacc  29340
tgaggttcct ctgcatctca ttatgccgct ctgagtctaa tctgaatatc tgggcctccg  29400
tgtgcagacc tgaggttcct ctgcatctca tgccgctctg cgggagtgtc tcattgactg  29460
cgtgatcatg caactctgag cctggtttgt cactgtctct gtctgtctgt ctctctcctg  29520
tctctctacc ttaacccaaa gctcaccctc tccctctgtc tctatatctc tctgtctctc  29580
tctctgtctg tccctaactc tgtctctaac tgtatctctg tctgtctcca actctgacct  29640
tctctctgcc tctccgtcac tgtctctcgg tctctctgtg tctgtctcgt tctctgtgtc  29700
tctgtgtctg tctctatata tctctgtctc ttacttaccc taatcctaaa cctctgtctc  29760
tccatctctg tgtctgtctc tgtctctctg tctctgcgtc tctgtatctc cgtgtctatc  29820
tgtgtctctc tgtccctaac tctgtctccg actctgtctc tctctctgtc tctatctctg  29880
tgtctgtctc actgtctgac tctccgtgtc tctaccttca ccctaaactt aaccctctct  29940
gtctctgtct ctatctctgt ctctctgtct ctgtcgctaa ctctatctct gtctctgtgt  30000
ttctctctct atatctctcc atctgtctct ccatctctgt ctctatctct ctgtgtttgc  30060
cagtctccat cgtctgtgtc tctgtgtctc tctgtctctg tgtctgtctc actttatatc  30120
tctctatctt tctgtcttac tgtctctgtg tctgtttctg tctctctgtc tccctttctc  30180
tctgtcagtc tggctctgta gctctgtctg tttctctatc tctccatcac tgtctccctc  30240
tctatctctc tctctctgtt tctttctgtc tcactgtctc tgtctctatg tctcactctg  30300
cctgtctctg actctgtgtc tctaaatctg tctctctgtc tctgtctgtt tcacttttc  30360
tatctctctc tgtctttctg tctctctgtc tccctttctc tctgtcagtc tggctctgta  30420
gctctgtctg tctgtttctc tgtctctcca tcactgtctc cctctctatc tgtctctctc  30480
tgtttctgtc tgtctttcgg tctcattgtc tctgtctcag tgtctgtctg tctcagtgtc  30540
tgtatctctc tgtctcgcag tctctgtgtc tctgtttctg tctctatctc gctgtctctc  30600
tgtctgtctc tctgtctctg tctctctcta actctgtcta acactgtctc tgtgtctctg  30660
tttctgtttt aaccctaacc ctaacctcac cctaacccta aacctctctg tctctccatc  30720
tctgtctctg tgtctctctg tctctgtctc tccgtgtctc tctaccttta accctaaccc  30780
taacctcacc ctaaacttaa ccctctctgt ctctacaact gtctctatat ctctctgtct  30840
gtctctgtgt ctgtctctct gtctctgtcg ctaactctat ctctctgtct ctgtgtttct  30900
ctctctacgt ctgtctctgt ctctatctct ctgtgtttgc ccgtctccat cgtctctctg  30960
tgtctctctg tctgtctctg tccctaactc tatctctaac tgtatctctc tttctgtgcg  31020
tgtctatctt tctttgtctc tctgtccgtc tccaactctg ttctgcctct cagtctctct  31080
gtctctatct gtttgtctct atatatctct gtctctccgt gtctctctac cttaacccta  31140
acctcaccct aaacttaacc ctctctgtct ctgtgtctgt ctctctgtct ctgtcgctaa  31200
ctctatctct gtctctgtgt ttctctctct atgtctctcc atctctgtct ctatctctct  31260
```

gtctttatct ctctgttttt gcctgtctcc atcgtctctc tgtgtctctc tgtctttctg 31320
cctctgtttc tgtctgtttc tctgtctctc catcactgtc tccctctcaa tctgtctctg 31380
tctctaagtt tctctgtctc tgtctgtctc tctttctctg tccctccatc tctgtatctc 31440
tctgtctcgc ataaccctaa ccctaaccct atctaaccct aaccctaacc cccctaaccc 31500
taatctaacc ctaaccataa ccctaaccct cctaacccta acctaacccc cctaacccta 31560
acctaacccc cctaacccta accctaaccc taacctaacc cccctaaccc taacctaacc 31620
cccctaaccc taaccctaac ctaacccccc taaccctaac ctaacccccc taaccctaac 31680
ctaaccaccc ccctaaccct aacctaaccc taacctaacc ctaacctaac cataacccta 31740
acctaaccct aaccataacc caaccctagc cctagccaaa acctgtctct ctgtctgtct 31800
ctctttcact ctcaggctct gtctgtctct ctctctctct gactgtttgt ctctctgtct 31860
ttctttctct gtccctgtct gtctgtctgt ctgtctctgt ttgtctctgt ctccctgtct 31920
gcctgtctct ctgtttgtct ctgtctccct gtttgtatgt ctgtctcttt atctctgtct 31980
ctgtctctct atctctctat atctgtatgt ctgtctgtct gaatctgtct ccctgtctgt 32040
ctgtctctct gtcactgtct ctctgtctgt ctctttcact ctcagtttct gtctctctgt 32100
ctgtctctgt ttgtctctgt ctctctgttt ctctgtcttt gtttgtctgt ctctctgtct 32160
gtctcactct ctgactctgt ctctctgtct gtatctctga ctctgtctgt ctctgtctcg 32220
ctatctgtcc ttctgactct ctgtctctct cagactgtct gtccctctgt ctctttgtct 32280
gtccctctgt ctctgtctct ccctgtctgt ctgtctctgt ctcgctgtcc ctttgtctgt 32340
ctctctgtct ctgtctgtct gtctctgtct cgctgtccct ttgtctttct gtctctgtct 32400
ctctgactct gtctctgtct gtctccgttt ccgtctctct gtctgtctgt ctctgtttcg 32460
ctgtcccttt gtctttctgt ctctgtctct gtctctctga ctctgtctct gtctgtctcc 32520
gtttccgtct ctctatctgt ctctctatct gtctcgctgt ctgtgtctgt gtctctctgt 32580
ctctgtatct ctgtctctct agctctgtct gtctccctgt ccctttgtct ctctgactct 32640
gtctccattt ctgtctctct atctgtctgt ctctctatct ctctctgtct gtctctctgt 32700
ctctaactct gtctgtctga ctctctgtct gtctctctgt ctctgtctgt ctgtctcgct 32760
gtccctttgt ctgtctctct gtctctgtct gtatctgtct gtctctaact ctgtctgtct 32820
gtgtctgtct gtctgactct ctgtctgtct atgtcttttt ccctgtctct ctatctctgt 32880
ctctctgtgt ctgtctgact ctctgtctct ctctgtctat gtctttctcc ctgtctctct 32940
gtctctgtct gtctctaact ctgtctgtat gtgcctgtct gtctgactct ctgtatctgt 33000
ctgtctctaa ctctgtcggt ctgtgtctgt ctgtctgact ctctgtctct ctgtctgtct 33060
atgtctttct ccctgtcgct ctgtctgttt gtctctctgt ctctgtctct ctatctctgt 33120
ctctctatct ctgtctctct atctctgtct ctctctcgga ctgtctctct gtctctgtct 33180
ctctctctct gtccctatgt ctgtctctct gtctgtctcg ctgtcccttt gtctgtctct 33240
ctgtctctgt ctctaactct gtctctctgt gtctgtctgt ctgactccct gtctatctgt 33300
ctgtctgtct ctctgtctct gtctctctct cggactgtct ctctgtctct ctgactctgt 33360
ctctctgtct ctgtctgtct ctaactctgt ctgtctgtct gtgtctgtct gactctgtat 33420
ctgtctgtct ctaactctgt gtctgtctgt gtctatgtct ctgtctctct atctctgtct 33480
ctctctcaga ctgtctctct gtctgtctct ctgtgaagta aagataatta gaagtgaagg 33540
taattagaga aaagaaaaat acctcgtctt gaataaaacc aacaacaata aacaacaaca 33600

-continued

```
ataaacaatc gcaaggttgc actgacgtcc tggggccact gggtggcgcc agagcatctg  33660
agtgcctcag tgtgcaaatg tgagcgtcgc attttaatgt ttatgtgaat ttgcatctct  33720
gtgtgcctca ttatgcaaat ctgtgcgagt tccctgggtc ctggttaaag tctctgtgag  33780
ttacctgagc gcctcattta aatggtgcag caccagagca accctctcag tgtgaagccc  33840
agacacaaaa cagaaatcaa ttcaaagatg tttcctttca aaaaattcaa gaaagaattt  33900
cacaaaaatt cccctgcatc ctaatttaaa cctgcacgag tttccaaggt gctgatttaa  33960
acctacaagt tccctggtaa aaacccgggc gtggtggctg agagaaacca agtctgtccc  34020
aaagccacca ggcctctaat ccctacctac cctccagaga cagagccagg tggatctctg  34080
agtcccaggc cagcctgctc tacagagcga gcttagagaa accctttctc ttaaaaacct  34140
gaaaagaaac taaaaataaa aatccaaaaa gaaagaaaca ggcagataaa taatcgttta  34200
acctccaaaa aattaaatct gaaaagtaat cagaaaagaa agaaaatatg ccaaatcttc  34260
gaaaaaaaat ctcaaatttc acagtgacgt tctatctcca cgagtttcac gggttctaat  34320
ttaaacctgc acagattccc tgattcctaa gttaaacctg cacgagtttt ggaaagatca  34380
ggaattcaag gcccacacct aaacatgata aaagcaatct acagcaaacc agtagccagc  34440
atcagagtaa atggagagaa gctggaagca atcccactaa aatcagggac gagacacggc  34500
tgcccactct ctccctacct cttcaacata gtacttgaag tattagccag agcaattcca  34560
caacaaaagg agatcaaggg gatacaaatt ggaaaagagg aagtcaaaat atcacttttt  34620
gcagatgata tgatagtata tataagtgac cctaaaaatt ccaccagaga actcctaaac  34680
ctgataaaca gctttggcga agtagctgga tataaaataa actcaaacaa gtcaatggcc  34740
tttctctata caaagaataa acaggctgag aaagaaatta gggaaacaac acccttctca  34800
atagtcacaa atagtataaa atatctcggc gtgactctaa ctaaggaagt gaaagatctg  34860
tatgataaaa acttcaagtc tctgaagaaa gaaattaaag aagatctcag aagatggaaa  34920
gatctcccat gctcatggag tggcaggatc aacattgtaa aaatggctat cttgccaaaa  34980
gcaatctaca gattcaatgc aatccccatc aaaattccaa ctcaattctt caacgaatta  35040
caaggagcaa tttgcaaatt catctggaat aacaaaaaac ctaggatagc aaaaactctt  35100
ctcaagggtt tgaaaaaaaa atcacaaatg ttgcagtgac gttctatctc catgagtttc  35160
acgggttcaa atttaaacct gcacagattc cctgattcct aatttaaacc tgcacagatt  35220
ccctgattcc taatttaaac ctgcacagag tttccaaggt gctgatttaa acctacaagt  35280
tccctggtaa aaacccgggc gtggtggcag agagaaacca agtctgtccc aaagccacca  35340
ggcctctaat ccctacctac cctccagaga cagagccagg tggatctctg agtcccaggc  35400
cagcctgctc tacagagcga gcttagagaa accctttctc taaaaaccta aaaataaact  35460
aaaagtaaaa actaaactaa aataagaata attggggaaa aaaccaagtt tcgcgagcac  35520
gggtgtctcg ggggttaaaa attacaaaat taaaatgttc aacagtcaaa aatacaaaaa  35580
taaaaattaa aattaaaact gaaaagaaaa atgacaaatc ttcaaataaa actcaaatat  35640
cgtagtgact ttctatctcc acgagttttg cgggttctaa tttaaacccg cacaaattac  35700
tgggttctaa attaaacctt taatttcaca ctcaaaaata gaaggtgaag ataattagag  35760
aaaagaaaaa tacctagtct tgaataaaaa catcaataaa aaattgcaag cctgcactca  35820
cgtcctgtcg ccactgggtg gcaccagagc caaagtctca cggtgaagca cagagaacac  35880
agatcttgga taaaaaccaa aaaacagatt ccctgcatcc taatttaaac ctgcacagat  35940
tccctgattc ctaatttaat cccacacgag ttcgcctgca tcctgattta aacctgcaca  36000
```

```
cattcccagg ttctaaatta aaccttgaat ttcacactca aaaataaaag gtgaagataa  36060
gtcgcaaaaa gaaaaatacc tagtcttgaa tgaaaacaac aataaaaata cggcaatagc  36120
ggcttgacaa cacatctaaa agctctagaa aaaggaagc aaactccccc aagaggagta  36180
gacagatggc aggaaataat caaactcagg ggggaaatca accaagtgga aacaagaaga  36240
actattcaag gaattaacca aacgaggagc tggttctttg agaaaatcaa caggatagat  36300
aaacccttag ccagactcac tagagggcac agggacaaaa tcctaatgaa caaaatcaga  36360
actgaaaagg gagacataac aacagatccg gaagaaatcc aaaacaccat cagaaatcaa  36420
aacacctgtg cctaaaaacc aaataataaa aattttttaa agatttgtaa agataaaatt  36480
aaaaaaaaat aattagaaaa aatataaagc attgacaaaa acctcccaaa attggaatgt  36540
ttattaaaaa ttacaaaata aaaatattaa acagtcaaaa atacaaaaat taaaattaaa  36600
attaaaactg aaaagaaaaa taaatgccaa atcttcaaaa aaatctccaa tatctcaggg  36660
acattctatc tccacgagct ttgcggcttc taatttaaac ctgcacgagt ttctctgcac  36720
cctaatttaa acctgtctct ctgtctgttt gtctgtctgt ctctctgtct ccctgtctct  36780
ctgtctgtct ctctgttaag taaagataat tagaagtgaa gataattaga gaaaagaaaa  36840
atacctcgtc tttgaagaaa accaacaata aacaatcgca aggttgcatg acgtcctgtg  36900
gccactgggt ggcgccagag catctgagcg cctcagtgtg caaatctgag cgttgcattg  36960
taaagtttct gcaaatttgc atctctgtga gcctcattat gcaaatctgt gcgagctccc  37020
tgggtcctgg ttaaagtctc tgtgagttac ctgagcgcct catttaaatg gtggagcacc  37080
agagacaaaa caaaaatcaa ttcaaagagt cagagagagg ctcatctccc tacacttcta  37140
caggctcaaa gggagcaggg gacgcggacc tgagacgccg cctgcccggg acgccactga  37200
ggaagccaca cccgccgtcg ggagcccggg ctgggattcg ggtcccagat tcgtccccat  37260
gaggcagaga aggtagggag gcgggggaca gagagatgac agagacccga gctgcggggg  37320
ccacggactc gggcttggtc cccgggtgga agaaagtgga agaaggaagg agaagggcgg  37380
ggacagagag acagacagaa acctgcatga gtttccaagg tgctgattta aacctacaag  37440
ttcccctggt aaaaatccgg taaaaaaagc atttgacaag atccaacacc cattcatgat  37500
aaaagtcttg gaaagatcag gaattcgagg cccacaccta accatgataa tagcaatcta  37560
cagcaaacca ggagccaaca tcaaagtaaa tggagagaag ctggaagcaa tcccactaaa  37620
atcagggacg agacacggct gcccactctc tccctacctc ttcaacatag tacttgaagt  37680
cctagccaga gcaattccac aacaacagga gatcacagtc accaggcctc tggtccctgc  37740
cctcgagaga gggacagagc caggtggatc tctgagtccc aggccagcct gctctacaga  37800
gcgagcttag agaaaccctt tctctaaaaa cctaaaaaga aactaaaagt aaaaactaaa  37860
ctaaaataag aataattggg gaaaaaaaca agtctcgcga gcacgggtgt ctcggggctt  37920
aagcagcaag aaagcaagtc tgcgaagatc caaaaattaa aatccaaaaa gaaagaaaca  37980
ggcaggtgaa tcaatgttta acctccaata aattaaaagt gaaaactaat cagaaaagga  38040
aaaaatatgc caaatcttcg aaaaaaaatc tcaaatgtcc acgagtttcg cgggttctaa  38100
tttaaacctg cacagattcc ctgattccta atttaaacct gcacagattc cctgattcct  38160
aatttaaacc tgcacagatt ccctgatttc taatttaaac ctgcacgagt ttgcaaggtg  38220
ctgatttaaa cctacaagtt cccctggtaa aaatccgggc gtggtggtcc aggccttcca  38280
tcccagccat ggggacacag acgcaggcag atctctgaat ccgaggtcag cctggtctcc  38340
```

agagcacatt gcgggacagc cagggctaca cagagaaacc ctgtggctaa aaaccaaata 38400
ataaattttt tttaaagatt tataaagata aaatttaaaa aataattaga aaaaaatata 38460
aagcattgaa aaacgctcca agaatggaat gtttatttaa aaattacaaa attaaaatgt 38520
tcaacagtca aaaatacaaa aattaaaatt aaaactgaaa agaaaaataa atgacaaatc 38580
ttcaaataaa actccaatct cgcagtgaca ttctatctcc acgagttttg caggtcctaa 38640
tttaatccca cacgagttcg cctgcatcct gatttaaacc tgcacaaatt cccatcttct 38700
aaattaaacc ttgaatttca cacttaaaaa caaaaggtga agataagtag cgaaaagaaa 38760
aatacctagt cttgaatgaa aacaacaata aaaaaacggc aatagcggct tgacaacaca 38820
tctaaaagcc ctagaaaaaa ggaagcaaac tcccccaaga ggagtagaca gatggcagga 38880
aataatcaaa ctcaggggtg aaatcaacca agtggaaaca agaagaacta ttcaaggaat 38940
taaccaaacg aggagctggt tctttgagaa aatcaacaag atagataaac ccttagccag 39000
actcactaga gggcacaggg acagtatcct aattaagaaa atcagaactg aaaagggaga 39060
cataacaaca gatccggaag aaatccaaaa caccatcaga aatcaaagca cctgtgccta 39120
aaaaccaaat aataaaattt ttttaaagat tggtaaagat aaaattaaaa aaaagtaatt 39180
agaaaaaata taaagcattg acaaaacccc acaaaattgg aatgtttatt taaaaattac 39240
aaaataaaaa tattcaacag tcaaaaattc aaatttaaga ttaaaattaa aattaacatt 39300
ctaaactcat ctccatgagt tttgcgggtt ctaatttaaa cctgcacgag tttctctgca 39360
ccctaattta aacctgtctc tctatctgtc tctctctctg ttaagtaaag atatttagaa 39420
gtgaagataa ttagagaaaa gaaaaatacc tcctcttgaa taaaaccaac aataaaaaat 39480
cgcaaggttg cagtgacgtc ctgtggccac tgggtggcgc cagagcatct gagcgcctca 39540
gtgtgcaaat ctgagagtcg cattttaaag tttctgcaaa tttgcatctc tgtgagcctc 39600
attatgcaaa tctctgtgag ttacctgagc gcctcattta aatggtggag caccagagca 39660
accctctcag tgtgaagccc agacacaaaa cagaaatcaa ttcaaagagt cagagagagg 39720
ctcatctccc tacacttcta caggtgcaaa gggagcaggg gacgcggacc attatataaa 39780
caaactcaaa ggcaaaaacc acatgatcat caacatgata aaagcaatct acagcaaacc 39840
agtagccaac atcagagtaa atggagagac gctggaagca atcccactaa aatcagggac 39900
gagacacggc tgcccactct ctccctacct cttcaacata gtacttgaag tattagccag 39960
agcaattcca caacaacagg agatcacagt caccaggcct ctggtccctg ccctcgagag 40020
agggacagag ccaggtggat ctctgagtcc caggccagcc tgctctacag agcgagctta 40080
gagaaaccct ttctccaaaa acctaaaaag aaactaaaag taaaaactaa actaaactaa 40140
aataattggg ggaaaaacca agtctcgcga aaacggtgtc tcggggttaa gccccgagaa 40200
agcaagtctg caaagatcca aaaattaaaa tccaaaaaga aagaaacagg caggtgaatc 40260
aatgtttaac ctccaataaa ttaaaagtga aaactaatca gaaaaggaaa aaatatgcca 40320
aatcttcgaa aaaaaatctc aaatgtccac gagtttcgcg ggttctaatt taaacctgca 40380
cagattccct gattcctaag ttaaacctgc acagattccc tgattcctaa tttaaacctg 40440
cacagagttt ccaaggtgct gatttaaacc tacaagttcc cctggtaaaa atccgggcgt 40500
ggtggcccag gccttccatc ccagccctgg ggacacagac gcaggcagat ctcagaatcc 40560
gaggtcagcc tggtctccag agcacattgc gggacagcca gggctacacc gagaaaccct 40620
gtggcaaaaa aaccaaataa tgaatttttt ttaaagattt gtaaggataa aattaaaaaa 40680
aataattaga aaaaatataa agcattgaca aaaccccccca aaattggaat gttaaaaaat 40740

```
tacaaaatat aaatattcaa cagtcaaaaa ttcaaattta agattaaaat taaaattaaa  40800
actgaaaaga aaaataaatg ccaaatcttc aaaaaaattt ccaatatcac agtgacattc  40860
tatctccacg agctttgcgg gttctaattt aaacctgcac gagtttctct gcaccctaat  40920
ttaaacctgt ctctctgtct gtctgtctgt ctgtctctct gttaattaga agtgaagata  40980
attacagaaa agaaaaatac ctcgtcttga agaaaaccaa caataaacaa tcgcaaggtt  41040
gcactgacgt cctttggcca ctgggtggcg ccagagcatc tgagcgcctc agtgtgcaaa  41100
tctgagcgtc gcattttaaa gtttctgcga atttgcatct ctgtgtgcct cattatgcaa  41160
atctgtgcga gctccctggg tcctggttaa aatctctgtg agttacctga gcgcctcatt  41220
taaatggagg agcaccagag acaaaacaga aatcaattca aagattcaga gagaggctca  41280
tctccctaca cttctacagg ctcaaaggga gcaggggacg cggacctgag acaccgcctg  41340
cccggggacg tcactgagga agtcacaccc ctcctgggga gccagggctg ggattcgggt  41400
cccagattcg tccccatgag gcagagaagg tagggaggcg ggggacagag agatgacaga  41460
gacccgagct gcgggggcca cggactcggg cttggtcccc gggtggaaga aagtaaaaga  41520
aggatggaga agggcgggga cagagagaca gacagaaacc tgcacgagtt aacaaggtgc  41580
tgatttaaac ctacaagttc ccctggtaaa aatccgggcg tggtggccca ggccttccat  41640
cccagccctg gggacacaga tgcaggcaga tctctgaatc cgaggtcagc ctggtctcca  41700
gagcacattg cgggacagcc agggctacac agagaaaccc tgtgtctaaa aaccaaataa  41760
taaaaatttt taaaatattt gtaaagataa aattcaaata aaactcaaat atcgcagtga  41820
cattctatct ccacgagctt tgcgggttct aatttaaacc tatacgagtt tctctgcatc  41880
ccaatttaaa cctgtttctc tgtctctctg tctgtctgtt tgttttttttg tttctgtctg  41940
tctgtctctg tctgtatccc tgagggcagg aaataatcaa actcaggggt gaaatcaacc  42000
aagtggaaac aagaagaact attcaaggaa ttaaccaaac gaggagctgg ttctttgaga  42060
aaatcaacaa gatagataaa cccttagcca gactcactag agggcacaga gacaaaatcc  42120
taattaacaa aatcagaaat gaaaagggag acataacaac agatcctgaa gaaatccaaa  42180
acaccatcag atccttctac aaaaggctat actcaacaaa actggagaac ctggatgaaa  42240
tggacaaatt tctgcacaga taccaggtac caaagttgaa tcaggatcaa gttgaccttc  42300
taaacagtcc catatcccct aaagaaatag aagcacttat caaaagtctc ccagcccaaa  42360
aaagcccagg accagatggg tttagtggag agttctatca ggccttcaaa gaagatctaa  42420
ttccagttct gaacaaacta tttcacaaaa tagaagtaga aggaactcta cccaactcat  42480
tctatgaagc cacaattact ctgataccta aaccacagaa agatccaaca aagatagaga  42540
acttcagacc aatttcactt atgaatatcg acgcaaaaat cctcaataaa attctcgcta  42600
accgaatcca agaacacatt aaagcaatca tccatcctga ccaagcctgc tctacagagc  42660
gagcttagag aaaccctttc tctaaaaacc taaaaagaaa ctaaaagtaa aaaccaaact  42720
aaaataagaa taattgggga aaaaaccaag tctcgcgaga acgggtgtct cggggttaag  42780
cctggagaaa tcaagtctgc gaagatccaa aaattaaaat ccaaaaagaa agaaacaggc  42840
aggtgaatca atgtttaacc tccaacaaat taaaactgaa aagtaatcag aaaaggaaaa  42900
aatatgccaa atcttcgaaa aaaaatctca aatgtccacg agtttcgcgg gttctaattt  42960
aaacctgcac agattccctg attcctaagt taaacctgca cagattccct gattcctagg  43020
ttaaacctgc acagagtttc caaggtgctg atttaaacct acaagttccc ctggtaaaaa  43080
```

-continued

```
tccgggcgtg gtggcccacg ccttccatcc cagccctggg gacacagacg caggcagatc  43140
tcagaatccc aggtcagcct ggtctccaga gcacattgcg ggacagccag ggctacacag  43200
agaaaccctg tgtctaaaaa ctaaataatg aaaatttttt aaagatttgt aaagataaaa  43260
taaaaaaaat aattagaaaa aatataaagc attgacaaaa acccccaaaa ttggaatgtt  43320
tatttaaaaa ttacaaaata aaaatattca acagtcaaaa attcaaattt aagattaaaa  43380
ttaaaattaa aactgaaagg aaaataaatg ccaaatgctc taaaaaatct caaatatcgc  43440
agtgacattc tatctccacg agctttgcag gttctaattt aaacctgcac gagtttctct  43500
gcaccctaat ttaaacctgt ctctctgtct gtctgtctct ctgttaagta aagataatta  43560
gaagtgaaga taattagaga aaagaaaaat acctcttctt gaagaaaggc aacaataaaa  43620
aataaaaata ttcaacagtc aaaaatacaa aagttgaaat taaaattaaa tttaaaactg  43680
aaaagaaaaa taaatgccaa gccttcaaaa aaatctccaa tatcacagtg acattctatc  43740
tccacgagct ttgcaggttc taatttaaac ctgcacgagt ttctctgcac cctaatttaa  43800
acctgtctct ctgtctgtct ctctgtgatg taaagataat tagaagtgaa aataattaga  43860
gaaaagaaaa atacctcctc ttgaataaaa ccaacaataa acaatggcaa ggttgcatga  43920
cgtcctttgg ccactgggtg gcgccagagc atctgagtgc ctcagtgtgc aaatctgaga  43980
gtcgcatttt aaagtttctg caaatttgca tctctgtgag cctcattatg caaatctgtg  44040
cgagctccct gggtcctggt taaagtctct gtgagttacc tgagcgcctc atttaaatgg  44100
tggagcacca gagacaaaac aaaaatcaat tcaaagagtc agagagaggc tcatctccct  44160
acacttctac aggctcaaag ggagcagggg acgcggacct gagacgccgc ctgcccgggg  44220
acgccactga ggaagccaca cccctcctgg ggagccaggg ctgggattgg ggtcccagat  44280
tcgtccccat gaggcagaga aggtagggag gcgggggaca gagagatgac agagacccga  44340
gctgcggggg acacggactc gggcttggtc cccgggtgga agaaagtgga agaaggaagg  44400
agaagggcgg ggacagagag acagacagaa acctgcacga gtttccaagg tgctgattta  44460
aacctacaag ttcccctggt aaaaatccgg taaaaaaagc atttcacaag attcaacacc  44520
cattcatgat aaaaagtctt ggaaagatca ggaattcaag gcccacacct aaacatgata  44580
aaagcaatct acagcaaacc agtagccagc atcagagtaa atggagagaa gctggaagca  44640
atcccactaa aatcagggac gagacaaggc tgcccactct ctccctacct cttcaacata  44700
gtacttgaag tattagccag agcaattcca caacaacagg agatcacagt caccaggcct  44760
ctggtccctg ccctcgagag agggacagag ccaggtgcat ctctgagtcc gaggccagcc  44820
tgctctacag agcgagctta gagaaaccct ttctctaaaa acctaaaaag aaactaaaag  44880
taaaaactca actaatataa gaataattgg ggaaaaaacc aagtctcatg agcacgggtg  44940
tctcggggtt aagcccggag aaagcaagtc tgcgaagatc caaaaattaa aatccaaaaa  45000
gaaaaaaaca ggcagataaa taaacgttta atctccaaaa acttaaatct gaaaagtaat  45060
cagaaaggga aaaaatatgc cgcaacttcg aaaaaaaatc tcaaatatct cagtgacatt  45120
ctatctccac gagctttgcg ggttctaatt taaacctgca cgagtttctc tgcaccgtaa  45180
tttcaacctg tctctctgtc tgtctctctg ttaagtaaac ataattagaa gtgaagataa  45240
ttagagaaaa gaaaaataca gcgtcttgaa tgaaaccaac aataaacaat cgcaaggttg  45300
cactgacgtc ctgtggccac tgggtggcac cagagcatct gagcgcctca gtgtgcaaat  45360
ctgagcgtca cgtttaaagt ttctgcaaat ttgcatctct gtgtgcctca ttatgcaaat  45420
ctgtgcgagc tccctgggtc ctggttaaaa tctctgtgag ttacctgagc gcctcattta  45480
```

aatggtggag caccagagac aaaacaaaaa tcaattcaaa gagtcagaga gaggctcatc 45540
tccctacact tctacaggcg caaagggagc aggggacgcg gacctgagac accgcctgcc 45600
cggggacgtc actgaggaag tcacacccct cctggggagc cagggctggg attcgggtcc 45660
cagattcgtc cccatgaggc agagaaggta gggaggcggg ggacagagag atgacagaga 45720
cccgagctgt gggggccacg gactcgggct tggtccccgg gtggaagaaa gtggaagaag 45780
gaaggagaag ggcggggaca gagagacaga cagaaacctg cacgagtttc caaggtgctg 45840
atttaaacct acaagttccc ctggtaaaaa tccggtaaaa aaagcatttg acaagatcca 45900
acacccattc atgataaaag ttttggaaag atcaggaatt cgaggcccac acctaaacat 45960
gataaaatgc acagattccc tgcatcctaa tttaaacctg cacagattcc ctgattccta 46020
atttacacct gcacagattc cctgattcct aatttgaacc tgcacagatt ccctgattcc 46080
taatttaacc ctgcacagat tccctgattc ctaatttaaa cctgcacaga ttccctgatt 46140
cctactttaa acctgcacag attccctgat tcctatttaa acctgcacag attccctgat 46200
tcctatttaa acctgcacag attccctgat tcctaattta aacctgcaca gattccctga 46260
ttcctaattt aaacctgcac agattccctg attcctaatt taaacctgca cagagtttcc 46320
aaggtgctgt tttaaaccta caagttcccc tggtaaaaat ccaggcgtga tgtcccacgc 46380
cttccatccc agccctgggg acacagacgc aggcggatct cagaatccga ggtcagcctg 46440
gtctccagag cacattgcgg gacagccagg gctacacaga gaaaccctgt gtctaaaaac 46500
caaattataa aaatttttaa agatttataa agagaaaatt taaaaaataa ttagaaaaaa 46560
tgacagtcaa aaatacaaaa gttaaaatta aaattgaaaa gaaaaataaa tgacaaatct 46620
tcaaataaaa ctccaatatc acagtgacat tctatctcca cgagttttgc aggttctaat 46680
ttaatcccac gcgagttcgc ctgcatccta atttaaacct gcacaaattc ccatgttcta 46740
aattaaacct tgaatttcac actcaaaaat aaaaggcgaa aagaaaaata cctagtctta 46800
aatgaaaaca acaataaaaa acggcaatag cggcttgaca acacatctaa aagctctaga 46860
aaaaaaggac gcaaactcac ccaagaggag tagacagacg gcaggaaata atcaaactca 46920
ggggtgaaat caaccaagtg gaaacaggaa gaactattca aggaattaat caaaggagga 46980
gctggttctt tgagaaaatc aacaggatag ataaaccctt agccagactc actagagggc 47040
acagggacta aatcctaatt aacaaaatca gaaaattagt gcagagatct atcagacctt 47100
caaagaagat ctaattccag ttctgcacaa actattccac aaaatagaag tagaaggaac 47160
tctacccaac tcattctatg aagccactat tactctgata cctaaaccac agaaagatcc 47220
agcaaagata gagaagttca gaccaatttc ccttatgaat atcgacgcaa aaatcctcaa 47280
taaaattctc gctaaccgca tccaagaaca cattaaagca atcatccatc ctgaccaagt 47340
aggttttatt ccagggatgc agggatggtt taatatacga aaatccatca atgtaatcca 47400
ttatataaac aaactcaaag acaaaaacca catgatcatc tcgtcagatg cagaaaaagc 47460
atttgacaag atccaacacc cattcatgat aaaagttttg gaaagatcag gaattcaagg 47520
cccacaccta aacatgctaa aagcaatcta cagcaaacca gtagccaaca tcaaagtaaa 47580
tggagagaag ctggaagcaa tcccactaaa atccaaaaat taaaatccaa aaagaaagaa 47640
acaggcagat aaataaacgt ttaacctcca caaaattaaa gataattaga agtgaagata 47700
attagagaaa agaaaaatac ctcgtcttga ataaaaccaa caataaaaaa atcgcaaggt 47760
tgcactgacg tcctgtggcc actgggtggc gccagagcat ctgagcgcct cagtgtgcaa 47820
atctgagcgt cgcattttaa tgtttatgtg aatttgcatc tctgtgtgcc tcattatgca 47880
aatctgtgcg agttccctgg ctcctagtta aagtctctgt gagttacctg agcgcctcat 47940
ttaaatggtg gagcaccaga gcaaccctct cagtgtgaag cccagacaca aaacagaaat 48000
caattcaaag atgtttcctt tcaaaaagtt caagaaagaa tttcacaaaa attcccctgc 48060
atcctaatga gtttccaagg tgctgattta aacctacaca agttccccgg taaaaacacc 48120
ggcgtggtgg ctgagagaaa ccaagtctgt cccaaagcca ccaggcctct aatccctacc 48180
taccctccag agacagagcc aggtggatct ctgagtccga ggccagcctg ctctacagag 48240
cgagcttaga gaaacccttt ctctaaaaac ctaaaaagaa actaaaaata aaaactcaac 48300
taaaataaga ataattgggg aaaacagcaa gtctcgcgag cacgggtgtc ttggggttaa 48360
gcctggagaa atcaagtctc tgaagatcca aaaattaaaa tccaaaaaga aagaaacagg 48420
cagataaata aacgtttaat ctccaaaaac ttaaatctga aaagtaatca gaaagggaaa 48480
aaatatcctg aaacttcgga aaaaaatctc aaatgtcgca gtgaagttct atctccacga 48540
gttttgcggg ttctaattta aacctgcaca gattccctga ttcctaattt aaacctgcac 48600
gagtttccaa ggtgctgatt taaacctaca agttcccctg gtaaaaatcc gggcgtgatg 48660
tcccacgcct tccatcccag ccctggggac acagacgcag gcagatctca gaatccgagg 48720
tcagcctggt ctccagagca cattgcggga cagccagggc tacaccgaga aaccctgtgt 48780
ctaaaaacca aataataaaa attttaaaga tttataaaga taaaattaaa aacaaataag 48840
tagaaaaaaa tataaagcat tgatattgac aaaacccccc aaaattggaa tgcttattaa 48900
aaaattacaa aataaaaata ttcaacagtc aaaaatacaa aaattaaaat taaaattaat 48960
ttaaaactga aaagaaaaat aaatgccaaa tcttcaaaaa aatctcaaat atctcagtga 49020
cattctatct cctcgagctt tgcgggttct aatttaaacc tgcacgagtt tctctgcacc 49080
ctaatttaaa cctgtttctc tgactgtctc tctgttaagt aaagataatt agaagtgaag 49140
ataattagag taaagaaaaa tacctcgtct tgaataaaac caacaataaa caatggcaag 49200
gttgcactga cgtcctctgg ccactgggtg gcgccagagc atctgagcgc ctcagtgtgc 49260
aaatctgaga gtggaatttt aaagtttcta caaatttgca tctctgtgtg cctcattatg 49320
caaatctgtg cgagtttcct gggtcctggt taaaatctct gtgagttacc tgagcgcctc 49380
atttaaatgg tggagcacca gagcaaccct ctcagtgtga agcccagaca caaaacagaa 49440
atcaattcaa agatgtttcc tttctaaaaa ttcaagaaac aatttcacaa aaattcctga 49500
gagaaaccaa gtctgtccca aagccaccag gcctctaatc cctacctacc ctccagagac 49560
agagccaggt gcatctctga gtccgaggcc agcctgctct acagagcgag cttagagaaa 49620
ccctttctct aaaaacctaa aaagaaacta aaaataaaaa ctcaactaaa ataagaataa 49680
ttgaggacta aaccaagtct cgcgagcacg ggtgtctcag ggttaagcct ggagaaagca 49740
agtctctgaa gatccaaaaa ttaaaatcca aaaagaaaga aacaggcaga taaataaacg 49800
tttaacctcc acaaaattaa agataataag aagtgaagat aattagagaa aagaaaaata 49860
cctcgtcttg aagaaaacca acaataaaca atcgcaaggt tgcagtgacg tcctgtggcc 49920
actgggtggc gccagagcat ctgagcgcct cagtgtgcaa atctgagcgt tgcattttaa 49980
agtttctgca aatttgcatc tctgtgtgcc tcattatgca aatctgtgcg agctccctgg 50040
gtcctggtta aagtctctgt gagttacctg agcgcctcat ttaaatggtg gagcaccaga 50100
gacaaaacag aaatcaattc aaagagtcag agagaggctc atctccctac acttctacag 50160
gcgcaaaggg agcaggggac agggacctga gacgctgcct gcccggggac cccactgagg 50220
aagccacacc cctcctgggg agcccgggct gggattcggg tcccagattt gtccccatga 50280
ggcagagaag gtagggagat gggggacaga gagatgacag agacctgagc tgcgggggcc 50340
acggactcgg gcttggtccc cgggtggaag aaagtggaag aaggaaggag aagggcgggg 50400
acagagagac agacagaaac ccggggacag cgagacacac ggaagccggg atggtgagtc 50460
tcgttcgcat gcagactcgg gcttggtccc aggtgagaaa aaggaagcag gaagcaggga 50520
gaaccaggac agggggacag acagatgcag agaaccgagc tgatttcaaa aattcaaaac 50580
aaaaaaccct gtctctaaaa aaccaaaaga aaaaaattac aaaatagata tcccggccgg 50640
gcgtcgtggc gcccgcacgc cttctatccc agccctcggg agtcagaggc agggggattg 50700
ctgagttgga ggccagcctg gtctacagcc tgagctccag gacagccagg gctacacaga 50760
gaaaccctgt ctcgaaaaac caaaaagaaa tcccaagcct taaaaacgta aaaacctcag 50820
aaattggagc gttgcagtaa cgtcctgttt ggaaaaatta ccaagccttc aagaagaccc 50880
gtgacgtcgc agggaagtcc tgcggccacc gggcggcgtc ttgggactga gtcacactgg 50940
gaggtcgcgt tgtccacctg ggtccctgag cccctgtggg cggctgtgcg tgtcagtggt 51000
cggcgctgcg tgtcctacct gacggcgtgc gtgcgtccgt ccgtccgtcc agcggggcga 51060
gggtcggtgg cacatacatc ttgaccacgg cgggtgaaca tcttgaccgc ggcggctcgt 51120
ccgtgtctgc gtggcgggtg cggcgggtcc tgcggatgcg tgtgcctggc ctgcctgccg 51180
tgtgtgccgt gtgtgccgcg tgtgcctggg cgggcgcggg gcccgcgtgt gtcctgtgtg 51240
ctgtggtggg tgcagcggtg cggtcggcgc aggcttccta ccttgtggag tccgtccgtc 51300
cgtcctgtgg ggatggcaga gacatcttga ccacggcgtc cgcttctacg tgtgtgcttt 51360
cgtgggtgac atcactgtgg gcggcggcag tgaccggtgg acgctggcgt gggatccagg 51420
tccataaaca gagaaacacg tgttagactt tcaaatcaca caacaaaaaa aataataaat 51480
aaaaaaaatt ggagtcgggc gtggtggtgc acacctttca tcccagcact cgggagccgg 51540
agacaggcag atttctgagt tggaggccag cctggtctac aaagtgagtt ccaggacagc 51600
cagggctaca cagagaaacc ctgttcgaaa aaccaaaaaa ctaaaataaa ataaaataaa 51660
aataataaga ataattaggg aaaaaaaacc atagccaggg ctataaagag aaaacctgtc 51720
ttgaaaaacc aaaaagtaaa ataaaaataa aataaaataa aataaaaata agaataaaaa 51780
ttagaataat taggaaaaaa atacaaaggt ctgaagttca aatcccagca accacgtggt 51840
ggctcacaac cacccgtaac gagatctgac tccctcttct cgagtgtctg aagacagcta 51900
cagtgcactt acatacaata aataaacatc ttttaaaaag agcaaaaaaa cttttaaaaa 51960
aagcaaaaaa aaaaaaaaaa aaaaaaaaaa attggagggt tgcagtgaca atccgtggcc 52020
acaaggtggc gcccctgagc aagtctacat tgccaggctg aagcacagtc taaccactgt 52080
gcttaaagtc tctaaccact ttctccaaaa agtaaaaatt aaattaaaaa ttaaaaataa 52140
aaaagagaat aattagggaa aaaaccatag ccaggactat aaagagaaac cctgtcttga 52200
aaaacgaaaa aaaaaatact gaaataaaaa agaataaaaa taaaacattt cgacgctgcc 52260
ctgacatact cccgccactg gcggacgcgc cccagccgag tgggcgtgtt gggatgaaac 52320
ccagagactc caagtctggg aagaaaaaaa accctaaaat atccaatcaa tagatcaata 52380
actccagcaa taaacgcatc agtgcctttg aaaggctcag acatcagaga ttaactacag 52440
ctcccagcat gccccggggc ccacttcctg ctgcagacgc ccctcagagt gaaacccata 52500
gagaaccatg gacccccgca gggcagtaaa actcccagca tgcctcgggg ctgagtcccc 52560
accactcaca ccagagcagc cctgtcagag tgaagggcag acccgcccat tcttaaaaca 52620
acaacaacaa caggggctgg cgagatggct cagtgggtaa gagcccccga ctgctcttcc 52680
agagctctga agttcaaatc ccagcgacca cgtggtggct cacaagcacc cgtaacgaga 52740
tctgacgccc tcttctcagt gtctgaagac agctacagtg cacttacata caataaataa 52800
acatctttta aaaagagcaa aaaaaaaact tttaaaaaaa gcaaaaaaaa acccagaaaa 52860
acaagaaaca attggagggt tgcagagcct atgtctcctc taagcaccag ctctaagtct 52920
ctaaccacca ggctacagtg tcctgtaacc accaggcata agtcgctgac caccaggcta 52980
cagtgtcctg taaccaccag gcataagtct ctaaccacca ggctacagtg tcctctaacc 53040
cccagctcta agtcgctgac caccaggcta cagtgtcctg taaccgccag ctctaagtcg 53100
ctgaccacca ggctacagtg tcctgtaacc gccaggcata agtcgctgac caccaggcta 53160
cagtgtcctg taaccgccag gcataactcg ctgaccacca ggctacagtg tcctgtaacc 53220
gccagctcta agtctctaac caccaggcta cagtgtcctg taaccgccag gcataagtcg 53280
ctgaccacca ggctacagtg tcctgtaacc gccaggcata agtcgctgac caccaggcta 53340
cagtgtcctg taaccaccag gcataagtct ctaaccacca ggctacagtg tcctgtaacc 53400
accaggtata agtctctaac cgccaggcta cagtgtcctg taaccgccag gcataagtct 53460
ctaaccacca ggctacagtg tcctgtaacc gccaggcata agtcgctgac caccaggcta 53520
cagtgtcctg taaccgccag gcataagtct ctaaccacca ggctacagtg tcctgtaacc 53580
gccagctcta agtctctaac caccaggcta cagtgtcctg taaccaccag gcataagtcg 53640
ctgaccacca ggctacagtt tcctgtaacc gccaggcata agtctctaac caccaggcta 53700
cagtgtcctc taacccccag ctctaagtcg ctgaccacca ggctacagtg tcctgtaacc 53760
gccagctcta agtcgctgac caccaggcta cagtgtcctg taaccgccag gcataagtcg 53820
ctgaccacca ggctacagtg tcctgtaacc gccagctcta agtctctaac caccaggcta 53880
cagtgtcctg taaccgccag gcataagtcg ctgaccacca ggctacagtg tcctgtaacc 53940
accaggtata agtctctaac cgccaggcta cagtgtcctg taaccgccag gcataagtct 54000
ctaaccacca ggctacagtg ccctgtaacc accaggcata agtcgctgac caccaggcta 54060
cagtgtcctg taaccgccag gcataagtct ctaaccacca ggctacagtg tcctctaacc 54120
cccagctcta agtcgctgac caccaggcta cagtgtcctg taaccgccag ctctaagtcg 54180
ctgaccacca ggctacagtg tcctgtaacc gccaggcata actcgctgac caccaggcta 54240
cagtgtcctg taaccgccag gcataagtcg ctgaccacca ggctacagtg tcctgtaacc 54300
gccaggcata actcgctgac caccaggcta cagtgtcctg taaccgccag ctctaagtct 54360
ctaaccacca ggctacagtg tcctgtaacc gccaggcata agtcgctgac caccaggcta 54420
cagtgtcctg taaccgccag gcataagtcg ctgaccacca ggctacagtg tcctgtaacc 54480
gccaggcata agtctctaac caccaggcta cagtgtcctg taaccgccag gcataagtct 54540
ctaaccacca ggctacagtg tcctgtaacc gccaggcata agtctctaac caccaggcta 54600
cagtgtcctg taaccaccag gcataagtcg ctgaccacca ggctacagtg tcctgtaacc 54660
gccaggcata agtctctaac caccaggcta cagtgtcctg taaccgccag gcataagtct 54720
ctaaccacca ggctacagtg tcctgtaacc accagctcta agtcgctgac caccaggcta 54780
cagtgtcctg taaccgccag gcataagtct ctaaccacca ggctacagtg tcctgtaacc 54840
accaggcaca agtcgctgac caccaggcta cagtgtcctg taaccgccag ctctaagtct 54900
ctaaccacca ggctacagtg tcctgtaacc gccaggcata agtctctaac caccaggcta 54960
cagtgtcctg taaccaccag ctctaagtcg ctgaccacca ggctacagtg tcctgtaacc 55020
gccaggcata agtctctaac caccaggcta cagtgtcctg taaccaccag gcacaagtcg 55080
ctgaccacca ggctacagtg tcctgtaacc gccagctcta agtcgctgac caccaggcta 55140
cagtgtcctg taaccaccag gcataagtcg ctaaccacca ggctacagtg tcctgtaacc 55200
gccaggcata agtctctaac caccaggcta cagtgtcctg taaccgccag gcataagtcg 55260
ctgaccacca ggctacagtg tcctgtaacc gccaggcata agtcgctgac caccaggcta 55320
cagtgtcctg taaccaccag gcataagtcg ctgaccacca ggctacagtg tcctgtaacc 55380
accaggcata agtctctaac caccaggcta cagtgtcctg taaccgccag gcataagtct 55440
ctaaccacca ggctacagtg tcctgtaacc accaggcata agtcgctgac caccaggcta 55500
cagtgtcctg taaccaccag gcataagtct ctaaccacca ggctacagtg tcctgtaacc 55560
accaggcata agtctctaac caccaggcta cagtgtcctg taaccgccag gcataagtct 55620
ctaaccacca ggctacagtg tcctgtaacc gccaggcata agtctctaac caccaggcta 55680
cagtgtcctg taacctccag gcataagtcg ctgaccacca ggctacagtg tcctgtaacc 55740
gccaggcata agtcgctgac caccaggcta cagtgtcctg taaccaccag gcataagtcg 55800
ctgatcacca ggctacagtg tcctgtaacc gccagctcta agtcgctaac caccaggcta 55860
cagtgtcctg taaccaccag ctctaagtct ctaaccacca ggctacagtg tcctgtaacc 55920
accagctcta agtctctaac caccaggcta cagtgtcctg taaccgccag gaataagtcg 55980
ctgaccacca ggctacagtg tcctgtaacc gccaggcata agtcgctgac caccaggcta 56040
cagtgtcctg taaccgccag gcataagtcg ctgaccacca ggctacagtg tcctgtaacc 56100
accaggcata agtcgctgac caccaggcta cagtgtcctg taaccaccag gaataagtct 56160
ctaaccacca ggctacagtg tcctgtaacc accaggcata agtctctaac caccaggcta 56220
cagtgtcctg taaccgccag gcataagtcg ctgaccacca ggctacagtg tcctgtaacc 56280
accaggaata agtctctaac caccaggcta cagtgtcctg taaccaccag gcataagtct 56340
ctaaccacca ggctacagtg tcctgtaacc accaggcata agtctctaac caccaggcta 56400
cagtgtcctc taacccccag ctctaagtcg ctgaccacca ggctacagtg tcctgtaacc 56460
gccaggcatg agtcgctgac caccaggcta cagtgtcctg taaccgccag gcataagtcg 56520
ctgaccacca ggctacagtg tcctgtaacc gccaggcata agtcgctgac caccaggcta 56580
cagtgtcctg taaccaccag gcataagtcg ctgaccacca ggctacagtg tcctgtaacc 56640
tccaggcatc agtcgctgac caccaggcta cagtgtcctg taaccgccag gcatcagtcg 56700
ctgaccacca ggctacagtg tcctgtaacc gccagacata agtcgctgac caccaggcta 56760
cagtgtcctg taaccgccag gcataagtct ctaaccacca ggctacagtg tcctgtaacc 56820
gccaggcata agtctctaac caccaggcta cagtgtcctg taaccaccag gcataagtcg 56880
ctgaccacca ggctacagtg tcctgtaacc accaggcata agtctaacca ccaggctaca 56940
gtgtcctgta accaccaggc ataagtctaa ccaccaggct acagtgtcct gtaaccgcca 57000
ggcataagtc tctaaccacc aggctacagt gtcctgtaac cgccaggcat aagtctctga 57060
ccaccaggct acagtgtcct gtaaccgcca ggcataagtc tctaaccacc aggctacagt 57120
gtcctgtaac cccagctct aagtcgctga ccaccaggct acagtgtcct gtaaccacca 57180
ggcataagtc gctgaccacc aggctacagt gtcctgcaac cgccaggcat aagtctctaa 57240
ccaccaggct acagtgtcct gtaaccgcca ggcataagtc gctgaccacc aggctacagt 57300
gtcctgtaac caccaggcat aagtcgctga ccaccaggct acagtgtcct gtaaccgcca 57360
ggcataagtc tctgaccacc aggctacagt gtcctgtaac cgccaggcat aagtctctga 57420
ccaccaggct acagtgtcct gtaaccgcca ggcataagtc gctgaccacc aggctacagt 57480
gtcctgtgac caccaggcta cagtgtcctg taaccgccag gcataagtct ctaaccacca 57540
ggctacagtg tcctgtaacc accaggcata agtcgctgac caccaggcta cagtgtcctg 57600
taaccaccag gcataagtcg ctaaccacca ggctacagtg tcctgtaacc accaggcata 57660
agtctctaac caccaggcta cagtgtcctg taaccgccag ctctaagtcg ctgaccacca 57720
ggctacagtg tcctgtaacc accaggcata agtcgctgac caccaggcta cagtgtcctg 57780
taactgccag gcatgagtcg ctgaccacca ggctacagtg tcctgtaacc accaggcata 57840
agtcgctgac caccaggcta cagtgtcctg taaccgccag gcataagtct ctaaccacca 57900
ggctacagtg tcctgtaacc gccaggcata agtctctaac caccagccta cagtgtcctg 57960
taaccaccag gaataagtcg ctgaccacca ggctacagtg tcctgtaacc gccaggcata 58020
agtctctaac caccagccta cagtgtcctg taaccaccag gaataagtcg ctgaccacca 58080
ggctacagtg tcctgtaacc gccaggcata agtctctaac caccaggcta cagtgtcctg 58140
taaccgccag gcataagtcg ctgaccacca ggctacagtg tcctgtaacc gccaggcata 58200
agtcgctgac caccaggcta cagtgtcctg taaccgccag gcatgagtct ctaaccacca 58260
ggctacagtg tcctgtaacc gccaggcata agtcgctgac caccaggcta cagtgcactt 58320
acatagaata aataaacatc tttaaaaaaa agcaaaaaaa aaattttaaa aaaagcaaaa 58380
aaaaaaaaac caaaaaaacc accaattgtt gcgctggcat aaacctccca cggcagaaat 58440
gaaagctaaa cacaccgtgt gccgttgccg tgacgtcccg tgcgccccgg gcggcgcccc 58500
agagcccgcg tccagcacaa actctcaaaa attaaaaata cgaaatgctt gggaaaaaaa 58560
accaagcctt caagaagacc cgtgacgtcg cagggacgtc ccgcggccac cgggcggcgt 58620
ctcgggaccg agccacactg ggaggtcgcg gtgtccaccc gggtccctga gcccctgtgg 58680
gcggccgtgc gtgtcagtgg tcggcgctgc gtgtcctacc tgacggcgtg cgcgcgtccg 58740
tccgtccgtc cagcggggcg agggtcggtg gcacatacat cttgaccgcg gcgggtgaac 58800
atcttgaccg cggcggctcg tccgtgtctg cgtggcgggt gcgggtcctg cggatgcgtg 58860
tgcctggcct gcctgccgtg tgtgccgtgt gtgccgcgtg tgcctgggcg ggcgcggggc 58920
ccgcgtgtgt cctgtgtgct gtggtgggtg cggcggtgcg ctcggcgcag gcttcctacc 58980
ttgtggagtc cgtccgtgcg tccgtgcgtc cgtgcgtccc gtgggcatgg cagagacatc 59040
ttgaccgcgg cgtccgcttc tgcgcgtgtg ggtgacgtcg ctgggggcgg cggccgtgac 59100
cggcggaggc tgaacagaga aacacgggtt agactttcca ttcacgccca cagaaaaact 59160
tacaacaaaa tttataaatt aaattaaatt aagaattaaa ttacaaataa ggacaagaat 59220
aattagggca gaaaccatag ctgcggctaa aagagaaacc ctgtctccaa aatcaaaaat 59280
taaaattaaa aaataaacaa aaatgaaaag gagaataatt acggaaaaaa cggtagccaa 59340
ggctataaag agaaatcctg tctggaaaag taaaaattaa aaataaaaca aaaaaaataa 59400
ttagtgaaaa atccacagcc aggtctatac agagaaaccc tgtcttaaaa aaaccaaaat 59460
taaaaaaaaa taaaccaaaa tgaaaataag aataattagg gaaaaaacgg tagccaaggc 59520
tctaaagaga aatcctgtgt gaaaaagtaa aaattaaaaa taaagctaaa agaaataatt 59580
agtgaaaaac ccacagccag gactatacag agaaacgcgt gctttaaaac atggcgctgc 59640
aactcccagc atgcctcggg gccgccttcc cgccactcac tctgaaagcc catagagaac 59700

```
cattgactac ggcaggacta caactcccag catgcctcgg ggccgccttc ccgccactca  59760
ctctgaaagc ccatagagaa ccattgacga cggcaggact acaactccca gcatgcctcg  59820
gggccgcctt cccgccactc actctgaaag cccatagaga accattgact acgcactaca  59880
agtcccagca ttcccggctc cgaccgagcc ttctcttccc gccgcagaca ggaagtgcct  59940
ccatcttaag tccgcacggt cggatcgagt ttaaaaaagc ccccaaatgc cccccagacc  60000
cccccagacc ccaattgtac gtcacggttc tgcagccggg gccccgggcg ggcgggcgcg  60060
gtggcggctg gggatcccgg gcgggcgcgc gggcgggcct cacgtcacgc ggcggcggcg  60120
gcggcggcgg gaaccgggga ccctggaggc ggctgcgggc cgagcaagcc ccgtccgtgc  60180
gcggccgagc ctgtggggaa gagagcgggg ctgagacgga ggcaggggga tggccgggag  60240
tgagcggaga aggcgggagc tcgggcggga cgcggcccgg ggccgcactc acctctcatg  60300
gcggcaggcg cggtccgctg ctcccgcccg cccgcccgcc cgcgcgggga aggccgggga  60360
ggccgaggcg gcggcggcgg aggcccgggg aggcggaggg gagccggcgg ggccgtgcgc  60420
gggcggcgga ggccgagtcc gatcgcgggg agacggcggg gagccgggga cgtccgcgga  60480
gctgcgagca catggcgatc ccaggagcga gtgtgcaggg acggccgcgg cgcctgcgcg  60540
gggggcgggg ccggggcggc ggccgcgaga gacgggcggc ggcggcggcc aatcgggagc  60600
ccggggcccg cgtgacgtca ccccgcggga ctcgggaggc cgcggtgacc ccgcccctgg  60660
cgggagcggc tctgtgtctc ctccctgtcg ccatggcgac gcaggcggcc aggcagcccc  60720
cgggctgggg aagggcttgg ttcccgccct gccagcacag gccggcctgc catctcagtc  60780
atccccctgc ctcagctctg cccctgggat tacaggcctg ggcgggtccc tgcctggggc  60840
cctgaggctc atgaacccca gagctgaatc cctgcatcca aacaaagcca agcaccccca  60900
aactcgtaac tgtgtgaggc tgggggatga ccatgagtga gtgtgtgtga ataaaataat  60960
aaaataaata aaatgcaaac acagcaccag ggcaggcggc ccagtgtgtg tgtcacaact  61020
gtgtgactgt gtgaggcagg gggatgtctg tgagtgattt tctggggcag ggtgatgatg  61080
ctgattgaat gtgtgagaca ggggcatgaa aatgagacag gggatgaagc tgagtgaatg  61140
tatgaggcag gggtttaact gtgagtgagt ttctgaggca gggggatgac agtgagtgaa  61200
tttctgaggc agggggatga ctgtgagtga ttttctgagg cagggggatg actgtaagtg  61260
attttttgaa gcagggagat gacagtgagt gaatttctga ggcaggggga tgactgtgag  61320
tgattttctg aggcaggggg atgactgtaa gtgatttttt gaagcaggga gatgactgtg  61380
agtgattttc tgaggcaggg ggatgactgt gagtgatttc tgctgattga atgtgtgagg  61440
caggggcatg aaaatgaggc aggagatgaa gctgagtgaa tgtatgaagc aggggttaac  61500
tgagtgagtt tctgaggcag gggatgact tttagtgtgt ttctgaggta ggggtttgat  61560
gctgagtgac tgtgtgacac aggagattga ccctgagagg ctgtatgagg caggggggatg  61620
ttagtgagtt tctctgtgag gcaggggat gacagtgagt gattttctga ggcaggggga  61680
tgaagcagag taactgtggg gcaggggat gtggctgtgt gactgtggga tgcaggggaa  61740
tgactgtgtg tgattttctg aggcagaggg ctgactgtaa gtgattttct gaggcagggg  61800
gatgactgtg agtgaatttc tgaggcaggg ggatcgctgt gagtgatttt ctgaggcagg  61860
agcatgatgc tgagtgagtg tctgaggcat agggatgaca gtgagtgatt ttctgacaca  61920
gggggatgaa gcagagtaac tgtgaggcag ggggatgtgg ctgtgtgact gtgtgaggca  61980
gggggatgaa tgtgtgtgat tttctgaggc agagggttga cagtgagtga ttttctgaat  62040
```

-continued catggagatg acagtgagtg attttctgag gcagggggat gactgtgagt gattttctga 62100
ggcaggggga tgaagcagag taactgtggg gcagggggat gtggctgtgt gactgtggta 62160
tgcaggggaa tgactgtgtg attttctgag gcagagggat gacagtgagt gattttctga 62220
ggcagagggc tgactgtgag tgaatttctg aagcaggttg ctcactgtga gtgattttct 62280
ggggcggggg gatcactgtg agtgaatgta tgaggcaggg ggctgactgt aagtgatttt 62340
ctgaggcagg gggatgtctg tgagtgattt tctgaggcag gggggatgact gtgagtgaat 62400 gtatgaggca ggggctgact gtaagtgatt ttctgaggca gggggatgac tgtgtgtgat 62460
tttctgaggc agtgggatga cagtgagtga ttttctgaca cagggggatg actgtgagtg 62520
attttctgag gcagggggat gactgtgagt gattttctga ggcagaggga tgacagtgag 62580
tgattttttg aggcaggggg ctgactgtaa gtgattttct gaagcagggg gctcactgtg 62640
agtgattttc tgaggcaggg ggatcactgt gagtgaatgt acgaggcagg ggaatgactg 62700
tgtgtgattt tctgaggcag gggggatgact gtaagtgatt ttctgaagca gggggctcac 62760
tgtgagtgat tttctgaagc ggggggatca ctgtgagtca atgtatgagg caggggggatg 62820 actgtaagtg attttctgaa gcagggggct cactgtgagt gattttctga ggcatgggga 62880
tcatgtgagt gaatgtatga ggcacggggc tgactgtaag tgaatttctg aggcaggggg 62940
ctgactgtga gtgaatttct gaggcagggg gatgactgtg agtgaatttc tgaggcaggg 63000
ggatgaatgt gagtgtgttt ctgaggcagg ggaatgttgt gagtgagtgt gtaagtcagg 63060
gggatgactg tgagtgattt tctgggccac ggggatgact gtgtttgagt ctctgaggca 63120
gggggctgac tgtaagtgat tttctgaagc aggggaagag tgtgtttgat tttctgaggc 63180
agggggatgg tagtgagttt ccgtgtgaag caggggggatg actgtgagtg attttctgaa 63240
gcagggggat gactgtgagt gattttctga ggcaggggga tcactgtgag tgattttctg 63300
aggcaggggg atgactgtga ttcattttat gagacaggga gatgactccc tgtgactgtt 63360
gaggcagggg cattactgtg aatgaatttc taaggcagag ggatgactgt gtgtgatttt 63420
ctgaggcagt gggatgactg tgagtgattt tctgaatcat ggagatgaca gtgagtgatt 63480
ttctgaggca gggggatgac tgtgagtgat tttctgaggc agggggatgt ctgtgtgtga 63540
ttttctgagg cagagggatg acagtgagtg attttctgag gcagggggat gaagcagagt 63600
aactgtgggg caggggggatg tggctgtgtg actgtggtat gcaggggaat gactgtgagt 63660
gattttctga ggcagaggga tgactgtgag tgattttctg aggcagaggg ctgactgtga 63720
gtgaatttct gaagcagggg gctcactgtg agtgattttc tggggcgggg ggatcactgt 63780
gagtgaatgt atgaggcagg gggctgactg taagtgattt tctggggcag ggtatgtct 63840 gtgagtgatt ttctgaggca gggggatgac tgtgagtgaa tgtatgaggc aggggctgac 63900
tgtaagtgat tttctgaggc agggggatga ctgtgagtga atgtatgagt caggggctgc 63960
ttgtgagtga ttttctgagg caggggggatg actgtaagtg attttttgaa gcagggagat 64020
gacagtgagt gaatttctga ggcaggggga tgactgtgag tgattttctg aggcaggggg 64080
atgactgtaa gtgatttttt gaagcaggga gatgactgtg agtgattttc tgaggcaggg 64140
ggatgactgt gagtgatttc tgctgattga atgtgtgagg caggggcatg aaaatgaggc 64200
aggagatgaa gctgagtgaa tgtatgaagc aggggttaac tgagtgagtt tctgaggcag 64260
ggggatgact tttagtgtgt ttctgaggta ggggtttgat gctgagtgac tgtgtgacac 64320
aggagattga ccctgagagg ctgtatgagg caggggggatg ttagtgagtt tctctgtgag 64380
gcagggggat gacagtgagt gattttctga ggcaggggga tgaagcagag taactgtggg 64440
gcagggggat gtggctgtgt gactgtggga tgcaggggaa tgactgtgtg tgattttctg 64500
aggcagaggg ctgactgtaa gtgattttct gaggcagggg gatgactgtg agtgaatttc 64560
tgaggcaggg ggatcgctgt gagtgatttt ctgaggcagg agcatgatgc tgagtgagtg 64620
tctgaggcat agggatgaca gtgagtgatt ttctgacaca gggggatgaa gcagagtaac 64680
tgtgaggcag ggggatgtgg ctgtgtgact gtgtgaggca gggggatgaa tgtgtgtgat 64740
tttctgaggc agagggttga cagtgagtga ttttctgaat catggagatg acagtgagtg 64800
tttttctgag gcagggggat gactgtgagt gattttctga ggcaggggga tgaagcagag 64860
taactgtggg gcagggggat gtggctgtgt gactgtggta tgcaggggaa tgactgtgtg 64920
attttctgag gcagagggat gacagtgagt gattttctga ggcagagggc tgactgtgag 64980
tgaatttctg aagcaggttg ctcactgtga gtgattttct ggggcggggg gatcactgtg 65040
agtgaatgta tgaggcaggg ggctgactgt aagtgatttt ctgaggcagg gggatgtctg 65100
tgagtgattt tctgaggcag gggggatgact gtgagtgaat gtatgaggca ggggctgact 65160
gtaagtgatt ttctgaggca gggggatgac tgtgtgtgat tttctgaggc agtgggatga 65220
cagtgagtga ttttctgaca caggggggatg actgtgagtg attttctgag gcagggggat 65280
gactgtgagt gattttctga ggcagaggga tgacagtgag tgattttctg aggcaggggg 65340
ctgactgtaa gtgattttct gaagcagggg gctcactgtg agtgattttc tgaggcaggg 65400
ggatcactgt gagtgaatgt acgaggcagg ggaatgactg tgtgtgattt tctgaggcag 65460
ggggatgact gtaagtgatt ttctgaagca gggggctcac tgtgagtgat tttctgaagc 65520
ggggggatca ctgtgagtca atgtatgagg caggggggatg actgtaagtg attttctgaa 65580
gcagggggct cactgtgagt gattttctga ggcatgggga tcatgtgagt gaatgtatga 65640
ggcacggggc tgactgtaag tgaatttctg aggcaggggg ctgactgtga gtgaatttct 65700
gaggcagggg gatgactgtg agtgaatttc tgaggcaggg ggatgaatgt gagtgtgttt 65760
ctgaggcagg ggaatgttgt gagtgagtgt gtaagtcagg gggatgactg tgagtgattt 65820
tctgggccac ggggatgact gtgtttgagt ctctgaggca gggggctgac tgtaagtgat 65880
tttctgaagc aggggaagag tgtgtttgat tttctgaggc agggggatgg tagtgagttt 65940
ccgtgtgaag caggggggatg actgtgagtg attttctgaa gcagggggat gactgtgagt 66000
gattttctga ggcaggggga tcactgtgag tgattttctg aggcaggggg atgactgtga 66060
ttcattttat gagacaggga gatgactccc tgtgactgtt gaggcagggg cattactgtg 66120
aatgaatttc taaggcagag ggatgactgt gtgtgatttt ctgaggcagt gggatgactg 66180
tgagtgattt tctgaatcat ggggatgaca gtgagtgatt cttttaagca gggggatgac 66240
tgtgagtgat tttctgaagc agggggatga ctgtgagtga ttttctgagg caggggggatg 66300
actgtgattc attttatgag acagggagat gactccctgt gactgttgag gcaggggcat 66360
tactgtgaat gaatttctaa ggcagaggga tgactgtgtg tgattttctg aggcagtggg 66420
atgactgtga gtgattttct gaatcatgga gatgacagtg agtgattttc tgaggcaggg 66480
ggatgactgt gagtgatttt ctgaggcagg gggatgaagc agagtaactg tgaggcatgg 66540
ggatgtggct gtgtgactgt ggtatgcagg ggaatgactg tgtgtgattt tctgaggcag 66600
agggatgact gtgagtgatt ttctggggcg gggggatcac tgtgagtgaa tgtatgaggc 66660
agggggctga ctgtaagtga ttttctgagg caggggtttg tctgtgagtg attttctgag 66720
gcagggggat gactgtgagt gaatgtatga ggcaggggct gactgtaagt gattttctga 66780

```
ggcaggggga tgactgtgtg tgattttctg aggcagaggg atgacagtga gtgattttct  66840
gacacagggg gatgactgtg agtgattttc tgaggcaggg ggatgactgt gagtgatttt  66900
ctgaggcaga gggatgacag tgagtgattt tctgaggcag gggctgact gtaagtgatt  66960
ttctgaagca gggggctcac tgtgagtgat tttctgaggc aatggggatc actgtgagtg  67020
aatgtatgag gcaggggctg actgtaagtg attttctgag gcagggggat gactgtgtgt  67080
gattttctga ggcagaggga tgacagtgag tgattttctg acacaggggg atgactgtgt  67140
gtgattttct gaggcagagg gatgacagtg agtgattttc tgacacaggg ggatgactgt  67200
gagtgatttt ctgaggcagg gggctgactg tgagtgaatt tctgaggcag ggggatgact  67260
gtgagtgaat ttctgaggca gggggatgac tgcgagtgat tttctgaggc agggggatga  67320
ctgtgggtga atatatgagg ctgggggttg actgcgagtg agtttctgag gctcccctcc  67380
ccccaggccg ctggccgcct ccatgacccc ctggcgggag cggctctgtg tctcctccct  67440
gtcgccatgg cgacgcaggc ggccaggcag cccccgggct ggggaagggc ttggttcccg  67500
ccctgccagc acaggccggc ctgccatctc agtcatcccc ctgcctcagc tctgcccctg  67560
ggattacagg cctgggcggg tccctgcctg gggccctgag gctcatgaac cccagagctg  67620
aatccctgca tccaaacaaa gccaaacacc ccccaaactc gtaactgtgt gaggcggggg  67680
gatgaccatg agtgagtgtg tgtgaataaa ataataaaat aaataaaatg caaacacagc  67740
gccagggcag gcggcccagt gtgtgtgtca cagctgtgtg actgtgtgag gcagggggat  67800
gtctgtgagt gattttctga ggcaggggca tgactgtgag tgattttatg tgagtgactg  67860
ttagtgtttg acgtaggggt ttgatgctga gtgactgtgt gacacaggag attgaccctg  67920
agaggctgtg tgaggcaggg ggatgttagt gagtttctct gtgaggcagg gggatgactg  67980
tgagtgattt tctgaggcag ggggatgaca gtgagtgatt ttctgacaca gggggatgaa  68040
gcagagtaac tgtggggcag ggggatgtgg ctgtgtgact gtgggatgca ggggaatgac  68100
tgtgtgtgat tttctgaggc agaggactga cagtgagtga ttttctgagg gagggggctg  68160
actgtaagtg attttctgag gcagggggat gtctgtgagt gattttctga ggcaggggga  68220
tgactgtgag tgaatgtatg aggcaggggc tgactgtaag tgattttctg aggcaggggg  68280
atgactgtgt gtgattttct gaggcagtgg gatgacagtg agtgattttc tgacacaggg  68340
ggatgactgt gagtgatttt ctgaggcagg gggatgactg tgagtgattt tctgaggcag  68400
agggatgaca gtgagtgatt ttctgaggca gggggctgac tgtaagtgat tttctgaagc  68460
agggggctca ctgtgagtga ttttctgagg catggggatc atgtgagtga atgtatgagg  68520
cacggggctg actgtaagtt aatttctgag gcagggggct gactgtgagt gaatttctga  68580
ggcaggggga tgactgtgag tgaatttctg aggcaggggg atgactgcga gtgattttct  68640
gaggcagggg gatgactgtg ggtgaatata tgaggctggg ggttgactgc gagtgagttt  68700
ctgaggctcc cctcccccca ggccgctggc cgcctccatg acccctggg ggagcggctc  68760
tgtgtctcct ccctgtcgcc atggcgacgc aggcggccag gcagcccccg ggctggggaa  68820
gggcttggtt cccgccctgc cagcacaggc cggcctgcca tctcagtcat ccccctgcct  68880
cagctctgcc cctgggatta caggcctggg cgggtccctg cctggggccc tgaggctcat  68940
gaaccccaga gctgaatccc tgcatccaaa caaagccaaa cacccccaaa ctcgtaactg  69000
tgtgaggctg gggatgacc atgagtgagt gtgtgtgaat aaaataataa aataaataaa  69060
atgcaaacac agcgccaggg caggcggccc agtgtgtgtg tcacaactgt gtgactgtgt  69120
gaggcagggg gatcactgtg agtgattttc tgaggcaggg ggatgattgt gattcatttt  69180
```

atgagacagg gagatgattc cctgtgactg ttgaggcagg ggcattactg tgaataaatt 69240
tctaaggcag aggcataact gtgagtgatt ttctgaggca gtgggatgac tgtgagtgat 69300
tttctgaggc agggggatga ctgttagtgt gtttttgacg taggggtttg atgctgagtg 69360
actgtgtgac acaggagatt gaccctgaga ggctgtgtga ggcaggggga tgttagtgag 69420
tttctctgtg aggcaggggg atgatgctga gtgagtgtgt aagtcagggg gatgactgtg 69480
agtgattttc tcggccacag ggatgactgt gtttgagtct ctgagacagg gggctgactg 69540
taagtgattt tctgaggcag gggaagagtg tgtttgattt tctgaggcag ggggatggta 69600
gtgagtttcc gtgtgaggca gggggatgac tgtgagtgat tttctgaggc agggggatga 69660
ctgtgagtga ttttctgagg caggggggatc actgtgagtg attttctgag gcagggggat 69720
gactgtgatt cattttatga gacagggaga tgactccctg tgactgttga ggcaggggca 69780
ttactgtgaa tgaatttcta aggcagaggg atgactgtga gtgattttct gagccagggg 69840
gatgttagtg agtttctgtg tgaggcaggg ggatgactgt gagtgatttt ctgaggccgg 69900
ggcatgactg tgagtgattt tctgaggccg ggcatgactg tgagtgattt tctgaatcat 69960
ggagatgaca gtgagtgatt ttctgaggca gggggatgac tgtgagtgat tttctgaggc 70020
agggggatgt ctgtgtgtga ttttctgagg cagagggatg acagtgagtg attttctgag 70080
gcagagggct gactgtgagt gaatttctga agcagggggc tcactgtgag tgattttctg 70140
gggcgggggg atgactgtga gtgaatgtat gaggcagggg ctgactgtaa gtgattttct 70200
gaggatgggg gatgactgtg agtgattttc tgaggcaggg ggatgacagt gagtgatttt 70260
ctgacacagg gggatgaagc agagtaactg tggggcaggg ggatgtggct gtgtgactgt 70320
ggtatgcagg gggatgactg tgagtgattt tctgaggatg ggggatgaca gtgagtgatt 70380
ttctgaggca gagggatgac agtgagtgat tttctgacac agggggatga ctgtgagtga 70440
ttttctgagg caggggggatg actgtgagtg attttctgag gcagagggat gacagtgagt 70500
gattttctga ggcaggaggc tgactgtaag tgattttctg aagcaggggg ctcactgtga 70560
gtgattttct gaggcggggg ggatcactgt gagtgaatgt atgaggcagg gggatgactg 70620
taagtgattt tctgaagcag ggggctgact gtgagtgaat ttctgaagcg gggggatcac 70680
tgtgggtgaa tgtatgaggc tgggggatga ctgctagtga atgtctgagg ctcccctccc 70740
cccaggccgc tggacgcctc catgaccccc tggcgggagc ggctctgtgt ctcctccctg 70800
tcgccacggc agggatatga ccgcgattaa ctgtgaggca ggggaatgaa gcgaagtgac 70860
tgaggcaggg ggatgactgt gattgaattt ctgaggcagg gggatgactg tgagtcagtt 70920
tctgaggcag gggggatgact ctgagtgagt gtgtgaggca gttggatggc actgattgtg 70980
ggtgtgaggc agggtgatga gtgtcagtga atttctgagg caggggggatg actgttagtg 71040 agtttctgag gcaggggtga cctggtttga atgtgtgagg caggggggtga tgctgagtga 71100 ctgtgtgaca caggagattg accctgagag gctgtgtgag gcagggggat gactgtgagt 71160
gaatttctga gacaggggga tgacagtgag tgattttctg aggcaggggg atgactgtga 71220
gtgactgtgt gaggcaggtg gatggcactg attgtgtgtg tgaggcaagg gtatgactat 71280
gattgaattt ttgaggcagg gggatgactt tgagtgactg tgtgaggcag gggatgact 71340 gtgagtgatt ttctgaggca gggggatgat tgtgggtgat tttctgaggc agggggctga 71400
ctgtgagtga atttctgagg cggggggatc actgtgggtg aatgtatgag gctgggggtt 71460
gactgcgagt gaatatctgg ggcaggggga tgacctggat tgaatgtgtg aggcaggggt 71520

-continued

```
aggaagctga gtgactgtgt gatgtagggc tatgacgctg agtgactgtg aggcaggggg  71580
atgaccctga gtgagtgtgt gaggcaggtg gatggcactg attgtgggtg tgaggcaggg  71640
ggatgactgt gagtgaattt ctgaggcagg gggatgactg tgagtgaatt tctgaggcag  71700
ggggatgact gtgagtgaat ttctgaggca ggggaatgac gctaagtgac tgtctgaggc  71760
agggggatga ctgtgagtgg ctgctgtggg ggagggtcag gtccgcacac ccgccgcagc  71820
agagcctgct gggagctcag cctctgcaca cacggacgga cggacagaca gacagacaca  71880
caggcagcca ggccttccag gtctgcttgc cagggctcag agcccagtgt caatcacact  71940
cggggccccg cccacccgga atcccccagg cagctgggcc aactgccacc ctgtgggagt  72000
gggggagagg tcaggcaggg agctgggccg tcgccatgga gacgacggcc tgggagcccc  72060
gccccgcctg cctgtcagtc accgaggctc cctggctccg cccacccgga atccccaggc  72120
agctgggcca actgccaccc tgtgggagtg gggggagaggt caggcaggga gctgggccgt  72180
cgccatggag acgaaggcct gggagccccg ccccgcctgc ctgtcagtca ccgaggctcc  72240
ctggctccgc ccacccggaa tcccccaggc cgctgggcca actgccaccc tgtgggagtg  72300
ggggagaggt caggcaggga gctgggccgt cgccatggag acgagggcct gggagccccg  72360
ccccgcctgc ctgtcagtca ccgaggctcc gggccccgcc ccctgtcagc tcagggattc  72420
cgcaggccag gcctgtgccc gcgtggccgg ctgtggatcc gtggtgctcc tgtgtgggcc  72480
gtgggctcca cgtcctggcc ccggtgggcg tgggggacac acggggtctc tgtgtctgtg  72540
cggccaggcc cggccgtgcc gggaactcac tgcgctacct agggctggcc gggaactcca  72600
atcatccccc tgtctcagct ctgaacgtga acgtgaacgc ctgtctgagg caggggggatg  72660
gcgccgagtg agcagtagag gcgaggcgcg gcctcgtgcg ggtttaggtc agcgcgcggg  72720
ggacagagtg aaggagccca cggcgcctcg tagccggagg tcgaggcggg cggcgaagcg  72780
gccgaggaca gggcggctgc agcgggcggc ggagccaagt agccgggcag tgaacgtgtg  72840
aggcaggggg atgaccgcga gtgactgtat gaggcagggg gatgaccgcg agtgactctg  72900
tgaggcaggg gcatgaccgt gagtgatgct aagtgactgt ctgaggcagg gggatgactg  72960
tgagtggctg ctgtgggcga gggtcaggtc cgcacacccg ccgcagcaga gcctgctggg  73020
agctcagcct ccgcacacag ggacggacag acagacagac acacacagac ccgcccacagc  73080
ctgggcacgc agccgcggga tttcccgcct gagacgaatc aatgaaatga agagcgcggg  73140
cggccccgat ctgatgacgt cacgcgtttc ctggtcgttc acgctgtgtg cggcagaggg  73200
cggaggcagg gggatgactc ccgcgagggg gaggctgaac cccgagtctc tcggcgcctg  73260
ggctgccgcg gctcacgccg ccgccggggt ctgacagggc tcgcgagagg cgggtcctgt  73320
tcagagcgag ctccgcgcgg cggctcgtct cggggtctgt gggcgggacc cgctgtcacc  73380
ccagccgacg gcctcggcct cggggtcgct atgagtgact gctgtgggtg aggcaggggg  73440
atgaccccga gtgactaact gtgaggcagg gggatgacgc tgagtgactg tctgaggcag  73500
ggggatgaca tgagtgactg ctgcgggtga ggcaggggga tgaccccgag tgactgtgag  73560
gcagggggat gacgctgagt gactgtctga ggcaggggga tgacatgagt gactgctgcg  73620
ggtgaggcag gggggatgacc ccgagtaact gtgaggcagg gggatgacgc tgagtgactg  73680
tctgaggcag gggatgaca tgagtgactg ctgcgggtga ggcaggggga tgagcccgag  73740
taactgtgag gcagggggat gacgctgagt gactgtttga ggcaggggga tgacatgagt  73800
gactgctgcg ggtgaggcag gggatgacc ccgagtaact gtgaggcagg gggatgacgc  73860
tgagtgactg tctgaggcag gggatgaca tgagtgactg tctgaggcag gggatgaca  73920
```

```
tgagtgactg tctgaggcag ggggatgaca tgagtgactg ctgcgggtga ggcaggggga  73980
tgaccccgag tgactgtgag gcaggggat gacgctgagt gactgaggca gggggatgac  74040
atgagtgact gctgcgggtg aggcaggggg atgaccccga gtaactgtga ggcaggggga  74100
tgacgctgag tgactgtctg aggcaggggg atgaccccga gtaactgtga ggcaggggga  74160
tgacgctgag tgagtgtctg aggcaggggg atgacatgag tgactgctgc gggtgaggca  74220
cggataggac cgcgactaac tgtgaggcag gggaatgatg ctgagtgact gtctgaggca  74280
gggggatgac atgagtgact gctgtgggtg aggcacgggt agcacagcga gtaactgtga  74340
ggcaggggga tgacgctgag tgactgtctg aggcaggtgg atgactgtga gtgattttct  74400
gatgcagggg atgactgtga gtgattttct gaggcagggg gatcgctgtg agtgatttgt  74460
gctgattgaa tgtgtgaggc aggggcatga aaatgaggca ggagatgaag ctgagtgaat  74520
gtatgaagca gggatttaac tgtgagtgag tttctgaggc aggggatga ctgtgagtgt  74580
gtttctgaca tagggggatg atcctgagtg actgtgtgac acaggagatg gaccctgaga  74640
ggctgtatga ggcaggggga taacagtgag tgattttctg aagcaggggt ttaactgtga  74700
gtgtgtttct aaggcaggag gataactgtg agtgattttc tgaggcagag gaatgactgt  74760
gagtcatttt ctaaggcagg ggatgactgt aagtgatttt ctgaggcagg gggatggttg  74820
tgagtgattt tctgaggcag tgagatggct gtgagtgatt ttctgaggca gggggatggt  74880
agagagtttc tgtgtgaagc aggggatga ctgtgagtga ttttctaagg caggggatga  74940
ctgtaagtga tttgtgctga ttgaatgtgt gaggcagggg catgaaaatg aggcaggaga  75000
tgaagctgag tgaatgtatg aagcagggat ttaactgtga gtgagtttct gaggcagggg  75060
gatgactgtt agtgtgtttc tgaggtaggg ctttgatcct gattgactgt gtgacacagg  75120
agatggaccc tgagaggctg tatgaggcag ggggataaca gtgagtgatt ttctgaagca  75180
ggggtttaac tgtgagtgag tttctaaggc aggaggatga ctgtgagtga ttttctgagg  75240
cagaggaatg actgtgagtc attttctaag gcagggggat ggctgtgagt gactgtgtga  75300
gtcgggggga tgatgctgag tgagtgtgtg aggcgggggga atgatgctga gtgattttct  75360
gaggcagggg ggtgactgta agtgattttt tgaagcaggg agatgactgt gagtgatttt  75420
ctgaggcagg ggcatgactg tgagggattt tctgaggcag gggatgaca gagagtgatt  75480
ttctgaggca gggggatgac tgtgagtgat tttctgaggc aggggatga cagtgagtga  75540
ttgtctgagg cagagggatg acagtgagtg attttctgac acaggggat gactgtgagt  75600
gattttctga ggcaggggga tgactgtgag tgattttctg aggcagaggg atgacagtga  75660
gtgattttct gaggcagggg gctgactgta agtgattttc tgaagcaggg ggctcactgt  75720
gagtgatttt ctgaggcaat ggggatcact gtgagtgaat gtatgaggca ggggctgact  75780
gtaagtgatt ttctgaggca gggggatgac tgtgtgtgat tttctgaggc agagggatga  75840
cagtgagtga ttttctgaca caggggatg actgtgtgtg attttctgag gcagagggat  75900
gacagtgagt gattttctga cacaggggga tgactgtgag tgattttctg aggcaggggg  75960
ctgactgtga gtgaatttct gaggcagggg gatgactgtg agtgaatttc tgaggcaggg  76020
ggatgactgc gagtgatttt ctgaggcagg gggatgactg tgggtgaata tatgaggctg  76080
ggggttgact gcgagtgagt ttctgaggct cccctccccc caggccgctg gccgcctcca  76140
tgaccccctg gcgggagcgg ctctgtgtct cctccctgtc gccatggcga cgcaggcggc  76200
caggcagccc ccgggctggg gaagggcttg gttcccgccc tgccagcaca ggccggcctg  76260
```

-continued

```
ccatctcagt catccccctg cctcagctct gcccctggga ttacaggcct gggcgggtcc  76320
ctgcctgggg ccctgaggct catgaacccc agagctgaat ccctgcatcc aaacaaagcc  76380
aaacaccccc caaactcgta actgtgtgag gcggggggat gaccatgagt gagtgtgtgt  76440
gaataaaata ataaaataaa taaaatgcaa acacagcgcc agggcaggcg gcccagtgtg  76500
tgtgtcacag ctgtgtgact gtgtgaggca gggggatgtc tgtgagtgat tttctgaggc  76560
aggggcatga ctgtgagtga ttttatgtga gtgactgtta gtgtttgacg taggggtttg  76620
atgctgagtg actgtgtgac acaggagatt gaccctgaga ggctgtgtga ggcaggggga  76680
tgttagtgag tttctctgtg aggcaggggg atgactgtga gtgattttct gaggcagggg  76740
gatgacagtg agtgattttc tgaggcaggg ggatgactgt gagtgactgt gtgaggcagg  76800
gggatgacac tgattgtgtg tgtgaggcaa ggggatgact gtcagtgatt ttctgaggca  76860
gggggatgac tttgagtgac tgtgtgaggc agggggatga ctgtgagtga ttttctgagg  76920
caggggaatg acaaggagtg attttctgag gcagggtgat cgctgtgagt gattttctga  76980
ggcagggggt tgactgtgag tgagtttctg aggcagggca gggcatcgtg gtgcccggac  77040
atcattaatc cctgcactct ggagtcagag gcagggggat gactgtgagt gtgtttctga  77100
ggttgagtga gggtgtgagg caggggcatg acgctgtgtg aggcaggggg ttgcctgtaa  77160
gtttctgagg cagggcaggg catcttggta cccggacgtc attaatccca gcactcggga  77220
gtcagaggca gggggatggc tgagttggag gccagcctgg tctacagcct gagctccagg  77280
acagccaggg ctacacagag aaaccctgtc tcgaaaaacc aaaaaacttt ctgaggcagg  77340
gggatgactg tgagtgtgtt tctgaggcag ggggatgact gtgagtgatt ttctgacaca  77400
ggggaatggc agtgagtgat tttctgacac agggggatga ctgtgagtgt gtttctgagg  77460
caggggcatg actgtgagtg attttctgag gcagggtgat gactgtgagt gattttatga  77520
tgctggggga tgagtatgag tgattttctg aggcaggggg ctgactgtga gtgattttct  77580
gaggcggggg gatcactgtg agtgaatttc tgaggcgggg ggatcactgt gagtgaattt  77640
ctgaggcggg ggatcactg tgggtgaatg tctgaggctc ccctcccccc aggccgctgg  77700
atgcctgtgg gtgtcacagc tgtgtgactg tgtgaggcag ggggatgact gtgagtgatt  77760
ttctgaggca gggggatgcc tgtgtgtgat tttctgaggc aggggcatgg tagagagttt  77820
ctgtgtgaag caggggggatg actgtgagtg attttctaag tcagggggat gactgtgagt  77880
gattttctga cgcaggggaa tgactgtgag tgattttctg acacagggag atgaagctga  77940
gtaactgtgg ggcaggggga tgttgatgtg tgactgtgag gcagggggat gactgtgagt  78000
gattttctga ggcaggggga tgaatgtgag tgattttctg aggcagtgga atgactgtga  78060
gtgagtttct gaggcggggg gatcactgtg ggtgaatgta taaggctggg gcatgactgc  78120
gagtgaacgt ctgaggctcc cctcccccca ggccgctgga cgcctccatg accccctggc  78180
gggagcggct ctgtgtctcc tccctgtcgc catggcaggg atatgaccgc gattaactgt  78240
gaggcagggg aatgaagtga agtgactgag gcagggggat gactgtgatt gaatttctga  78300
ggcaggggga tgacagtgag tgattttctg aggcaggggg atgactgtga gtgactgtgt  78360
gaggcaggtg gatggcactg attgtgtgtg tgaggccagg ctatgactat gattgaattt  78420
ttgaggcagg gggatgactt tgagtgactg tgtgaggcag ggggatgact gtgagtgatt  78480
ttctgaggca ggggggtgac tgtgggtgat tttctgaggc agggggctga ctgtgagtga  78540
atttctgagg cggggggatc actgtgggtg aatgtatgag gctgggggtt gactgcgagt  78600
gaatatctgg ggcaggggga tgacctggat tgaatgtgtg aggcaggggt aggacgctga  78660
```

gtgactgtgt gatgtagggc tatgacgctg agtgactgtg aggcaggggg atgattctaa 78720
ttaatagtat taggcagggg gtgatgctga gtgactgtgt gaggcagggg gatgaccgcg 78780
attaactgtg aggcagggga atgacgctaa gtgactgtct gaggcagggg gatgactgtg 78840
agtggctgct gtgggggagg gtcaggtccg cacacccgcc gcagcagagc ctgctgggag 78900
ctcagcctcc gcacacacgg acggacggac agacagacag acacacaggc agccaggcct 78960
tccaggtctg cgtgccaggg ctcagagccc agtgtcaatc acactcgggg ccccgcccac 79020
ccggaatccc ccaggcagct gggccaactg ccaccctgtg ggagtggggg agaggtcagg 79080
cagggagctg ggccgtcgcc atggagacga gggcctggga gccccgcccc gcctgcctgt 79140
cagtcaccga ggctccctgg ctccgcccac ccggaatccc ccaggcagcc gggccaactg 79200
ccaccctgtg ggagtggggg agaggtcagg ggatgacgct gagtgactgt gggaggcagc 79260
gcatgactgt gagtgatttt ctgaggcagg gagatgactg tgtctgagtc tctgaggcag 79320
ggggatgatg ctgattgaat gtgtgaggca ggggcctgaa aatgaggcag gggattaagc 79380
tgagtgaatg taggatgcag gggtttaagt gtgagtgcgt ttctgaggca gggggatgac 79440
tgtgagtgac tgtgggaggc agcgcatgac tgtgattgat tttctgaggc agggagatga 79500
ctgtgtctga gtctctgagg caggggggatg atgctgattg aatgtgtgag gcaggggcct 79560
gaaaatgagg caggggatga agctgagtga atgtcggaat gacagcataa gaaaaatata 79620
aaaatatttc cacgtcgctg cttctccttt attctccccc cccacccccc ccccccgcgc 79680
acaccaccga catcggaccc ggatgacaaa acgaatcccc accctcccga ccccgacccc 79740
taaccccagc ccaacgatgt gataaaaaca gaaacgatgg ctgacatggg atgtttggcc 79800
cggggttcac ccacacgcaa acagcaggcg agtgacataa aaaaataatc atgttgggga 79860
aaaacccatg tgtttgtttt cccttgtggt ggtgacatcc aacctgggcg ggtgaccccc 79920
aagcaccggc ccgacccagg ggggtcaggc cacagaagaa caagtgcaac gtgtgaaaaa 79980
actgtgccta cggttcacac atacgcaaac agcgacgagc agtcaatgac agtctaagaa 80040
aactataaaa aagaatttcc gtgtcgccgg tcacgaccgc cgcattctcc tctgtcacca 80100
ccgggtggcg acagagagca cgccgggaaa aacctccgct ccgggagtcc tcccaggggt 80160
cggagtctgc gaggggaaag cgacgaggag gggacagacg cccgagatcg actccagatg 80220
aggccagatg tcttccgggg tggcagaatc gagaacgtga cgagaagcgc tgttttccaa 80280
acgtttctct tgctggcgtc gtcgtcgtcg agacgttctc acaaattttc agaggaaaat 80340
gaaacatttt ccaccgaggt gtccgtgttt aagatgtgaa gtcgttttaa gtcgctatca 80400
aaatattcat ctgggtatca atgatacagt cacagctgaa atgtctccac tcacatcgga 80460
gtgaggaagc ccgcgggctt ccttattagg ctcaagacgg cttctgcttt agccgtctat 80520
ccggttcttc taagcggtcg tgcccagcct ggcctcagta tggaatagaa ttttctgaag 80580
cagggggatg accctgagtg accgtgtgag acagggggat gactgtgagt gattttctga 80640
ggcaggggga tgaccctgag tgaccgtgtg aggcaggggg atgactgtga gtgattttct 80700
gaggcagggg gatgactgtg agtgattttc tgaggcgggg ggatgactgt gaatgatttt 80760
ctgaggcagg gggatgaccc tgagtgaccg tgtgaggcag ggggatgacc ctgagtgacc 80820
gtgtgagaca gggggatgac tgtgagtgat tttctgaggc agggggtgac tgtgagtgat 80880
tttatgatgc tgggggatga gtatgagtga ttttctgagg cagtgggatg actgtgagtg 80940
attttctgag gcagaaggat gactgtgagt gattttctga agcgggggtg atcactgtga 81000

-continued atgattttct gaggcagggg gatgattgtg agtgattttc tgaggcaggg ggatgaccct 81060
gagtgaccgt gtgaggcagg gggatgactg tgagtgattt tctggacaga ttggggaaga 81120
tgtcacgacg ctctggaagc ctgagtttct cgaccccata aacagcggcc tccacctgtg 81180
tccctccccg gggccgctgt ggggccgggt ccctcaaggt cgctgctccg tacagtccag 81240
atggtccggg atgggcagac ccgtgacgat ggtcagacac ttgttccaca cggtgaaggt 81300
ggggcacacg ggctgcgcga gcgccgcgtg gaaggtgtgg aggtggacgg agctcagagc 81360
gtcgtagaag gcgatggagc cgttgtcgta gtccagcagg acgccgacgc gcctgaggtg 81420
aggggccggc gcgatggggg tctccttgcc gtcgtgtcgc accgcccagt ggttgtggca 81480
gcggcagagg gcccaggacg ccgcgttctt cccgatccac tcgtgtttcg gcgccgatct 81540
gtacgccagg ccgatggcgt acctgccgag aaaaaaaaga aaatcacatc gcctgtcggt 81600
gagatttgct cgtggtccac aggtgttttc tttttaaagt gatcctttat tggcgatcac 81660
actcccttta agtctttacg tctaaatatg tctgtctgtc cttcctaaac acattagagg 81720
tggacggcgg ccggtgtgtc gaccgacctt ctggtctgca gcttaagtgt caccagagaa 81780
tctcgatttt ccattccttc actgccccgt ttctctcctg tgcatgcccg tgcagacggg 81840
tggacagaca gacagacaga gggacggaca gatagacaaa agatggacag acagatggac 81900
agaagagcag acagactgat ggacagaaac agacagagag aagggcagac aggtagacgg 81960
atgggcagac agacagacag agggacggac agatagacaa aagatggaca gacagatgga 82020
cagaagagca gacagactga tggccagaaa cagacagaga gaagggcaga caggtagacg 82080
gatggacaga cagacagaca gagggacgga cagatagaca aaagatggac agacagatgg 82140
acagaagagc agacagaccg atggacagaa acagacagag agaagggcag acaggtagac 82200
ggatggacag acagacagac agagggacgg acagatagac aaaagatgga cagacagatg 82260
gacagaagag cagacagact gatggacaga aacagacaga gagaagggca gacaggtaga 82320
cggatggaca gacagaggac aggtggacag atggacagaa gacagatgga cacacaggga 82380
cagacaggtg gatccagacg gagacggcct accatgtgct tccgctggtg accacttccc 82440
agtagtgacg gccgctgtcg atgaacacgt tgccagccac tccgtagctc ccctgaccag 82500
cgaagcgctc cggcgcgtga ctcttcttag aggacgactc gtcgcgctcg acagtcaggt 82560
tgtcgtggga caccttcagc ttgcgatgag ccgatttggg atccagtcta aacggctgac 82620
ctgaaggcga gttcaccaga gagagagaca ccaagagcac ggttgactgg aaagatgaca 82680
ggtagcgtga cctcatttac atttaagagt ctgaaacaag ggctcaaggg agagagctgc 82740
ctaaatgcca acagcaacgc ctaggttttc tatatttgga tttattaata cacataataa 82800
gcagagttga catattctgg gttcacacat atgcaaagag tggtgagcca tcaacgataa 82860
taaaagaaaa acgaacgtgc acgtagatgc tttgaaaaag aatcaacgct cacggaaacc 82920
aaaaacaagt gtcctttgaa aaaaagaaaa tcggacggtc acgaccaccg cattctcctc 82980
tgtcaccacc gggtggcgac agagagcacg cagggaaaaa acttcctcca aggggtcgga 83040
tctgcctgct tcatcccggc cagggtgagg ggaagccggc caggctggcg gatccgaccc 83100
ggcgaggcgg tcgcgttttc catcggtcgg tccccgggag gttgtactct gtgagataca 83160
ggaagtgcct ccattttgga caggaagtcg ggcccaggcg ctcatgggag ctgtagtgcg 83220
tctaggctag ggcccagcgc cgatctccgg ggccacccgg tggcgagaaa cgcgcaagtg 83280
cacccccggt tctctgcctc gcggggacgg atctgggacc cgaaggcccc aattgagaac 83340
ctcgatgcgg ctgctgggaa cctcagtgtt tcacatcggt ccttgattca cttgtgtgag 83400

```
gctgtcagtg aggcccagga cggaaaacgt aaaagaaagg tggggagcag cctcagcccc  83460
aaaggcaagc agccgtgaga tggcagctca gccgagttca cagcactcac tgttggtctt  83520
cagctttccg ggctcactgc tactgaagca gggggatgac cctgagtgac cgtgtgaggc  83580
agggggatga ctatgagtga ttttctgagg caggggggatg accctgagtg accatgtgag  83640
gcagggggat gactgtgagt gattttctga ggcaggggga tgaccctgag tgaccatgtg  83700
agacatgggg atgactgtga gtgattttct gaagcagggg gatgaccctg agtgaccatg  83760
tgagacaggg ggatgactgt gagtgatttt ctgaagcagg gggatgaccc tgagtgacca  83820
tgtgagacag ggggatgagt gtaagtgatt ttctgaggca gggggatgac tgtgagtgat  83880
tttctgaggc agggggatga ccctgagtga ccatgtgaga caggggggatg actgtgagtg  83940
attttctgag gcagggggat gaccctgagt gaccatgtga gacaggggga tgactgtgag  84000
tgattttctg aggcaggggg atgactgtga gtgattttct gaggcagtgt aagctggcag  84060
ctcagccgag tccacagcac tcactgttgg tcttcagctt tccgggctca ctgctacggc  84120
tgcccgcctg gttgatggcc ttcaccgtga agatatactt ggtgccactt tgcaggccgt  84180
gcacggtgta gtggttctgc ttgatgttgg gcacgatcat ccagctgtcc gccgagttac  84240
acagacctgc ggagccgagg agacaggtgc cgtcacaggc cacgtctgca gaatggcaga  84300
ttatttggac attgaacatt ggaaaacgga gagctttctg gctctttatg tggcttgatc  84360
aataaaacac tgctcagcgt gctacctcta tggagagttc acttcgtacc atatacgttc  84420
tctttgcgcg ttccgctttt ctgccacact tttctctatt ccgtacaaac aatcctaatt  84480
aatatctaca attttaacct ctgataatac attttacgta agagtggttg agtttggata  84540
tctatgttat gaggtgatca atggattcac agtgtgtatg tggttaccgg cttctttttt  84600
aaaactacat ccgggctggt gagatggctc agtgggtaag agcacccgac tgctcttccg  84660
aaggtccaga gttcaaatcc cagcaaccac atggtggctc acaaccatcc gtaacaagat  84720
ctgactccct cttctggagt gtctgaagac agctacagtg tacttacata taataaataa  84780
ataaatcttt aaaaaaaaaa actacatcca tgtggttttc cggaggttgt taatttcatg  84840
ggtatttagt cagctgttct catgactgcg atacaagtga gcattatcca ttccttgaac  84900
aggaaagaga agccgataaa tattgtcatc atgttcagtc ctcatcatct cctttctgtg  84960
ttgagatccc ttcacccagc tcatctgaaa acagtcgtcg aacgcggaag ggaatcagcc  85020
gagagatact cactgacaac attggcttgt ccggtgaata tggtgtactg gagctcgtag  85080
gagaccacgc tgaactcgtc ctctgaggtc cagtggacgg tgatggtgtc ataggaagcg  85140
gtgcagagct cttctctaat cgtgggagcg ttgggagctg tggacatcac acgcatgtca  85200
gcggagcagc agataccatt aggacgacaa tttggaggta ttcgactgtt gaagcaggtc  85260
ttcctcctaa acaggtctag cacatttact aacaggaggt tttggttcca gagcgctcag  85320
ccgtctactt aaagaatgtt tcagggttta tctgttgttg atttttctaa gcggtgtgac  85380
taaagccagc cagccggccg ctaagacgtc acctcgattt atcatgagaa tatatttatg  85440
agagtaagag aacaatagct tcttgtgtat gaagaaagat agatcagaga aaaagtaacc  85500
atggcagact ttcataatgt cattctcatt tggtaggggg tggggggtgg aaatcttact  85560
aatcaaggac tataggatcg acattttagg tattgtagga cagacttctg ctctcgcacc  85620
tacttaaccc tgccattaga gcggatgtag atgatttgta cgtaaagagt acgaccagac  85680
tctcataaaa tcttatttac aaaacagcca cagggcctga tttggcttga aacccactat  85740
```

-continued

```
gccaatctct cgtccacacg ccaccagcta ttttaaaaaa tatcacggtg atctgctaag  85800
aaatcaacaa gtcatttaaa ttcttccttt atctttattt tcttgtccct gtttctactt  85860
ggtctgtgtt atttaggtta gaatacagcg cggacattca tctttatagg actatcagat  85920
agcatttcag agactgaagc acgtgtatgg gttttagaag ataatcgact caatggtaaa  85980
gtgaatagac actgtactag agagaacata gaagagagta agacgatacc tgttaggtaa  86040
tccagacact ctagcagttt cttctcccgg gaaaaatcca aggcaaaagt gtcaaacgtg  86100
tcattgaggt tgatttcggg aattaggacc tgggaggatg cagttgccat ggagactctg  86160
tcatttaaac aagacactgt tttaagaaat gtcaaggtgg cttttatcac cactgtgaag  86220
gagtgagaac aaaaccaaag gaaaagaaat atcagggttt taaaaagcac cccctctgaa  86280
aaggcgtcac gtgcgaacgc aaacaacctc acagagaaag cagaggaatt gggagaggta  86340
acccggtgcc accccccccc cttctttaaa atatccgaaa aagtccccac ggaagcagaa  86400
gaatcttcat atttcgtgct gctgtgtatt tgacagcccg gcccggtcac atcgaacccc  86460
ggccagaagc gcacagcttc aggcatctct tcacacatct gtctgggaaa ctgtctgttc  86520
ctttcagact cgcccctgcc ccacttccaa ggggagtctc cagaatttca aactgcatca  86580
aaggcagagt gaagattaaa aaagaatgtc tccagatctt ggattagttt aatcaattac  86640
tagcccctct ctaaaataaa catgaaaagg gggggagggg ttgtctggct ctttctcgtt  86700
ctcccgctat tcgccttttt tcccctaccg tcttcccaac agatgccacg ggaaatattc  86760
ctgagctttc tcagaaattc cccagtcggc acacaatctc gtccctacgc tcagattttc  86820
tggtgagtgc tcccttgtat aaagcgtaaa gcaaggtatg tgtgtctgtc tcctgtgtgc  86880
tcttgagttc atttggaaag tgactgacag cagaacaatc tagcgggtgc taaaatgcaa  86940
gtaattatgt ttacacaaag aaaaccatgt cttgaataat gctactactg agcatagaga  87000
atgatctaga cttattttga tgtgttttat ggttttgttg agttcaagct gaaggctgtc  87060
acggaaaggg ttttatcatg tcgaaggaaa gcgttcttag ctggagcaaa ccagccgaag  87120
cttccattct ctctggcact cgacctctaa cagaaaacaa gtcagtcgga gagcaaggcc  87180
gaccggtcag tcccacgcag atatgagcca ccatcagcct gacagcttcc cagctgtccc  87240
tgcacccacc tctcagtgat attctttgct gtctgtagaa aacgggcgtg gtcattttcc  87300
ttcagcgagt gctccgcttg cgagatgagc gatgcagacc tctcaaggca ctgtttacag  87360
tttgcaatct gctgagctaa cttgcggagc ctgatcacct ggaacgagag aagcacggcg  87420
ggcgaggtca cacgttaagg atcgatcgct tgggaggtgg ctcagggctg aacccttcag  87480
aggcgtgagg tctgttctgt ctaagcagag agaggttgaa atccggaagg caaatttttg  87540
gaacttgaac tttcagtctt tggagaagcc ttagtcacct gtttgatgag gagacactaa  87600
ttcgtgtcag tgtgacacta actcacacta gcatcgctca ttacttctct gttgaagggg  87660
ggaaaggtgt ccgctggcaa gtgacaaacg gtcaccgaat ctcttccttc tgccatccta  87720
cctaatgact tcaggacctt agagaaccct ggaactctct ccatctcagg ttttcaatat  87780
gcctttaaga aaataaaaca tgtctgtagg tgtgaattcg aggcttaagt taaaaacagt  87840
gaaaaaaaac cctacaaagt tctttgtaat ccacgtaata aagttgtgac atgaaagcat  87900
taggtattcc tattttccat actgcctaaa acctgtgtat gaaattaaca gagagggagc  87960
attttcccat tgattgatat ttttcttatt ggactgatga gagaaagcca aaaaaagcac  88020
agctgggcca tttcctctca ctgtaaacgt catttccagt cactttgtgc agcatggtaa  88080
aaacacatcg ttcattgtaa aggtaggtct tgtccctatc aggagaagtg tgtacccgag  88140
```

tcgaacaaaa taacaccatt tcacaccaga tagaacagag cctctggcaa cattatctag 88200
agagtcgagg cagccctcta gcctaactca gggtgttaga acacatctat taggaactgt 88260
cagaggaagg gagaattcca gaaggataag ttaatagtct caaccataaa ccagatgagt 88320
ggaatattta attatataac ataaagaaga tttaaatggt acggccaagt tgaaggcaga 88380
tgataaaatt ctcaccaaac gagatgaggt cagactactc ttctggcttc atttcatgtc 88440
actctcttag cctttgaata ggcacagcag agaccacacg tctcaaaaat gacggctctt 88500
caatgtcata tttttcaggt ttttcctctg aggctatgtg gagattaacg gtgatgttta 88560
aggacaagaa gaataaccga aacaggagat attgatgtaa aagaaattga gagcatactg 88620
tgaaactgcc acgatcttct cgagtggact tccatgtaga gcgtactttt cattacaggt 88680
cagttgacag ttgcctcgga gattcacaaa cactgtgtgc gatagaatca gctggggatc 88740
tttcccagga aaactctaga tgtctgggca catcctctgg cattctagtt aaggagctgc 88800
cattggcaga gccacagtaa tttgcatttg aacgagcaac gcatgttttt aagtctccgg 88860
gtgatgaatg actagtatgg tcgggaccag catttcaaat atcaatctcg ctttaatctt 88920
tgagtccatg gacatctgtc atgcttgaat gtcactcaga ccctttttgtc ccttcttacc 88980
tcgatggaac tccccaggca gaggccaaaa ctcagtcccc acggaagcag aagaatattc 89040
atatttcgtg ttgctgtgta tttaacagcc tggcccggtc acatcgaacc ccagcaagaa 89100
gcgcatcaat gataataaaa gataataaaa aagaaaaacg aacgtgcacg cagatgcttt 89160
ccaaaagaat caacgctcac ggaaaccaaa aacaagtgtc ctttgaaaaa aaggaaaatc 89220
gaacggtcac gaccaccgca ttctcctctg tcaccaccgg gtggcgacag agagcacgcc 89280
gggaaaaaaa aacttcctcc gaggggtcgg attgcccaat ttcttctgta gctgttttct 89340
gtcacataat tgtctacgag tttacctcca aaacttattg attgcattcc cgtctgtgtg 89400
tttcttcttt gagtcctttt ttgtctgtga tttctttatc tctaaactgt ttcttttcag 89460
gtctgcgtcc tcttctgcaa aacgaatctt accggaaatt agataatgct gctgattttg 89520
ctggctgtgc ttttagaaac tcaagatttc ttggcttgct tcggaaatga gctcagcacc 89580
tcagttttaa agaaaagaat ctgaaaatag cttcttgttc tccttggtgt gctctaatgg 89640
ttttactttt ctgctttccc ctaaccaggc tcctgggctc agcgctctgc aatccaatct 89700
cactgtggac tcctgtctca tctctgtgtc tctgaggcac ctgtctggtg tgataataga 89760
atgagtggag tacgggtcct cttaacgact gacttgttcc agaacctcag aactgaagtc 89820
tgccaaaagc tatgatgcca ggcagacatc ggcaatactc tcttcccgtc cctcgtaatg 89880
aataagaagc cttctgcagt ctgtggcgct gaggcacagg cctggtttct gccttccatc 89940
cgatccaaag caattccaga ttcttccagg atgtttttta ggcacaggca tcggaactgc 90000
aggcatgccc gtatctcttc aaccatgcct gtgcttccag ccacagttgt ggcattgcac 90060
tttcatgcca ttcctgcttc accgaaatgc tgctctcatt tcactcttca ccgttggagt 90120
ccatgtctat taatggtgta tgtctgcagc ggagtgagtg ctacaaaaga tggactctac 90180
ctataatcat ggcccaaact ggaatacctt ttattactat cctctagctc ctgaaaggaa 90240
accccaggcc gtgaaattca agctgcagct gagtaagggt aagtaagtac ggttgctgca 90300
gaggtatgaa aaagtgccac tgcaatctga agatggactc ttagcgaagt ccacatcggc 90360
accttgggaa tctttcagta tgctaccttc cataccaaag gaactttgta gatgtctagg 90420
ttaagaatct taaggggttg gggtggtcca ggatcgtctg ggtaatctct acataattcc 90480

```
taaggtcttt atgacagaga gacaggacgg ttcatgtcag tgaagtagat agcaggatga  90540
agacagaagg cagagtgcta atgacttagt tgtgagccaa ggaccatgga tgacctccag  90600
aaacttgaca agacaagcat agcttactaa cattgccttt aacctatgta gcctttagta  90660
cagtgagact gctctcagac atcagaacag taagataatc aataagaagg ttctaagcta  90720
cacagttttg gtaatgtgta atagtacgat agaaaccatc ataagaagaa tacagaacca  90780
attaaacagg agaacagagg ctttttaaaa aaatttttg agctacattg catagattaa  90840
caaatatacc aaatgtaaat ttcttacact tccagattac tagaccgtta aattcgagaa  90900
tttatcacca caaaaataag tgtttgaggt gatgaatatg ttacttagct tgatttaatt  90960
attatacatt ctattcatga accacagaat catgtcgtat ccaccaacat gtacacgtgt  91020
aacttgtcaa tttaacatta aaacgataaa ttttctaaag aaatttatgt gggcatgtag  91080
agtattgatc ctggcatgca accacttgac aatagcagat tatcttcttg gaacataata  91140
gcaactaacc atggcagaaa aacaggcatc tgagaaacta ggagacgaaa ggaatgagag  91200
atgagtccac atgatgaaag aagatgcact atgcggaagt atattctcag tagattctag  91260
gtggacactt actgccagag gcattgagca aacatggtgc catgctattg ggaattttaa  91320
gaaatatgaa taattctctt tcggttcttc actactcttt gtcgagtatt ttactacagc  91380
aacacaaaat ggaccaaggc aggtagttaa gaagggatta tgacgaatgc agagagtacg  91440
atttgttttt aactttcaaa gctgtagatg ttggagagaa agtatatatt cttcaggtga  91500
gaaatacaga accttttat caaggaaacc ataccttgcc ttctttaatc tttgttccaa  91560
taatttgtct tcgttgctga atgatttcaa tgagaagatc acattcttct gtcagtttgg  91620
cttcttgacg ggatgcattg acctacagga tgaataaaat ggcattcatc ggaatttgat  91680
cttagccatt ctgagtggct gtgaggtgga atctcagggt tgttttgatt tgcatttccc  91740
tgatgattaa ggatgctgaa cctttttttt ttcaggtgct tctcagccat tcggtattcc  91800
tcaggtgata gcccaaaaaa cttagaatac ccaagataca agatacaatt tgcaaaacac  91860
atgaaactca agaagaacga agaccaaagt gtggacactt tgccccttct cagaactggg  91920
aacaaaacac ccatggaagg agttacagag acaaagtttg gagctgagac gaaaggtgga  91980
ccatctagag actgccttat ccagggatcc accccataat cagcttccaa acgctgacac  92040
cattgcacac accagcaaga ttttatcgaa aggacccaga tatagctgac gaaatccagg  92100
cccatccatg ttcctgaaaa tgtgaagact ccattctttt tatggcagaa tacaattccc  92160
atatgtgtat ataccatatt cttaaaatcc actcttctgt caagggaact ttaggttgat  92220
tctatatctt agctattgta aatagtatag caataaatat ggctgagcaa gtatctctat  92280
gttaggatat ggagtccttt gggtacatga ccaggatttg tataactagt tgtgtgtgtg  92340
tgtgtgtgtg tgtgtgtgtg tgtgtgtgtg tgtgtgtgtg tgtatttgta taactagttg  92400
tgtgtgtgtg tgtgtgtgtg tacccttcaa actgagcttc attgtgaata cactactttg  92460
cattgccacc agcagtgtat aaaggttcct ttcacttctg tattcacacc agcatctgtt  92520
gttgtatcta ataggacttt agaaacattc tttttttttt tttttcctc attggaccat  92580
gtctggctga agtgagttag ccacctacag gctttcaaag cagaacttcc cgattcatcc  92640
tgccaaaagg atatactcat tcgagagatg gcttcctgtt ggtacacaga aggaacactg  92700
aagtaagcct gggacaggat aaagccaatg tgtcagagac aggaaatctt acttctgagt  92760
attcagggag aaaggagcat tgctcaatgc actaggaatt ctacaaaaat ggttaccccc  92820
cccctgagat tacacagcct aggaaccatg ctggccctca atcagtgcaa ttttgaaact  92880
```

```
gcaccgctgc accactaaac aattacactt tccttttaag gctgttaacc tttctgtctg  92940
gtagttttaa acacagttat ctacactgta tatttgccta aaagcagtct ttatggcacc  93000
atcacaagct gggtcattcc atactcattt aaattaaggg aacccagaga aaggaggcga  93060
cattcacata tgatgtcctg taagtgtggt tatttggact ccagagcact tgtctctgta  93120
tatctgtaac tttgattctg catctgatta taaagtggat agttttattt aaaaagcatg  93180
gtccggctct cccatttaac tcgaaaaaga gacacactaa aggagttaat tccaaagtgg  93240
ataaattgat attttggcca gtaagatgag ggcatgaggg gaaagctgca ctcacgtcag  93300
ctctgtgccc cactgtgctc tgccgaccag gtgcaaagag aaatatgagg atctgagggt  93360
gctttggttt ttattgccaa aggcagccgt gatgaacatt ccagaccctg gggcagaagt  93420
tagacagagc tgccagaagg aacaatgaaa gggatcctaa tagtttagtt tgtacataaa  93480
accgagccaa ggagaactga gtaagcacag acggtattac tgtaatacat ctgatatgtt  93540
tacatcgacg ttttactctg caactctctc atagtgtggc agttcttttg cacctgtgtt  93600
ctgggaattc tacaacttga actggagaaa acaatttcac tatagttttg gccatagaag  93660
ggtttatgaa tgctgacaat gatccaatta cgttgttaac ctttttgggc tttatgcatg  93720
aatgggagtt tgctggtata gtttaatacg acccagagtc caactccaaa taataccgca  93780
cagcaacctg acaaggtgtc aaatggagtg ggaatctatc acttctcttg aagtagcaat  93840
gaactaaaaa tctcaataca actttagata ctacagttgc tcactacagg atctagctca  93900
tccagattat acacgtccaa atgatgtaaa cagcacgcat gtgtgtgtgt gtgtatgctt  93960
atgtgtatgt ttctctgtgt gcatttgtgg tgtgtgtgtg tgtgtgtgtg tgtgtgtgtg  94020
tgtgtgtatt tgaatgctgg cctctatcca atgctctggt ctggatgatg caattgccat  94080
tgtctccaaa aaaaaataga atgttttccc atttggaaat ggcacaatta attgaagcag  94140
aaatgctcat ctttacttgc agtttggcat tatttcaaag tttataaata atgattttta  94200
ggcttgatca atgatttaaa gtcttctgca cacctatcca ttcattttaa caaagaattc  94260
tctgcagtgt tttacatcat tcaagataat ttatccccat caatcctcta gtaaaaaaac  94320
tatgattaat tcattcacaa aatatctagt gctccatatg caaatgatgg gaggtcacag  94380
aaggccagaa aaggaagaaa ctttcaaaac agaccaaaaa gggggtgggg ggaccaaaaa  94440
gagagccaca gagaattgga aaatccagtg aaggtggatt acaggacaga aagatggctt  94500
gtcaggtaag ggagcttgct tctaggcctg aggacttgaa ttcagtcctt ggaatataca  94560
cagtggagga gagggccaat tgccaaaatt gttttctgat cttcacataa gggatatagt  94620
taacatgtac attctcacac acatgtataa acacacagac acacacagac acacacacgg  94680
ttaaattttt gaggcgatta caaacaatga ggctagcaca ctgacaatct gctggatttg  94740
accttgggta aggatgatta gtcagatggg cctctatctt ccagaaacca cagttgcaat  94800
tatttacaag tttttacttg ttccccatta ctatctcaat gtggattgat actcaaatca  94860
ccaacaattc cccaattggt cttttatgtt atatttgcta taaaaacaag agtaatggct  94920
cttggtattt tcttaagtaa taaaatcggc tttctgattt ttctaagaaa attgggaaga  94980
cagtgtgata atgagagctg tattccatat ttgacttaca cagagtaaat tctgagacta  95040
attctgttta aaatttaaat agaatatttt tccatttatt ggtagtcagc agctcactat  95100
gttacccagg ctctccctga agaatccatc ctctgccaga aaatccccag tgctgattgt  95160
gtgtgtgtgt gtgtgtgtgt gtgtgtgtgt gtgatcacat ccatatcctg accacaaacc  95220
```

-continued

```
tcaatcactt ctcataagct tgttttatgc tccagataac agtaacttca aacttgacct  95280
gagggagctt ttactgtaat actctcctgg aggaaacaaa gcagaacaga ttaaaaacct  95340
attgtttcta aaaccccaga cagcaactta acacaaacag tttgttggga ggctctctga  95400
agttgctctt tcaatgcctc tcattcccaa gccccaaact gccttggact ttacactgtt  95460
tcttttctag ttttaaaaaa ccagcactta cacaatcaca aggccatttc atttgcttgc  95520
cctctttggt taaataagtt attaaaacaa tcagggagcg gaccttcaag agtttccatt  95580
tttaaaagaa agcggaagtg aacccctggg aggaggggtg aacttatgag gatgtaacat  95640
ttcctactaa ggcctgagaa agaattcatt gattgaattt acaacaatga ggagttacct  95700
ctgtgctgtg agttttctta gctcccgcta gcctgggaat gttattttcc tcacgaattc  95760
tcagactcgg aagacatgga caacttcggg aagaggaaaa ggaagaacta gagtctagga  95820
acctatgatg tgaagcagga aattcttttc aactgtactg actgaaaaga atagcttgct  95880
ggtgcccaac atattccagc acctctttgg aagtccctta atagtgtggc attttcccat  95940
ggatgggtga ttattttgca ggaagataaa ataaaaaagg taaaggacag gaaagaacat  96000
ggcgccaaat gaagtaaaaa gaaataaaag aaagagatga ctgctcctgg gtatggtaga  96060
ggagaaaggt ttttatagat acgtggggga gcatagccag aggcaagaac cttagagaga  96120
gagtctggag tggacatgaa cacactgcca tgtgtcatgt gaggagaaag gtgaaggagg  96180
gcaagagaga ggtgagagag aagaaccacg ttcaggagtc aggaggctca aagttacaaa  96240
gagaaaggat aaccaaagtg gttggattat ttagggagga gcggcctgtg ccagagagtt  96300
cagagtaagg gttgaggaat gccacccagg tgggtcctat aacagggagg gactggtgga  96360
tacagggaac ttgggggcca ggtctgttgt gatatgttag ataggtatct cagccatttg  96420
tcccaggttt caaacatagc acagattatt tttcaaatag ctacaaatat caatttctga  96480
aatgagttag gttttaagtg cgaagccaac aaaatctatg tgcttcttga aatgttgttg  96540
taccttcaag aaccaatttc caactcaggt accaaatgaa acgcttctca accctcatct  96600
ctccagagct gctccttagc tatctttcct tcatgcatgc ctttcatttt tccagaagac  96660
acacacacac acacacacac acacacactc tctctctctc tctctctctc tctctctttc  96720
tttctttctt cttttttttt tggttgtttt tttcggaaca gggtttctct gtatagccct  96780
ggatgtcctt tgtagatcag gctggcctcg aactcagaaa tccacctgcc tctgcctccc  96840
aagtgctggg attaaaggcg tgcgccccca ccgcccggca tcctttttct ttaatgcttc  96900
ctgctccctt ttttatatac cagggcatga tatcctcttt ggttcaaata gcttttatga  96960
ctctgatggc tccttcctca gtcaattatc acaaaataac ttggaattcc tttttaaaaa  97020
gtattctttg agaatattaa taattaggat aaatgtaata gtagatactg ttcctgccat  97080
ttttctactc ataaataatt acctagtact tacttagaat acacttactt ccactccaaa  97140
ggatttacaa agcagcaggt aaatagatac tcttaaattt tgttaagaat tacttctaat  97200
ggtatgtacg actgttttta aaatggccac aattaattga gtaatttttt ttttaatgag  97260
tatcttaact agaacaatat ctgatccctg gaaataaata atctggtggt aagtttcttg  97320
aatttatttc ccatctgaaa attactatac atgataggat ataattttac atcacattac  97380
aatgaataat attttgtaaa ttccagtcat actaaaattg cattaggaac atggcattag  97440
ttctgaaaac attaccagcc ataatgcaaa ccagacacta atgctttgag aagtaacttg  97500
ctgaaatggg atgaaataat cacgcgatac ataaaccatt tataggattt accttaaagc  97560
acaggtgatt tgtttttact gaagagaaat aattctttct tattattcca aacatcaagc  97620
```

-continued

```
gccatcgcat cataaaaata aaatatggca catgaacatt ctatttttca tccttttatt  97680
catattcgct ttgctatgaa ataacgaaaa catcatgcat cttcactatt atttcccata  97740
ttgtctaatc aacaaggtac aaacaaatgc agtttcagta gatgagaaag gtcaaggttc  97800
tgcaacttgc agtcgccttc acgttgcatg ctgcgcctga gcagcataaa agacagaagt  97860
atcatttagt gccaaaagga aagggtctga ggcatgaacc cgagagccaa tcctttcaac  97920
ttccattctc taacttttct ttctccatat accatattca tcagcactta agtgaccaac  97980
agttaaaacg gatggtttag gcaaggaaaa acacctctct tgttagtcct aaatactgca  98040
gaaatttaga gcttgaaaaa ttggccaaca gacttacttc tcagtaacca gttttaaatt  98100
tccaatcatg aagagggtaa aatcacaacc tttatgaaca caaaatattt taaaccttac  98160
acggaatctc caatatttac ataaaagaga agcttttaag ctgagtgtat ttgaaagctt  98220
agctttattg tgctggggaa tgtaccatca tcaacaccat tgaatgacat aaaataagct  98280
gatatcccca aatccttttt tattagatat tttcttcatt tacatttcaa atgctatccc  98340
gaaagtcccc tctaccttcc cccacccccc cccgccctgc tccccgaccc tcccaaatac  98400
tggaattttt aaagacagta cttctgaaat ctataggaca agttcaagtc ctggctactc  98460
attaaattcc ataagctttc aggcaaatcg taccccccttt cctctctgtg tgtcttcatt  98520
tctgtggact ggttgagatg tgtgcatgtg gaagcctaag gacaaccttg ttgtcatctc  98580
tcagacacca tcccaccatc taccttttttt tctttggtgg tcagggtttc tcattggcct  98640
ggaacttatc aagtatgcta gcctaaacgg tcagtgaggg cctacctgct ctccttggcg  98700
cagagattac aagcatgaac caccctgact tgtgatttgt tttagaaact taggttctag  98760
ggatcaaact tgggtcctca tgcttgtaag tcaaaccctt taatgcctgg acaatttcat  98820
tggtccccac ttctttcttc ctttcttact ttcacttgca cttgtcactc tggtaagtgg  98880
cattctttcc tgtttgtacc ctgactcctc gatggtaatg tgatggagaa atactgagtt  98940
gacttctact caggctattg tgttacttaa gtgtggttgc tctctgctcc tatgtgaagc  99000
tctttagaat tagaaccagc ccatgctctt ccagtgagtg aaagactaga tcacattgct  99060
taaaatcctt gaacttagat gtgcacctga ataaaggtaa gcatagttct gtctttatga  99120
aagatccata agtgatatcg atataacgtc ttgtttggtt gttgtcgttc cagaattggg  99180
gcagaagtgc agattgatta ctgaatatct ttgctatcta aggtttgata tctatagtta  99240
tgcaaataca accaattaga ggatgggctg taaaaactgt acatgtgaac tacggccaca  99300
gtcagggaaa ggactcgtgc tattattcca tctttgattc tatctatgac atatggctga  99360
gcaagtatct ctatgttagg atatggagtc ctttgggtac atgaccagga tttgtctaac  99420
tagttgtgtg tgtatgtgtg tgtgtgtgtg tgcgtctatt tctttttatt ggggaattga  99480
gtcgattgat attaagagat attaagttaa agtaattgtt gcttccaatt agtataaata  99540
tacaaagata aatcataaca aaatattaag aatgacaaga atagaaaacg tcctatttta  99600
ttttactaca cacacacaca cacacacaca cacacaaaca cacacacact ttcacatgtt  99660
taatgtatat ataggttgac atattctggg ttcacacata tgcaaagagt ggtgagccat  99720
caacgagaat aaaagaaaaa cgaacgtgca cgtagatgct ttcaaaaata atcaacgctc  99780
acggaaacca aaaacaagtg tcctttgaaa aaaagaaaat cgaaaggtca cgaccaccgc  99840
attctcctct gtcaccaccg ggtggcgaca gagagcacgc cgggaaaaaa aaaaaaaaaa  99900
cttcctccaa ggggtcggat ctgcctgctt catcccggcc agggtgaggg gaagccggcc  99960
```

-continued

```
aggctggcgg atccgacccg gcgaggcggt cgcgttttcc atcggtcggt ccccgggagg 100020
ttgtactctg tgagatacag gaagtgcctc cattttggac aggaagtcgg gcccaggcgc 100080
tcatgggagc tgtagtgcgt ctaggctagg gcccagcgcc gatctccggg gccacccggt 100140
ggcgaaaaac acgcaagtgc acccccggtt ctctgcctcg tggggacgga tctgggaccc 100200
gaaggccagc cctggttcca gacgagcggt gtggccgtgt cggcggcgtc cccgggcaga 100260
cgggggttca ggtccgcgcc cgccgctcca ggttgtacct gtagaagttc agggacagag 100320
cctctctctg tctctctctc tctgtgtcta agtctctctc tctgtccctc tgtctgactc 100380
taagtctctc tcctcctcct cctcctcctc ctcctccctt ccacccgggg ctgcctggcg 100440
tcggcgtccg ccatcgaggg acccatcccg gcttccacga gtcccgcagc ccccggctct 100500
cccttctcct cccttctcct cccttctcct tccttctcct gcttccttct tccatcccgg 100560
cctgcctggc ctctgccgtg gcccgcgcag ctcggctctc tgcgtctgtc tgtcccccctg 100620
tcctggttct cccttctcca tcttccttct tccatcccgg cctgactggc ctctgccgtg 100680
gcccgcgcag ctcaggtctc tgcgtctgtc tgtccgtccc cctgtcctgg ttctcccttc 100740
tccttccttc tcccttcttc tccccgggga ccaagcccga gtccgtgtcc cgcgcagtct 100800
gggtctctct gtccccctat ccccctgtcc ccctgtcctg gttctccctg cttccttctg 100860
ctccccgggg accaagcccg agtctgcatc cgaccgagac gcaccatccc ggcttccgtg 100920
tgtctctctg tccccgggtc tctgtctgtc aacctccctt ctccttcctt cttccaccca 100980
gggaccaagc ccgagtccgt gtcccgtgta gttcgggtct ctctgtcccc ctgtccccct 101040
gtcctggttc tcccttcttc ttccatcccg gcctgcctgg tctctgccgt ggcccgcgca 101100
gctcgggtct ctgcgtctgt ctgtccccct gtcccggttc tccctgctcc tgcttccttc 101160
ttctccccgg ggaccaagcc cgagtctgca tccgaccgag acgcaccatc ccggcttccg 101220
tgtgtctctc tgtccccggg tctctttgtc tccatccttc ctccactttc ttccacccag 101280
ggaccaagcc cgagtccgtg tcccgcgcag tctgggtctc tctgccccac tgtccccctg 101340
tcctggttct cccttctccc ttcttccatc ccggcctgcc tggcctctgc catggcccgc 101400
gcagctcggg tctctgcgtc tgtctgtccc cctgtcctgg ttcttccttc tcccttcttc 101460
catcttcctt cttccatccc ggcctgcctg gtctctgccg tggcccgcgc agctcgggtc 101520
tctctgtccc cctgtccccc tgtcctggtt ctccctgctt cctgcttcct tctccccggg 101580
gaccaagccc gagtctgcat ccgaccgaga cgcaccatcc cggcttccgt gtgtctctct 101640
gtccccgggt ctctgtctgt caatctccct tctccttcct tcttccaccc agggaccaag 101700
cccgagtccg tgtcccgcgc agtctgggtg tctctgtccc actgtccccc tgtcccggtt 101760
ctcccttatc ctgcttcctt cttccatccc ggcctgcctg gtctctgccg tggcctgcgc 101820
agctcgggtc tctgcgtctg tctgtccccc tgtcccggtt ctcccttctc cttccttctc 101880
attccttctc cttccttctc cccggggacc aagcccgagt ctgcatccga ccgagacgca 101940
ccatcccggc ttccgtgcgt ctctctgtcc ccgggtctct ctgtctccat ccttcctcca 102000
ctttctccca cccagggacc aagcccgagt ccgtgtcccg cgcagtctgg gtctctctgt 102060
ccccctgtcc ccctgtcccc ctgtcctggt tctccctgct cctgcttcct tcttctcccc 102120
ggggaccaag cccgagtctg catccgaccg agacgcacca tcccggcttc cgtgcgtctt 102180
gctgtccccg ggtctctgtc tgtcaacctc ccttctcctt ccttcttcca cccggggacc 102240
aagcccgagt ccgagtcccg tgtagttcgg gtctgtctgt ccccctgtcc ccctgtcctg 102300
gttctccctt ctccttcctt ctccctgctt ccttcttctc cccggggacc aagcccgagt 102360
```

ctgcatccga ccgagacgca ccatcccggc ttccgtgcgt ctcgccgtcc ccgggtctct 102420
gtctgtctcc atccttcctc cactttcttc cacccgggga ccaagcccga gtccgtgtcc 102480
cccgcagctc aggtctctgt catctctctg tcccccccgt ctccctacct tctctgtctc 102540
gtggggtcga atctgggacc cgaaccccag cccgggttcc cgacgagagg tgtggctctg 102600
tcattggggt ccccgggcag gcggcgtctc aggtctgcgt cctccgctcc cgttgtacct 102660
gtagaagtgt aggagacgag cctctctctg tctctctgtc tctgtgtctc tctgtctaag 102720
tctctctcct cctcccttcc acccggggct gcctggcgtc ggcgtccgcc atcgagggac 102780
ccatcccggc ttccgcgagt cccgcagccc ccggctctcc cttctccttc cttccttcag 102840
acccggcctg cctggtgctt ggccaccacc tgtgcagccc cgggtctgtc tctctgtctg 102900
tccatcctcg cttcaggccg gggcccagcc cgagagacat cggcccggcc cgtgcatcct 102960
ccctgcctcc cccccccccc cgctgtctct gtctcccccc cctctgtccc atctccctcc 103020
ctcctcaccc ggcctgcctg gcgctgccca tggcctgtgc agcctgggtc tgtgtgtctg 103080
tcctggtcct cgctttcttc cttcagaccc ggcctgcctg gtgcttggcc aacacctgtg 103140
cagtttgggg tctgtccatc tgtctctgtc ccagtctctg cctgtctgtc cctgtctgtc 103200
cctcctccct tcagacagac ccggcctgcc tggtgcttgg ccaacagctg tgcagctcag 103260
gtctgtccat ctgtctctgt cccagtctct ctgcctgtct gtcccggtct ctccttctta 103320
aatcttaaag gaaaaatctt aaaggaaaaa gagtccagcc cgctcctccc ctcgcctgtg 103380
ctcccgctct tcccgactcc cgaaccccga accgaccgcc tgtctgtccc ggactcagtc 103440
agctccggac cgagtccgtc tctctgtcct tctggcagga cgcagacaca cacgcctcac 103500
cccacccaga ccgcagccag ccccggccgg ctcggtccgt ccccgctcgt cccggagccc 103560
gtgcacccgc gcaccgtccg cgcgtaagac agcccgagtc tgagtccgtg cggatgtgcc 103620
gggtggggga tggggtggtg tgcgtgtgag gtagaccaga agtccagaga gaggaaagga 103680
cggacgggcg ggggtgaggt gagggggtgg gggggaagag cgggagcacg ggcgagggga 103740
ggagcgggct ggactctttt tcctttaaga tttttccttt aagatttttc ctttaagatt 103800
tttcctttaa gatttttcct ttaagatttt tcctttaaga tttttccttt aagatttttc 103860
ctttaagatt tttcctttaa gatttttcct ttaagatttt tcctttaaga tttttccttt 103920
aagatttttc ctttaagatt tttcctttaa gatttttcct ttaagatttt tcctttaaga 103980
tttttccttt aagatttttc cttgttaaga tttttccttg ttaagatttt tccttgttaa 104040
gatttttcct ttttaaggtc ttttaagaga cctttggtgt cttttttttt tttactttt 104100 ttttccgctt tctttttgc ctttccattc tgaccttctc tgtctctcgc gttagaccgg 104160
aaggggcgtg ttctgacact ttaggggcgg gtctaaggga agaggggtgt ggtctgacac 104220
ttttttttta attcttttt tctccgcttt cttgggtggc ttttccattc tgacctcctc 104280
tgtctctccc tctcaggggg gtgtgtctta gcccagaagg ggcgtgtctc agagcaggag 104340
gggtgtggtc tgacactttt taaaaaactt atttttcctt tttttccctt ttttcctgct 104400
ttctggggtg gcttttccat tgtgaccttc tctgtcgctc tcgttagggc gtgtcctgac 104460
acttaagggg cgggtctaag ggaagagggg tgtggtctga cacttttttt taaattccgc 104520
tttcttgggt ggctccctcc ctctcagtag gatgtgtctt agcccagaag gggcgtggtc 104580
tagtactttg ggggcgtgtc ttagacagga aggggtctcc tctcacactt tggggagtgg 104640
tctcagagca ggaggggtgt ggtctgacac ttttttaaaa actttttttt ccttttttc 104700

-continued gctttcttgg gtggattttc cattctgact ttctctgtct ctgtccattt agggtttttt 104760
tgtcctacta ttctcatcac actctctgtc tgtggaccga aaaggggtgt gatctcacac 104820
tttaggggcg tgtctaaggg aagaggggtg tggtctgaca cttttttttt aaattccttt 104880
tttctcccgc tttcttgggt ggcttttgca ttctgacttt ctctgtccct ctctcttagc 104940
ccagaagggg cgtggtctta gacaggaagg ggtctcatct cgcactttgg gggcctttgg 105000
gggcgtgtct cagagcagga ggggtgtggt ctgacgcttt aggggcgtgt cttaaaccgg 105060
gaggggtgtg gtctgacact tttttaaaaa cttttttttc ccttttttttc gctttcctgg 105120
ggggatttc cattctgact ttctctgtct ctgtccattt agggtttttt gtctcactat 105180
tctcacactc tgtctgtgga tgggaggaag gggcgtggtc tcacgcttta gaggcgggtc 105240
ttacactggg aggggtctga agatggcctt ctttttaaac tctcatctct gccacagaag 105300
gctgtgcttc cttcctgtac tttttggagg caggaaggga cctggtctca cactttaggg 105360
gcggttttta cattttcttt atcgtccctg tcttttctgt tccgtctgtc gcagaaggaa 105420
gacacacaca catttgcata tccatttcaa ctgcaatttt attgaggggg acatgtctgt 105480
acgcagtcag gccctgttgg cgtgctcctt cctccgtgag aatcgctccg tcctggcggc 105540
ctcggcgaca cgcgcacctg gaaaagacgg gaagagaggg aggggggtca gcgtctgtgg 105600
acgggaccgt ggcgactcgc tgtttaaggg tgtgagtgtt tggacacccc gcctaattgg 105660
agtgtgaggc ggcctcattg tgctaatcat cagttgcgtg tctgctgcct ccgtgtgcag 105720
acctgaggtt cctctgcatc tcattatgct gctctgagtc taatctgaac atctgggcct 105780
ccgtgtgcag acctgaggtt cctctgcatc tcatgccatt cactgtcctg gtttgtcaag 105840
gtctctgtct ctctctctcc gtgtctctac ctgaacccaa agctcaccct ctccctctgt 105900
ctctatatct ctctgtctct ctctgtctgt ctgtctgtcc ctaactctgt ctctaactgt 105960
atctctgtct gtctttctgt atctgtgtct ctgtttctgt ctctctgtct ccctttctct 106020
ctgtcagtct ggctctgtct ctctctgtct gtttctctgt ctctccatca ctgtctccct 106080
ctctatctgt ttctctgtcc ctccatctct gtatctgtgt ctgtatctct ctgtctcgca 106140
gtctctgtgt ctctgtttct gtctctatct ggctgtctct ctgtctccct ttctttctgt 106200
tggtctggct ctgtctgtct ctctgtctct ctgtctctgt ctaacactgt ctctctctgt 106260
gtctctgttt ctgtctgtct cactttctct atctctctct gtctttctgt ctgtcttact 106320
gtctctgtct ttctgcctct gtctcccttt ctctctgtca gtctggctct gtatctctgt 106380
ctgtctgtct ctgtcgctgt ctgtttctct gtctctccat cactgtctcc ctctctatct 106440
gtctctctct atgtctctgt gtctgtctat ttatctctgt ctctttctct ctctgtttct 106500
aactctgtct ctgtctctcc gtgtctctct accttaaccc taacctcacc ctaaccctaa 106560
acctctctgt ctgtttgtct ctgtctctcc atctctgtct ctatctctct gtgtctctct 106620
gtctctgtct ctccgtgtct ctctacctta accctaacct caccctaacc ctaaacctct 106680
ctgtctctcc atctctgtct ctgtgtctct ttccctaact ctgtctctaa ctgtatctct 106740
ctgtctctcc gtctctgtct ttctctccgt gtctatcttt ctttgtctct ctgtccttaa 106800
ctctgtctgt ctccaactct gttctgcctc agtctctctg tctctatctc tgtgtctgtc 106860
tccctctcta tctgtctcta tatatctctg tctcactctg tctctgtctc tctaccttaa 106920
cactaatcat aacctcaccc taaacttaac cctctctgtg tctgtctctg tctctatctc 106980
tctgtctctg tgtttctctc tctatgtctc tcgatctctg tctttctgtt tctccatctc 107040
tgtctctatc tctctgtgtt tgcctgtctc catcgtctgt ctcactttat ctatatctgt 107100
ctttctgtct ctgtgtctgt ttctgtctct ctgtcagtct ggctctgtag ctctgtctgt 107160
ctatttctct gtctctccat cactgtctcc ctctctatct ttctctctct gtgtctctgt 107220
tctgtctgtc tatctatctc actgtctctg tctctctgtg tctctatgcc tgtctctgac 107280
tctgtgtctc taaatctgtc tctctgtctc tgtctgtttc actttttcta tctctctctg 107340
tctttctgtc tctctgtctc cctttctctc tgtcagtctg gctctgtagc tctgtctgtc 107400
tgtttctctg tctctccatc actgtctccc tctctatctg tctctctctg tttctgtctg 107460
tctttcggtc tcattgtctc tgtctcagtg tctgtctgtc tcagtgtctg tatctctctg 107520
tctcgcagtc tctgtgtctc tgtttctgtc tctatctcgc tgtctctctg tctgtctctc 107580
tgtctctgtc tctctctaac tctgtctaac actgtctctg tgtctctgtt tctgttttaa 107640
ccctaaccct aacctcaccc taaccctaaa cctctctgtc tctccatctc tgtctctgtg 107700
tctctctgtg tctgtctctc cgtgtctctc taccttaacc ctaacctcac cctaacccta 107760
aacctctgtg tctctccatc tctgtctctc tgtctctctg tgtctctctg tctctgtctc 107820
tccgtgtctc tctaccttaa ccctaacctc accctaaccc taaacctctc tgtctctcca 107880
tctctgtctc tctctctctg tgtctctctg tctctgtctc tccgtgtctc tctaccataa 107940
cactaacctc accctaaccc taaacctgtc tgtctctcca tctctgtctc tatctccctg 108000
tgtctctctg tctctgtctc tccgtgtctc cgtctctcta tctgactctc tctctgactc 108060
gctgtctgtg tctctctgtc tctgtatgtc tgtctctata gatatctgtc tctctgtgtc 108120
tctgtgtgtc tctgactctg tctcaatctg tgtctctgta tctgtctgtc tatctatctc 108180
actgtctctg tctctctgtc tctctctctg tctgtctgac tctctgtctg tctctctgtc 108240
tctgtctgtc tcgctgtccc tttgtctgtc tctctgtctc tgtctctctg tctctgtatc 108300
tgtctgtctc taactctgtc tgtgtctgtc tgtctgactc tctgtctgtc tatgtctttt 108360
tccctgtctc tctatctctg tctctctctc ggactgtctc tgtctctttg actctgtccg 108420
tatgtgtcta tctctctgtc tctgtctgtc tctaactctg tctctctgtg tctgtctgtc 108480
tgtctctctc tgtctatgtc tttctccctg tctctctgac tgtgtttgtc tctctgtctc 108540
tgtctctctc tcggactgtc tctctgactc tgtctctctg actctgtccc tatgtctgtc 108600
tctctgtctc tgtctgtctc actgtccctt tgtctgtctc tctgtctctg tctctctgtc 108660
tctgtttgtc tctaactctg tctgtgtctg tctgtctgtc tgtatctgtc tgtctctaac 108720
tctgtctctc tgtgtctgtc tgactgtctg tctctctcta tgtctttctc cctgtctctc 108780
tatctgtttg tctctctgtc tctgtctctc tatctctgtc tctctgactg tctctctgtc 108840
tctgtctctc tctttctgtc actatgtctg tctctgtctg tctgtctcgc tgtgcctttg 108900
tctgtctctg tctctctgtc tctctttgtc tctaactctg tctgtatgtg tctgtctgtc 108960
tgactctctg tatctgtctg tctctaactc tgtcggtctg tgtctgtctg tctgactctc 109020
tgtctgtcta tgtctttctc cctgtctctc tgtctgtttg tctctctgtc tctgtctctc 109080
tatctctctc tcggactgtc tctctgtctc tgtctctcta tctctctctc ggactgtctc 109140
tctgtctctc tctctctgtc tctatctgtc tctaactgtc tctctgtgtc tgtctgactc 109200
cctgtctctg tctgtctgtt tgtctctctg tctctgtctc tctctcggac tgtctctctg 109260
actctctctc tctgtctctg tctctaactc tgtctgtgtc tgtctgtctt tctctctgtc 109320
tctgtctgtc tggctgtccc tttgtgtgtc tctctgtctc tgtctctctg tctctgtctg 109380
tctctaactc tgtctgtctg actctctgtc tctctgtctg tctatgtctt tctccctgtc 109440

-continued tctctgtctg tctgtttgtc tctctgtctc tgtctctctg tctgtctgtc tctaactctg 109500
tctgtctgtc tctgtctctc tgtctctgtc tgtctctaac tctgtctgtc tgactctctg 109560
tctctctgtc tgtctatgtc tttctccctg tctctctgtc tgtctgtttg tctctctgtc 109620
tctgtctctc tatctctgtc tgtctctaac tctgtctgtc tgtctctgtc tgtctctctg 109680
tctctgtctg tctcgctgtc cctttgtgtg tctctctgtc tctgtctctg tctgtctcta 109740
actctgtctg tctgtctctg tctgtgtctg tctgtctgac tctctgtcta tgtctttctc 109800
cctgtctgtc tgtctgtctg tctctctgtc tctgtctctc tctcggactg tctctctgtc 109860
tgtctctctg actctgtctc tctgtctctg tctgtctcta actgtctgtc tgtgtctgtc 109920
tgactccgta tctgtctgtc tctaactctg tgtctatgtc tctgtctctc tatctctgtc 109980
tctctctcag actgtctctc tgtctgtttg tctccctatc tctgtctctc tctcagactg 110040
tctctctgtc tgtctctctg tgaagtaaag ataattagaa gtgaaggtaa ttagagaaaa 110100
gaaaaatacc tcgtcttgaa taaaaccaac aacaataaac aacaacaaca ataaacaatc 110160
gcaaggttgc actgacgtcc tggggccact gggtggcgcc agagcatctg agtgcctcag 110220
tgtgcaaatc tgagcgtcgc attttaatgt ttatgtgaat ttgcatctct gtgtgcctca 110280
taatgcaaat ctgtgcgagt tcactgggtc ctagttaaag tctctgtgag ttacctgagc 110340
gcctcattta aatggtggag caccagagca accctctcag tgtgaagccc agacacaaaa 110400
cagaaatcaa ttcaaagaat tgaattctaa aaattcaaaa aagaatttca caaaaattcc 110460
cctgcatcct aacgagtttc caaggtgctg atttaaacct acacaagttc cctggtaaaa 110520
acccgggcgt ggtggctgag agaaaccaag tctgtcccaa agccaccagg cctctaatcc 110580
ctacctaccc tccagagaca gagccaggtg gatctctgag tcccaggcca gcctgctcta 110640
cagagcgagc ttagagaaac cctttctcca aaaacctgaa aagaaactaa aaataaaaat 110700
ccaaaaagag agaaacaggc agataaataa tcgtttaacc tccaaaaaat taaatctgaa 110760
aagtcatcag aaaagaaaaa aaatatgcca aatcttcgaa aaaaaatctc aaatttcaca 110820
gtgacgttct atctccacga gtttcacggg ttctaattta aacctgcact agttttggaa 110880
tctgattcct aatttaaacc tgcactagtt ttggaaagat caggaattca aggcccatac 110940
ctaacatgat aaaagcaatc tacagcaaac caggagccaa catcaaagta aatggagaga 111000
agctggaagc aatcccacta aaatcaggga ctagacaagg ctgcccactc tctccctacc 111060
tcttcaacat agtacttgaa gtattagcca gagcaattag acaacaacag gagatcaagg 111120
ggatacaaat tggaaaagag gaagtcaaaa tatcactttt tgcagatgat atgataatat 111180
gtatacgtga cccaaaaatt ccaccagaga actcctaaac ctgataaaca gcttcggtga 111240
agtagctgga tataaaatta actcaaacaa gtcaatggcc tttctctaca caaagaataa 111300
acaggctgag aaagaagtta gggaaacaac accccttctca atagtcacaa ataatataaa 111360
atatcttggc gtaacgttaa ctaaggaagt gaaagatctg tatgattaaa aagttcaaat 111420
ctctgaagaa agaaattaaa gaagatctca gaagatggaa agatctccca tgctcatgga 111480
ttggcaggat caacattgta aaaatggcta tcttgccaaa agcaatctac agattcaatg 111540
caatccccat caaaattcca actcaattct tcaacggatt agaaggagca atttgcaaat 111600
ttatctggaa taacaaaaaa cctaggatag caaaaagtct tctcaagggt ttgaaaaaaa 111660
atctcaaatg tcgcagggac cttctatcta cacgagtttc gcgggttcta atttaaccct 111720
gcacagattc cctgattcct aatttaaacc tgcacgagtt tccaaggtgc tgatttaaac 111780
ctgtacaagt tccctggtaa aaacccgggc gtggtggctg agagaaacca agtctgtccc 111840
aaagccacca ggcctctaat ccctacctac cctccagaga cagagccagg tggatctctg 111900
agtcccaggc cagcctgcta tacagagcca gcttagagaa accctttctc caaaaacctg 111960
aaaagaaact aaaaataaaa actcaactaa aataagaata attggggaaa aaaccaagtc 112020
tcgcgagcac gggtgtctcc ggggttaaaa attacaaaat taaaatgttc aacagtgaaa 112080
aaaatacaaa aataaaaatt aaaattaaaa ctgaagaaaa atgacaaatc ttcaaataaa 112140
actcaaatat cgtagtgact ttctatctcc acgagttttg cgggttctaa tttaaacctg 112200
cacaaattac tgggttctaa attaaaccat taatttcaca ctcaaaaata gaaggtgaag 112260
ataattagag aaaagaaaaa tacctagtct tgaataaaaa caacaataaa aaattgcaag 112320
cctgcactga cgtcctgtcg ccactgggtg gcgccagaga cagagtctca cggtgaagca 112380
cagagaacac agatcttgca taaaaaccaa aaaacagatt ccctgcatcc taatttaaac 112440
ctgcacagat tccctgattc ctaatttaat cccacacgag ttcgcctgca tcctgattta 112500
aacctgcaca cattcccagg ttctaaatta aaccttgaat ttcacactca aaaataaaag 112560
gtgaagataa gtcgcgaaaa gaaaaatacc tagtcttgaa tgaaaacaac aataaaaata 112620
cggcaatagc ggcttgacaa cacatctaaa agctctagaa ctaaaggaag caaactcacc 112680
caagaggagt agacagatgg caggaaataa tcaaactcag gggtgaaatc aaccaagtgg 112740
aaacaagaag aactattcaa ggaattaacc aaaccaggag ctggttcttt gagaaaatca 112800
acaagataga taaaccctta gctagactca ctagagggca cagggacaaa atcctaatta 112860
acaaaatcag aactgaaaag ggagacatga caacagatcc ggaagaaatc caaaacacca 112920
tcagaaatca aaacacctgt gcctaaaaac caaataataa aattttttaa agatttgtaa 112980
agataaaatt aaaaaaaaat aattagaaaa aatataaagc attgacaaaa tcccccaaaa 113040
ttggaatgtt tatttaaaaa ttacaaaata aaaatattca acagtcaaaa attcaaaaca 113100
aaaaaccctg tctcgaaaaa aattttttgt ctctgtatgt ctgtgtctct gtctccctgt 113160
ctctctgtct ccctgtcttt gtctgtctgt ctctctgtta agtaaagata attagaagtg 113220
aagataatta gagaaaagaa aaatacctcg tcttgaataa aaccaaccat aaacaatggc 113280
aaggttgcac tgacgtcctg tggccactgg gtggcgccag agcatctgag cgcctcagtg 113340
tgcaaatcta agcctcgcat ttcaaagttt ctgcaaattt gcatctctgt gagcctcatt 113400
atgcaaatct gtgcgagctc cctgggtcct ggttaaagtc tctgtgagtt acctgagggc 113460
ctcatttaaa tggtggagga ccagacacaa aacaaaaatc aattcaaaga gtcagagaga 113520
ggctcatctc cctacacttc tacaggcgca aagggagcag gggatgcgga cctgagatgc 113580
cgcctgcccg gggacgccac tgaggaagcc acacccctcg tcgggagccc gggctgggat 113640
tcgggtccca gattcgtccc catgaggcag agaaggtagg gaggcggggg ggacagagag 113700
aggacagaga ccagagctgc tcgggccacg gacaggaatc aggaattcaa ggcccacagc 113760
taaacatgat aaaagcaatc tacagcaaac caggagccag catcagagta aatggagaga 113820
agctggaagc aatcccacta aaatcaggga ctagacaagg ctgcccactc tctccctacc 113880
tcttcaacat agtacttgaa gtattagcca gagcaattcc acaacaacag gagatcaagg 113940
ggatacaaat tggaaaagag gaagtcaaaa tatcactttt tgcagatgat atgatagtgt 114000
atataagtga ccctaaaaat tccaccagag aactcctaag cctgataaac agcttcgccg 114060
aagtagctgg atataaaatt aactcaaaca agtcaatggc ctttctctac acaaagaata 114120
aacaggctga gaaagaaatt agggaaacaa cacccttctc aatagttaca aatagtataa 114180

-continued aatatcttgg cataatgcta actaaggagg tgaaagatct gtatgataaa aacttcaagt 114240
ctctgaagaa agaaattaaa gaagatccca gaagagcgag cttagagaaa ccctttctct 114300
aaaaacctaa aaagaaacta aaaataaaaa tccaaaaaga aagaaacagg cagataaata 114360
atcgtttaac ctccaaaaaa ttaaatctga aaagtcatca gaaaagaaaa aaaaatgcca 114420
aatcttcgaa aaaaatctca aatatctcag tgacgttcta tctccacgag ttttgcgggt 114480
tctaatttaa tcccacacga gttcgcctgc atcctgactt aaacccgcac aaattcccag 114540
gttctaaatt aaaccttgaa tttcacactc aaaaataaaa ggtgaagata agtcgcgaaa 114600
agaaaaatgc ctagtcttga atgaaaacaa caataaaaaa acggcaatag cggcttgaca 114660
acacatctaa aagctctaga aaaaaaggaa gcaaactcac ccaagaggag tagacagatg 114720
gcaggaaata atcaaactca ggggtgaaat caaccaagtg gaaacaagaa gaactattca 114780
aggaattaac caaacgagga gttggttctt tgagaaaatc aacaagatag ataaaccctt 114840
agctagactc actagagggc acagggacaa aatcctaatt aacaaaatca gaactgaaaa 114900
gggagacatg acaacagatc ctgaagaaat ccaaaacacc atcagaaatc aaaacacctg 114960
tgtctaaaaa ccaaataata aaaatctttt aaagatttgt aaagataaaa tttttaaaga 115020
ataattagaa aaaaatataa agcattgaca aaacccccca aaattggaat gtttatttaa 115080
aaattacaaa ataaaaatat tcaacagtca aaaattcaaa acaaaaaacc ctgtctcgaa 115140
aaaaattttt tgtctctgta tgtctgtgtc tctgtctccc tgtctctctg tctgtctctc 115200
tctattaagt aaagataatt agaattgaag ataattagag taaagaaaaa tacctcctct 115260
tgaagaaaac caacaataaa aaatcgcaag gttgcactga cgtcctgtgg ccactgggtg 115320
gcgccagagc atctgagctc ctcattgtgc aaatctgagc ctcgcatttt aaagtttctg 115380
caaatttgca tctctgtgag cctcattatg caaatctgtg cgagctccct gggtcctggt 115440
taaaatctct gtgagttacc tgagggcctc atttaaatgg tggagcacca gagacaaaac 115500
aaaaatcaat tcaaagagtc agagagaggc tcatctccct acacttctac aggcgcaaag 115560
ggagcagggg acgcggacct gagatgccgc ctgcccgggg acgtcactga ggaagtcaca 115620
cccctcgtcg ggagcccggg ctgggattcg ggtcccagat tcgtccccat gaggcagaga 115680
aggtagggag gcgggggaca gagagaggac agagacacga gctgcggggg ccacggactc 115740
aggcttggtc cccgggtgga agaaagtgga agaaggaagg agaagggcgg ggacagagag 115800
acagacagaa acctgcacga gtttccaagg tgctgattta aaccgacaag ttcccctggt 115860
aaaaatccgg gcgtggtggc ccaggccttc catcccagcc ctggggacac agacgcaggc 115920
agatctctga atccgaggtc agcctggtct ccagagcaca ttgcgggaca gccagggcta 115980
cacagagaaa ccctgtgtct aaaaaccaaa taataaaaaa cttttaaaga tttgtaaaga 116040
taaaataaaa aaaataatta gaaaaaatat aaagcattga aaaaaaccat ccaaaattgg 116100
aatgtgtatt aaaaaattac aaaattaaaa tgttcaacag tcaaaaatac aaaaattaac 116160
attgaaactg aaaagaaaaa taaatgacaa atcttaaaat aaaactcaaa tatctcagtg 116220
acattctatc tccacgagtt ttgcgggttc taatttaatc ccagaggagt tcgcctacat 116280
cctgacttaa acccacaaaa attcccatgt tctaaattaa accttgaatt tcacactcaa 116340
aaataaaagg tgaagataag tagcgaaaag aaaaatacct agtcttgaat gaaaacaaca 116400
ataaaaatac ggcaatagcg gcttgacaac acatctaaaa gctctagaac taaaggaagc 116460
aaactcaccc aagaggagta gacagatggc aggaaataat caaactcagg ggtgaaatca 116520
accaagtgga aacaagaaga actattcaag gaattaacca aacgaggagc tggttctttg 116580
agaaaatcaa caagatagat aaacccttag ctagactcac tagagggcac agggacaaaa 116640
tcctaatgaa caaaatcaga actgaaaagg gagacataac aacagatcct gaagaaatcc 116700
aaaacaccaa cagatccttc tacaaaaggc tatactcaac aaaagtggaa aacctggacg 116760
aaatggacaa atttctgcac agataccagg taccaaagtg taatcagggt caagttgacc 116820
atctaaacag tcccatatca cctaaagaaa tagaagcagt tataaatagt ctcccaacca 116880
aaaaaagccc aggaccagac gggtttagtg cagagttcta cagattccct gattcctaat 116940
ttaaccctgc acgagtttcc aaggtgctga tttaaaccta caagttcccc tggtaaaaat 117000
ccgggcgtgg tggcccaggc cttccatccc agtcctgggg acacagacgc aggcagatcg 117060
ctgaatccca ggtcagcctg gtctccagag cacattgcgg gacagccagg gctacacaga 117120
gaaaccctgt gtctaaaaac caaataataa aaatttttta aagatttatg aagataaaat 117180
taaaaaaata attagaaaaa tataaagcat tgaaaaaaac catccaaaaa tggaatgtat 117240
attaaaaaat tacaaaatta aaatgttcaa cagtcaaaaa tacaaaaatt aaaattaaaa 117300
ttgaaactga aaagaaaaat aaatgacaaa tcttcaaaaa atctcaaata tcgcagtgac 117360
attctatctc cacgagcttt gcgggttcta atttaaacct tcacgagttt ctctgcaccc 117420
taatttaaac ctgtctctct gtctctgttt ttttgtttct gtctgtctgt ctctctgtct 117480
gtatccctga gcgcaggaaa taatcaaact caggggtgaa atcaaccaag tggaaacaag 117540
aagaactatt caaggaatta accaaacgag cagctggttc tttgagaaaa tcaacaagat 117600
agataaaccc ttagctagac tcactagagg gcacagggac aaaatcttaa tcaacaaaat 117660
cagaaaatta gtgcagagtt ctatcagacc ttcaaagaag atctaattcc agttctgcac 117720
aaactattcc acaaaataga agtagaaggt cctctaccca actcacttta tgaagccact 117780
attactctga tacctaaacc acagaaagac ccaacaaaga aagagaactt cagaccaatt 117840
tcccttatga atatcgatgc aaaaatcctc aataaaattc tcgctaacca aatccaagaa 117900
cacattaaag caatcatcca tcctgaccaa gtaggtttca tcccagggat gcagggatgg 117960
tttaatatac ggaaatccat caatataatc cattatgtaa acaaactcaa agacaaaaac 118020
cacatgatca tctcgttaga tgcagaaaaa gcatttgaca agatcaacac ccattcatta 118080
taaaagttct ggaaagatca ggaattcaag gcccacagct aaacatgata aaagcaatct 118140
acagcaaacc aggagccagc atcagagtaa atggagagac gctggaagca atcccactaa 118200
aatccaaaaa ttaaaatcca aaaagaaaga aacaggcagg tgaatcaatg tttaacctcc 118260
acaaaattaa agataattag aagtgaagat aattagagaa aacaaaaata cctcctcttg 118320
aagaaaacca acaataaaaa atcgcaaggt tgcactgacg tcctgtggcc actgggtggc 118380
gccagagcat ctgagctcct ccttgtgcaa atctgagcgt cgcattttaa agtttctgca 118440
aatttgcatc tctgtgagcc tcattatgca aatctgtgcg agctccctgg gtcctagtta 118500
aaatctctgt gagttacctg agcgcctcat ttaaatggag gagcaccaga cacaaaacag 118560
aaatcaattc aaagagtcag agagaggctc atctccctac acttctacag gcacaaaggg 118620
agcaggggac ggggacctga gaagccgact gcccggggac cccactgagg aagccacacc 118680
cctcgtcggg agcccgcgct gggattgggg tcccagattc gtccccatga ggcagagaag 118740
gtagggaggc ggggggacag agagatgaca gagaccggag ctgcgggggc cacggactca 118800
ggcttggtcc ccgggtggga gaaagtggaa gaaggatgga gaagggcggg gacagagaga 118860
cagacagaaa cctgcacgag tttccaaggt gctgatttaa acctacaagt tcccctggta 118920
aaaatccggt aaaaaaagca tttggcctca gtgtgaagcc cagaggcaaa acagaaatca 118980
atttttgtat aggtttaatt cttgtataga tttaaacctt gtataggttt aaatcaggcc 119040
tctggtccct gccctgagag agggacagag ccaggtggat ctctgagtcc caggccagcc 119100
tgctctacag agcgagttta gagaaaccct ttctctaaaa acctaaaaag aaactaaact 119160
aaaataagaa taattgggaa aaaaaaccaa gactcgcgag cacgggtgtc tcggggttaa 119220
gtcccgagaa agcaagtctg caaagatcca aaaattaaaa tacaaaaaga aagaaacagg 119280
caggtgaatc aatgtttaac ctccaaaaaa ttaaaactga aaagtcatca gaaaaggaaa 119340
aaatatgcca aatcttcgaa aaaaaatctc aaatgtggca gtgacgttct atctccacga 119400
gtttcgcggg ttctaattta aacctgcaca gattccctga ttcctaattt aaacctcaca 119460
gattccctga ttcctaattt aaacctgcac agattccctg tttcctaatt taaacctgca 119520
cagattccct gattcctaat ttaaacctgc acagattccc tgattcctaa tttaaacctg 119580
cagagattcc ctgattccta atttaaacct gcacagattc cctgattcct catttaaacc 119640
tgcacagatt ccctgcatcc taatttaaac ctgcacagat tccctgcatc ctaatttaaa 119700
cctgcacaga ttccctgatt cctaatttaa acctgcacag attccctgat tcctaattta 119760
aacctgcaca gattccctga ttcctaattt aaacctgcac gagtttccaa ggtgctgatt 119820
taaaccgaca agttcccctg gtaaaaatcc gggcgtggtg gcccaggcct tccatcccag 119880
ccctggggac acagagtccg gcagatctct gaatccgagg tcagcctggt ctccagagca 119940
cattgcggga cagccagggc tacacagaga aaccctgtgg ctaaaaacta aataatgaaa 120000
aatttttaaa gatttgtaaa gataaaataa aaaaaataat tagaaaaaat ataaagcatt 120060
gacaaaaccc cccaaaattg gaatattaaa aaattacaaa ataaaaatat tcaacagtca 120120
aaaattcaaa tttaagatga aaattaaaat taacattcta tctccatgag ttttgcgggt 120180
tctaatttaa acctgcacga gtttctctgc accctaattt aaacctgtct ctctgtcttt 120240
ctctctgtta agtaaagata tttagaagtg aagataatta gagaaaagaa aaatacctca 120300
tcttgaagaa aaccaacaag aaacaatggc aaggttgcac tgacgtcctg tggccactgg 120360
gtggcgccag agcatctgag cgcctcagtg tgcaaatctg agcatcacat tttaaagttt 120420
ctgcaaattt gcatctctgt gtgcctcatt atgcaaatct ctgtgagtta cctgagggcc 120480
tcattgaaat ggtggagcac cagagcaacc ctctcagtgt gaagcccaga cacaaaacag 120540
aaatcaattc aaagagtcag agagaggctc atctccctac acttctacag gcgcaaaggg 120600
agcaggggac gcggaccatt atataaacaa actcaaagac aaaaaccaca tgatcatctc 120660
atcagatgca gaaaaagcat ttgacaagat ccgacaccca ttcatgataa aagtcttgga 120720
aagatcagga attcaaggcc cacacgtaaa catgataaaa gcaatctaca gcaaaccagg 120780
agccagcatc agagtaaatg gagagaagct ggaagcaatc ccactaaaat cagggacgag 120840
acaaggctgc ccactctctc cctacctctt caacatagta cttgaagtat tagccagagc 120900
aattccacaa caacaggaga tcaaagtcac caggcctctg gtccctgccc tgagagaggg 120960
acagagccag gtggatctct gagtcccagg ccagcctgct ctacagagcg agcttagaga 121020
aaccctttct ccaaaaacct aaaaagaaac taaaaataaa aatccaaaaa gaaacaggca 121080
gataaataaa cgtttaacct ccaaaaaatt acatctgaaa agtaatcaga aaagaaaaaa 121140
atatgccaac tcttcgaaaa aaatctcaaa tgtcgcagtg acgttctatc tccacgagtt 121200
tcgcaggttc taatttaaac ctgcacagat tccctgattc ctaatttaaa cctgcacaga 121260
ttccctgatt cctaatttaa acctgcagag attccctgat tcctaattta aacctgcaca 121320
gattccctga ttcctaattt aaacctgcac agattccctg catcctaatt taaacctgca 121380
cagattccct gattcctaat ttaaacctgc agattccctg attcctaatt taaacctgca 121440
cagattccct gattcctaat ttaaacctgc acagattccc tgattcctaa tttaaacctg 121500
cacagattcc ctgattccta atttaaacct gcagattccc tgattcctaa tttaaacctg 121560
cacagattcc ctgattccta atttaaacct gcacagattc cctgattcct aatttaaacc 121620
tgcacagatt ccctgattcc taatttaaac ctgcagattc cctgattcct aatttaaacc 121680
tgcacagatt ccctgattcc taatttaaac ctgcacagat tccctgattc ctaatttaaa 121740
cctgcacaga ttccctgatt cctaatttaa acctgcagat tccctgattc ctaatttaaa 121800
cctgcacaga ttccctgatt cctaatttaa acctgcacag attccctgat tcctcattta 121860
aacctgcaca gattccctga ttcctcattt aaacctgcac agattccctg attcctcatt 121920
taaccctgca cagattccct gattcctcat ttaaacctgc acagattccc tgattcctca 121980
tttaaacctg cacagattcc ctgattccta atttaaacct gcacagattc cctgattcct 122040
aatttaaacc tgcacagatt ccctgcatcc taatttaaac ctgcagattc cctgattcct 122100
aatttaaacc tgcacagatt ccctgattcc taatttaaac ctgcacagat tccctgattc 122160
ctcatttaaa cctgcacaga ttccctgatt cctaatttaa acctgcacag attccctgat 122220
tcctaattta aacctgcaga ttccctgatt cctaatttaa acctgcacag attccctgat 122280
tcctcattta accctgcaca gattccctgc atcctaattt aaacctgcac atattccctg 122340
attcctcatt taaacctgca cagattccct gattcctaat ttaaacctgc acagattccc 122400
tgattcctca tttaaacctg cacagattcc ctgattcctc atttaaacct gcacagattc 122460
cctgattcct aatttaaacc tgcacagatt ccctgattcc tcatttaaac ctgcacagat 122520
tccctgattc ctaatttaaa cctgcacaga ttccctgatt cctaatttaa acctgcacag 122580
attccctgat tcctaattta aacctgcaca gattccctga ttcctaattt aaacctgcac 122640
agattccctg attcctaatt taaacctgca cagattccct gattcctaat ttaaacctgc 122700
acagattccc tgcatcctaa tttaaacctg cccagattcc ctgattccta atttaaacct 122760
gcacagattc cctgattcct aatttaaccc tgcacagatt ccctgattcc taatttaaac 122820
ctgcagagat tccctgattc ctaatttaaa cctcacagat tccctgattc ctaatttaaa 122880
cctcacagat tccctgattc ctaatttaaa cctgcacaga ttccctgatt cctaatttaa 122940
acctgcacga gtttccaagg tgctgattta aacctacaag tttccctggt aaaaatccgg 123000
gcgtggtggc ccaggccttc catcccagcc ctggggacac agacgcaggc agatctctga 123060
atcccaggtc agcctggtct ccagagcaca ttgcgggaca gccagggcta cacagagaaa 123120
ccctgtgtct aaaaaccaaa taataaaaat tttttaaaga ttggtaaaga taaaataaaa 123180
aaaaataatt agaaaaaata taaagcattg acaaaaaccc ccaaaattgg aatgttaaaa 123240
aattacaaaa tataaataat caacagtcaa aaattcaaat ttaagattaa aattaaaatt 123300
aaaactgaaa agaaaaataa atgccaaatc ctctaaaaaa tctcaaatat ctcagtgaca 123360
ttctatctcc acgagttttg cgggttctaa tttaatccca cacgagttcg cctgcatcct 123420
gacttaaacc cacacaaatt cccatgttct aaattaaacc ttgaatttca cactcaaaaa 123480
taaaaggtga agataagtcg cgaaaagaaa aatgcctagt cttgaatgaa aacaacaata 123540
aaaatacggc aatagcggct tgacaacaca tctaaaagct ctagaactaa aggaagcaaa 123600
ctcacccaag aggagtagac agatggcagg aaataatcaa actcaggggt gaaatcaacc 123660

-continued

```
aagtggaaac aagaagaact attcaaggaa ttaaccaaag gaggagctgg ttctttgaga 123720
aaatcaacaa gatagataaa cccttagcta gactcactag agggcacagg gacaaaatcc 123780
taatgaataa aatcagaact gaaaagggac acatagcaaa gtctgcgaag atccaaaaat 123840
taaaatccaa aaagaaagaa acaggcagat aaataaacgt ttaacctcca caaaattaaa 123900
gataattaga agtgaagata attagagaaa acaaaaatac ctcttcttga agaaaaccaa 123960
caagaaacaa tggcaaggtt gcagtgacgt cctgtggcca ctgggtggcg ccagagcatc 124020
tgagctcctc attgtgcaaa tctgagtgtt gcattttaaa gtttctgcga atttgcatct 124080
ctgtgagcct cattatgcaa atctgtgtga gttccctggg tcctggtaaa agtctctgtg 124140
agttacctga gagcctcatt taaatggtgg agcaccagag caaccctctc agtgtgaagc 124200
ccagacacaa aacagaaatc aattcaaaga tgtttccttt caaaaaagtc aagaaacaat 124260
ttcaaaaaat ttcctccgca tcctaaaaag tttccaaggt gctgatttaa acctgtacaa 124320
gttccctggt aaaaacccgg gcgtggtggc tgagagaaac caagtctgtc ccaaagccac 124380
caggcctcta atccctaccc accctccaga gacagagcca ggtggatctc tgagtcccag 124440
gccagcctgc tctacagagc gagtttagag aaaccctttc tccaaaaacc taaaaagaaa 124500
ctaaaaataa aaactcaact aaaataagaa taattgggga aaaaaccaag actcgcgagc 124560
acgggtgtct cggggttaag cccccagaaa gcaagtctgc aaagatccaa aaattaaaat 124620
ccaaaaagaa agaaacaggc aggtgaatca atgtttaacc tccaataaat taaaactgaa 124680
aagtaatcag aaaaggaaaa aatatgctga aatttcgaaa aaaaatctca aatgtggcag 124740
tgacgttcta tctccacgag tttcgcgggt tctaatttaa acctgcacag attccctgca 124800
tcctaattta aacctcacag attccctgat tcctaattta aacctgcaca gattccctga 124860
ttcctaattt aaacctcaca gattccctga ttcctaattt aaacctgcac agattccctg 124920
aaacctaatt taaacctcac agattccctg catcctaatt taaacctgca cagattccct 124980
gattcctaat ttaaacctgc acagagtttc caaggtgctg atttaaccct acaagtttcc 125040
ctggtaaaaa tccgggcgtg gtggcccagg ccttccatcc cagccctggg gacacagacg 125100
caggcagatc tctgaatccc aggtcagcct ggtctccaga gcacattgcg ggacagccag 125160
ggctacacag agaaaccctg tgtctaaaaa ccaaataata aatttttttt aaagattggt 125220
aaagataaaa taaaaaaata attaggaaaa atataaagca ttgacaaaac cccccaaaat 125280
tggaatgttt atttaaaaat tacaaaataa aaatattcaa cagtcaaaaa ttcaaattta 125340
agattaaaat taaaactgaa aagaaaaata aatgccaaat cctctaaaaa atctcaaata 125400
tctcagtgac attctaacaa catgagcttt gcgggttcta atttaaacct gcacgagttt 125460
ctctgcaccc taatttaaac ctgtctctct gtctttctct ctgttaagta aagatattta 125520
gaagtgaaga taattagaga aaagaaaaat acctcttctt gaagaaaacc aacaagaaac 125580
aatggcaagg ttgcactgac gtcctgtggc cactgggtgg cgccagagca tctgagctcc 125640
tcagtgtgca aatcttagag tcacatttta aagtttctgc aaatttgcat ctctgtgagc 125700
ctcattatgc aaatctgtgc gagctccctg ggtcctggtt aaaatctctg tgagttacct 125760
gagcgcctca tttaaatggt ggagcaccag agacaaaaca aaaatcaatt caaagagtca 125820
gagagaggct catctcccta cacttctaca ggcgcaaagg gagcagggga cgcggacctg 125880
agacaccgcc tgcccgggga cgccactgag gaagtcacac cccttgtcgg gagcctgggc 125940
tgggattggg gtcccagatt cgtccgcatg aggcagagaa ggtagggagg cgggggggaca 126000
gagagatgac agagacccga gctgcggggg ccacggactc gggcttggtc cccgggtgga 126060
```

agaaagtgga agaaggaagg agaagggcgg ggacagagag acagacagaa acctgcacga 126120
gtttccaagg tgctgattta aacctacaag ttcccctggt aaaaatccgg taaaacaagc 126180
atttgacctc agtgtgaagc ccagaggcaa aacagaaatc aatttttgta taggtttaat 126240
tcttgtatag atttaaacct tgtataggtt taaatcaggc ctctggtccc tgccctgaga 126300
gagggacaga gccaggtgga tctctgagtc ccaggccagc ctgctctaca gagcgagctt 126360
agagaaaccc tttctccaaa aacctaaaaa gaaactgaaa gtaaaaactc aactaaaata 126420
agaataattg gggaaaaaac caagtctcgc gagaacgggt gtctcggggt taagccccca 126480
gaaagcaagt ctgcgaagat ccaaaaatta aaatccaaaa agaaagaaac aggcaggtga 126540
atcaatgttt aaccttcaat aaattaaaac tgaaaagtaa tcagaaaagg aaaaatatat 126600
gctgaaattt caaaaaaaaa aaactcaacg tcacagtgac tttctatctc cacgagtttt 126660
gcgggttcta atttaaacct gcacagattc cctgattcct catttaaacc tgcacagatt 126720
ccctgattcc tcatttaaac ctgcacagat tccctgattc ctaatttaaa cctgcacaga 126780
ttccctgatt cctaatttaa acctgcacag attcgctgat tcctaattta aacctgcaca 126840
gattccctga ttcctaattt aaacctgcac agattccctg attcctaatt taaacctgca 126900
cgagtttcca aggtgctgat ttaaacctac aagtttccct ggtaaaaatc cgggcgtggt 126960
ggcccaggcc ttccatccca gccctgggga cacagacgca ggcagatctc agaatccgag 127020
gtcagcctgg tctccagagc acattgcggg acagccaggg ctacacagag aaaccctgtg 127080
tctaaaaacc aaataataaa atttttaaag atttgtaaag ataaaataaa aaaaaataat 127140
tagaaaaaat ataaagcatt gacaaaaccc cccaaaattg gaatgtttat ttaaaaatta 127200
caaaataaaa atattcaaca gtcctagttt aggagttctg tggtggaatg tttaggttca 127260
cttatatata ctatcatatc atctgcaaaa aagtgatatt ttgaattctt cttttccaat 127320
ttgtatccac ttggtctcct ttcgttgtca aattgctctg tctaggactt caagaacaat 127380
gttgaatagg tagggagaaa gtgggcagcc ttgtctagcc actgatttta gtgggattgc 127440
ttccagcttc ataccattac atttgatgtt gggtactgat ttactgtaaa ttgcttttat 127500
cctgttatgc cttgaattcc tgatccttcc aagactttta tcatgaatgg gttttggatt 127560
tacttaaatg atttctttgc atctaatgag aagatcatgt ggttttgtct ttgaggttgt 127620
ttatataatg gattatgttg atggattgcc atatattaaa ccatccctgt acacctggta 127680
taaaacctac ttggtaaggt tgaatgaaat ttttaatgtg ttcttggata tgattaggga 127740
taattttact gagtattttt gtttcaatat tcataagggc gattgttcta aagttcttta 127800
tctttgttgg atctttctgt ggtttaggta tcagagtaat atggcttcat agaatgagtt 127860
gggtagagta ccttctactg ctattttgtg gaatttttgt gcagaactgg atttagatat 127920
tctttgaagg tctgacagaa ctctgcacat taaacccatc tgttcctggg ccttttttttt 127980 ttttttttgg ttgggagact attaatccct ccttctattt ctttagggta tatgggactg 128040
tttagatcgt taacttgatc ctgttttaac tttgttacct ggtatctgtc tagaaatttg 128100
tccattttgt ccatgttatc ctgttctgtt gagtatagcc tgtggtagaa ggatctgatg 128160
gtgttttgga tttcttcagg atctgttttt atttctctct tttcaattct gattttgtta 128220
attaggatgc tgtctctgtg ccttaaggga tgctagctaa gggtttatct atcttgttga 128280
ttttctaaaa gaaccagctc ctctttggtt gattctttaa gtagttcttg tttccacttg 128340
gttaatttca cccctgagtt tgattatttc cttccatcta ctcctcttga gtgaatttgt 128400
ttcctttatt ctggagattt tttatgtgtt ttcaagctgc ttgtatgtgc tctctctggt 128460
ttcttttttg aggcactcaa atgtatgagt ttccctctta gtaatgattt cattgagtct 128520
cataagttag ggaatgttat ggctttattt tcattaaact ctaaaatgtc tttaatttcc 128580
ttctatatcc cttccttgac caaggtatca ctgaaaagac tgttgttcat tttcaaagta 128640
aacgttggct ttccattatt tatgttgtta ttgaagatca atcatcctta gtccttggtg 128700
gtctgatagg atgttttgga caattgcaat atttttatc agttgaggcc tgttttatga 128760
ccaattatat ggtcaatttt ggaaaaggta cgatgatgtg ctgagaaaaa gttacatcct 128820
tttgtttcag gataaatgtt ctgtagatat ctattaagtc catttgttta ataacttccg 128880
ttagtttcac tgtgtccctg tttagtttct gtttccaaaa tatgtccatt gataaaagtg 128940
gtttttttaag cctcccacta ttattgtgtg agctgcaatg tgtgctttga gctttcttta 129000
atgaatgaga atgcccttgc atttggagca tagatattca gatttgagag ttcctcttgg 129060
aagattttaa ctttgctgag tatgaagtgt ccttctttgt cttttttgat aactttaggt 129120
tggaaatcaa ttttaatcga tatttgaatg gttactccag ctgatttctt cagaccattt 129180
gcttggaaaa ttattttcta gcctttcact ctgagatagt gtctgtcttt ttccctgaga 129240
tgggtttcct gtaagcagca gactattggg tcctgttttt atagccagtc tatgtctttt 129300
tattggggac ctgaatccat tgatattaag agttattaag gaaaagtaat tgttgcttgg 129360
tatcattttt gttgttagag tttgcattct gttcttgtgg ctgtcttctt tttggtttgt 129420
tgagggatta ctttcttgct ttttctaggg cgtggtttct gtccttgtat tgttattttt 129480
ttctgttatt attctttgaa gggctggatt tatggaaaat taatgtgtga atttgttttt 129540
tatcgtgaaa tactttggtt tctccatcta tggtaattga gagtttggct gggtttaata 129600
gcctgggctg gcatttgtgt tctcttagta tctgtataat atctgtccag gatcttctgt 129660
ctttcatagt ctctggtgaa aagtctggtg taattctgat aggcctgcct ttatatgtta 129720
cctgaccgtt ttcccttact acttttaaca ctatatctct atttagtgta tttcttcttc 129780
tgattattat gtgtcaggag gaatttcttt tctggtccag tctatatgga attctgtagg 129840
cttcttttat attcatgggc atgtgtttct ttaggtttga caagttttct tctataattt 129900
ttttgaagat atgtgctggc cctttaagtt gaaaatcttc attctcatct actcctatta 129960
ccagtaggtt tagacttcat attgtgttct ggatttcctg gatgtttgag ataagatctt 130020
ttgcattttg tattttattt gattgttgtg ccgatgttct ctatggaatc ttctgcatct 130080
gtcattctct cttccatgtc ttgtattctg gtgctgatac tcgcatctat ggttccagat 130140
ttcttgccta ggtattctat ctccagcgtt gcctcacttt gggttttctt tattgtgtct 130200
acttcacttt ttaggtcttg gatggtttta ttcaattcca tcacctgttt ggtcgtgttt 130260
tccttcaatt ctttaagttt tttttttttt ttgcttcctc ttaaggttct acctatttag 130320
cagtattctc ctgtatttct ttaagtgagt tattaaagtc cttcttgatg tcctctacca 130380
tcaacctgag atatgctttt aaatctggga ctacctttc gggtgttttg gcgtttccag 130440
gactgggtga ggtgggagtg ctgtaattct gatgatggtg agtggtcttg gtttctgtta 130500
gtaagattat tatgtttgcc tttcatcatc tggtaatctc tggagttagt tgttataatt 130560
gtgtctggtt atatcttgtt cctcagtgat tatgttatcc tctatcagca gacctgggag 130620
acttgttttc tcctgagttt cagtgttcag agtactctat gcaggcaaga tctccacttg 130680
cagagaaggg gcccagatat ctggtgtttg aaccttcctc ctggcacatg ttgtgatcca 130740
ctcactagag atactaacat cccatggaga gtcctgtggg gacctttggg gtgtccacag 130800
actctgccgc caaggtgccc agtgctgtcg tggactggaa gggacttgtg accctggtca 130860
gaccggtttc tctgatcacc taattaatgc agtcacaggt cctgcttgat aggattggag 130920
cagaagttgt tttccactca ccaaaggtct taagatctgg tggatgtttc tgtgaggacc 130980
ttggggttgt cctcagtctc tgcccaaaat gttgcccagg tgctggcaca gaccagaggg 131040
acttgtgacc attgtcaggc cagtttttct gcttccctaa ttaatgcagt ctcagatcct 131100
gtgagattgg attggagcag aggttgtttt ccattcacga gaggtcttat gatcctaaaa 131160
agggtcttgt ggggacctta ggagtgtctg cagactccga tcccaatgtg ccctgttgct 131220
ggcttgtcag tctctctctt atggtacacc ttctctgcct ccttaaagag atgttgtaaa 131280
gataatgttt tcagactctc tagatgctgt aaccttttcc taatttcaga agaggactgc 131340
cgtatagaag ccatgacacc tgttacttgc tggcacgctg aagtagggtc aaagatagtg 131400
taacacttct atacctttaa gaggtagtct aaaatcactg ctgggggctc ctttttctct 131460
tgtaggatct ctattacctt ggccaaattg gtggggcacc tgccagctcc tttcagtcct 131520
attatcagag cccagcagaa aattgtcaat tgctccatat ggtcagtttt gtcaggacat 131580
gtcagaggga aggctgcatc tatttcattc agaagtttta ttggtagtca attggcccac 131640
agcatgctct ttctttcctc tcagaatccg atccttctcc tctgtggtga aagaacctgt 131700
aaaagctgct gacagtcatc acaagtaggc tgaagagaga atatgagaga ttccattaga 131760
ttagcaaggc tagatgggtt ttcaaagaag gggagtgtga tttaccttct agttatagag 131820
ataagaggag taaaaaggcc attactgaag gggctgcagt tgtctggggt ccgctggatg 131880
agggtcataa gtacacaaag gcagtgcgat ggttgagtcg ggtcctctgg gctttgagct 131940
ccctggtctt gggctttagc aactggtccc tccccaaaat ctagtggcac cctgttgaga 132000
gttcttgtgg gggaccagtt gggaatatgc gggtggggtg ctgtgccatt ttggaggttc 132060
ttctaattct ggatagatct tgggagaaac cgagggctgc agttcaactg ctgccagatt 132120
taactttttt tttcccctct ggatggcaga ggtccaggac tggggagcct ggattattct 132180
tttgaaacaa aggctttaaa caggatggga gaggggggat cctctgctaa ttttttctag 132240
atgagaacgt agggcactca atctagctga gaccctggtc ccctctgtaa aacaacttta 132300
agagctgaaa acagatccaa accaagggtg ccctctagtg gccaactaac atcaaagctg 132360
gccattccat agagcagaaa gttctctaaa atctatttca gccatccacc gagacaatgt 132420
gagtcttagt cttaatttca gtcctgtgca caagggtcag tccaaggggc atgctaattg 132480
tcggtcccat catcaaagtt acatagaggg gaaaaaccaa tatatacaca caaaaagatt 132540
acaataacca agaccaggcc ccaataagat ggccgagaga gcacacactc acttggcacc 132600
cagtaacaga aacagacagc cgagtgagca cacactcact tggcaccctg ataggaaatc 132660
tccaggtatc cttggaactc cctcagaact ggggagtgag ttttttctga atttttatct 132720
ccttgtcctt ggcaaaggaa ggcaggcatc tctggttgta aagtatagaa acaaaatgct 132780
tttttgctgc ctatagagag caaagagctt cttcctagct gtattttcag agatcaggga 132840
aaacaagctt ggggaatgtc taggggcttt atcttactgg gagatatact ttaagttaga 132900
aactcacagt aggatatttt ttctacaaca cacaaaactt tacacagaag attattacaa 132960
ttatttataa taaatatata atatttgatt tgaaccaaat gtcatatcca tataaaatac 133020
atggtagtat tacaaaaaaa ttgtaatatt tactttaaac aatttataca tttacacccc 133080
acagcacttc ttcataactg tactaccctt tctgagatcc ttcttcttcc caaatagtcc 133140
ctctcttatt tttataatgg ttctcctttt cttttgtgta tatatggaaa catctcatgc 133200
aggtggttgt attgtactcg ttgctatgtt tttgtgatca caaagtctaa aggaccacaa 133260
tctgttcatg aactacatat ataagagcat ctgaccctga gttgctcttt ttcctgaatc 133320
tacttctcca gtcaagggat cacaaacacc acttttgaag tactctattg aaatgggata 133380
aaattgaata tattgtacca tatcttcatc tgtttctacc tgaggtgata tattctcatc 133440
tttgtcaaat gctgggctct gtactatatg gacaacagaa aatggaaaca taatatgcta 133500
tattagtaaa agggaataaa gttttaatga tttgaatttc tcaggaaata ctgcccatgt 133560
gaatttttga aatagctttg agaaatgaca taattgaata catgatatcc ggtatagtta 133620
tagattagaa gtaaggtttc caaattatag ggccattgaa tatctttacc aatattataa 133680
aaaaaaaaaa cttccctaac ttaaagaaag ataatctcat gaatatacaa gaagcctaca 133740
gaacgccaaa ttatttggac cagaaaaaaa aaatcctgcc atcatataat agtcaaaaca 133800
ccaaatgcac aaaacaaaga aagaatatta aaaggagtaa gggtaaatgg tcaagtaata 133860
tataaagcaa gatctatcag gattacacat aacttctccc ctgagactat gaaagccaga 133920
aaatctaggg cagatgtcat acagaatgta agagagcaga aatgccagcc aagactacta 133980
tatgaagcaa aactttttaa catagcttga gactacaagg tattctgtga caaaaccata 134040
tttacatagt atcttccaat gcatccagca cttcaaacga taataaagag acaattccaa 134100
tataacgagg gaaattacac tcaagaaaaa gcaagaaatt aaacttgaag gaaacctaaa 134160
agaagataga tacatgaaca aaattccaac tctaataaca aaaataacag gaagcaacaa 134220
gaacttttcc ttagtatctc ttaatatcag tggattcagt tcaccagtaa aaaggcatag 134280
aataacaaaa tggatgtgta agcaatattc agcacaccag aaacaaacac caaggacaaa 134340
gtcagacatt acctcagact aaaagcctgg aaaaatcttt ccaagcaaat aatcccaaga 134400
aataagctgg agcagccata ctaatatcaa ataaaattca ctttcaaccc aaagttatta 134460
aaaaaggcaa ggagggaaac ttcatattca ttaaagttaa tatttaccaa gatggactcc 134520
caaatctaaa catttatact ccaaatgcaa tgacatccac atagataaaa gaaactttag 134580
taagctcaaa acacacgttg taccacacac aataatattg gaagacttca acacccctcc 134640
ctcattaatg gacagatcct gtaaactaaa actaaaaaga tacacggtga aactcacaga 134700
atttatgtaa caaatacatt tagttcatat ctatagaaca ttttatccaa aaagaaacga 134760
atgtcccttc ttctcatcac ctcacgatgc cttctccaaa attgaccaaa cactcagtca 134820
caaaacatgc ctcaacagat ataaaattat tgaaataatg tcatgcttcc tatcagatca 134880
ccacagacta aggctgatct tcaacaataa catgaataat tgaaaaccta catacacgtg 134940
gaatgtgtac aacaatctag tcagtgacaa aacagtcaag gaagaaatct agaactaaat 135000
taaagacttt ttagagttta atgaaaatgt agctacaaca tactgcatgt tatgggacac 135060
aataaaaata gccctaagat ggactctcat agctctctct gaatgcctct aaaaaaaacc 135120
ggagagagga tataggagta ggttgacaac ccaccttaac actatagaac aaaaggaagc 135180
aaattcaccc aaaaggagtt gaagtcaaga aataatcaag ctcagtgcta aaatcaacca 135240
agtggaaaca aaggaacaat acaaaaataa tcaaacaaac tgggagcttg ttctttgaga 135300
aaatcaacaa gatagataaa ccattagaca gacaaaatac agaacacaag aacagtatcc 135360
aatttagcaa aaccagaaat gaaaagggag aaataacaac agaaatttag taaatttgaa 135420
atatcaaaag atccaaatac aaggctgtac tcaacaaaac tgaaaaatct ggataaaatg 135480
gacacttatc tagacagata ccaggtacca aattcaaatc aggatcagat aaaccctgta 135540

-continued attacttcta ccactgtgaa aagccgccct catggtcgcc attacgagat ggtgctgaca 135600
acaccattgt caccattgct catggtgagt gcacgcaggc gtcaggatat ctttccatta 135660
cctgagccct gactctccca tggcatcatc aggctgattg tgggcatcca atcccggtgg 135720
tgcacgtccc caaccatact tctaaccata cttcacagcc tatataaggg aggggttttc 135780
tgctctctgg gtctcctgtc ttgaagctgt tcatctatct ctggagatgt attaaagctt 135840
tactacagaa agatctgagt gtcctggatg cattcttgct ggcaagatgg tagcgtgggt 135900
catctggtgc cagaaaccca ggatcaacat cgctggcatt gaggagaacc cctgaagaag 135960
ggatggattc agaactgcag gaaaaaggta agttcgcaga ggtatatctg atcgtgaacc 136020
tcttatccct tttgatttca gtcttaatct agatgcaact taggaacggg cagtagaagc 136080
tctagttttg gttgccctgg cgctcattct gtttcttatt ctgtccatcg aggctggtgc 136140
tgaaatttga ggtccatcgc ggctggtgct gaaaaatgag gtgttgtcag tccaacatag 136200
ataagtggca gcactgaggt atcttctaag ccttccatag ataagggagc agagcgctgt 136260
gtttactttc actttgctta aggaatacta taagtcgggt gtagatcagc cgcaggcact 136320
cattctatca tgggcttctc acagtcagtg atcaccacat tacaggcagt gctaaagcaa 136380
cgtgatctgc aggttgcctc ccatatgctg cagaattttg ttaaggaggt ggatcgcatt 136440
tctccctggt atgcctattt ggggtcacta actgtagcct tatagaataa gctaggaagg 136500
gaccttgacc ataagcatga agagggagac ttacgcctgg gcaccaaggc aatttggaag 136560
ctgataaaaa actgtctaga ggatgaaacc tgccaaccag ccaatgtgga gggacaggga 136620
atactagaag aggttcagga cagtatgtga gaaaactaac agaatgagag aaagggagct 136680
cgaaaaaaga aagacacgtc taagaaaaag ggccctccca gggattcaga aggaagggga 136740
gagagaaaag agggcagtaa aactgatcct ctactaagaa aaagccacac atgtaattca 136800
acattgcctt gaagcttgga gtgcttgggg acaacccaaa tttcttagaa cagataatgg 136860
actggcctac acctctcaat aatttcaaca gttctggcta cagaggaatg taatttattt 136920
aactggtttg ccatacaggg acaaggcatt gtggaacatg cccaccacac tcttataacc 136980
taccttatca aactaaaagg ctgagtcgat gaggccccgc ccttaacact gagagtggcc 137040
gtctccatgg tactctttac tcttaatttt ttgaatattg atgaacaagg ccacactgca 137100
cctgatcatc actgttcaga acgaaacagt tctagagaaa tgatcaaatg gaaagatatc 137160
ttaaccggaa aatggagatg cccggatcct attttaataa gatccagggg agttatttgt 137220
gtctttccac aggaagaaga caatcctctt tgggttccag aatgcctcat ctaaaggatc 137280
tccccttcag aagatgtgga caaaagaggg aatactgaaa caaagatgga tactgaccct 137340
tctactggag atcctggttc ctagtatatc gggggaattg tgttggggta ttatgtccac 137400
ctttcccctg cccatgcctg tcatgcacag tgcacaagtg tttccacatt tctttactac 137460
tgatagggag cttcaacttg ccttttttatc attagatggg caaattcaga ctctgatgga 137520
aaacagaacg tttccctcaa aagttgcata tgtagcagag gatggactag taagtcatca 137580
atgggaggag agacacttgt tcttgtaaag ttcctatgac caagttttgg gaatgcctgg 137640
gtcaggaatt gggagtgggt gtgcttgttg gagagcaggg tgagagggga gaggactggg 137700
atttttggag gggaaaatag aaaagagaat aacatttgaa atgtaaaaaa aaataataat 137760
aataaaaaaa gaatgaatta aattatttgt agtattcttg aaataaattc aagttttaca 137820
aatatattat tggaacaatg ttcaggtatt ttcctttggc agaataataa caagttattt 137880
tttatcaata tattgtgact acaatgccaa gaatagttat atgtgttgct aaaactcggg 137940
tataggaata tatagatata ggtaaaattt caaatgaatt atacaaaatc tcttagaaaa 138000
gacttcttac aattcaggtg actaggaaaa agtctagtga actgcaggac acgcaattaa 138060
tacccaaacc agaatatgca ataaccttca gaaagagact cctctgaaat atttatgtca 138120
tcttcttcat catcaaagtc caaaagtaat aagtaatctc ctttggaatc accatcattt 138180
tcttaacagc cattcttctc ttaaaaacta taatgtcttc ttagttaaaa aaaaatggaa 138240
aaaaaggaaa aaaaatctta gtaatctgaa tccaaaggta tcatttaagt agttaaaaat 138300
atcaaaaatg aaataattat atgcacttcc tctttccagt tcctccatgt atcccattta 138360
tcatgtccct ctccctcaaa acattgtttt aaaatcttat taacttactt ctttaagaaa 138420
ctcctttaga accagagcta acaatatgtc agatcccagt ttaaataagg ggaaaaaggc 138480
cagccttgaa tatgtgagac ttcttaacta cccaaagacg atgagcaaaa tgtatttgca 138540
tttaatttct gagtcatctg attcttgttc ctatttccca cagattcttt ttaaacaaaa 138600
cattagcaat tttgtttatc agtgtgtctc tgtctttaaa taaactcaca ctgctatcaa 138660
gatagataat gaatatggta actgtatatt catttgagaa gacccaaagc tccctcaaca 138720
atcaacaccc aacagcacca gcacccacac agaaagacct tctattggag aaagcaggga 138780
tttggggaag acttggtttt caaatatctg gagattgtaa gtccaaggcc agcccaaacc 138840
aagacagcct gagctaaaac gaagaaccca tcctacagaa gggaaacgga gagaaaaggc 138900
tgatctccat ggtgcaagtc tttaatagaa atacttgggg aatgagaggg aggatctgtg 138960
gtaagaatcc atcttagaag acttatgaat cttctgcatt gtctgctctc attcttttca 139020
tttattcttc ctatgccact cccctttctg tagtatccat acagtctcta ccaaagaaat 139080
acacactaga gaagacagtg agggtagagg aatcctcagt gtgtctctaa tagattttgg 139140
actacacaca ggaaaagtgc caatttcaac cctaaggcct cttacagcaa ataggacaat 139200
cgccaagact cctcaccaat ggcaccctga tcccctgacc cccagtcctg cagccggctc 139260
tctgatcctc tccctaggct tcaagcttgt gtcctacaag ggctttcaat cctctaagcc 139320
cctgtcctgt tcaatcctgt gcaatgaata tgatcctcct ccttcattta accctcagaa 139380
gccataggaa atgccgatca ggaggctttt cctcacagag tggcctcctg ggactgagat 139440
ttcccaccac tcacacatct gttaatagtc caattatcct gatcagagct ggttatcagt 139500
tccaggtctt tcaaaagtga actccttcac aaccgaaccc ttccttgctt ggctctcaat 139560
gaaaaaaaca aaacaaaaaa aaaacaaaaa aaaaaaacaa agcaaaacaa aacaaacaaa 139620
caaaaaaaac taagcaaaaa aacaaaacaa aaacaaaaac acaaagaaaa aacaaaacaa 139680
aaccaaaaaa caaataaaaa actaaacaaa taaaaaacaa aacaaaaaca aaaacaaaaa 139740
caataacaaa acaaaaagaa aaagaaaaac aaacaaaaga aaaagtaaca aacaatcaaa 139800
caaacaaaca aacaaaacgt tatcaggaga gacctagatg gtgtactctg aggacccttt 139860
atgatgccag atggagaaaa caggtctcat ccagggattt cactgtttgg ctgaatatac 139920
cctgtgtatg ctgtcatgga gtaccaggca ccattgattg gaagggagtt ctcaggaggt 139980
ggaaaagagc taccatcttt aagacaaatg atttccaatt actaggttga aaagcatttg 140040
cagacttgaa aaacatgaac aaatgtgtaa catatgaaag cactggaaat ggcactacta 140100
atttcaactg taatattttt ttttgttatt tatttatgtg cataaaatta aaatgtgtgc 140160
actttttctg tatgtacata cctacaacag aagagtccat gctgtcctaa tagatctgaa 140220
aataacatcc agattcccta caatccctga taaactccca cctccacctt cctagtactg 140280

-continued agcttgatta caagagtgtg ctaggatgtg caggcccttt ctccctcact tatgtgctag 140340
gctgcccagc cccttttat ccccttatgtg ctagagtgct catacccctct ctctcattta 140400 tgcctctatg gcctacagag gctgaaagag agcagtgatt ctctaaaact gtggctgtgc 140460
ataaattgta agccactatg tgtgtgcatt gtgcccggtc ctcttcacag aacaggtgct 140520
gtttgtttgt ttgtttgttt gtttgtttgt tttattattt tttgagagag ggttactctg 140580
tgtagacctg gctgtcctgg aactcactct gtataccaag ctggtctcag actcacaaat 140640
tattggcctc tgccacccaa gtgatgggat taaaggcata aaccaccact gcccaaacaa 140700
cagttgcttt tatcagctaa tttttccatt tttcaactaa tctagtgtgt acttcatgta 140760
tctttagggc atttctccca tttactttca aggtggaggg tgtttccacc ggaacaggga 140820
tccaaagtgg gatccgtgcc accatggcac gggtgttctt tgttacatcc caacattgag 140880
aaatccaaca agaatcattg gaacagactt caaaagaatc acttgaaaga atataaacaa 140940
gaaagggggg taaacacaga ctgggggaga tgtataatta atctggttta ccaaagtttt 141000
attgaatcca gtgatctcta cacagatatt agtatgtcca taagagtcct gggaggcatc 141060
atgtattccc caatgctgag caaatcttga gatgccaata aaagaagcct ttacaactgc 141120
tcctccctgg ataaaattca aaggatttag ttctctacaa ctgccattga ctccacaaag 141180
cacccacttg tgaaaaggat gcattctaaa gtcctgtatg aaaaatctct ttttcataac 141240
aaattccttc tctgggtcat ctgtcatgtt gaaagaaaag gaaaaagttt tactctgatc 141300
tgcccaacaa atgatggagg atcgataatc agaccaaagc aggatcagcc cttcatcttc 141360
caagatacaa tgaggggcta tttttgtttg gtggggatgt cctttttctg aaaagttagg 141420
tggtagaaat gtaccattaa cctaaattgc ctcttgccaa aaggtccgat tttataaaggt 141480 tatatctaca ttggaagtat cttgggttgt gctcacccaa cctcctcggt gctcattaaa 141540
cttccctaaa gctcgggctg ggaggttgat acaatttctg gtccattaat ttgaaaacat 141600
aaagacccct gttctagtaa ggagtgattt tctcctaatg gtgctcgagt gggatcatag 141660
gttaaatatg gcaaatccac tgttttatta gtagtaaaga attttggaaa aactatagca 141720
tcatggcgaa ctgacattgg tttagggaaa gtcgagagaa tagcccttct ctgttcaccc 141780
attatactag aaacctgaga caagttcagc attgtcagga tcaggaacag tcctggggag 141840
gtcagcatct tctgcaccat ccttgatgaa tatcctgcgg gtgagtcgtt ccggcagcca 141900
atatgggttg tcctcactct gtggaaaaac acaaacagct ccccaggata tgattaagat 141960
aggatccagg cctttccaca gaccagttaa aacatccttc cctttgacca tttcttttgg 142020
tctatcaggg tctgagttat gtcactcagc tacagaacgt ccctgctcgt tgagattcaa 142080
aaaattaagt gtgaagagtg acatagatac tgctactctt ggcactgaga gcagagtctc 142140
atcaactccc cctttttgtt ttataagata agacttgagt gtgtggtggg cacattccac 142200
aatgccttgt ccttgaggat tataaggaag gccagtcaag tgactgacat ccatttgatg 142260
acaaaattat tcaaatttag tagaagtata tgctgcccat tatccgtttt aagaattgtg 142320
ggcttgccca aagcactcca ctcttctagg cagtgctgta taacatgaga ggctttttcc 142380
cctgttaaag atgtggcaaa cattacacca ttgcaggtat caatggaaat atgtaaatac 142440
tgatttataa tggctattgc aggtggcacg cacggctctt cttaaggatt gcttgtggca 142500
cgcacgcgat tgctcgggac atggcactac acagccgtct atataaaaat gaaaatgtaa 142560
ttaaggataa aagtgataca ggagaaatgg ggaacaattc aaggaggaga agatagggat 142620
aaatttgcta aaactcattt atgtgtatgc agaaagttct tacccaacaa atttaaaaca 142680
aagtaagtaa gtaagtaagt aagtaaataa atagaaaaat atatgtgtat gcacatgcat 142740
acacgatagg catttgtgta tgtgtgtgtg tgtgtgtgtg tgtgtgtgtg tgtgtgtgtg 142800
tgtgtgcata tatgggtgta ggtatgtagc acctgttact agaggaatgc aatcatgcag 142860
tatctttctt tatgttgtat gatgcagtgt gttgattaga atatcttttg cccaagggat 142920
gtggcactat tacgatcttt aagtggcact attattatct ttaagtgctc cttagccatt 142980
ttagactgtt ctgaattgac atatctattt agatatatac cccatatttg attggtttat 143040
ttcgtttctt gagttcttta tatatttagg atattagccc tttattggat gtgaggttag 143100
ttaagatttt ttctccagtc tgtagcttga tgattagtct catcgcctat atgttttgct 143160
tacagaagct ttccagtttc atgaggtcac atttatgaac tgttgatctt agagcatgaa 143220
tcacgggaga tgtttttagg acatttccct ctctgtgtca atgagtttat cttctattag 143280
attcagtgca tcttatttta tgttgataat cgtgttcaac ttgaaactga gctttgtgca 143340
aggtgatcag tatggatttt tttgttcatt tttcaacata cagactgcaa attagaacag 143400
cacaatttat tgaaaatcct ttcttttttc catcgtatat atatccatat atattttgct 143460
tctttgtcaa atatcaagtg accataaatg tgtggttttc tttctggatc ttcagttcta 143520
gtccactgat ccatctgtca gtctctgtat caataccata tagttttgat ttgttttgtt 143580
ttgttttgtt ttcttttaat cacttttgct ctatagtaga gtttgaagtc caggattgct 143640
ctgagccagg atagcagtgg agtcacagag taggaccctg gcaatggctt taaaatcgaa 143700
gtgtcccagg gctttctagc tttcaaattg tacttaaatg ctgatgataa cttctaaaaa 143760
gtaataggtc tttctgaggg taggctggct taggtgatta acacctgtag cctaacagag 143820
gaggattaac aatgcagcct tttttctagc tcagcaggaa ttgctgggct ctaattttga 143880
gcctactagc cagatgtcac tggaagagaa ggaatttata gaagtgatta tagaagttat 143940
tacttggtta taaaaatatt ttttatgaaa gttatataag gggaaaagca gaaagatcct 144000
aagtgctgaa agggaaaaat tcttctaagt ggggaaaagg aaaaaaaaaa gtctaagtgg 144060
agaaaggcaa aaaaaaaaaa atcttctctc ttgatttttc tcgtctcttt gtcctcagca 144120
cttatacata tttcagaata catgaccaca tgttacaaag ttcatcaact gtctcagatc 144180
aataggtaca ctgaaggtat caaaccataa ctaagatatt agtgaagttt tgtataggta 144240
aaaccaatcc atattttacc ttttacccta gaacatataa taaatcgtta gttcccttct 144300
gatgaccttt ggttaattgt tatacaacct cttgtaatgt gctctgagta ggagaaagcc 144360
tagttactat ctaagagcaa ttagccagtg acacttggaa aactggcagt tctcattgca 144420
gttttgacta tcagaaaaag gacctaatag ccccttttagt ttggggagaa ttttattgag 144480
tatttttgca ttgatataca aaagagaagt tggtctgaag ttgctttaat ctggaatcaa 144540
ttcaccaata aaaacaaata gactaacaga ctggatatat aaacaataca caacattttg 144600
ctgcataaaa gaaacccacc tcagggacaa aaccagatac tacctcatag taaaaggctg 144660
gaaaacaatt ttccaagcaa atggtctgaa gaaataagct ggagtagaaa ttctaatata 144720
gaataaaatc aatttccaac ccaaagttat caaaaaagac aagaagggac agttaatgct 144780
catgaaatgt aaaatcttcc aagatgaacc ctcaattctg aatatctatg ctccaaatgc 144840
aatggcatcc acattcatta aagaaacttt agtaaaactc aaatcactca ttgcactgca 144900
caccataata gtgggagact tcaacaaccc gctcttatca atagaaagat cctggaaata 144960
gaaactaaac agagacacat tgaagataac agaatttatg aaacaaatgg atttaataga 145020
tatctacaga acattttacc ctaaaacaaa aggttataac ttcctcttag cacttcatgg 145080
taccttctcc acaatagacc acaatcagtc ataaaacagg actcaacaaa aatattgaaa 145140
gtatcccata caccctatca catcaccatg gaggaaggct gatcttcaat aacaacataa 145200
atagtagaaa gccaacattc agttgaaagc tgaacaacac tctactcaat gataacttcg 145260
tcaaggaaga aataaagaag aaataaaaca ctttttagag tttaatgaaa atgaagggac 145320
aatataccca aacttatggg acacaatgaa tgtagtccca caaagaaaac caaaagctct 145380
gagtgccacc aaaaagaaac cagagagagc acacactaag agcttgacag cacacctaaa 145440
agctctagaa caaaaggagg caaatttaca agggggagta gatagcagaa aataatcaaa 145500
ctcagagctg gaatcaacca agtgggcaca aaaagaacta ttcaaagtat caatcaatac 145560
aggagcctgt tctttgagaa tagtatcaag atagatacac ccttagcaag acgaactaga 145620
gggcacaggg atagtatcct aattaacaaa atcataaatg aaaagggaga cataagacca 145680
gaacctgagg aaatcctagg catcatcaca tcctactaca aaaggctata ctaaacaaaa 145740
ctggaaaact tggacaaaat ggacaatttt ctagacagaa atcaagtacc agagttaaat 145800
acagatcaga ataaagatct aaacagcccc atatccccta aagaaataga agcagtcact 145860
aatactctcc caaccaaata atgcccagga ccacccttat gggtttagtg cagagttcga 145920
tcagaccttc aaaaaagaac taattccaac tgttctcaaa ctatttcaca aaatagaaac 145980
agaacgtact ctattcaatt cattctatag aagccaaaat ttctctgata actaaaccat 146040
ataaagtccc aacaaaatag aggacttcag atcaatttcc cttatgaata ttgatgcaaa 146100
aatattcaat aaagtccatg caaactgaat ctaagaacat atcacaaaga tc 146152

<210> SEQ ID NO 3
<211> LENGTH: 98755
<212> TYPE: DNA
<213> ORGANISM: Homo sapiens

<400> SEQUENCE: 3
ccgaacccga acccgaaccc gaacccgaac ccgaacccga acccgaaccc taaccctaac 60
cctaacccta accctaaccc taaccctaac cctaacccta accctaaccc taccctaacc 120
ctaaccctaa ccctaaccct aaccctaacc ctaaccctaa ccctaaccct aaccctaacc 180
accctaaccc taaccctaac cctaacccta accctaaccc taacccttaa ccctaaccct 240
aaccctaacc ctaaccctaa ccctaaccct aaccctaacc ctaaccctaa cccaacccca 300
accccaaccc caaccccaac cccaacccta acccaaccct aaccctaacc ctaaccctaa 360
ccctaaccct aaccctaacc ctaaccctaa ccctaacccc aaccccaacc ctaaccctaa 420
aaccctaacc ctaaccctaa ccctgaccct aacccctaac ccctaaccct gaccctgacc 480
ctgaccctga ccctgaccct gaccctaacc ctaacccaac cctaacccta accctaaccc 540
taaccctaac cctaccctac ccctgaccct gaccctgacc ctgaccctga ccctaacccc 600
taaccctaac cctcaccctc accctcaccc tcaccctcac cctcacccta accctaaccc 660
taaccccaac cctcattatt ctcggctgca aagaggaagg atctttaccg tggatgtggc 720
ccccagttgt cccaaaatga agcagtgccc ccaacgtctg tggagaggca tgcgctgctc 780
caccttcgcg atgtcccccg cgtctgtgct gagcagaatg cagctccgtc atcgcgttcc 840
ccccgaagtc tctgcagagg aaaacggagc tcctccttcg cgatgctctc caggtctgcg 900
ctgaggggaa cgcagctccg ccctcgcaaa ggcatagagc catcgcaggc gcagaaaaaa 960

-continued

```
acgtcggtgc agcgcaggcg cagagaaaaa cgacggcgcg tccctggggg gcgcggcgca   1020
ggccgagaga ggcatgccac cgtggcgccg gggcgtgggg cgcggcgcag acgcagagac   1080
gcacgccggc gcggcgccgg gatgggagcg cggcccaggc gcagacacgg acggcagcgt   1140
ggcgcctggc ccgaggcgcg acgcaggccc agagacacac ggcggcgcgg cgccatgatg   1200
gggccccgcg caggcgcaga gacggatggt ggcgcggcgc aggcgcagag aaaaacgcca   1260
gcgcggggcg gggggcgtgg cgcaggcaca ggcgcagaga cggaggcggg cgcggcgcag   1320
gcgcagagac ggaggcgggc gcggcgcagg cgcagagacg gacgccgccg cggcgcaggc   1380
gcagagacgg acgccgccgc ggcgcaggcg cagagacgga cgccgccgcg gcgcaggcgc   1440
agagacggac gccgccgcgg cgcaggcgca gagacggacg ccgccgccgc gcaggcgcag   1500
agacggacgc cgccgcggcg caggcgcaga gacggacgcc gccgcggcgc cgtggcgggg   1560
gcaagagtca cgcggagaga tgcacggctg cgtggcgcag gcgcagagaa aaacgccggc   1620
gcgtccccga tgggcgcggc ggaggcccag agacgcacgc cggcgcggcg ccggggcggg   1680
ggtcggggcg caggcgcaga gaaaaacgcc ggcgcggcgc cggagcgggg gcgcggcgca   1740
ggcgcagaga cccacgccgg ggcgggggcg cggcgcaggc gcagagacgc acgccggggc   1800
gggggcgcgg cgcaggccca gagacgcacg ccggcgcggc accggggcgg gagctccgcg   1860
caggggcaga aaaggacgct ggcgcggcgc agacgcagaa aaaaaatggc ggcgcagcgc   1920
aggcgccgag aaaagcgcca gcgccggggg tcgcggcgca ggcgcagaga aaaacgccag   1980
cgcggcgccg gcgcaaagac gggcgcaggc gcagagtcgg gcgctggcgc gtcgccgagg   2040
tgggggcgcg atgcacgcgc agagacgcac ggctgcgtgg cgcagacgca gagaagaacg   2100
cgagcgcggc gccgaggaca aggcgcaggc gcggagacgc acgccagcgc gggggcgagg   2160
cgcaggcgcg gagatgcact ccgccaggcg cggggagggg ggcgcggcgc aggcgcagtg   2220
acgcacgccg cctggggcgc agcgcagaga taggcggaac ctcagtaatc tgaaaagcca   2280
ggttgccccc tccttgcggc cgggcactaa agggcccact tgctgaaggc gctgtgccag   2340
cgtgccccct gctggtgact ggggcaactg cagggttctc ttgcttccat tagtggccag   2400
cggcccctgc tggctgcggg gcaccgcagg gtcctcttgc acacagtata gtggcggcat   2460
gccgcctgct ggcagctggc gacattgcag ggccctcttg ctcatagtat agtgacagga   2520
cgcccgcctg ctggcagctg gggacactgc cggccactct tgctccaagt gtagtggctg   2580
ttggctcccc tgctggcagc tggggacact gccgggccct cttgcttgca gtttactggg   2640
ggcacgcccc cttctggccg cttggggcac tacaggatgc tcttgctcac agtgtagtgg   2700
cagctcgccg cctgctggca accagggtac tgcagggttc tcttgctcat ggtgtggtgc   2760
ccgtccacca cctgctggca gctaaggaca ctgcagggcc ctcttgctca gagtgtagtc   2820
gtcgtacacc ccctgctggc agctggggat gctgccggga cttttgctgg cactgtcgtg   2880
gcagcacact acctgcaggc cgatggggac tatgcaggga cctcttgttc agggtgtgag   2940
ggctggcacg ccctactggc cgcctcctgc accacttaaa gtcggagcgc cagttgttaa   3000
gcaccatcag ttctggaaat tgaaactgaa atggagctat tactgaggag agttgatgtc   3060
ccagttcttg tctaacttgg aagaaagatt tttcaccaag aggcagtaaa aacatggcag   3120
ataacttcat tgaaaacaaa tacagtgtaa agagcttatt gtagaataat agggaggagt   3180
gggctgattg tgcaggaaaa cagcctgaga gtcctgtgca gggaatttta ttttggactt   3240
cttcacattt ctgcctctgt ctcaagtctc cacctgtttt ctttgtctgg ttttcctgct   3300
actgccttag gtccctgagt tgccccactt aggcttatgg gacctcctca ctgttggttg   3360
```

```
aggcacatgt gtggtgatca atccgaatcc actctggtac caggctcctt ccccccatcc   3420
caggcaggct gacagcggtc atgtttctgc ctacagcgcc tgcctatctc ttttgaatgt   3480
ccttctctac cctactctgt acttatggtg ccaggtttct cttaagaatg tcccctttgt   3540
ccttcttatc agcatgtagc cagcaatatt gtgacatttt tactgcagag tgaatgatga   3600
ctggggcatc ttaaatggag ttctggggtg tttctttctg cataggtacc tctgcagtag   3660
tagtttccaa aatacttttg gtaattttta accttaaagt taaccttaaa gttaagctaa   3720
gtaaaagatt tgcattaaat atctagacca tttataaata agatacaata ctaaaacatt   3780
actgaagata aataattcaa gtttacatac ttttggctac ttatttttac agagaaacta   3840
aagatatttt agcccattaa taaacatgtt tttgtctacc acactgagaa attgtactat   3900
gaggaaacac atccctctag atgttgggag atggtatact catacatttt ctaacctact   3960
atagaatgct aacatatgac agtttataac tgtctacttc ctagttttct ctggaaaata   4020
aaagattact aagtattaaa attataatca atatgtgtaa ataaaactac tggaaataat   4080
agaataacta gaaacaactc tatgcaaagc atgcaagaaa agtagtgcat gttttgcaag   4140
taaagtagga cgtatttttt ataaggaaaa ccatacaaaa gatacaaata aaaagagata   4200
cctagccttc cctgtgttat atttgtatgg gtaaaatgtc atgttttcag aaattatata   4260
aaattcctgg aaatttgtca atgttctcct tatccatgct atgtgccagt atagagttat   4320
gagtcataat tccaattatt attttaaatg ttgtgctggg tgcagtggct cacgtctgta   4380
atcccagcac tttgggaggc ctaggcaggt ggatcacaag gtcaggagat cgagaacatc   4440
ctggctgaca tggtgaaacc ccatctctac taaaaataca aaaaattagc caggcgtggt   4500
ggtgggcacc tgtactccca gctactcagg aggctgaggc agaagaatgg catgaaccag   4560
ggaggcagag cttgcagtga gccaagatag cgccactgca ctccagcatg ggcaacagag   4620
cgagactctg tctctaaata aataaataaa taaataaatg ttgtatccca cagaaaaaat   4680
cgaatatcct tgtcagttgt ggtataatga actctcatca gatctttcat cacagccatt   4740
tcatattctt tatcatttag atattatttc cccctgatgc tttcctgaaa gctcctgcaa   4800
tcagctacag gtcagaatgt tcatctccat cacgggattc cctctgagac acacagaaaa   4860
gagtatgcaa gatagtctgg ttataggctt ctgatgatat tgtttaaata actttaagac   4920
catacacttc gctcagtgaa gatctccaga agtctgcttc agaaattgat gggttcatga   4980
cactgctaac ccaagatgca acaagactgg aattgattac atggtactga atgaactgat   5040
gaaaattgat tataatttta tagctttttg gagcattgct ggttctttaa tgttctagtt   5100
tctggactta agaaatctct ttctcttaac ctaactgtaa catacaattt agtagattat   5160
acttttgaaa acagaagtga agcatttatc ttttttcccc tgcctgattt ttccagaatt   5220
ttgaaatcct tactgaacac tcttattttc acgatgatat agttgttagc aaaagtccaa   5280
taagaatctg ttcaccttga acagagacct cagaaataat gccgcatatc tacaaccatc   5340
tgatctttga caaacctgac aaaaacaagc aatggggaaa ggattcccta tttaataaat   5400
ggtgctggga aaactggcta gccatatgta gaaagctgaa actggatccc ttccttacac   5460
attatacaaa aattaattca agatggatta aagacttaca tgttagacct aaaaccataa   5520
aagccctaga agaaaaccta ggcaatacca ttcaggacat aggcatgggc agggacttca   5580
tgtttaaaac accaaaaaca atggcaacaa aagccaaaat gcacaaatgg gatctaatta   5640
aactaaagag cttctgcaca gcaaaaaaaa acctactgtc agagtgaaca ggcaacctac   5700
```

-continued

```
aaaatgggag aaaattttca caacctactc atctgacaaa gggctaatat ccagaatcta   5760
caatgaacac aaagaaattt acaagaaaaa aacaaacaac cccatcaaaa agtgggcgaa   5820
ggatgtgaac agacacttct caaaagaaga catttatgca gccaaaagac atgtgaaaga   5880
atgctcatca tcactggcca tcagagaaat gcaaatcaaa atcacaatga gacaccatct   5940
cacaccagtg agaatggcga tcattaaaaa gtcaggaaac aacaggtgct ggagaggatg   6000
tggagaaata ggaacacttt tacactgttg gtgggactgt aaactagttc aaccattgta   6060
gaagatggtg tggcgattcc tcagggatct agaactagaa ataccatttg acccagccat   6120
cccattactt ggtatatacc caaaggagta taaatcatgc tgctataaag acacatgcac   6180
acgtatgttt attgcggcac tattcacaat agcaaagact tggaaccaac ccaaatgtcc   6240
aacaatgata gactggatta agaaaatgtg gcacatatac accatggaat actatgcagc   6300
cataaaaaat gaagagttca tgtcctttgt agggacatgg atgaagctgg aaaccatcat   6360
tctcagcaaa ctatcacaag gacaaaaaaa ccaaacactg catgttctca ctcataggtg   6420
ggaattgaac aatgagaata catggacatg ggaaggggaa catcacactc cagggactgt   6480
tgtggggtgg ggggggaggg gggagggata gcattaggag atatacctaa tgctaaatga   6540
cgagttaatg ggtacagcac accaacatgg cacatgtgca catgtataca tatgtaacaa   6600
acctgcacat tgtgcacatg taccctaaaa cttaaactat aataataata aaataaaata   6660
aatttaccaa aataataata ccaataccaa tgtgctctag ttttgtcaga tcatgaatgc   6720
atcatgcatc ccaataaaag attattgaac ataaaaaaaa tctgtttacc ttataacagg   6780
acataattgg aaatttttgt tatattatca aggtttttac tggaatatca tatttaggaa   6840
atgtacctaa gatcacttat gaccagcaat tttaaggaag taaggttgac ttttatgcag   6900
acagtgctta caaagcactc tgagaaatga gaaaattctt cttcaaaaat tataaaaagt   6960
cacaatttct tactatgaga ttgctatcca ctatttatat gtgtgtgtgt gtgtgtgtgt   7020
gtgtgtgtgt gtgtcttcca agtcagttgt cctagcttgc tccagcatgc ctggacagaa   7080
ctagacaagc cccagcccat agtgcatgcc attccttatt tggagatgct tccttaacta   7140
tccctgggca acttcctgtt ctttctttgt tctattcccc ttacctaatt aataaagttt   7200
taaactaata gccaactggg taaagtgtaa aatgtgaggt cttattccag ccaatggaaa   7260
ctgcacacag cagtagggta gacacataag gttataagta actctgtctc ctttgttcgg   7320
tgtgttcttc tggctggaca gctattgagt agcacccttt ctgcagaaag taaagctcac   7380
cttgctaaga gatcatttgt tcccatgtta attctttttt ttttttcctt ttttggaaca   7440
tcaaaaactt cattcccaac agcactctga gaaaagccag cctgatacct agattacagg   7500
gttcacagcc ttacaggtta gtaaggaagg tcatttcctg gtaggcccag gaatttaggg   7560
atattttggg ggcctcaaga agagaggaat tcacacaaag ctataaggac tgcagctgaa   7620
atttgatagt atgttcttag cttggctttt agcctgaata aggcctttaa aagtcaaatc   7680
tgagattcta tatgaaaact tccagcaaag aaacttgaaa gcacctatgt ggtcatcgcc   7740
tgttcttgct gcaattacat aaataatcaa gcaaaatcta ataaaacaag acttattttt   7800
aaaacaagaa tagtcttact ttgattatga taaaaaatga tggttactac caagagaaat   7860
tttatatttc aaaggaaaac tataacatgg ccgggcatgg tggcacatgc ctataattcc   7920
agcactttgg gaggccagga gttcaagacc agcctgggca acatggtaaa accctgtttc   7980
taccaaaaat acaaaaatta gttgggtatg atggcatgtg cctgtagtcc cagctaatca   8040
ggaagctgag gagggaagat cgtttgcacc caggaggtag aggttgcagt gagctgagat   8100
```

-continued

```
tgcacctttg cactccagcc tgggtgacag agccagaccc tgtctcaaaa aaaatgtttt   8160
taaaggaaaa ctacagcctt tgtgggttat cagattctag tcttgtttct tgtttctggg   8220
ctgtttttac ctctttgtaa actagatcct gccatctgat gaattctgtc ccacaatgat   8280
acttggggag caagaagcca attattgtct ctcctactaa tgtatctatt gtcagttaat   8340
ttgatggtca ccaaccctgg aacaaagtta gaagaggaag gttttgctcc ccaaaatgca   8400
taaccaaatt gtggtacatt catgcaatgg aatgctactt agccatagaa aggaacaagc   8460
tatcaactca cacaaagaca tgagcgactc ttgcatgcac attgctaagt ggaagaagac   8520
agtgtgagga gcatacacac agtgtgacct catttaatga gacactggag aaggcaaact   8580
acacagatgg gaagccattg gctccatggg gtgggggtta gaagcattcc atattatact   8640
tattagtggg atacctgcca caatgcattt gtcaaaatat gcagaatttt acagccaaat   8700
ggttaaagaa aactctattc aaattaaata aaattactca ggatgtggag tatctcagga   8760
cagaatacat catgtgaaaa agaatttaac tatgctacaa attactatct tttggatgtg   8820
gcttgtcccc gcaaaaactc atattgaaat ttgaccccca ctgtgtcagt gtggggcgat   8880
ggggcctagg ggaagatgtt tgggtcatgg tgatggatct ctcatgaata gattaatgta   8940
ctccgatggg ggtgaatgag ttctgctctc acaggaatgg attaattcct gcaggagtag   9000
gtagttaaaa agagtctggc ttccttggct tccctcttgc tttcactttt gctatgtgat   9060
ctctggtgca ccccttgctc cccttccact ttccaccatg aggtgaaaaa gactgaagcc   9120
ccccagatgc aagtgcccaa tctcagacat tccagccaca aatattgtgg gccaaatgaa   9180
ccttttttac ttataaatta cccagcctca ggtattctgt tacagaagca cgaaatggac   9240
taagacacaa atggaggtaa aaactcactg aaggtgtagg gaaaatgatg ttgacctaag   9300
tcactttgaa aatgaataga atctgtaggc cgaaggcaaa tgaactatac ttcatcattg   9360
gattccattt tataaagttc tttccagcag aagcaattgt taacagttgt aaaaccacag   9420
tatctgtatc tggaataaaa caatgactta cataagttgc agatggtagg aaccagatct   9480
ctcactggtg aagtgggagg ttacaaatta gcaaggtgag aaggctagaa tgattcatgt   9540
gatagtagat cagaggtgga gacatcaacg ttataggaaa agaaagagag atcagactgt   9600
tactgtgtcc atgtagaaag ggaagacata agaaattcca ttttgatctg taccttgaaa   9660
aatttctttg ctgagatgct gttaatttgt aactttgccc cagccacttt gccccaactt   9720
tgagctcaca aaaacatgtg ttatatggaa tcaaggttta agggatctag ggctgtgcag   9780
gatgtgcctt gttaacaaaa tatttacaag cagtatgctt ggtaaaactc attgccattc   9840
tctagtctca ataaaccagg ggcacaatgc actgcaaaaa gccacaggga cctctgccct   9900
ggaaagccgg gtattgtcca aggtttgtcc ccatgtgata gtctgaaatg tggcctcatg   9960
ggataagaaa gacttgacca tcccccagcc tgacacccat aaagggtctg tgctgaggtg  10020
gattagtaaa agaggaaagc ctcttgcagt tgagatagag gaaggccacc atttcctgcc  10080
tgcccctggg aacttgatgt ctcggtataa aacccgattg tacacctgtt caattctgag  10140
ataggaggaa aaccacccta tggtgggagg tgagacatgt tggcagcaat gctgtctagt  10200
tattctttac tccactgaaa tgtttgggtg gacagtaaca taaatctggc ctacatgcac  10260
atccaggcat agtacctacc cttgaactta attatgacat agattctttt gctcacatgt  10320
ttttttgctg acctcctcct tattatcacc ctgctctcct acagcattcc tcttgctgag  10380
ataatgaaaa taataatcaa taaaaactga gggaactcag agaccggtgc tggtgcatgt  10440
```

-continued

```
ccttggtatg ctgagagcca gtcccctggc cccacttttc tttctctata ctttgtctct  10500
gagtcttatt ttttttctca gtctctcatc ccatctgacg agatataccc acaggtgtgg  10560
aggagcaggc cacccccttca tctgccaccc aatgtgggtg cctttctcta ggatgaaggt  10620
atgctaagaa tgtgagcatt gaggacagtc gagagattcc tgagtacatc caccatcagc  10680
cttgcggtaa gcttgtgcgc tcagagaaac ccagggtaac aatggggcaa actgaaagta  10740
aatatgcctc ttatctcagc ttcatcaaaa ttctcttaag aagaggggga gttaaagctt  10800
ctacagaaaa tctaattaca ctatttcaaa caatagaacg attctgccca tggtttccag  10860
aacagggaac tttagattta aaagactggg aaaaattggc aaagaattaa gcaagtaggg  10920
aaggtaaaac catcccactt acagtatgga atgattgggc cattattttt tatttattta  10980
tttatttatt tatttattta tttatttatt tattttgaga cagagtctcg ctctgtcgcc  11040
caggctggag tgtagtggcg cgatctcagc tcactgcaag ctctgcctcc tgggctcacg  11100
ccattctcct gcctcagcct cccgagtagc tgggactaca ggcgcccgct gcgatgctgg  11160
gccattgtta aagcaacttt agaatggttt caagtagaag aagacagcat ttcagtttct  11220
gctgcctctg aaagctgtgt aatagattgt gaagaggcgg ggacaaaatc taggaaatga  11280
atggaaagtt catattgtaa atatgtagca gagccggtaa tggctcggtc aatgcaaaat  11340
gttgactaca atcaattaca ggaggtaata tatcctgaaa cattaaaatt aaaaggaaaa  11400
agtccagaac catcggggcc attggggcta aaagcatgat ggccacctcc tcctcagccc  11460
agtgacttct gggggaggga gcctgaaact aggcttgctg cgacttggct cgaggcactc  11520
attattgtcc aacctacagt tcactgtggt gaaggagcaa ttcagactca ccctgcagct  11580
tcctgtatag gtcaaacagt ggccgctccc taaggaaaag ttgggggtgc tacataaaat  11640
agttaaaaag ctattttata aaggacatgt ttcacccact ttctgtcttt agaattctcc  11700
tgtttttgta attcagaaaa aatcaggcag atggcgcatg ctaactgact taagagccat  11760
taatgcagta attcaaccta tgaggcctct ccaacccgtg ttgccctctc cagccacgat  11820
ctcctttaat tataattgat ctgaaggatt gctttttac catttctctg gcaaaacagg  11880
attttgaaaa atttgctttt actataccag ccataaataa taaagaacca gccaccagat  11940
ttcagtggaa agtgttgcct cagggaatgc ttaatagtcc aattatttgt cagacttttg  12000
tagctcaagt tcttcaacca gttagagaca agttttcaga ctgttatgtc attcattatg  12060
ttgatatttt gtgtgctgca gaaacaagag gcaaattaat tgactgttac acatttctgc  12120
agaggttgca aacgcagatt cagacctcta ctccttttca ttatttggga atgcaagtag  12180
aggaaagaaa aattaaacca caacaaatag aaataagaaa agacacatta agaacattaa  12240
atgactttca aaaattgcta ggagatatta attggattcg gccaactcta ggcatcccta  12300
cttatgccat gtcgaatttg ttctctatct tgagagggta tccagacttg aatagtaaaa  12360
gaacattaac tccagaggca gctaaggaaa ttgaattagt tgaagaaaaa attccgtcag  12420
cacaagtaaa tagaatagat cacttagccc cactccaact tttgattttt gctactgtac  12480
attctccaac aggcattatt gttcaaaata cagatcttgt ggagtggtca ttctttcctc  12540
acagtacaat taagactttt acattgtact tagatcaaat ggctacatta attggtcagg  12600
gaagactacg aatagtaaaa ttgtgtggaa gtgacccaga taaaatcatt gttcctttaa  12660
acaaggaaca ggttagacaa gcctttatca attctgctgc atggcagatt ggtcttgctg  12720
cttttgtggg aattgttgat catcattacc caagaacaaa aatcttccag ttttcaaaat  12780
tgactacttg gattttacct aaaattacca gacataaacc tttagaaaat gctctgatgg  12840
```

```
tgtttactga tggttccagc aatggaaaaa tggcttaccc caggccaaaa gaatgaatca  12900
ttgaaactca atatcactca gctcaaagag cagaattggt tgctgttatt tcagtgttac  12960
aagattttaa tcagcctatt aacattgttt cagattctgc atatgtagta caggctacaa  13020
aggatgttga gacagcccta atcaaatgta gtatggatga tcagttgaat cagctgttta  13080
attttttaca ataaactgta agaaaaagaa atttcccatt ttatattact catattcaag  13140
cacatactaa tttaccaggg ccttaactaa gggaaatgaa caagctgact tgctagtatc  13200
atctgccttc atggaagcac aagaacgtca tgctctgact catgtaaatg caacaggatt  13260
aaaaaataaa tttgatatca catggaaaca ggcaaaaaat attgtacaac attgtactga  13320
gtgtcaagtc ctacacctgc ccactcagga ggcaggactt aatcccagag gtttatgtcc  13380
taatgcatta tggcaaatgg atgtcacaca tgtaccttca tttggaaaat tgtcatttgt  13440
ccatgtgatg gttgatactt gttcacattt catatgggca acctgctaga cagaaaatgt  13500
acttcccatg ttaaaagaca tttattatct tgttttgctg tcatgggagt tccagaaaaa  13560
attaaaacag ataatggacc aggctactat agtaaagcat tccaaaaatt cttaaatcag  13620
tggaaaatta cacatacaac aggaatccct tataattccc aaggacaggc cataattgaa  13680
agaaataata ggacactcaa agctcaattt gttaaacaaa aaaggaaaaa gagagtaagg  13740
agtataacac tccccagatg caacttaatc tagcactcta tactttaatt tttttaaaca  13800
tttatagaaa taagaccact acttctgcag aacaacattt tactggtaaa aagaacagcc  13860
cacatgaggg aaaactgatt tggtggaaag atcaaaaata agacatgaga aataggtaag  13920
gtgataacat gtgggagagg ttttgcttgt gtttcaccag gagaaaatca gcttcctgtt  13980
tggataccca ctagacattt gaaattctac aatgaaccca tcagagatgc aaagaaaagt  14040
gcctccgtgg agatggaaaa cccgcaatgg agcaccatcg actcgccagg tgaacaaaat  14100
ggtgatatca gaagaacaga tgaagttgcc atccaccaag aaagtggagc tgctgacctg  14160
ggcccagcta aagaagctga cacagttagc tgaaaaaaag cctgaagaat acaaggttaa  14220
cacaaactcc agagaatatg ctgcttgcag ctttaatgat tgtaccaacg gtggtaagtc  14280
tccctatgtc tgcaggagca gctgcagcta attatactta cttggcctat gtgcctttcc  14340
caccccttaat tcggacagtc acttggatag ataatcctat tgaagtatat gttaataata  14400
gtgcatgggt accaggcccc acagatgacc gtggccctgc ccaacctgaa gaagaaggaa  14460
tgatgataaa catttccatt gggtatcatt atcctcctat ttgcctgggg aaagcaccag  14520
gatgcttaat acctacaacc caaaattggt tggtagaagt acctactgtc agtgccatca  14580
gcagatttac ttatcacatg gtaagtggaa tgtcactcag gccacagata aataatttac  14640
aggatttttc ttatcaaaga tcattacaat ctaggcctaa ggggaagcct tgccccaagg  14700
aaattcccaa agaatcaaaa agcccagaag tcctagtttg ggaagaatgt gtggctgata  14760
ctgcagtggt actacaaaac aatgaatttg gaactattat aaactgggct ccttgaggcc  14820
aattatatca tagttgtgca ggccagactc aaccatgttg acaggtccca tccatctggc  14880
ccattaatct ggcctatgaa aggctggacc aggtttatag taggttagaa tcactctatc  14940
catggaaatg gggtgtgtaa aacccccctta tatgctagtt gtaggaaaca gagttattaa  15000
accagattcc caaactataa cctgtgaaaa ttgtagattg tttacttgca ttgattcaac  15060
tttggattgg caacactgta ttctgctagt gagggcaaga gagggcgtgg ggatccctgt  15120
gtccatggac caacagtggg agggttcccc atccatccat attttaacag aagtattaaa  15180
```

-continued

```
aggagttcta actagatcca aaagattcat ttttactttg attgcagtga ttatgggtct  15240
tatcacagct actgctgcgg ctgctggaat tgctttacac tcctctgttc aaactgcaga  15300
atatgtgaat aattggcaaa agaattcctc aaaattgtgg aattctcata cccaaataga  15360
tcaaaaattg gcaaaccaaa ttaatgatct tagacaaact gtaatttgga ttggagatag  15420
gctcatgagc ttggaatacc tttttcagtt acagtgtgac tggaatacat cagatttttg  15480
tattacacct cgagcttata atgaatctga acatcactag gacatggtga gatgccatct  15540
acaaggaaga gaagataatc ttaccttaga gatttcaaaa ttaaaagaac aaatttttga  15600
ggcatcaaaa gcccagttaa atctggtacc agaaaactgag gcaatcatga aagctgttga  15660
tagcctcaca aatcttaacc ctgccacttg ggttgaaaac attggaagtt ccaccattga  15720
aatttttgta ttaatccttg tatgtccgtt ctctctgttg ttagtctaca ggtgtatcca  15780
gcagctctgg agagacagtg accagtgaga atggaccatg atgaccatgg cagttttgtc  15840
aaaaagaaaa gggggatatg tagggaaaag agagatcaga ctgttactgt gtctatgtag  15900
aaagggaaga cataagaaat tccattttga tctgtacctt gaaaaattgt tttgctgaga  15960
tgctgttaat ttgtaacttt gccccagcca ctttgcccca actttgagct cacaaaaaca  16020
tgtgttatat ggaatcaagg tttaagagat ctagggctgg gcaggatgtg ccttgctaac  16080
aaaatattta caagcagtat gcttggtaaa actcattgcc attctctagt ctcaataaac  16140
caggggcaca atgcactgca aaaagccaca gggacctctg ccctggaaag ccgggtattg  16200
tccaaggttt gtccccatgt gatagtctga aatgtggcca catgggatga gaaagaccgg  16260
actgtccccc agcctgacac ctgtaaaggg tctgtgctga ggtggattag taaaagagga  16320
aagccacttg cagttgagat agaggaaggc cactgtttcc tgcctgcccc tgggaactta  16380
atgtctcggt ataaaacccg attgtacata tgttcaattc tgagatagga ggaaaactgc  16440
cctatggtgg gaggcgagac atgttggcag caatgctgcc tcgttattct ttactccact  16500
gagatgtttg ggtgggaaga aacataaatc tggcccacgt gtacatccag gcatagtacc  16560
tccccttgaa cttaattatg atatagattc ttttgctcac gtgttttttt gctgaccttc  16620
tccttattat caccctgctc tcctactgca ttcctcttgc tgagataatg aaaataataa  16680
tcaataaaaa ctgagggaac tcagagaccg gtgctggtgc aggtccttgg tatgctgagt  16740
gcaggtcccc tgggcccact attctttctc tatagtttgt cttgtatctt atttcttttc  16800
tcagtctctc atcccacctg atgagatata cccacagatg tggagggcca ggccacccct  16860
tcaaacataa acttatgttt agtttaatat agatacacac agttctacat agaaaacttt  16920
ataatcaggt gtgtataggt aggttagaca cacacatata cttcctagca ttgctaatga  16980
gggacaagat acaatgtgct aattcaacag ccagatgtaa gttttcctac cattctgaaa  17040
ggaatcaggc tctttgaaga aatgtctgat actagaactg ggacagtaaa tataggagcc  17100
aggataatct tgaagtatca gaaagtaagt actaaaaaaa attaaaatat atcaaagaaa  17160
aataagagcc aataataaca gctaccgaag gccaacacag gaatgaattg tgcaacacaa  17220
tgctgcagtg ttgaataata actgaagctt aaagtaatta tctaggtgtc tgtatttgta  17280
tacataggtg aataagctaa tggagttgca tagaaatctc ctttgcaaaa gaattccaaa  17340
taattgatgt agacactcag ccatcaggaa ggtggagcca actcctcact ccatgagtgt  17400
gggctctgca tagtgacttg ctccaaaaga acacatgcag tatggacaag gaggaaaaat  17460
aacttcacag tggagaaacc tgacaaacag tagctctgcc aaatgatcca agtgaacatc  17520
aaaaatgaca gtttaccttg agaacatgaa gtgaaaatgg gggacattct acaaaattcc  17580
```

```
tgaccaatcc tcctcagtac tgtcaaggtc atcatgagat ggaaagcctg acacactgtc  17640
acagccagga agagcctatg tgatgactac atgtcgtgcg ggatcctgga tgggatcctg  17700
ggtcagagta agacagacct aagggagtcc aaatgaaatg tgaactttag ttaataatag  17760
tctatcagta ttggttcatt aactgtgaca aattatgtaa gatattaata agccatgtga  17820
gacacactga tagaagatgt taatgagagg aaactaggtt gtggctacat gggaaatctc  17880
tgcttttttt ttttttttt ggtaatttct gtgtaagtaa aaaaaaaaga tgtaaaataa  17940
aactttattt aaaacctttt tatatttttt aatgcttcct tgcttaatta tttataccgt  18000
gaattactag taattgacac tgttaactag tcctgttttt ttaaataaga gcatttatga  18060
cacaaaaaat taaacagtgc agactgatat ataaatcaaa acaaacgctc tgtatatgtt  18120
ttctgttaca gtagtaacac atatgtgtaa acttaattat cgtatttttg tcttgtgcta  18180
tggttgtgtc ctggttcatt ctctaaaatg ctgatcacct tagaccagga aaaaaaataa  18240
acttacagga tctgtttcaa ttcatggcta aatattttca aaagagtgac tgtaaaaata  18300
tgttccaatg gcaaattgat tcattgtgat gggatcactt attctaaaga cttcttgtct  18360
ttactttgtt cccatgccta ccttttagcc ataatacaac agaatcaaat attggccatt  18420
gggaaaaaat attcaaagaa agaaagaatg tgaacagaac ttacaaccat gatgattcaa  18480
tgttttacca caatgctttc taaaaataag agtgtaaaag gatattcaaa gtcaatttcc  18540
tcagcgaggc tttgcagaaa atgaggaaac taaagaaaca aaaatggcag gacgttctac  18600
gggtgatttt agatgttgct atgttttatg ggaaaaaaat actttacctt ttaaagaatc  18660
actaagaatt attggaaacc caaactctgg aatgtttgca aatttagttg agcttctgtg  18720
taattatgtc tatgtagcta ggcatgaagt tgatgatttt ttaaaaatct ttgccttatt  18780
tgtgtaataa aatacacaat aaataattaa tgctcatagg aaaacatgtt agaccttgtg  18840
aagggaaaat aaatcttggg gacccaaaat cgctaagcta aagggaaaag tcaagctggg  18900
aactgcttag ggcaaatctg cctcccattc tatccaaagt cacccatctg ctcaccgaga  18960
caaatgcata tctgattgcc tcatttggag agggtaatca gcaaagcaaa agaatgaaac  19020
catttgtctc ttacctactt atgacctgga agccccctgt ctggccttct cacctttctg  19080
gactgaacca atgtacatct tgcacatatt gattgatgtc tcatgtctcc ctaaagtgta  19140
taaaaccaag ctgtgcctcg accaccttgg gcccatgttg tcaggacttc ctgaggaggc  19200
atcatggggg cgcatcctca aacttggcaa gtaaactttc taaaaaatcc gagagctgtt  19260
tcagattttc agggttcata catgtaatat agtatgtcaa tgtttataaa acagacatta  19320
ttctgtctac tattacaact atgctgccaa ttaaccttag actttctcaa caaaataaaa  19380
aatgatgagg taccaacaat atatttaaac ttaaataatg ttgcaagttt taatatgcct  19440
acttttcaat ttttcaatac tatttttact actttaacac tgtaagaaaa atgagcaact  19500
aaaacatgaa taaaagtgtt tacagggggt gcacatgttt cctccagcct ctgcccatcc  19560
ccagctttca tcccaactct tctgatggtg gctctaagca tttcccctgt ctctatacca  19620
agatctctcc ccagaaacaa gcccaaatct taccatatgt tatggcacgc tatggtgatg  19680
agaagcgatg agcagccgaa gcctcaagga aaggatgctt ttgtaaaaca agacttgtag  19740
aataaaacat gtgaaagtaa agcccatggc agagctccct cctcagcaca tggggagcag  19800
acaggaagct tttgcctcac cttcctcaat ggccagcagc cacgtctgcc caggtcagtc  19860
ttaaggacaa tgaaactctg gtcttcactg tagacatgct acactaccag gtgctccaaa  19920
```

-continued

```
gccatggtga cccaccctcg ggtgggtcct gaggagaaca aagctctggt tctaatccta  19980
accctaaccc tgtcccaaga ctttgaccct gaacctaaac actgatccct accctgggcc  20040
ccaattctca cccttacttt gaccctgatt ttgatcttga ccctgacctt gaccccacct  20100
ctaaccatat ttctggccct gactctgacc cagatcctaa tcctaaccct aaccctaacc  20160
ctattattat ctttacgatc tatctctaat cttaccctct agtgctaaat agctgtatcc  20220
aacagcactt ttaaactgtt taacttcttt tccttgaatt ctctaaggat atcctaaagg  20280
agatgtcatt atgtattttg cattccctct gagtggtatg gcttcagata tgcagttcta  20340
atactttgca agacataaaa agtttggagg gaaatagcac cgggttgtta gggatgcatg  20400
tttgcattca tgatagtcat tggtgctgtt ctccaaatat tttcagttca tttgtttgtg  20460
aatgcattct gactgttcca tcccacctac ttaaattttc ccatggccac atgacttttt  20520
tgtttgtttg tttgtttttt gccaacggag gtgagaagaa ataacatgtg actttttcag  20580
aagaaatctc caagaaacag agttctattc cgcatgcttt tttctttttt ctatagcaat  20640
ggggatctta ttgatggtcc ctccttccgt ctggattcct gtgttaggat gacacagcac  20700
agagctacct cacatctgac ccatgatgag atgtaaataa atgaggaaaa agatttttga  20760
accactgaaa tttggaggtt gtttgtcacc acagtttaac ctagccccca ttgactgatg  20820
cagggctgaa gaatgagtct gaactggatc tggacaagac atgtgaagag cactgcaggc  20880
tgagtaaaac tcaagtgttg tctcaaagat aacagtgagc acaatatgtt attagggtga  20940
gtgtgggata aataaggtat atcaggtgag aataatgaga aactcaactt caaaagatgg  21000
tgctgatttg gactgtggag agattcaaat gccctgctta gcatttgaga ttgtgatggt  21060
tgaacaaact aattaagagc ccaaaatgaa ggcttgggat aaatatctga gggtgtctaa  21120
tatcccaatt tttcatccta gagtgggcag agtccttgat cccattctag ggagacttcc  21180
aaaagaaaaa agacctgcat ttcttcaaca acccacattg agagactttc ctgcactttt  21240
gacctatggt taacactcct cacctttcat tctgtcatca gtgttttggg gaaacacctt  21300
taactctcta tgatttacag gttatgaagt ggcccttata attccttcca ggggtggaaa  21360
agactaatga tgatggtgtc tgagctcaca gccacaagcg ggcatgtgtg ttcagcagcc  21420
atgtggctca tgtgctagga gcttactaaa tacaatgttc tacatcattg cttaacacaa  21480
ggggagatgc tcctgactca gagggtttaa ttgctcacct gcttcttttt ctgccctctt  21540
gggctcctaa aatgaaaaga atcctggggt gataaagtga gtcaaagggg tgccagccac  21600
atcacagcaa aatagattcc taaaaaaatc cctggcctaa gatgacagcc ttggctggat  21660
aagtttgaat gtgctgatag tggacatggt agaatgaagg tggttgaaat gttcatatta  21720
aagaacttct acccagattg caagaaaaga gagaggaatg gagatggcag catgattccc  21780
tataataaaa gcagatgatt taagatcagt tatctttgtt ctgaaaaaaa taaagacaga  21840
aacaaaagtt tagcctgagg ctacaattaa ttgggcaata agtgagaggc acatatggca  21900
tagacagatt taaacatttc tcccttatat taatacaaat actaaaatta caaataaatt  21960
gattccaaat aaaacaaata tttaaaaaac ttaatgaata aacaccggag tctacagtag  22020
tgttcgaagg agatctcaca aacaagtttg gtttttgaag gttagaactg atggtctaga  22080
gaattcatat cattccagag agagaaagag aggaattttt taaaaagaac acttgcagtg  22140
tttgaagtga caaaggctgc tgtgacaaaa aggaagggaa agggaatttt ttttaaaaaa  22200
gcaagcaaca acaacaaaac cccacaaaaa agcagacaac aaacaaacaa aaaacagagg  22260
aagaagtcaa aacatgctgg gctgtgacta cttccaggaa ggggctacaa gaggcagctg  22320
```

```
gaaattctat ttgctttgca actgtgagtt ttccggcctg cttcctttct aaagtatatt  22380
actttgtttt tggttcatga agttatccat ttctgttttc tggaacagct atgtattttc  22440
tttatctatc atctatctac ctgcctatca tctatctatc tatttactat ctatcttttc  22500
tacctttcac tatcaagagc ttgggtcaag caggatagaa ttccagtgta tgttcactct  22560
accatttaaa acaagagctc ttgtaggcat tctccaacac atcataaacc tgagctttct  22620
aaaacagggt gtggcaaact accattcatg ggccatgtct gacatagtct gcgtttgtaa  22680
gaaaagttgt aatgggacac agccacatac atgtgttaca taatgtctct ggctactttc  22740
atggtataac ggaagagctg agtcattgag agagggacca catggcttgg aaaacttaaa  22800
atatttaaca tttagccctt cgcagaaaat atttgctgac tcttgttttt aaagatctct  22860
gtttagaatg ctaactattg ccttctggat agaatcacaa ctctttacca caatcaacac  22920
agcttcaacc ctgcttctat atccagcctc atctattatt tccgctcctc ctccttattt  22980
tccttctggc catgctgatg gattgccagc ttcccagatg tgcaagaatc tctcctccct  23040
tcccgacatt ctcatgctct ccctctgcct ctcaagaact tcctgtccca tctctcatga  23100
cgaatctctt cttcattctt taagatgcag ctcctttgct ccttccttaa agatgtctgt  23160
ctggctctat tttgggtgac atgctccttc tgcatctccc agagccagcc tgtgtgtgtc  23220
agctacagca tttatttgca tctctgtgtc atatatcacc aaatctgcct aagcttgcgt  23280
gagtcactgc atgacaactt cagcctccac cagcattgtc cccactaacc atgaggctta  23340
gatatttgtc cagtatgctc ggggttgtgg agtggtagca gtaaccaact ggtgagcatc  23400
atttcttaca tcagaatcaa atctgtagat ctctgcaatt cataagtatt tggagtttaa  23460
aattagcata aagattttct ttaaaataag aacaaatggc ttgagtaggc ttttggaatg  23520
tataatactt ctgctggctc ctttcagtgt tcagtattcc cacatgaatc taaacacaac  23580
tctgctctta gtagctgtgt gaccctggga aagtcactca atctccctca gctaaatttt  23640
gttgtgtgag taatgagaag agagttgtga tttgtattta gtgagtaata acaaacaaaa  23700
ggcatttagc tttctggaac ctggtatgta gtagatcctc atgaaatact aactctgttg  23760
ataaaactag actgaaagaa gctttcaaag tcaacagcag tatcatgcag ggaaggatgt  23820
agatgagaag ctgctgctgc tgctgctgca gcctacagct cctggaggcc cgttttgtcc  23880
atgatttagc aggaatgcac tacctttcca tgaggagaca ctgcccacag aaaccaaggc  23940
cattctttga agacaaacat gttttaatag cctttacatt atgtaatagt gtaatataaa  24000
taataattta tttacattat tctgttataa cttttgtaca gagctttaca cctagatatt  24060
ctgaagttgg tggtctgtga gtggcatcaa gtggtgagtg acacactctg accttgggta  24120
gaacaacaca agcattctta tacaccaata acagacaaac agagagccaa atcatgagtg  24180
aactcccatt cacaattgct tcaaagagaa taaaatacct aggaatcaaa cttacaaggg  24240
atgtgaagga cttcttcaag gagaactaca aaccactgct cgatgaaata aaagaggaca  24300
caaacaaatg gaacaacatt ccatgctcat ggataggaag aatcaatatc atgaaaatgg  24360
ccatactgcc caaggtaatt tatagattca atgccatttg catcaagcta ccaatgaatt  24420
tctttgcaga attggaaaaa actactttaa agttcatatg gaaccaaaaa agagtctgca  24480
ttgccaagac aatcctaagc caaaagaaca aacctggagg catcacacta cctgaattcg  24540
aactatacta caaggctaca gtaacaaaaa cagattggca ttggtaccaa aacagagata  24600
tacaccaatg gaacagagca gagccatcag aaataatacc acacatctac aaccatctga  24660
```

```
tctttgagaa acctgacaaa aacaagcaat ggggaaagga ttccctattt aataaatggt  24720
gcttggaaaa ctggctagcc atacatagaa agctgaaact ggatcccttc cttacacttt  24780
atacaaaaat taattcaaga tggattaaag acttacatgt tagacctaaa accataaaaa  24840
ccctagaaga aaacctaggc aataccattc aggacatagg catgggcaag gacttcatgc  24900
ctaaaacacc gaaagcaatg gcaacaaaag ccaaaatgca caaatgggat ctaattaaac  24960
taaagagctt ctgcacagaa aaagaaacta ccatcagagt gaacaggcaa cctacagaat  25020
gggagaaaat ttttgcaatc tacccatctg acaaaggact aatatccaga atctacaaag  25080
aactcaaatt tataagaaat aaaacaaaca acctcatcaa gaagtgggca aaggatatga  25140
acagacactt ctcaaaagaa ggcattttgt gcagccaaca gacacgtgaa aaaatgctca  25200
tcactggcca tcagagaaat gcaaatcaaa accacaatga gataccatct cacaccagtt  25260
agaatggcga tcattaaaaa gtcaggaaac aacaagtgct ggagaggatg tggagaaata  25320
ggaacacttt tacactgttg gtgggactgt aaactagttc aaccattgta gaagatggta  25380
tggtgattcc tcaaggatct agaactagaa ataccatttg atccagccat cccattactt  25440
ggtatatacc caaaggatta taaatcatgc tgctataaag acacatgcac acgtatgttt  25500
atcgcagtgc tattcacaac agcaaagact tggaaccaac ccaaatgtcc atcaatgata  25560
gactggatta agaaaatgtg gtacatatac accatggaat actgtgcagc cataaaaaag  25620
gatgagttca tttcctttgt aggggcatgg atgaagctgg aaaccatcat tctcagcaaa  25680
ctatcacaag cacaagaaac caaacactgc atgttctcac tcataggtgg gaattgaaca  25740
atgagaacac ttggacacag gaaggggaac atcacacacc ggggcctgtt gtggggtgga  25800
ggaagggggg agggaaagca ttaggagata tacctaatgt aaatgacgag gtaatgggtg  25860
tagcacacca acatggcaca tgtatacata tgtaacaaac ctgcacgttg tgcacatgta  25920
ccctagaact taaagtataa taataaaaaa aagagtgaaa aaaataaaga agcccatgag  25980
aaagatctcc atcaagttca cgcggaatga actccagcaa gacctggaaa atgctcagtt  26040
ccacaaaata tctgcgtcca aatactttga gtgcacagct ctggcatcag gttactgtga  26100
ggacagaccc tgagatggat ttctggatgg aggctgctgc tggaggagac aatgtcactg  26160
cagatggctc atgctgctcc catgctgcag gggccagtga tttggggctc ccacctgctg  26220
tcccgttggg gaactgcgga gattcacccc agctgggtgg actctgctgt gtctcctgtc  26280
aagaatctcc tcagcttacc ttggtttttc ctttttaaat actctctggt gttttcctct  26340
ccagtggggg ctgcatctca ccttagaaga aaagattttc caactagggg ctgtcttggt  26400
agctggtcca gaagaaggtc tcctctctct ggagtgaggt ccagccaagt aactccagcc  26460
agaactctca ctgagtgcgg ctggatctgc cctgctctcc tcccatcctc ctgtggactg  26520
tggaaaccca tccatgccct atgcaaagtc ctgcatctca gactgtaaaa tggcagaagc  26580
tgaatttaaa ataaatgatt atattgactc tatgagggaa acagagttct gaggtaggca  26640
attggtaagc aagcaattat gtgtaacttg ttagaacact agggtgtttt ttgtcttact  26700
gattattttc tggttaacag gctggctagg agccagaggg agagaaagct ggctgggaat  26760
tgagaggcat gaagtcacct cagtcccaac atttccatgt aaatgatgat gcgagatggg  26820
ctggtggcag gagtccctgg aaatcctcac aatctcagct tttaacttct gtaaaatatt  26880
atgtcattta tgatctcttt aacaaataac tttttttcta attataaaag tgtatattct  26940
ctttggagga tctttggtga atataaaatg agttataaga aaaagaaaaa ttcataattt  27000
tatcactcaa attttgataa ttatattcct gcacttttaa tgaaatgtag aaattttaga  27060
```

```
ttatactgta cataaaatgt ttctgttttt tcatccaata ttggatcata aacgtcttac  27120
atggcataaa ctatatatgt aaatcaacta tttccacacc tggatgcttg atttaaccct  27180
ccttatactg ttagccattt aaatgatttc tactttatcc tatgaataac acttccacca  27240
gttattattc ttatatataa ctcattcaat catttcataa tcttgttgag catttattta  27300
taatttggtt gcctattacc tgagtggatt gtggttatat gtttatatgc ttattccaaa  27360
tatagtgcta agattagcat tagagacaac aaaatattta caggttttga aactagaagg  27420
agccaaacaa atccatgatc cagctctgca tactctcacc cagccttagt tctctcacac  27480
agaaagtgaa gacagtgcta tttgccttgt ggcattgctg tgaacttaaa gaaggcaccg  27540
attgtacaca cagcagtgcg cagaccgtgg aaggctgggc tccgaccaac tctaaggaca  27600
atcaccatcg gatgccccac gatcctactc tcaggatgcc catatgccat atgccatgtg  27660
agtgtcactc agtgaacaca tatttgttga ttataaatta ctcccatgct gttttctttg  27720
ttttacatgt tcacaaatct gtaaaaaacaa agttacaatt atgaaattaa aagttaacta  27780
aaggaggaga ttttcattat ctctgaaatg taaccccccca aatccagatt ataaagcaag  27840
gaaatgtctt atggcccaac acttgccatc aatacttttt ttatgttagt gggcagggga  27900
gggtagtgaa aatgaaggaa tcagagctcc gatgggtgca cattgtcttc cctacaaatc  27960
cattgcttgt ccagccttcc ttcctcattg gggctgctct atccttttcc acacatttga  28020
actgctcccc tgtaggcctt tctcatttgc tttacttcct agtctgaatt ccatgggacc  28080
cacatttaag gagaggggaa caactctggg actggaggaa gatcacctta tgagttatac  28140
ctgcctcctt cctctacagt gaacggtctc tggtgtccct gggtgttcag tttctttcca  28200
ctcatgtgtt actgactgtt caggtggcaa atggcccatg acctttatgg gattaaaaag  28260
aaaaaaaata aaaagctgtg tttctttttt tttaactttt attttaggtt agggggtaca  28320
cgggagggtt tgttatacag ttaaatacgt gtcacagggg tttgttgtac ctgttatttc  28380
atcatccagg tattaggccc agtatccaat agttatcttt tctgctcctc tccctcctcc  28440
caccctcccc ccatcaagta gaccccagtg tcttttgttt ccttctttgt gttcacaagt  28500
tcttatcatt tagctcccac ttataagtta gaacatgctg tatttggttt tctgttcctg  28560
cgttagtttg ctaaggataa taccccttcag cttcatccat actaatgcaa aagacataat  28620
ctcattcttt tttatggctg catattattc catggtgtat atgtagcaca ttttctttat  28680
ccaatccgtg actgatgagt atttgggttg attctatgtc tttgctattg tgaatagtgc  28740
tgcaatgaac atttgcatgc atgtaacttc atggtagaat gatttatatt catctgggta  28800
tataaccagt aatgggattg ctaggtcaaa tgttgtagtt ctgcttttag ctctttgagg  28860
aatcaccata ctgctttcca ccacagttga attaacttac actcccacca atggtgtata  28920
catgttcact tttccctgca atcttgccaa cttctgttag ttttttagtt tttagtaata  28980
gccattctga ctggtgtgag atggtgcctc actgtggttt tgatgagcat ttctctagtg  29040
atcagtgatc tagagctttt ttccatatgt ttgtttgcca cgtttgcctt tttttttttt  29100
ttttttctta gcccgagtct cgctctgtca cccaggccag agtgcagtgg tgcgatctca  29160
gctaactgca agctctgcct ccttggttca cgccattctc ctgcctcagc ctcccaagta  29220
gctgggacta caggtgcctg ccaccacacc cggctaattt tttgtatttt tagtagagac  29280
ggggtttcac catgttagtc aggatggtct caatctcctg acgttgtgat ccaccctcct  29340
tggcctccca aaatgcagga attacaggcg tgagccacca cgcccggcac acatgtttgt  29400
```

-continued

```
ctcctttgga gaagtgtctc tttatgtcct tggcccactt tttaatgggg ttgtttttct  29460
cttgtaaatt tgtttaagtt ccttatagat gctggatatt agacctttgt cagatgcata  29520
gtttgtaaat actttctccc aatctgcaag ttgcctgttt actttgttga tagtttcttt  29580
tgctgtgtag aagctcttta gtttaactag atcccacgtc aatttttgct ttcattgcta  29640
ttgcttttgt tgtctttgtc atgaaatctt tgcctgtcct tatgtccagg atggtattgc  29700
ctaggttgtc ttccagggtt tttatatttt tgggttttac acttaagtct ttaatccatc  29760
ctgagttcat ttttgtgtat ggtgtaagaa aggggcccag ttcaatcttc agcatgtggc  29820
tagccagtta tcccagcacc atttattgaa cggagtctcg agtcccggtc ttttgtcccg  29880
gaggaaaccg cccactccct gggccccgga accggggcga atgggtggtg ccccgccggc  29940
cggcgcggcg gctgtgggcc cagccctcag cccgcgccgg acgctgaccg ttttcccgga  30000
gggcgggggt cccgctactc ccggaggccg aggaccgctt ttcctccctg ccttcctccc  30060
cccgtccgtc cccggctccc tcccgcccgc ccccagtccc tgcgtcgctc tgtctctccc  30120
tccgttcctc cctgcctccc tgcctccctg cctccctcct aacgtccctc cgcccgtcct  30180
tccgcccctc taggtctccc gttcctctct ccatctctgc ccgccttccc tcccgcctgg  30240
aacgctcagc gtccccggtg tgcgccgggc ctggggtctg cgttccgccg ccaggcgctc  30300
cgtgctggca gctgggcggc tgcaggggcc cgggcgggcg ggcgacggtg gcgcgggggc  30360
gcagaggagg cgagccgccg gagcggtgtc aggcccggac gctgcgcggg gcccggtgtt  30420
tcgcgggacg gggtctcca cccagcccag gggacgacgc gttttccggg ggtgggggt  30480
gggggtgggg agggggcggt caggcggcgg ggtgggctgg tggagaggca ggagagctct  30540
gcccgggctg ctcccacagc ccaggcggct gcccgcaaac ccgcgcgtgc gcagtaggcg  30600
gcccacctgc tggtacctgg gccggctctg ggatccccgg gatgcccagg aaagaatggc  30660
agttctccgc ggtgtggagt ctctcaccgg gcctggacct agaaggcagg aatcccaggc  30720
cggtcagccc ggtggagggg gcggggcgga gacacgcccc tccgtagcca gccaggtgtt  30780
ccccgcgaaa gagaggccac cgccctgccc cgaaccaccc gaccccgtcc caaccccgcg  30840
tcctaaagct cctccagcag agcccggtat tcttcctcgc tgaggggtgc ttccagcgag  30900
gcggcctctt ccgaggcctc cagctccccc ggggcctccg tttctaggag aggttgcgcc  30960
tgctgcagaa actccgggct cgccaggagc tcatccagca gcaggccgca ggggagtgca  31020
gaccagggcg ccggctcctg gagcgcctgg gagggcgccg ggatgccttg catctgcccc  31080
tgccgcgcgg aggcggaggc gtccgggggc gcgggctggg gaggtggagc tgccccggct  31140
tggggttccc acgccgcccc ggcgacctgg ggaccccggc cccagcccca ccacggactc  31200
ccctgggacg tgggtggcgc aagcacccct tggccctgcg gccccgcttg agcgggccca  31260
ggctgtgcca ccgcgcaggg gcccggcagg ccgtcgcgct gcgggtcccg gtcctcccgg  31320
cttttgcccg ggtgcggagg ccaccgagga gcctgagggt gggagagcgc cccgtccgga  31380
ggagccgggg cggcgtaggc gaaatccccg cgcgccgggg caggttggga gaccccctct  31440
gccggcgcgg cctggctggg ctgcagcgcg ggggcggccc tcgctgcctg gctcacgaaa  31500
gcccccctgtg ggagagcccc aggcgcgcag ggcacgtggg gtgcgggaag ccccgttccc  31560
cacgcgccgg tgtgggcgaa ggcgacccac gagggagcag ggtgaccccc gccgggggcc  31620
gcgctgcaca ggccgcctgc ctgcgcgggc gccctgccac cctgtcccgg gtgcctggcc  31680
cttcgattct gaaaccagat ctgaatcctg gactccggga ggcccgtctc tctggccagc  31740
tcctcccggg cggcgatgcc tggaaagcga tccttctcaa aggctcggag gagcagggcg  31800
```

gtctgggatc cggtgacggc ggtccgcttt cgccggcctt ctggcgggcc gcgtctcccg 31860
ggccagggcc gagattcccg ccggtgctgc ctcagctggc gtgacctctc attctgaaac 31920
caaatctgga ccctgggctc cggaatgccg atggcctggg ccagccgttc tctggtggcg 31980
atgcccgggt acgggttccg ctcaaagcag gctcgcaggg cctcgctttg gctcggggtc 32040
caaacgagtc tccgtcgccg tcctcgtccc cgggcttccg cggggagggt gctgtccgag 32100
ggtgtcggga gggccatcgc ggtgagcccc ggccggaatt tcacggacgg acgcgggcag 32160
agagaggccg gcgggctccc gtgcacctca gccggactgt gcactgcggc aggtgcagcc 32220
aggaggcctg cccggacagc cagccagcca gccagccgcc cttgtaaagg cccacaggca 32280
ggcaggctcc accccttcat gaatggcggt gagccccct gggacagccc gccccacccc 32340
ggaagggacc cagggcgtcg aggcctgggg ccggccggcg gggtggtggt ggtggtggtg 32400
gtgggggggg ggggtggtgg gggagggcgt ggtggcggtg gtggtggtgg ggccggagag 32460
acgaagagga agggggagag gggggagggg ggaggggggc gcgtttcggg ggccggctct 32520
ccggacctct ccagggatcc cgcgggaacg ggaagccgct ctctgggctc ccacgcgtcg 32580
gcagcaggga gaaaccagcc tgggagggtg gaggggagtg tggaactgaa cctccgtggg 32640
agtcttgagt gtgccaggcc ctctctccgt gaaggaggca atgcctgtgg gcgtcgccgt 32700
tgccgggacg gtctcgcaca cgcaggcgtg tggctctcgt tcatttccac gtagaagacc 32760
agagcgagac cccagagagg agatgcctcc ccggcgtgat ggcctgacga tggattcccg 32820
cgtgcggcaa cgtggggagt ctgcagtgtg gccggtttgg aacctggcaa ggagagcgaa 32880
ggcaccatgc cgggcttgca cccttccctg catgtttccg ggtgcccgca gagctccggg 32940
agcaaacagt cggcatggcc agcctttcgg gggccggaga gacgtgagca acaggccgcc 33000
ttgcggaggg caaagccacg cggaaaccaa aatcacgcct ccgtcgtcct gcgtgtggct 33060
cctccgtggc cggggctgtc ggcctcgcgc cgcgttgcag ggctcagcct ggggatgtgc 33120
ggtctgtgaa ccgcgcgggt gaagacccga cggcaacccg agtcccggtc ttttgtcccg 33180
gaggaaaccg cccactccct gggcccccgga accggggcga atgggtggtg ccccgccggc 33240
cggcgcggcg gctgtgggcc cagccctcag cccgcgccgg acgctgaccg ttttcccgga 33300
gggcgggggt cccgctactc ccggaggccg aggaccgctt ttcctccctg ccttcctccc 33360
cccgtccgtc cccggctccc tcccgcccgc ccccagtccc tgcgtcgctc tgtctctccc 33420
tccgttcctc cctgcctccc tgcctccctg cctccctcct aacgtccctc cgcccgtcct 33480
tccgcccctc taggtctccc gttcctctct ccatctctgc ccgccttccc tcccgcctgg 33540
aacgctcagc gtccccggtg tgcgccgggc ctggggtctg cgttccgccg ccaggcgctc 33600
cgtgctggca gctgggcggc tgcaggggcc cgggcgggcg ggcgacggtg gcgcgggggc 33660
gcagaggagg cgagccgccg gagcggtgtc aggcccggac gctgcgcggg gcccggtgtt 33720
tcgcgggacg ggggtctcca cccagcccag gggacgacgc gttttccggg ggtggggggt 33780
gggggtgggg agggggcggt caggcggcgg ggtgggctgg tggagaggca ggagagctct 33840
gcccgggctg ctcccacagc ccaggcggct gcccgcaaac ccgcgcgtgc gcagtaggcg 33900
gcccacctgc tggtacctgg gccggctctg ggatccccgg gatgcccagg aaagaatggc 33960
agttctccgc ggtgtggagt ctctcaccgg gcctggacct agaaggcagg aatcccaggc 34020
cggtcagccc ggtggagggg gcggggcgga gacacgcccc tccgtagcca gccaggtgtt 34080
ccccgcgaaa gagaggccac cgccctgccc cgaaccaccc gaccccgtcc caaccccgcg 34140

-continued

```
tcctaaagct cctccagcag agcccggtat tcttcctcgc tgaggggtgc ttccagcgag  34200
gcggcctctt ccgaggcctc cagctccccc ggggcctccg tttctaggag aggttgcgcc  34260
tgctgcagaa actccgggct cgccaggagc tcatccagca gcaggccgca ggggagtgca  34320
gaccagggcg ccggctcctg gagcgcctgg gagggcgccg ggatgccttg catctgcccc  34380
tgccgcgcgg aggcggaggc gtccgggggc gcgggctggg gaggtggagc tgccccggct  34440
tggggttccc acgccgcccc ggcgacctgg ggaccccggc cccagcccca ccacggactc  34500
ccctgggacg tgggtggcgc aagcacccct tggccctgcg gccccgcttg agcgggccca  34560
ggctgtgcca ccgcgcaggg gcccggcagg ccgtcgcgct gcgggtcccg gtcctcccgg  34620
cttttgcccg ggtgcggagg ccaccgagga gcctgagggt gggagagcgc cccgtccgga  34680
ggagccgggg cggcgtaggc gaaatccccg cgcgccgggg caggttggga gaccccctct  34740
gccggcgcgg cctggctggg ctgcagcgcg ggggcggccc tcgctgcctg gctcacgaaa  34800
gcccccctgtg ggagagcccc aggcgcgcag ggcacgtggg gtgcgggaag ccccgttccc  34860
cacgcgccgg tgtgggcgaa ggcgacccac gagggagcag ggtgaccccc gccgggggcc  34920
gcgctgcaca ggccgcctgc ctgcgcgggc gccctgccac cctgtcccgg gtgcctggcc  34980
cttcgattct gaaaccagat ctgaatcctg gactccggga ggcccgtctc tctggccagc  35040
tcctcccggg cggcgatgcc tggaaagcga tccttctcaa aggctcggag gagcagggcg  35100
gtctgggatc cggtgacggc ggtccgcttt cgccggcctt ctggcgggcc gcgtctcccg  35160
ggccagggcc gagattcccg ccggtgctgc ctcagctggc gtgacctctc attctgaaac  35220
caaatctgga ccctgggctc cggaatgccg atggcctggg ccagccgttc tctggtggcg  35280
atgcccgggt acgggttccg ctcaaagcag gctcgcaggg cctcgctttg gctcggggtc  35340
caaacgagtc tccgtcgccg tcctcgtccc cgggcttccg cggggagggt gctgtccgag  35400
ggtgtcggga gggccatcgc ggtgagcccc ggccggaatt tcacggacgg acgcgggcag  35460
agagaggccg gcgggctccc gtgcacctca gccggactgt gcactgcggc aggtgcagcc  35520
aggaggcctg cccggacagc cagccagcca gccagccgcc cttgtaaagg cccacaggca  35580
ggcaggctcc accccttcat gaatggcggt gagcccccct gggacagccc gccccacccc  35640
ggaagggacc cagggcgtcg aggcctgggg ccggccggcg gggtggtggt ggtggtggtg  35700
gggggggggg gtggtggggg agggcgtggt ggcggtggtg gtggtggggc cggagagacg  35760
aagaggaagg gggagagggg ggagggggga ggggggcgcg tttcgggggc cggctctccg  35820
gacctctcca gggatcccgc gggaacggga agccgctctc tgggctccca cgcgtcggca  35880
gcagggagaa accagcctgg gagggtggag gggagtgtgg aactgaacct ccgtgggagt  35940
cttgagtgtg ccaggccctc tctccgtgaa ggaggcaatg cctgtgggcg tcgccgttgc  36000
cgggacggtc tcgcacacgc aggcgtgtgg ctctcgttca tttccacgta gaagaccaga  36060
gcgagacccc agagaggaga tgcctccccg gcgtgatggc ctgacgatgg attcccgcgt  36120
gcggcaacgt ggggagtctg cagtgtggcc ggtttggaac ctggcaagga gagcgaaggc  36180
accatgccgg gcttgcaccc ttccctgcat gtttccgggt gcccgcagag ctccgggagc  36240
aaacagtcgg catggccagc ctttcggggg ccggagagac gtgagcaaca ggccgccttg  36300
cggagggcaa agccacgcgg aaaccaaaat cacgcctccg tcgtcctgcg tgtggctcct  36360
ccgtggccgg ggctgtcggc ctcgcgccgc gttgcagggc tcagcctggg gatgtgcggt  36420
ctgtgaaccg cgcgggtgaa gacccgacgg caacccgagt cccggtcttt tgtcccggag  36480
gaaaccgccc actccctggg ccccggaacc ggggcgaatg ggtggtgccc cgccggccgg  36540
```

-continued

```
cgcggcggct gtgggcccag ccctcagccc gcgccggacg ctgaccgttt tcccggaggg  36600
cgggggtccc gctactcccg gaggccgagg accgcttttc ctccctgcct tcctcccccc  36660
gtccccggct ccctcccgcc cgccccccagt ccctgcgtcg ctctgtctct ccctccgttc  36720
ctccctgcct ccctgcctcc ctgcctccct cctaacgtcc ctccgcccat ccttccgccc  36780
ctctaggtct cccgttcctc tctccatctc tgcccgcctt ccctcccgcc tggaacgctc  36840
agcgtccccg gtgtgcgccg ggcctggggt ctgcgttccg ccgccaggcg ctccgtgctg  36900
gcagctgggc ggctgcaggg gcccgggcgg gcgggcgacg gtggcgcggg ggcgcagagg  36960
aggcgagccg ccggagcggt gtcaggcccg gacgctgcgc ggggcccggt gtttcgcggg  37020
acgggggtct ccacccagcc caggggacga cgcgttttcc gggggtgggg ggtgggggtg  37080
gggagggggc ggtcaggcgg cggggtgggc tggtggagag gcaggagagc tctgcccggg  37140
ctgctcccac agcccaggcg gctgcccgca aacccgcgcg tgcgcagtag gcggcccacc  37200
tgctggtacc tgggccggct ctgggatccc cgggatgccc aggaaagaat ggcagttctc  37260
cgcggtgtgg agtctctcac cgggcctgga cctagaaggc aggaatccca ggccggtcag  37320
cccggtggag ggggcggggc ggagacacgc ccctccgtag ccagccaggt gttccccgcg  37380
aaagagaggc caccgccctg ccccgaacca cccgaccccg tcccaacccc gcgtcctaaa  37440
gctcctccag cagagcccgg tattcttcct cgctgagggg tgcttccagc gaggcggcct  37500
cttccgaggc ctccagctcc cccggggcct ccgtttctag gagaggttgc gcctgctgca  37560
gaaactccgg gctcgccagg agctcatcca gcagcaggcc gcaggggagt gcagaccagg  37620
gcgccggctc ctggagcgcc tgggagggcg ccgggatgcc ttgcatctgc ccctgccgcg  37680
cggaggcgga ggcgtccggg ggcgcgggct ggggaggtgg agctgccccg gcttggggtt  37740
cccacgccgc cccggcgacc tggggacccc ggccccagcc ccaccacgga ctcccctggg  37800
acgtgggtgg cgcaagcacc ccttggccct gcggccccgc ttgagcgggc ccaggctgtg  37860
ccaccgcgca ggggcccggc aggccgtcgc gctgcgggtc ccggtcctcc cggcttttgc  37920
ccgggtgcgg aggccaccga ggagcctgag ggtgggagag cgccccgtcc ggaggagccg  37980
gggcggcgta ggcgaaatcc ccgcgcgccg gggcaggttg ggagaccccc tctgccggcg  38040
cggcctggct gggctgcagc gcgggggcgg ccctcgctgc ctggctcacg aaagcccccct  38100
gtgggagagc cccaggcgcg cagggcacgt ggggtgcggg aagccccgtt ccccacgcgc  38160
cggtgtgggc gaaggcgacc cacgagggag cagggtgacc cccgccgggg gccgcgctgc  38220
acaggccgcc tgcctgcgcg ggcgccctgc caccctgtcc cgggtgcctg gcccttcgat  38280
tctgaaacca gatctgaatc ctggactccg ggaggcccgt ctctctggcc agctcctccc  38340
gggcggcgat gcctggaaag cgatccttct caaaggctcg gaggagcagg gcggtctggg  38400
atccggtgac ggcggtccgc tttcgccggc cttctggcgg gccgcgtctc ccgggccagg  38460
gccgagattc ccgccggtgc tgcctcagct ggcgtgacct ctcattctga aaccaaatct  38520
ggaccctggg ctccggaatg ccgatggcct gggccagccg ttctctggtg gcgatgcccg  38580
ggtacgggtt ccgctcaaag caggctcgca gggcctcgct ttggctcggg gtccaaacga  38640
gtctccgtcg ccgtcctcgt ccccgggctt ccgcggggag ggtgctgtcc gagggtgtcg  38700
ggagggccat cgcggtgagc cccggccgga atttcacgga cggacgcggg cagagagagg  38760
ccggcgggct cccgtgcacc tcagccggac tgtgcactgc ggcaggtgca gccaggaggc  38820
ctgcccggac agccagccag ccagccagcc gcccttgtaa aggcccacag gcaggcaggc  38880
```

-continued tccaccccttt catgaatggc ggtgagcccc cctgggacag cccgccccac cccggaaggg 38940
acccagggcg tcgaggcctg gggccggccg gcggggtggt ggtggtggtg gtggtggggg 39000 ggggggtgg tgggggaggg cgtggtggcg gtggtggtgg tggggccgga gagacgaaga 39060
ggaaggggga gagggggag gggggagggg ggcgcgtttc gggggccggc tctccggacc 39120
tctccaggga tcccgcggga acgggaagcc gctctctggg ctcccacgcg tcggcagcag 39180
ggagaaacca gcctgggagg gtggagggga gtgtggaact gaacctccgt gggagtcttg 39240
agtgtgccag gccctctctc cgtgaaggag gcaatgcctg tgggcgtcgc cgttgccggg 39300
acggtctcgc acacgcaggc gtgtggctct cgttcatttc cacgtagaag accagagcga 39360
gaccccagag aggagatgcc tccccggcgt gatggcctga cgatggattc ccgcgtgcgg 39420
caacgtgggg agtctgcagt gtggccggtt tggaacctgg caaggagagc gaaggcacca 39480
tgccgggctt gcacccttcc ctgcatgttt ccgggtgccc gcagagctcc gggagcaaac 39540
agtcggcatg gccagccttt cgggggccgg agagacgtga gcaacaggcc gccttgcgga 39600
gggcaaagcc acgcggaaac caaaatcacg cctccgtcgt cctgcgtgtg gctcctccgt 39660
ggccgggtct gtcggcctcg cgccgcgttg cagggctcag cctggggatg tgcggtctgt 39720
gaaccgcgcg ggtgaagacc cgacggcaac ccgagtcccg gtcttttgtc ccggaggaaa 39780
ccgcccactc cctgggcccc ggaaccgggg cgaatgggtg gtgccccgcc ggccggcgcg 39840
gcggctgtgg gcccagccct cagcccgcgc cggacgctga ccgttttccc ggagggcggg 39900
ggtcccgcta ctcccggagg ccgaggaccg cttttcctcc ctgccttcct ccccccgtcc 39960
gtccccggct ccctcccgcc cgcccccagt ccctgcgtcg ctctgtctct ccctccgttc 40020
ctccctgcct ccctgcctcc ctgcctccct cctaacgtcc ctccgcccgt ccttccgccc 40080
ctctaggtct cccgttcctc tctccatctc tgcccgcctt ccctcccgcc tggaacgctc 40140
agcgtccccg gtgtgcgccg ggcctggggt ctgcgttccg ccgccaggcg ctccgtgctg 40200
gcagctgggc ggctgcaggg gcccgggcgg gcgggcgacg gtggcgcggg ggcgcagagg 40260
aggcgagccg ccggagcggt gtcaggcccg gacgctgcgc ggggcccggt gtttcgcggg 40320
acgggggtct ccacccagcc caggggacga cgcgttttcc gggggtgggg ggtgggggtg 40380 gggaggggc ggtcaggcgg cggggtgggc tggtggagag gcaggagagc tctgcccggg 40440
ctgctcccac agcccaggcg gctgcccgca aacccgcgcg tgcgcagtag gcggcccacc 40500
tgctggtacc tgggccggct ctgggatccc cgggatgccc aggaaagaat ggcagttctc 40560
cgcggtgtgg agtctctcac cgggcctaga cctagaaggc aggaatccca ggccggtcag 40620
cccggtggag ggggcggggc ggagacacgc ccctccgtag ccagccaggt gttccccgcg 40680
aaagagaggc caccgccctg ccccgaacca cccgaccccg tcccaacccc gcgtcctaaa 40740
gctcctccag cagagcccgg tattcttcct cgctgagggg tgcttccagc gaggcggcct 40800
cttccgaggc ctccagctcc cccggggcct ccgtttctag gagaggttgc gcctgctgca 40860
gaaactccgg gctcgccagg agctcatcca gcagcaggcc gcaggggagt gcagaccagg 40920
gcgccggctc ctggagcgcc tgggagggcg ccgggatgcc ttgcatctgc ccctgccgcg 40980
cggaggcgtc cgggggcgcg ggctggggag gtggagcttc cccggcttgg ggttcccacg 41040
ccgccccagc gacctgggga ccccggcccc agccccacca cggactcccc tgggacgtgg 41100
gtggcgcaag cacccccttgg ccctgcggcc ccgcttgagc gggcccaggc tgtgccaccg 41160
cgcaggggcc cggcaggccg tcgcgctgcg ggtcccggtc ctcccggctt ttgcccgggt 41220
gcggaggcca ccgaggagcc tgagggtggg agagcgcccc gtccggagga gccggggcgg 41280

-continued cgtaggcgaa atccccgcgc gccggggcag gttgggagac cccctctgcc ggcgcggcct 41340
ggctgggctg cagcgcgggg gcggccctcg ctgcctggct cacgaaagcc ccctgtggga 41400
gagccccagg cgcgcagggc acgtggggtg cgggaagccc cgttccccac gcgccggtgt 41460
gggcgaaggc gacccacgag ggagcagggt gaccccccgcc gggggccgcg ctgcacaggc 41520
cgcctgcctg cgcgggcgcc ctgccaccct gtcccgggtg cctggccctt cgattctgaa 41580
accagatctg aatcctggac tccgggaggc ccgtctctct ggccagctcc tcccgggcgg 41640
cgatgcctgg aaagcgatcc ttctcaaagg ctcggaggag cagggcggtc tgggatccgg 41700
tgacggcggt ccgctttcgc cggccttctg gcgggccgcg tctcccgggc cagggccgag 41760
attcccgccg gtgctgcctc agctggcgtg acctctcatt ctgaaaccaa atctggaccc 41820
tgggctccgg aatgccgatg gcctgggcca gccgttctct ggtggcgatg cccgggtacg 41880
ggttccgctc aaagcaggct cgcagggcct cgctttggct cggggtccaa acgagtctcc 41940
gtcgccgtcc tcgtccccgg gcttccgcgg ggagggtgct gtccgaaggt gtcgggaggg 42000
ccatcgcggt gagccccggc cggaatttca cggacggacg cgggcagaga gaggccggcg 42060
ggctcccgtg cacctcagcc ggactgtgca ctgcggcagg tgcagccagg aggcctgccc 42120
ggacagccag ccagccagcc agccgccctt gtaaaggccc acaggcaggc aggctccacc 42180
ccttcatgaa tggcggtgag ccccccctggg acagcccgcc ccaccccgga agggacccag 42240
ggcgtcgagg cctggggccg gccggcgggg tggtggtggt ggtggtggtg gggggggggg 42300
gtgggggggg agggcgtggt ggcggtggtg gtggtggggc cggagagacg aagaggaagg 42360
gggagagggg ggagggggga gggggcgcg tttcgggggc cggctcttct gacctctcca 42420
gggatcccgc gggaacggga agccgctctc tgggctccca cgcgtcggca gcagggagaa 42480
accagcctgg gagggtggag gggagtgtgg aactgaacct ccgtgggagt cttgagtgtg 42540
ccaggccctc tctccgtgaa ggaggcaatg cctgtgggcg tcgccgttgc cgggacggtc 42600
tcgcacacgc aggcgtgtgg ctctcgttca tttccacgta gaagaccaga gcgagacccc 42660
agagaggaga tgcctccccg gcgtgatggc ctgacgatgg attcccgcgt gcggcaacgt 42720
ggggagtctg cagtgtggcc ggtttggaac ctggcaagga gagcgaaggc accatgccgg 42780
gcttgcaccc ttccctgcat gtttccgggt gcccgcagag ctccgggagc aaacagtcgg 42840
catggccagc ctttcggggg ccggagagac gtgagcaaca ggccgccttg cggagggcaa 42900
agccacgcgg aaaccaaaat cacgcctccg tcgtcctgcg tgtggctcct ccgtggccgg 42960
gtctgtcggc ctcgcgccgc gttgcagggc tcagcctggg gatgtgcggt ctgtgaaccg 43020
cgcgggtgaa gacccgacgg caacccgagt cccggtcttt tgtcccggag gaaaccgccc 43080
actccctggg ccccggaacc ggggcgaatg ggtggtgccc cgccggccgg cgcggcggct 43140
gtgggcccag ccctcagccc gcgccggacg ctgaccgttt tcccggaggg cgggggtccc 43200
gctactcccg gaggccgagg accgcttttc ctccctgcct tcctcccccc gtccgtcccc 43260
ggctccctcc cgcccgcccc cagtccctgc gtcgctctgt ctctccctcc gttcctccct 43320
gcctccctgc ctccctccct ccctcctaac gtccctccgc ccatccttcc gcccctctag 43380
gtctcccgtt cctctctcca tctctgcccg ccttccctcc cgcctggaac gctcagcgtc 43440
cccggtgtgc gccgggcctg gggtctgcgt tccgccgcca ggcgctccgt gctggcagct 43500
gggcggctgc aggggcccgg gcgggcgggc gacggtggcg cgggggcgca gaggaggcga 43560
gccgccggag cggtgtcagg cccggacgct gcgcggggcc cggtgtttcg cgggacgggg 43620

```
gtctccaccc agcccagggg acgacgcgtt ttccgggggt ggggggtggg ggtggggagg  43680
gggcggtcag gcggcggggt gggctggtgg agaggcagga gagctctgcc cgggctgctc  43740
ccacagccca ggcggctgcc cgcaaacccg cgcgtgcgca gtaggcggcc cacctgctgg  43800
tacctgggcc ggctctggga tccccgggat gcccaggaaa gaatggcagt tctccgcggt  43860
gtggagtctc tcaccgggcc tggacctaga aggcaggaat cccaggccgg tcagcccggt  43920
ggagggggcg gggcggagac acgcccctcc gtagccagcc aggtgttccc cgcgaaagag  43980
aggccaccgc cctgccccga accacccgac cccgtcccaa ccccgcgtcc taaagctcct  44040
ccagcagagc ccggtattct tcctcgctga ggggtgcttc cagcgaggcg gcctcttccg  44100
aggcctccag ctcccccggg gcctccgttt ctaggagagg ttgcgcctgc tgcagaaact  44160
ccgggctcgc caggagctca tccagcagca ggccgcaggg gagtgcagac cagggcgccg  44220
gctcctggag cgcctgggag ggcgccggga tgccttgcat ctgcccctgc cgcgcggagg  44280
cggaggcgtc cgggggcgcg ggctggggag gtggagctgc cccggcttgg ggttcccacg  44340
ccgcccccggc gacctgggga ccccggcccc agccccacca cggactcccc tgggacgtgg  44400
gtggcgcaag cacccccttgg ccctgcggcc ccgcttgagc gggcccaggc tgtgccaccg  44460
cgcaggggcc cggcaggccg tcgcgctgcg ggtcccggtc ctcccggctt ttgcccgggt  44520
gcggaggcca ccgaggagcc tgagggtggg agagcgcccc gtccggagga gccggggcgg  44580
cgtaggcgaa atccccgcgc gccggggcag gttgggagac cccctctgcc ggcgcggcct  44640
ggctgggctg cagcgcgggg gcggccctcg ctgcctggct cacgaaagcc ccctgtggga  44700
gagccccagg cgcgcagggc acgtggggtg cgggaagccc cgttccccac gcgccggtgt  44760
gggcgaaggc gacccacgag ggagcagggt gaccccccgcc gggggccgcg ctgcacaggc  44820
cgcctgcctg cgcgggcgcc ctgccaccct gtcccgggtg cctggccctt cgattctgaa  44880
accagatctg aatcctggac tccgggaggc ccgtctctct ggccagctcc tcccgggcgg  44940
cgatgcctgg aaagcgatcc ttctcaaagg ctcggaggag cagggcggtc tgggatccgg  45000
tgacggcggt ccgctttcgc cggccttctg gcgggccgcg tctcccgggc cagggccgag  45060
attcccgccg gtgctgcctc agctggcgtg acctctcatt ctgaaaccaa atctggaccc  45120
tgggctccgg aatgccgatg gcctgggcca gccgttctct ggtggcgatg cccgggtacg  45180
ggttccgctc aaagcaggct cgcagggcct cgctttggct cggggtccaa acgagtctcc  45240
gtcgccgtcc tcgtccccgg gcttccgcgg ggagggtgct gtccgagggt gtcgggaggg  45300
ccatcgcggt gagccccggc cggaatttca cggacggacg cgggcagaga gaggccggcg  45360
ggctcccgtg cacctcagcc ggactgtgca ctgcggcagg tgcagccagg aggcctgccc  45420
ggacagccag ccagccagcc agccgccctt gtaaaggccc acaggcaggc aggctccacc  45480
ccttcatgaa tggcggtgag ccccccctggg acagcccgcc ccacccccgga agggacccag  45540
ggcgtcgagg cctggggccg gccggcgggg tggtggtggt ggtggtgggg gggggggtg  45600
gtgggggagg gcgtggtggc ggtggtggtg gtggggccgg agagacgaag aggaaggggg  45660
agagggggga ggggggaggg gggcgcgttt cgggggccgg ctctccggac ctctccaggg  45720
atcccgcggg aacgggaagc cgctctctgg gctcccacgc gtcggcagca gggagaaacc  45780
agcctgggag ggtggagggg agtgtggaac tgaacctccg tgggagtctt gagtgtgcca  45840
ggccctctct ccgtgaagga ggcaatgcct gtgggcgtcg ccgttgccgg gacggtctcg  45900
cacacgcagg cgtgtggctc tcgttcattt ccacgtagaa gaccagagcg agaccccaga  45960
gaggagatgc ctccccggcg tgatggcctg acgatggatt cccgcgtgcg gcaacgtggg  46020
```

gagtctgcag tgtggccggt ttggaacctg gcaaggagag cgaaggcacc atgccgggct 46080
tgcacccttc cctgcatgtt tccgggtgcc cgcagagctc cgggagcaaa cagtcggcat 46140
ggccagcctt tcgggggccg gagagacgtg agcaacaggc cgccttgcgg agggcaaagc 46200
cacgcggaaa ccaaaatcac gcctccgtcg tcctgcgtgt ggctcctccg tggccgggtc 46260
tgtcggcctc gcgccgcgtt gcagggctca gcctggggat gtggggtctg tgaaccgcgc 46320
gggtgaagac ccgacggcaa cccgagtccc ggtcttttgt cccggaggaa accgcccact 46380
ccctgggccc cggaaccggg gcgaatgggt ggtgccccgc cggccggcgc ggcggctgtg 46440
ggcccagccc tcagcccgcg ccggacgctg accgttttcc cggagggcgg gggtcccgct 46500
actcccggag gccgaggacc gcttttcctc cctgccttcc tccccccgtc cccggctccc 46560
tcccgcccgc ccccagtccc tgcgtcgctc tgtctctccc tccgttcctc cctgcctccc 46620
tgcctccctg cctccctcct aacgtccctc cgcccatcct tccgcccctc taggtctccc 46680
gttcctctct ccatctctgc ccgccttccc tcccgcctgg aacgctcagc gtccccggtg 46740
tgcgccgggc ctggggtctg cgttccgccg ccaggcgctc cgtgctggca gctgggcggc 46800
tgcaggggcc cgggcgggcg ggcgacggtg gcgcgggggc gcagaggagg cgagccgccg 46860
gagcggtgtc aggcccggac gctgcgcggg gcccggtgtt tcgcgggacg ggggtctcca 46920
cccagcccag gggacgacgc gttttccggg ggtgggggt gggggtgggg agggggcggt 46980
caggcggcgg ggtgggctgg tggagaggca ggagagctct gcccgggctg ctcccacagc 47040
ccaggcggct gcccgcaaac ccgcgcgtgc gcagtaggcg gcccacctgc tggtacctgg 47100
gccggctctg ggatccccgg gatgcccagg aaagaatggc agttctccgc ggtgtggagt 47160
ctctcaccgg gcctggacct agaaggcagg aatcccaggc cggtcagccc ggtggagggg 47220
gcggggcgga gacacgcccc tccgtagcca gccaggtgtt ccccgcgaaa gagaggccac 47280
cgccctgccc cgaaccaccc gaccccgtcc caaccccgcg tcctaaagct cctccagcag 47340
agcccggtat tcttcctcgc tgaggggtgc ttccagcgag gcggcctctt ccgaggcctc 47400
cagctccccc ggggcctccg tttctaggag aggttgcgcc tgctgcagaa actccgggct 47460
cgccaggagc tcatccagca gcaggccgca ggggagtgca gaccagggcg ccggctcctg 47520
gagcgcctgg gagggcgccg ggatgccttg catctgcccc tgccgcgcgg aggcggaggc 47580
gtccgggggc gcgggctggg gaggtggagc tgccccggct tggggttccc acgccgcccc 47640
ggcgacctgg ggaccccggc cccagcccca ccacggactc ccctgggacg tgggtggcgc 47700
aagcacccct tggccctgcg gccccgcttg agcgggccca ggctgtgcca ccgcgcaggg 47760
gcccggcagg ccgtcgcgct gcgggtcccg gtcctcccgg cttttgcccg ggtgcggagg 47820
ccaccgagga gcctgagggt gggagagcgc cccgtccgga ggagccgggg cggcgtaggc 47880
gaaatccccg cgcgccgggg caggttggga gaccccctct gccggcgcgg cctggctggg 47940
ctgcagcgcg ggggcggccc tcgctgcctg gctcacgaaa gccccctgtg ggagagcccc 48000
aggcgcgcag ggcacgtggg gtgcgggaag ccccgttccc cacgcgccgg tgtgggcgaa 48060
ggcgacccac gagggagcag ggtgaccccc gccgggggcc gcgctgcaca ggccgcctgc 48120
ctgcgcgggc gccctgccac cctgtcccgg gtgcctggcc cttcgattct gaaaccagat 48180
ctgaatcctg gactccggga ggcccgtctc tctggccagc tcctcccggg cggcgatgcc 48240
tggaaagcga tccttctcaa aggctcggag gagcagggcg gtctgggatc cggtgacggc 48300
ggtccgcttt cgccggcctt ctggcgggcc gcgtctcccg ggccagggcc gagattcccg 48360

-continued

```
ccggtgctgc ctcagctggc gtgacctctc attctgaaac caaatctgga ccctgggctc  48420
cggaatgccg atggcctggg ccagccgttc tctggtggcg atgcccgggt acgggttccg  48480
ctcaaagcag gctcgcaggg cctcgctttg gctcggggtc caaacgagtc tccgtcgccg  48540
tcctcgtccc cgggcttccg cggggagggt gctgtccgag ggtgtcggga gggccatcgc  48600
ggtgagcccc ggccggaatt tcacggacgg acgcgggcag agagaggccg gcgggctccc  48660
gtgcacctca gccggactgt gcactgcggc aggtgcagcc aggaggcctg cccggacagc  48720
cagccagcca gccagccgcc cttgtaaagg cccacaggca ggcaggctcc acccccttcat  48780
gaatggcggt gagcccccct gggacagccc gccccacccc ggaagggacc cagggcgtcg  48840
aggcctgggg ccggccggcg gggtggtggt ggtggtggtg gggggggggg gtggtggggg  48900
agggcgtggt ggcggtggtg gtggtggggc cggagagacg aagaggaagg gggagagggg  48960
ggagggggga ggggggcgcg tttcgggggc cggctctccg gacctctcca gggatcccgc  49020
gggaacggga agccgctctc tggggctccca cgcgtcggca gcagggagaa accagcctgg  49080
gagggtggag gggagtgtgg aactgaacct ccgtgggagt cttgagtgtg ccaggccctc  49140
tctccgtgaa ggaggcaatg cctgtgggcg tcgccgttgc cgggacggtc tcgcacacgc  49200
aggcgtgtgg ctctcgttca tttccacgta gaagaccaga gcgagacccc agagaggaga  49260
tgcctccccg gcgtgatggc ctgacgatgg attcccgcgt gcggcaacgt ggggagtctg  49320
cagtgtggcc ggtttggaac ctggcaagga gagcgaaggc accatgccgg gcttgcaccc  49380
ttccctgcat gtttccgggt gcccgcagag ctccgggagc aaacagtcgg catggccagc  49440
ctttcggggg ccggagagac gtgagcaaca ggccgccttg cggagggcaa agccacgcgg  49500
aaaccaaaat cacgcctccg tcgtcctgcg tgtggctcct ccgtggccgg ggctgtcggc  49560
ctcgcgccgc gttgcagggc tcagcctggg gatgtggggt ctgtgaaccg cgcgggtgaa  49620
gacccgacgg caacccgagt cccggtcttt tgtcccggag gaaaccgccc actccctggg  49680
ccccggaacc ggggcgaatg ggtggtgccc cgccggccgg cgcggcggct gtgggcccag  49740
ccctcagccc gcgccggacg ctgaccgttt tcccggaggg cgggggtccc gctactcccg  49800
gaggccgagg accgcttttc ctccctgcct tcctccccccc gtccccggct ccctcccgcc  49860
cgcccccagt ccctgcgtcg ctctgtctct ccctccgttc ctccctgcct ccctgcctcc  49920
ctccctccct cctaacgtcc ctccgcccat ccttccgccc ctctaggtct cccgttcctc  49980
tctccatctc tgcccgcctt ccctcccgcc tggaacgctc agcgtccccg gtgtgcgccg  50040
ggcctggggt ctgcgttccg ccgccaggcg ctccgtgctg gcagctgggc ggctgcaggg  50100
gcccgggcgg gcgggcgacg gtggcgcggg ggcgcagagg aggcgagccg ccggagcggt  50160
gtcaggcccg gacgctgcgc ggggcccggt gtttcgcggg acgggggtct ccacccagcc  50220
caggggacga cgcgttttcc gggggtgggg ggtgggggtg gggaggggc ggtcaggcgg  50280
cggggtgggc tggtggagag gcaggagagc tctgcccggg ctgctcccac agcccaggcg  50340
gctgcccgca aacccgcgcg tgcgcagtag gcggcccacc tgctggtacc tgggccggct  50400
ctgggatccc cgggatgccc aggaaagaat ggcagttctc cgcggtgtgg agtctctcac  50460
cgggcctgga cctagaaggc aggaatccca ggccggtcag cccggtggag ggggcggggc  50520
ggagacacgc ccctccgtag ccagccaggt gttccccgcg aaagagaggc caccgccctg  50580
ccccgaacca cccgaccccg tcccaacccc gcgtcctaaa gctcctccag cagagcccgg  50640
tattcttcct cgctgagggg tgcttccagc gaggcggcct cttccgaggc ctccagctcc  50700
cccggggcct ccgtttctag gagaggttgc gcctgctgca gaaactccgg gctcgccagg  50760
```

agctcatcca gcagcaggcc gcaggggagt gcagaccagg gcgccggctc ctggagcgcc 50820
tgggagggcg ccgggatgcc ttgcatctgc ccctgccgcg cggaggcgga ggcgtccggg 50880
ggcgcgggct ggggaggtgg agctgccccg gcttggggtt cccacgccgc cccggcgacc 50940
tggggacccc ggccccagcc ccaccacgga ctcccctggg acgtgggtgg cgcaagcacc 51000
ccttggccct gcggccccgc ttgagcgggc ccaggctgtg ccaccgcgca ggggcccggc 51060
aggccgtcgc gctgcgggtc ccggtcctcc cggcttttgc ccgggtgcgg aggccaccga 51120
ggagcctgag ggtgggagag cgccccgtcc ggaggagccg gggcggcgta ggcgaaatcc 51180
ccgcgcgccg gggcaggttg ggagaccccc tctgccggcg cggcctggct gggctgcagc 51240
gcgggggcgg ccctcgctgc ctggctcacg aaagcccccct gtgggagagc cccaggcgcg 51300
cagggcacgt ggggtgcggg aagccccgtt ccccacgcgc cggtgtgggc gaaggcgacc 51360
cacgagggag cagggtgacc cccgccgggg gccgcgctgc acaggccgcc tgcctgcgcg 51420
ggcgccctgc caccctgtcc cgggtgcctg gcccttcgat tctgaaacca gatctgaatc 51480
ctggactccg ggaggcccgt ctctctggcc agctcctccc gggcggcgat gcctggaaag 51540
cgatccttct caaaggctcg gaggagcagg gcggtctggg atccggtgac ggcggtccgc 51600
tttcgccggc cttctggcgg gccgcgtctc ccgggccagg gccgagattc ccgccggtgc 51660
tgcctcagct ggcgtgacct ctcattctga aaccaaatct ggaccctggg ctccggaatg 51720
ccgatggcct gggccagccg ttctctggtg gcgatgcccg ggtacgggtt ccgctcaaag 51780
caggctcgca gggcctcgct ttggctcggg gtccaaacga gtctccgtcg ccgtcctcgt 51840
ccccgggctt ccgcggggag ggtgctgtcc gaaggtgtcg ggagggccat cgcggtgagc 51900
cccggccgga atttcacgga cggacgcggg cagagagagg ccggcgggct cccgtgcacc 51960
tcagccggac tgtgcactgc ggcaggtgca gccaggaggc ctgcccggac agccagccag 52020
ccagccagcc gcccttgtaa aggcccacag gcaggcaggc tccacccctt catgaatggc 52080
ggtgagcccc cctgggacag cccgccccac ccccggaaggg acccagggcg tcgaggcctg 52140
gggccggccg gcggggtggt ggtggtggtg gtgggggggg ggggtggtgg gggagggcgt 52200
ggtggcggtg gtggtggtgg ggccggagag acgaagagga aggggggagag gggggagggg 52260
ggaggggggc gcgtttcggg ggccggctct tctgacctct ccagggatcc cgcgggaacg 52320
ggaagccgct ctctgggctc ccacgcgtcg gcagcaggga gaaaccagcc tgggagggtg 52380
gaggggagtg tggaactgaa cctccgtggg agtcttgagt gtgccaggcc ctctctccgt 52440
gaaggaggca atgcctgtgg gcgtcgccgt tgccgggacg gtctcgcaca cgcaggcgtg 52500
tggctctcgt tcatttccac gtagaagacc agagcgagac cccagagagg agatgcctcc 52560
ccggcgtgat ggcctgacga tggattcccg cgtgcggcaa cgtggggagt ctgcagtgtg 52620
gccggtttgg aacctggcaa ggagagcgaa ggcaccatgc cgggcttgca cccttccctg 52680
catgtttccg ggtgcccgca gagctccggg agcaaacagt cggcatggcc agcctttcgg 52740
gggccggaga gacgtgagca acaggccgcc ttgcggaggg caaagccacg cggaaaccaa 52800
aatcacgcct ccgtcgtcct gcgtgtggct cctccgtggc cgggtctgtc ggcctcgcgc 52860
cgcgttgcag ggctcagcct ggggatgtgg ggtctgtgaa ccgcgcgggt gaagacccga 52920
cggcaacccg agtcccggtc ttttgtcccg gaggaaaccg cccactccct gggccccgga 52980
accggggcga atgggtggtg ccccgccggc cggcgcggcg gctgtgggcc cagccctcag 53040
cccgcgccgg acgctgaccg ttttcccgga gggcgggggt cccgctactc ccggaggccg 53100

-continued

```
aggaccgctt ttcctccctg ccttcctccc cccgtccgtc cccggctccc tcccgcccgc  53160
ccccagtccc tgcgtcgctc tgtctctccc tccgttcctc cctgcctccc tgcctccctg  53220
cctccctcct aacgtccctc cgcccatcct tccgcccctc taggtctccc gttcctctct  53280
ccatctctgc ccgccttccc tcccgcctgg aacgctcagc gtccccggtg tgcgccgggc  53340
ctggggtctg cgttccgccg ccaggcgctc cgtgctggca cctgggcggc tgcaggggcc  53400
cgggcgggcg ggcgacggtg gcgcgggggc gcagaggagg cgagccgccg gagcggtgtc  53460
aggcccggac gctgcgcggg gcccggtgtt tcgcgggacg ggggtctcca cccagcccag  53520
gggacgacgc gttttccggg ggtgggggt gggggtgggg atggggcggt caggcggcgg  53580
ggtgggctgg tggagaggca ggagagctct gcccgggctg ctcccacagc ccaggcggct  53640
gcccgcaaac ccgcgcgtgc gcagtaggcg gcccacctgc tggtacctgg gccggctctg  53700
ggatccccgg gatgcccagg aaagaatggc agttctccgc ggtgtggagt ctctcaccgg  53760
gcctagacct agaaggcagg aatcccaggc cggtcagccc ggtggagggg gcggggcgga  53820
gacacgcccc tccgtagcca gccaggtgtt ccccgcgaaa gagaggccac cgccctgccc  53880
cgaaccaccc gaccccgtcc caaccccgcg tcctaaagct cctccagcag agcccggtat  53940
tcttcctcgc tgaggggtgc ttccagcgag gcggcctctt ccgaggcctc cagctccccc  54000
ggggcctccg tttctaggag aggttgcgcc tgctgcagaa actccgggct cgccaggagc  54060
tcatccagca gcaggccgca ggggagtgca gaccagggcg ccggctcctg gagcgcctgg  54120
gagggcgccg ggatgccttg catctgcccc tgccgcgcgg aggcggaggc gtccgggggc  54180
gcgggctggg gaggtggagc tgccccggct tggggttccc acgccgcccc ggcgacctgg  54240
ggaccccggc cccagcccca ccacggactc ccctgggacg tgggtggcgc aagcacccct  54300
tggccctgcg gccccgcttg agcgggccca ggctgtgcca ccgcgcaggg gcccggcagg  54360
ccgtcgcgct gcgggtcccg gtcctcccgg cttttgcccg ggtgcggagg ccaccgagga  54420
gcctgagggt gggagagcgc cccgtccgga ggagccgggg cggcgtaggc gaaatccccg  54480
cgcgccgggg caggttggga gaccccctct gccgtcgcgg cctggctggg ctgcagcgcg  54540
ggggcggccc tcgctgcctg gctcacgaaa gccccctgtg ggagagcccc aggcgcgcag  54600
ggcacgtggg gtgcgggaag ccccgttccc cactcgccgg tgtgggcgaa ggcgacccac  54660
gagggagcag ggtgaccccc gccgggggcc gcgctgcaca ggccgcctgc ctgcgcgggc  54720
gccctgccac cctgtcccgg gtgcctggcc cttcgattct gaaaccagat ctgaatcctg  54780
gactccggga ggcccgtctc tctggccagc tcctcccggg cggcgatgcc tggaaagcga  54840
tccttctcaa aggctcggag gagcagggcg gtctgggatc cggtgacggc ggtccgcttt  54900
cgccggcctt ctggcgggcc gcgtctcccg ggccagggcc gagattcccg ccggtgctgc  54960
ctcagctggc gtgacctctc attctgaaac caaatctgga ccctgggctc cggaatgccg  55020
atggcctggg ccagccgttc tctggtggcg atgcccgggt acgggttccg ctcaaagcag  55080
gctcgcaggg cctcgctttg gctcggggtc caaacgagtc tccgtcgccg tcctcgtccc  55140
cgggcttccg cggggagggt gctgtccgag ggtgtcggga gggccatcgc ggtgagcccc  55200
ggccggaatt tcacggacgg acgcgggcag agagaggccg gcgggctccc gtgcacctca  55260
gccggactgt gcactgcggc aggtgcagcc aggaggcctg cccggacagc cagccagcca  55320
gccagccgcc cttgtaaagg cccacaggca ggcaggctcc acccccttcat gaatggcggt  55380
gagccccccct gggacagccc gccccacccc ggaagggacc cagggcgtcg aggcctgggg  55440
ccggccggcg gggtggtggt ggtgggggg gggggggggg ggggagggcg tggtggcggt  55500
```

ggtggtggtg gggccggaga gacgaagagg aagggggaga ggggggaggg gggagggggg 55560
cgcgtttcgg gggccggctc tccggacctc tccagggatc ccgcgggaac gggaagccgc 55620
tctctgggct cccacgcgtc ggcagcaggg agaaaccagc ctgggagggt ggaggggagt 55680
gtggaactga acctccgtgg gagtcttgag tgtgccaggc cctctctccg tgaaggaggc 55740
aatgcctgtg ggcgtcgccg ttgccgggac ggtctcgcac acgcaggcgt gtggctctcg 55800
ttcatttcca cgtagaagac cagagcgaga ccccagagag gagatgcctc cccggcgtga 55860
tggcctgacg atggattccc gcgtgcggca acgtggggga gtctgcagtg tggccggttt 55920
ggaacctggc aaggagagcg aaggcaccat gccgggcttg caccccttccc tgcatgtttc 55980
cgggtgcccg cagagctccg ggagcaaaca gtcggcatgg ccagcctttc gggggccgga 56040
gagacgtgag caacaggccg ccttgcggag ggcaaagcca cgcggaaacc aaaatcacgc 56100
ctccgtcgtc ctgcgtgtgg ctcctccgtg gccgggtctg tcggcctcgc gccgcgttgc 56160
agggctcagc ctggggatgt gcggtctgtg aaccgcgcgg gtgaaaaccc gacggcaacc 56220
cgagtcccgg tcttttgtcc cggaggaaac cgcccactcc ctgggccccg gaaccggggc 56280
gaatgggtgg tgccccgccg gccggcgcgg cggctgtggg cccagccctc agcccgcgcc 56340
ggacgctgac cgttttcccg gagggcgggg gtcccgctac tcccggaggc cgaggaccgc 56400
ttttcctccc tgccttcctc cccccgtccg tccccggctc cctcccgccc gcccccagtc 56460
cctgcgtcgc tctgtctctc cctccgttcc tccctgcctc cctgcctccc tgcctccctc 56520
ctaacgtccc tccgcccatc cttccgcccc tctaggtctc ccgttcctct ctccatctct 56580
gcccgccttc cctcccgcct ggaacgctca gcgtcccggt gtgcgccggg cctggggtct 56640
gcgttccgcc gccaggcgct ccgtgctggc agctgggcgg ctgcaggggc ccgggcggcg 56700
ggcgacggtg gcccgggggc gacagggagg aggcgagccg ccggagcggt gtcaggcccg 56760
gacgctgcgc ggggcccggt gtttcgcggg acgggggtct ccacccagcc caggggacga 56820
cgcgttttcc gggggtgggg ggtgggggggt ggggatgggg cggtcaggcg gcggggtggg 56880
ctggtggaga ggcaggagag ctctgcccgg gctgctccca cagcccaggc ggctgcccgc 56940
aaacccgcgc gtgcgcagta ggcggcccac ctgctggtac ctgggccggc tctgggatcc 57000
ccgggatgcc caggaaagaa tggcagttct ccgcggtgtg gagtctctca ccggcctgga 57060
cctagaaggc aggaatccca ggccggtcag cccggtggag ggggcggggc ggagacacgc 57120
ccctccgtag ccagccaggt gttccccgcg aaagagaggc caccgccctg ccccgaacca 57180
cccgaccccg tcccaacccc gcgtcctaaa gctcctccag cagagcccgg tattcttcct 57240
cgctgagggg tgcttccagc gaggcgcctc ttccgaggcc tccagctccc ccggggcctc 57300
cgtttctagg agaggttgcg cctgctgcag aaactccggg ctcgccagga gctcatccag 57360
cagcaggccg caggggagtg cagaccaggg cgccggctcc tggagcgcct gggagggcgc 57420
cgggatgcct tgcatctgcc cctgccgcgc ggaggcggag gcgtccgggg ggcgcgggct 57480
ggggaggtgg agctgccccg gcttggggtt cccacgccgc cccggcgacc tggggacccc 57540
ggccccagcc ccaccacgga ctcccctggg acgtgggtgg cgcaagcacc ccttggccct 57600
gcggccccgc ttgagcgggc ccaggctgtg ccaccgcgca ggggcccggc aggccgtcgc 57660
gctgcgggtc ccggtcctcc cggcttttgc ccgggtgcgg aggccaccga ggagcctgag 57720
ggtgggagag cgccccggct ccggaggagc cggggcggcg taggcgaaat ccccgcgcgc 57780
cggggcaggt tgggagatcc cctctgccgg cgcggcctgg ctgggctgca gcgcgggggc 57840

```
ggccctcgct gcctggctca cgaaagcccc ctgtgggaga gccccaggcg cgcgcatccc  57900
aatgtctccc catctcccct cacacacttc tgacttgagg cacaatagat ttataaataa  57960
tggcatgaca agggtctcca gaagtgtgca cagattttcc cagatcccca aaagcaatgc  58020
caaactagtc agatcattta tgttctcaca agattctggg aggattttgc ctgtgagttc  58080
gaatgcactt taagattctg ggagggagag aaaaagcctt aggggattgc agagtagaat  58140
aagcataaga caggaaatgt tcctctgtta cagcaaggaa aatagaagta ggctttctga  58200
aaacagtttg cactggagca gagatgacca cagtatattc aaactctggc cttgtccgtg  58260
acgtttaata gggtttttg tttttctctt gtaaattttt ttttcattgg tgcagaaatt  58320
tgatgaagtc tggcttacag cctgtccact gcagtttatt ttttcaccca gaacagtaac  58380
tgggctaatg agaaaatgcc caactcccag tatctccttc aggagagaat taaaacagta  58440
gaatatgtgt tgaaatgttt ggctttttga taaattgtct aatgactaga ttctttctct  58500
cctgatgtgg agtgctgaag gacatgatgg agtcatatag atgacagttt gtgtctgctg  58560
agaagaaaga tgagtgtttg ctacagcact agtgaaactg caataccaca gacagccaac  58620
tggggaagaa aatagacaat agaatctaaa atacattgag aaaaaattct ctttaacttg  58680
gaaacacagc gaagtccaga gaaaatatat ttgggaatgt gtttgtgaag cacctagaat  58740
ctatagcctg gactattgct gtcggtatcc ccctttactg agccagtctt taaatgctag  58800
atttgatgag tgctgtatag atccccagat ctctttaaaa aaaaaaaatc acaaggcaca  58860
cagagaaggc agaaaatatt ccccattgga agaaaaacat aaatattcag aaactgaatt  58920
ttaacaaata aagatttttt gcatatctga tggagaactt aaaataatca tcttatgcat  58980
tctcagtgag caaaactata acagaaagag acaactgagt gaaatttaaa aataacgaat  59040
gagcaaaata tcaacaaaga gataaaaact atttttaaaa acccaacaga aatcatagag  59100
ttgaagaata taataactga gttttataaa ttcactacag agacacaaca gcgaacaatg  59160
gagcagaaaa aagaaaattg aacatatatt attcacaaat attgagtcct ggaaactaat  59220
attttaaaga atgggaaaat tacgggtgaa atataagact tactggacac catcaagtag  59280
accaatacat tcagagatag agtcttttaa aaagaataga gggagaaaat ggcataaaca  59340
ttatttcaga gaaaaagcgg ggatgctaag aactttccag atttcaaagc gatgaaagaa  59400
aaaatactag caaccaataa taattgatct gggaaatact gtatttcaaa attagaaaaa  59460
aataaagact ttcaaagatt aaaataaaaa agctgaggtt gttaactact agaataaccc  59520
taggaaaaaa aatgctaaag agagttaatt atgttgaaaa attaaatgat gctggacagc  59580
atcataaaac cacatgaaaa tataaagctc tctgttcaat gtaaatatat acacagatat  59640
acaattttct actataatgg tgcattaaat tcttaaatct ctgtgaaaat acaaatcata  59700
tataaagata caatttgtaa tgttaagaaa gtgacggaag taaaaatgaa tatattttgt  59760
atgttgttaa ggtgaagttg aaggcaaaag ccatttgccc tggggacctt agcaatgggc  59820
aagggaggag gcaaggctgc cattttctct ccctcatttc ttccatctcc ccttactctg  59880
catagggatt tttcttggtc tgcaggaata gtcaatgggc caggctctgt cctgcgtgca  59940
caaacacaca cacacacaca ggtgcaggtg ggcatggcat gtatacgcgg aacctgggat  60000
tttaatttta aaatttttaa aaagtgggaa accaaggatt tttggcatga ttctcaggac  60060
tttgggctgg ggaaagggta agtctttgct ttctgccatg tggcatgcca tcagttgttg  60120
gggctttctc cctcaaggtg tcccccaagg agattgtgca ggagatttac ccggtgctca  60180
tggtccgtga agacatgtgt caccgcacct gcttctcact gcccctggac agcaacatgc  60240
```

-continued

```
tggaccactt ctcagagatg tgcaacattg aggagcggca ggagggctca gggctgtgtg  60300
tgagggaagg ctgttttgga agttcggtgg actgccttgg ggacggcccc cagaagcagg  60360
gccaggaagc acttccccac ttctctgagg gctctgcgtc agatgagagc atgaaggtgg  60420
gattggagct gcgctctgct tgtcaggctg tcacaccagc accttctaac ttcacaaccc  60480
gtgagttaaa gaacagcgtt ctgattccaa aaaaaatgag gcagtaccaa gccaggcttg  60540
atatcagccc aacaaaattc tataaagaaa aataatgttt aaaaaaaaag aaagaaaagc  60600
ttcacagcct ttgagtaggg aagtctgccc cgtgcagcac tgccaactgc tgaggtgaga  60660
ttggcatggt tgtaaagcaa aagttctcat gcactcaagt tacctgcggg gaagctactc  60720
atgttctcag ggtctacctg cttgttaaga gcaattgtga aaaagatctg tagctcaatg  60780
tgtcccataa ttgatcacag aacctttcct ttttcccaaa agaaccacca ttaaaatatc  60840
gtgaaacaca cattggaaga cagtgctgaa cttgtgcatc ctgaaaagtt cttaggacac  60900
ccctgcatga gggctgcccc tggacagcag ggcaaggttg tggaggcccc agagctctga  60960
aagctatgcc tacccaagac actagtgcac aaagaggaag tggccttgtg gctccccaag  61020
acctgcctgt gcttcagagg catttggcag aaggtttctt gttaacaagg atccttgcag  61080
gaaggagaga gagagagaca gaaagagaca tacagagaga gagactgtgt gtgtgtgtgt  61140
gtgtgtgttt gtgtgtgtgt gtgtgtgtgc tgaaaccaga actccacctt atgtgtttat  61200
tgtggaattt gaaaatgaaa gcctaaagtt gaaaactaaa atcacacatg accgcaccct  61260
gccaactatt tactgtctga gaagggtcgt tccagggtgt aggacccggg taacaccctt  61320
ttcccttcct tcctgaaaga gctacacaca ctgctcaaag cctgtatcca catgttccat  61380
gtccaagacg agctcaagag cctggaccca tctgccactt tcagcagggt taactgcagc  61440
tgcttgttct tcctgagcat cttctccaat ggtgacctga gagttgaggg aggcattggc  61500
gccaggattg aacagaggaa aagggagcac ggacactcag gtggtgagga ccaggccatc  61560
tcacctggag ggttctggcc ctgagacatc cagacaagca tcacatttag gtgcagacag  61620
ctggccttgg gtggctctgt gcttgtcacc ggcctcgggt ccctcaaaca gtggaaatgg  61680
aagaatggct tgggaaatgg ccccatcaac tgtgtgtcac ctgagcacat tctcccaggg  61740
gtccaggagg ggccatcgtg tctccagaac cagaactgga aggtccaact tccaggggaa  61800
gcaaggaaga gtgttcttag tgaagtggag ggcctcacag caagatgcct ggcttaatca  61860
agcttggaca tgcctgaagc atgttcagtg actaaaagtg cctaccatga gcagctggaa  61920
cccactccct gagagcttca agatgcatgg gtacctcatg tacctgtttg taattacagc  61980
caaggaccag caggcagcat tactgcatcc acatggggct tttactggaa ccagtaagtc  62040
tctgccagcc cctcacaggc tcctgggatg ccactcattc tgcgtctatg gacagacaac  62100
caggacactt gctcagtgcc cacccactcc ttgtggccca cagcccatca ctcaacccca  62160
gccccaccat cccctgcttc ctaagccatt cctcatgcca gaagaaaagg caataccttt  62220
gtcccacagc ctctgccttg tgtcatgtca tgtgggcgta tggaatgaac tggccagcct  62280
aaactccagt gcttatgcct gaggaatctg tccccactgt ctgagtcccc ctctagggag  62340
ctgtcagtgg gggagagagc agccctggaa gagaggccca cgtgcttctg tttgacttca  62400
gggcagcctc tcagggcaag aacccagaga agatggtggc ctcacagaag cctgtggcag  62460
ggctctgggc ttggtggctg aacatctccc tctttgctgc cagccatggg gcccagaacc  62520
acccattcat gagggtcacc accacattgc aggtgtgcag ctggacggct ccccaggcag  62580
```

agcctgccat ggactccatg cacacagagg atgcacacct tgaggctgga ctatgaggag 62640
aacattcctg aagaggtgca tgaagcctgg tcctgccctc actgggaacc cccttccctc 62700
tgggtaccag atagaattct atgcactttc ctggaggctc catgctggtc tgttcatttg 62760
gaagtttgag gctgtccatg aggaagtaac aaaaagagat atctcagagc aggttgtgag 62820
gcacaggctg agcccttgcc tagtccctcc ctagtccctt tgcagagccg gggctggaac 62880
aaggacctgt ggataatgag ggaactgctc tgcaataacc ggcctgagca gctgcttcaa 62940
gaaacagcca caatcgaggc acctatagcc tctggtgagt gactggcagc ctcaggccca 63000
cctgccatct gtgagcaggt tttcttgcta acagaatgaa agcaaagaaa gctggaataa 63060
gcccagccct ctcaggcacc ttgaagtctg ttggggttcc ttgcaaagcc ttctagcctt 63120
ctgcttcttg gcagcccaca caagcacctt tttccagcct ctaatgcttt gatgctctgg 63180
aaggagaggg ccctagtttt cactaggcta tggggccagg cctatccagc tccctacttc 63240
cactaacaac cacagggctc tcacctgggc acacactgcc cagccatagc ccttctaagg 63300
cagaagatca tttgtcttgc agtttcagct tgctagggct taaaagttat cagtgctgtt 63360
attaagatag agaagtgaga tcatcagcac aggtgacagc acagcccggg ctgctgggga 63420
ggctgaggga gagtgtccag cctattctgc cagctgggcc ttgccagggg tgtctcgtga 63480
cccagtccct tagagaaaca tgcagacatc tcagcaagga gctggaaggt gcagatcagg 63540
gcagcccagc accactgatg gtggagtggg gctacctccc atcaagctgt gtctccacag 63600
ctgacccgtg gagccaggag gtgatttaca acatctgcaa ggcagtcagc cccatcagct 63660
ctatgccctt caacattcac ttcaactcaa acatcccacc agaaagcagt ggggactggc 63720
caatgcagca gccctgcaaa gtggaacaga tcatcctggg gtggggaatc tggggcctgc 63780
ctgctcatct gagcactgct ccctgggtgt gtgctctgca ggacccctga aggagggctg 63840
tgagctcatc agggagaccc tgagcctgtg gaacatgcct gaggccatgt ccatggggat 63900
ttgtgcctac ttgcacctcc ttgctcatct cactacgcta ttggtgactg tgctgaggtg 63960
ggcctcgagc atcccctggg ctgtgtcagc acagggctct gggcctggcc tggcattgag 64020
ggacggcaaa taaggggcct gggtttgcat tgtcgcctcc tgtggttcca gaaaatgagg 64080
aggtccagac ctgcagtact ggaaccctat caaaggggtt aggaggccgc tcactttccc 64140
tcagggcccc atgtggagga gctgagggag gttaaggaga ccctggggac tcacttgttc 64200
tgtctgggct tcccccagct ccaccctttg ataaccattt tctgggaaga gctcaggaac 64260
ctctcgtgct gtagtgaggt ggggccttcc ctcacagggt attggtgagg aggcattctg 64320
agactctgtg agtgagaagc taacacagtg cctgagaata ctcatgggag ctgtcatcct 64380
ctgtgaccat cacgtgacct tgtagtgttc agactgcctg gcctggcctt gggcttggta 64440
aggctgtttt ggggttagct gctttagact cccacttttt ttgcattcaa acagtgactg 64500
ttttagtgtt tgtctatggg tttaaaaaat cctaatattt catttatagt agtttcagct 64560
tgtatgtatg tatttgtata aattttatta gaagaaagag ggcttaaggc aacagcattt 64620
taagaaggtc ttaatggggc atagactttt atgtcacaac agctaatact gacctctttt 64680
tctacctttg cataaagtat acgtaggaag tgtagccaga ggtggtgagg ctaagtgtct 64740
agagctgagc tgctgggctt gcttgctggc ctgcagtcag gtggactctg gctgtgaggc 64800
agtgcccacc ctggatctac atccccccacc ccctctcctt agtccctgag taaccaacac 64860
aaggcagtgc taataagcag gggagtgatg ggcattggga accccaatac tatccgggaa 64920
gatctgaagg ccatctgggc tggggctgtt gggggtaggg gctgtggctg ccttggcttg 64980

```
tcagggtgcc acccacagat gtgcctgccc tgtgctgctt ctccagcagc cggctgccta  65040
tggccctgag cctgtcacac catgcttgct acctcatgct acttgtgttt gaaaaaccat  65100
cccaagatgg tgctgctgga tgtgagtgct gaaaaggggg cagcaccttt gtcctggggg  65160
attaggagct gaccagattc ctcctgactc cctcccgaaa caagtggggc tggtgctgca  65220
atcaatgatg ccccccagaa gatgtgtttg cactggctga acaaatacat gatgcagagg  65280
cctaaatgaa gacacatgaa tggggtgtgt agacatcagc tagcagctgg gaaacaggtg  65340
tctctcaggc ctctcattct tcagcaagtg tggaatgtgc ccatgccctt gagtgtatac  65400
atctggagtg tatacatctg gctgttgctt ttgctgccac tatccccagg cccaatctgg  65460
cttaaagtcc aggttttaag taaaaaagat aagaggattt tctgtgttct gggataggaa  65520
gccagggatc tgtgtagggc tgcagttggg tgcacattag ttttgtgaca ggatgagagc  65580
tgcagtggtt ttattaatcg tgatagcctg ggctggttgt agcttcaggt gaggggaggg  65640
agtcagcagt ggtggtcccg gagacatcca tgtgcccagc cctggccttc ctgccctcag  65700
gcacagcaaa aggcaccgcc acaggccccg acttccttct ctactctctg cagcccagat  65760
gggaaaactt ggaggctaca atctgaatat atttttctcc cattttaacc cgagctgcct  65820
aacacacagt gggggcaggg tgggtgaagg gcctggggga aagcagggct ggatcatgga  65880
tcccggggga aatttagaga tacagaagtg gctgtcacct ctctgtggaa cccagctcca  65940
tacctggtcc ttgccacacc gccctttcta cagagaatag ttccggggcg tttggggatc  66000
cctatggccc cgggtggctt cctgtccccc gctgcctgtg ctgcttccct tggctgctgg  66060
cagagcccaa catggaggag gaggttgcag ccctgggagc ctgagggagc tcttcccttg  66120
cctgctggca gagcccaaca tggaggagga ggttgcagcc ctgggagcct gagggagctc  66180
ttcccttggc ctgctggcag agcccaacat ggaggaggag gttgcagccc tgggagcctg  66240
agggagctct tcccttgacc tgctggcaga gcccaacatg gaggaggagg ttgccgccct  66300
gggagcctga gggagctgcg tctgactggg gcttctgcct gggggtttgc aaagagctac  66360
ttatgaatat agtctctcca gattccttgt ttcaaaggaa gtgagcatga gctagcaagt  66420
gtagcaaccc cacagctgat aaacaacttt gtcttggttt taaaccatca catcttcatt  66480
tcacattgga ataaagtaag tgaaacctgc tactccagcc ttgcccatgt gttctgtaac  66540
ccagtctcct ttggttgtga gggctattgt cagaaatgtt ataagaaaag attatgccat  66600
aaattaaatc aaatgtaaaa ttatgcttat aatgtcactt gagtgaaagg taagagggta  66660
gagtcacagg cactcagctg gggtttaccc acccatcact taccacactc ataagagtgt  66720
gacacaggtg aatgtcactt gacattggtg acagaagaga aaaggctggc atgaaggcca  66780
ggtaggggag aggtgccagg ctgtggggcc aggccctggg cgatgctgga cctgtgaggt  66840
cactgaacat ctaactgccc aggcactggc ccttttcaca tcagttgagg taagaggatg  66900
ggggagcact ctctggaagt cacactgcac tgggagaatg gaggagagtc tacaactcac  66960
catcctagtg taggttttag agtgagatgg actgtcttgg agagctaatg aaatgggagg  67020
aaagcagtcc cccaggtgca tctgagggcc acagcctatg aagtaagcag tgtgtgtggg  67080
agtggcctgt ccctgtgaga ggagaagttt aaagttatta cagctggtgg ctgctgctca  67140
gccatccctc tgcagagcag gcaggtcctc agctgcatgt atatctgaat gtcttttgga  67200
gtgtttagag agtcctctat gtcttagaaa ttttgaaaag aaaaacaaat ttcaattcta  67260
atgtttatta gtttccctga gccaactgga aaaaaaatgt ccttcacctt gaagttttaa  67320
```

gtgacaccca agggtagcca ccagtgtctc agccactgaa gccttgtgca tgctcccact 67380
accagtttga tttgcagcct catggttgtg ttgtactaaa tgttctttct tctggccttg 67440
tccagtgaaa acggttcaca tggctaacac cacttcttga gatacgggca ccatgtaaag 67500
ctgagaatgg attgggttag ttactattgt gcctcctcct cacccgagag gcccatttct 67560
cctggttgat tcattaagtg tattagtgct gtcagtcgcc tttggacaac tcaaatgaca 67620
agtggctgtt gtttcataaa gaaaatgaag gctttagatg tgaaacactc cttttctctt 67680
ctgcttctct taggtgaaag attttatttt tttaaaaagg gtacatagtc gtatcccagc 67740
aggtgtagtg tgataactgg catgtgctag gctatggttt cagtgtgtat gggcaattct 67800
tcaagatgga aaaccaagtt tcactgagtt gctggagccg cactcacctt ccctccacat 67860
ccccaccatg ggcttccact ttcctcccgg gcttgaattt ttttcacatc catattgttt 67920
atacacacac acacacacac acacacacac acacacacac acacacatct gtctgtcagt 67980
gcagtggctg aatcatgggt cagtgcagcc tcaaactctt aggctcgagt gatcctttca 68040
catcagcttc tcaaatagcg aggactacac tacaggcatg caatgctaca cccagccaat 68100
taaaaaaaat tttttgtaga aactgagcct acttatgttg cccaaactgg tcttgaactc 68160
ataggatcca gcgatcatcc caccttggcc tcccaaattg tttacattac aggtgtgagc 68220
taccaaactc agccaaaaat attttttaaa gaacagttac aaccaaatta tgagttatga 68280
ttgtgccact gccctccagc ctgggcacca gagcaagacc ttgtatccaa aaataaagca 68340
aaacaaaaca agaacaaaaa accttataac caaattaaac ttcgaagatt gtgtcatctg 68400
tgtccctctc tgccctccag ttatcaccgt taaatataat ggttattgag aaaacggtta 68460
gatattatta agaaatttct atatctactc cagctgagaa taggtattct gatgtggcca 68520
aaacattttc tcactgctac cttcagggtc taaactagca gacaaaatca ggacacctgc 68580
agaggacagt tggccatttt caaatagaaa cagaaatacc cccattaatg agagtaatcc 68640
agtgattttc agaaagacaa gtcagactga catgcagcac agtcagggca caattaccct 68700
ggaataatca cttcacacag aatggttgtg gagcctttct aagatgagca aatatgggca 68760
acatcattct tgcttattta ttcccagccc ccgctgcccg ccttattctg gcctgattct 68820
ggcccgcctg ataatggcca ccccacaatg tggtcagcag tgaggtgcag cgtggtgaga 68880
gaggggcttc agggatggga tgagggtctt tcctgcatta tgaaaatgcc taataagttg 68940
ttgaaaagat gtccaaatgt tctacttcct acccttaaat agctgctaag atgcatgact 69000
caacagatcc tggtaaggga aagagcatgc gcatttcaag tctcagctca cttcttaatt 69060
agctgtgata ctctgcgcat gtgaccccaa ctattcgagc ctgtttgcct gtccacccaa 69120
gacaatccta agcaaaaaca actggtagct ggaggcatca tgctaccaga cttcaaacta 69180
tacttcaagg ctacagtaac caaaacacca cggtactggt accaaacaga tatatagacc 69240
aatggaacag aacaaagacc tcagaaataa caccacacat ctacaaccat ctgatcttcg 69300
acaagcctga caaaaacaag caatggggaa agattttcta tttaacaaat ggtgctgaaa 69360
aaactggcta gccatatgca gaaaacagaa actgcacccc ttccttacac cttaaacatt 69420
atctcaagat ggattaaagt cttaaatgta aaaccccaaa ccataaaaac cctagaagaa 69480
aacctaggca ataccattca ggacataggt atgagcaaag acttcatgac taaaatacca 69540
aaagcaattg caacaaaagc caaaattgac aaatgagatc taattaaaga gcttctgcac 69600
agcaaaagaa gctatcatca gagtgaaagg caacctacag aatgagaaaa tttttgcaat 69660
ctatccatct gacaaaggtc taacatctgg aatctacaag gaactcaaat gaattcacaa 69720

```
gaaaaaaaaa accatcaaaa agtgggcaga ggatatgaac agactcttct caaaagaaga  69780
tatttgactg agtgtggtgg ctcacacctg taatcccagc actttggaac gtggaggcag  69840
gtggatcatg aggtcaggag tttgagacca gcctggccaa catgctgaaa tcttgtctct  69900
actgaaaaca caaaaaatta gccagacata ttggcaggtg cctgtaatcc cagcttctcg  69960
ggaggctgaa gcaggagaat cacttgaacc cgggaaacag atgttgcagt gagccaagat  70020
cctgccactg cattccagcc tgggtgacag agcaagactt cgtctcaaag aagaagaaga  70080
agaaggagaa gaaggagaag aagaagacat ttatgtggcc aaaaaatatt ttaaaaaatc  70140
tcatcatcac tggttattag agaaaggcaa atcaaaacca caatgagata ccatctcaca  70200
ccagttggaa tggcaattat taaaaagtca ggaaacaaca gatgctggtg aggctgtgga  70260
gaaacagaaa cgtttttaca ctgctggagg gagggtaaat tagttcaacc attgtggaag  70320
acagtgtggt gattcctcaa ggatctacaa gcagaaatac catttgaccc agcaatccca  70380
ttactgggta tatatccaaa ggaatataaa tcattctact ataaagacac atgcacattt  70440
acgtttattg cagcactgtt tacaatagca aagacttgga accaacccaa atgcccatca  70500
atgatagact ggaaaaagaa aatgtggcac atatacacca tggaatacta tgcagccata  70560
aaaaagaata agttcatgtc ctttgcaggg acgtgagtga agctggaaac cattatcctc  70620
agcaaactaa cacagggaac aggaaaccaa acaccatatg ttctcactca tatgtgggag  70680
ttgaacaatg agaacagatg tacaccggaa ggaaacatca cacgctgggg cctgttaggg  70740
ggttggggtc aaggggaggg agagcattag gacaaatatc taatgcacgt ggggcttaaa  70800
acctaaatgg caaggttgac ggtgcagaaa accaccatgg cacatgtaaa cctctgtaac  70860
aaacctgcac gttctgcaca tgtatcccaa aacttaaagt aaaacaaaga aacaaacaaa  70920
aatgcactaa cgctcagggt gagtggggca ggggccgggg tggggtgcgg atgggtgggt  70980
cctggcgttt tattcaatca gtggcgctgg tgtgggaacc acccaatcgg gcgcacagtt  71040
tgagaagaga ggagggcgtg gcttccggcg tttggcgggg cctttgtctc tcgctggtgc  71100
tggtgcagga gcttgggatc catctcctct ttcgcctcct ccaccttggg aaatccagac  71160
aactccctca cagcccctgt tgccctgtga atctgtaggt ccttggggac acacagttaa  71220
ggtgctgtta ccatggggtg gtctttgctc ccagagcgcc caagatggtg gcgggccact  71280
tccataattt tggcaggcca cttccaagat ggtggcaagc ctcctgttct ctgacctggg  71340
gctcttggcc tcacggattc caaggaatgg aatcttgagc catgcggtga gtgttatagc  71400
tctattagaa gctgtgggtc acggaagaga accgtggaac ccagtgacta gtgttcagct  71460
tgattaggat gaacccaggc gcttagctgt gcaggaacaa tggcaagcct tcagcccgat  71520
cgggagtggc aatggatgcc tcgctggatc aggagcagag cggacacctt gctagccagg  71580
atggtcttga tctcctgacc ttgtgatccg cccgcctcgg cctcccaaag tgctgggatt  71640
acaggtgtga gccatcgtgc ccagccaaga actgtcttca caacaactgg tgctggggaa  71700
attaggtacc cacatgtaaa agaatgaacc tgtgcccttc acttatactg taagaaaaaa  71760
ttaactaact ggatcaaata cctaaatgta agagctaaaa ctacaaaatt cttagaataa  71820
aatatagggg aaacacgtca taacactgga tttggcagtt tttttttttt aaacaggaca  71880
cccacaacac aagaaacaaa agaaaaatag acgaatagga atctatccag aatatgcaaa  71940
gaacaattca gcaacaataa aacaaactac ttgtttaaaa tattggcaaa aacttaagca  72000
gacatttctc taaaaattat gtaaagtagc taataagcac atgaaaagac actcaacaaa  72060
```

-continued

```
actcatcatt agtgaaatgc aaatctaacc ccaaatgaca tatcacttaa tacccatcag  72120
catagctact accaaaagaa aaaaaaaaac agaaaatccg aagtgttggt gaggacgtgg  72180
agcaattaga atccttgtac actgttggtg gaaatgtaaa atgctgcagc tgctataaaa  72240
taacaacaca gtaactaaaa aatttacaca taaaatcacc atacgatcca gcaatttcac  72300
atctgggtat gcagcaaaag atatgaaagc aaagacacaa aataatatac atacacctag  72360
gttcatagca gcattactca catcaccaaa aaggtgtttg aattactcaa gtgttgtttg  72420
aattaccatc aatgattaat agataaaatg tgatttatac atagagtgga atgttattca  72480
gttatgtaaa ataaggaaat tctgacacat ggtacgtcat gcatgaacct taaggacatt  72540
gtgcaaagtg acatgagcca gtcataaaag gacaaatact gaatcattcc acttatgaga  72600
tacttagagt agttaaattc tagaaaccca aatagaagag tagttcttag gagctagagg  72660
gggagtaaca aggagcttat ttaatgggta tagagttttg tttctgcaag ttgaaagaag  72720
gtccctatga gtggtaatga cagttgcaaa acaatgtgaa agtagttaat ttttctgagc  72780
tgcacactta aaatagctaa aatggttaat tttatgtata ctttaccaca atgtaaaaaa  72840
taattttaaa ataaactata gctatctgca atatcatgaa ttaatatcat aaatataatg  72900
ttgcatagaa gaaagtagat gtaaaagtat acatattaca caatctcact gttataaaat  72960
ccaaaaagtg aacacaactg agcttctggc ttccagtaat aatgaagtaa agtagtttgt  73020
tgaacacttc acagataact ataacaaagc tctttggtca cagggctgca gcactgcaat  73080
cccagcatgc accaggctca gggagagtgc gctaatcact ggaggaaggg acgaggctcc  73140
gcgcctctcg ctggtcttgc tgggagatgc agtctcataa acactcccag ccctttggtc  73200
acagggctgc gagcactgca atcccagcat gcaccaggct cagggagagt gcgctaatca  73260
ctggaggaag ggacgaggct ccgcgcctct cgctggtctt gctgggagat gcagtctcat  73320
aaacactccc agccctttgg tcacagggct gcagcactac aatcctagca tgcaccgggc  73380
tccgggaaag tgcgcgtcac cggaggaaga ggcagggctg tgcgcgcctc cctaggattg  73440
ttggaagatg cattctcata aacactccca accctttggt caaagggcta caggactaca  73500
atcccagcat gcaccaggct ccagggcgag gcgcagccct ggaagaaggg gcagagtggt  73560
acccgcccca cctaatatgc tgggagctgt agtccgttac ctactctcag cctgtttgtc  73620
ggtaagcttc agagctataa tcccagcatg taccgggatc cggggtccat agccctggag  73680
ggaggggcag agcggtgtgg acttcccggt gtccaaagca ctgctgagtt ctgatgctat  73740
gccgactctt tgcaaggaga gtgagtacag aggtgcacct ggagggcagg tctgggctga  73800
gcattgagga gggtattacc ctacaaagat accttacctt ttcccaaatc gggcgggttg  73860
tcctcacccg cttggcccta tccttctcag gttcctcttt cagttgcacc cagggttctt  73920
tccagaggag tacgtcttct gcagcccagg gtgctgcctt ctttcctaaa ctgcgtgaga  73980
actttcctga tgtccaagac actgtcattg tgccgcagcc ctcttttttc tctagccaga  74040
gcacgcactc aaccgttttt gagagaaatc ttccacctgg cctgcttgtg agcagcttca  74100
gagctctgca ggggtgacaa gggctgtggc ttcttggaaa ggtcactttc aatggcgcct  74160
ttttcacgaa tgtgaaagtc taggcatcag aaaggttaat tattgggttg cataaaatct  74220
gctaagagca aaggaaaaaa ccccatttct gaggcgtgag tcttgtgagc cattttcatc  74280
aacccactta agtggacaag ctccaaaatg caacctgaag ctactgagta tttaggcatt  74340
ttacacttga aatcattggt ctcatctcaa gtcaggcctg gcttgccagt ggctcagagc  74400
cacaaatggg acctgatacc tcaggaacag atagtgttcc agctttaccg gaggaacttt  74460
```

```
taagacgtgg agcacttggg gtcatttgaa acccgctatc ttcagtaggg acttttaatt  74520
ctacagagca tgtgcatttt gattttatgt gtcctcaagc tgaccctttg ttcattttaa  74580
tagtaaaaaa cacattcctg ggtggagatt taagatgcta gtgaggcatg caatgtatgc  74640
acaaatatgt acagctactg cacatgtata accagaagac cagtcagaac atgcttaccg  74700
taacacttct ttccaccttc ttatgaaata atcatgcaaa actcccataa agagggtttc  74760
tccagcaata attaatgctg tctcactttt atgagcaggc tgccctggaa tctctttctc  74820
agactgtacc ggctattctg cacttaattt tcaaaatatt ctttttggg caataaatta  74880
tgctgtactt cttttgctgt gtgtctcttg tttaaattat tttaaactaa gaagataaga  74940
accaaggtat tacatcagcc atcaacattt ctggtgccat gacctgcgga gacgtttgtc  75000
tgcttcatta atttcagttt ccctttactt gcagtgaata ctatggcagt ttcagactac  75060
ctggttaact atcgctgctg gttccagcgc tgttccagta aagttctggg ggaaacgttt  75120
ttaagtcacc cgcattcttt agagagagaa tatatgtccg ctctcctttt ctctgcggct  75180
tctgtagtat cgataaatac gctaaccaca tgggttgccc tcaacatttc atatttgggc  75240
tatttgccgc tcattttcac atctttctgg ccacagttta gactcagctt gtcgtttgct  75300
gtccgttcag caatactcga tcgccaccta gtggctattg taatttattt tctggtcagg  75360
ttttctgttt acaaaatttt tgttttgttt tgagcagcac attaagagaa ccctgtccct  75420
tcaggcttta tgcatttccc agctccttga aattgttctt caaccggctt tctttgctga  75480
acaaaagatg cacagtcaag cagatgccaa gtcgtaggga ttgcatctga gcattccagg  75540
tgttgtaact gggcatcaca aatggcaaac cagtgaatta gagcaaggct tgtcagccag  75600
acatctgccc cccagcccgc agtgggggtc atctccgtag ggctggagat gtccaccgct  75660
gggggagcta ggacggtgta tggcaaatgc ctatgacctc ctagagcttc agttaatggg  75720
gtttcgaggg gatgcgctgg acccccttggt gttttcactt ggctcatgag gacgcccaca  75780
gcctcctgga cttcagtaaa tgttctgtca ttgcaggatt ctctcggcac catgggagct  75840
gcttcctcta ctgtcactga aacacccctg ggatgtatat ctaaaaatta gaacagcttt  75900
tggctaaatg aacttagaaa aaagaaaacc ttatcttctt ttgtaatact atttagcctg  75960
cctacagatt agctgacaaa acatggctgg agaatgagac tgtgagcttt aactccatcc  76020
tacagctaga tcttttctgt agcaatcagg gaaaatggtc tgaagtaccc tatgtgcaag  76080
ccgttctggc ctgacaacaa aatccagctc tacgcagcac ctgtgggcta aagcctagta  76140
agccagaaag cccctcagaa caattggaag atcatctctt attaagggga agggacccca  76200
gaccccacag cccaacacca gctccagaca ggggcactca ggggtccaca cctcctttag  76260
aatccccagc atccccacac tatcagagtc ttctgtagaa tctaagcttg tttcacctcc  76320
tccttatgct cctttctatc ggcctttgcc aggtacaata gagaccagcc cagctgcagt  76380
tactcacagt gggacttcac accatccagg gccagagaaa tttctcccct tacagaaagt  76440
cccaaatgga gagaggacca tcagagtgct tgttctactc tcaataaata atctaatcca  76500
atataagcaa caactctgat ggccctcaga caacttcagc gcatttactg aaggcttcca  76560
ggctctaact ttgaccacca ttcaactgta ccgtccataa atggaccgaa tgactgctgc  76620
caacttagct gcacaaaatt ttgcttatta gcaaaaaata gaaaatactt aaaacgtttg  76680
ttgctttcac cattttaatg caaaatactt ttgcagcata aatgtcacca taaggtggag  76740
ccttgggaat ccagtataaa ctatctcaga aaacctcaat gggtctgcaa caagcagcag  76800
```

```
agggcctcaa tagacttcaa caatgtctgg actccatggc cactgtagtc cgacaaaagc  76860
aaaaagcctg ggatcttctc ccagccgggc aaggaggaac atgtttatat ctaaaagagg  76920
aatgctgttt ttgagatcaa tcagcccggc ttagtccaag aaaatattaa aaatatcatc  76980
acccaggcag acaaaattga atctctatga acttccatgg gaccatgaaa gcaacgtcta  77040
ttacctgcct tactctcttt aatagtaaca gccattacta tactttcagc ttttactttt  77100
gttccaattt tgtttaaaat gttaactgat ttcttgctct cttgcttacg gcaactccat  77160
gtttgcatga tggttttgca aggctttcaa catttggctg ccaacatctt gcccactggt  77220
tccacgaatt acatggttta cacccagtta gatcacacag gaagaaactt tagggcccag  77280
actaggtaga aataacaccc actcagcagg aaacagctcc agaaaaagtg acctagcccc  77340
tcaacctcca atatgattat gaccctaaga tctcttaggg ggaaactgag gcagaataga  77400
tcagaatagt caagaaaatg accatgatct cgggatacag aaatgtgggg aaattataaa  77460
tagaactacc atatgatgca gcaatctcat tgctgggttt atatcaaaag gaaacaaaat  77520
aagcatgtca aaaaagataa ctgcactctc atgtttatta agcagtattc aaaataaccc  77580
aaaccactat ttcttctaag tatttctaaa tttacctttt tttcatatat tacaccctaa  77640
acttttaaag gtttcatgtc tggtttccaa tttctgaaac ttacaagtca ctgattcttt  77700
gttgccttcc tatttagagt ctggtaaaac aattaaatgc tttttatttc ttctcaatct  77760
aatcttcata tataaatata tttatatttt ctattaattt gccttctata acatatatga  77820
ctacattaat tgtgatcagc atttcacttt actagccctc tttttggctc agcctatttt  77880
aatatgtaat ttgtatgttg tacattaaat tgttttacaa ccctttcaat actttacttt  77940
tcatttgcct cttttccaaa gatagcttga caagctcgta gtttctttcc acattatttt  78000
ggtttcttgt ttttccatta tattgactta aacatttaaa tataaattca atatctgaga  78060
tttatgtgcc atataatttc ttctgatgct tcaccccagt agctcatctc cttgtgtgtg  78120
acataattta taatttaatc ctcacatatg ggagacaccg cattccaatg cctgcaggca  78180
gtttctcttt gtttattcca tttgccttgt cagaagggaa caacccacac ggacctgaca  78240
ttcttgtaat caggcacatc tgagtggagc cctggtctct taggttgatt acttctctgg  78300
atcattacct ttatttactt ccagtcctgg gaggttttct taatttcctt tcaactatat  78360
taggcattct gtgaattctt gtaacttctt ggtgatttta attgtctgca ttaagtgttt  78420
aaagtatatt atttttctga aaagcagaaa tatcaataat tgcatatatg agtgaaatat  78480
tttacataga ttttctatgg catctatcac catgagaaat tccaagtttt tttcatttga  78540
aacacccctc tcatcaatag accatattgt aataatttgt agagtgtgat tacttttata  78600
ccattagaaa attaattata tattatgtac atatttttga aatactccac tgcaataaat  78660
agtatatggt cagaagtatt gttttctcta acctaaaact aatatgagta aaattatcta  78720
cctgaattca gaccttttgg cttcaatggc cattctgtct cattagcact tccctgatcc  78780
ataaaagaca tcattcgtac tttctgctta attcataatt tattgaaatg agtaatttaa  78840
tgttataatg ttttatggca atttaggaca ttttcaataa atatattgag ctcaaggccc  78900
tggctaagta ttccttttgt gctcaaaatc agatttttct ggcacaactt cattgcctgc  78960
aatggtattt ataaaaagta tgaatgccag cacatggact atttcaatac tgtactcatt  79020
ttttcatgta taaacatttc attagctatg aaacaaacca aatacaaatg ctgaatgtac  79080
agtatatatc aacaaatgca gattcttcac ctaagaaaac aataaaagac gaattttctg  79140
tgacatgtca cctgttcatt agttctttaa tatgatttag gctattccaa atataagaaa  79200
```

atgtatgcat cactatttat gttgtctcaa cacatttttt atctaggtcc tgaaggacag 79260
aaaaaagaat gtatattgtc agatttattt ttatagattt tagatgtttc ttttgctgta 79320
ttttctgtgc atactactat gaatatatgg agacaaggac aaatgagcat ttaagtggtt 79380
atatgaattt tgcttatatg gctaattgct tatatggatg ttgtaaatga caagataaaa 79440
tagtaaagtt tggtaaactt atctgtgccc tgtgaacttt agttcactta ctgtataact 79500
taattcagtc actaataatt aatttaaaaa gtgtttttta aaaactgcaa accacatttt 79560
attacacatt tctgaatcag gaaggggtaa actgtgacac agctttctca tgccactgac 79620
ttttttgggg agaaacattc tgcaataaaa taagagtttc caaactctat ttataaaaaa 79680
gcttgagttt tcttctgtga ttaaccttca ctcctcagtc ccttttaccc aaggaatggt 79740
tcctaggtca tcttttggaa gtttagtttc tggaaagttt tcggcaaacc tctcctgagc 79800
tttgtcccag ttgttgttgt tcttgttttg gagaaggtga gtctctttaa ttgaggatgg 79860
tttgtctgtc tccaatcctg catgtgtttg ccaaggctga agctgtactg gagtttttat 79920
tctcccacca tccttcccca ggccttctcc tgttttcaac acatcttttt caacatcttc 79980
tgacctttgt tgctatcagt aatttcagaa tgaacagatg caggagcatc atctctttgg 80040
aaatttcctt cacttccaat ctgctcccta tgttttccag ctctatcttt atatttttga 80100
ttctccagta tcttatcatc tttgtagtct gtattctgta aaccatattt tactcgtata 80160
tttttaaaat ccttttcttc tttccaactc gtttccttct tagttaatga tggaccaaca 80220
aatgattcat ctttcttgtc aaggaaaagg tgagctctaa cctgccctgg ttcacatcca 80280
acacagctat tactgccagt gtgaatgtaa taagataaca cagtgtctcc aactttcact 80340
ttatctccat gctcaggttc ataaggctca catttagttt tcagctgaac aatccatttt 80400
acattaacaa ttgttccatt ttgactgtct gatccaaaag gacataactt tgtaagtcaa 80460
ggtcaaaata gatttctgca tgaaacttac accaacttca gggatttgga aagtatgctc 80520
catatcattt tctcttccaa ttgtagcagg ttttgcagca gtaatgatga agaatgatcc 80580
tgtctgtagc acaggtgatc taatgacaat cactctcata tatgaggcca cactttttcc 80640
tcatcttcct cctcagtatc ttttgcagtt gcattgcctt tactggtaat gccttcatca 80700
taactaccct cggtctgaga gtctgtaatt tcaccttctt ctggttcact atcagtctct 80760
gtgattttct catccttaaa gatgaattga gatgttttca ttaaaaggag attccatagg 80820
atttccacta aatggaacag tgaattttgg ggattatttt tgtgatgaat gcctattttg 80880
gcttttttttt tttcacattt gtgaaattgt ctttcccgtt gcagcttgta tgttcaacac 80940
tgaaggcttc ttgatcctct gaattcaaat ccttttcctc atcgtttttt tgtagaagaa 81000
tcctttcttt tctcaatttt tcgtttttgt ttcgtgctat aagtctgata aggttgcaaa 81060
tctactcgag aatgaaatcg atagcgacaa ctttccacat cacagtggta ataaattaaa 81120
tcataatata tttgattctc agaatcttaa tagaaaccag tgctgtggtc aaaatacagt 81180
ccagtatttt catcatcact aaatccagtc tgtgacaaag ccgcttccgc tgcagctctc 81240
aaacttccag ctaatgacga accttctaag gacgtatctt gtgctgctaa tgcagatgct 81300
ggctcctgtg aattggaggc agatgaccct cttgtctaca cttaacattt gctgtcctat 81360
cagtaccagg gtgagtgtca ttttctactt ataactggtc gttagaattc aaagcaggac 81420
tttcaatatc ctgatcttgc tgatttgaca gttcagtcac tcactttatt tggaagacta 81480
acgtcattag ggtaggtctg ataataataa tctgagattg accaaggagc atggttctct 81540

```
gcgagtactt ctacatcaga cttttattac ctccatgtct cccacagcgg agtacgttac  81600
tgagttcttc cagctgcgtg cggagctcct ggcggttgct cgtgtcgctc tgagcagccg  81660
tcctgggcga ggccatagct tctcccgttc ccgcacctgc cgcctgcagc tccgcgttcg  81720
ggttccagct tctccgccct ccttctccgc tgggccagct cgggctcggg gagggggagg  81780
agcggccaca gcgaaggcgc tggcggcggc tacgggcaga ggccgcgagt tcgggaccag  81840
acggctgcgt tctcggaggg gctgcgcggg gccggagcgg gggccggcgg agccacagcc  81900
ccgggggcgc gcgggcagcc acaggcagcc tccccggcca ggaggccccg aaacgcggag  81960
cctgacgggg ctgcggcaag agcaggggga cggcgatggc cctgccggat ctgcgtgcct  82020
ggaatccggg gaacgactgc gccttcccca gccccggggg cgcgggagga gcgtcgaagt  82080
ccaggggcca gaagcgctcc ggccgttccc gagttgagct gcgaacagcg gccaagcgtg  82140
ttttaaatcg agcttccgtg tggcgagcta tgacctgctg gttactctta tttttttct  82200
ccattcgttg agctatgatt gacaaattga aaagtgtgta tttttagggt gtacaataga  82260
gtgttttgag atgtcagtgg tctttaaatc acctcagtta agctagttag cctgtctatc  82320
ccctcacata gtgaatacgc ctctgtgtgt ggtgagagca cctgagatct actcttgcag  82380
caaatttcaa gtacacagta ttgttaacta tagtcactat tctgtacgtt aggtccccag  82440
cagttactca ccttgtaact gaaggtgcgc cccttccatg gaaatcttcc cactttcccc  82500
acttcctagc ccatgggaac cagcgttcta ctgtttccat ggctttttta aatttttatt  82560
tactttttta gattttacat acaaacgaga tcatgcagta gttgtctttc tgtattcagc  82620
ttatttcact tagcataatg tcttcaagat ttatcaatat tgttgtggat gaaagagttt  82680
catttttatt aaagctgaaa ttatgtctct cagtttatct gtatcagagg aatgcagata  82740
cccttgatga tcctgatttt atgtcctttg gctatatact cctaattggg attaatggta  82800
gttctagttt aacaatttta aggaacctcc atactgtttt tcataatagc tgcaccaatt  82860
gacatcctca gcaacagtgc acaagtgttc tctttttcca caccctaaca ctttttatct  82920
tttgactttt tgataatagg tatccaaaca ccacgataag gtgatacctc attgtgattt  82980
taattactgt gataattagt gatgttgagc atttttttata tacctgctgg ccatttgtat  83040
atctttggaa aaattgctat ttatatattt tgcccaatta ttaatcaaga aattgctttt  83100
aattctgctg tgggtttttt gtattgatta ctatgacata tattttggat agtaacatat  83160
tatcctacat atggtttaca aatattttct cccattccat ataatgcctt tatattttgc  83220
tgattgtttc ctttattgtg cagaaaattt ttactttgac atagttccac ttgtttattt  83280
ttgcttttgt tgactgcgct cctggtgtca aatccgaaac atcattgcca tgaccagtgt  83340
caaggaggct tttccccatt ttttttttta gaggattcat gatttcagtt cttatgttta  83400
agtctttatt tcatttcaaa ttcattttgt gatgacatga gagaaaggtt tactttttgt  83460
ctgtgcatat cgagtttttc ctacaccact ccttgatgtg tttatccttt ctccattctg  83520
tgggattggt cgaatgtata tttgtgagtt tatttctggg tcctctattc tgttctattg  83580
gtttttatgt aggtactata ctgtattaat gactacagct ttgtaatata gtttgaaatc  83640
aggaagtgtg aggctttcag cctttttgtt cttctcagta tttggctatt tgaggtcttt  83700
tgtggttcca tactaatttt aaaattgtcg ttctacattt taataaaatg gcattaaaat  83760
tttgataaaa atttaactct gtagatcact ttgtgtagta tggatatttt aacaatatta  83820
atttttagaa tccatgaaca catatttccc attttgtatt cttcattttc tttcctcaac  83880
attttatagt tttcagtatg cagatctttc atattctttg ttaactcatt cctaagtatt  83940
```

```
tcattctatt tgataatatt gtaaatggaa ctatctttat tcctgtttca gatattttgt  84000
tgttactgta aaaaaaatgc aactgatgtt catatgttaa tattgtatcc tgagaattta  84060
ctgacttagt tggttagtta taacaggttt tttttttct ggtaaaatgg tggttattct  84120
gaattctggt taaactttaa attgataatt gctattatca tttcaaaatt atttaaaata  84180
tgaccagatg gattcctgct ttcatgaatt caatggaatt caaatcttcc catttaaaat  84240
aattttgtct ggttgaccta gaccccgggg atcgggggca ccccgtggga gcccggagat  84300
tcgcctgggg gtgggaggga gaagccgtca gagagggggc tgagctgggg aagcagagag  84360
gggctcgggg acagccggga ggagagaggg tcgtgtcgga gacccagtgg ggagagagaa  84420
tgggccggaa aaggaggaag ggtgagagtg ggcaacagga cggcttcccg gcgcggcagg  84480
gaactttgct gaaactgcgg gccccaggga ccagcgcggg cagggtggga gggagtggag  84540
aggacccagc agacccgaag gtcagtgtgg agaaagggac gtttcccggt tccttcgtct  84600
ctgcccagcg ttctgcgggc gtggccccct ccaggggcag gggaggaggt ggctcccggc  84660
gggctcggag aactaagggg cgcacacccg cttcgcaggg ccggggtgac aggggaagcc  84720
tgagacggct gcggatctcg ctggccccgt gggtgggcgc gggggacgcg ggaggggccg  84780
agctcacggg gccagcgccg gggcctgcag gtggccctgg aggaatctgc aagcacccgc  84840
ccgtgcagcg ggccttccgg gagaccagtg tggacagcgc cctggacacg cccttcccag  84900
ctggaacatc tgtgaggctg gaatttaagc tccggcagac agggaagcgg ctggaggaag  84960
gcctggaaga aacccaagtg caaagcccag cccgagagga ggaagcagaa atgcctgacc  85020
tgcgtcaaaa tggactgtga ggataaggtt ctgggcagga tggttcgctg ccctccagag  85080
acgcagactc ggcgggagcc tgaggagcac caggggggccg ggtgcagccc ggcggagcgg  85140
gcggtgagga ccccacggct gccgcttccc tgcacggttc gcctcctcca aggcccggcc  85200
cccagcggag cccagcgctg aatcgcatgg cgccccctgg agccctggcg gggaaaacca  85260
gtggaagacc cacctcccag ggagaggacc ccactgtatc cccagataat aaaactgtcc  85320
tctcccccaa aaaataaata aataattttg tctggtcttt gaaaatgtgt atcccctgtg  85380
tactggtcaa aatgctgccc atttatctat atgcctaatt agccaacttt ttaatgaagt  85440
tatttaacat tctttttat tatgaaacaa aacagtaaat ttgttaatgg ttttaatatc  85500
atctaatatg attgaaaata tgtcaatttt tcattgccaa agaatctttg tgttatttat  85560
tttactctgt tatgtattct gtccataaag gtctaagtgg cttagaatct tgcctaacat  85620
attgtatgtg ctaagtacta actactctaa ttcatcaaat tatctttcta taccattctt  85680
aaaatacaat attattttct atttattttt attaaaattt tttgcctaat ctaattattt  85740
atgaaaatta tgaggtctat tcagtttgtc ctcttgataa aagccaaagt tttttttttt  85800
ctctcttttt ttttttttg agacggagtc tccctctgtt ccccaggctg gagtgcagtg  85860
acacaatctc ggctcaccac aacctccgct tcccgggttc aagtgattct cctgcctcag  85920
cctcccaagt agctaggact acaggcatgt gccaccacgc ctggctaatt tttgtatttt  85980
tagtagagat ggggtttcac tatattggcc aggctggtct tgaactcctg accacgtgat  86040
ccgccctcct cagcctccca aagtgctggg attataggct tgagccacct caccaggcct  86100
ttttttttat ctctttatta atacgtgaga gagtacaaat gccgctccct tacagaagca  86160
tgttgcatag tgatgaagta tgggcttttg gtgtgacaat catctgaatg ttgtttattg  86220
tcccaattag ttattttctc attcctaaac cctctccaac ctcccatctt tctgagtctc  86280
```

cagtgtctat ttttccagtc tctatatcca agtgtatgct taattgagtt cccacttaca 86340
actgagaaaa tactgaattt gattttctgt ttctgagttt tttcacttac agtaatggcc 86400
tccggtttta ttcatgttgt tgcaaaagac atgattttat tcttcatggc tgagtagcat 86460
tccatggtat acttgtatag cacattttct ttattcgatt attgattgat aaatttaaat 86520
tgatttcata tatcggctat tatgaatagt gctgtgataa acatgtcagc atgggtattt 86580
tctttatgta acaaattgtt ttcctttggg tagataccaa gtagtgggag tgctgaatca 86640
aatggaagtt ctatttttag tctattttga aatctccata ctgttttcca gaggttgtag 86700
aaagttactt tcccacaaac aatgtataag tgttctcttt tccctgtatc cttgccgata 86760
gctcattttt ctgcttttta gtaatagcca ttctgcaggg tgtaagttgg tatctcattg 86820
tggtttttaa ttggcatttc tctgatcatt gacaaggttg agcatctttt acgtgcttgt 86880
tgaccattga ccatcagtgt ctttcttttt tttaatgttc atgttctttg cttgcttttt 86940
aatgaggtta cttgttttat ttttgttgag ttgtttgagt tccttgcata ttctggacat 87000
tagatctttg tcacatgcaa aactcgtaaa catttatctc attccatagg ttttctgttc 87060
actgtgttaa ttaggaagct cattttcagg agctttttag tttaattgag ttgctgttgt 87120
ctatttttgt tattgttaca tctgcttttg agatcttagt cataaattct ttgtccaagt 87180
caatgtctag aagagtttat cctagagttt cttctagcat ttttatagtt tcaggtctta 87240
cattttagtc ttttaatcca tattgagttg atttttgtat atggtgggac ataggggtcc 87300
cattccattc ttctgcatac ggaaatataa tttttccagc acaatttgtt gaataggatg 87360
tcatttctcc agtgtgtgtt tttgttgact ttgtaaaaga tcagtcattt gtaggtatgt 87420
ggctttattt ctaggttctc tattctgtac cattgatcta tgtgtcgatt tatatcagta 87480
ccatgctgtt ttggttacta cagccttcta gcataatttt aagtcagata atgtaatatc 87540
tccagcttta ttctctttgc ttagatttgc tttgactatt caggctcttt ttgtggttcc 87600
ataagaattt tagtgggttt tttttctaat tttataaaaa ataccattgg cattttggta 87660
ggaattgcat ttaatatgta gattgttttg ggcagtagag tcattttatt gatcataatt 87720
cttccaatcc ataagcatgg gatgtttttc tcatttgtgt catgtacaat ttctttcatc 87780
agtgttttgt agttttcctt gaagggatcg ttcatctctt tgaccaattg tatttctaag 87840
cattttacct ttttttgtag ctattgtaaa aggaagtgac tttttaattc agttctcagc 87900
ttgatcatca ttagtgtata aaaatgctat caacttttgt acgttgattt ttgcatcctg 87960
aaacattatt aaatttattt atcaaatctg agtttttttgg tggtctttag aatttttgta 88020
tatatgatat tatattatca tcaaagaggg acaatttgac tttctaatta caaccacata 88080
gatgctccca ccaagatcaa tagacagagt ctctggggag ggcacaagtg atggtatttc 88140
tttaagctgg ccatgtgatt atggctggaa gcatgggccg agagccactt agctaagcct 88200
tgcctctcaa gtctgtctgt ctttctttct ttcttccttt ctttctttct gtctgtctgt 88260
ctttctttct tttctttcga cagagttttc actcattgta caggcaggag tgcagtggca 88320
ccatcttggc ccactgcaac ctccacctcc caggttcaag ggattctgca gtctcagcca 88380
cccgagtagc taggattaca ggcaccagcc accacacctg gctaattttt gtatgtttta 88440
gtagagacat ggtttggcca tgttgcccag gctggtcttg aactcctgac ctcaggttat 88500
ctgcccactt ccgcctccca aagtgttggg attacaggca taagtcacca cacccggctg 88560
cctctcaagt ttcaatgtgc atatgaatta tttccgattc caggctctct cttagtaatg 88620
tgattctgca ggtttggaag cggtccatga attggcttct ttaaaaagtc tcctcttaat 88680
gctgatgttt cttccactac atccaatata gtagcactca gctagagaaa gtaggcacag 88740
cacagagctc ctgacaccca acactgttac cacaacacaa atacttttgg ctcaaagtgg 88800
aagccaccaa tcgccatttt caaacatgtc attttctgct ggctctttgc agtttagaaa 88860
gcctagagaa ggcatcaatg tttgagtaag tctgcatttg gaaaacatgt acacatgagt 88920
taatacaatg tttattgagc acatactatg tgttcagaag tctgttacag agcactgttc 88980
aggaaacatt acatgatgtg agttaatcct catagcaccc tggggagttg ggtgctaagt 89040
tttctgtaat tttcaggact taaatgaagg gcctagcatt tctatttttt cttccatttt 89100
aaaaattatt tacctggaaa ataaaatgtg cagaataaaa gctatatcga cagatgaagg 89160
gatagagaaa aaaggatgaa ctgttcagag agatgtttta tatttatatt taccttcttg 89220
tgccttgtgg agcagctact gaatttgcag gaatggaaaa caagttgcta ggtgaggtgt 89280
ctctagaagc gctggcttca atgaaaaaga aagtataacc ccccaatata gaattatttg 89340
cttccactta tctgcttttc cattttagga aattgtgggc accagctcag gagaggcagc 89400
aggagccccc gcccgaatct ctggtctcct ttaatgagtt ctgtgagaga agattctagg 89460
gtgaggccag acctggatga ggccttagaa gagggtggat ctgggcaggg ctggaacaga 89520
aagtggaccc catgtttctg atgttcatgc tggtggagta tttccagttc tgtctttcct 89580
aagccttccc aacagagact tgactcttag agcttgtgta attttaatct gttttagcca 89640
cttccctgtc aatttttata acacatgata acaagaaact taagcaaaac tcttagggtt 89700
ttttaggaca attatatgag aagctaaaaa cttattttta ccaagataaa agaaatagaa 89760
ataatcacaa caacaacaat aattcttctg tccatgaata gtccttcagg tagtgacatc 89820
ggaactcaag gaacagcata agggaaatgg agcaaatgca gccaaggccc cctgtgcagc 89880
tcccttctcc cttccgacta caggatgctg aattcagcca ttaatccatt tcccttccga 89940
ccacaggatg ctgaattcag ccattaatcc atttcccttc cgaccacagg atgctgaatt 90000
cagccattaa tccgtttccc ttccgaccac aggatgctga attcagccat taatctgttt 90060
gctctagatg aaaagttact ggacagtaga aaccatgaat tcttcatctg tttttctgat 90120
ggtcatgtga tatagtttag atgtcccctc caaatctcat attgaatttt aatccccaat 90180
gtggcaggtg ggacctgggg aggaggtggt tgaatcactg ggtgagtccc tcatggatct 90240
gtgccatcct tgtgatagtg agtactcgtg agatctggtt gtttagaagt gtggcccatc 90300
cctcccccat ctttcttgtt tctgcttcta ccatgtgaga tgcctgcttc tctttcacca 90360
tgattgtaag cttccccagg ccttcccaga agcagacgct ggtgctatgc ttcctgtaca 90420
gcctgcagaa ccatgagcca atcaaactct tttcttataa attacccagt ctcaggtttt 90480
ttaaatagca atgcaagaat agcttaatac ctcatatgaa aagaaagcaa ttgatatatt 90540
taccagtttg agtacttacc agtttgagtc tccagacctc tgccttgctt caactcaaag 90600
aacaggaagg gagcaacctc catctactgc tcctgattat gggagaatct tcagttcatc 90660
ttaaaacatt tcagtcaaaa gcaccgtgtt ttatgtagaa gaatgagggt gtctgaaaga 90720
atgggtctct ttatttattt ttatttctga gacagggtct ctttccctgt cattctggct 90780
ggggtgcagt ggttcactgc agctttgaca ttctgtgctc cagcgattct cccacctcag 90840
cctcccaagt agctgggacc acacgtgcac actaccacaa ccagataata tttgtatatt 90900
tggcagagat gaggtttttc tatgttgagc atgctggtct tgaactcctg agctcaagtg 90960
atcctccagc ctctgccttt caaagtgctg gaattacagg tgtgagccac cacaccgggc 91020
agatgggtct taactgattt taatcaggat acatgagcat ggaagacatg cccttaattt 91080
ttttcctaat acaatatttg acagttatat aactatgatt tttttattcc tgtgattcat 91140
aaggatatga tagtaaaagg ccttgaaagc ctgtaggaaa aaagtgctat attgtgcttg 91200
aaaccacctt ttactctgaa agcaagtgcc atccagatac atcttttgag aagatatttt 91260
ctcctgctgc attttagtca aacagctgag tgtgtcttga agtagttttt tgatttttaa 91320
caggacaagt gtattttcta agaccccaaa ctcaggagtg gccatggggc aaatcaccgc 91380
tgcacacatg gaatgcatgc acagcaaatg catttctcat cccgaaccag gggttgttcc 91440
ccctgggtgc acacaggaat caccagggag gcttttaaaa ttacctaaac tcaaaaggca 91500
atagataagt gaactcagaa tccctgcagt gggacctgag ccatagtgct gtttaaagct 91560
ctctgggtga ctatggggta caaccaagcc cccaaactgc tgctttaaat cagcctcttc 91620
gggtgaacta gtggcaaatg gtttcctgaa atgaatggtt taaatcagcc ttttctggtg 91680
aactagtggc aaatggtttc ctgaaatgaa tggtttaaat cagcctcttc cggtgaacta 91740
gtggcaaacg ggttcctgaa ataaatggaa agatttgctg ctgggttgtg ctcttctgat 91800
cttacctgca ttacctactt ttccttgccg aactgacctc tgctacgtat tttattcctg 91860
attcaatcca gttctactca taccaaatgc atagtatgca ctaggtgccc ttgcattgct 91920
gaacctcacc gtggggagag gactttgctg aataataatt gcatcctaaa aaaactcaaa 91980
atactggact caaatgatcc tcctgccttg gcctcccaag agctgagact gtaggcatga 92040
gccaccgtgc ttggcctata ccctaaaaaa ttaaaactat cttacttact aaattgatgt 92100
aaacatggga agacctagaa ggtcaccgaa gtgttacaac ataagtaaat accttggaat 92160
attaatatcc atctgatgat gccccgagaa aacatgtccc actttaaaac agtacaaaac 92220
agtgctatta ttctgagata tgaagttaaa attttgtgca aataggtaat atttaaattt 92280
ttatatatgt ataacattca tgcagaaaga cgtatacaaa gaaatcatgt aaagttcaat 92340
gaattattac aaagtgaaca cacgtgtgta acctagaaat agaaccagct tcacagatgt 92400
cctggtaacc actttctctc ttttgctccc ccaaagtcac taagatctta agagctaaca 92460
gtgtagatca actttgtatt attatacatg ttttattaca gaaaatttaa aacatacaca 92520
aaataaaaga aacagtacaa taggcctgtt acccaggctc aacaacaact aataacatgc 92580
caattttgtg ttatctatac ttcaactcat ttctcacaca gactttgtta tttattatta 92640
ttttttgtgg tataaaatgt gtgctcattg aaggtaaaat cttggctgag cacaatggct 92700
taagcctgtg taatcccatc actttggaat gacaaggcag gaggatcatt tgaggtcagg 92760
agtttgagag cagcctgggc agcatagtga gaccacatct ttattaaatt ttttttttaa 92820
ttaatcaggc gcggtggtgc atgcctgtag ttccagctac ttggtatgtt gacatagcag 92880
gatcccttga ttctacgagt ttgaggctac agtgagttgt gattgtgcca ctgcacatca 92940
gcctgggtga cagagtgaga ctctgtctca aaaaaaaaat aaataaaggt tcgaccttaa 93000
ctagcttttt acacataaac acacccatat aagcaatccc tcttttaaca atagaagtac 93060
caaactaaaa atcattagtg tgaacccact tttaactcag actttatctt ttaataagtt 93120
tcttttcttt tttttttttt tgaggtaaga tgtgcactca ttgaaaggtc taatcttggc 93180
tgggcatggt ggctcacatt cgtaacctca tcactttgga agccagagct caggagtttg 93240
agaccagcct aggcaacata acaaggcctc actggggcaa gagagtgaga cctcatctct 93300
acaacaattt tttaaaagtt agttgggcat agtggtgcac acttctagtc acagctattt 93360
gagaggctga cttgggagga tcactggagt ctgggaggtc aaggctgcag tgagctgtga 93420

-continued

```
ttgcaccact gcactccttc cagagggaca gagtgaggct ctgtcaaaaa aaggtacaat  93480
tttaactgta catgtttgat acatcaacac atccatataa acaatccctc tcttaaaaat  93540
aaaagtaccc aatttaacag ttattaatat tcatatgaat tacctagaag ctttttgttt  93600
gttttggttt ggatttttat tgaaagggga cacctagaaa tgtcatttac aatctagatt  93660
ttgataaaaa taaggctgag ttttttcttt ttttgagatg gagttttgct ctgtcgccca  93720
gctggagtgc agtggattga tctcggctca ccaaaacttc tgcctcccgg gttcaagcaa  93780
tcctcctgcc tcccaactag ctgggactac aggcatgagc caccacattc agctaatttt  93840
tttttttgta tttttagtgc agatggggct tccttatgtt ggctaggcta gccttgaact  93900
cctgacctaa ggtgatccac ccgccttggc ctcgcaaagt gctgggatta caggcataag  93960
ccaccatgcc cagccagtcc taagttttgc ctgagaattt ctctttctaa gaaagtacat  94020
catatggcag ttacaaggtc tcttttgtct aaaataaata gaatttaata aataaaaatt  94080
taaaaaattt acctgagatt aaaggacaaa taaaaacaca tgggtaatat gttctctgta  94140
ggaatatatt ttaacaatga cataaattat taataatcac taaatgttgt aataatttat  94200
taactaaaat taacaaaatt cctattacga tatctaggaa aatactttct tagagtaaaa  94260
tattctcata tcttgagaga gcattggtta aaaacagcaa agatgtgcaa gtcgatgtct  94320
tatcaagtac ttactatcac gtaagtagca gacccctctt cacagctttt acagagttat  94380
ccaaaacgca gtcatttaca caagagcaga caattttcct agctttctat tgagtttata  94440
ggttaatgtt gttacaaaat ttatgaaatt acctgaccaa attttatata ttatttcata  94500
atatatcaaa atttatttag atgtcaaatt tcatatcata atattataat atataacgat  94560
atcatattat gataagttcc atttactttc agacaatttc actaggcagt gtctgtctac  94620
cactaattct tttttcgttc cactatttgc acaggcagca cagctgggaa aacacagact  94680
cacccaacac agtctcttcc ctgtgacttt ctcctcctca aggaatcagt tcatcagtca  94740
atcaagtcat ttgggactgg aggctgagta ctccttaaca tagaaggtct cgttcctgca  94800
tgctttcctc agcagagggg gagacaagaa ggtcctttta ggggacactt gcttggacat  94860
agactaggct agttggaggg ctctgaccag cagagacaga ctccgccgca gtaggaaggg  94920
atgaggcagc tgttctgaac ctggagctcc accacacctt gtcctgtctc actgaggcag  94980
ttttgagagg ctgccctgga atacgtcttg ctggtggatg ttgagaatca atgtgggctt  95040
tgacgggatt caggtggtgt ccgcagtgtg aagacaggag ctgatgttca gaatctaggc  95100
tgtttgtctt gtgatcagtt gggttacctg tttgagacca agtccatttt cactagggag  95160
ggctgaataa agcccacaga acacaatggc gctcccagga tgactgagga agggtgagaa  95220
tgggggaaag tttttccacc gagacttttt gctacctcag gaatcggggg ctaattaggt  95280
tagcactgac tcaacctaat caattcaatt ttattgcatt tgatctaatt atcttcccca  95340
tttttaaggt aggaagggcc atttcatttg gtatttattt tttctctgca tttttatttc  95400
atcatatatg tgtggaccta atacaatcaa ccataatttg acatttgttg tttccaagca  95460
tttaagaaat tataatatct atgcatacaa tgttaacact atgtataata aattctcttt  95520
ctgtgcaaaa tatataacat atgacaatat aggcatgttt aattgtgcat cttgaaaggt  95580
gaacaggatc ataaatcctt ccaggtagga actgggacag aaataggaag aaatgcttcc  95640
ccgattttcc ggtccctgtg ctcccggttc tttgttttct ggacaccatg acaggatcct  95700
gaaaatgtct ccctttaact gtgtctaggt ccccagtaga actacagcaa gaaacttctg  95760
```

```
attgaggctc taagaagcgg caggaatgag aaaactcttc agccaataag agtaagccac  95820
gcccagccga gggacgtata aaaggcaggt ctagcagact aacccacact ctgcctttgg  95880
acgtgagaga gagcgcacct ttcacttgag cttcaacatg ggaaagggaa atgaagactc  95940
cgatctccac tgctcctcca tccagtgctc cactgaccag ccccctttcc aacagatctc  96000
ctttacagaa aagggctcag atgagaagaa accattcaaa gaaaaaggca agaccgcctt  96060
ctcccattcc agtgagaagc acatacaaag gcaaggtaag gccttgggct gctcctgtgg  96120
agtctggaag gagggttgga atcagggata ctgagctgtg tctttagcag ggttttattt  96180
tgagatttgg ggatgggaaa tggcttagtg ccctcagggg acttgagaaa tgtgttcact  96240
cgtgacactg gcagaagagc ttcacatgaa agactgatcc gcaaaaatgc atcagagata  96300
gactgtggga ctctgcctag ggagaggtga gtcacctaaa ccttctcttg cagcaggatc  96360
ggagcccaat ccaaacaagg agaattctga ggaaaccaag ctcaaggccg ggaacagcac  96420
tgctggatca ggtaagattt gactctttca aggtgagaag ggacagggaa gcaacacagg  96480
ctcccctggc aaggaaactg ggagctcctt ggcagccagg gccgtacaga tcctggacac  96540
tggagaacag aagagagctg gggtttggtg gtaacctcag ctcctgtgtg tccaggatgg  96600
actaggaatt tcagggtgtt cagttggagg cactttctca aactctcatt gtgttcacag  96660
aaccagagtc cagctcatat cgggaaaact gcaggaaaag aaaaatgagt tccaaggaca  96720
gctgccaaga cacagcaggt agaatcttgg tgtttgttgt tggtggtggt ggtttttttg  96780
tttttggttt gccccaaaag gcaaataatc aggaaacttt tatacgaggc ttgagcggaa  96840
agggagttac ttattgacga gtaaattttt gagatcttag cactctgaga atatttgggg  96900
actcacaggg ggttcagcct cacttcattc cagtgctgag atggtcagga aggagtggga  96960
gagacaagtg gggttcacct gggtgtacag ggggttctgg aaatcagggt ctgtggggac  97020
tgctctggtg agtctctcac atgctttctt tgcagggaac tgtccagaaa aggagtgcag  97080
cttgtcattg aataaaaaat caagatcctc cactgctgtg cacaacagtg aaatccagga  97140
gacctgtgat gcccaccata ggggacattc cagggcttgc actgggcaca gcaagcggca  97200
taggtctcgg gccctaggag tccaaacacc gtcaattcga aaaagcttgg tgacttctgt  97260
gcgagctatg tcagaggctg tttatcaaga cctagcccag gtgtgggcac agcagatcca  97320
ttctccactt acctgtgagc agctgacact gctcactcgg ctccgggggc ctctgtgtgc  97380
ccaggtgcag accttgtatt ccatggccac ccaggcagct tatgtcttcc ctgctgagag  97440
ctggcttgtc ccagccacac tgccaggtcc tggggaatca gccctggata gagaagccca  97500
tcccttccct gggcaggaga taactgagac tgtcagtgga tcagatgagg ctaagctgtg  97560
agcaccctga ccctattcag cagagatgca gctctgggaa tgagaacaag gatctgcttc  97620
ttctcagatt cttccagatg accagcagtg acaattttag acacactgtg ttaataaatg  97680
acagaacctg aagaagtcat aggaaagaaa cttgagcggt atactcagaa tggtgagagc  97740
cctgaatttt gcagaccgct aagactatag acaaatttta tatttcatgt tagacatttg  97800
atgccttttg gatgtctgat gacagtcatg catttctata taatcagaaa aacattagaa  97860
tgtaatcgtg aatttgcata ttttagattg tagaaaagta aatataaaat tatgtgctcc  97920
ttttttgttt tttttttttt ttgagacagt cttgctatgt tacccaggct ggagtgcagt  97980
ggcacaatct tagctcactg caacctctgc ttcctgggtt caaacaattc tcatgcctca  98040
gcctcccaag cagctgggac tacaggcatg tactgctatg cctggctaat tttttttttc  98100
ctgtattgtt agtagagaca gagttttgtc actttggcca ggttggcctc gaactcaggt  98160
```

gatctgccag cctccgcctc ccaacgtgct gggattacag gcatgagccg ccttaccaag 98220
aaattgcttc tcttttaatc cagaaaaggt tgtaggctct cactcttcca gcctgaaccc 98280
atggagtact aatatccaca aaccattaat agcactccct gtgggaaaat gtctatatat 98340
ttttagtttg atataattat agtaaaatta ctatgcaagc tgtttacttt taatatttct 98400
acataaaatt taagtcaaga tatagtaaat ggtaaatgat tgtacttatt tattgacctg 98460
cctcatgttt catttcattt taaacatcct aaatttatat tttattatat tttatacatt 98520
tcaattgatt gtactatatt gcaggatatg gagatttcat cacgtactac aatacagtgt 98580
attttgttat atttgacgta tattctactt gtattttgta ctgagatcat acactatttc 98640
attatctaag tgtattaatt gtttggttgc tttataattt tcattttatg taatgaaata 98700
aacaatgttg tttggaattt taaatttctt tcatatggaa tttgtattta ataaa 98755

<210> SEQ ID NO 4
<211> LENGTH: 16
<212> TYPE: DNA
<213> ORGANISM: Artificial Sequence
<220> FEATURE:
<223> OTHER INFORMATION: synthetically generated oligonucleotide

<400> SEQUENCE: 4
cacgtctata caccac 16

<210> SEQ ID NO 5
<211> LENGTH: 16
<212> TYPE: DNA
<213> ORGANISM: Artificial Sequence
<220> FEATURE:
<223> OTHER INFORMATION: synthetically generated oligonucleotide

<400> SEQUENCE: 5
taaccctaac cctaac 16

<210> SEQ ID NO 6
<211> LENGTH: 16
<212> TYPE: DNA
<213> ORGANISM: Artificial Sequence
<220> FEATURE:
<223> OTHER INFORMATION: synthetically generated oligonucleotide

<400> SEQUENCE: 6
tctctgtctc tgtcgc 16

<210> SEQ ID NO 7
<211> LENGTH: 40
<212> TYPE: DNA
<213> ORGANISM: Artificial Sequence
<220> FEATURE:
<223> OTHER INFORMATION: synthetically generated oligonucleotide

<400> SEQUENCE: 7
tgcactgacg tcctgtggcc actgggtggc gccagagcat 40

<210> SEQ ID NO 8
<211> LENGTH: 40
<212> TYPE: DNA
<213> ORGANISM: Artificial Sequence
<220> FEATURE:
<223> OTHER INFORMATION: synthetically generated oligonucleotide

<400> SEQUENCE: 8
taatctgaat atctgggcct ccgtgtgcag acctgaggtt 40

<210> SEQ ID NO 9
<211> LENGTH: 40
<212> TYPE: DNA
<213> ORGANISM: Artificial Sequence
<220> FEATURE:
<223> OTHER INFORMATION: synthetically generated oligonucleotide

<400> SEQUENCE: 9
gtctctgtgt ctgtctctct gtctctgtcg ctaactctat 40

<210> SEQ ID NO 10
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 10
ctcagagccc agtgtcaatc ac 22

<210> SEQ ID NO 11
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 11
cacgaccgct tagaagaacc gg 22

<210> SEQ ID NO 12
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 12
gagacggcct accatgtgct tc 22

<210> SEQ ID NO 13
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 13
gtgagtgctg tgaactcggc tg 22

<210> SEQ ID NO 14
<211> LENGTH: 23
<212> TYPE: DNA
<213> ORGANISM: Artificial Sequence
<220> FEATURE:
<223> OTHER INFORMATION: synthetically generated oligonucleotide

<400> SEQUENCE: 14
cagggcctga tttggcttga aac 23

<210> SEQ ID NO 15
<211> LENGTH: 23
<212> TYPE: DNA
<213> ORGANISM: Artificial Sequence
<220> FEATURE:
<223> OTHER INFORMATION: synthetically generated oligonucleotide

<400> SEQUENCE: 15
gaagagtagt ctgacctcat ctc 23

<210> SEQ ID NO 16
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 16
cagggcatga tatcctcttt gg 22

<210> SEQ ID NO 17
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 17
cattcaatgg tgttgatgat ggtac 25

<210> SEQ ID NO 18
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 18
ggttagaata cagcgcggac attca 25

<210> SEQ ID NO 19
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 19
gtgaatctcc gaggcaactg tc 22

<210> SEQ ID NO 20
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 20
gagcgcctca gtgtgcaaat ct 22

<210> SEQ ID NO 21
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 21
actgggtggc gccagagcat 20

<210> SEQ ID NO 22
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 22
ctccgtgtgc agacctgagg tt 22

<210> SEQ ID NO 23
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 23
ccctacctac cctccagaga 20

<210> SEQ ID NO 24
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 24
tctctgtctc tgtcgctaac 20

<210> SEQ ID NO 25
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 25
taaccctaac cctaacccta 20

<210> SEQ ID NO 26
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 26
ttagggttag ggttagggtt 20

<210> SEQ ID NO 27
<211> LENGTH: 26
<212> TYPE: DNA
<213> ORGANISM: Artificial Sequence
<220> FEATURE:
<223> OTHER INFORMATION: synthetically generated oligonucleotide

<400> SEQUENCE: 27
tggaggttaa acgattattt atctgc 26

<210> SEQ ID NO 28
<211> LENGTH: 19
<212> TYPE: DNA
<213> ORGANISM: Artificial Sequence
<220> FEATURE:
<223> OTHER INFORMATION: synthetically generated oligonucleotide

<400> SEQUENCE: 28
acgagtttcc aaggtgctg 19

<210> SEQ ID NO 29
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 29
ctgctacttc aactcctggt gtgc 24

<210> SEQ ID NO 30
<211> LENGTH: 23
<212> TYPE: DNA
<213> ORGANISM: Artificial Sequence
<220> FEATURE:
<223> OTHER INFORMATION: synthetically generated oligonucleotide

<400> SEQUENCE: 30
aggcgaattg ggatgtagct cag 23

<210> SEQ ID NO 31
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 31
gcatatgttg tgttttacag 20

<210> SEQ ID NO 32
<211> LENGTH: 18
<212> TYPE: DNA
<213> ORGANISM: Artificial Sequence
<220> FEATURE:
<223> OTHER INFORMATION: synthetically generated oligonucleotide

<400> SEQUENCE: 32
gcaacaaatt gataagca 18

<210> SEQ ID NO 33
<211> LENGTH: 30
<212> TYPE: DNA
<213> ORGANISM: Artificial Sequence
<220> FEATURE:
<223> OTHER INFORMATION: synthetically generated oligonucleotide

<400> SEQUENCE: 33
taaccctaac cctaacccta accctaaccc 30

<210> SEQ ID NO 34
<211> LENGTH: 39
<212> TYPE: DNA
<213> ORGANISM: Artificial Sequence
<220> FEATURE:
<223> OTHER INFORMATION: synthetically generated oligonucleotide

<400> SEQUENCE: 34
gtagacccac gacatactca gcaccggcct caccccatt 39

<210> SEQ ID NO 35

<211> LENGTH: 40
<212> TYPE: DNA
<213> ORGANISM: Artificial Sequence
<220> FEATURE:
<223> OTHER INFORMATION: synthetically generated oligonucleotide

<400> SEQUENCE: 35
aaggccagcc gcggttccag acctgcggtg cggccgtgtc 40

<210> SEQ ID NO 36
<211> LENGTH: 40
<212> TYPE: DNA
<213> ORGANISM: Artificial Sequence
<220> FEATURE:
<223> OTHER INFORMATION: synthetically generated oligonucleotide

<400> SEQUENCE: 36
taatctgaat atctgggcct ccgtgtgcag acctgaggtt 40

<210> SEQ ID NO 37
<211> LENGTH: 40
<212> TYPE: DNA
<213> ORGANISM: Artificial Sequence
<220> FEATURE:
<223> OTHER INFORMATION: synthetically generated oligonucleotide

<400> SEQUENCE: 37
ttgggggcgt gtctcagagc aggaggggtg tggtctggca 40

<210> SEQ ID NO 38
<211> LENGTH: 40
<212> TYPE: DNA
<213> ORGANISM: Artificial Sequence
<220> FEATURE:
<223> OTHER INFORMATION: synthetically generated oligonucleotide

<400> SEQUENCE: 38
gtctctgtgt ctgtctctct gtctctgtcg ctaactctat 40

<210> SEQ ID NO 39
<211> LENGTH: 40
<212> TYPE: DNA
<213> ORGANISM: Artificial Sequence
<220> FEATURE:
<223> OTHER INFORMATION: synthetically generated oligonucleotide

<400> SEQUENCE: 39
aaagccacca ggcctctaat ccctacctac cctccagaga 40

<210> SEQ ID NO 40
<211> LENGTH: 40
<212> TYPE: DNA
<213> ORGANISM: Artificial Sequence
<220> FEATURE:
<223> OTHER INFORMATION: synthetically generated oligonucleotide

<400> SEQUENCE: 40
cctggagaaa tcaagtctgc gaagatccaa aaattaaaat 40

<210> SEQ ID NO 41
<211> LENGTH: 40
<212> TYPE: DNA
<213> ORGANISM: Artificial Sequence
<220> FEATURE:
<223> OTHER INFORMATION: synthetically generated oligonucleotide

<400> SEQUENCE: 41
tgcactgacg tcctgtggcc actgggtggc gccagagcat 40

<210> SEQ ID NO 42
<211> LENGTH: 40
<212> TYPE: DNA
<213> ORGANISM: Artificial Sequence
<220> FEATURE:
<223> OTHER INFORMATION: synthetically generated oligonucleotide

<400> SEQUENCE: 42
ctgaccacca ggctacagtg tcctgtaacc gccaggcata 40

<210> SEQ ID NO 43
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 43
cgtcccgtag acaaaatggt 20

<210> SEQ ID NO 44
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 44
ttgatggcaa caatctccac 20

<210> SEQ ID NO 45
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 45
cacagtgatg tcacccacga 20

<210> SEQ ID NO 46
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 46
gtgagaatcg ctccgtcctg 20

<210> SEQ ID NO 47
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 47
ggacgagagg ggacaaagga 20

<210> SEQ ID NO 48
<211> LENGTH: 21
<212> TYPE: DNA

<213> ORGANISM: Artificial Sequence
<220> FEATURE:
<223> OTHER INFORMATION: synthetically generated oligonucleotide

<400> SEQUENCE: 48
ggtcaaacct ggactctggc a 21

<210> SEQ ID NO 49
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 49
gaagtgggac aggaagtgag 20

<210> SEQ ID NO 50
<211> LENGTH: 17
<212> TYPE: DNA
<213> ORGANISM: Artificial Sequence
<220> FEATURE:
<223> OTHER INFORMATION: synthetically generated oligonucleotide

<400> SEQUENCE: 50
cgggaacagg aagtggc 17

<210> SEQ ID NO 51
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 51
ccagtctaat ggtgacctgg g 21

<210> SEQ ID NO 52
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 52
tgagagtcag catgcaccag 20

<210> SEQ ID NO 53
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 53
taccgaggac cacggactaa 20

<210> SEQ ID NO 54
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 54
aatacacggt gcctcttccg 20

<210> SEQ ID NO 55
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 55
caggtatcca tggccccgat gggc 24

<210> SEQ ID NO 56
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 56
ctcggtctct cgaatcggat ccgac 25

<210> SEQ ID NO 57
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 57
gagttatggg cactgcattt tagca 25

<210> SEQ ID NO 58
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 58
ttgttaaacg caggctagat cctga 25

<210> SEQ ID NO 59
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 59
cgccatttta tagacttctg agcag 25

<210> SEQ ID NO 60
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 60
cctaattctt ggcgtaactg gctcg 25

<210> SEQ ID NO 61
<211> LENGTH: 25
<212> TYPE: DNA
<213> ORGANISM: Artificial Sequence
<220> FEATURE:

-continued

<223> OTHER INFORMATION: synthetically generated oligonucleotide

<400> SEQUENCE: 61
atgcttagga agagggacaa atgca 25

METHODS OF REDUCING EXPRESSION OF X-INACTIVATION ESCAPEE GENES AND AUTOSOMAL GENES

CLAIM OF PRIORITY

This application is a § 371 National Stage Application of PCT/US2016/064438, filed Dec. 1, 2016, which claims the benefit of U.S. Provisional Patent Application Ser. No. 62/261,698, filed on Dec. 1, 2015. The entire contents of the foregoing are hereby incorporated by reference.

FEDERALLY SPONSORED RESEARCH OR DEVELOPMENT

This invention was made with Government support under Grant No. R01-GM58839 awarded by the National Institutes of Health. The Government has certain rights in the invention.

TECHNICAL FIELD

Described herein are inhibitory nucleic acids, e.g., antisense oligonucleotides (ASO) against PAR-TERRA RNA and TERRA of autosomal origin, and methods of use thereof to downregulate: (i) expression of escapee genes on the inactive X chromosome (Xi), e.g., in cells and subjects with supernumerary X chromosomes, (ii) expression from the active X chromosome (Xa), (iii) expression a network of autosomal genes involved in growth control and apoptosis, and (iv) expression of the genetic locus associated with FSHD (facioscapulohumeral muscular dystrophy) and other subtelomeric autosomal genes.

BACKGROUND

The mammalian genome is ubiquitously transcribed and the ends of telomeres are no exception. In spite of their heterochromatic properties, telomeric ends actively synthesize a heterogeneous population of long noncoding RNAs dubbed "TERRA" (Azzalin et al., 2007; Schoeflner and Blasco, 2007; Zhang et al., 2009). TERRA transcripts range in size from 100 bases up to >9 kb and contain the canonical telomeric repeat sequence, UUAGGG, as well as sequences unique to the sub-telomeric region of each chromosome. The function of TERRA has generated major interest in light of its association with human diseases, such as cancer and the ICF syndrome (immunodeficiency, centromere instability, and facial anomalies) (Maicher et al., 2012; Azzalin and Lingner, 2015). Elegant studies have pointed to a number of telomere-associated functions. Telomeres are well-defined nucleoprotein complexes that cap the physical ends of linear chromosomes and protect them from unprogrammed shortening and genetic rearrangements (Blackburn et al., 2006; Sfeir and de Lange, 2012; Bernardes de Jesus and Blasco, 2013; Doksani and de Lange, 2014; Azzalin and Lingner, 2015). The reverse transcriptase activity of the RNA-containing telomerase complex enables regeneration of chromosomal ends that are lost with every DNA replication (Lingner et al., 1997). However, TERRA's activity does not appear to be directly related to telomerase activity (Schoeftner and Blasco, 2007; Redon et al., 2010; Redon et al., 2013). Rather, TERRA seems to keep telomere length in check (Sandell et al., 1994; Luke et al., 2008; Maicher et al., 2012; Pfeiffer and Lingner, 2012; Pfeiffer et al., 2013; Wang et al., 2015), regulate recombination (Balk et al., 2013; de Silanes et al., 2014; Yu et al., 2014), and serve as a scaffold for recruitment of HP1, histone methyltransferases, and shelterins to telomeric heterochromatin (Deng et al., 2009). Thus, TERRA is an integral part of the telomeric architecture.

Cytological studies indicate that only about half of detectable TERRA transcripts are localized to telomeres (Le et al., 2013). The remaining half is presumed to be "free" in the nucleoplasm. Nevertheless, investigation into TERRA function has focused almost exclusively on telomeres, though early observations noted a large cluster of TERRA transcripts near the inactive X-chromosome (Xi) of somatic female cells (Schoeftner and Blasco, 2008; Zhang et al., 2009). TERRA RNA is also concentrated next to the Y-chromosome (Zhang et al., 2009).

SUMMARY

Telomeric repeat-containing RNAs (TERRA) are highly conserved long non-coding RNAs transcribed from telomeric ends of eukaryotic chromosomes. TERRA has so far only been ascribed function in telomere biology. Genome-wide binding sites for TERRA have now been identified, and show that TERRA localization is not cis-limited, nor is TERRA function confined to telomeres. Transcriptomic analysis shows that TERRA depletion results in dysregulation of TERRA target genes. Described herein is a subclass of TERRA transcripts specific to the sex chromosomes. Dubbed PAR-TERRA, these transcripts originate within the pseudoautosomal region (PAR) and mediate two special sex-linked processes. First, in somatic cells, PAR-TERRA prevents spreading of Xist RNA away into genes that escape silencing on the inactive X (Xi). PAR-TERRA renders X-linked escapee genes immune to Xist RNA. Depleting PAR-TERRA leads to downregulation of escapees. We also show that depleting PAR-TERRA reduces expression of the Xa gene and various target autosomal genes, especially those involved in apoptosis and cell cycle regulation. Thus, the methods can also be applied to downregulate a network of autosomal genes involved in growth control and apoptosis. Provided herein is evidence that PAR-TERRA sets up a specialized privileged compartment that aids in boosting transcriptional activity specific genes across the genome. Thus, PAR-TERRA may be targeted to turn down (i) expression of escapee genes on the inactive X chromosome (Xi), e.g., in cells and subjects with supernumerary X chromosomes, (ii) expression from the active X chromosome (Xa), or (iii) expression a network of autosomal genes involved in growth control and apoptosis. The present methods include using inhibitory nucleic acids, e.g., antisense oligonucleotides (ASO) against PAR-TERRA RNA to downregulate expression of these classes of genes.

Thus, provided herein are isolated inhibitory nucleic acids targeting PAR-TERRA, preferably wherein the inhibitory nucleic acid is modified, and compositions comprising the isolated nucleic acids.

Also provided are methods for decreasing expression of an Xi escapee gene in a cell, preferably a cell of a subject have a supernumerary X chromosome. The methods include administering to the cell an inhibitory nucleic acid targeting PAR-TERRA, preferably wherein the inhibitory nucleic acid is modified.

Further, provided are methods for decreasing expression of Xa genes in a cell, preferably a cell of a subject having a supernumerary X chromosome. The methods include administering to the cell an inhibitory nucleic acid targeting PAR-TERRA, preferably wherein the inhibitory nucleic acid is modified.

Also provided are methods for treating a subject who has a disorder of sex chromosome aneuploidy associated with a supernumerary X chromosome. The methods include administering to the subject an inhibitory nucleic acid targeting PAR-TERRA, preferably wherein the inhibitory nucleic acid is modified.

Also provided is a composition described herein, e.g., comprising an inhibitory nucleic acid targeting PAR-TERRA, for treating a subject who has a disorder of sex chromosome aneuploidy associated with a supernumerary X chromosome.

In some embodiments described herein, the subject has 46,XY, 47,XXY, 48,XXYY, 48,XXXY, 47,XXX, 48,XXXX or 49,XXXXX aneuploidy.

In some embodiments described herein, the cell is from a subject who has 46,XY, 47,XXY, 48,XXYY, 48,XXXY, 47,XXX, 48,XXXX or 49,XXXXX aneuploidy.

Also provided are methods for decreasing expression of X-linked, autosomal growth control or apoptosis genes, and sub-telomeric autosomal genes in a cell (e.g., out D4Z4, DUX4, FRG1, and FRG2 for FSHD, from Chr4). The methods include administering to the cell an inhibitory nucleic acid targeting PAR-TERRA, PAR, or TERRA, preferably wherein the inhibitory nucleic acid is modified.

In addition, provided are methods for decreasing expression of autosomal genes in a cell. The methods include administering to the cell an inhibitory nucleic acid targeting PAR-TERRA or an autosome-specific TERRA (e.g., TERRA species originating with the subtelomeric region of an autosome and comprising autosome-specific 5' sequences), preferably wherein the inhibitory nucleic acid is modified. In some embodiments, the inhibitory nucleic acid targets Chr4-specific TERRA. In some embodiments, expression of FRG1, FRG2, DUX4, and the long noncoding RNAs of forward and reverse orientations from the macrosatellite repeat, D4Z4 is decreased. In some embodiments, the cell is from or in a subjection who has facioscapulohumeral muscular dystrophy (FSHD). Thus, in a specific example the methods include targeting the Chr4 region associated with facioscapulohumeral muscular dystrophy (FSHD), which is located in the subtelomeric region of human Chr4 and contains coding genes FRG1, FRG2, DUX4, and the long noncoding RNAs of forward and reverse orientations from the macrosatellite repeat, D4Z4. FSHD is caused by ectopic expression of these genes when the D4Z4 repeat contracts and becomes “activated”. Thus, PAR-TERRA or Chr4-specific TERRA can be targeted to downregulated the associated subtelomeric genes. Other subtelomeric genes, e.g., as shown in FIG. 4A,B, from 5 chromosomes are shown (Chr1,3,8,18,19), can also be targeted.

In some embodiments described herein, the inhibitory nucleic acid does not comprise three or more consecutive guanosine nucleotides or does not comprise four or more consecutive guanosine nucleotides.

In some embodiments described herein, the inhibitory nucleic acid is 8 to 30 nucleotides in length.

In some embodiments described herein, at least one nucleotide of the inhibitory nucleic acid is a nucleotide analogue.

In some embodiments described herein, at least one nucleotide of the inhibitory nucleic acid comprises a 2'O-methyl, e.g., wherein each nucleotide of the inhibitory nucleic acid comprises a 2'O-methyl.

In some embodiments described herein, the inhibitory nucleic acid comprises at least one ribonucleotide, at least one deoxyribonucleotide, or at least one bridged nucleotide.

In some embodiments described herein, the bridged nucleotide is a LNA nucleotide, a cEt nucleotide or a ENA modified nucleotide.

In some embodiments described herein, each nucleotide of the inhibitory nucleic acid is a LNA nucleotide.

In some embodiments described herein, one or more of the nucleotides of the inhibitory nucleic acid comprise 2'-fluoro-deoxyribonucleotides and/or 2'-O-methyl nucleotides.

In some embodiments described herein, one or more of the nucleotides of the inhibitory nucleic acid comprise one of both of ENA nucleotide analogues or LNA nucleotides.

In some embodiments described herein, the nucleotides of the inhibitory nucleic acid comprise comprising phosphorothioate internucleotide linkages between at least two nucleotides, or between all nucleotides.

In some embodiments described herein, the inhibitory nucleic acid is a gapmer or a mixmer.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

REFERENCE TO SEQUENCE LISTING

This application includes a sequence listing submitted herewith in electronic format. The entire content of this files is hereby incorporated by reference.

DESCRIPTION OF DRAWINGS

The patent or application file contains at least one drawing executed in color. Copies of this patent or patent application publication with color drawing(s) will be provided by the Office upon request and payment of the necessary fee.

Figure 1A:
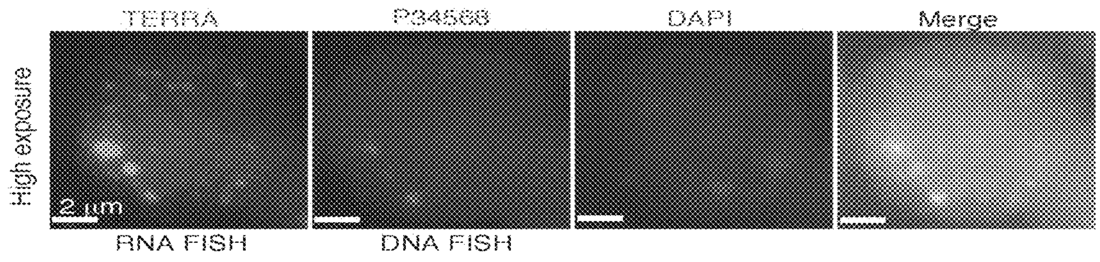
FIGS. 1A-H. Telomeric RNAs produced by the sex chromosomes

A. TERRA RNA FISH followed by PAR DNA FISH using P34567 probes, which are subsets of BAC RP24-500I4 DNA. Higher exposure of TERRA RNA FISH revealed that multiple TERRA foci were sparely distributed across the nucleus in mES cells. DAPI detects nuclear DNA.

B. Map of the PAR and relative positions of BAC clones, RP24-143B12 and RP24-500I4. Locations of internal (TTAGGG) repeats shown in red. Dotted purple lines, incompletely assembled regions.

C. TERRA RNA FISH followed by PAR DNA FISH (n=204) using P34567 probes in ES cells. Lower exposure of TERRA RNA FISH showed that the dominant TERRA foci were colocalized with PAR DNA. 80-90% of TERRA signals localized to ChrX and Y.

D. Percent colocalization of PAR and TERRA signals. n=139 (male); 209 (female).

E. Two color RNA FISH detecting TERRA (Alexa488, green) and PAR transcripts (Cy3, red) in ES cells. Nick-translated BAC DNA was used to detect PAR RNA.

F. Top panel: Map of sub-BAC probes and PCR amplicons. Left panel: Northern blot analysis of PAR-TERRA RNA using either TERRA or 36K oligo probes in ES cells on differentiation days 0-12, as indicated. GAPDH, loading control. Right panel: Primer extension using an antisense TERRA oligo probe with PCR amplification using PAR-specific primer pairs located at 33, 36, and 39 k (kb) from the end of BAC RP24-500I4TERRA. +, with RT; –, without RT.

G. Northern blot analysis of PAR-TERRA in ES cells using TERRA-specific or PAR-specific oligo probes, as shown in panel F.

H. Higher exposure RNA FISH indicating colocalization of TERRA and PAR signals at both large and small foci in ES cells. Three-color RNA FISH (upper panel): TERRA oligo probe; PAR-specific probes, 47k and 22k. Two-color RNA FISH (lower panel): TERRA oligo probe; PAR specific probe, 31k. DAPI was used for nuclear staining. Right graph, quantitation of colocalization.

FIGS. 2A-I. Mapping genomic PAR-TERRA binding sites by ChIRT-seq

A. To capture the PAR-TERRA transcripts, five DNA oligo probes were used: 22k, 31k, 34k, 36k, and 47k. Each probe has multiple alignments to the RP24-500I4 BAC DNA around the telomeric repeats.

B. RNA slotblot analysis showing that TERRA-AS and PAR-31-AS probes specifically captured TERRA RNA by ChIRT. Total RNA was extracted from beads after ChIRT hybridization without RNase H elution.

C. Quantitative PCR showing the enrichment of PAR DNA in TERRA-AS ChIRT and PAR ChIRT, but not TERRA-S ChIRT in ES cells. TERRA-AS ChIRT used antisense DNA oligos against TERRA, TERRA-S ChIRT used TERRA sense probes as a control, and PAR ChIRT used PAR probes for the PAR transcripts.

D. Enrichment of PAR DNA following TERRA ChIRT was observed only when elution was performed with RNaseH. Enrichment was abolished in the RNase A pre-treated control (Pre-RNaseA).

E. Table of ChIRT results indicating the number of PAR and TERRA binding sites in ES cells on different days of differentiation and in MEFs. Different normalization methods produced similar results, as shown.

F. Scatterplot analysis comparing log2 coverages of TERRA and PAR ChIRT in indicated samples. Pearson's r shown. ChIRT results were normalized to input unless otherwise indicated.

G. TERRA ChIRT-seq showed enrichment for telomeric repeats DNA in female ES cells. Samples captured by TERRA-AS or TERRA-S. No-RNAseH for the TERRA-AS capture is also shown as a control.

H. Pie charts show relative representation of various genomic regions in TERRA (top) and PAR (bottom) ChIRT-seq experiments in female ES cells.

I. CEAS analysis shows significant over-representation of introns and noncoding regulatory regions. Exons are under-represented. ***, P<0.001 (one-sided binomial test). The genome reference was obtained from the ChIRT-seq input.

FIGS. 3A-D. X-linked PAR-TERRA RNA binds in cis and in trans to multiple chromosomes.

A. ChIRT-seq tracks showing PAR-TERRA enrichment at the ends of various chromosomes in female ES cells (top) and MEFs (bottom). TERRA ChIPT-seq data was normalized to input (TERRA/input), no-RNase H control (TERRA/no RNase H), or the sense control (TERRA/sense).

B. Magnified views of the female ES PAR-TERRA ChIRT-seq results for the pseudoautosomal regions of ChrX and ChrY.

C. Female ES ChIRT-seq tracks showing PAR-TERRA enrichment on multiple autosomes. Red bars, internal TTAGGG repeats. Grey bars, sequence gaps.

D. ChIRT-seq tracks of female ES cells showing PAR-TERRA binding to non-telomeric autosomal regions.

FIGS. 4A-G. Transcriptome analysis of PAR-TERRA-depleted cells.

A. Northern blot analysis of TERRA RNA shows depletion by treatment with gapmer LNA against TERRA or PAR in ES cells. Control, scramble LNA gapmer (Scr KD).

B. RNA FISH detecting TERRA (Alexa-488, green), or PAR (Cy5, cyan blue) after LNA knockdown in ES cells.

C. Venn diagram of genes affected by TERRA versus PAR KD. Number of genes in each circle and overlapped region is indicated. 56 genes are shared between TERRA and PAR KD in female ES cells; 36 in MEF.

D. Heatmap of differentially expressed genes in TERRA KD, PAR, and Scr KD. 56 shared genes were examined for ES cells; 36 shared genes for MEF. Scale in Log10 FPKM.

E. Heatmap of differentially expressed genes in TERRA KD, PAR KD, and Scr KD ES cells or MEFs. 8 genes were shared in both ES cells and MEFs.

F. Probability density function for the 565 genes with and 14,724 genes without PAR-TERRA binding sites in the structural gene ±10 Kb of flanking sequence, with respect to their likehood of changing gene expression following PAR-TERRA KD. Log2 fold-change (AFPKM) is plotted. After PAR-TERRA KD, there is a net downregulation for the group of genes with PAR-TERRA binding sites. Kolmogorov-Smirnoff (KS) test, P<0.0001.

G. Cumulative fraction that genes with or without PAR-TERRA sites would be up- or down-regulated following PAR or TERRA KD, as indicated. P-values determined by $\chi^2$ analyses.

FIGS. 5A-F. PAR-TERRA protects escapees and genes of the subtelomeric/pseudoautosomal regions from silencing.

A. RNA-seq shows downregulation of subtelomeric genes following TERRA KD in ES cells. ChIRT-seq and post-KD RNA-seq tracks are shown.

B. RT-qPCR confirms that Tmx3 and Wls are downregulated upon TERRA KD in MEFs.

C. Whole-ChrX view of PAR-TERRA binding sites. Two regions (boxes) show high-level binding. Escapee genes shown below the chart.

D. Table showing the numbers of total and ChrX PAR-TERRA binding sites in female ES cells and in MEFs.

E. Probability density functions for escapees (n=15), Xi genes (n=438) subject to XCI. Escapee genes have higher PAR-TERRA binding densities relative to genes subject to XCI (P<0.001 for TERRA density, P<0.05 for PAR density, KS test).

F. RT-qPCR of pseudoautosomal genes following PAR or TERRA KD. P-values determined by the Student t-test.

FIGS. 6A-I. TERRAs regulate the gene expression on the PAR

A. Dynamics of Xist RNA spread following PAR-TERRA KD in female MEFs. Shown are tracks for Xist CHART-seq after Scr, TERRA, or PAR KD, and tracks for PAR-TERRA ChIRT-seq. Yellow-shaded region corresponds to the PAR-TERRA and Xist boundaries within Mid1.

B. Metagene analysis of PAR-TERRA density across XCI-repressed (n=438) and escapee genes (n=15). Relative PAR-TERRA density from PAR or TERRA ChIRT in MEFs was produced by CEAS analysis.

C. Scatterplot analysis comparing Xist coverage (log2 scale) in PAR-TERRA KD female MEFs relative to Scr KD on ChrX. The transcriptomic profiles are highly similar (Pearson's r>0.90). Outliers (dots) map to the "borders" of pseudoautosomal genes. Xist coverage files were normalized to the corresponding ChrX median values, and individual dots in the scatterplot represents an average of two biological replicates.

D. Metagene analysis of Xist density across XCI-repressed (n=438) and escapee genes (n=15) after TERRA KD or Scr KD in MEFs.

E. RNA FISH detecting TERRA (Alexa-488) and Xist (Cy3, red) in MEFs cells. 87% show colocalization (n=139).

F. 3D DNA FISH to determine the colocalization frequency of PAR (Cy3), the Xic (Ftx-Jpx probe; Cy5) and Hprt (FITC). A colocalization event is scored when two signals show overlapped pixels in 3D space. N=276 nuclei. P, determined by two-tailed Fisher's exact test.

G. 3D DNA FISH to determine the frequency of PAR-Xic colocalization after PAR-TERRA KD. A colocalization event is scored when two signals show overlapped pixels. N=256-272 nuclei. P, determined by two-tailed Fisher's exact test.

H. 2D model: PAR-TERRA protects escapees from Xist silencing by setting up a privileged compartment and walling off Xist at the 5' end of escapee genes. When PAR-TERRA is depleted, Xist spreads into the privileged compartment.

I. 3D Model: PAR-TERRA as an organizing center. PAR-TERRA forms a privileged nuclear compartment next to the Xist cloud. The Xi is partitioned spatially into a silent domain and an active domain for escapees.

FIGS. 7A-I. TERRAs regulate Xic pairing in mES cells

A. PAR-TERRA ChIRT-seq tracks of the Xic pairing center (red bar) in MEFs and in ES cells on d0, d3, and d7 of differentiation. Note prominent ES-specific PAR-TERRA peaks at the pairing center.

B. Cumulative frequency curves of inter-allelic differences measured between Xic-Xic, telomere-telomere, and Hprt-Hprt (bottom). Measurements were taken on DNA FISH experiments (representative DNA FISH image is shown) which detected Xic (Xist), TeloX (RP23-461E16, ChrX telomeric BAC), and Hprt (Cy5). ES cells on d0 and d4 shown. Normalized distance (ND)=distance/d, where d=2 X (nuclear area/$\pi$)0.5. ND 0.0-0.2 are shown. n=109-120. P values were determined using the KS test.

C. Cumulative frequency curves for inter-allelic telomeric distances for ChrX (TeloX) or Chr2 (Telo2) on day 4 of ES differentiation. n=120-158. P values were determined using the KS test.

D. PAR-to-PAR pairing during female and male ES cell differentiation. n=246-385. P values were determined using the KS test.

E. Cumulative frequency of paired PAR DNA (TERRA RNA signals) in male ES cells on d0 versus d4. DNA FISH shows that, on d4 of differentiation, the PAR's of ChrX and ChrY were frequently colocalized (one dot) or very close in 3D space (2 neighboring dots of <0.2 ND). N=149 (d0); 176 (d4). P value was determined using the KS test.

F. Cumulative frequency curves show that TERRA knockdown disrupted telomeric pairing in both female and male ES cells at 6 hr post-transfection at d4 of differentiation. P values were determined using the KS test. n=235-336.

G. Cumulative frequencty curve shows that TERRA knockdown disrupted Xic-Xic pairing in female ES cells at 3 hr post-trasfection on d4 of differentiation. P=0.001 (KS test). n=326-377.

H. Cumulative frequency curves indicate an increase in Xic-telo distances after 3 hours of TERRA KD in d4 female ES cells. P=0.009 (KS test). n=174-214.

I. Model: Without wishing to be bound by theory, it is believed that PAR-TERRA forms an organizing center to facilitate X-X pairing. (1) Prior to cell differentiation, the two female X-chromosomes are separated. (2) During early cell differentiation, trans-interactions between two telomeres bring the sex chromosomes in close promixity. (3) PAR-TERRA also drives the intra-chromosomal interactions between the Xic and the telomere in cis. (4) These events bring the Xic pairing center to the same juxta-telomeric compartment, accelerating the homology search between the two Xic pairing centers by the reduced effective search space. The pairing event induces initiation of XCI in female cells. In male cells, the telomeric pairing interaction also occurs, but is not followed by Xic pairing; thus, XCI is not initiated.

FIGS. 8A-E. Cytological analysis of PAR-TERRA transcripts. This figure relates to FIGS. 1A-H.

A. DNA FISH detecting PAR DNA using P34568 sub-probes of BAC RP24-500I4 DNA (Cy3, red), and X chromosomes (FITC labeled X painting probes, green) on metaphase spread in female ES cells. P345678 probes mark on the end of X chromosomes.

B. Electrophoresis of PCR products amplified from BAC RP24-500I4 DNA. The pools of P3, P4, P5, P6, and P8 PCR produces were used for generating P34568 sub-probes to detect PAR DNA in DNA FISH experiments.

C. RNA FISH detecting TERRA RNA in various human (lower panel) and mouse (upper panel) cell lines.

D. PAR-TERRA RNA is localized next to the Xist cloud. RNA FISH detecting TERRA (Alexa-488, green), 14-31k (Cy5, cyan blue), and Xist (Cy3, red) in MEFs (upper panel). Image of the overexposed TERRA foci (green) to display moderate intensity of TERRA foci was shown in the lower panel. False color for I4-31k (red, lower panel).

E. RNA FISH detecting TERRA (Cy5, cyan blue), Xist (FITC, green), the PAR transcripts with DNA oligo probes: I4-47k (Alexa-488, green) and I4-22k (Cy3, red) in MEFs (hybrid strain cas/mus, Xist clouds specifically on mus alleles), female ES cells (hybrid strand, cas/mus) and male ES cells (mus/mus). I4-22k probes only mark on cas alleles.

Figure 9A:
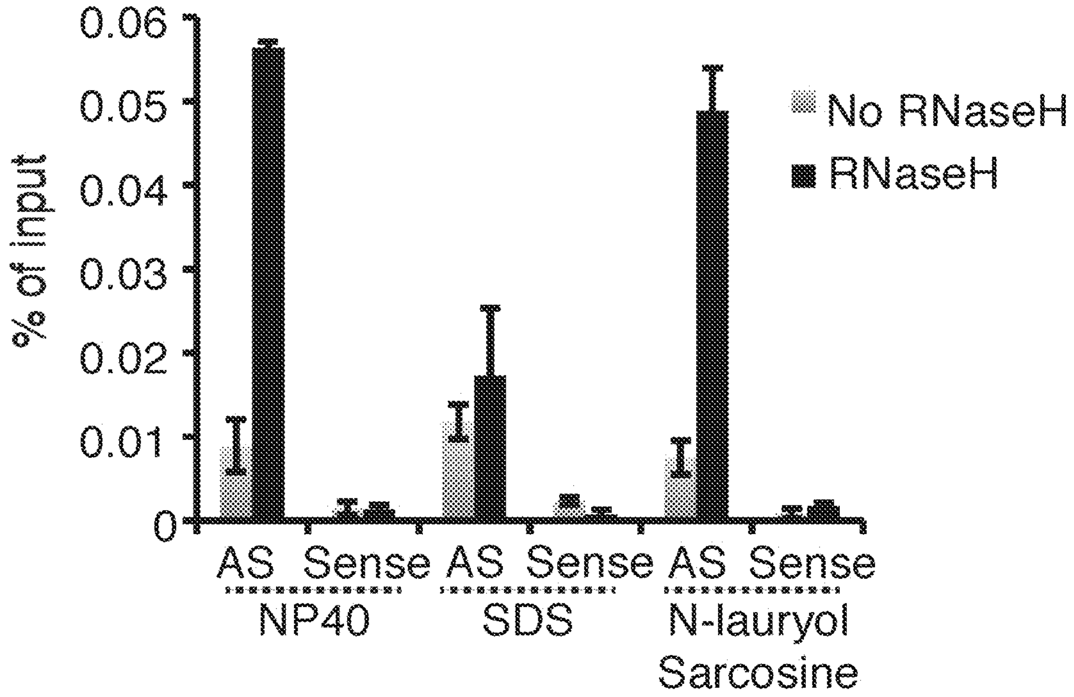
Figure 9B:
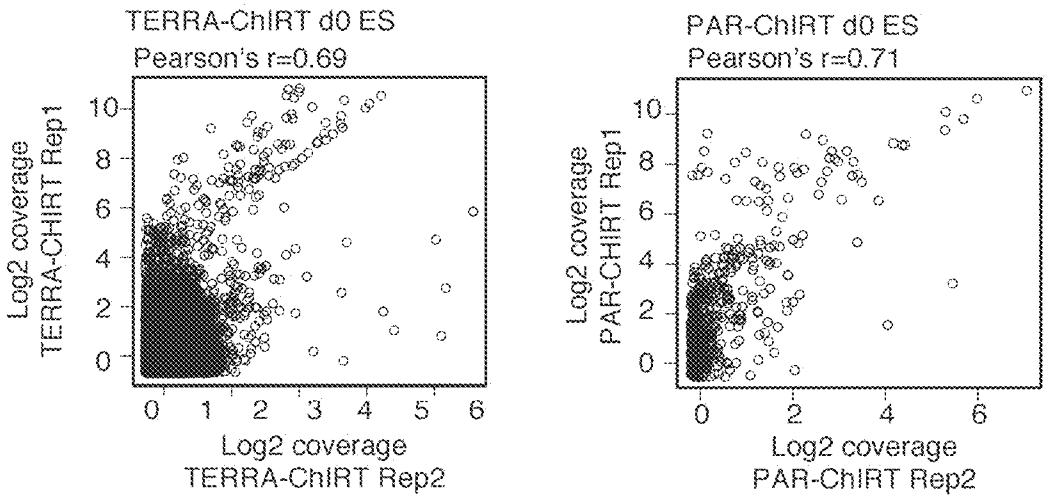

FIGS. 9A-C. ChIRT-seq statistics. This figure relates to FIG. 2.

A. Quantitative PCR showing the enrichment of PAR DNA following ChIRT using oligo probes TERRA-AS (AS) that targets to TERRA transcripts or sense probes. Various detergents (0.1% NP40, or 0.1% SDS, or 0.1% N-lauryol Sarcosine) were added separately during the final DNA elution. NP40 retains RNase H activity better than other detergents in ChIRT elution.

B. Scatterplot comparing log2 coverages of biological replicates for PAR and TERRA ChIRT-seq analysis in ES cells. Pearson's r shown. Replicate 1 (Rep1) was normalized with input. Replicate 2 (Rep2) was normalized to RNaseA pre-treated control.

C. Read statistics for two biological replicates of the PAR-TERRA ChIRT-seq analysis.

Figure 10:
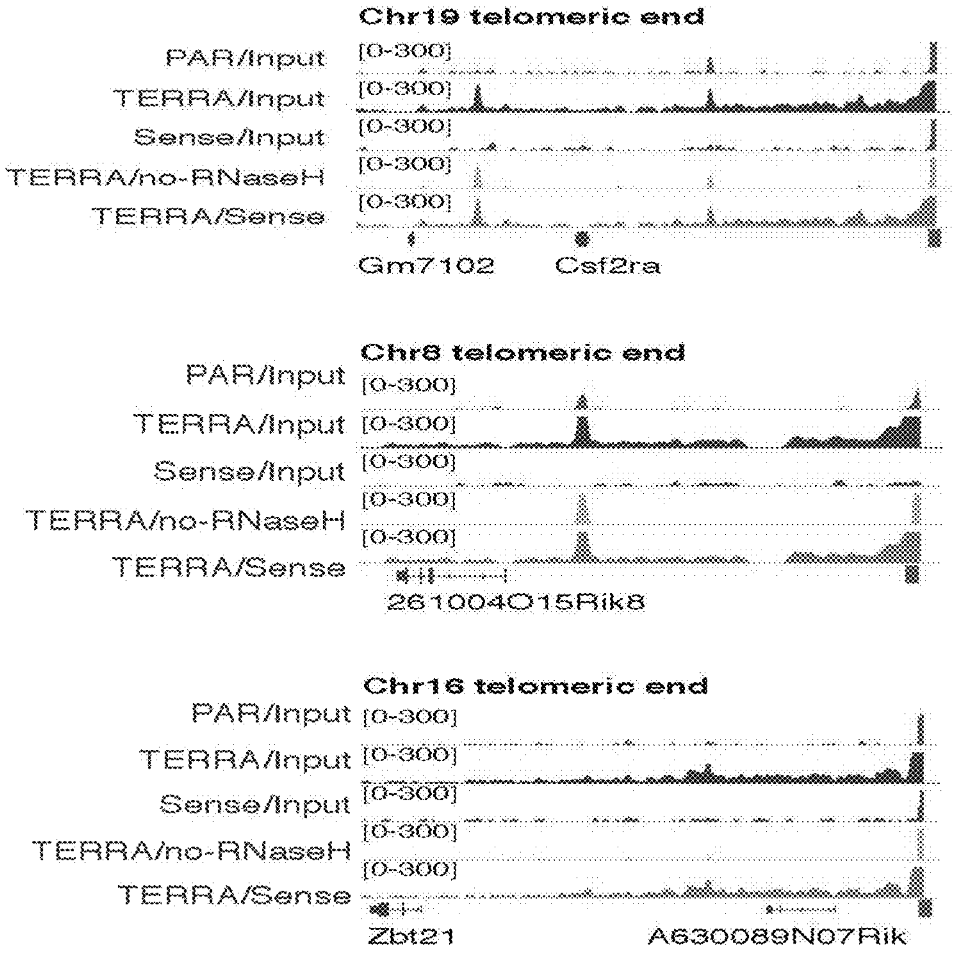

FIG. 10. PAR-TERRA RNA binds subtelomeric regions of select autosomes.

This figure relates to FIG. 3. ChIRT-seq tracks showing PAR-TERRA enrichment at the subtelomeric regions of Chr19, 8, and 16 in ES cells.

Figure 11A:
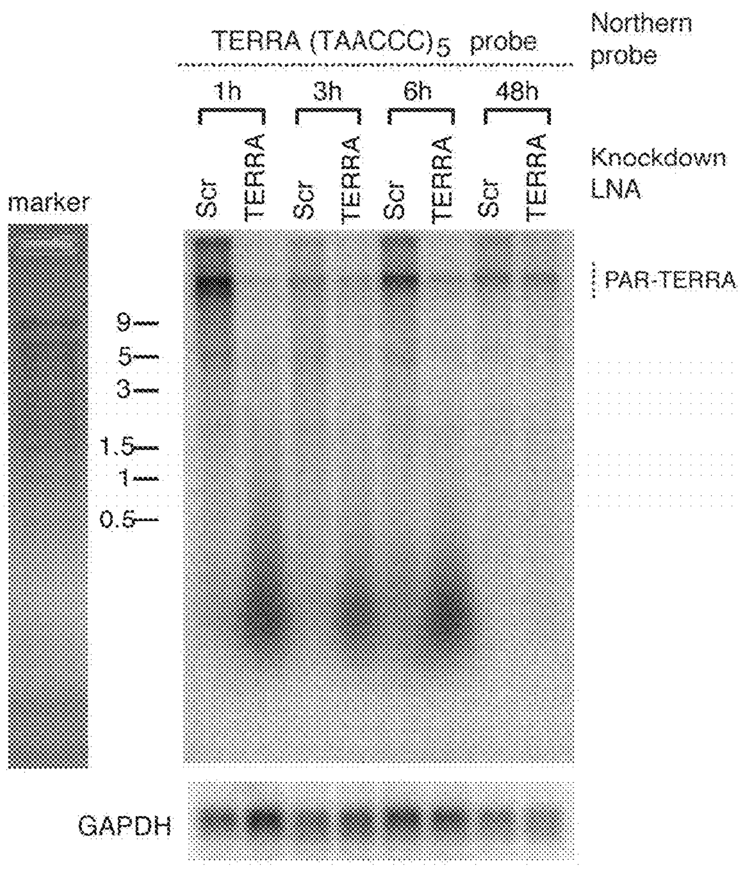
Figure 11B:
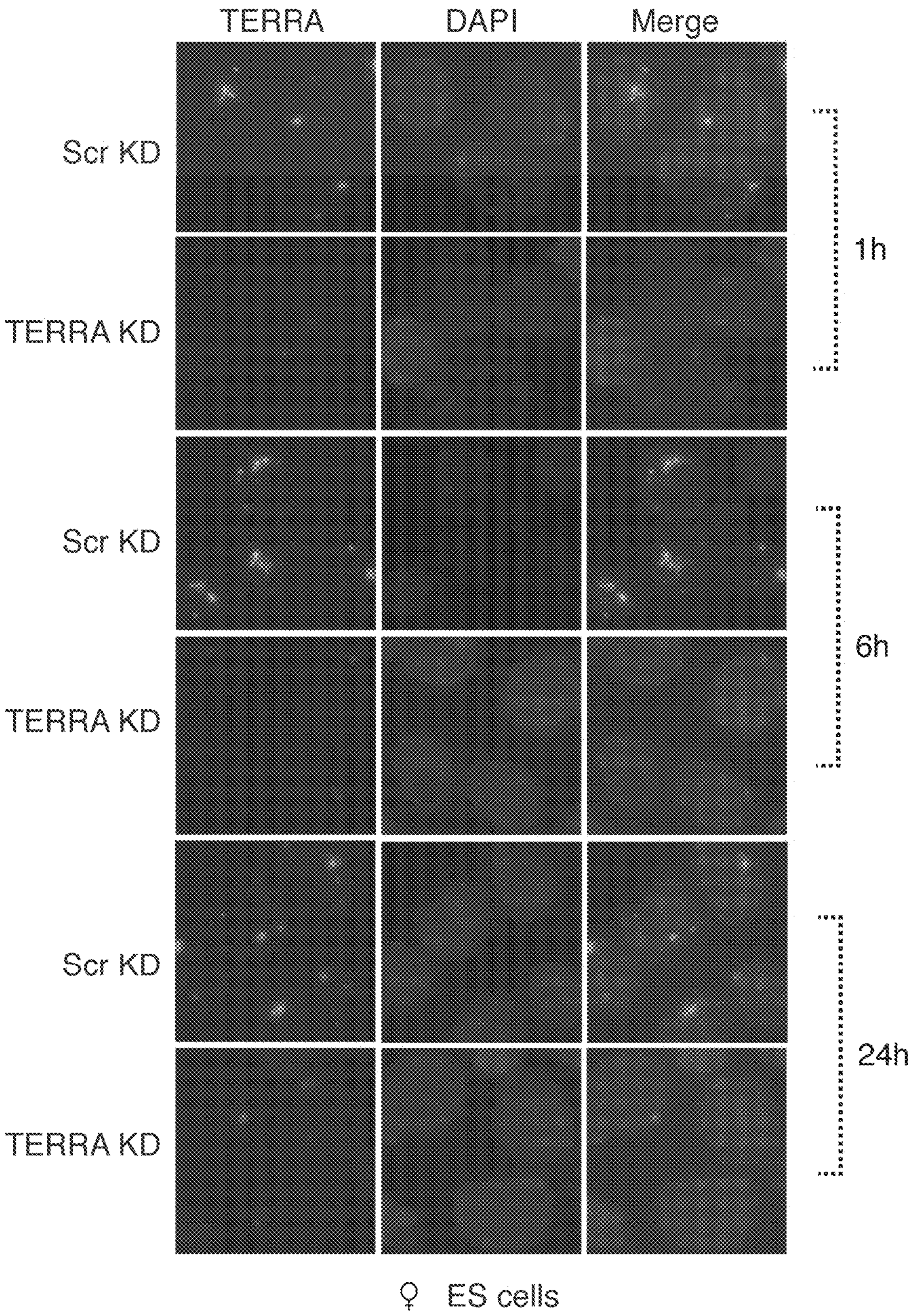
Figure 11C:
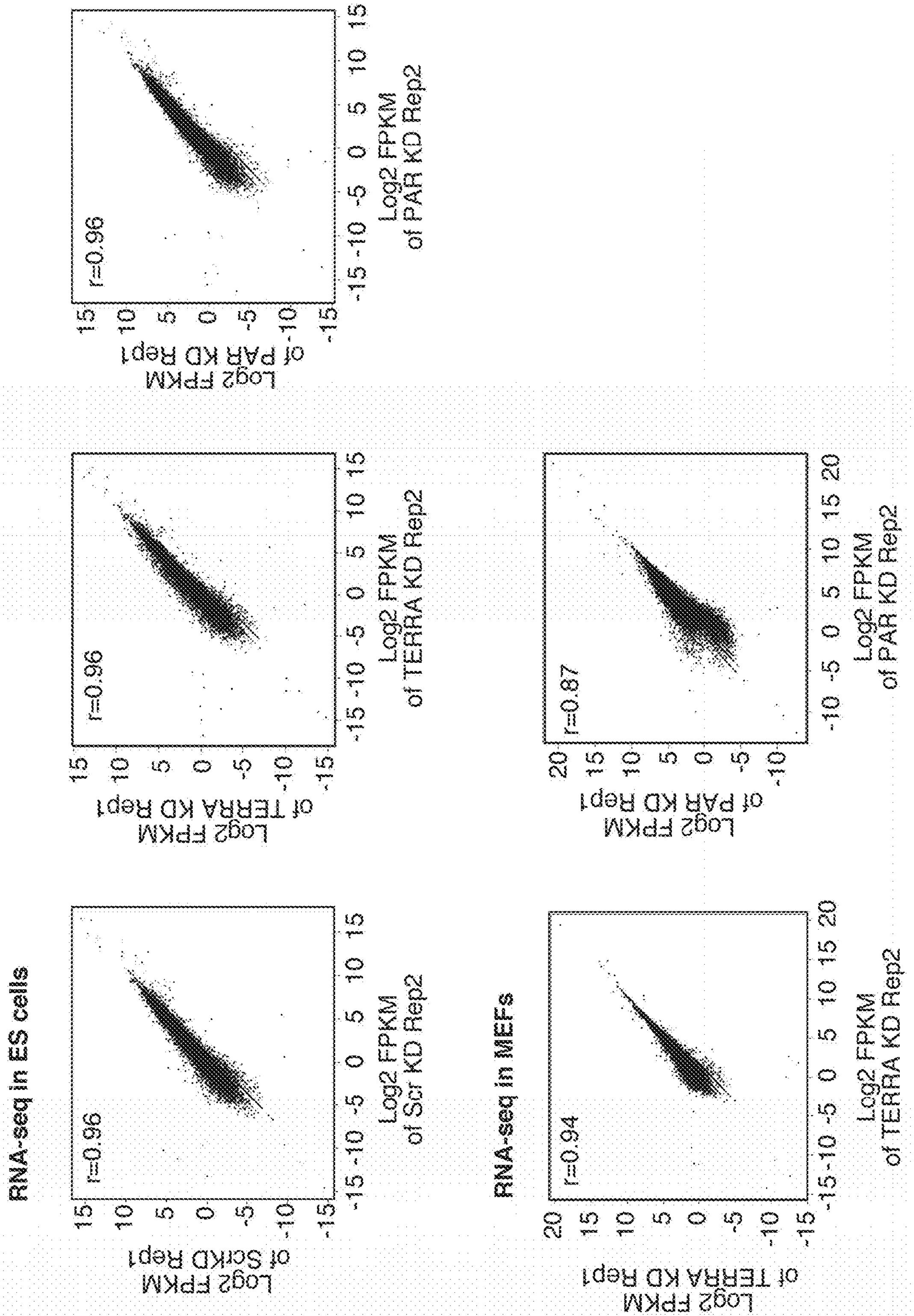

FIGS. 11A-C. PAR-TERRA knockdown by LNA gapmers. This figure relates to FIG. 4.

A. LNA gapmers efficiently knocked down PAR-TERRA in ES cells after 1 to 48 hours.

B. RNA FISH detecting TERRA (Alexa-488, green) after LNA transfection at various time points in ES cells.

C. As shown by scatterplots comparing log2 FPKM values, there is good correlation between biological replicates of RNA-seq biological replicates after PAR-TERRA KD in ES cells and MEFs. Pearson's r as shown.

Figure 12A:
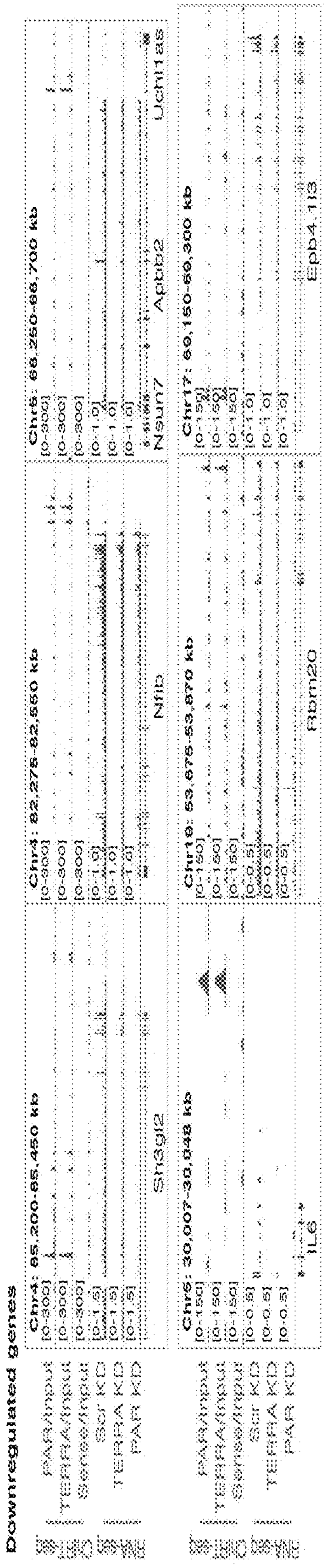
Figure 12B:
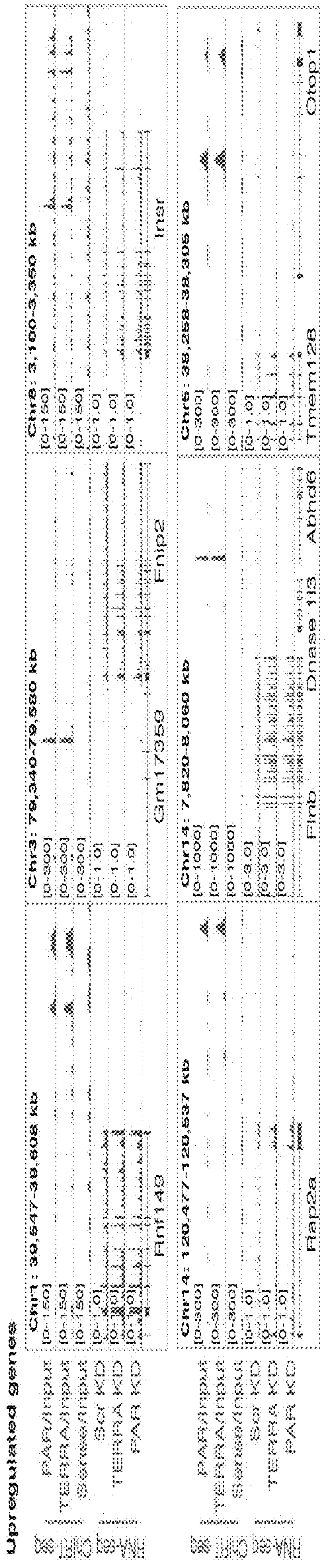

FIGS. 12A-B. Analysis of gene expression following PAR-TERRA knockdown. This figure relates to FIG. 5.

A. ChIRP-seq tracks (red) for PAR-TERRA binding sites near differentially downregulated genes after PAR-TERRA KD in ES cells. RNA-seq coverage are FPM-normalized and tracks are shown in blue.

B. ChIRP-seq tracks (red) for PAR-TERRA binding sites near differentially upregulated genes after PAR-TERRA KD in ES cells. RNA-seq coverage are FPM-normalized and tracks are shown in blue.

Figure 13A:
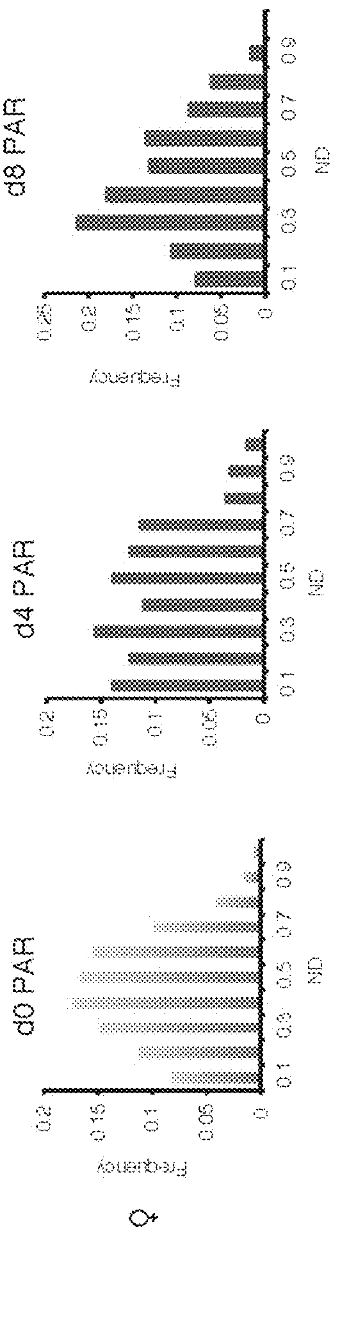
Figure 13B:
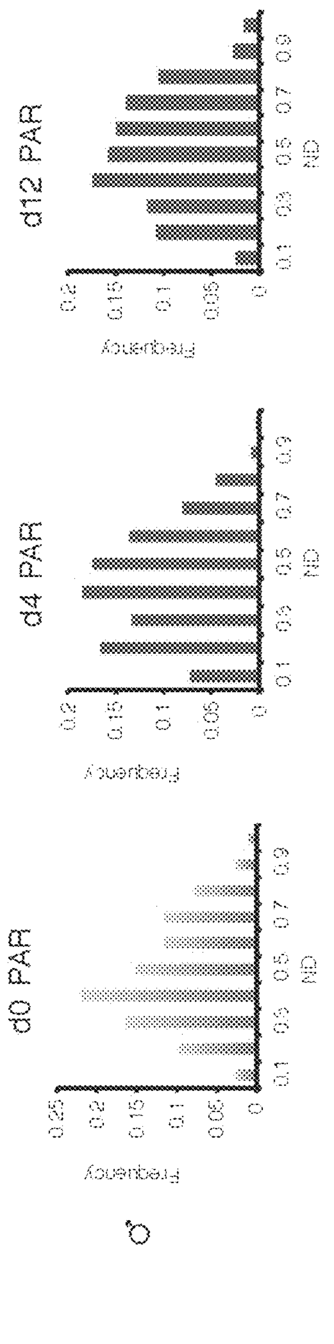

FIGS. 13A-B. Telomeric pairing analysis: Whole distributions of inter-PAR distances. This figure relates to FIG. 7.

A. Distributions of PAR-PAR distances in female ES cells on days 0, 4, and 8 of differentiation. Normalized distance (ND)=PAR-PAR distance/d, where d=2 X (nuclear area/π) 0.5.

B. Distributions of PAR-PAR distances in male ES cells on days 0, 4, and 8 of differentiation.

DETAILED DESCRIPTION

XCI is an epigenetic pathway that results in silencing of one X-chromosome in the female cell to compensate for unequal X-chromosome number between male (XY) and female (XX) cells (Starmer and Magnuson, 2009; Lee, 2011; Wutz, 2011; Disteche, 2012). The pathway is controlled by long noncoding RNAs (lncRNA) of the X-inactivation center (Xic). During early development and as recapitulated by differentiating embryonic stem (ES) cells, the X-to-autosome ratio is assessed and the XCI pathway is induced only when there is more than one X-chromosome in a diploid nucleus. This "counting" mechanism has been proposed to involve a titration of the X-linked Jpx lncRNA and autosomally encoded CTCF protein (Sun et al., 2013). In parallel, a transient interaction ("pairing") between two female X-chromosomes mediates the mutually exclusive choice of Xi and Xa (active X) (Bacher et al., 2006; Xu et al., 2006), with the subsequent action of Tsix lncRNA blocking XCI on the designated Xa (Lee et al., 1999) and the action of Xist lncRNA inducing whole-chromosome silencing on the designated Xi (Brown et al., 1992; Penny et al., 1996). Xist spreads along the Xi and recruits silencing complexes (Zhao et al., 2008; Wutz, 2011). With the exception of a small class of genes that escape XCI, nearly all 1000 genes on the Xi are subject to silencing. Although significant progress has been made, many aspects of XCI mechanism continue to elude understanding.

TERRA's affinity for sex chromosomes led the present inventors to hypothesize that TERRA might have non-telomeric functions; based on its association with sex chromosomes, possible roles surrounding the process of X-chromosome inactivation (XCI) were investigated. TERRA's association with the X-chromosome provides a new and potentially relevant avenue for exploration. Here we generate a map of TERRA's genomic binding sites, identify multiple non-telomeric targets, and interrogate the relationship of X-linked target sites to sex chromosome biology.

Figure 1B:
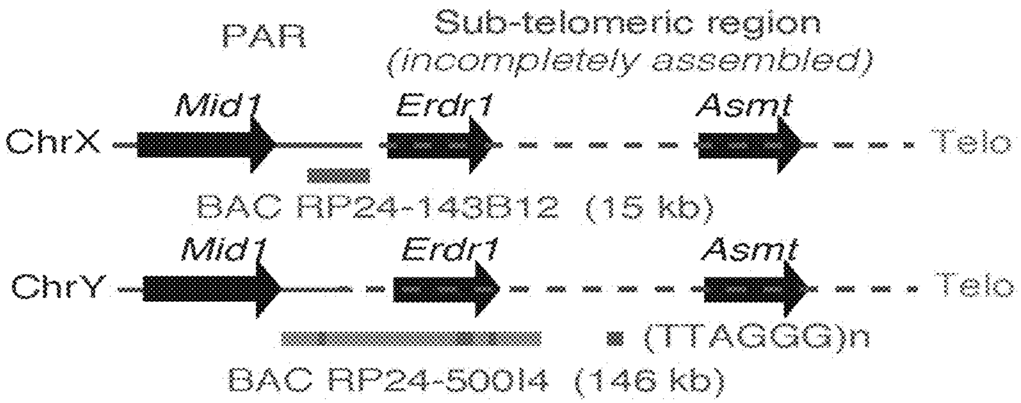
Figure 1C:
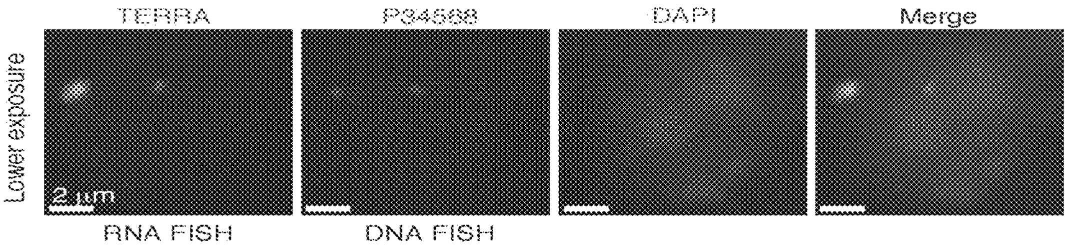
Figure 1D:
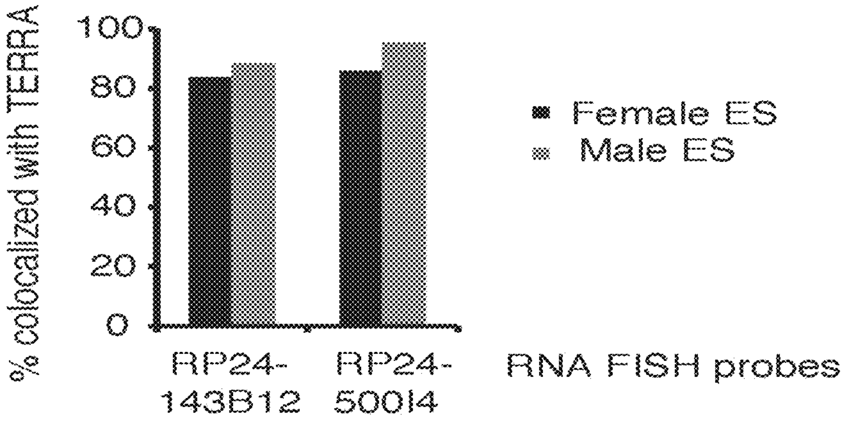
Figure 1E:
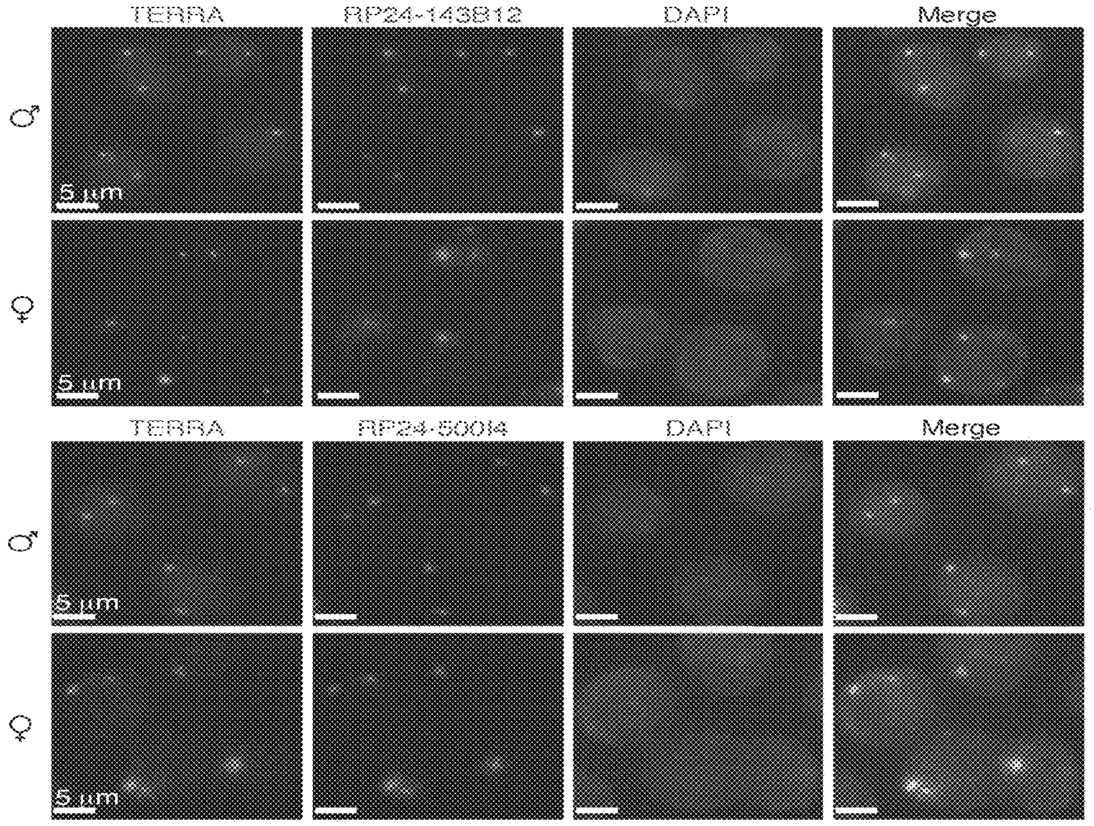
Figure 1F:
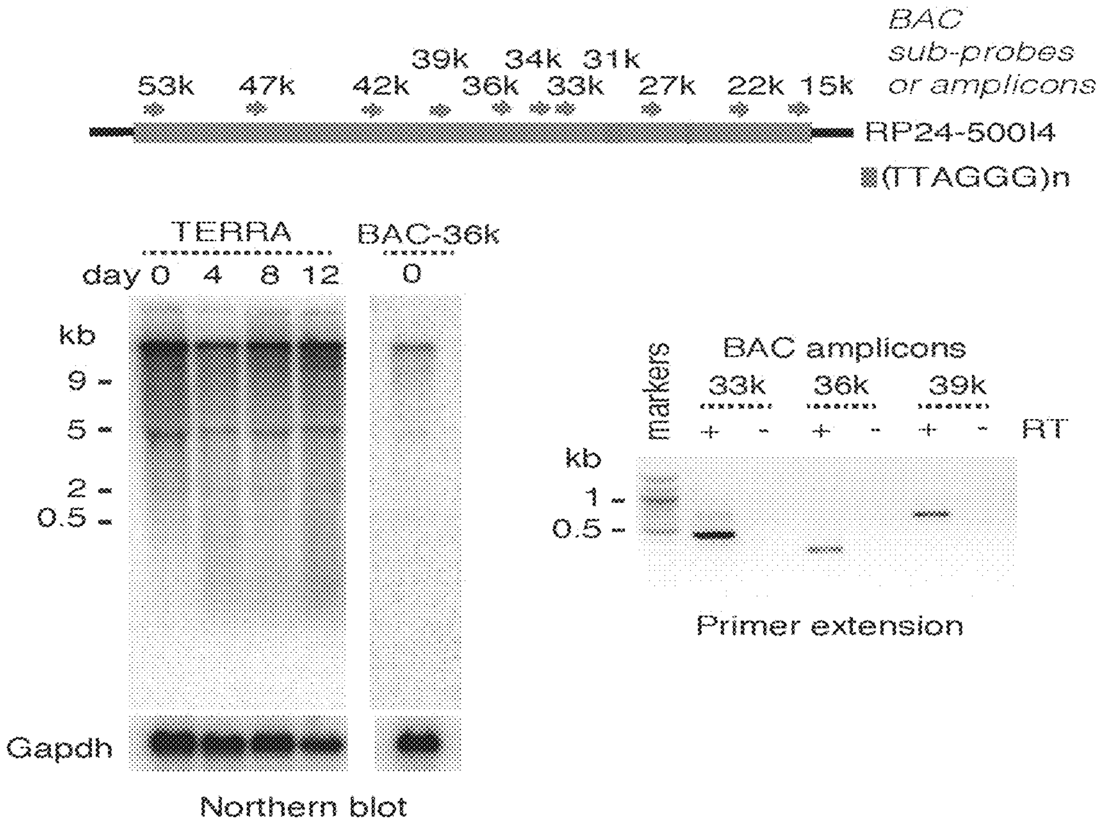
Figure 1G:
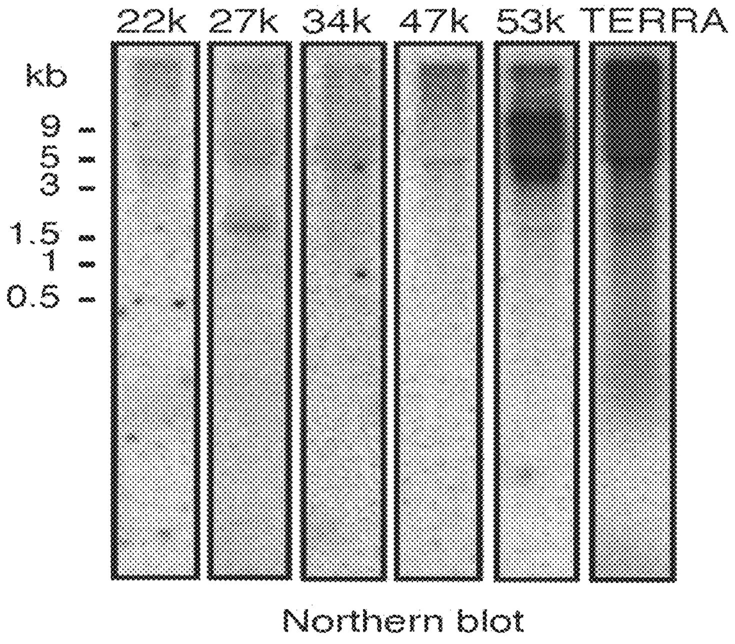
Figure 3A:
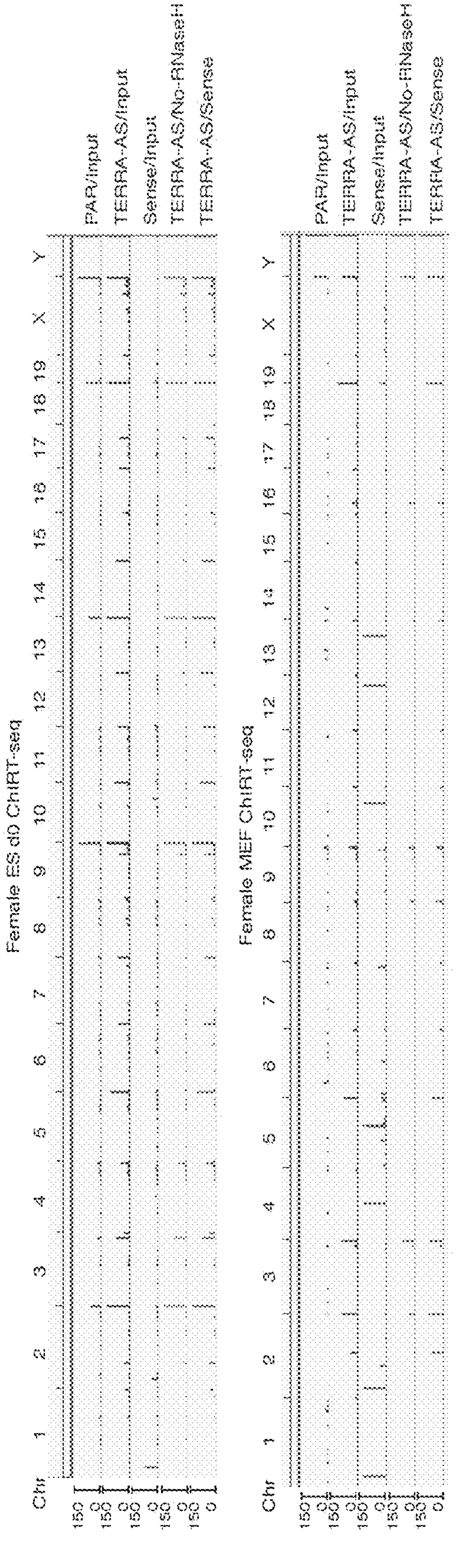
Figure 3B:
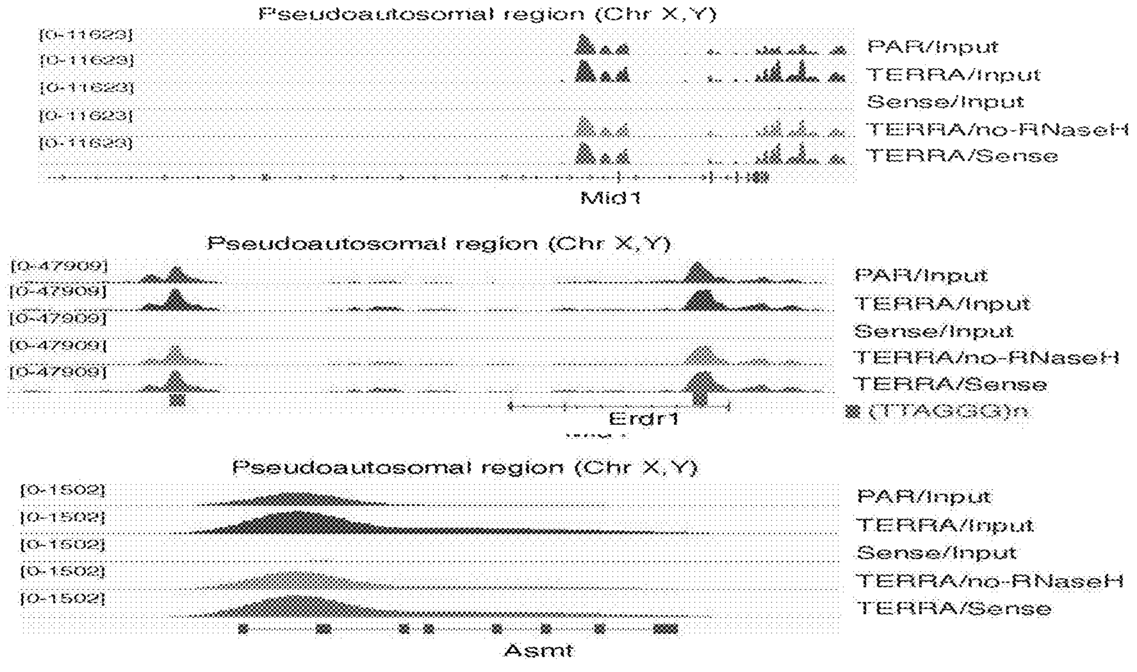
Figure 3C:
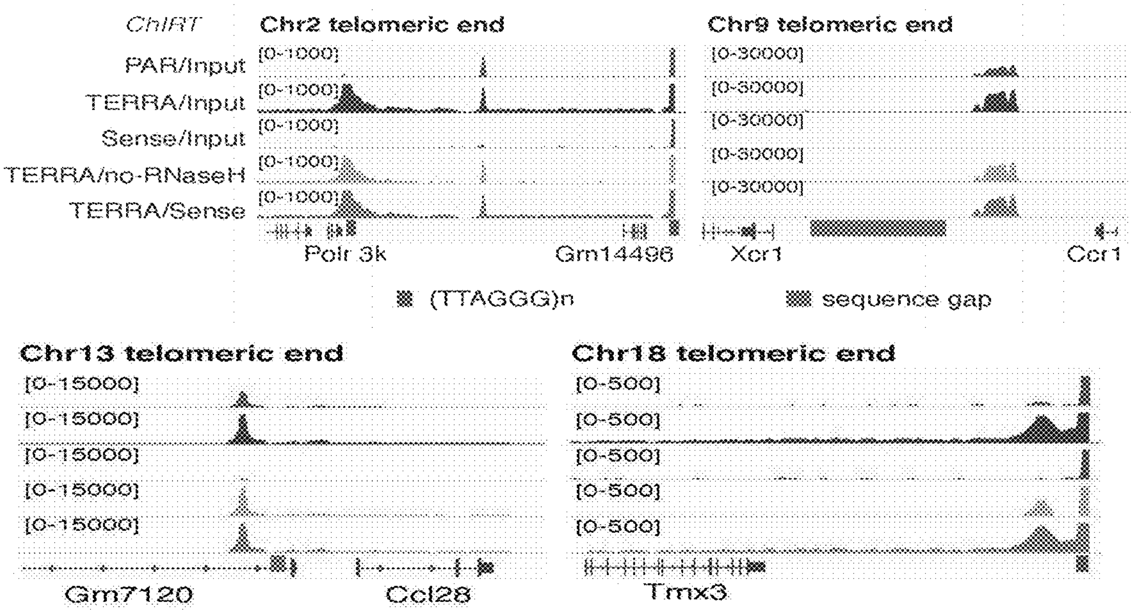
Figure 3D:
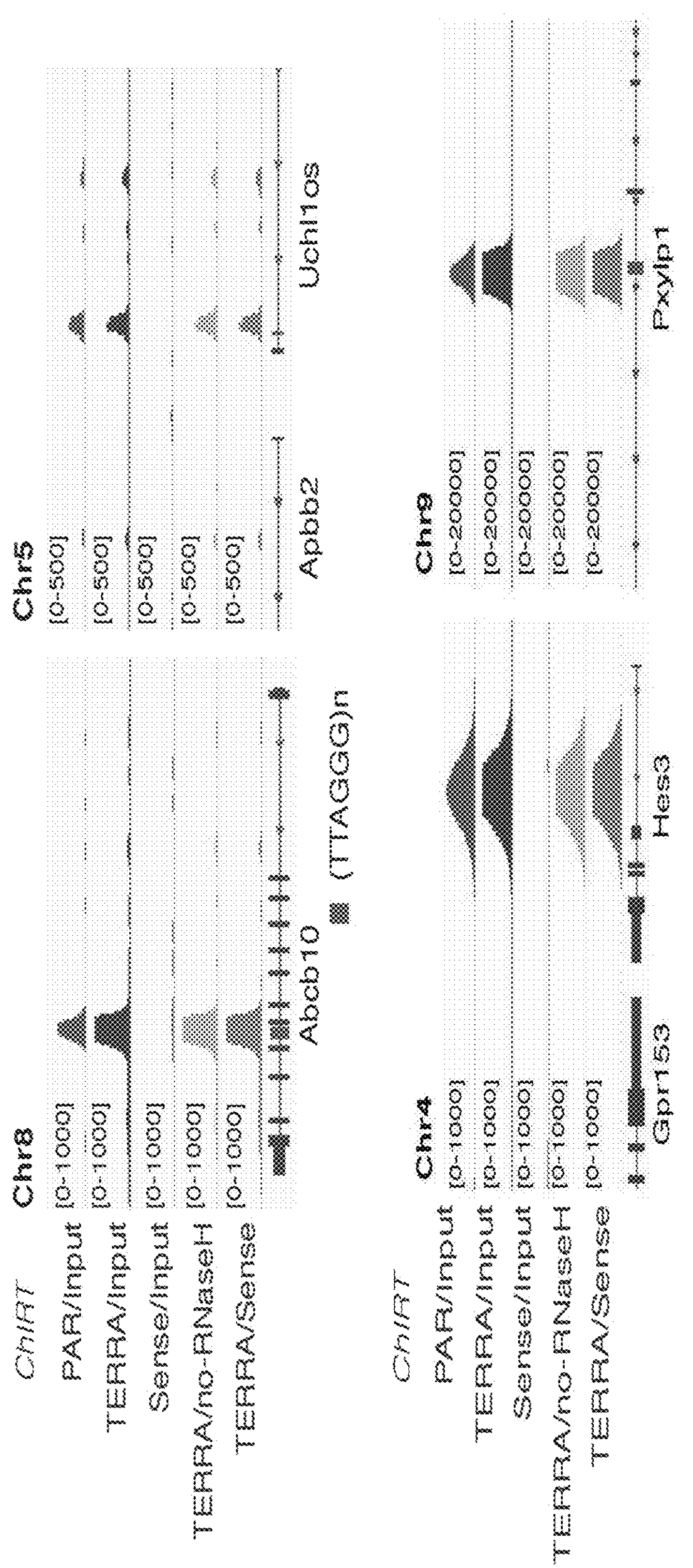
Figure 4A:
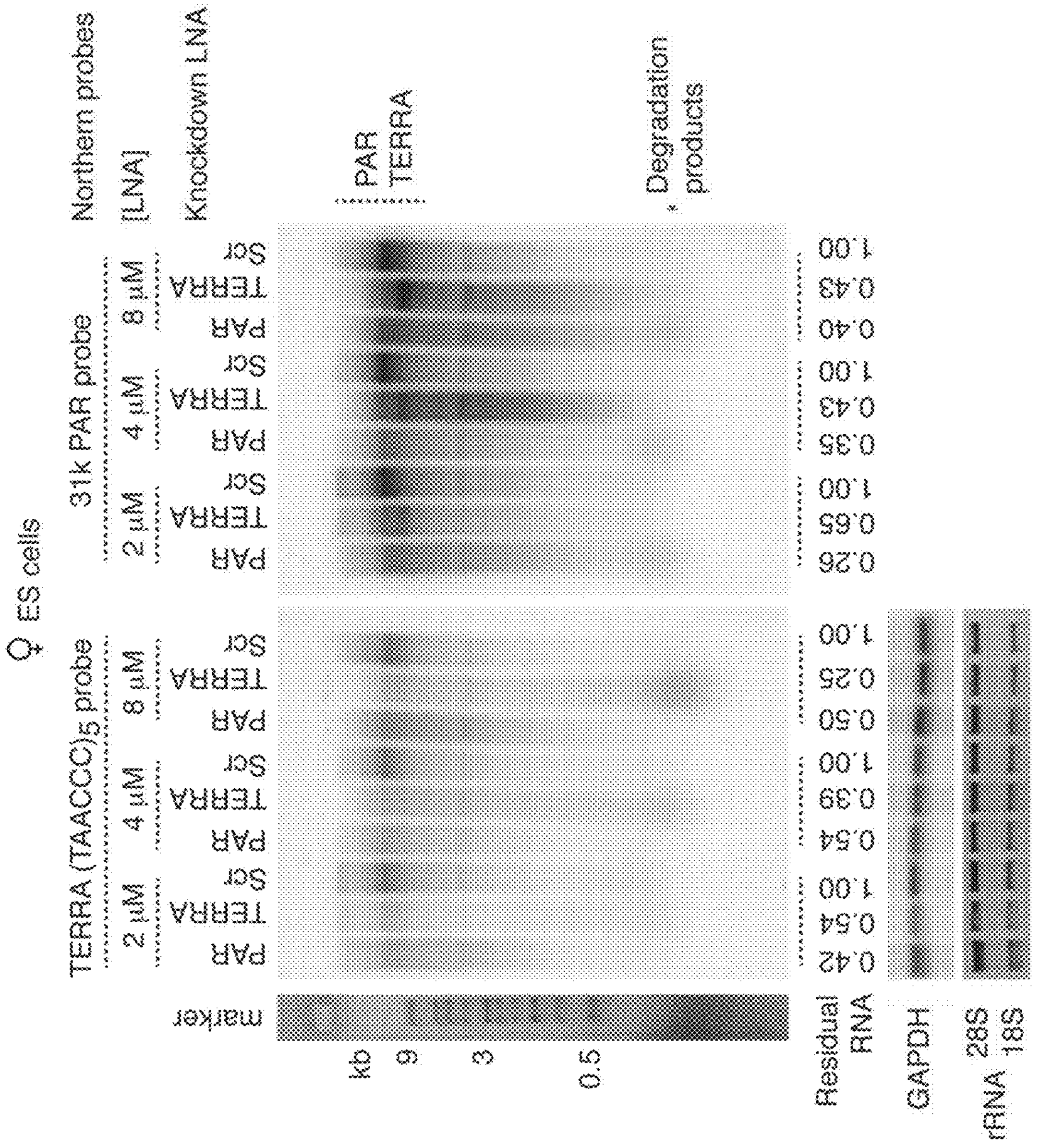

Here we have shown that TERRA function is not confined to telomeres, nor is it cis-limited in action. TERRA is predominantly expressed from the sex chromosomes and originates at least in part from the sub-telomeric region known as the pseudoautosomal region (PAR). Several lines of evidence argue that X- and P-linked "PAR-TERRA" is a continuous transcript and that PAR-TERRA comprises a major subclass of telomeric RNAs. First, similar results are obtained by Northern blot analysis using PAR and TERRA oligo probes (FIG. 1F,G). Second, primer extension indicates that TERRA and PAR RNA sequences are physically continuous (FIG. 1F). Third, RNA FISH experiments using TERRA and PAR probes demonstrate overlapping RNA signals (FIG. 1A,C,E,H). Fourth, ChIRT analysis indicates that nearly all TERRA-binding sites are also PAR-binding sites (FIG. 3,S3). Furthermore, knocking down PAR sequences using LNA gapmers results in TERRA depletion as well (FIG. 4A,B). FISH analysis demonstrates that PAR-TERRA establishes a compartment next to the telomeric ends of each sex chromosome, with a large PAR-TERRA RNA focus localizing next to but not overlapping the Xist RNA domain.

Figure 4B:
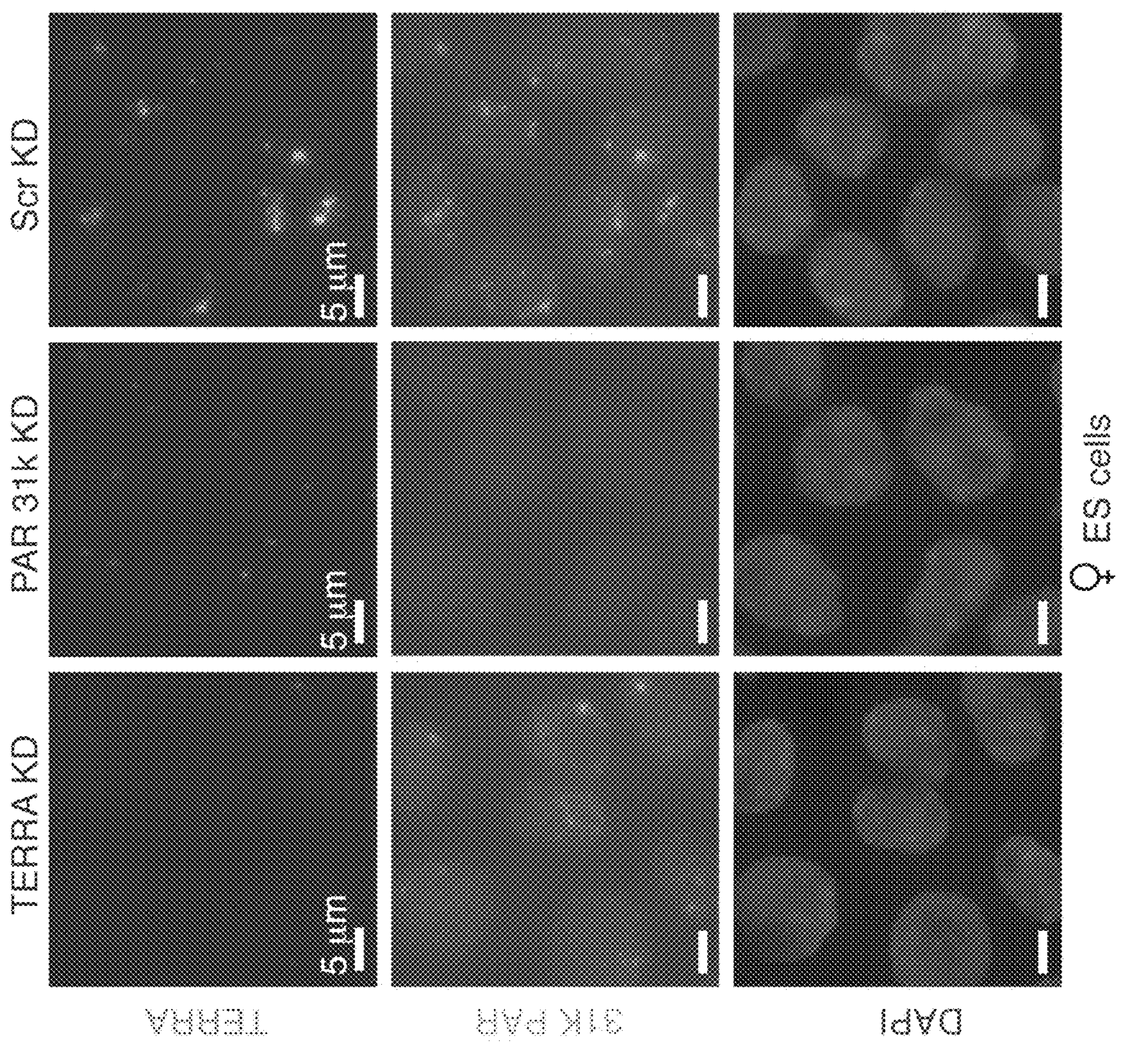
Figure 4C:
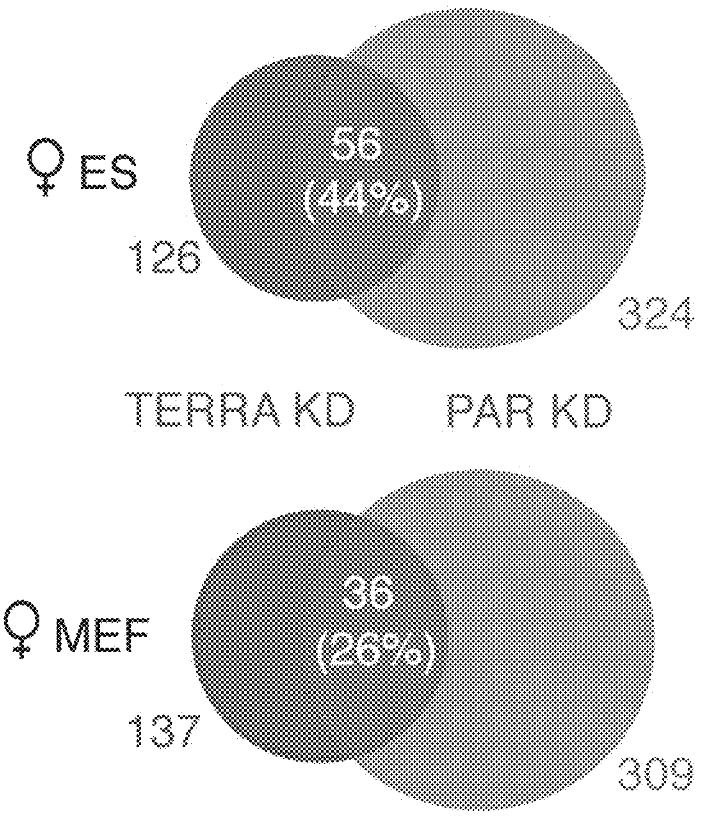
Figure 4D:
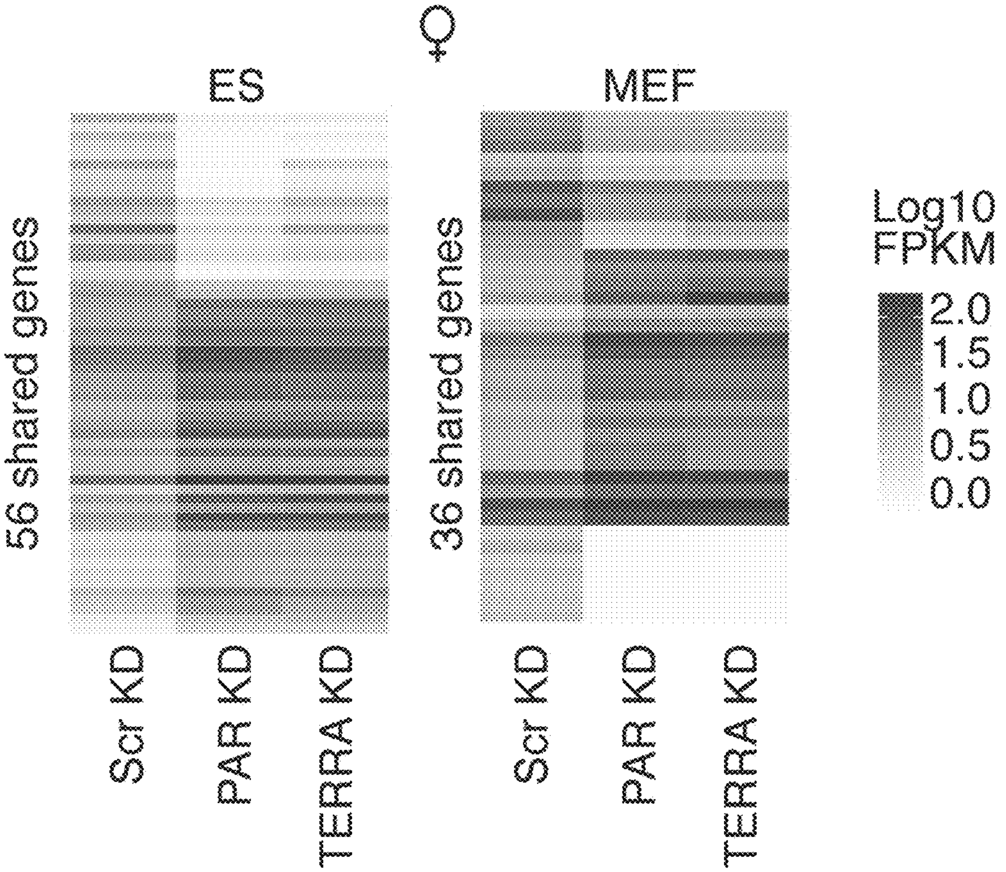
Figure 4E:
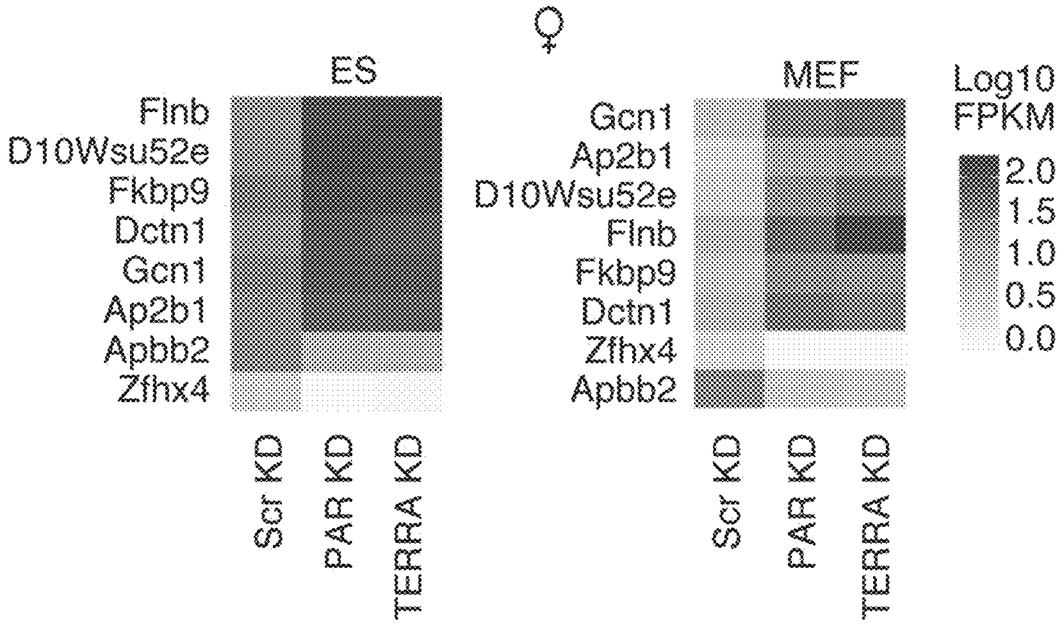
Figure 4F:
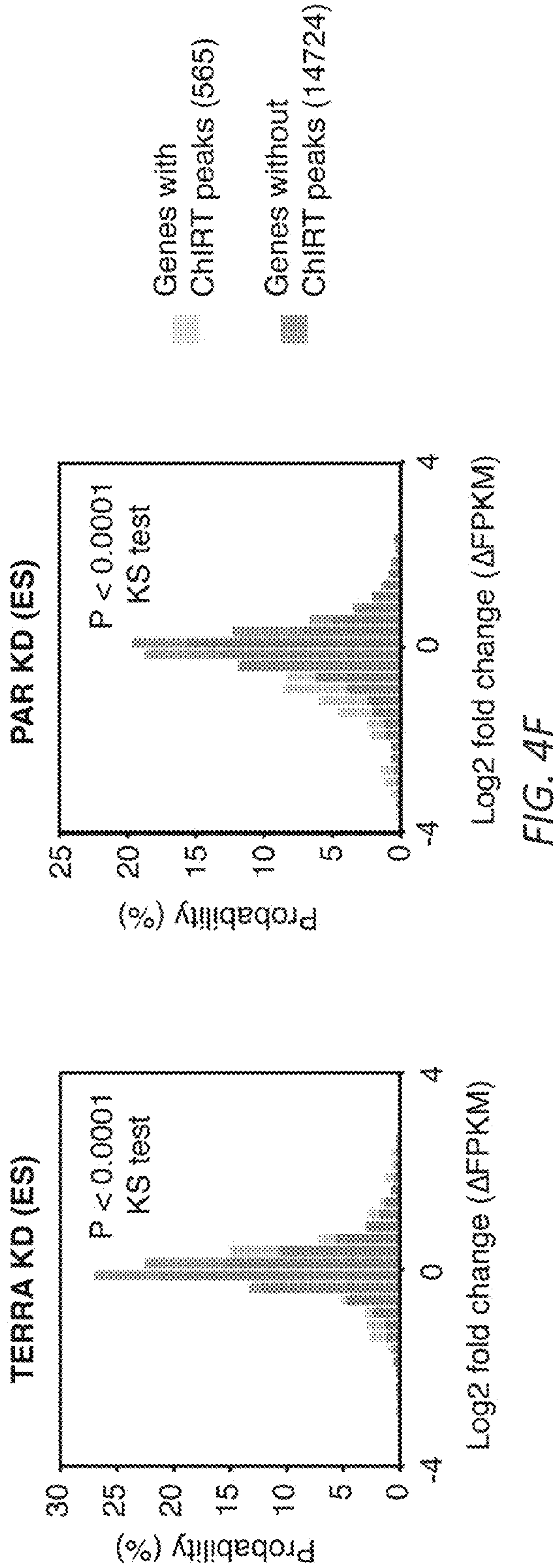
Figure 4G:
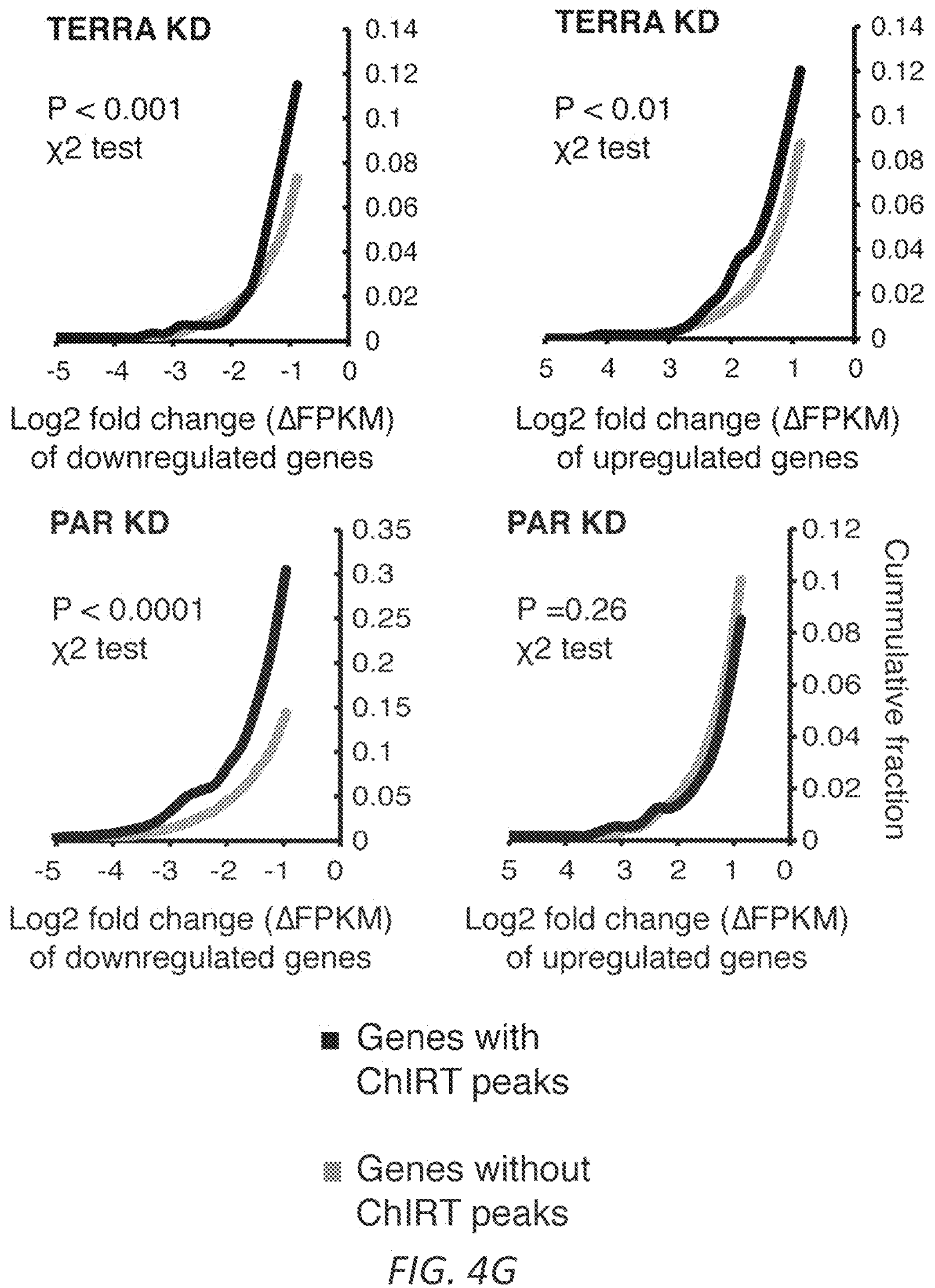
Figure 5A:
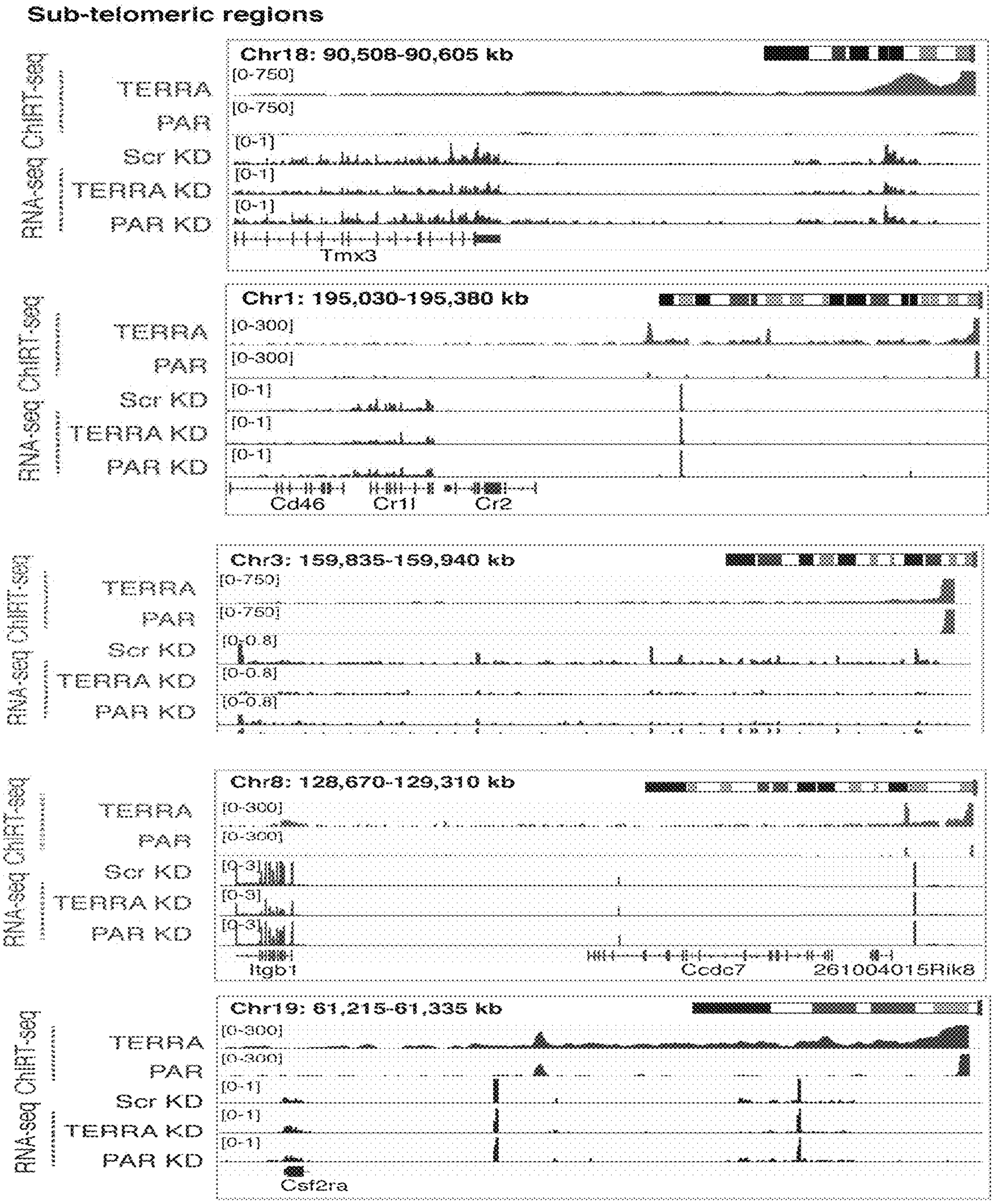
Figure 5B:
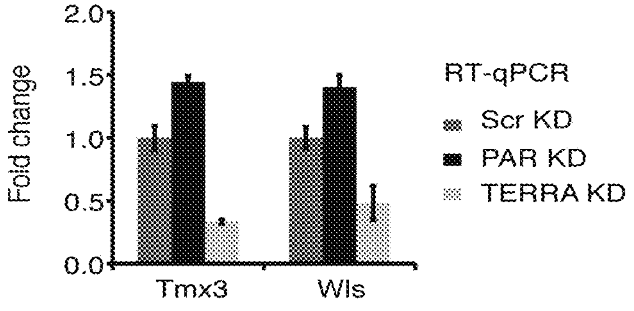
Figures 5C, 5D:
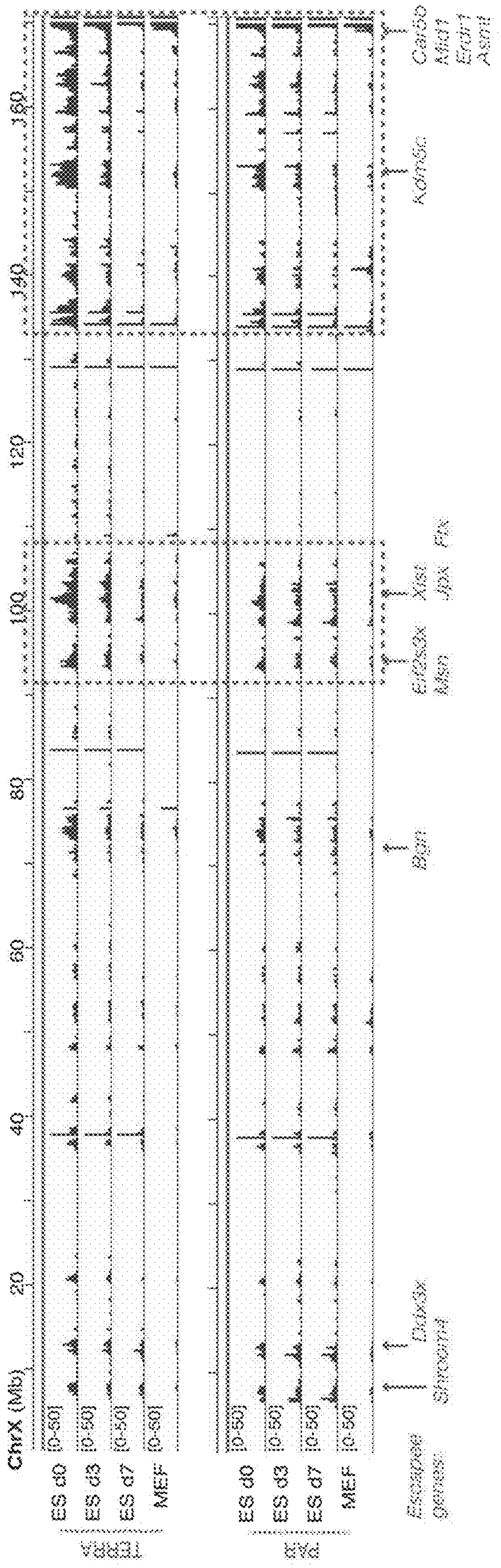
Figure 5E:
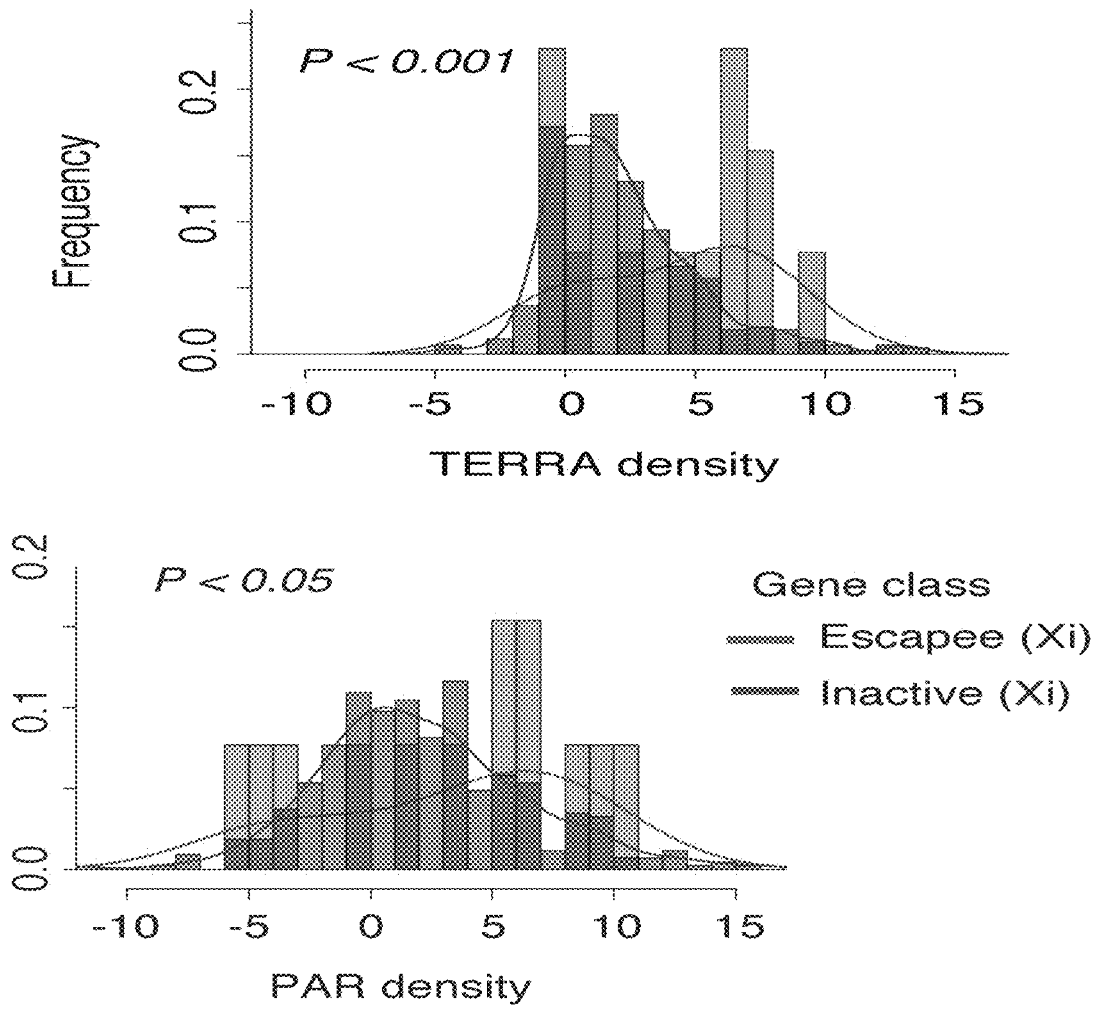
Figure 5F:
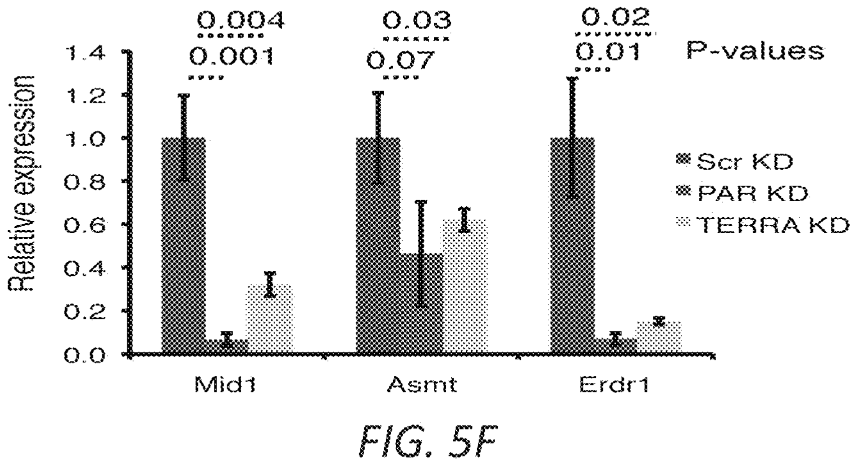
Figure 6A:
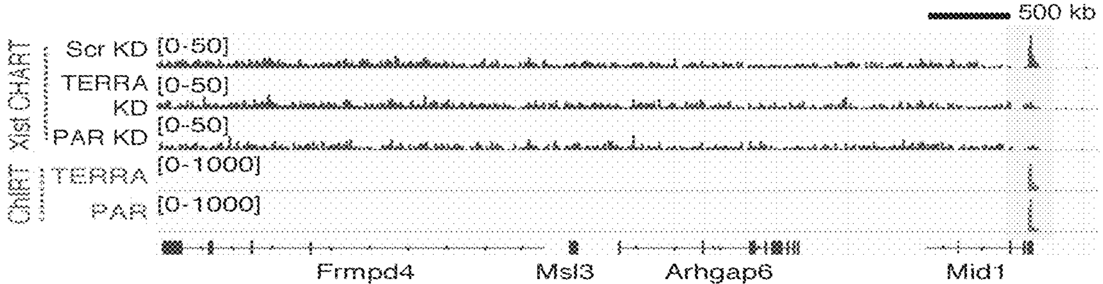
Figure 6B:
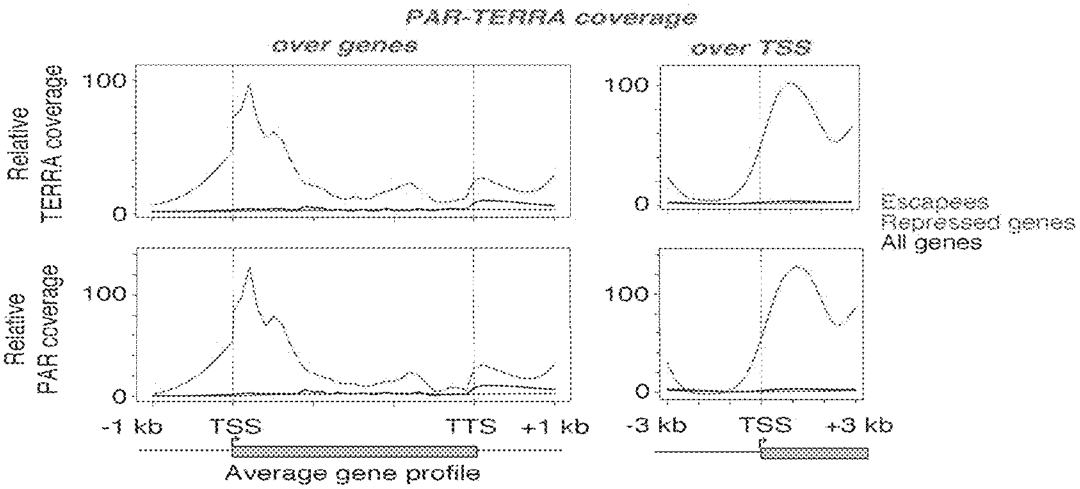
Figure 6C:
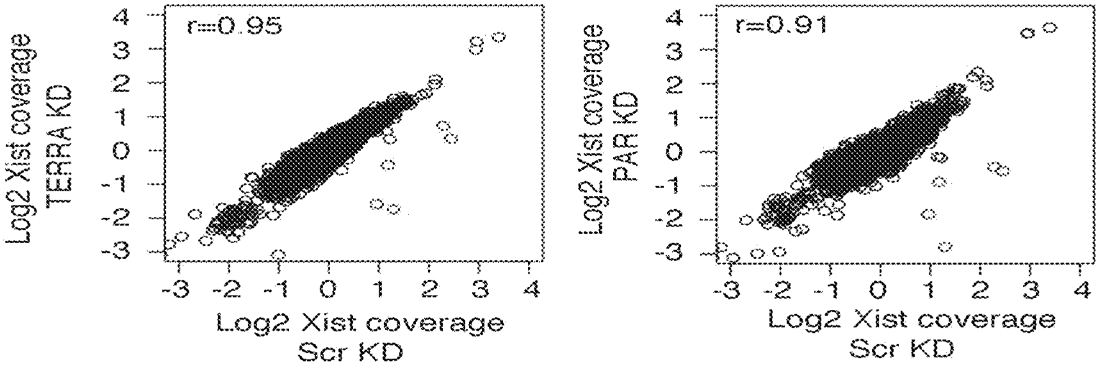
Figure 6D:
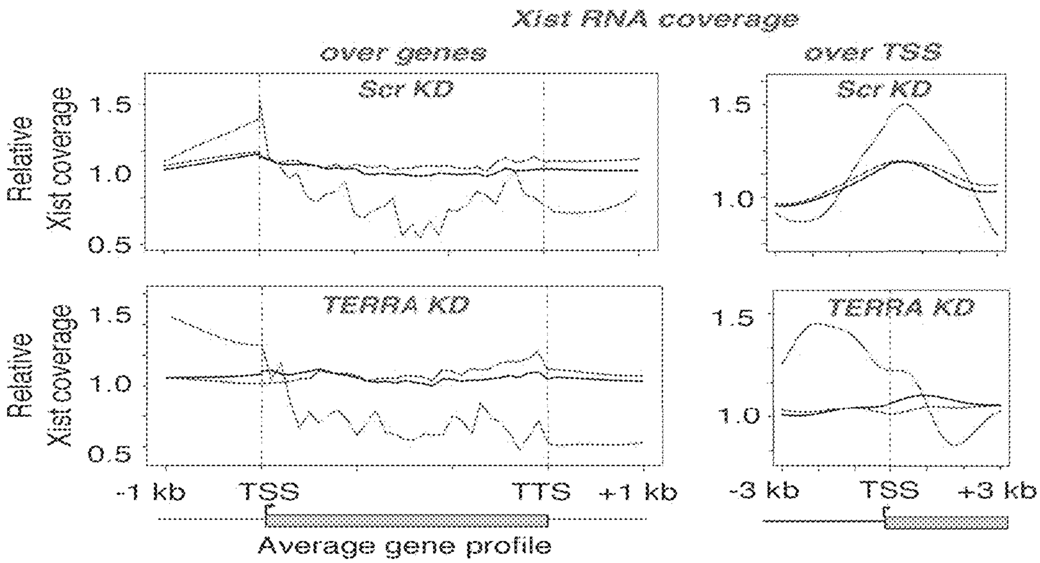
Figure 6E:
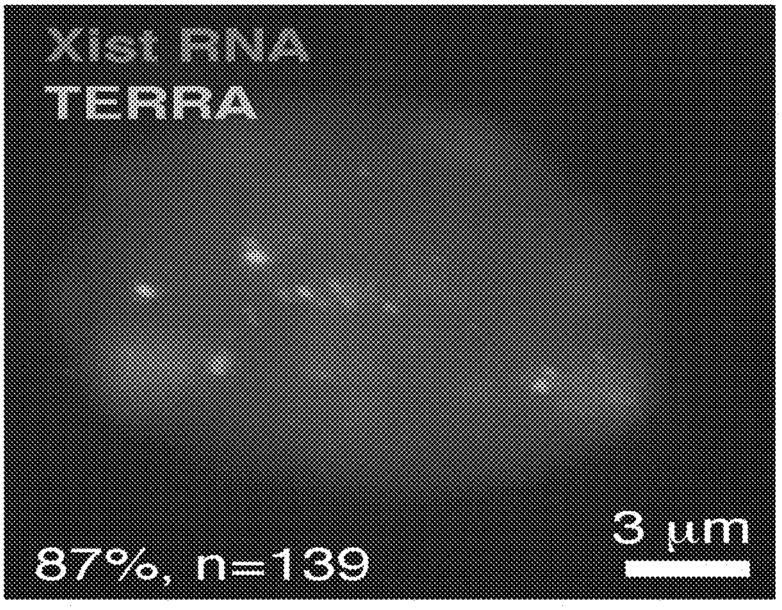
Figure 6F:
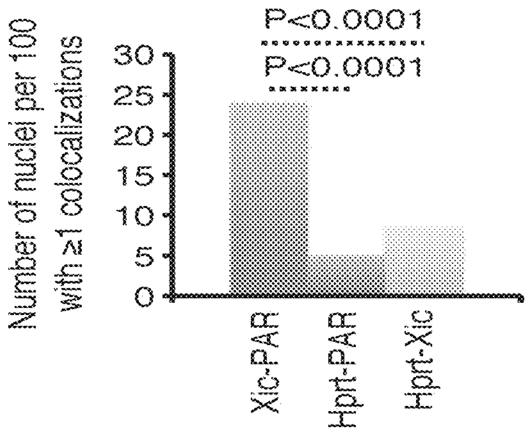
Figure 6G:
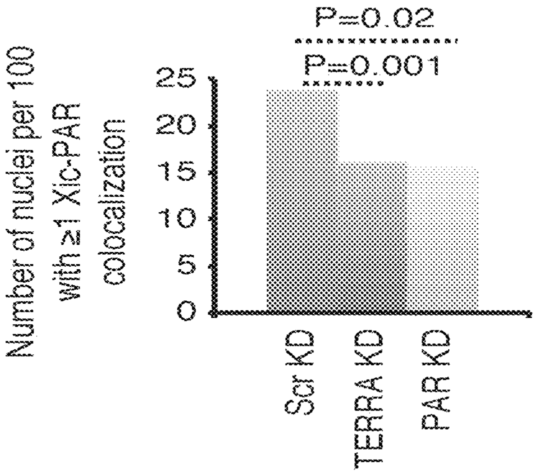
Figure 6H:
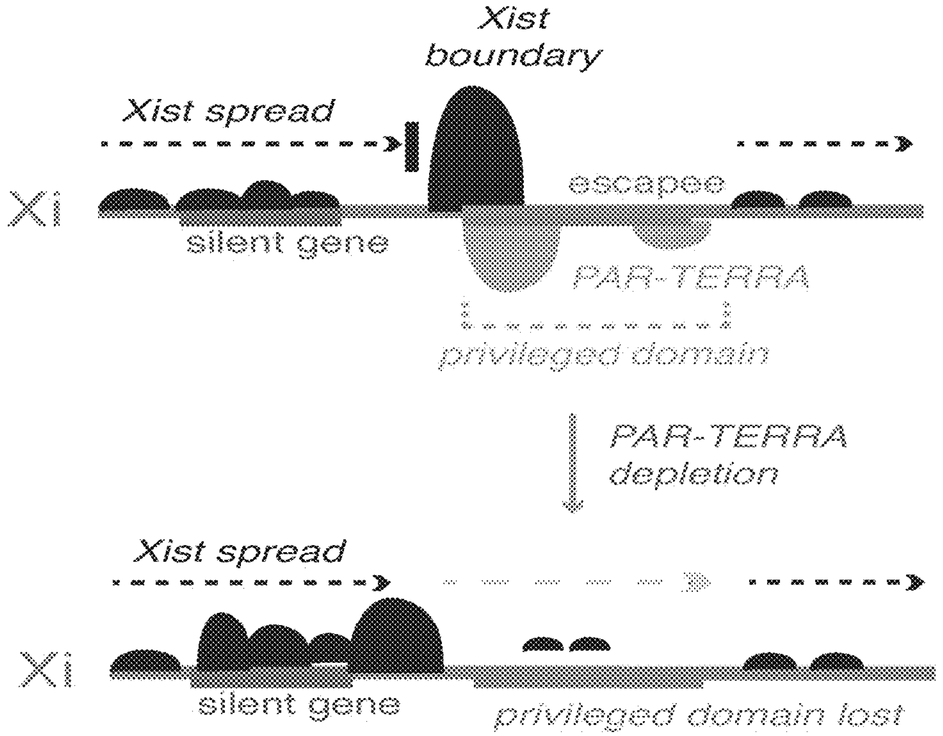
Figure 6I:
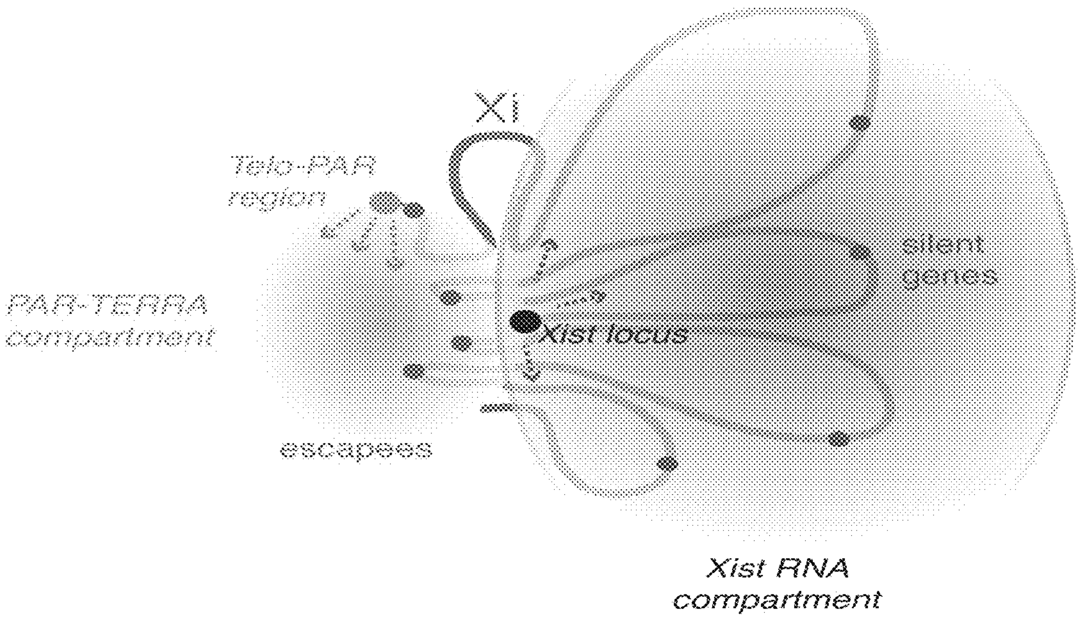
Figure 7A:
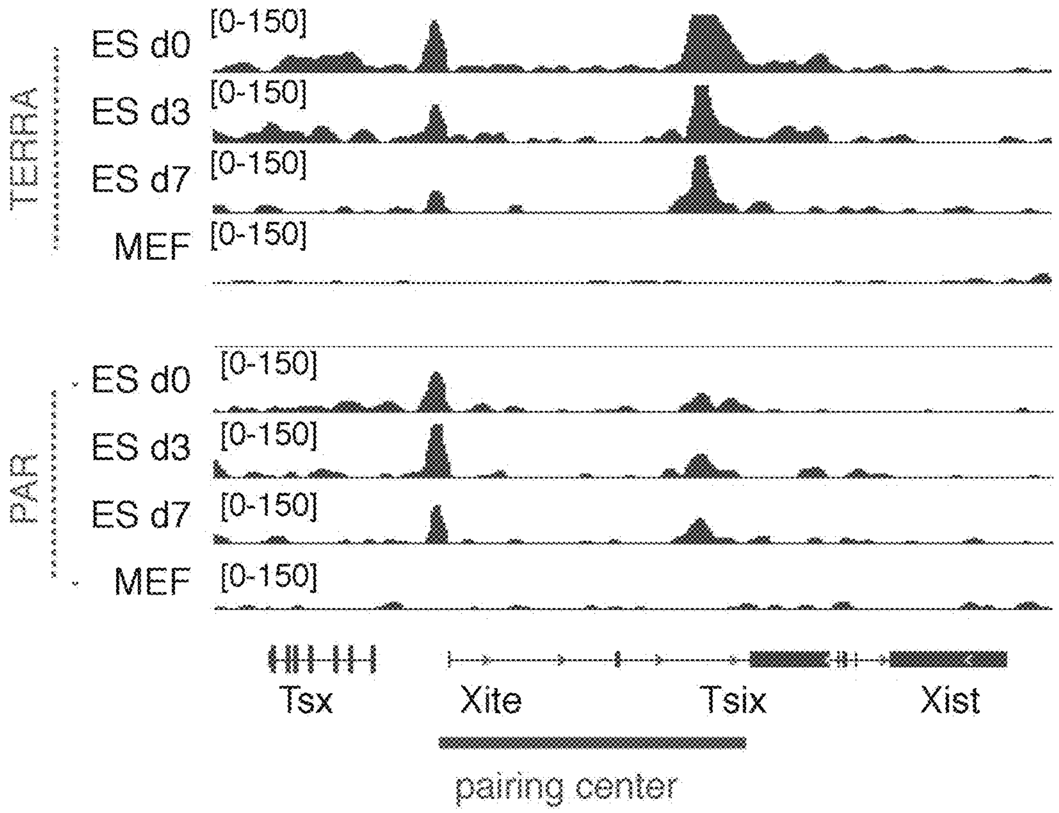
Figure 7B:
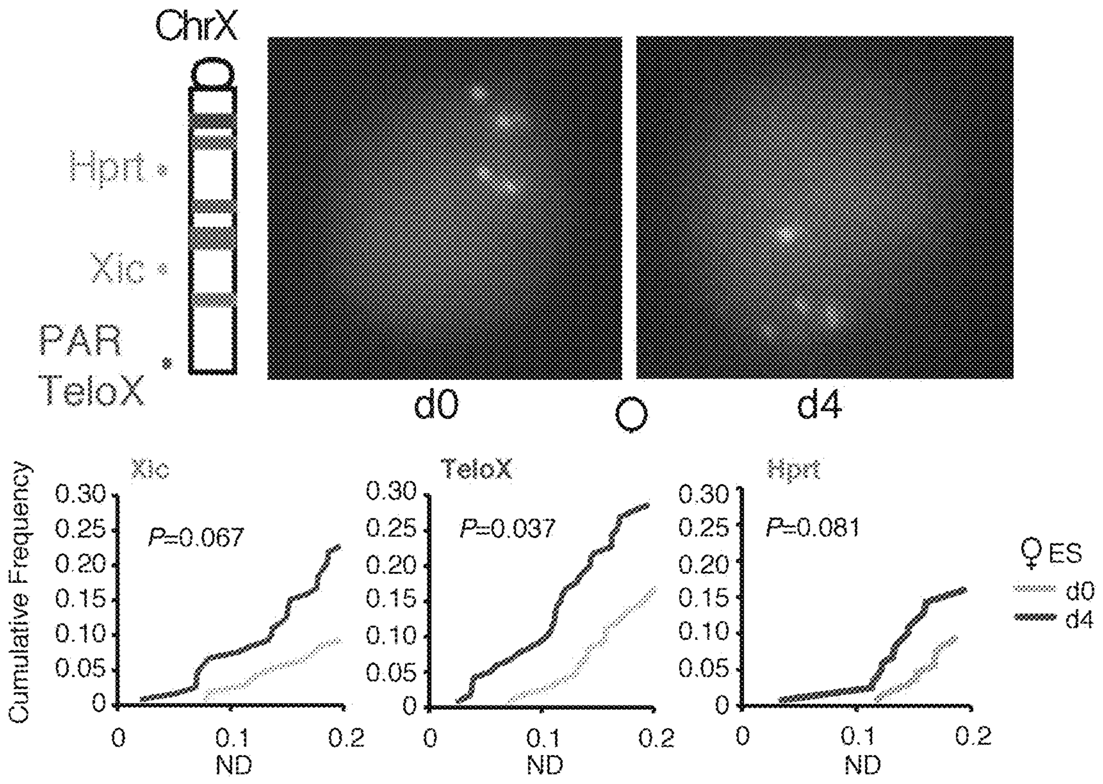
Figure 7C:
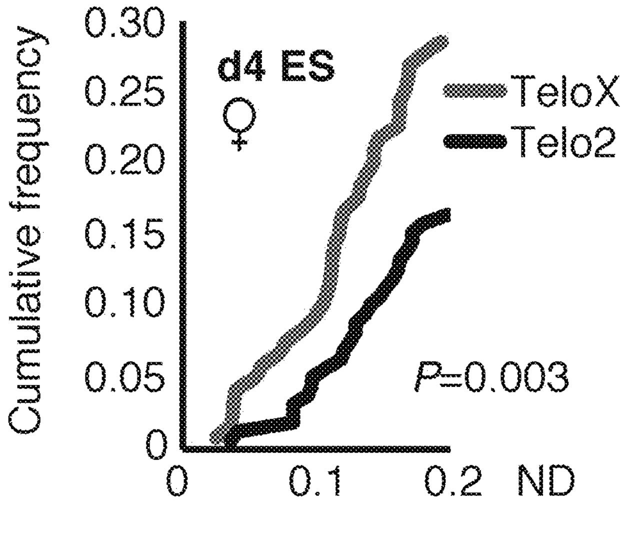
Figure 7D:
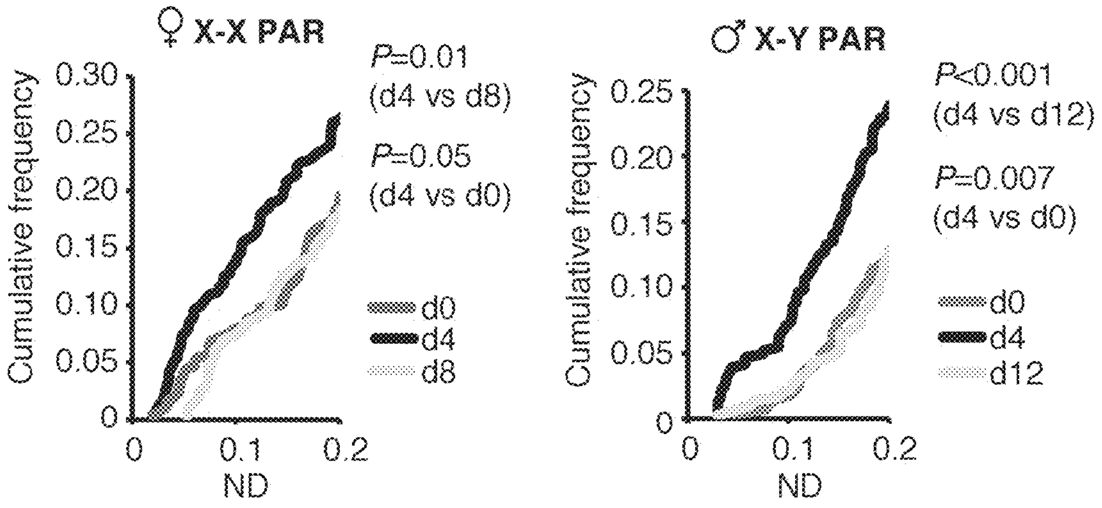
Figure 7E:
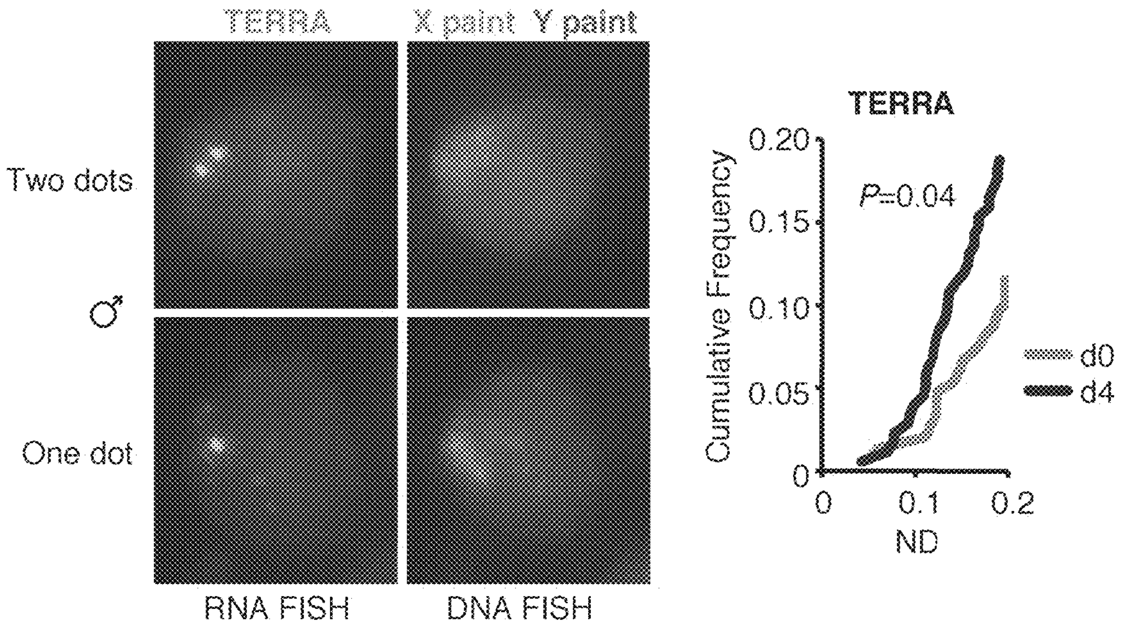
Figure 7F:
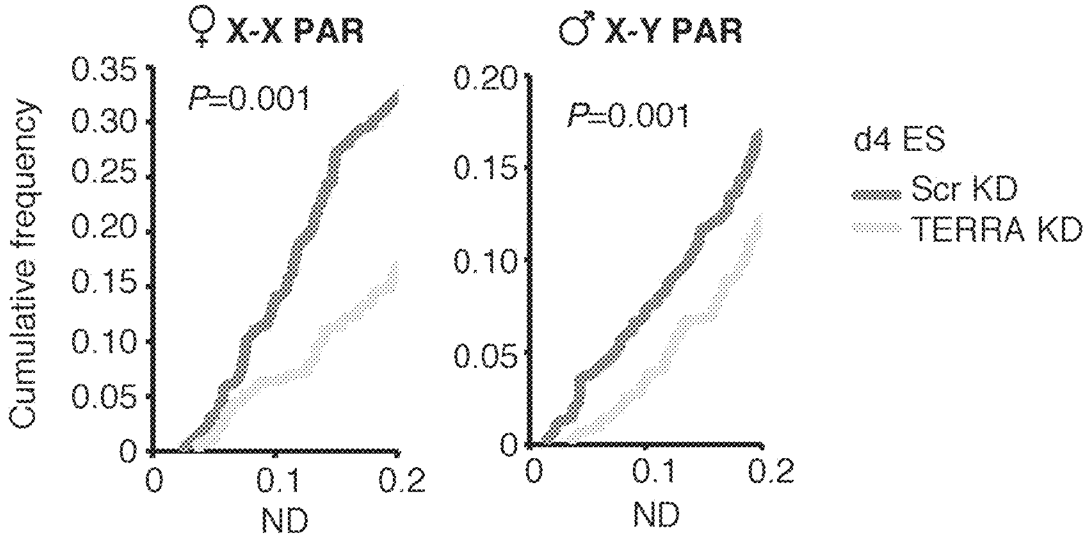
Figure 7G:
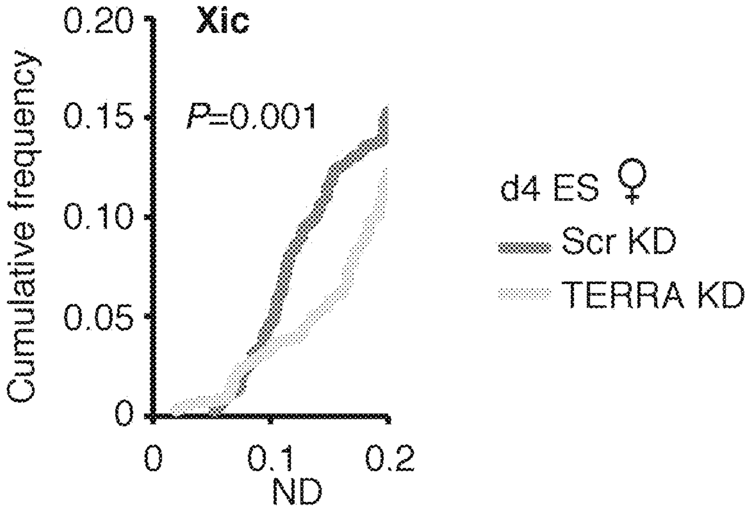
Figure 7H:
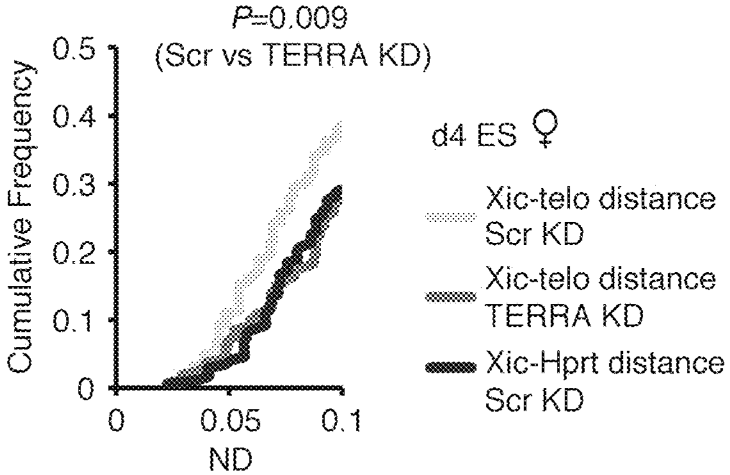
Figure 7I:
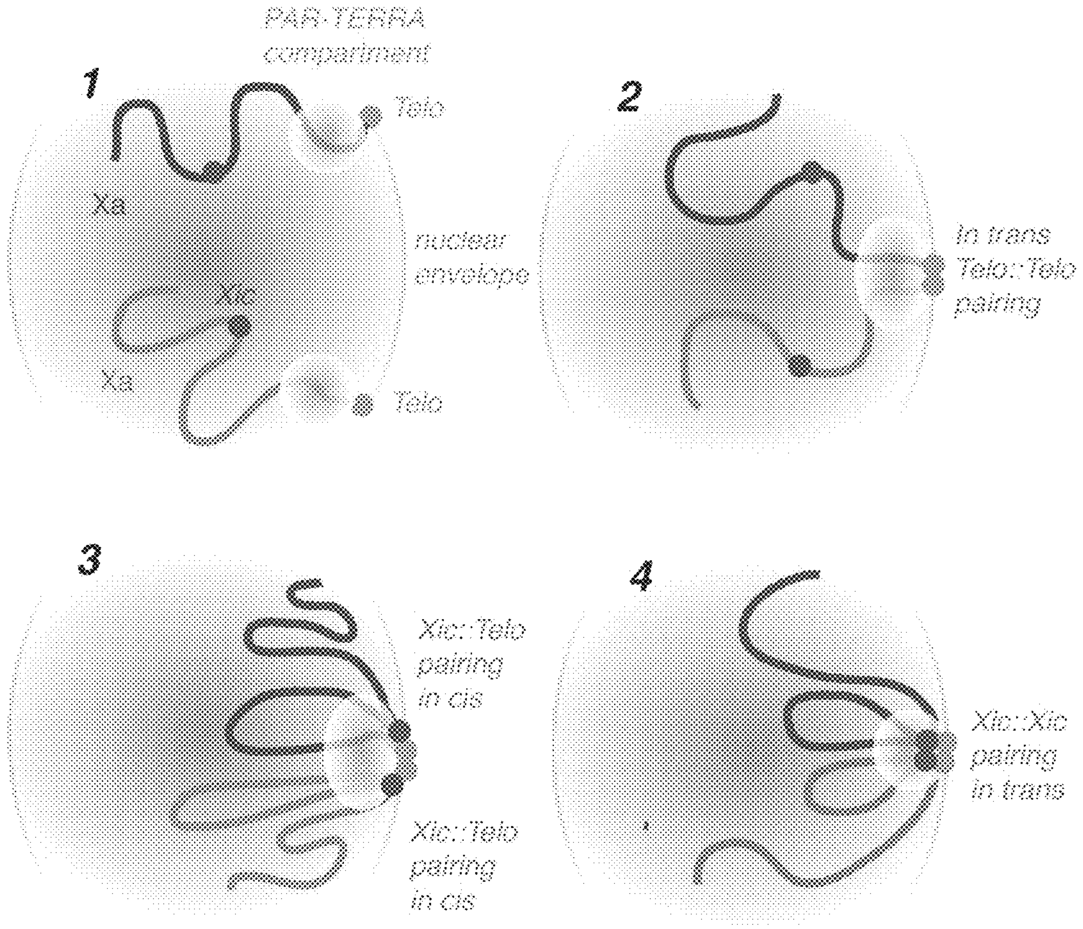

We postulate that PAR-TERRA is as an organizing center for two XCI-related processes (FIG. 6H-I, 7I). First, PAR-TERRA regulates gene regulation on a global scale (FIG. 4). Altogether, we identified hundreds of TERRA-binding sites throughout the genome in MEFs, of which 30-94 are X-linked. High PAR-TERRA coverage occurs near escapee genes, including genes of the pseudoautosomal region (FIG. 5). Perturbation experiments demonstrate that X-linked PAR-TERRA sites promote expression of escapee genes on the Xi. In the pseudoautosomal region, PAR-TERRA appears to protect genes from telomeric position effects. Analysis of Xist RNA localization indicated that Xist RNA is often enriched within defined peaks near escapees (Simon et al., 2013), such as the prominent peaks seen at Mid1 (FIG. 6A). These peaks suggest that Xist RNA may be sequestered at "boundaries" near escapee genes and be prevented from entering privileged loci. The idea of a boundary near escapees has been explored previously, with CTCF emerging as a candidate regulator (Filippova et al., 2005; Horvath et al., 2013). The loss of these Xist-enriched boundaries following PAR-TERRA depletion argues that PAR-TERRA also aids in formation of the Xist boundaries. We therefore propose a model in which PAR-TERRA holds Xist RNA in check and brings escapee genes into a privileged juxta-telomeric compartment that is permissive of transcription (FIG. 6H-I).

Methods of Reducing Expression of X-linked Escapee Genes

The present methods include using antisense oligonucleotides (ASO) against PAR-TERRA RNA to downregulate expression of escapee genes. In humans, all chromosomes may have the capacity to produce TERRA transcripts, each from their own subtelomeric regions. These subtelomeric regions are chromosome-specific; therefore, the X and Y subtelomeric region (also called pseudoautosomal region) are distinct from autosomes. Sex-chromosome-specific effects can be achieved by targeting the PAR end of the telomeric transcript. Without wishing to be bound by theory, knocking down PAR, TERRA, or PAR-TERRA with an inhibitory nucleic acids, e.g., an ASO, may disrupt the organizing center and thereby induce escapee gene downregulation. These inhibitory nucleic acids can therefore be used to treat disorders of sex chromosome aneuploidy, e.g., Klinefelter Syndrome (XXY) and Triple X Syndrome (XXX), or any other condition that results in extra copies of all or part of the X-chromosome (e.g., unbalanced X-autosome translocations). While individuals with extra X chromosomes are mostly dosage compensated due to the counting mechanism (XXX women have two Xi's; XXY men have 1 Xi), they have uncompensated dosage of the 15% of X-linked genes that escape XCI.

Escapee genes include those listed in Table A.

TABLE E

Escapee Genes

Human Escapee Genes

PR48; CALB3; SYAP1; HDHD1A; T54860; BC014382; AA348446; DKFZP564I1922; PRKX; Hs.431292; ITM2A; SRPX2; KIAA1817; MDS031; FLJ23018; HSU24186; Hs.271686; WBP5; TRPC5; TNFSF5; Hs.122516; Hs.404298; ARMCX4; FLJ11016; Hs.333016; DOCK11; LOC203427; CITED1; PLP1; PLCXD1; SLC25A6; LOC375793; ASMTL; DHRSX; FLJ43159; FLJ39679; CD99; XG; GYG2; ARSD; ARSE; Hs.399941; FLJ43700; AA971220; NLGN4X; FLJ12417; STS; Hs.186498; Hs.495638; PNPLA4; Hs.495641; Hs.348675; MGC17403; RAB9A; SEDL; Hs.41434; AA952971; FAM51A1; PIR; TMEM27; CA5BL; CA5B; AP1S2; Hs.121592; Hs.431654; CTPS2; Hs.431102; CXORF15; RBBP7; EIF1AX; EIF2S3; ZFX; Hs.458197; Hs.128084; USP9X; Hs.282780; Hs.86849; Hs.229338; DDX3X; MAOA; DUSP21; Hs.232417; AA130835; UBE1; INE1; JARID1C; A009X24; KIAA0522; Hs.87752; RPS4X; XIST; FLJ31610; F03810; PLXNB3; AVPR2; IKBKG; N74477; GPM6B; MGC39350; FUNDC1; SH3BGRL; L1CAM; GAB3; Hs.86443; TBL1X; GPR143; SMC1L1; RIBC1; Hs.258828; FLJ38564; NAP1L3; ZD89B07; SYTL4; Hs.527551~; ARHGAP4; RENBP; PCTK1; GRPR; CHM; HEIL2; HCFC1; OFD1; CRSP2; CLCN4; Hs.157695; MORF4L2; MYCL2; BRS3; ARD1; CXORF12; AF069137; Hs.108029; SH3KBP1; USP11; WAS; XEDAR; MAGEE1; ATP7A; Hs.445729; NXF3; LOC340544; PLS3; CUL4B; DXYS155E; MKRN4; 23809; MSL3L1; ASB11; NHS; PHEX; TIMP1; MLLT7; PIN4; COX7B; RAB40A; COL4A6; FLJ36576; UTP14A; COVA1; PLAC1; LOC159090; MAGEA8; ABCD1; C6.1A; CLIC2; PDZK10; REPS2; CDKL5; Hs.435570; Hs.446513; RS1; PHKA2; N53651; Hs.444490; ACATE2; TAB3; Hs.177986; BCoR; SYP; CCNB3; LOC51248; FLJ20105; Hs.37464; ABCB7; Hs.182171; BTK; RPL36A; GLA; BEX1; FLJ21174; NXT2; FLJ22679; Hs.425072; AMMECR1; Hs.61094; PAK3; LHFPL1; FLJ22965; UPF3B; MCTS1; GPC4; PHF6; MOSPD1; Hs.436787; CDR1; SLITRK2; LOC347512~; ZNF185; M78874; HCA127; FLJ34366; FLJ12525; FMR1; IRAK1; TKTL1; VBP1; Hs.522189~; KIAA1280; MID1; Hs.187608; ARHGAP6; H48827; M62076; GLRA2; EUROIMAGE 35971; CXorf23; SAT; AA601738; DMD; AA461044; FLJ42925; TM4SF2; FLJ43479; ATP6AP2; ZC35F11; SLC9A7; RGN; SLC38A5; GATA1; KCND1; GRIPAP1; FLJ21687; HADH2; UREB1; DT1P1A10; FGD1; Hs.13041; LOC90736; MAGEH1; W68846; DKFZp686L07201; LOC92249; Hs.38448; MSN; STARD8; EFNB1; PJA1; ACRC; GPR23; FLJ13042; TM4SF6; ARMCX1; ARMCX2; Hs.53997; MGC23947; RAB9B; FLJ33516; CLDN2; AI650369; H66935; PRPS1; PSMD10; APG4A; CHRDL1; KLHL13; NKAP; PEPP-2~; ODZ1; XPNPEP2; CXorf9; Hs.269127; FHL1; Hs.205436; FLJ38034; ATP11C; Hs.112784; Hs.127679; Hs.31542; LDOC1; CD99L2; PNMA5; SYBL1; G06389; TIMM8A; HPRT1; FAM9C; AW448933; UBQLN2; FLJ31204; PGPL; SHOX; ZBED1; KAL1; IL9R; IL9R Mouse Escapee Genes 1810030O07Rik; 5530601H04Rik; 5730416F02Rik; Abcb7; Aff2; Bgn; Car5b; Col4a6; Cox7b; Cxx1b; Ddx3x; Dkc1; Dmd; Dusp9; Eda; Eif2s3x; Fgf13; Firre; Frmpd4; Ftx; Gm5124; Gyk; Hmgb3; Il1rapl1; Irak1; Jpx; Kdm5c; Kdm6a; Kif4; Lage3; Mageb16; Mageb18; Mbtps2; Mid1; Msn; Naa10; Ndufb11; Ngfrap1; Nono; Pbdc1; Pdha1; Plp2; Pola1; Praf2; Prickle3; Rbbp7; Rbm10; Reps2; Rpl39; Rps4x; Sept6; Shroom4; Slc16a2; Slc25a5; Usp11; Wbp5; Xist; Flna; Ikbkg; Hcfc1; Huwe1; Maged1; Ogt; Asmt; and Erdr1

305 escapees in human, and 65 escapees in mouse
human escapees defined as Xi/Xa > 0.1 based on allele specific PCR in this paper: (Nature, 2005, Laura Carrell & Huntington F. Willard) X-inactivation profile reveals extensive variability in X-linked gene expression in females
#mouse escapees defined as Xi/Xa > 0.1 or Xi read counts >5 in MEF RNA-seq Table B provides a list of escapee genes in the human pseudoautosomal region (PAR) of the X chromosome. Annotated gene name and full gene description are shown. Whether or not there is a Y-chromosome homologue is noted in the third column.

TABLE B

| Human PAR genes or Y orthologues or pseuodogene | | |
| --- | --- | --- |
| PR48 | Protein phosphatase 2A 48 kDa subunit | Pseudoautosomal; Y identity |
| PLCXD1 | Phosphatidylinositol phospholipase C, X domain 1 | Pseudoautosomal; Y identity |
| SLC25A6 | Solute carrier family 25, member 6 | Pseudoautosomal; Y identity |
| LOC375793 | Hypothetical protein with EST support | Pseudoautosomal; Y identity |
| ASMTL | Acetylserotonin O-methyltransferase-like | Pseudoautosomal; Y identity |
| DHRSX | Dehydrogenase/reductase (SDR) family | Pseudoautosomal; Y identity |
| FLJ43159 | mRNA of unknown function | Pseudoautosomal; Y identity |
| FLJ39679 | mRNA of unknown function | Pseudoautosomal; Y identity |
| CD99 | CD99 antigen | Pseudoautosomal; Y identity |
| DXYS155E | Lymphocyte surface protein | Pseudoautosomal; Y identity |

TABLE B-continued

| Human PAR genes or Y orthologues or pseudogene | | |
|---|---|---|
| PGPL | Pseudoautosomal GTP-binding protein-like | Pseudoautosomal; Y identity |
| SHOX | Short stature homeobox | Pseudoautosomal; Y identity |
| ZBED1 | zinc finger, BED domain containing 1 | Pseudoautosomal; Y identity |
| SYBL1 | Synaptobrevin-like 1 | Pseudoautosomal; Y identity |
| IL9R | Interleukin 9 receptor | Pseudoautosomal; Y identity |
| RPS4X | Ribosomal protein S4, X isoform | Y orthologue |
| UBE1 | Ubiquitin-activating enzyme E1 | Ancestral Y homolog |
| JARID1C | Jumonji, AT rich interactive domain 1C | Y orthologue |
| RAB9A | Ras-related GTP-binding protein | Y homology by BLAST |
| SEDL | Spondyloepiphyseal dysplasia, late | Y pseudogene |
| CXORF15 | Chromosome X open reading frame 15 | Y orthologues |
| EIF1AX | Eukaryotic translation initiation factor 4C | Y orthologue |
| ZFX | Zinc finger protein X-linked | Y orthologue |
| USP9X | Ubiquitin specific protease 9, X isoform | Y orthologue |
| DDX3X | DEAD/H box 3, X-linked | Y orthologue |
| DUSP21 | Dual specificity phosphatase 21 | Y orthologue |
| OFD1 | Oral-facial-digital syndrome 1 gene | Y pseudogene |
| CRSP2 | Cofactor required for Sp1 transcriptional activation | Y pseudogene |
| TAB3 | TAK1-binding protein 3 | Y pseudogene |
| BCoR | BCL6 co-repressor | Y pseudogene |
| FAM9C | Family with sequence similarity 9, member C | Y homology by BLAST |
| HDHD1A | Haloacid dehalogenase-like hydrolase domain 1 | Y pseudogene |
| NLGN4X | Neuroligin 4 | Y orthologue |
| STS | Steroid sulfatase | Y pseudogene |
| TBL1X | Transducin (beta) like 1 | Y orthologue |
| GPR143 | G protein-coupled receptor 143 | Y pseudogene |
| KAL1 | Kallmann syndrome 1 sequence | Y pseudogene |
| AA348446 | ESTs | Y homology by BLAST |
| DKFZP564I1922 | Adlican | Y pseudogene |
| PRKX | Protein kinase, X-linked | Y orthologue |
| XG | Xg blood group | Y pseudogene |
| GYG2 | Glycogenin 2 | Y pseudogene |
| ARSD | Arylsulfatase D | Y pseudogene |
| ARSE | Arylsulfatase E | Y pseudogene |
| Hs.399941 | ESTs | Y homology by BLAST |
| FLJ43700 | Hypothetical protein with mRNA & EST support | Y homology by BLAST |

The sequence of human PAR-TERRA is provided herewith as SEQ ID NO:1. The sequence of mouse PAR-TERRA is provided herewith as SED ID NO:2. In some embodiments, the sequence of an oligo targeting TERRA is 5'-TAA CCC TAA CCC TAA C-3' (SEQ ID NO:5); or PAR-TERRA is 5'-TCT CTG TCT CTG TCG C-3' (SEQ ID NO:6).

Method of Reducing Expression of from non-Xi Genes

TERRA forms a special compartment for gene activation, not only for escapees on the Xi but also for autosomal genes and subtelomeric genes on autosomal ends, of which Chr 1, 3, 4, 8, 18, and 19 are shown herein (see, e.g., FIGS. 4, 5A-B). PAR-TERRA and various Chromosome-specific TERRAs (produced from the subtelomeric regions) are also used to regulate genes outside of the Xi. The present methods can be applied to downregulate a network of Xa and subtelomeric autosomal genes involved in growth control and apoptosis, and other processes relevant to human disease. Two examples include active X (Xa) genes and the FSHD subtelomeric region of human Chromosome 4. The Xa also produces PAR-TERRA from its pseudoautosomal region and has multiple targets outside of its pseudoautosomal region. Targeting PAR, TERRA, or PAR-TERRA can reduce expression from the Xa. PAR-TERRA and TERRA also target thousands of autosomal sites with closely linked genes. A specific example include the Chr4 region associated with facioscapulohumeral muscular dystrophy (FSHD), which is located in the subtelomeric region of human Chr4 and contains coding genes FRG1, FRG2, DUX4, and the long noncoding RNAs of forward and reverse orientations from the macrosatellite repeat, D4Z4. FSHD is caused by ectopic expression of these genes when the D4Z4 repeat contracts and becomes “activated”. Thus, PAR, TERRA, or PAR-TERRA or Chr4-specific TERRA could be targeted to downregulated the associated subtelomeric genes.

In addition, PAR-TERRA knockdown resulted in downregulation of genes enriched for cell cycle and apoptosis genes (see Example 5). Thus, targeting PAR, TERRA, or PAR-TERRA transcripts can be an effective method of treating cancer and other human diseases where the X-chromosome and various growth control genes are frequently overexpressed. The sequence of human Chr4 FSHD region is provided herewith as SEQ ID NO:3.

Disorders of Sex Chromosome Aneuploidy

The present methods can be used to reduce expression of escapee genes in subjects with disorders of sex chromosome aneuploidy in which at least one extra X chromosome is present (referred to herein as a supernumerary X chromosome). The term Klinefelter syndrome (KS) describes a group of disorders in which at least one extra X chromosome is present in addition to a normal male karyotype, referred to in standard genetics nomenclature as 46,XY. Related to the KS group is 47,XXY aneuploidy, which is the most prevalent disorder of sex chromosomes in humans with a prevalence of about 1:500. Rarer sex chromosome aneuploidies include 48,XXYY and 48,XXXY (about 1:17,000 to 1:50,000); 49,XXXXY (about 1:85,000 to 1:100,000) births. See, e.g., Visootsak and Graham, Orphanet J Rare Dis. 2006; 1: 42; Targaltia et al., Acta Paediatr. 2011 June; 100(6):851-60). Triple X syndrome (47,XXX) is a disorder in which at least one extra X chromosome is present in addition to a normal female karyotype; 48,XXXX and 49,XXXXX have also been described (Schoubben et al., Eur J Pediatr. 2011 October; 170(10):1325-7). Conditions resulting from unbalanced X-autosome translocations or cancers (and other human diseases) with X-chromosomal aneuploidies may be treated similarly using the technology. These conditions can result in a large number of deleterious physical, psychological, and intellectual effects in affected individuals (see, e.g., Visootsak and Graham, Orphanet J Rare Dis. 2006; 1: 42; Schoubben et al., Eur J Pediatr. 2011 October; 170(10): 1325-7; Targaltia et al., Acta Paediatr. 2011 June; 100(6): 851-60).

Inhibitory Nucleic Acids Targeting PAR-TERRA or Other Chromosome-specific TERRA

The methods and compositions described herein can include nucleic acids such as a small inhibitory RNA (siRNA) or LNA that targets (specifically binds, or is complementary to) PAR, PAR-TERRA, or other chromosome-specific TERRA (e.g., Chr4-specific, as produced from the subtelomeric region of human Chr4 which is associated with facioscapulohumeral muscular dystrophy (FSHD)) RNA. Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, molecules comprising modified bases, locked nucleic acid molecules (LNA molecules), antagomirs, peptide nucleic acid molecules (PNA molecules), and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., U.S. Ser. No. 62/010,342, WO 2012/065143, WO 2012/087983, and WO 2014/025887. However, in some embodiments the inhibitory nucleic acid is not an miRNA, an stRNA, an shRNA, an siRNA, an RNAi, or a dsRNA.

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required.

Routine methods can be used to design an inhibitory nucleic acid that binds to the target sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the RNA sequence. For example, a specific functional region can be targeted, e.g., a region comprising a known RNA localization motif (i.e., a region complementary to the target nucleic acid on which the RNA acts). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

Once one or more target regions, segments or sites have been identified, e.g., within a sequence known in the art or provided herein, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a RNA molecule, then the inhibitory nucleic acid and the RNA are considered to be complementary to each other at that position. The inhibitory nucleic acids and the RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the inhibitory nucleic acid and the RNA target. For example, if a base at one position of an inhibitory nucleic acid is capable of hydrogen bonding with a base at the corresponding position of a RNA, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Inhibitory nucleic acids that hybridize to an RNA can be identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids), as well as WO 2012/065143, WO 2012/087983, and WO 2014/025887 (inhibitory nucleic acids targeting non-coding RNAs/supRNAss), all of which are incorporated herein by reference in their entirety.

Antisense

In some embodiments, the inhibitory nucleic acids are antisense oligonucleotides. Antisense oligonucleotides are typically designed to block expression of a DNA or RNA target by binding to the target and (without wishing to be bound by theory) halting expression at the level of transcription, translation, or splicing. Antisense oligonucleotides of the present invention are complementary nucleic acid sequences designed to hybridize under stringent conditions to an RNA. Thus, oligonucleotides are chosen that are sufficiently complementary to the target, i.e., that hybridize sufficiently well and with sufficient specificity, to give the desired effect.

siRNA/shRNA

In some embodiments, the nucleic acid sequence that is complementary to an target RNA can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc NatlAcadSci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $min^{-1}$ in the presence of saturating (10 mM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

Modified Inhibitory Nucleic Acids

In some embodiments, the inhibitory nucleic acids used in the methods described herein are modified, e.g., comprise one or more modified bonds or bases. A number of modified bases include phosphorothioate, methylphosphonate, peptide nucleic acids, or locked nucleic acid (LNA) molecules. Some inhibitory nucleic acids are fully modified, while others are chimeric and contain two or more chemically distinct regions, each made up of at least one nucleotide. These inhibitory nucleic acids typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the inhibitory nucleic acid into which they are incorporated more resistant to nuclease digestion than the native oligodeoxynucleotide; these modified oligos survive intact for a longer time than unmodified inhibitory nucleic acids. Specific examples of modified inhibitory nucleic acids include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are inhibitory nucleic acids with phosphorothioate backbones and those with heteroatom backbones, particularly CH2—NH—O—CH2, CH, —N(CH3)—O—CH2 (known as a methylene (methylimino) or MMI backbone], CH2 —O—N (CH3)—CH2, CH2—N (CH3)—N (CH3)—CH2 and O—N (CH3)—CH2 —CH2 backbones, wherein the native phosphodiester backbone is represented as O—P—O—CH,); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the inhibitory nucleic acid is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid inhibitory nucleic acid mimetics are described in Wang et al., J. Am. Chem. Soc., 2000, 122, 8595-8602.

Modified inhibitory nucleic acid backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, $SCH_3$, F, OCN, $OCH_3$ $OCH_3$, $OCH_3$ $O(CH_2)n$ $CH_3$, $O(CH_2)n$ $NH_2$ or $O(CH_2)n$ $CH_3$ where n is from 1 to about 10; C1 to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an inhibitory nucleic acid; or a group for improving the pharmacodynamic properties of an inhibitory nucleic acid and other substituents having similar properties. A preferred modification includes 2'-methoxyethoxy [2'-0-$CH_2CH_2OCH_3$, also known as 2'-O-(2-methoxyethyl)] (Martin et al, Helv. Chim. Acta, 1995, 78, 486). Other preferred modifications include 2'-methoxy (2'-0-$CH_3$), 2'-propoxy (2'-$OCH_2$ $CH_2CH_3$) and 2'-fluoro (2'-F). Similar modifications may also be made at other positions on the inhibitory nucleic acid, particularly the 3' position of the sugar on the 3' terminal nucleotide and the 5' position of 5' terminal nucleotide. Inhibitory nucleic acids may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given inhibitory nucleic acid to be uniformly modified, and in fact more than one of the aforementioned modifications may be incorporated in a single inhibitory nucleic acid or even at within a single nucleoside within an inhibitory nucleic acid.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an inhibitory nucleic acid mimetic that has been shown to have excellent hybridization properties, is referred to as a peptide nucleic acid (PNA). In PNA compounds, the sugar-backbone of an inhibitory nucleic acid is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. Nos. 3,687,808, as well as 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the inhibitory nucleic acid. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Locked Nucleic Acids (LNAs)

In some embodiments, the modified inhibitory nucleic acids (including ASOs) used in the methods described herein comprise locked nucleic acid (LNA) molecules, e.g., including [alpha]-L-LNAs. LNAs comprise ribonucleic acid analogues wherein the ribose ring is "locked" by a methylene bridge between the 2'-oxgygen and the 4'-carbon —i.e., inhibitory nucleic acids containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herein.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA; for example, a series of inhibitory nucleic acids of 10-30 nucleotides spanning the length of a target RNA can be prepared, followed by testing for activity. Optionally, gaps, e.g., of 5-10 nucleotides or more, can be left between the LNAs to reduce the number of inhibitory nucleic acids synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of more than four LNA residues, should be avoided where possible (for example, it may not be possible with very short (e.g., about 9-10 nt) inhibitory nucleic acids). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O-N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning; A Laboratory Manual 3d ed. (2001); Current Protocols in Molecular Biology, Ausubel et al., eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, ed. Elsevier, N.Y. (1993).

Pharmaceutical Compositions

The methods described herein can include the administration of pharmaceutical compositions and formulations comprising an inhibitory nucleic acid that targets PAR-TERRA RNA and other chromosome-specific TERRA RNAs.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy,* 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; *Remington: The Science and Practice of Pharmacy,* 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as *Remington: The Science and Practice of Pharmacy,* 21st ed., 2005.

Various studies have reported successful mammalian dosing using complementary nucleic acid sequences. For example, Esau C., et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by Krützfeldt J., et al., (2005) Nature 438, 685-689, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., compositions for providing cholesterol homeostasis. For example, the inhibitory nucleic acids can be co-administered with drugs for treating or reducing risk of a disorder described herein.

EXAMPLES

The invention is further described in the following examples, which do not limit the scope of the invention described in the claims.

Experimental Procedures

The following materials and methods were used in the Examples below.

FISH

Cells were cytospun onto glass slides and permeabilized with CSK buffer containing 0.5% Triton X-100, and fixed in 4% paraformaldehyde. DNA oligos probes for RNA FISH were ordered from Integrated DNA Technologies. For TERRA: $(TAACCC)_7$-Alexa488-3' and 5'-Cy5-$(TAACCC)_7$. For I4 oligos: I4-47k 5'-Alexa488-TGC ACT GAC GTC CTG TGG CCA CTG GGT GGC GCC AGA GCAT (SEQ ID NO:7); I4-22k: 5'-Cy3-taa tct gaa tat ctg ggc ctc cgt gtg cag acc tga ggt t (SEQ ID NO:8); I4 31k: 5'-Cy5-gtc tct gtg tct gtc tct ctg tct ctg tcg cta act cta t (SEQ ID NO:9). DNA oligo probes for RNA-FISH were mixed at the final concentration 0.5 pmol/μl in hybridization solution (50% formamide, 2×SSC, 2 mg/ml BSA, 10% Dextran Sulfate-500K). BAC DNA probes and PCR-PAR probes were labeled with fluorophore-dUTP using nick translation, used 1 ng/μl for RNA-FISH and 50 ng/μl for DNA FISH at the final concentration in hybridization buffer. Hybridization was carried out at 42° C. overnight for RNA FISH. Slides were washed with 2×SSC/50% formamide for 5 min three times at 44° C., and then wash with 2×SSC for 5 min twice at 44° C. For DNA FISH, slides were treated with 0.4 mg/ml RNase A in PBS at 37° C. for 1 hr, washed with PBS, incubated with 0.1 N HCl for 10 min. Slides were washed in PBST (0.2% Tween 20 in 1 × PBS) at RT for 5 mins, and then the denaturation was carried out in 70% formamide/2×SSC at 80□C for 15 mins. Slides were then washed with PBS, dehydrated with EtOH, and air dried. Hybridization was carried out at 37° C. overnight for DNA FISH, and washing condition was the same as for RNA-FISH with additional wash in 0.1×SSC for 5 min at 44° C. For metaphase spread, cells were incubated with 50 ng/ml Colcemid for 2 hr, harvested, washed with PBS, incubated in cold 0.056M KCl on ice for 30 min and fixed in methanol/acetic acid (3:1). Metaphase spread chromosomes were spread on glass slides, air dried and fixed in 4% formaldehyde.

For pairing assay, digital images were obtained with the Nikon and processed using Volocity software (PerkinElmer). In brief, z sections were captured at 0.2 μm intervals and 3D images were projected on a single two-dimensional plane. Distance of Xic-Xic, PAR-PAR (x), and the nuclear areas (A) was analyzed using Volocity software. Only nuclei with two resolvable X signals were scored (single dots were excluded). 'Normalized distance' (ND) is defined as x/d, where d is the nuclear diameter, defined as $2(A/\pi)^{0.5}$. PCR-PAR PCR primer pairs were used as follows:

| Primer | Sequence | SEQ ID NO: |
|---|---|---|
| P3-F: | CTCAGAGCCCAGTGTCAATCAC, | 10 |
| P3-R: | CACGACCGCTTAGAAGAACCGG | 11 |
| P4-F: | GAGACGGCCTACCATGTGCTTC, | 12 |
| P4-R: | GTGAGTGCTGTGAACTCGGCTG | 13 |
| P5-F: | CAGGGCCTGATTTGGCTTGAAAC | 14 |
| P5-R: | GAAGAGTAGTCTGACCTCATCTC | 15 |
| P6-F: | CAGGGCATGATATCCTCTTTGG | 16 |
| P6-R: | CATTCAATGGTGTTGATGATGGTAC | 17 |
| P8-F: | GGTTAGAATACAGCGCGGACATTCA | 18 |
| P8-R: | GTGAATCTCCGAGGCAACTGTC | 19 |

ChIRT-seq Analysis

The PAR-TERRA ChIRT protocol was modified from the original ChIRP and CHART protocols (Chu et al., 2011; Simon et al., 2011) as follows: (i) We used a minimum number of capture probes to reduce off-target effects. (ii) We also increased the shearing size to 0.5-3 kb to preserve integrity of long noncoding RNAs. (iii) Because we observed that RNaseH is not active in SDS buffer, we used NP40 instead of SDS or N-lauroyl sarcosine in the final DNA elution; we used a lower concentration of NP40 detergent to better preserve RNaseH activity (FIG. 9A).

Specifically, mouse ES cells were grown to 80% confluency and feeder cells were removed. 15 millions of cells were spun down and washed with PBS once. Cells were resuspended in 10 ml of PBS and then another 10 ml of 2% of glutaraldehyde were added to fix cells at room temperature for 10 min. Crosslinking was then quenched with 0.125 M glycine for 5 min. Cells were than spun down at 2000 g for 5 min at 4° C. Cells were then washed with cold PBS and then spun down again. Cell pellets were immediately frozen in liquid nitrogen and stored at −80° C. Mouse ES cells at embryonic body stages (Day3, Day7) were trypsinized, filtered with cell strainers (40 μm). The following steps were prepared as the same as undifferentiated ES cells. Cells were thaw out on ice, and were resuspened in 1 ml of swelling buffer (0.1 M Tris pH 7.0 10 mM KOAc, 15 mM MgOAc, 1% NP40, 1 mM DTT, 1 mM PMSF, 100 U/ml Superase-In[Ambion]) for 10 min on ice. Cells were then dounced and pelleted at 2500 g for 5 min. Nuclei was further lyzed in nuclear lysis buffer (50 mM Tris pH 7.0, 10 mM EDTA, 1% SDS, 1 mM DTT, 1 mM PMSF, protease inhibitor, 100 U/ml Superase-In) on ice for 10 min, and sonicated using Bioruptor until DNA size 0.5-3 kb (it usually takes 1.5 hr and depends on the cell numbers). Cell lysates were then spun down at 13,000 rpm for 5 min to remove insoluble debris. Cell lysates were then frozen in liquid nitrogen and stored in −80° C. Streptavidin-magnetic Cl (Life Technologies) beads were blocked with 500 ng/ul yeast total RNA, and 1 mg/ml BSA for 1 hr at 37° C., and respuspended in 1X hybridization buffer (1 volume of lysis buffer plus 2 volume of 2X hybridization buffer). Cell lysates were diluted in two times volume of 2X hybridization buffer (750 mM NaCl, 1% SDS, 50 mM Tris pH 7.0, 1 mM EDTA, 15% Formamide, 1 mM DTT, PMSF, protease inhibitor, and 100 U/ml Superase-In), and were preclean with Streptavidin-magnetic Cl beads at 37° C. for 1 hr (100 μl of beads for 1 ml lysates). Precleaned lysates were incubated with pooled probes (100 pmol for 3 ml of diluted cell lysates) at 37° C. for 3 hr. Three hundred microliters washed/blocked Cl beads were added per 100 pmol of probes, and the whole reaction was mixed for another 1 hr at 37° C. DNA probes for ChIRT were ordered from Integrated DNA Technologies and labeled with 3' biotin-TEG. PAR DNA probe sequences were listed as follows: 36K: gagcgcctcagtgtgcaaatct (SEQ ID NO:20), 47K: ACTGGGTGGCGCCAGAGCAT(SEQ ID NO:21), 22K: ctccgtgtgcagacctgaggtt (SEQ ID NO:22), 34K: ccctacctaccctccagaga (SEQ ID NO:23), 31K: tctctgtctctgtcgctaac (SEQ ID NO:24). TERRA-AS probe sequence: TAACCCTAACCCTAACCCTA (SEQ ID NO:25). TERRA-sense probe sequence: TTAGGGTTAGGGTTAGGGTT (SEQ ID NO:26). Beads: biotin-probes: RNA:chromatin adducts were captured by magnets, washed five times at 37° C. for 5 min with wash buffer (2×SSC, 0.5% SDS, 1 mM DTT, 1 mM PMSF), and then washed twice for 5 min at room temperature with 0.1% NP40 buffer (150 mM NaCl, 50 mM Tris pH 8.0, 3 mM $MgCl_2$, 10 mM DTT, 0.1% NP40). DNA was then eluted twice for 20 min in 450 μl of 0.1% NP40 buffer with 200 U/ml RNase H (NEB) at room temperature. DNA for no RNase H controls was eluted in 0.1% NP40 buffer without RNaseH. Eluted DNA was treated with RNase A (1 mg/ml) at 37° C. for 1 hr, and then was treated with proteinase K (1 mg/ml) and supplied addition of SDS to 0.5% at final concentration at 55° C. for 16 hr. DNA was extracted with phenol/chloroform using phase lock gel tubes. For pre-RNaseA treatment control, cell lysates were treated with RNase A at 37° C. overnight before hybridization. For RNA elution after hybridization, beads:biotin-probes:RNA:chromatin adducts were washed 5 time in wash buffer, then treated with proteinase K in PK buffer (100 mM NaCl, Tris pH 7.0, 1 mM EDTA, 0.5% SDS) at 55° C. for 30 min. Beads suspension was boiled at 90° C. for 5 min, and then RNA was extracted using TRIzol (Invitrogen). Primer pairs for q-PCR were used as followed: PAR-DNA-F: TGGAGGTTAAACGATTATTTATCTGC (SEQ ID NO:27), PAR-DNA-R: ACGAGTTTCCAAGGTGCTG (SEQ ID NO:28); Hprt-F: CTGCTACTTCAACTCCTGGTGTGC (SEQ ID NO:29), Hprt-R: AGGCGAATTGGGATGTAGCTCAG (SEQ ID NO:30).

PAR-TERRA ChIRT-seq Analysis

PicoGreen (Life Technologies) was used to estimate the concentration of eluted DNA. Before library construction, equal amount of lambda DNA (0.015 pg of PCR products, ~250 bp) was added as spike-in control into eluted DNA samples. The PCR primers sequences for lambda DNA are as follows: Lambda 5-F, 5'-GCA TAT GTT GTG TTT TAC AG-3' (SEQ ID NO:31); Lambda 5-R, 5'-GCA ACA AAT TGA TAA GCA-3' (SEQ ID NO:32). Following the removal of adaptor sequences and PCR duplicates, paired-end 50 bp sequencing data was aligned to mouse reference genome (GRCm38/mm10 and NCBI37/mm9) using the software Novoalign (v3.00.02) (Li H. (2013) Aligning sequence reads, clone sequences and assembly contigs with BWA-MEM. arXiv:1303.3997v1 [q-bio.GN]). The coverage files were generated using R software library SPP software (Kharchenko et al., 2008) with smoothing using 500 bp bins with a 100 bp step size to generate control-subtracted, normalized read densities. Controls include input, sense-ChIRT, and TERRA-ChIRT without RNase H elution (no RNase H). These data were visualized using IGV software to display all tracks with a mean windowing function and scales indicated in each figure. Other methods to generate normalized coverage files, including the generation of conservative enrichment and maximum likelihood estimates, resulted in similar distribution patterns. Scatter plots for correlation analysis used input—normalized coverage produced by SPP, windowed by 3 kb bins and filtered out unenriched bins with an averaged density smaller than 4. Peaks were called by MACS (1.4.2)(Zhang et al., 2008) software using normalization to indicated controls (e.g., input, sense, no RNaseH or pre-RNaseA), and filtered by peak length greater than 1 kb. Metagene profiles were produced by software CEAS (0.9.9.7) (Shin et al., 2009) using 2 fold enriched over input wig files and bed files produced by MACS peak calling.

TERRA Knockdown

Mouse ES cells (female, 16.7, cas/mus hybrid) were grown to 70% confluency, and then trypsinized, and feeder cells were removed. A total of $2\times10^6$ mES cells were transfected with LNA gapmer oligos at a concentration of 2~8 μM in 100 μl nucleuofector solution using A30 program (nucleuofector kits, Lonza). A total of 2 ml of feeders-conditional medium (medium from feeders grown in mES medium for 6-18 hr) was added to the cells, and the cells were plated on gelatinized plates. LNA gapmers were designed and synthesized by Exiqon with modified LNA bases and phosphothiolated backbone modification. The LNA sequences were as follows: Scr, 5'-CAC GTC TAT ACA CCA C-3' (SEQ ID NO:4); TERRA, 5'-TAA CCC TAA CCC TAA C-3' (SEQ ID NO:5); PAR, 5'-TCT CTG TCT CTG TCG C-3' (SEQ ID NO:6). SV40T transformed MEFs (cas/mus hybrid) were used for TERRA LNA knockdown.

RNA-seq Analysis

Total RNA was isolated using TRIzol (Invitrogen), depleted of DNA by DNase treatment (TURBO DNase, Ambion), depleted of ribosomal RNA (Ribominus Eukaryote Kit v2, Invitrogen), purified greater than 200 nucleotides using mirVana RNA extraction kit (Ambion), and fragmented in first strand synthesis buffer (NEB) containing magenisium at 95° C. for 10 min to a median size 150-200 bp. cDNA were reversed transcribed with random primers (with Actinomycin D) using Superscript III (Invitrogen) at 50° C. for 30 min. The following steps such as second strand synthesis, end repaired, dA-tailing, adaptor ligation, USER enzyme digestion, double size selection (0.6x-1.2x AMpure XP beads), and library amplification were performed according to NEBUltra Directional RNA library preparation protocol for Illumina (NEB). Sequencing of purified libraries was carried out on an Illumina HiSeq instrument for paired 50 nucleotides reads. After removal of adaptor sequences by Trim Galore, reads were aligned to mouse genomes (GRCm38/mm10 and NCBI37/mm9) using Tophat2. After removal of PCR duplicates, data was analyzed using either Cuffdiff 2 (Trapnell et al., 2013). Differential expression was called using Cuffdiff 2 with a threshold of q-Value<0.05. Coverage of RNA-seq was normalized by per million mapped reads as FPM value shown in the tracks. Allelic RNA-seq analysis was described previously (Simon et al., 2013). Briefly, reads were aligned to allele-specifically to 129S1/SvJm (mus) and CAST/EiJ (cas) using Tophat2. All reads mapping to gene bodies were summed for cas, mus and comp tracks, and PCR duplicates were removed. Differential expression between sets of genes in KD samples was analyzed using R library EdgeR (3.4.2) within by HOMER (4.8) software (Heinz et al., 2010) using function analyseRepeates.pl to generate count numbers on mus tracks for gene expression on Xi (mus).

Northern Blotting Analysis

DNA sequences for Northern probes were listed as follows:

| Probe | Sequence | SEQ ID NO. |
|---|---|---|
| TERRA | TAACCCTAACCCTAACCCTAACCCTAACCC | 33 |
| GAPDH | GTAGACCCACGACATACTCAGCACCGGCCTCACCCCATT | 34 |
| 14-15k | aaggccagccgcggttccagacctgcggtgcggccgtgtc | 35 |
| 14-22k | taatctgaatatctgggcctccgtgtgcagacctgaggtt | 36 |
| 14-27k | ttgggggcgtgtctcagagcaggaggggtgtggtctggca | 37 |
| 14-31k | gtctctgtgtctgtctctctgtctctgtcgctaactctat | 38 |
| 14-34k | aaagccaccaggcctctaatccctacctaccctccagaga | 39 |
| 14-42k | cctggagaaatcaagtctgcgaagatccaaaaattaaaat | 40 |
| 14-47k | TGCACTGACGTCCTGTGGCCACTGGGTGGCGCCAGAGCAT | 41 |
| 14-53k | CTGACCACCAGGCTACAGTGTCCTGTAACCGCCAGGCATA | 42 |

All oligo probes were end labeled using T4 polynucleotide kinase. I4-31k oligos were used for PAR-TERRA transcripts in FIG. 4B. Total RNA was extracted using TRIzol followed by acid phenol extraction. Total RNA (5 μg) was loaded in each lane. Hybridization was carried out at 42° C. overnight using ULTRAhyb-Oligo hybridization buffer (Ambion).

Quantitative RT-PCR

Total RNA was isolated using TRIzol (Invitrogen), treated with TURBO DNase (Ambion), and reverse-transcribed with random primers using Superscript III reverse transcriptase (Invitrogen). qRT-PCR was perform using iQ SYBR Green Supermix (Bio-Rad). Expression levels were normalized to GAPDH levels. Primer pairs were used as follows:

| Primer | Sequence | SEQ ID NO: |
|---|---|---|
| GAPDH-F | CGTCCCGTAGACAAAATGGT | 43 |
| GAPDH-R | TTGATGGCAACAATCTCCAC | 44 |
| Erdr1-F | CACAGTGATGTCACCCACGA | 45 |
| Erdr1-R | GTGAGAATCGCTCCGTCCTG | 46 |

-continued

| Primer | Sequence | SEQ ID NO: |
|---|---|---|
| Mid1-intron1-F | GGACGAGAGGGGACAAAGGA | 47 |
| Mid1-intron1-R | GGTCAAACCTGGACTCTGGCA | 48 |
| Asmt-F | GAAGTGGGACAGGAAGTGAG | 49 |
| Asmt-R | CGGGAACAGGAAGTGGC | 50 |
| Wls-F | CCAGTCTAATGGTGACCTGGG | 51 |
| Wls-R | TGAGAGTCAGCATGCACCAG | 52 |
| Tmx3-F | TACCGAGGACCACGGACTAA | 53 |
| Tmx3-R | AATACACGGTGCCTCTTCCG. | 54 |

XIST CHART-seq Analysis

The Xist CHART was modified from the original XIST CHART protocols (Simon et al., 2011). We used 7 oligo probes to target Xist RNA:

| Oligo | Sequence | SEQ ID NO: |
|---|---|---|
| Xist-503 | CAGGTATCCATGGCCCCGATGGGC | 55 |
| Xist-1895 | CTCGGTCTCTCGAATCGGATCCGAC | 56 |
| Xist-3322 | GAGTTATGGGCACTGCATTTTAGCA | 57 |
| Xist-5799 | TTGTTAAACGCAGGCTAGATCCTGA | 58 |
| mXist-1240 | CGCCATTTTATAGACTTCTGAGCAG | 59 |
| mXist-935 | CCtaattcttggcgtaactggctcg | 60 |
| mXist-5651 | ATGCTTAGGAAGAGGGACAAATGCA | 61 |

In detail, 20 million cells were crosslinked by with 1% formaldehyde for 10 min at room temperature. Crosslinking was then quenched with 0.125 M glycine for 5 min. After washing 3 times with PBS, crosslinked cells were re-suspended in 2 ml of sucrose buffer (0.3 M sucrose, 1% Triton-X-100, 10 mM HEPES pH 7.5, 100 mM KOAc, 0.1 mM EGTA), dounced 20 times with a tight pestle, and kept on ice for 10 min. The following steps were using polystyrene tubes,glass pipettes, and DNA LoBind microtubes (Eppendorf) to avoid cell clumps sticking onto the walls of tubes or pipettes. Nuclei were collected by centrifugation at 1,500 g for 10 min on top of a cushion of 5 ml glycerol buffer (25% glycerol, 10 mM HEPES pH7.5, 1 mM EDTA, 0.1 mM EGTA, 100 mM KOAc). Nuclei were further cross-linked with 3% formaldehyde for 30 min at room temperature. After washing three times with PBS, nuclei were extracted once with 50 mM HEPES pH7.5, 250 mM NaCl, 0.1mM EGTA, 0.5% N-lauroylsarcosine, 0.1% sodium deoxycholate, 5 mM DTT, 100 U m121 SUPERasIN (Invitrogen) for 10 min on ice, and centrifuged at 400 g for 5 min at 4 uC. Nuclei were resuspended in 270 μl of sonication buffer (50 mM HEPES pH 7.5, 75 mM NaCl, 0.1 mM EGTA, 0.5% N-lauroylsarcosine, 0.1% sodium deoxycholate, 5 mM DTT, 10 U/ml SUPERasIN, and sonicated in microtubes using Covaris S2 sonicator at 10% duty cycle, 200 bursts per cycle, intensity 3 for 5 min. The size of chromatin fragments was 0.2~3 kb. Fragmented chromatin was subjected to hybridization immediately. Hybridization, washing and elution were performed similarly to TERRA-ChIRP protocol. In brief, beads were blocked by yeast tRNA and BSA. 320 μl of 2X hybridization buffer (750 mM NaCl, 1% SDS, 50 mM Tris pH 7.0, 1 mM EDTA, 15% Formamide, 1 mM DTT, PMSF, protease inhibitor, and 100 U/ml Superase-in) was added into 160 μl lysates, and then this 1X hybridization lysate was precleaned by 60 μl of blocked beads at room temperature for 1 hr. After removal of the beads, 7 probes (labeled with 3' biotin-TEG) for Xist RNA (3.66 pmol/per probe) were added into the 1X hybridization lysate and incubate at room temperature for overnight. Beads:biotin-probes:RNA:chromatin adducts were captured by magnets, washed once with 1X hybridization buffer at 37° C. for 10 min, washed four times at 37° C. for 5 min with wash buffer (2×SSC, 0.5% SDS, 1 mM DTT, 1 mM PMSF), and then washed twice for 5 min at room temperature with 0.1% NP40 buffer (150 mM NaCl, 50 mM Tris pH 8.0, 3 mM $MgCl_2$, 10 mM DTT, 0.1% NP40). DNA was then eluted twice for 20 min in 450 μl of 0.1% NP40 buffer with 200 U/ml RNase H (NEB) at room temperature.

Metagene Analysis

Escapee genes are as previously described (Carrel and Willard, 2005; Yang et al., 2010; Pinter et al., 2012). Xist itself is excluded as an escapee in the metagene analysis. "Repressed" genes are all other genes on the Xi which have an FPKM>1.0 on the Xa. The normalized coverage files produced from SPP were used for metagene analysis with CEAS software.

Example 1

Identification of Sex-linked PAR-TERRA Transcripts

Figure 8A:
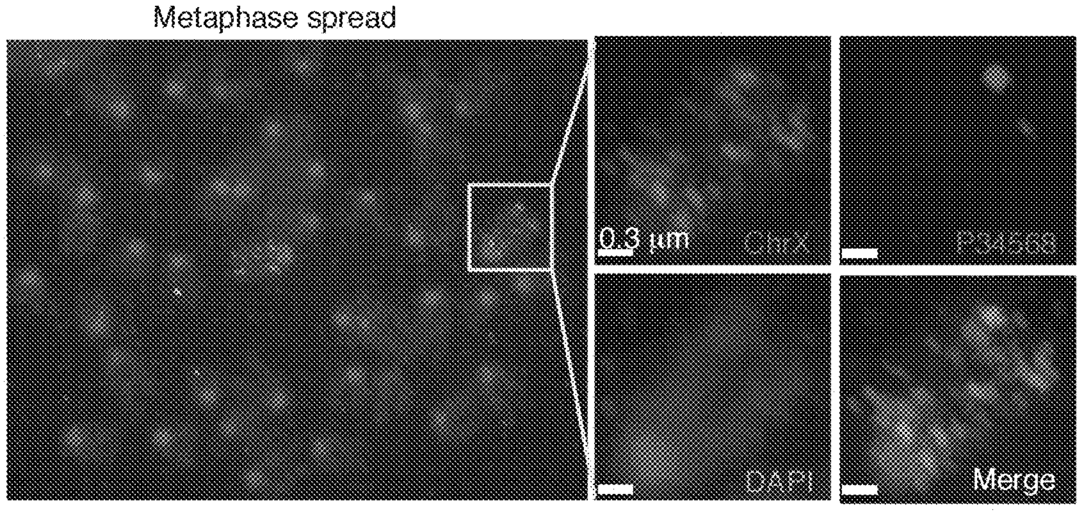
Figure 8B:
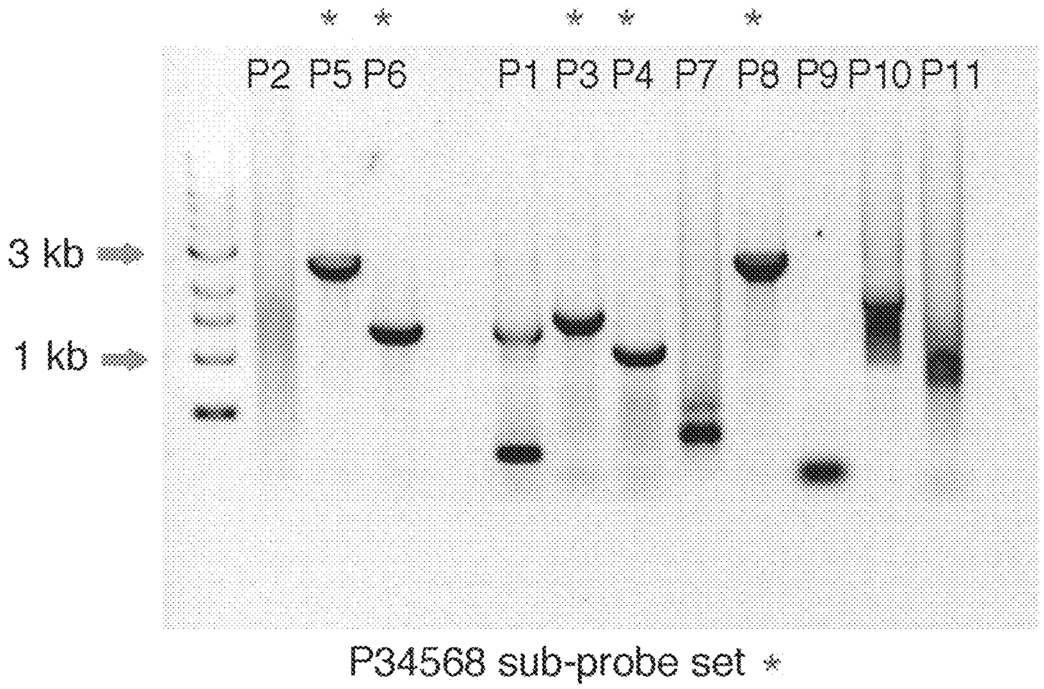

RNA fluorescence in situ hybridization (FISH) using TERRA oligo probes showed that TERRA can be seen, in high-exposure and higher contrast images, as multiple foci in the nuclei of ES cells (FIG. 1A). Consistent with our previous report (Zhang et al., 2009), two of the speckles were especially prominent. To confirm their colocalization next to the sex chromosomes, we performed serial RNA-DNA FISH using probes from the pseudoautosomal region (PAR) of the sex chromosomes. The PAR represents the only homologous region between chromosomes (Chr) X and Y. Because PAR genes are shared between the sex chromosomes, these genes are not subject to XCI. At the commencement of this project, the most distally mapped X- and Y-linked gene was the PAR gene, Mid1 (Erdr1 and Asmt were partially assembled in recent months). We obtained two BAC clones mapping to Mid1—the 15 kb BAC RP24-143B12 and the ~146 kb RP24-500I4. RP24-500I4 contains several internal telomeric repeats, two of 40 bp and the third of 314 bp (FIG. 1B). To isolate PAR-specific probes, we subcloned the BACs, generated unique PCR fragments, and identified a set of unique probes consistenting of P3, P4, P5, P6, and P8 (P34568; FIG. 8A,B). Serial RNA-DNA FISH showed that the large TERRA foci indeed mapped to the PAR in ES cells. Quantitation of RNA FISH intensities indicated that sex chromosome-associated TERRA RNA accounted for ~80-90% of total TERRA transcripts and the finer speckles ~10-20% of detected signals (FIG. 1A,C).

Although cytological analysis shows that TERRA RNA localizes to the ends of most, if not all chromosomes (Azzalin et al., 2007; Schoeftner and Blasco, 2008), the origin of TERRA transcription is not fully known. TERRA may be transcribed by all telomeres and retained in cis, or it may be transcribed by only a few loci but localized in trans to multiple distant sites. A murine transcriptomic study indicates that TERRA is synthesized predominantly from the end of Chr18 (de Silanes et al., 2014). Because sub-telomeric sequences of some chromosomes, including Chr X and Y, have not been fully sequenced or assembled, determining additional transcriptional origins for TERRA is possible.

Figure 8C:
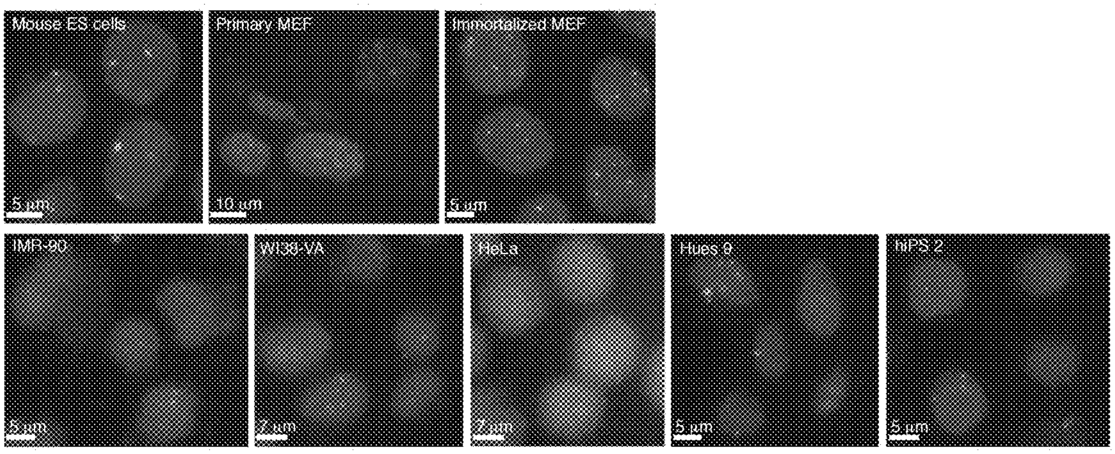
Figure 8D:
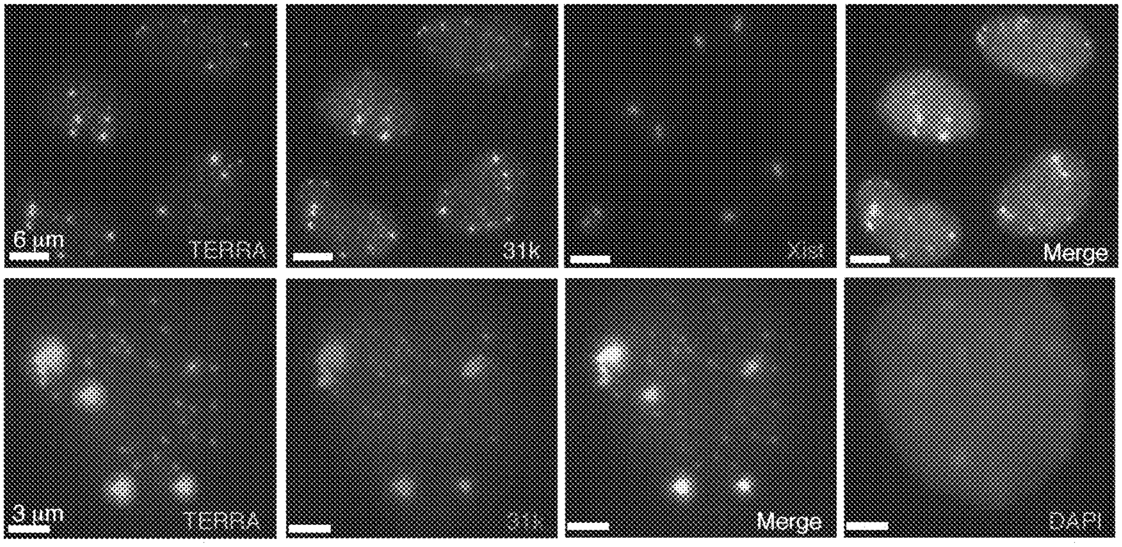

To determine whether the sub-telomeric region of ChrX and ChrY could contribute to sex-linked TERRA transcription, we carried out RNA FISH to compare signals arising from PAR versus TERRA probes. The PAR and TERRA RNA clusters looked nearly identical in male and female ES cells (FIG. 1D,E), raising the possibility that PAR and TERRA may extend—at least in a fraction of total transcription—as a single long noncoding RNA. On Northern blot analyses, an antisense TERRA oligo probe detected a smear of signals from 100 bp to>9kb (FIG. 1F, left panel), consistent with TERRA being of heterogeneous size (Azzalin et al., 2007; de Silanes et al., 2014). However, we observed a dominant species in ES cells of>>9 kb, indicating that some TERRA transcripts may originate much further upstream in relation to the telomeric repeats. Primer extension using an antisense TERRA oligo probe gave positive amplification by RT-PCR using PAR-specific primer pairs located at 33, 36, and 39 kb from the end of BAC RP24-500I4 (FIG. 1F, right panel), demonstrating that PAR-initiated RNAs is physically contiguous with at least a fraction of TERRA-containing RNA. We then repeated Northern analysis using sub-BAC walking probes to verify the physical contiguity and observed smears of high molecular weight transcripts similar to those observed with TERRA probes (FIG. 1F,G). The pattern was especially similar with probes 22k, 27k, 34k, 36k, and 47k. Two-color RNA FISH using BAC sub-probes showed that >90% of large RNA clusters were coincident with TERRA foci in ES cells (FIG. 1H) as well as in MEF (FIG. 8C). In MEFs, ~93% of PAR and TERRA clusters (n=285) localized next to, but generally did not overlap with, the Xist cloud (FIG. 8D). Henceforth, we refer to the TERRA transcripts of PAR origin as “PAR-TERRA”, to distinguish them from TERRA transcripts intrinsic to the TTAGGG repeats and to those originating within sub-telomeric regions of autosomes.

Figure 8E:
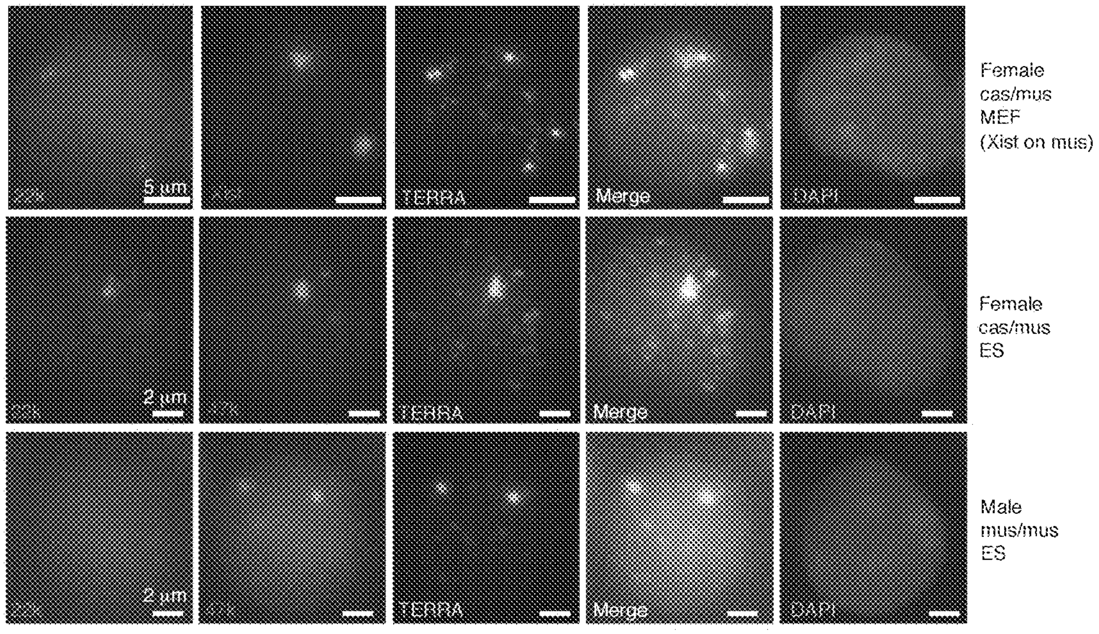

TERRA foci were similarly observed in various human cells (FIG. 8C). In mice, PAR-TERRA expression showed some strain-specific variation. For example, PAR-TERRA signals were detectable with the 22k probe in hybrid ES and MEF cells of mixed *Mus musculus* (mus) and *Mus castaneus* (cas) origin. Using the 22k probe, however, PAR-TERRA could not be detected in cells of pure *musculus* origin (FIG. 8E). This is consistent with the PAR being variable in sequence between mouse strains (Soriano et al., 1987). As a consequence, the two large TERRA foci were often asymmetric in size in hybrid 16.7 female ES cells, with *Mus musculus* cluster being smaller than the *Mus castaneus* cluster. In J1 male ES cells, TERRA RNAs on both Chr X and Y were usually smaller, consistent with their being of *Mus musculus* origin. We conclude that a substantial fraction of sex-linked TERRA transcripts originates in the pseudo-autosomal region (PAR-TERRA). The X-linked origin could have been missed previously (de Silanes et al., 2014) because pseudoautosomal sequences and assembly were not available until recently.

Example 2

Mapping Genome-wide Targets of TERRA and PAR RNA by ChIRT-seq

Figure 1H:
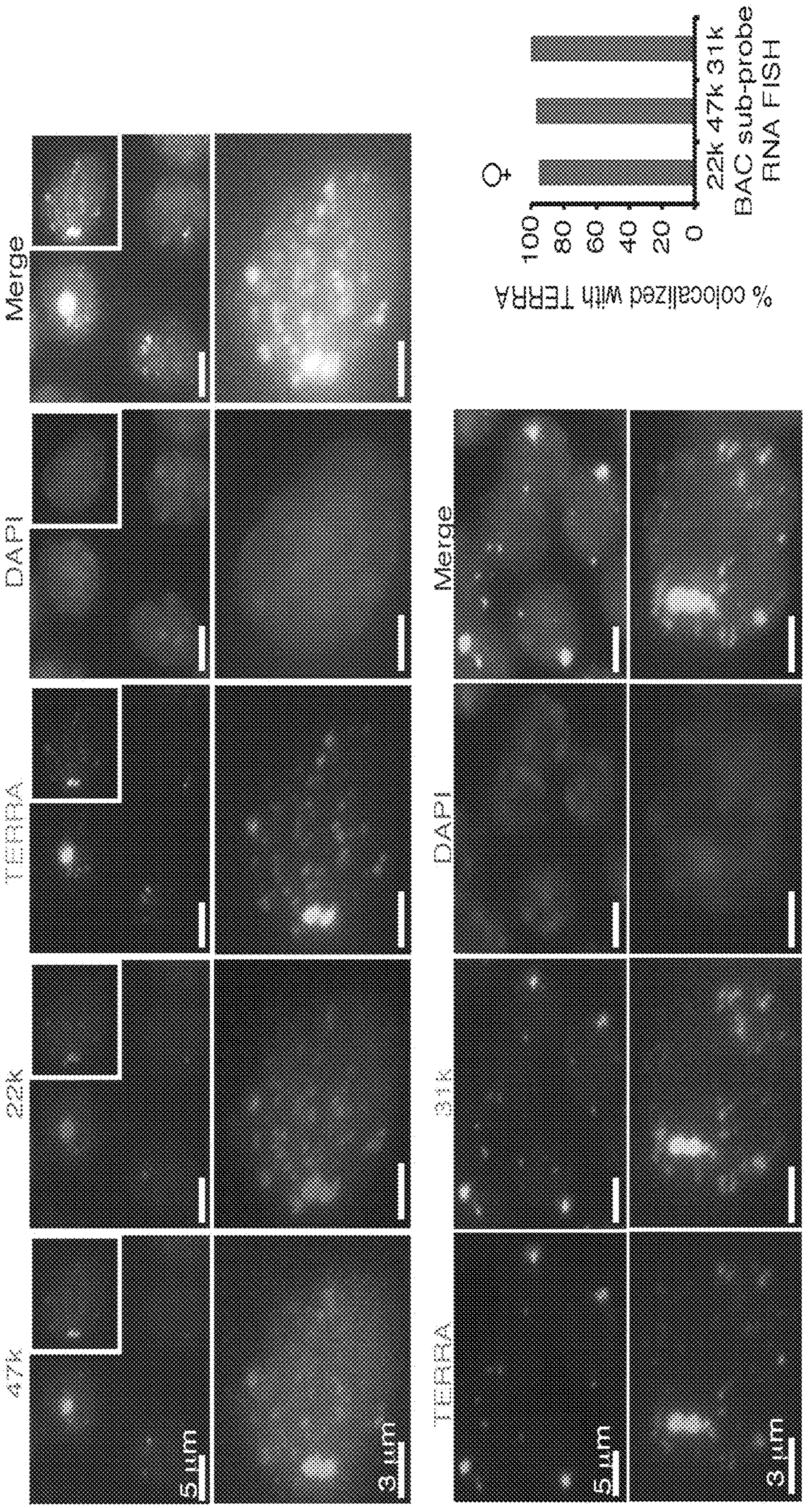
Figure 2A:
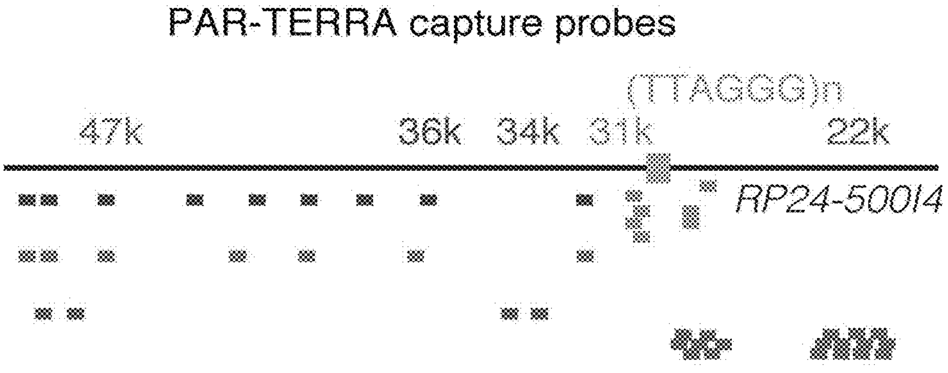
Figure 2B:
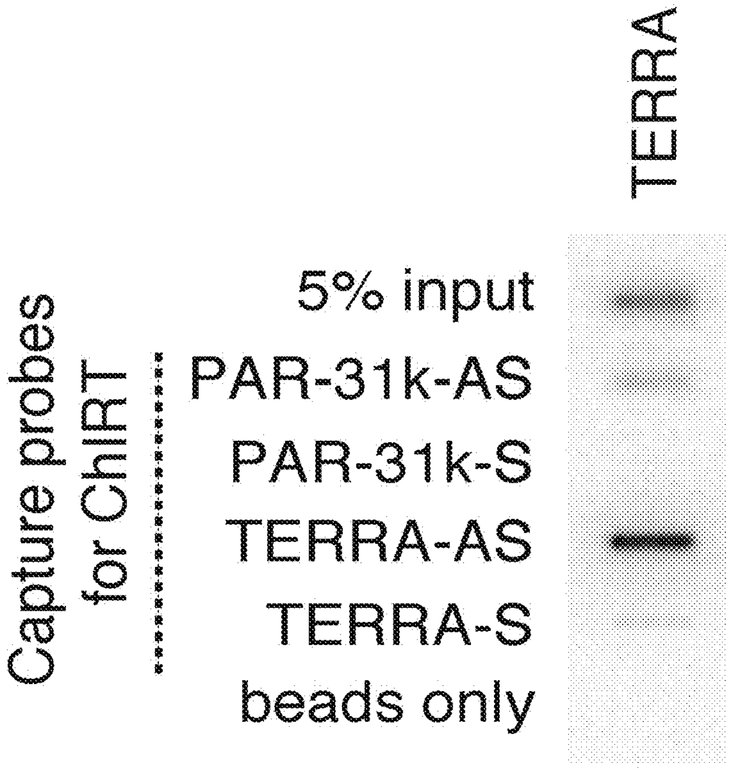

Although RNA FISH showed that >90% localized in cis to Chr X and Y, additional foci throughout the nucleus were clearly evident (FIG. 1H). Because the probes were PAR-specific, this finding indicated that PAR-TERRA could diffuse away from the sex chromosomes and possibly localize elsewhere in the nucleus. To identify genome-wide targets of TERRA and PAR RNA, we captured RNA-bound genomic sites by merging elements of ChIRP (Chu et al., 2011) and CHART (Simon et al., 2011) to achieve high specificity of chromatin pulldown (henceforth “ChIRT”). Because capture probes could potentially interact with DNA rather than RNA, we included an RNaseH elution step (FIG. 9A). Several DNA-based capture probes were designed: (i) TERRA antisense (TERRA-AS), to capture transcripts containing UUAGGG, (ii) PAR, to capture PAR-TERRA transcripts, and (iii) TERRA sense (TERRA-S, the reverse complement), to control for background. Slot blot analysis showed that both TERRA-AS and 31k-PAR-AS probes captured TERRA RNA after ChIRT, whereas the corresponding sense probes did not (FIG. 2B). Quantitative PCR indicated that PAR sequences were enriched relative to Hprt sequences after ChIRT using TERRA-AS and PAR-AS probes, but not when the TERRA-S probe was used (FIG. 2C). The enrichment was dependent on RNaseH treatment and was abolished by RNase A treatment (FIG. 2D), indicating that the pulldown was mediated by interaction between the DNA capture probes and RNA targets.

We then performed deep sequencing of ChIRT-seq pull-downs to identify genome-wide binding sites. To rule out artifacts due to direct probe hybridization to genomic DNA rather than the intended RNA target, we sequenced two critical controls: (i) an RNaseH-control in which RNaseH was omitted in the elution step, which would in principle preclude elution of RNA-dependent interactions; and (ii) a TERRA-S control, which would not hybridize to TERRA RNA but could potentially pull down contaminating DNA (in addition to any potential antisense-TERRA transcripts). We collected ES cells on differentiation days 0, 3, 7 (d0, d3, d7) and MEFs for ChIRT-seq. Approximately 30 million 50-bp paired-end reads were obtained for each library. After removing PCR duplicates, >70% of reads uniquely mapped to the mouse genome. Biological replicates showed a high degree of correlation (FIG. 9B,C).

We used MACS software to call statistically significant enrichment peaks signifying genomic binding sites of TERRA and PAR transcripts (FIG. 2E). To call enrichment peaks, we normalized ChIRT reads to (i) input library, (ii) TERRA-S library, or (iii) no-RNaseH library. The results were highly similar with each method of normalization (FIG. 2F), and MACS called a similar number of peaks (FIG. 2E). Major enrichment at telomeric repeat DNA in the TERRA-AS pulldown relative to TERRA-S and no-RNaseH controls provided a validation of our ChIRT method (FIG. 2G). Across the genome, we observed >2,000 peaks of TERRA binding in day 0 and day 3 ES cells, 1,800 peaks in d7 differentiating ES cells, and ~500 peaks in MEFs (FIG. 2E). Peaks called in the sense ChIRT samples did not overlap those called for TERRA or PAR (FIG. 2F), and could represent either background or binding of a putative antisense TERRA transcript. Similarly for PAR RNA, we observed thousands of binding sites in ES cells and hundreds in MEFs. Overall, PAR-TERRA binding sites were enriched in noncoding space, including upstream regulatory regions, introns, and intergenic space, whereas binding in exons was depleted (FIG. 2H,I).

Figure 2F:
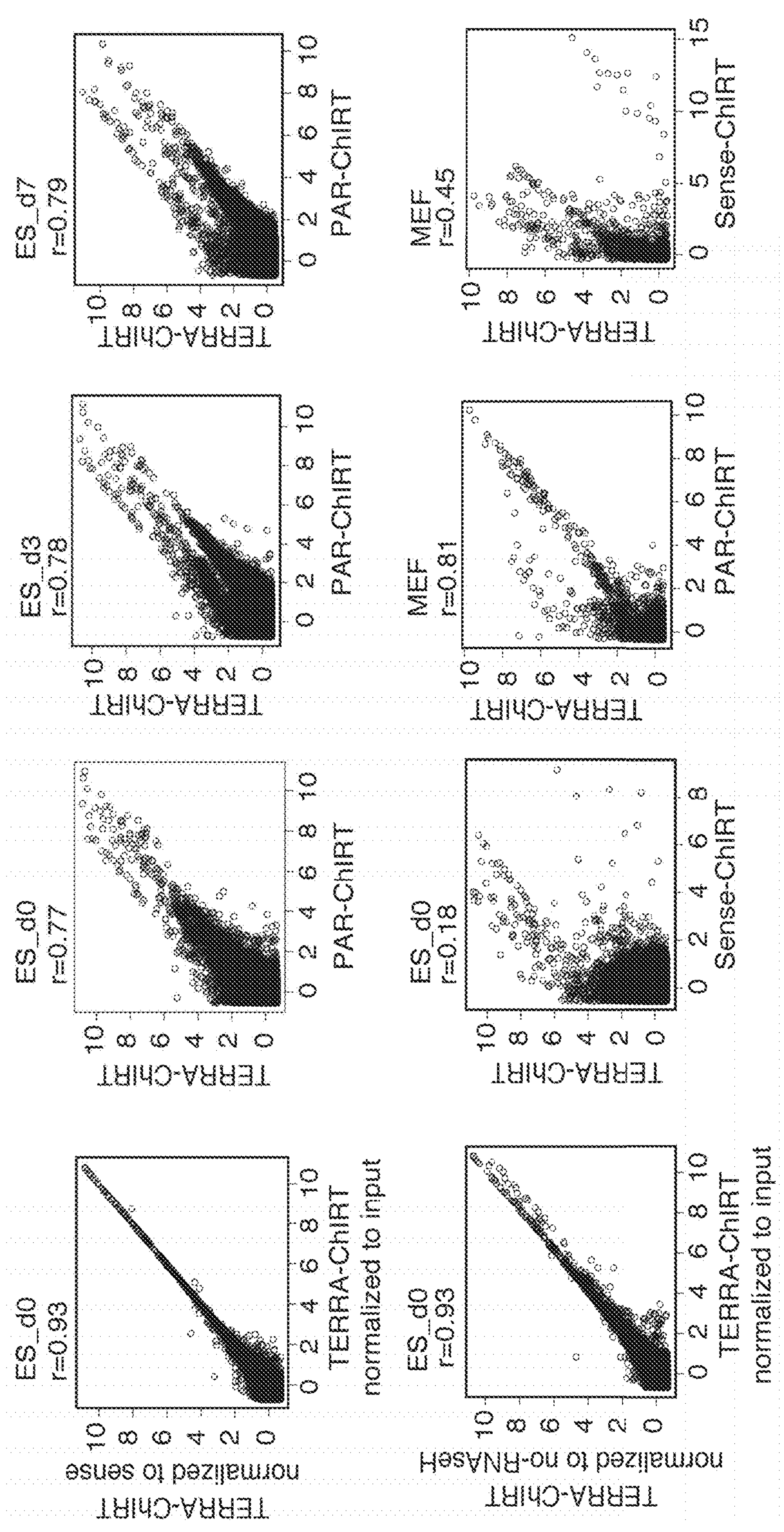
Figure 2G:
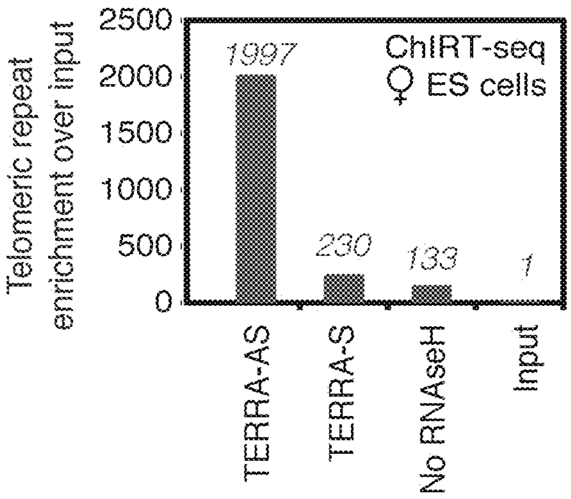
Figure 2H:
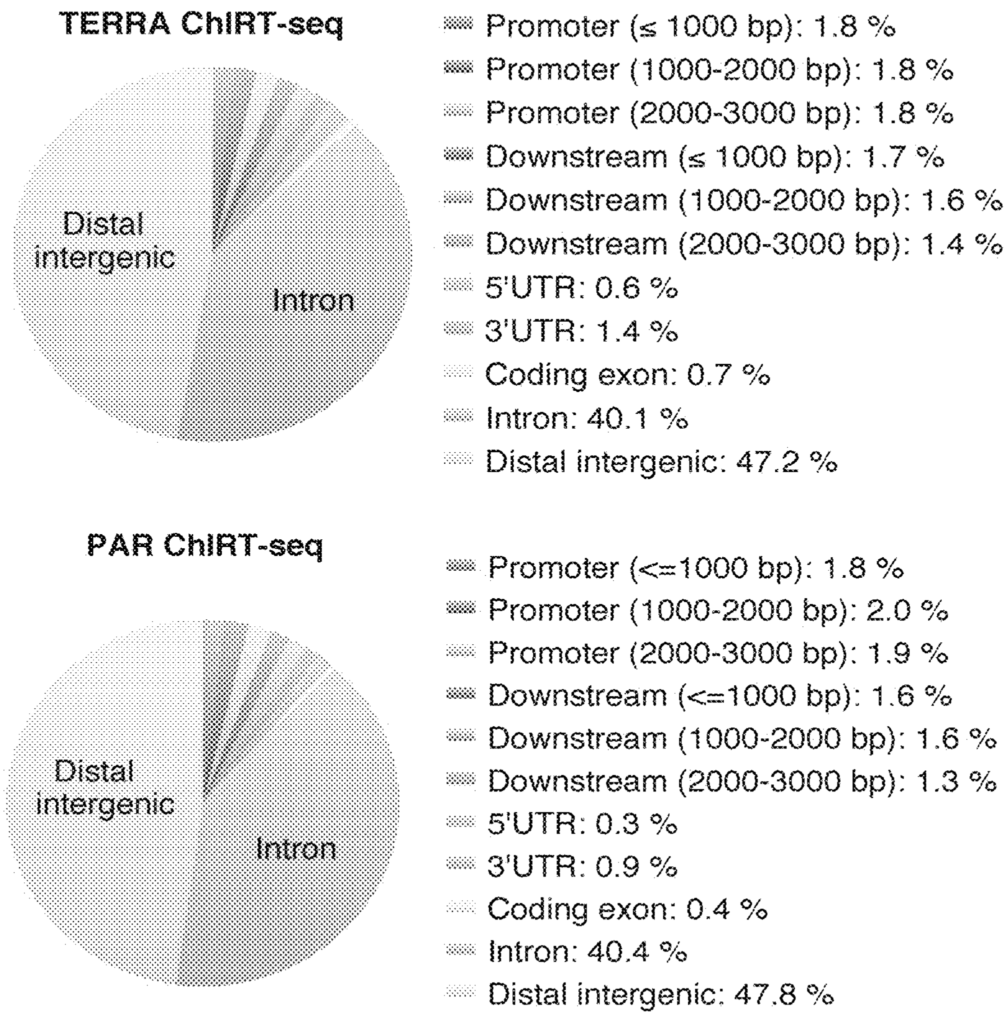
Figure 2I:
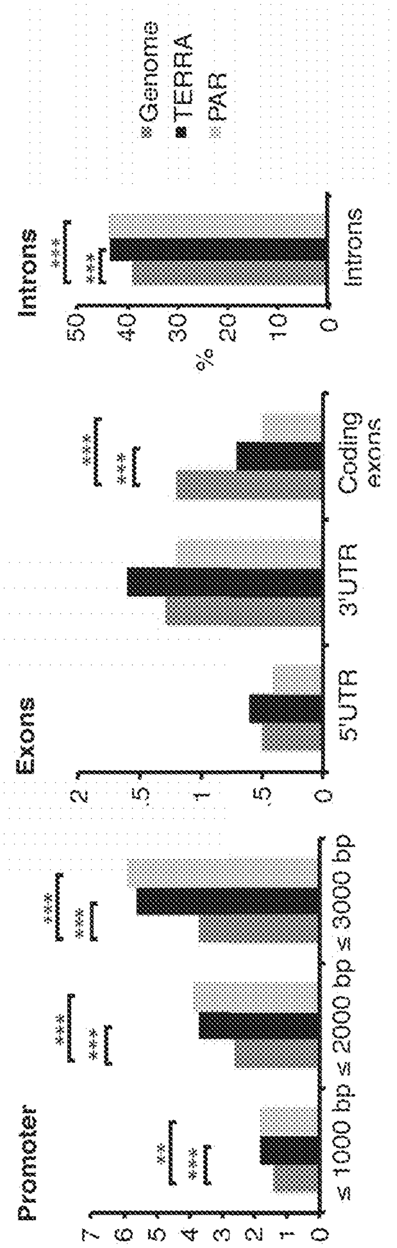

There was considerable overlap between TERRA and PAR ChIRT profiles, with high Pearson’s r values in correlation plots for d0 and d3 ES cells and for MEFs, but not for comparisons to sense-ChIRT controls (FIG. 2F). There was also a high degree of similarity between biological replicates (FIG. 9B,C). In ES cells and MEFs, whole-genome views demonstrated strongest overall enrichment of both TERRA and PAR RNAs at telomeric ends, inclusive of sub-telomeric regions—regions with unique sequence that enabled unambiguous alignment of paired-ends TERRA reads to the specific chromosome ends (FIG. 3A). Intriguingly, the X-linked RNAs could diffuse to autosomes and bind their telomeric ends (FIG. 3A, PAR track). In MEFs, the number of TERRA and PAR targets decreased overall, but telomeric ends remained enriched. Control TERRA-S pulldowns did not resemble TERRA-AS pulldowns and showed no significant enrichment at telomeres. These results demonstrated the specificity of the TERRA and PAR pulldowns and argued against artifacts of genomic DNA hybridization. Taken together, our findings demonstrate that telomeric RNAs (i) are indeed produced from the sex chromosomes and (ii) bind both in cis and in trans to their site of synthesis.

Table 1 provides a list of X-linked genes with the highest PAR-TERRA binding. Top binders are defined as the top quartile in terms of PAR-TERRA density over the gene. There are 452 active genes in the MEF cell line. Mm10 coordinates are used. Start and stop positions of the gene target, along with the gene name and transcribed strand are shown. RNA-seq FPKM refers to gene expression in frequency per kilobase per million reads. Mean TERRA coverage over the gene is also shown.

TABLE 1

PAR-TERRA binding sites on the mouse X-chromosome in MEFs

| mm10 assembly | Start | End | gene name | FPKM | strand | Mean of TERRA coverage |
|---|---|---|---|---|---|---|
| chrX | 169685246 | 169990797 | Mid1 | 1.39743 | + | 203.232 |
| chrX | 169311530 | 169320343 | Hccs | 27.2857 | – | 64.2334 |
| chrX | 167207093 | 167209218 | Tmsb4x | 454.052 | – | 24.1368 |
| chrX | 152336851 | 152342484 | Tspyl2 | 28.3268 | – | 13.6914 |
| chrX | 166499814 | 166510478 | Tceanc | 2.77384 | – | 13.1733 |
| chrX | 74270815 | 74273135 | Rpl10 | 82.0002 | + | 12.988 |
| chrX | 74270815 | 74273135 | Snora70 | 201.378 | + | 12.988 |
| chrX | 74273216 | 74282333 | Dnase1l1 | 1.20938 | – | 12.9053 |
| chrX | 134601285 | 134607054 | Hnrnph2 | 44.022 | + | 11.0383 |
| chrX | 74369218 | 74373349 | Slc10a3 | 10.7721 | – | 10.2314 |
| chrX | 153498231 | 153501558 | Ubqln2 | 81.5338 | + | 10.2078 |
| chrX | 73673132 | 73682500 | Slc6a8 | 57.6063 | + | 10.028 |
| chrX | 168795098 | 169304435 | Arhgap6 | 1.7761 | + | 9.93581 |
| chrX | 134588168 | 134601005 | Gla | 10.9353 | – | 9.78217 |
| chrX | 168654117 | 168673902 | Msl3 | 7.40496 | – | 9.71429 |
| chrX | 134686518 | 134697772 | Armcx4 | 9.21521 | + | 9.7044 |
| chrX | 152233229 | 152274354 | Kdm5c | 101.365 | + | 9.38192 |
| chrX | 101449108 | 101453541 | Itgb1bp2 | 1.18288 | + | 8.99717 |
| chrX | 101429650 | 101448593 | Nono | 123.217 | + | 8.59172 |
| chrX | 74313032 | 74320149 | Fam50a | 52.844 | + | 8.43926 |
| chrX | 94636068 | 94638561 | Gspt2 | 18.0414 | + | 8.38342 |
| chrX | 166457251 | 166479867 | Rab9 | 44.5493 | – | 8.34863 |
| chrX | 74282696 | 74290151 | Taz | 20.6918 | + | 8.29363 |
| chrX | 99136129 | 99148991 | Efnb1 | 8.80092 | + | 8.27655 |
| chrX | 152004583 | 152016295 | Ribc1 | 8.85901 | – | 8.25976 |
| chrX | 101254527 | 101260873 | Foxo4 | 35.4845 | + | 7.89614 |
| chrX | 152144267 | 152225236 | Iqsec2 | 3.55372 | + | 7.89114 |
| chrX | 13281021 | 13293983 | Ddx3x | 202.014 | + | 7.79031 |
| chrX | 74365717 | 74368548 | Ubl4 | 27.821 | – | 7.72789 |
| chrX | 152001895 | 152004442 | Hsd17b10 | 58.1856 | + | 7.67299 |
| chrX | 101532734 | 101601789 | Taf1 | 47.7176 | + | 7.64038 |
| chrX | 152016427 | 152061973 | Smc1a | 57.1067 | + | 7.62341 |
| chrX | 152294827 | 152327493 | 2900056M20Rik | 1.73042 | – | 7.3519 |
| chrX | 150571506 | 150588149 | Apex2 | 30.0146 | – | 7.27157 |
| chrX | 151803281 | 151935417 | Huwe1 | 161.224 | + | 7.14147 |
| chrX | 20688492 | 20699877 | Cdk16 | 89.5491 | + | 6.96555 |
| chrX | 101404383 | 101420685 | Zmym3 | 53.5806 | – | 6.93208 |
| chrX | 103560909 | 103623754 | Ftx | 6.13111 | – | 6.83641 |
| chrX | 134748454 | 134751419 | Armcx6 | 1.47279 | – | 6.69088 |
| chrX | 8061170 | 8074760 | Suv39h1 | 10.5102 | – | 6.59123 |
| chrX | 109095406 | 109162467 | Sh3bgrl | 11.0008 | + | 6.35196 |
| chrX | 94535473 | 94542074 | Maged1 | 150.771 | – | 6.24733 |
| chrX | 96096044 | 96168553 | Msn | 125.765 | + | 6.23976 |
| chrX | 73483634 | 73495936 | Bgn | 131.985 | + | 6.19272 |
| chrX | 163909159 | 163929546 | Ap1s2 | 22.2628 | + | 6.12689 |
| chrX | 106015699 | 106022450 | Cox7b | 81.8186 | + | 6.02631 |
| chrX | 74013913 | 74023936 | Irak1 | 54.9015 | – | 5.97292 |
| chrX | 74013913 | 74023936 | Mir5132 | 28310 | – | 5.97292 |
| chrX | 166523006 | 166585716 | Egfl6 | 2.75673 | – | 5.89232 |
| chrX | 101274090 | 101298934 | Med12 | 16.9166 | + | 5.74426 |
| chrX | 74223460 | 74246534 | Flna | 119.321 | – | 5.66957 |
| chrX | 139779680 | 139782353 | Ripply1 | 9.2593 | – | 5.66923 |
| chrX | 94188708 | 94212651 | Eif2s3x | 13.3916 | – | 5.62242 |
| chrX | 140539528 | 140600522 | Tsc22d3 | 4.01031 | – | 5.60397 |
| chrX | 74254838 | 74257747 | Emd | 131.791 | + | 5.52669 |
| chrX | 94074630 | 94123407 | Zfx | 14.4577 | – | 5.457 |

TABLE 1-continued

PAR-TERRA binding sites on the mouse X-chromosome in MEFs

| mm10 assembly | Start | End | gene name | FPKM | strand | Mean of TERRA coverage |
|---|---|---|---|---|---|---|
| chrX | 8138974 | 8147963 | 2900002K06Rik | 2.48279 | + | 5.45401 |
| chrX | 8138974 | 8147963 | Rbm3 | 21.0491 | − | 5.45401 |
| chrX | 151047232 | 151096543 | Fgd1 | 81.8043 | + | 5.44937 |
| chrX | 151047232 | 151096543 | Tsr2 | 23.1259 | − | 5.44937 |
| chrX | 57383347 | 57393036 | Rbmx | 15.7016 | − | 5.4457 |
| chrX | 73916869 | 73921944 | Naa10 | 94.1038 | − | 5.41574 |
| chrX | 74297096 | 74304721 | Atp6ap1 | 57.5415 | + | 5.33398 |
| chrX | 100622905 | 100625907 | Pdzd11 | 67.6827 | − | 5.24963 |
| chrX | 166440824 | 166452543 | Trappc2 | 5.95827 | + | 5.23482 |
| chrX | 101640063 | 101684351 | Ogt | 82.85 | + | 5.19793 |
| chrX | 74329065 | 74344689 | Plxna3 | 6.81077 | + | 5.15815 |
| chrX | 73716596 | 73738287 | Abcd1 | 9.8525 | + | 5.05484 |
| chrX | 7884243 | 7894492 | Slc35a2 | 8.80274 | + | 5.05244 |
| chrX | 7919821 | 7928607 | Eras | 53.4302 | − | 5.03256 |
| chrX | 7919821 | 7928607 | Pcsk1n | 14.3249 | + | 5.03256 |
| chrX | 73437314 | 73459029 | Haus7 | 37.766 | − | 5.03236 |
| chrX | 7894518 | 7899269 | Pqbp1 | 101.762 | − | 4.95918 |
| chrX | 140948424 | 140956711 | Psmd10 | 16.0633 | − | 4.86065 |
| chrX | 160502165 | 160598878 | Phka2 | 10.5119 | + | 4.82787 |
| chrX | 159627407 | 159975917 | Sh3kbp1 | 13.5148 | + | 4.81242 |
| chrX | 9654269 | 9662983 | Dynlt3 | 8.16616 | − | 4.77036 |
| chrX | 60891365 | 60893430 | Sox3 | 5.66273 | − | 4.76974 |
| chrX | 73778962 | 73786897 | Idh3g | 186.084 | − | 4.72145 |
| chrX | 142317992 | 142390535 | Acsl4 | 25.1009 | − | 4.71533 |
| chrX | 164373547 | 164402647 | Figf | 2.67737 | + | 4.70077 |
| chrX | 7823842 | 7836503 | Kcnd1 | 5.67212 | + | 4.6921 |
| chrX | 163935442 | 163958666 | Zrsr2 | 32.212 | − | 4.68589 |
| chrX | 159372194 | 159385699 | Eif1ax | 160.42 | + | 4.667 |
| chrX | 150983132 | 151017322 | Gnl3l | 79.5544 | − | 4.63998 |
| chrX | 7722248 | 7728201 | Wdr45 | 57.6147 | + | 4.57451 |
| chrX | 7762660 | 7775202 | Tfe3 | 88.3365 | + | 4.55791 |
| chrX | 101377336 | 101385624 | Gjb1 | 7.30102 | + | 4.55117 |
| chrX | 155213138 | 155216409 | Sat1 | 31.7602 | − | 4.49062 |
| chrX | 164419786 | 164433915 | Piga | 14.5205 | + | 4.46376 |
| chrX | 73686182 | 73716175 | Bcap31 | 136.655 | − | 4.34133 |
| chrX | 7728570 | 7731063 | Praf2 | 45.3074 | + | 4.32855 |
| chrX | 136139044 | 136140437 | Bex4 | 54.8305 | + | 4.31599 |
| chrX | 134585653 | 134588062 | Rpl36a | 1.66059 | + | 4.30142 |
| chrX | 134804141 | 134809221 | Armcx2 | 20.2464 | − | 4.29013 |
| chrX | 73853779 | 73880834 | L1cam | 1.33532 | − | 4.26027 |
| chrX | 58030627 | 58036630 | Zic3 | 68.0886 | + | 4.24685 |
| chrX | 159532667 | 159593081 | A830080D01Rik | 43.9242 | + | 4.19267 |
| chrX | 7899397 | 7907652 | Timm17b | 31.5895 | + | 4.06939 |
| chrX | 142853473 | 142966728 | Ammecr1 | 13.3866 | − | 4.01434 |
| chrX | 164070702 | 164076049 | Siah1b | 49.6673 | − | 3.99607 |
| chrX | 150806420 | 150814339 | Maged2 | 15.8384 | − | 3.94816 |
| chrX | 100626064 | 100727271 | Kif4 | 34.3476 | + | 3.93177 |
| chrX | 75095853 | 75130949 | Dkc1 | 136.814 | + | 3.90988 |
| chrX | 75095853 | 75130949 | Mpp1 | 38.769 | − | 3.90988 |
| chrX | 37091833 | 37110322 | Upf3b | 39.8344 | − | 3.88822 |
| chrX | 12936872 | 12938541 | AA414768 | 7.27643 | + | 3.8628 |
| chrX | 48411048 | 48463132 | Elf4 | 16.0656 | − | 3.8481 |
| chrX | 7959259 | 7967910 | Gata1 | 1.29963 | − | 3.77677 |
| chrX | 134308162 | 134362639 | Cenpi | 16.8886 | + | 3.77197 |
| chrX | 134059348 | 134086821 | Cstf2 | 45.5011 | + | 3.75403 |
| chrX | 51003913 | 51018018 | Rap2c | 14.0536 | − | 3.69198 |
| chrX | 8238667 | 8252406 | Ftsj1 | 29.4 | − | 3.68661 |

Top 25% of TERRA mean coverage over gene
Total active gene 452

Example 3

PAR-TERRA Localizes in cis and in trans

Although TERRA and PAR ChIRT profiles were very similar, ChIRT analysis revealed heterogeneity in the telomeric RNAs. Some binding sites were dominated by TERRA RNA (e.g., telomeric ends of Chr 3,4,5, etc), while others showed prominent peaks of both TERRA and PAR RNA (FIG. 3). A distinct PAR-TERRA species was further supported by the nearly identical ChIRT profiles at these sites of overlap (examples shown in FIG. 3B-D), as well as by the above molecular analyses indicating a physical contiguity (FIG. 1F,G). PAR-TERRA binding was especially notable at the subtelomeric end (pseudoautosomal region) of the sex chromosomes (FIG. 3B). Mid1, Erdr1, and Asmt are tens of kilobases away from the TERRA DNA sequence [(TTAGGG)n telomeric repeat], but nevertheless demonstrated prominent TERRA peaks. The intronic regions and 3' end of Mid1 contained some of the strongest PAR-TERRA peaks in the genome. The gene body of Asmt was also a strong binding site. By far the strongest peaks were found in Erdr1, which itself contains two short stretches of (TTAGGG)n repeats. [Note: It should be emphasized that these TERRA reads could be unambiguously assigned to the Erdr1 repeats—and not telomeric repeats—because pair-end sequencing enabled utilizing the unique sequence at one end to align the other repetitive end.] These results demonstrated that PAR-TERRA not only localizes in cis to the telomeres of sex chromosomes, but also spreads locally in cis to emcompass genes of the pseudoautosomal region.

Intriguingly, PAR-TERRA also targeted sites in trans. Magnified views showed strong PAR-TERRA binding peaks in the sub-telomeric regions of Chr 2, 9, 13, and 18 (FIG. 3C), and more moderate binding peaks in the sub-telomeric regions of Chr 8 and 19 (FIG. 10). Additionally, PAR-TERRA targeted internal regions of autosomes. Many binding peaks occurred within genes, especially within introns, as exemplified by Abcb10,Uchl1os, and Hes3 (FIG. 3D). PAR-TERRA also targeted internal (TTAGGG)n telomeric repeats which occur at a number of locations throughout the genome (one example shown in FIG. 3C; NOTE: The reads could be assigned unambiguously to the internal repeats because of pair-end sequencing, in which the unique end is used to align the repeat end). We conclude that TERRA and PAR-TERRA transcripts are not confined to telomeric ends of mouse chromosomes.

Example 4

Epigenomic Regulation by PAR-TERRA

Because PAR-TERRA accounts for the vast majority of TERRA transcripts in the nucleus and has both X-linked and autosomal targets, we examined its effect on gene expression on a genome-wide basis. We perturbed PAR-TERRA expression using knockdown (KD) approaches to avoid undesirable consequences of genetically deleting telomeres. Neither siRNA nor shRNA resulted in knockdown. On the other hand, single-stranded antisense oligonucleotide (ASO) locked nucleic acids (LNA) gapmers led to substantial depletion of TERRA after 12 hours in ES cells, as shown by Northern blot analysis (FIG. 4A, 11A) and RNA FISH (FIG. 4B, 11B). ASO's to TERRA sequences and PAR-specific sequences (31k) achieved similar results. At optimal LNA concentrations, at least 75-90% of PAR-TERRA were degraded as quantitated by Northern analysis (FIG. 4A, 11A). RNA FISH showed a substantial depletion of both TERRA and PAR signals in >86% of nuclei (n=217) after 6 hours (4B, 11B). Notably, treating with 31k-PAR gapmers dramatically reduced TERRA RNA FISH signals (FIG. 4B). Conversely, administering TERRA gapmers also reduced PAR FISH signals. These data provide strong support for the idea of a continuous PAR-TERRA transcript and the conclusion that PAR-TERRA accounts for the majority (~90%) of telomeric transcripts in ES cells.

We then carried out transcriptomic analysis on two biological replicates of ES cells after 12 hours of PAR-TERRA depletion (FIG. 4, 11C). Analysis of the biological replicates of TERRA-specific and PAR-specific KD's revealed overlapping transcriptomic changes (FIG. 4C). Analysis using Cuffdiff2 uncovered 126 differentially expressed genes after TERRA KD and 324 after PAR KD in ES cells, among which 56 genes were shared between the TERRA- and PAR-specific KD cells. In MEFs, TERRA KD led to 137 significant changes and PAR KD led to 309, among which 36 genes were shared. Among the shared genes for each cell type, the changes in gene expression after PAR and TERRA KD were very similar (FIG. 4D). Among 8 genes that were shared between female ES cells and MEFs, the expression changes were also highly similar (FIG. 4E).

On the other hand, there was a significantly increased probability that genes with PAR-TERRA binding sites would be downregulated by PAR-specific KD (FIG. 4F). The probability density function for 565 genes with PAR-TERRA binding sites was significantly different from that for the 14,724 genes without a PAR-TERRA site (FIG. 4F; KS test P<0.0001). PAR KD resulted in net downregulation of genes with PAR-TERRA binding sites (left-shift of red distribution). Among all downregulated genes after PAR KD, the degree of downregulation was significantly more pronounced for those with PAR-TERRA sites (FIG. 4G, right panels; $X^2$ test, P<0.001), possibly indicative of a direct effect on PAR-TERRA target genes. In contrast, among the upregulated genes, there was no signifcant difference between genes with and without a PAR-TERRA site ($\square^2$ test, P=0.26), suggesting that upregulation may be an indirect consequence. These data argue that PAR-TERRA RNA exerts a direct positive effect on target genes.

The non-overlapping transcriptomic changes for TERRA-versus PAR-specific knockdowns may suggest the presence of a gene class targeted by TERRA-intrinsic transcripts (containing only UUAGGG repeats), rather than by PAR-TERRA. Consistent with this, we observed a number of autosomal genes—particularly those within sub-telomeric regions—where TERRA RNA was the predominant bound form (FIG. 5A). At such genes, TERRA KD consistently resulted in gene downregulation, as shown by RNA-seq and confirmed by RT-qPCR (FIG. 5B). Such autosomal sub-telomeric genes might therefore be controlled by TERRA transcripts produced in cis, perhaps in addition to some contribution from X-linked PAR-TERRA in trans. We proposed that genes responsible for facioscapulohumeral muscular dystrophy (FSHD) can be controlled in this way. The FSHD locus is located in the subtelomeric region of human Chr4 and contains coding genes FRG1, FRG2, DUX4, and the macrosatellite repeat, D4Z4. FSHD is caused by ectopic expression of these genes when the D4Z4 repeat contracts and becomes "activated". Thus, PAR-TERRA or Chr4-specific TERRA could be targeted to downregulate the associated subtelomeric genes.

Example 5

PAR-TERRA Protects Pseudoautosomal Genes and Escapees from XCI

ChrX has a large number of PAR-TERRA sites (FIG. 3A). In d0 ES cells, ChrX harbors 84-86 PAR-TERRA sites; in MEFs, ChrX harbors 30-94 sites, with one broad domain at the distal end of ChrX, another around the X-inactivation center, and several additional hotspots in more proximal regions of ChrX (FIG. 5C,D). Intriguingly, PAR-TERRA densities were greater at escapees than at genes subject to XCI (FIG. 5E; P<0.05). Escapees play important roles in human disease (e.g., XO Turner Syndrome) and generally have ChrY homologues that render XCI unnecessary for these genes (Berletch et al., 2010; Berletch et al., 2011; Deng et al., 2014). Escapee genes are located throughout ChrX, and may occur singly or in clusters (Berletch et al., 2011; Lopes et al., 2011). In humans, 15% of X-linked genes escape silencing, whereas approximately a dozen or so genes escape XCI in mice (Carrel and Willard, 2005; Yang et al., 2010). Their association with PAR-TERRA raised the possibility that PAR-TERRA could regulate escape from XCI.

To test this idea, we performed quantitative RT-PCR. Significantly, PAR-TERRA KD resulted in downregulation of all pseudoautosomal genes, including Mid1, Erdr1, and Asmt (FIG. 5F). This downregulation was confirmed by RNA-seq analysis and was similar to the downregulation at sub-telomeric regions of autosomes after TERRA KD (FIG. 5A,B). Thus, one of TERRA's cis functions may be to protect sub-telomeric genes from position effects of telomeric heterochromatin. To examine Xi-specific changes, we performed allele-specific RNA-seq analysis using a hybrid MEF clonal cell line in which the Xi is always of *Mus musculus* origin and the Xa is of *Mus castaneus* origin (Pinter et al., 2012). RNA-seq analysis confirmed downregulation of PAR genes and additional known escapees outside of the PAR, such as Shroom4, Kdm6a, 1810030O07Rik, as well as escapees (Fgf13, Mbtps2, Huwe1, Sept6, Aifm1, and Kif4) observed in our cell line. We concluded that PAR-TERRA promotes expression of escapee genes on the Xi.

We next investigated the mechanistic relationship between PAR-TERRA and escapees. While escapee gene bodies generally have low Xist coverage, their flanking regions are often marked by high Xist coverage suggestive of a boundary that sequesters Xist and prevents it from entering escapee loci (FIG. 6A, Mid1 shown)(Simon et al., 2013). Intriguingly, metagene analysis revealed that PAR-TERRA was highly enriched at the transcriptional start sites (TSS) of escapee genes, where the Xist boundary occurred (FIG. 6B). For example, Mid1 was marked by a sharp border of Xist RNA beyond which Xist coverage dropped off dramatically (FIG. 6A). To determine how PAR-TERRA affected Xist spreading near escapees, we carried out CHART-seq of Xist following knockdown of PAR-TERRA for 6 hours. Scatterplot analysis of Xist coverages in 40-kb windows showed that Xist binding changed very little for nearly all Xi loci (FIG. 6C, Pearson's r>0.90), with the notable exception of outliers corresponding to some escapees (FIG. 6C, red dots). Upon PAR-TERRA KD, we observed decreased accumulation of Xist at the TSS and a shift to flanking regions (FIG. 6D). Taken together, these data suggest that PAR-TERRA protects escapees from silencing by sequestering Xist at the TSS of escapees, thereby preventing the spread of Xist into upstream regulatory regions and into the TSS regions of escapees.

Given that ~90% of PAR-TERRA foci occurred next to but did not overlap the Xist cloud (FIG. 6E; 8D)(Zhang et al., 2009), we considered the possibility that PAR-TERRA might organize a privileged, transcription-permissive compartment next to the Xi. We noted that PAR has a higher colocalization rate with other escapees, such as Fix and Jpx, than with genes subject to XCI, such as Hprt (FIG. 6F; $P<0.0001$). Depleting PAR-TERRA resulted in a statistically significant decrease in colocalization frequency (FIG. 6G; $P<0.02, 0.001$). These data are consistent with the idea of a privileged compartment that is geographically close to the pseudoautosomal region.

Gene ontology (GO) analysis was performed, restricted to differentially expressed genes in TERRA KD (P adjusted value<0.05 in DEseq2 analysis). The top 10 enriched biological process terms are listed in Table 2, in the upregulated gene set or in downregulated gene set in MEFs.

TABLE 2

| Category | Term | Count | PValue | Benjamini |
|---|---|---|---|---|
| MEF up-regulated | | | | |
| GOTERM_BP_FAT | GO: 0007155~cell adhesion | 25 | 9.28E−08 | 0.911919899 |
| GOTERM_BP_FAT | GO: 0022610~biological adhesion | 25 | 9.54E−06 | 0.006157583 |
| GOTERM_BP_FAT | GO: 0030029~actin filament-based process | 12 | 1.12E−04 | 0.047233272 |
| GOTERM_BP_FAT | GO: 0034330~cell fuction organization | 6 | 1.35E−04 | 0.042637379 |
| GOTERM_BP_FAT | GO: 0030036~actin cytoskeleton organization | 11 | 2.94E−04 | 0.073349276 |
| GOTERM_BP_FAT | GO: 0034329~cell function assembly | 5 | 2.95E−04 | 0.061751534 |
| GOTERM_BP_FAT | GO: 0010810~regulation of cell-substrate adhesion | 6 | 3.97E−04 | 0.070796403 |
| GOTERM_BP_FAT | GO: 0034621~cellular macromolecular complex subunit organization | 13 | 5.34E−04 | 0.082874247 |
| GOTERM_BP_FAT | GO: 0001944~vasculature development | 13 | 8.40E−04 | 0.087939941 |
| GOTERM_BP_FAT | GO: 0034622~cellular macromolecular complex assembly | 12 | 6.75E−04 | 0.083770541 |
| MEF down-regulated | | | | |
| GOTERM_BP_FAT | GO: 0007049~cell cycle | 27 | 2.17E−08 | 2.99E−05 |
| GOTERM_BP_FAT | GO: 0051726~regulation of cell cycle | 14 | 2.06E−06 | 0.001425534 |
| GOTERM_BP_FAT | GO: 0007348~regulation of mitotic cell cycle | 10 | 2.42E−06 | 0.00111682 |
| GOTERM_BP_FAT | GO: 0008219~cell death | 21 | 3.42E−06 | 0.001182773 |
| GOTERM_BP_FAT | GO: 0012501~programmed cell death | 20 | 4.72E−06 | 0.001304329 |
| GOTERM_BP_FAT | GO: 0016265~death | 21 | 4.86E−06 | 0.001120723 |
| GOTERM_BP_FAT | GO: 0006915~apoptosis | 19 | 1.41E−05 | 0.002783689 |
| GOTERM_BP_FAT | GO: 0051130~positive regulation of cellular component organization | 10 | 1.74E−05 | 0.00300798 |
| GOTERM_BP_FAT | GO: 0033043~regulation of organelle organization | 11 | 1.81E−05 | 0.002783466 |
| GOTERM_BP_FAT | GO: 0022402~cell cycle process | 17 | 2.36E−05 | 0.00325865 |

Example 6

TERRA Facilitates Homologous Sex Chromosome Pairing

In mammals, pairing between two homologous chromosomes rarely occurs outside of meiosis. An exception is the X-chromosome, which undergoes transient homologous interactions prior to the initiation of XCI in ES cells (Bacher et al., 2006; Xu et al., 2006). Their transient pairing via the noncoding Tsix and Xite loci is proposed to result in mutually exclusive selection of Xa and Xi and, thereby, to ensure upregulation of Xist RNA from a single ChrX (Xu et al., 2006). To date, only a few regulatory factors have been identified, including a 15-kb "pairing center" from which the noncoding Tsix and Xite RNAs are produced (Xu et al., 2007). Tsix and Xite RNAs work together with the chromosomal architectural protein, CTCF, to establish the paired state (Kung et al., 2015). How the two X-chromosomes search and identify each other during the pairing process is not known.

Interestingly, PAR-TERRA ChIRT revealed strong PAR-TERRA binding sites in Xite and Tsix (FIG. 7A). These peaks grabbed our attention because they occurred within the pairing center and were specific to ES cells. To test a role in pairing, we knocked down TERRA and measured inter-chromosomal distances in a 3D DNA FISH assay (Xu et al., 2006; Kung et al., 2015). We measured inter-allelic distances at the telomere, the X-inactivation center (Xic), and a distant locus, Hprt. Using Xic probes mapping to Tsix/Xist, we observed a left shift in the cumulative frequency curve between days 0 and 4 of differentiation, indicating an increase in the number of nuclei displaying inter-allelic distances of <0.1 nuclear diameters (ND) or <1 micron (FIG. 7B, 13A), a distance implying the occurrence of pairing, as previously determined (Bacher et al., 2006; Xu et al., 2006). By contrast, the number of such events increased minimally between Hprt alleles. Curiously, however, when measured between the telomeres (TeloX) or between PAR, there was also a significant increase in allelic colocalization events. The degree of left shift indicated a very robust telomeric pairing (FIG. 7B). Telomeric pairing was X-specific and was not observed between homologous autosomal telomeres (FIG. 7C, Chr2 telomere shown). Moreover, the time window of telomeric pairing overlapped with that for Xic-Xic pairing.

This unexpected relationship raised the possibility that the X-telomeres may be involved in somatic X-X pairing. Since the 1920's, the telomere has been suspected to facilitate homology searching during meiotic chromosome pairing, where a single telomeric "bouquet" (a clustering of telomeric ends of all chromosomes) nucleates synapsis and enables synaptic extension along the length of homologous pairs (Maguire, 1984; Rockmill and Roeder, 1998; Reig-Viader et al., 2013; Xiang et al., 2014). During male meiosis, Chr X and Y also pair in spite of their limited homology, and they do so via their pseudoautosomal region—the only region of homology between the two sex chromosomes.

We explored the possibility that telomeric clustering could also mediate sex chromosome pairing in non-meiotic cells. First, given the occurrence of meiotic X-Y pairing, we asked whether somatic telomeric pairing extends to the X and the Y. Indeed, during differentiation, the inter-PAR and inter-telomeric distances between Chr X and Y shifted to the left, much in the same way as those observed for X-X telomeric pairing (FIG. 7D, 13B). This colocalization of telomeres/PARs was also transient, occurring on day 4, but not on day 0 or 12. Serial RNA/DNA FISH showed that, while the paired telomeric signals of the sex chromosomes were very close (<1 μm between two dots) or overlapped (one dot), the rest of the two chromosomes were not paired, as visualized by Chr X and Y painting probes (FIG. 7E). These data demonstrate that somatic telomeric pairing is not limited to the two female X-chromosomes. Transient homologous chromosome pairing also occurs between Chr X and Y during differentiation of male ES cells.

We asked whether X-X and X-Y pairing might be controlled by PAR-TERRA in cis. To examine telomeric pairing, we assessed pairing frequencies between telomeres on d4 after treating cells with LNA gapmers to degrade TERRA RNA. Significantly, we observed a right shift of inter-telomeric (PAR-PAR) distances in TERRA KD cells relative to control cells that were administered a scrambled (Scr) LNA. These results demonstrated a loss of telomeric colocalization when TERRA RNA was depleted (FIG. 7F). Telomeric X-X pairing in female cells and X-Y pairing in male cells were both affected. Therefore, TERRA RNA is required for somatic telomeric pairing of sex chromosomes. Given the presence of PAR-TERRA binding sites at the pairing center, we investigated whether Xic-Xic pairing in female cells might also be affected by the loss of TERRA. We treated differentiating female ES cells with TERRA LNAs and measured inter Xic distances at day 4. Relative to cells treated with the control Scr LNA, there was a significant right shift of colocalization frequencies between the Xic alleles after TERRA KD (FIG. 7G), indicating a loss of pairing. Thus, both types of trans-interactions—telomeric pairing and Xic-Xic pairing—require the function of TERRA.

These data lead to the notion that PAR-TERRA RNA could facilitate homologous interchromosomal interactions by inducing co-clustering of crucial pairing sites. Because the pairing center (FIG. 7A) and the pseudoautosomal region (FIG. 2H) are both major hotspots of PAR-TERRA binding, we examined the possibility that intra-chromosomal cis-interactions between the Xic and telomere could bring the Xic to the juxta-telomeric compartment, which in turn would bring the two Xic's in close proximity due to the action of telomeric pairing. Indeed, DNA FISH using Xic and sub-telomeric (PAR) probes showed that the Xic and telomere frequently colocalized on day 4 (FIG. 7H). This co-clustering depended on TERRA RNA, as knocking down TERRA abolished the Xic-telomeric interactions (FIG. 7H). We conclude that both (i) cis-interactions between the Xic and the telomere and (ii) trans-interactions between two telomeres require TERRA RNA. We propose that TERRA RNA tethers the ends of sex chromosomes to facilitate inter-chromosomal interactions between the Xic's (FIG. 7I).

REFERENCES

Azzalin, C. M., and Lingner, J. (2015). Telomere functions grounding on TERRA firma. Trends Cell Biol 25, 29-36

Azzalin, C. M., Reichenbach, P., Khoriauli, L., Giulotto, E., and Lingner, J. (2007). Telomeric Repeat Containing RNA and RNA Surveillance Factors at Mammalian Chromosome Ends. Science 318, 798-801

Bacher, C. P., Guggiari, M., Brors, B., Augui, S., Clerc, P., Avner, P., Eils, R., and Heard, E. (2006). Transient colocalization of X-inactivation centres accompanies the initiation of X inactivation. Nature cell biology 8, 293-299

Balk, B., Maicher, A., Dees, M., Klermund, J., Luke-Glaser, S., Bender, K., and Luke, B. (2013). Telomeric RNA-DNA hybrids affect telomere-length dynamics and senescence. Nat Struct Mol Biol 20, 1199-1205

Berletch, J. B., Yang, F., and Disteche, C. M. (2010). Escape from X inactivation in mice and humans. Genome biology 11, 213

Berletch, J. B., Yang, F., Xu, J., Carrel, L., and Disteche, C. M. (2011). Genes that escape from X inactivation. Human genetics 130, 237-245

Bernardes de Jesus, B., and Blasco, M. A. (2013). Telomerase at the intersection of cancer and aging. Trends in genetics: TIG 29, 513-520

Blackburn, E. H., Greider, C. W., and Szostak, J. W. (2006). Telomeres and telomerase: the path from maize, Tetrahymena and yeast to human cancer and aging. Nature medicine 12, 1133-1138

Brown, C. J., Hendrich, B. D., Rupert, J. L., Lafreniere, R. G., Xing, Y., Lawrence, J., and Willard, H. F. (1992). The human XIST gene: analysis of a 17 kb inactive X-specific RNA that contains conserved repeats and is highly localized within the nucleus. Cell 71, 527-542

Carrel, L., and Willard, H. F. (2005). X-inactivation profile reveals extensive variability in X-linked gene expression in females. Nature 434, 400-404

Chu, C., Qu, K., Zhong, F. L., Artandi, S. E., and Chang, H. Y. (2011). Genomic maps of long noncoding RNA occupancy reveal principles of RNA-chromatin interactions. Molecular cell 44, 667-678 de Silanes, I. L., Grana, O., De Bonis, M. L., Dominguez, O., Pisano, D. G., and Blasco, M. A. (2014). Identification of TERRA locus unveils a telomere protection role through association to nearly all chromosomes. Nat Commun 5, 4723

Deng, X., Berletch, J. B., Nguyen, D. K., and Disteche, C. M. (2014). X chromosome regulation: diverse patterns in development, tissues and disease. Nat Rev Genet 15, 367-378

Deng, Z., Norseen, J., Wiedmer, A., Riethman, H., and Lieberman, P. M. (2009). TERRA RNA binding to TRF2 facilitates heterochromatin formation and ORC recruitment at telomeres. Molecular cell 35, 403-413

Disteche, C. M. (2012). Dosage compensation of the sex chromosomes. Annual review of genetics 46, 537-560

Dixon, J. R., Selvaraj, S., Yue, F., Kim, A., Li, Y., Shen, Y., Hu, M., Liu, J. S., and Ren, B. (2012). Topological domains in mammalian genomes identified by analysis of chromatin interactions. Nature 485, 376-380

Doksani, Y., and de Lange, T. (2014). The role of double-strand break repair pathways at functional and dysfunctional telomeres. Cold Spring Harbor perspectives in biology 6, a016576

Filippova, G. N., Cheng, M. K., Moore, J. M., Truong, J. P., Hu, Y. J., Nguyen, D. K., Tsuchiya, K. D., and Disteche, C. M. (2005). Boundaries between chromosomal domains of X inactivation and escape bind CTCF and lack CpG methylation during early development. Dev Cell 8, 31-42

Heinz, S., Benner, C., Spann, N., Bertolino, E., Lin, Y. C., Laslo, P., Cheng, J. X., Murre, C., Singh, H., and Glass, C. K. (2010). Simple combinations of lineage-determining transcription factors prime cis-regulatory elements required for macrophage and B cell identities. Molecular cell 38, 576-589

Horvath, L. M., Li, N., and Carrel, L. (2013). Deletion of an X-inactivation boundary disrupts adjacent gene silencing. PLoS genetics 9, e1003952

Kharchenko, P. V., Tolstorukov, M. Y., and Park, P. J. (2008). Design and analysis of ChIP-seq experiments for DNA-binding proteins. Nature biotechnology 26, 1351-1359

Kung, J. T., Kesner, B., An, J. Y., Ahn, J. Y., Cifuentes-Rojas, C., Colognori, D., Jeon, Y., Szanto, A., Del Rosario, B. C., Pinter, S. F., et al. (2015). Locus-Specific Targeting to the X Chromosome Revealed by the RNA Interactome of CTCF. Molecular cell 57, 361-375

Le, P. N., Maranon, D. G., Altina, N. H., Battaglia, C. L., and Bailey, S. M. (2013). TERRA, hnRNP A1, and DNA-PKcs Interactions at Human Telomeres. Frontiers in oncology 3, 91

Lee, J. T. (2011). Gracefully ageing at 50, X-chromosome inactivation becomes a paradigm for RNA and chromatin control. Nat Rev Mol Cell Biol 12, 815-826

Lee, J. T., Davidow, L. S., and Warshawsky, D. (1999). Tsix, a gene antisense to Xist at the X-inactivation centre. Nat Genet 21, 400-404

Lingner, J., Hughes, T. R., Shevchenko, A., Mann, M., Lundblad, V., and Cech, T. R. (1997). Reverse transcriptase motifs in the catalytic subunit of telomerase. Science 276, 561-567

Lopes, A. M., Arnold-Croop, S. E., Amorim, A., and Carrel, L. (2011). Clustered transcripts that escape X inactivation at mouse XqD. Mammalian genome: official journal of the International Mammalian Genome Society 22, 572-582

Luke, B., Panza, A., Redon, S., Iglesias, N., Li, Z., and Lingner, J. (2008). The Rat 1p 5' to 3' exonuclease degrades telomeric repeat-containing RNA and promotes telomere elongation in Saccharomyces cerevisiae. Molecular cell 32, 465-477

Maguire, M. P. (1984). The mechanism of meiotic homologue pairing. Journal of theoretical biology 106, 605-615

Maicher, A., Kastner, L., Dees, M., and Luke, B. (2012). Deregulated telomere transcription causes replication-dependent telomere shortening and promotes cellular senescence. Nucleic Acids Res 40, 6649-6659

Merkenschlager, M., and Odom, D. T. (2013). CTCF and cohesin: linking gene regulatory elements with their targets. Cell 152, 1285-1297

Penny, G. D., Kay, G. F., Sheardown, S. A., Rastan, S., and Brockdorff, N. (1996). Requirement for Xist in X chromosome inactivation. Nature 379, 131-137

Pfeiffer, V., Crittin, J., Grolimund, L., and Lingner, J. (2013). The THO complex component Thp2 counteracts telomeric R-loops and telomere shortening. EMBO J 32, 2861-2871

Pfeiffer, V., and Lingner, J. (2012). TERRA promotes telomere shortening through exonuclease 1-mediated resection of chromosome ends. PLoS genetics 8, e1002747

Pinter, S. F., Sadreyev, Yildirim, E., Jeon, Y., Ohsumi, T. K., Borowsky, M., and Lee, J. T. (2012). Spreading of X chromosome inactivation via a hierarchy of defined Polycomb stations. Genome research 22, 1864-1876

Redon, S., Reichenbach, P., and Lingner, J. (2010). The non-coding RNA TERRA is a natural ligand and direct inhibitor of human telomerase. Nucleic Acids Res 38, 5797-5806

Redon, S., Zemp, I., and Lingner, J. (2013). A three-state model for the regulation of telomerase by TERRA and hnRNPAl. Nucleic Acids Res 41, 9117-9128

Reig-Viader, R., Brieno-Enriquez, M. A., Khouriauli, L., Toran, N., Cabero, L., Giulotto, E., Garcia-Caldes, M., and Ruiz-Herrera, A. (2013). Telomeric repeat-containing RNA and telomerase in human fetal oocytes. Hum Reprod 28, 414-422

Reig-Viader, R., Vila-Cejudo, M., Vitelli, V., Busca, R., Sabate, M., Giulotto, E., Caldes, M. G., and Ruiz-Herrera, A. (2014). Telomeric repeat-containing RNA (TERRA) and telomerase are components of telomeres during mammalian gametogenesis. Biol Reprod 90, 103

Rockmill, B., and Roeder, G. S. (1998). Telomere-mediated chromosome pairing during meiosis in budding yeast. Genes & development 12, 2574-2586

Sandell, L. L., Gottschling, D. E., and Zakian, V. A. (1994). Transcription of a yeast telomere alleviates telomere position effect without affecting chromosome stability. Proceedings of the National Academy of Sciences of the United States of America 91, 12061-12065

Schoeftner, S., and Blasco, M. A. (2007). Developmentally regulated transcription of mammalian telomeres by DNA-dependent RNA polymerase II. Nature cell biology 10, 228-236

Schoeftner, S., and Blasco, M. A. (2008). Developmentally regulated transcription of mammalian telomeres by DNA-dependent RNA polymerase II. Nature cell biology 10, 228-236

Sfeir, A., and de Lange, T. (2012). Removal of shelterin reveals the telomere end-protection problem. Science 336, 593-597

Shin, H., Liu, T., Manrai, A. K., and Liu, X. S. (2009). CEAS: cis-regulatory element annotation system. Bioinformatics 25, 2605-2606

Simon, M. D., Pinter, S. F., Fang, R., Sarma, K., Rutenberg-Schoenberg, M., Bowman, S. K., Kesner, B. A., Maier, V. K., Kingston, R. E., and Lee, J. T. (2013). High-resolution Xist binding maps reveal two-step spreading during X-chromosome inactivation. Nature 504, 465-469

Simon, M. D., Wang, C. I., Kharchenko, P. V., West, J. A., Chapman, B. A., Alekseyenko, A. A., Borowsky, M. L., Kuroda, M. I., and Kingston, R. E. (2011). The genomic binding sites of a noncoding RNA. Proceedings of the National Academy of Sciences of the United States of America 108, 20497-20502

Soriano, P., Keitges, E. A., Schorderet, D. F., Harbers, K., Gartler, S. M., and Jaenisch, R. (1987). High rate of recombination and double crossovers in the mouse pseudoautosomal region during male meiosis. Proceedings of the National Academy of Sciences of the United States of America 84, 7218-7220

Starmer, J., and Magnuson, T. (2009). A new model for random X chromosome inactivation. Development 136, 1-10

Sun, S., Del Rosario, B. C., Szanto, A., Ogawa, Y., Jeon, Y., and Lee, J. T. (2013). Jpx RNA activates Xist by evicting CTCF. Cell 153, 1537-1551

Trapnell, C., Hendrickson, D. G., Sauvageau, M., Goff, L., Rinn, J. L., and Pachter, L. (2013). Differential analysis of gene regulation at transcript resolution with RNA-seq. Nature biotechnology 31, 46-53

Wang, C., Zhao, L., and Lu, S. (2015). Role of TERRA in the Regulation of Telomere Length. Int J Biol Sci 11, 316-323

Wutz, A. (2011). Gene silencing in X-chromosome inactivation: advances in understanding facultative heterochromatin formation. Nat Rev Genet 12, 542-553

Xiang, Y., Miller, D. E., Ross, E. J., Sanchez Alvarado, A., and Hawley, R. S. (2014). Synaptonemal complex extension from clustered telomeres mediates full-length chromosome pairing in Schmidtea mediterranea. Proceedings of the National Academy of Sciences of the United States of America 111, E5159-5168

Xu, N., Donohoe, M. E., Silva, S. S., and Lee, J. T. (2007). Evidence that homologous X-chromosome pairing requires transcription and Ctcf protein. Nat Genet 39, 1390-1396

Xu, N., Tsai, C. L., and Lee, J. T. (2006). Transient homologous chromosome pairing marks the onset of X inactivation. Science 311, 1149-1152

Yang, F., Babak, T., Shendure, J., and Disteche, C. M. (2010). Global survey of escape from X inactivation by RNA-sequencing in mouse. Genome research 20, 614-622

Yu, T. Y., Kao, Y. W., and Lin, J. J. (2014). Telomeric transcripts stimulate telomere recombination to suppress senescence in cells lacking telomerase. Proceedings of the National Academy of Sciences of the United States of America 111, 3377-3382

Zhang, L. -F., Ogawa, Y., Ahn, J. Y., Namekawa, S. H., Silva, S. S., and Lee, J. T. (2009). Telomeric RNAs Mark Sex Chromosomes in Stem Cells. Genetics 182, 685

Zhang, Y., Liu, T., Meyer, C. A., Eeckhoute, J., Johnson, D. S., Bernstein, B. E., Nusbaum, C., Myers, R. M., Brown, M., Li, W., et al. (2008). Model-based analysis of ChIP-Seq (MACS). Genome biology 9, R137

Zhao, J., Sun, B. K., Erwin, J. A., Song, J. J., and Lee, J. T. (2008). Polycomb proteins targeted by a short repeat RNA to the mouse X chromosome. Science 322, 750-756

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of decreasing expression of an Xi escapee gene, or decreasing expression of Xa genes, in a cell, the method comprising administering to the cell an inhibitory nucleic acid targeting PAR-TERRA.

2. The method of claim 1, comprising decreasing expression of Xa genes in a cell.

3. The method of claim 2, wherein the cell is in a subject who has a disorder of sex chromosome aneuploidy associated with a supernumerary X chromosome, the method comprising administering to the subject an inhibitory nucleic acid targeting PAR-TERRA.

4. A method of decreasing expression of autosomal genes in a cell, the method comprising administering to the cell an inhibitory nucleic acid targeting PAR-TERRA or an autosome-specific TERRA, optionally TERRA species originating within the subtelomeric region of an autosome and comprising autosome-specific 5' sequences, optionally wherein the inhibitory nucleic acid is modified.

5. The method of claim 4, wherein the inhibitory nucleic acid targets Chr4-specific TERRA.

6. The method of claim 5, wherein expression of FRG1, FRG2, DUX4, and the long noncoding RNAs of forward and reverse orientations from the macrosatellite repeat, D4Z4, is decreased.

7. The method of claim 5, wherein the cell is from or in a subject who has facioscapulohumeral muscular dystrophy (FSHD).

8. The method of claim 3, wherein the subject has 46,XY, 47,XXY, 48,XXYY, 48,XXXY, 47,XXX, 48,XXXX or 49,XXXXX aneuploidy.

9. The method of claim 1, wherein the cell is from a subject who has 46,XY, 47,XXY, 48,XXYY, 48,XXXY, 47,XXX, 48,XXXX or 49,XXXXX aneuploidy.

10. A method of decreasing expression of X-linked or autosomal growth control or apoptosis genes in a cell, the method comprising administering to the cell an inhibitory nucleic acid targeting PAR-TERRA, PAR, or TERRA, optionally wherein the inhibitory nucleic acid is modified.

* * * * *